(12) United States Patent
Crosignani et al.

(10) Patent No.: US 8,273,769 B2
(45) Date of Patent: Sep. 25, 2012

(54) PHENOXY ACETIC ACID DERIVATIVES

(75) Inventors: Stefano Crosignani, St. Genis-Pouilly (FR); Catherine Jorand-Lebrun, Contamine-Sarzin (FR); Christophe Cleva, La Tour (FR); Adeline Pretre, Saint Julien En Genevois (FR)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 13/147,389

(22) PCT Filed: Feb. 9, 2010

(86) PCT No.: PCT/EP2010/051567
§ 371 (c)(1),
(2), (4) Date: Aug. 2, 2011

(87) PCT Pub. No.: WO2010/092043
PCT Pub. Date: Aug. 19, 2010

(65) Prior Publication Data
US 2011/0288066 A1    Nov. 24, 2011

Related U.S. Application Data

(60) Provisional application No. 61/207,778, filed on Feb. 17, 2009.

(30) Foreign Application Priority Data

Feb. 12, 2009   (EP) .................................. 09152711

(51) Int. Cl.
| | |
|---|---|
| A61K 31/426 | (2006.01) |
| A61K 31/44 | (2006.01) |
| A61K 31/4427 | (2006.01) |
| A61K 31/428 | (2006.01) |
| A61K 31/4164 | (2006.01) |
| A61K 31/216 | (2006.01) |
| C07D 233/56 | (2006.01) |
| C07D 333/04 | (2006.01) |
| C07D 333/52 | (2006.01) |
| C07D 277/22 | (2006.01) |
| C07D 277/64 | (2006.01) |
| C07D 231/12 | (2006.01) |
| C07D 213/30 | (2006.01) |
| C07C 69/76 | (2006.01) |

(52) U.S. Cl. ........ 514/336; 514/645; 514/365; 514/407; 514/445; 514/543; 546/268.1; 548/146; 548/152; 548/300.1; 548/302.7; 560/100

(58) Field of Classification Search .................. 514/336, 514/345, 365, 407, 445, 543; 546/268.1; 560/8, 100; 548/146, 152, 300.1, 302.7
See application file for complete search history.

(56) References Cited

FOREIGN PATENT DOCUMENTS
WO   WO 2007/062773   6/2007

OTHER PUBLICATIONS

Kanazawa, C. et al. "Phosphazene base-catalyzed intramolecular cyctization for efficient synthesis of benzofurans via carbon-carbon bond formation" Chemical Communications, 2009, pp. 5248-5250, vol. 35.*
Kanazawa, C. et al. "Phosphazene base-catalyzed intramolecular cyclization for efficient synthesis of benzofurans *via* carbon-carbon bond formation" *Chemical Communications*, 2009, pp. 5248-5250, vol. 35.
Woltering, T. J. et al. "Synthesis and characterization of 8-ethynyl-1,3-dihydrobenzo[bj[1,4]diazepin-2-one derivatives: Part 2. New potent non-competitive metabotropic glutamate receptor 2/3 antagonists" *Bioorangic & Medicinal Chemistry Letters*, 2008, pp. 1091-1095, vol. 18.
Written Opinion in International Application No. PCT/EP2010/051567, Apr. 16, 2010, pp. 1-10.

* cited by examiner

*Primary Examiner* — Joseph K. McKane
*Assistant Examiner* — Janet L Coppins
(74) *Attorney, Agent, or Firm* — Saliwanchik, Lloyd & Eisenschenk

(57)   ABSTRACT

The present invention provides phenoxyacetic acid derivatives of Formula (I) for the treatment of CRTH2 related disorders and disease selected from asthma, atopic dermatitis and inflammatory dermatoses.

12 Claims, No Drawings

PHENOXY ACETIC ACID DERIVATIVES

The present invention relates to phenoxy acetic acid derivatives of Formula (I) and its ester derivatives, for use as pharmaceutical active compounds, as well as pharmaceutical formulations containing such phenoxy acetic acids. Said derivatives are useful for the treatment and/or prevention of diseases such as asthma, atopic dermatitis and inflammatory dermatoses. Specifically, the present invention is related to the use of phenoxy acetic acid derivatives for the modulation of CRTH2 activity. The present invention furthermore relates to methods of the preparation of phenoxy acetic acid derivatives.

In one aspect, the invention provides compounds of Formula (I)

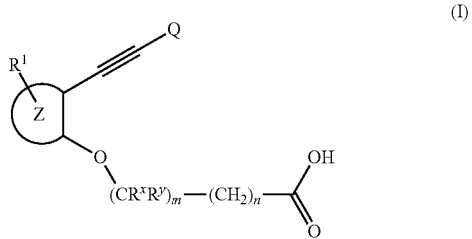

as well as its ester derivatives, its geometrical isomers, its optically active enantiomers, diastereoisomers and its racemates forms, and tautomers, or a pharmaceutically acceptable derivative thereof,
wherein:
$R^1$ is H, Hal, A, CN, $NO_2$, OA, $CF_3$, $OCF_3$, Ar or Het,
Q is Ar, Het,
n is 0, 1, 2, 3, or 4,
m is 0, 1 or 2 wherein n+m is not 0,
Z is phenyl, naphthyl or pyridinyl,
A is branched or linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$— groups may be replaced by O, $NR^3$ or S and/or by CH=CH— or —C≡C— groups, or denotes cycloalkyl or cycloalkylalkylen having 3 to 7 ring C atoms,
Hal is F, Cl, Br or I,
Ar denotes a monocyclic or bicyclic, unsaturated or aromatic carbocyclic ring having 6 to 14 carbon atoms which may be unsubstituted or monosubstituted, disubstituted or trisubstituted or tetrasubstituted by Hal, A, —$CH_2OA$, —$CH_2OR^3$, —$CH_2SO_2A$, —$OR^3$, $CF_3$, —$OCF_3$, —$N(R^3)_2$, $NO_2$, —CN, —$NR^3COA$, —$NR^3COAr'$, —$NR^3SO_2A$, —$COR^3$, CON$(R^3)_2$, COHet, —$SO_2N(R^3)_2$, —SOA, —$SO_2A$, Het, or by $SO_2T$, SOT, Ar',
T denotes —$(CH_2)_p$—Ar' or —$(CH_2)_p$-Het',
p is 0, 1, 2, 3 or 4,
Ar' denotes a monocyclic or bicyclic, unsaturated or aromatic carbocyclic ring having 6 to 14 carbon atoms which may be unsubstituted or monosubstituted, disubstituted or trisubstituted by Hal, A, —$CH_2OA$, —$CH_2OR^3$, —$OR^3$, —$CF_3$, —$OCF_3$,
Het' denotes a monocyclic or bicyclic, saturated, unsaturated or aromatic heterocyclic ring, having 1 to 4 N, O and/or S atoms, which may be unsubstituted or monosubstituted, disubstituted or trisubstituted by Hal, A, $CH_2OA$, $OR^3$, $CF_3$, $OCF_3$,
Het denotes a monocyclic or bicyclic or tricyclic, saturated, unsaturated or aromatic heterocyclic ring, having 1 to 4 N, O, S atoms, and/or 1 $SO_2$ and/or CO groups and/or NO groups, which may be unsubstituted or monosubstituted, disubstituted or trisubstituted or tetrasubstituted by Hal, A, $CH_2OA$, $OR^3$, $CF_3$, $OCF_3$, $N(R^3)_2$, $NO_2$, CN, $NR^3COA$, $NR^3SO_2A$, $COR^3$, $SO_2N(R^3)_2$, SOA, $SO_2A$, $SO_2T$,
$R^3$ is H or A,
$R^x$, $R^y$ independently denote H, a linear or branched alkyl having 1 to 8 carbon atoms optionally substituted with OH, Hal, CN, or $R^x$ and $R^y$ together form a carbocyclic ring having 3 to 7 carbon atoms, optionally substituted by OH, Hal, CN,

BACKGROUND OF THE INVENTION

Prostaglandin D2 (PGD2) has long been associated with inflammatory and atopic conditions, specifically allergic diseases such as asthma, rhinitis, conjunctivitis and atopic dermatitis (Lewis et al. (1982) J. Immunol. 129, 1627). PGD2 belongs to a class of compounds derived from the 20-carbon fatty acid skeleton of arachidonic acid. In response to an antigen challenge, PGD2 is released in large amounts into the airway as well as to the skin during an acute allergic response. The DP receptor, which is a member of the G-protein coupled receptor (GPCR) subfamily, has long been thought to be the only receptor of PGD2. DP's role in allergic asthma has been demonstrated with DP deficient mice (Matsuoka et al. (2000) Science 287, 2013-2017). However, despite intense interest in the role of PGD2 in the inflammatory response, a direct link between DP receptor activation and PGD2-stimulated eosinophil migration has not been established (Woodward et al. (1990) Invest. Ophthalomol. Vis. Sci. 31, 138-146; Woodward et al. (1993) Eur. J. Pharmacol. 230, 327-333).

More recently, another G-protein coupled receptor, referred to as "Chemoattractant Receptor-Homologous molecule expressed on T-Helper 2 cells" (CRTH2) (Nagata et al. (1999) J. Immunol. 162, 1278-1286, Hirai et al. (2001) J Exp. Med. 193, 255-261) has been identified as a receptor for PGD2 and this discovery has begun to shed light on the mechanism of action of PGD2. CRTH2, which is also referred to as DP2, GPR44 or DLIR, shows little structural similarity with the DP receptor and other prostanoid receptors. However, CRTH2 possesses similar affinity for PGD2. Among peripheral blood T lymphocytes, human CRTH2 is selectively expressed on Th2 cells and is highly expressed on cell types associated with allergic inflammation such as eosinophils, basophiles and Th2 cells. In addition, CRTH2 mediates PGD2 dependent cell migration of blood eosinophils and basophiles. Furthermore, increased numbers of circulating T cells expressing CRTH2 have been correlated with the severity of atopic dermatitis (Cosmi et al. (2000) Eur. J. Immunol. 30, 2972-2979). The interaction of CRTH2 with PGD2 plays a critical role in the allergen-induced recruitment of Th2 cells in the target tissues of allergic inflammation. Compounds that inhibit the binding of CRTH2 and PGD2 should therefore be useful for the treatment of allergic diseases.

Allergic disease, like asthma, and inflammatory dermatoses represent a major class of complex, and typically chronic, inflammatory diseases that currently affect about 10% of the population and that number appears to be increasing (Bush, R. K., Georgitis J. W., Handbook of asthma and rhinitis. 1st ed. (1997), Abingdon: Blackwell Science. 270). Atopic dermatitis is a chronic skin disease, wherein the skin becomes extremely itchy. It accounts for 10 to 20 percent of all visits to dermatologists. The increasing incidence of allergic diseases and inflammatory dermatoses worldwide underscores the need for new therapies to effectively treat or prevent these diseases. Currently, numerous classes of pharmaceutical agents are widely used to treat these diseases, for example, antihistamines, decongestants, anticholinergics, methylxanthines, cromolyns, corticosteroids, and leukotriene modulators. However, the usefulness of these agents is often limited by side effects and low efficacy.

It has been reported recently that 3-sulphur-substituted indole derivatives (A) exhibit CRTH2 activity (WO 04/106302, AstraZeneca AB) and are potentially useful for the treatment of various respiratory diseases.

WO 04/096777 (Bayer Healthcare AG) relates to pyrimidine derivatives, which are useful for the treatment of diseases mediated by CRTH2.

WO 04/035543 and WO 05/102338 (Warner-Lambert Company LLC) disclose tetrahydrochinoline derivatives as CRTH2 antagonists (C), which are also described to be effective in the treatment of neuropathic pain.

Specific tetrahydrochinoline derivatives as CRTH2 modulators are also provided by WO 04/032848 (Millennium Pharmaceutical Inc.) and WO 05/007094 (Tularik Inc.). These tetrahydrochinoline derivatives are said to be useful for treating disorders associated with allergic inflammation processes.

Patent applications WO2005115382, WO2007062678, and WO2007062773 also provides phenoxyacetic acid derivatives as ligands of CRTH2 receptors.

The invention further provides a pharmaceutical composition comprising a compound of Formula (I), together with a pharmaceutically acceptable excipient or carrier.

The invention further relates to a kit or a set comprising at least one compound of Formula (I), preferably in combination with immunomodulating agents. Alternatively, the kit consists of separate packs of:

(a) an effective amount of a compound of the formula (I) and/or pharmaceutically usable derivatives, solvates and stereoisomers thereof, including mixtures thereof in all ratios, and (b) an effective amount of a further medicament active ingredient.

The invention further relates to the use of compounds of Formula (I) for the preparation of a medicament for the treatment and/or prevention of diseases selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropathic pain, and other inflammatory diseases such as chronic obstructive pulmonary disease (COPD), rheumatoid arthritis, multiple sclerosis, osteoarthritis, and inflammatory bowel disease (IBD) such as ulcerative colitis and Crohn's disease and other diseases or disorders associated with CRTH2 activity. Specifically the present invention is related to the use of compounds of Formula (I) for the modulation, notably the inhibition of CRTH2 activity.

The invention further relates to a method for treating and/or preventing a patient suffering from a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropathic pain, and other inflammatory diseases such as chronic obstructive pulmonary disease (COPD), rheumatoid arthritis, multiple sclerosis, osteoarthritis, and inflammatory bowel disease (IBD) such as ulcerative colitis and Crohn's disease and other diseases and disorders associated with CTRH2 activity, by administering a compound according to Formula (I).

The invention further relates to the use of compounds of Formula I for the preparation of a pharmaceutical composition.

The invention finally relates to novel compounds of Formula I as well as to methods to synthesize these molecules.

In another embodiment, the present invention provides compounds of Formula (IA)

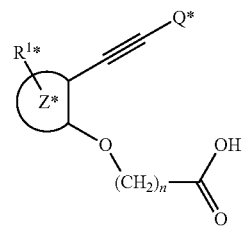

(IA)

As well as its ester derivatives, its geometrical isomers, its optically active enantiomers, diastereoisomers and its racemates forms, and tautomers, or a pharmaceutically acceptable derivative thereof.

Wherein $R^{1*}$ is H, Hal, A, CN, $NO_2$, OA, $CF_3$, $OCF_3$, $Q^*$ is $Ar^*$, $Het^*$, n is 1, 2, 3, or 4, $Z^*$ is phenyl or pyridinyl, A is branched or linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$— groups may be replaced by O, $NR^3$ or S and/or by CH=CH— or —C≡C— groups, or denotes cycloalkyl or cycloalkylalkylen having 3 to 7 ring C atoms, Hal is F, Cl, Br or I, $Ar^*$ denotes a monocyclic or bicyclic, unsaturated or aromatic carbocyclic ring having 6 to 14 carbon atoms which may be unsubstituted or monosubstituted, disubstituted or trisubstituted by Hal, A, $CH_2OA$, —$CH_2OR^3$, $OR^3$, $CF_3$, $OCF_3$, $N(R^3)_2$, $NO_2$, CN, $NR^3COA$, $NR^3SO_2A$, $COR^3$, $SO_2N(R^3)_2$, SOA, $SO_2A$, Het, or by $SO_2T$, T denotes —$(CH_2)_p$—Ar' or —$(CH_2)_p$-Het', p is 0, 1, 2, 3 or 4, Ar' denotes a monocyclic or bicyclic, unsaturated or aromatic carbocyclic ring having 6 to 14 carbon atoms which may be unsubstituted or monosubstituted, disubstituted or trisubstituted by Hal, A, —$CH_2OA$, —$CH_2OR^3$, —$OR^3$, —$CF_3$, —$OCF_3$, Het' denotes a monocyclic or bicyclic, saturated, unsaturated or aromatic heterocyclic ring, having 1 to 4 N, O and/or S atoms, which may be unsubstituted or monosubstituted, disubstituted or trisubstituted by Hal, A, $CH_2OA$, $OR^3$, $CF_3$, $OCF_3$, $Het^*$ denotes a monocyclic or bicyclic, saturated, unsaturated or aromatic heterocyclic ring, having 1 to 4 N, O and/or S atoms, which may be unsubstituted or monosubstituted, disubstituted or trisubstituted by Hal, A, $CH_2OA$, $OR^3$, $CF_3$, $OCF_3$, $N(R^3)_2$, $NO_2$, CN, $NR^3COA$, $NR^3SO_2A$, $COR^3$, $SO_2N(R^3)_2$, SOA, $SO_2A$, $SO_2T$, $R^3$ is H or A, In a preferred embodiment, the invention provides compounds of Formula (Ia):

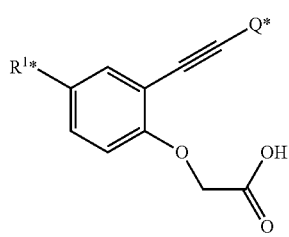

wherein R¹* and Q* are as above defined, as well as their ester derivatives, their geometrical isomers, their optically active enantiomers, diastereoisomers and its racemates forms, and tautomers, or a pharmaceutically acceptable derivative thereof.

In a preferred embodiment, the invention provides compounds of Formula (Ib):

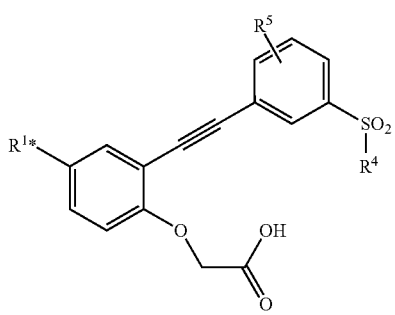

Wherein R¹ is as above defined
R⁴ is N(R³)₂, A or T,
R⁵ is H, Hal, A, CF₃, SO₂A, SO₂N(R³)₂, or SO₂T,
with A, T and R³ being as above defined, as well as their ester derivatives, their geometrical isomers, their optically active enantiomers, diastereoisomers and its racemates forms, and tautomers, or a pharmaceutically acceptable derivative thereof.

In another preferred embodiment, the invention provides compounds of Formula (Ic):

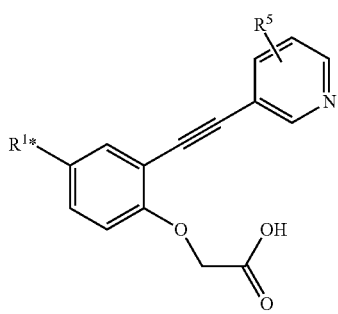

wherein R¹* and R⁵ are as above defined.

In another preferred embodiment, the invention provides compounds of Formula (Id):

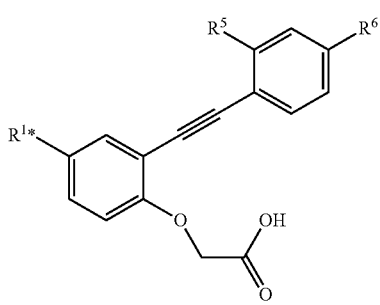

wherein R¹* is as defined above, R⁵ is Hal, and R⁶ is A, CH₂OA, as well as their ester derivatives, their geometrical isomers, their optically active enantiomers, diastereoisomers and its racemates forms, and tautomers, or a pharmaceutically acceptable derivative thereof.

In another preferred embodiment, the invention provides compounds of Formula (Ie):

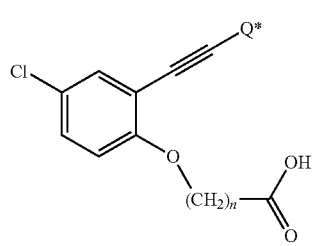

wherein Q* and n are as above defined, as well as their ester derivatives, their geometrical isomers, their optically active enantiomers, diastereoisomers and its racemates forms, and tautomers, or a pharmaceutically acceptable derivative thereof.

In another preferred embodiment, the invention provides compounds of Formula (If)

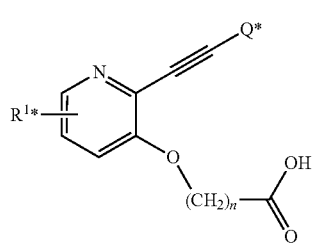

wherein Q*, R¹* and n are as above defined, as well as their ester derivatives, their geometrical isomers, their optically active enantiomers, diastereoisomers and its racemates forms, and tautomers, or a pharmaceutically acceptable derivative thereof.

In another preferred embodiment, the invention provides compounds of Formula (Z):

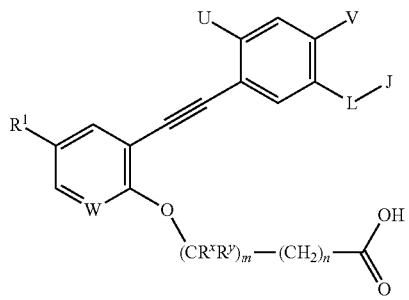

Wherein $R^1$, $R^x$, $R^y$, m and n are as defined under Formula (I),
L denotes $SO_2$, SO, or O, preferably $SO_2$;
W denotes C or N, preferably C,
U denotes H, Hal, $R^Z$,
V denotes H, Ar', $R^Z$, $COR^Z$, $CONHR^Z$, and if linked to J also —CO—, —$CONR^Z$, or an arylen,
J denotes $R^Z$, $NHR^Z$, $N(R^Z)_2$, $(CH_2)_sAr'$, whereby s is 0 or 1; and if linked to V also —$NR^Z$, or $(CH_2)_sAr''$; whereby an arylen denotes a di-, tri-, or tetravalent Ar' group, or when L is O, J also denotes H,
and wherein J and V may be linked to each other to form a ring.
$R^Z$ denotes a linear or branched alkyl or alkenyl having 1 to 6 carbon atoms, optionally substituted by OH, or $OCH_3$;
Ar" denotes an arylen which may be further substituted by 1 or 2 groups selected from $OR^3$, Hal, $CF_3$ wherein $R^3$ is as above defined.
as well as their ester derivatives, their geometrical isomers, their optically active enantiomers, diastereoisomers and their racemates forms, and tautomers, or a pharmaceutically acceptable derivative thereof.

Ar preferably denotes a monocyclic or bicyclic aromatic carbocyclic ring having 6 to 14 carbon atoms which may be unsubstituted, monosubstituted or disubstituted by Hal, A, $CH_2OA$, $OR^3$, $CF_3$, $OCF_3$, $N(R^3)_2$, $NO_2$, CN, $NR^3COA$, $NR^3SO_2A$, $COR^3$, $SO_2N(R^3)_2$, SOA, $SO_2A$, $SO_2T$, wherein T is as defined above.

More preferably, Ar is selected from the following groups:

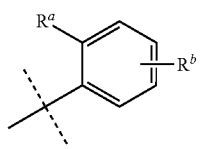

wherein $R^a$ denotes H, alkyl having 1 to 6 carbon atoms, Hal, $CF_3$, —$OR^3$, and $R^b$ denotes H, Hal, $CF_3$, —$SO_2N(R^3)_2$, —$SO_2R^3$, $CH_2OR^3$, $SO_2T$.

Het preferably denotes a monocyclic or bicyclic, saturated, unsaturated or aromatic heterocyclic ring, having 1 to 3 N, O and/or S atoms, which may be unsubstituted or monosubstituted, disubstituted or trisubstituted by Hal, A, $CH_2OA$, $OR^3$, $CF_3$, $OCF_3$, $N(R^3)_2$, $NO_2$, CN, $NR^3COA$, $NR^3SO_2A$, $COR^3$, $SO_2N(R^3)_2$, SOA, $SO_2A$, $SO_2T$, wherein T is as above defined.

More preferably, Het denotes a monocyclic, unsaturated or aromatic heterocyclic ring, having 1 to 3 N, and/or S atoms, which may be unsubstituted, monosubstituted or disubstituted by Hal, A, $CH_2OA$, $OR^3$, $CF_3$, $OCF_3$, $N(R^3)_2$, $NO_2$, CN, $NR^3COA$, $NR^3SO_2A$, $COR^3$, $SO_2N(R^3)_2$, SOA, $SO_2A$, $SO_2T$, wherein T is as above defined.

More preferably, Het denotes one of the following groups:

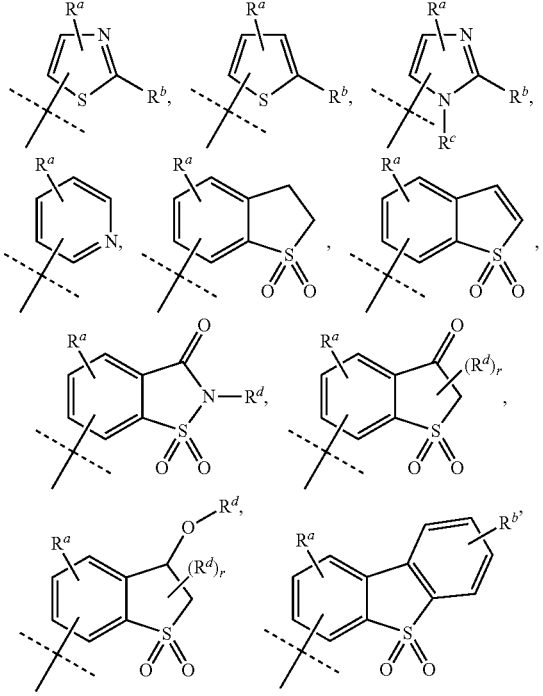

wherein $R^a$, $R^b$ independently from one another denotes an alkyl group having 1 to 6 carbon atoms, H, Hal, CN, $CF_3$, —OMe, —OEt, $(CH_2)_qCH_3$, —$SO_2NH(CH_2)_qCH_3$, —$SO_2(CH_2)_qCH_3$, —$SO_2NH(CH_2)_qOH$, —$SO_2(CH_2)_qOH$, —$SO_2NH(CH_2)_qO(CH_2)_qCH_3$, —$SO_2(CH_2)_qO(CH_2)_qCH_3$, or $SO_2T$ wherein q denotes 0, 1, 2, 3 or 4;
$R^c$ denotes H, Me, or Et,
$R^d$ denotes H or a branched or linear alkyl having 1 to 6 carbon atoms,
and r is 0, 1, 2 or 3.

Q is preferably Ar, more preferably a phenyl group.

Most preferably, when Q is Het, Het denotes one of the following groups:

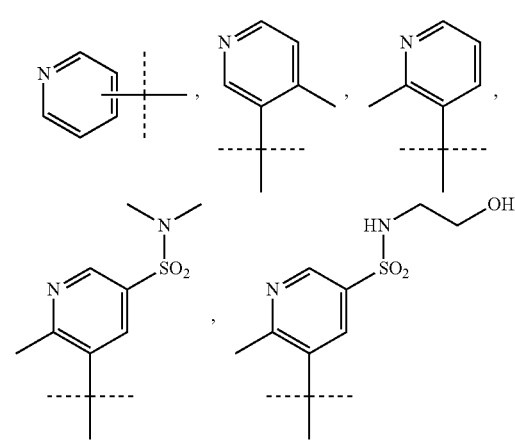

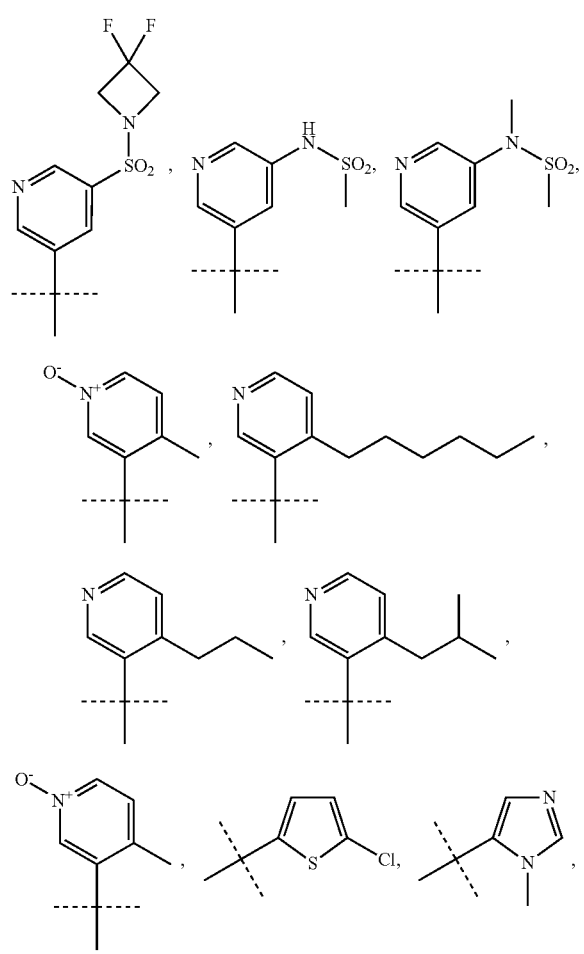
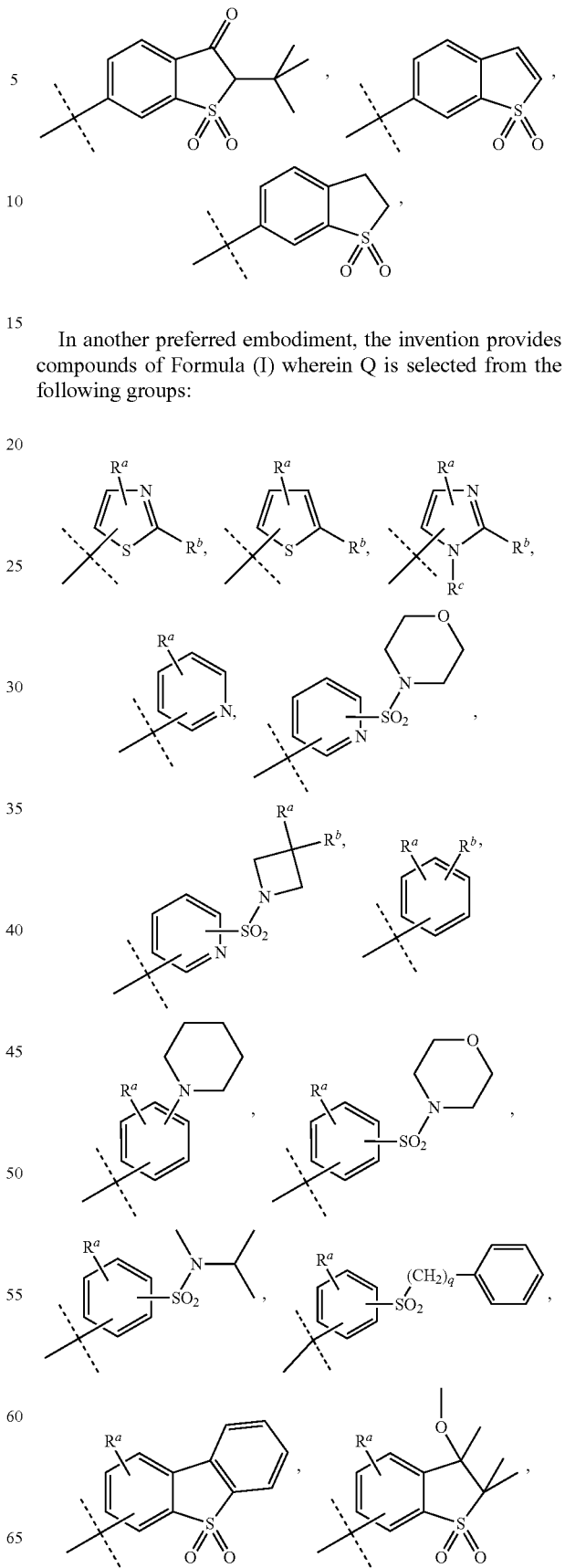
In another preferred embodiment, the invention provides compounds of Formula (I) wherein Q is selected from the following groups:

-continued

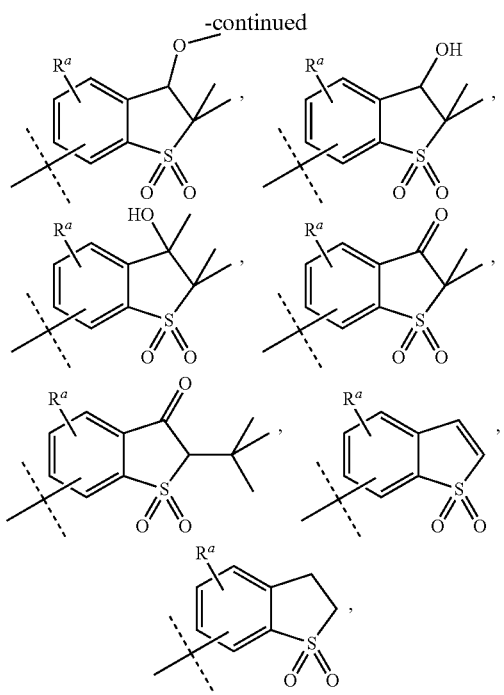

Wherein $R^a$, $R^b$ independently from one another denotes H, Hal, CN, OH, $CF_3$, —OMe, —OEt, $(CH_2)_qCH_3$, —$(CH_2)_q(CH)(CH_3)_2$, —$SO_2NH(CH_2)_qCH_3$, —$SO_2NH(CH_2)_qC(CH_3)_3$, —$SO_2N(C_2H_5)_2$, —$SO_2(CH_2)_qCH_3$, —$SO_2(CH)(CH_3)_2$, $SO_2(CH_2)_qCH(CH_3)_2$, —$SO_2NH(CH_2)_qOH$, —$SO_2(CH_2)_qOH$, —$SO_2NH(CH_2)_qO(CH_2)_qCH_3$, —$SO_2(CH_2)_qO(CH_2)_qCH_3$, $N(CH_3)$—$SO_2$—$(CH_2)_qCH_3$, —Ar', —$(CH_2)$ Ar', or $SO_2T$, wherein q denotes 0, 1, 2, 3 or 4, and wherein $R^x$ denotes H, Me, Et.

Most preferably, when $R^1$ is Het, $R^1$ denotes one of the following groups:

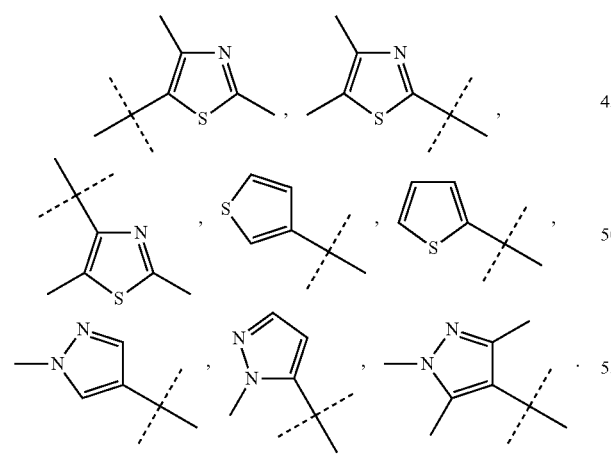

Otherwise $R^1$ preferably denotes H, Cl, F, CN, —$CH_3$, —$CF_3$, or a phenyl group optionally substituted by an alkyl having 1 to 6 carbon atoms, and most preferably H, Cl, or a phenyl group optionally substituted by an alkyl having 1 to 6 carbon atoms.

A preferably denotes a branched or linear alkyl having 1 to 6 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$— groups may be replaced by O, $NR^3$ or S.

Het' preferably denotes a monocyclic saturated, heterocyclic ring, having 1 to 3 N, and/or O atoms, which may be unsubstituted or monosubstituted, disubstituted or trisubstituted by Hal, A, $CH_2OA$, $OR^3$, $CF_3$, $OCF_3$.

Most preferably, Het' denotes one of the following groups:

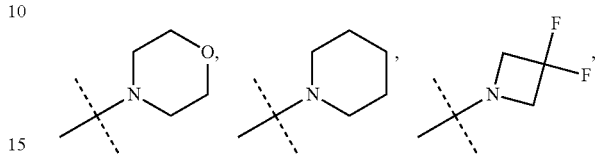

Ar' preferably denotes a phenyl group.
n is preferably 1 or 2
—$OR^3$ preferably denotes one of the following groups: —OH, $O(C_1-C_6)$alkyl, most preferably, OH or OMe.

An "alkyl" or "alky group" denotes a linear or branched carbon chain having 1 to 6 carbon atoms. Preferably, an "alkyl" or an "alkyl group" denotes a linear or branched carbon chain having 1 to 4 carbon atoms.

The term "ester" or "ester derivatives" refers to compounds of Formula (I) wherein one or more carboxylic function is protected with an alkyl, Ar, Het or benzyl group, preferably with a tert-butyl group.

The term "arylen" refers to a divalent monocyclic or bicyclic, unsaturated or aromatic carbocyclic ring, having 6 to 14 carbon atoms. "Arylen" preferably refers to a phenylene group optionally substituted with $OR^3$, Hal, and/or $CF_3$, wherein $R^3$ is as above defined.

In a preferred embodiment, the invention also provides compounds of Formula (I') or (IA')

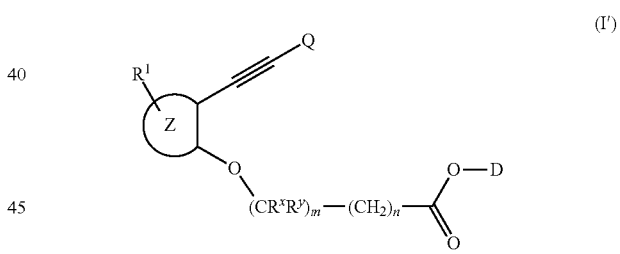

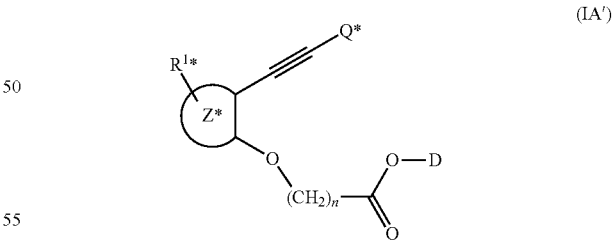

wherein D denotes an alkyl, a benzyl group, Ar or Het.
D preferably denotes an alkyl, preferably tert-butyl, or a benzyl group.

In another preferred embodiment, the invention provides compounds of Formula (IA) wherein $R^{1*}$ is as defined under (IA) and wherein $Q^*$ denotes a phenyl optionally substituted with Hal, —OMe, CN, $CF_3$, —$SO_2NH(CH_2)_qCH_3$, —$SO_2(CH_2)_qCH_3$, —$SO_2NH(CH_2)_qOR_3$, —$SO_2(CH_2)_qOR_3$, —$(CH_2)_qCH_3$, —$(CH_2)_qOR_3$, wherein q and $R^3$ are as above defined.

In another preferred embodiment, the invention provides compounds of Formula (IA) wherein R¹* is as defined under Formula (IA) and wherein Q* denotes a phenyl optionally substituted with an alkyl having 1 to 6 carbon atoms.

In another preferred embodiment, the invention provides compounds of Formula (IA) wherein R¹* is as defined under Formula (IA) and wherein Q* denotes a pyridinyl optionally substituted with Hal, —OMe, CN, CF₃, —SO₂NH(CH₂)$_q$CH₃, —SO₂(CH₂)$_q$CH₃, —SO₂NH(CH₂)$_q$OR₃, —SO₂(CH₂)$_q$OR₃, —(CH₂)$_q$CH₃, —(CH₂)$_q$OR³, wherein q and R³ are as above defined.

In another embodiment, the invention provides compounds of Formula (IA) wherein R¹* is as defined under Formula (IA) and wherein Q* denotes a thienyl optionally substituted with Hal, —OMe, CN, CF₃, —SO₂NH(CH₂)$_q$CH₃, —SO₂(CH₂)$_q$CH₃, —SO₂NH(CH₂)$_q$OR₃, —SO₂(CH₂)$_q$OR₃, —(CH₂)$_q$CH₃, —(CH₂)$_q$OR³, wherein q and R³ are as above defined.

In another embodiment, the invention provides compounds of Formula (IA) wherein R¹* is as defined under Formula (IA) and wherein Q* denotes an imidazol optionally substituted with Hal, —OMe, CN, CF₃, —SO₂NH(CH₂)$_q$CH₃, —SO₂(CH₂)$_q$CH₃, —SO₂NH(CH₂)$_q$OR₃, —SO₂(CH₂)$_q$OR₃, —(CH₂)$_q$CH₃, —(CH₂)$_q$OR³, wherein q and R³ are as above defined.

In another preferred embodiment, the invention provides compounds of Formula (IA) and related formulae wherein Q* is as defined above and wherein R¹* is Hal, —(CH₂)$_q$CH₃, CN, CF₃, —O(CH₂)$_q$CH₃, wherein q is 0, 1, 2, 3, or 4, preferably 0, 1 or 2.

In another preferred embodiment, the invention provides compounds of Formula (I) wherein Q denotes a phenyl or a pyridinyl optionally substituted with Hal, —OMe, —OH, —CN, —CF₃, —SO₂NH(CH₂)$_q$CH₃, —SO₂(CH₂)$_q$CH₃, —SO₂NH(CH₂)$_q$OR³, —SO₂NR³(CH₂)$_q$OR³, —SO₂(CH₂)$_q$OR³, —(CH₂)$_q$CH₃, —(CH₂)$_q$OR³, —SO₂(CH₂)$_q$C(CH₃)₂, SO₂(CH₂)$_q$Ar, SO₂N(CH₃)₂, NR³CO(CH₂)$_q$CH₃, wherein q and R³ are as defined under Formula (I).

The preferred compounds of the invention are selected from the following group:

| Ex. | Formula |
|---|---|
| 1 | (4-chloro-2-(phenylethynyl)phenoxy)acetic acid structure |
| 2 | (4-chloro-2-((4-chlorophenyl)ethynyl)phenoxy)acetic acid structure |
| 3 | (4-chloro-2-((3-chlorophenyl)ethynyl)phenoxy)acetic acid structure |
| 4 | (4-chloro-2-((2-chlorophenyl)ethynyl)phenoxy)acetic acid structure |
| 5 | (4-chloro-2-((2-fluorophenyl)ethynyl)phenoxy)acetic acid structure |
| 6 | (4-chloro-2-((2-methoxyphenyl)ethynyl)phenoxy)acetic acid structure |
| 7 | (4-chloro-2-((3-(trifluoromethyl)phenyl)ethynyl)phenoxy)acetic acid structure |
| 8 | (4-chloro-2-((2,4-difluorophenyl)ethynyl)phenoxy)acetic acid structure |

-continued

| Ex. | Formula |
|---|---|
| 9 | 2-[4-chloro-2-[(2-trifluoromethylphenyl)ethynyl]phenoxy]acetic acid |
| 10 | 2-[4-chloro-2-[(5-chlorothiophen-2-yl)ethynyl]phenoxy]acetic acid |
| 11 | 2-[4-chloro-2-[(1-methyl-1H-imidazol-2-yl)ethynyl]phenoxy]acetic acid |
| 12 | 2-[4-chloro-2-(pyridin-4-ylethynyl)phenoxy]acetic acid |
| 13 | 2-[4-chloro-2-(pyridin-2-ylethynyl)phenoxy]acetic acid |
| 14 | 2-[4-chloro-2-(pyridin-3-ylethynyl)phenoxy]acetic acid |

-continued

| Ex. | Formula |
|---|---|
| 15 | 2-[4-chloro-2-[(4-methylpyridin-3-yl)ethynyl]phenoxy]acetic acid |
| 16 | 2-[4-chloro-2-[[3-(N-ethylsulfamoyl)-4-methylphenyl]ethynyl]phenoxy]acetic acid |
| 17 | 2-[4-chloro-2-[[3-(propylsulfonyl)phenyl]ethynyl]phenoxy]acetic acid |
| 18 | 2-[4-chloro-2-[[3-(methylsulfonyl)phenyl]ethynyl]phenoxy]acetic acid |
| 19 | 2-[4-chloro-2-[[3-[(3-hydroxypropyl)sulfonyl]phenyl]ethynyl]phenoxy]acetic acid |
| 20 | 2-[4-chloro-2-[[3-[(2-hydroxyethyl)sulfonyl]phenyl]ethynyl]phenoxy]acetic acid |

-continued

| Ex. | Formula |
|---|---|
| 21 | 3-[(4-chloro-2-(carboxymethoxy)phenyl)ethynyl]-4-fluorobenzonitrile |
| 22 | 2-(4-chloro-2-{[(2-methylpyridin-3-yl)]ethynyl}phenoxy)acetic acid |
| 23 | 2-{4-cyano-2-[(2-chlorophenyl)ethynyl]phenoxy}acetic acid |
| 24 | 2-(4-chloro-2-{[(2,4-dimethylthiazol-5-yl)]ethynyl}phenoxy)acetic acid |
| 25 | 2-(4-chloro-2-{[4-fluoro-3-(hydroxymethyl)phenyl]ethynyl}phenoxy)acetic acid |
| 26 | 2-(4-chloro-2-{[3-fluoro-4-(hydroxymethyl)phenyl]ethynyl}phenoxy)acetic acid |

-continued

| Ex. | Formula |
|---|---|
| 27 | 2-{2-[(2-chlorophenyl)ethynyl]-4-methylphenoxy}acetic acid |
| 28 | 2-(4-chloro-2-{[2-fluoro-3-(hydroxymethyl)phenyl]ethynyl}phenoxy)acetic acid |
| 29 | 2-(4-chloro-2-{[(4-pentylpyridin-3-yl)]ethynyl}phenoxy)acetic acid |
| 30 | 2-(4-chloro-2-{[2-fluoro-5-(methoxymethyl)phenyl]ethynyl}phenoxy)acetic acid |
| 31 | 2-(4-chloro-2-{[(4-methyl-1-oxidopyridin-3-yl)]ethynyl}phenoxy)acetic acid |

-continued
| Ex. | Formula |
|---|---|
| 32 | 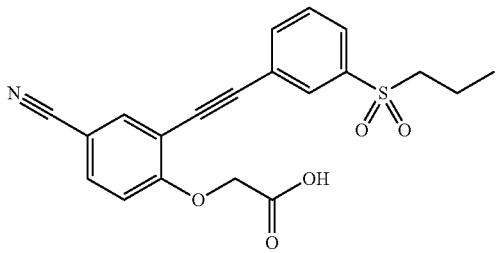 |
| 33 | 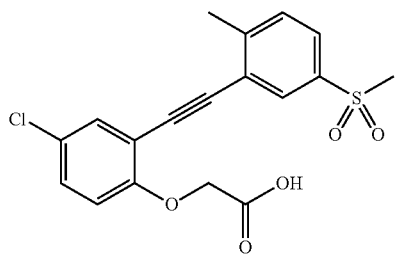 |
| 34 | 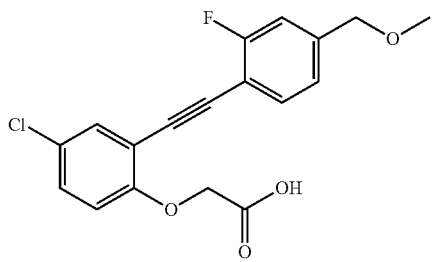 |
| 35 | 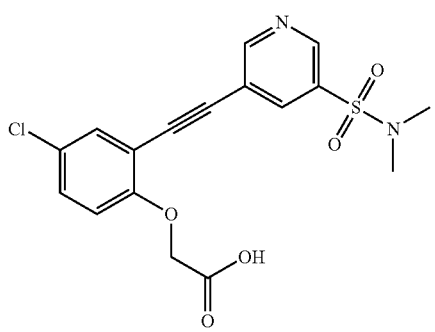 |
| 36 | 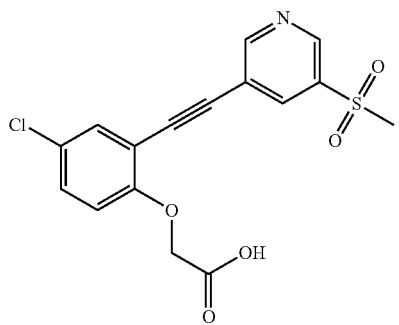 |
-continued
| Ex. | Formula |
|---|---|
| 37 | 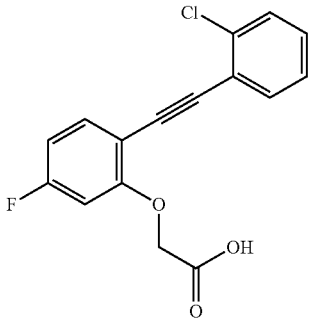 |
| 38 | | 
| 39 | |
| 40 | |
| 41 | |
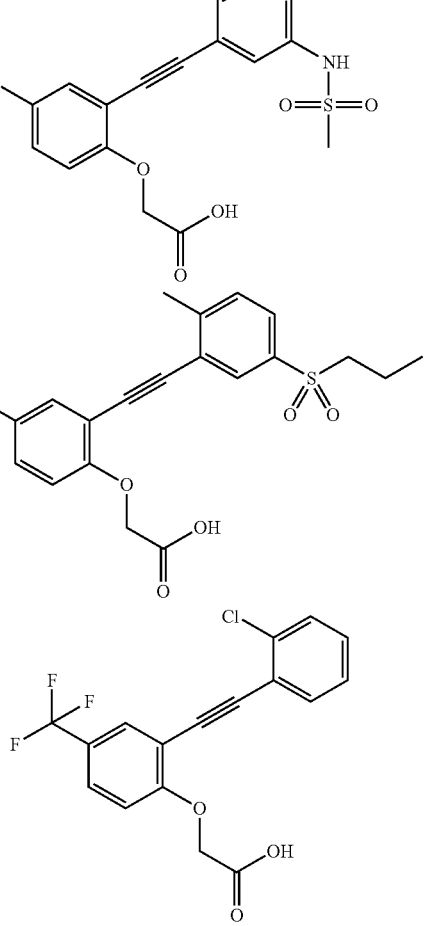

-continued
| Ex. | Formula |
|---|---|
| 42 | 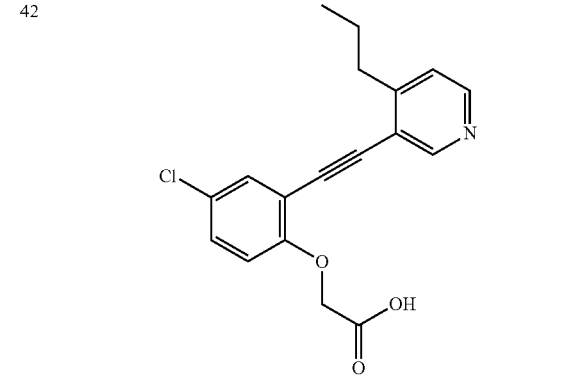 |
| 43 | 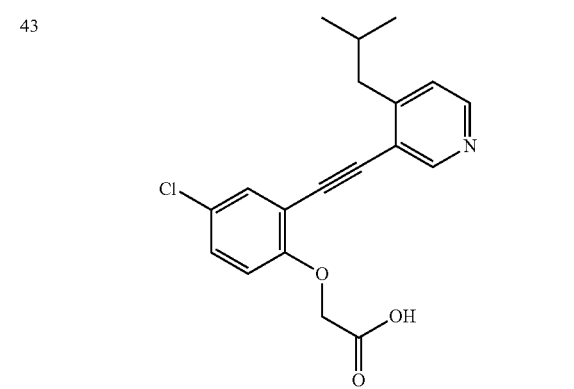 |
| 44 | 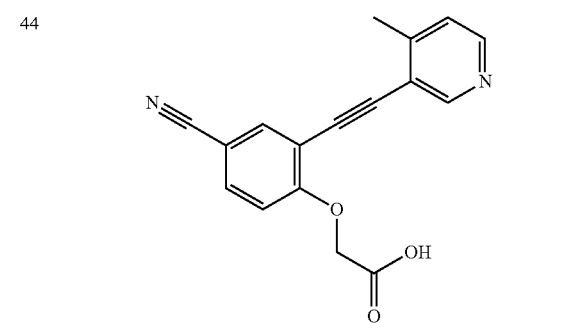 |
| 45 | 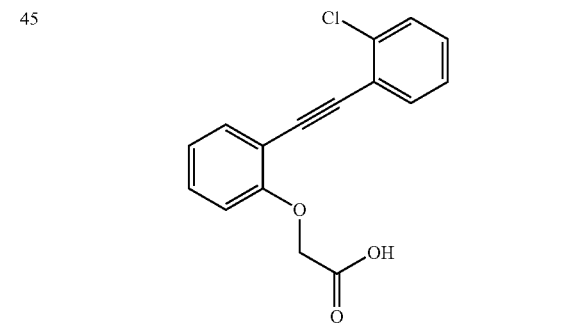 |
-continued
| Ex. | Formula |
|---|---|
| 46 | 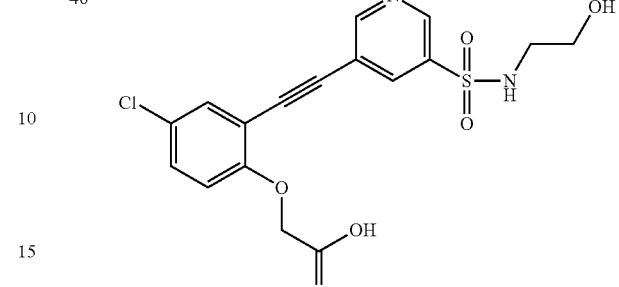 |
| 47 | 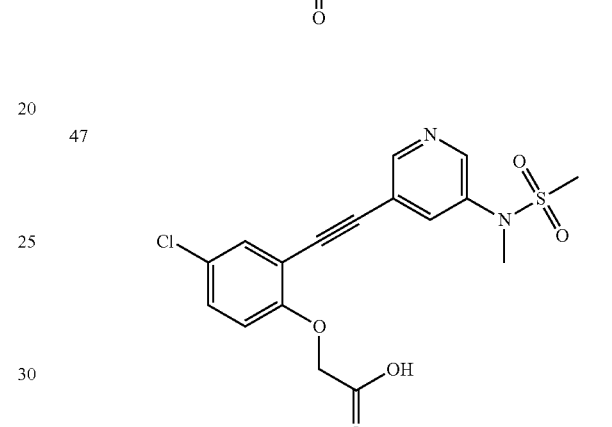 |
| 48 | 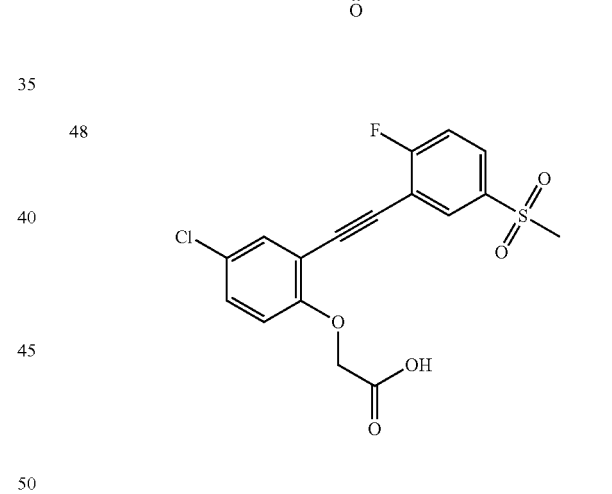 |
| 49 | 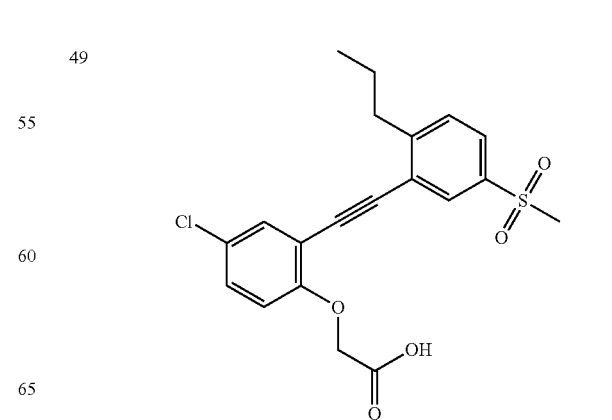 |

23
-continued
| Ex. | Formula |
|---|---|
| 50 | |
| 51 | |
| 52 | |
| 53 | |
| 54 | |
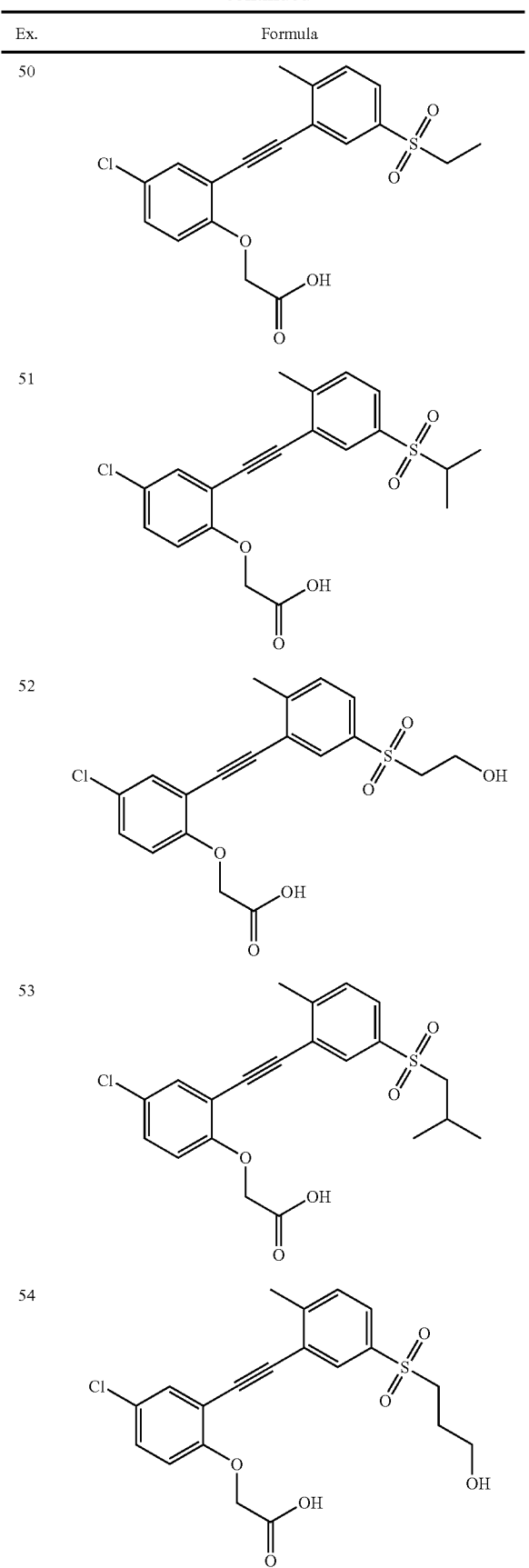
24
-continued
| Ex. | Formula |
|---|---|
| 55 | |
| 56 | |
| 57 | |
| 58 | |
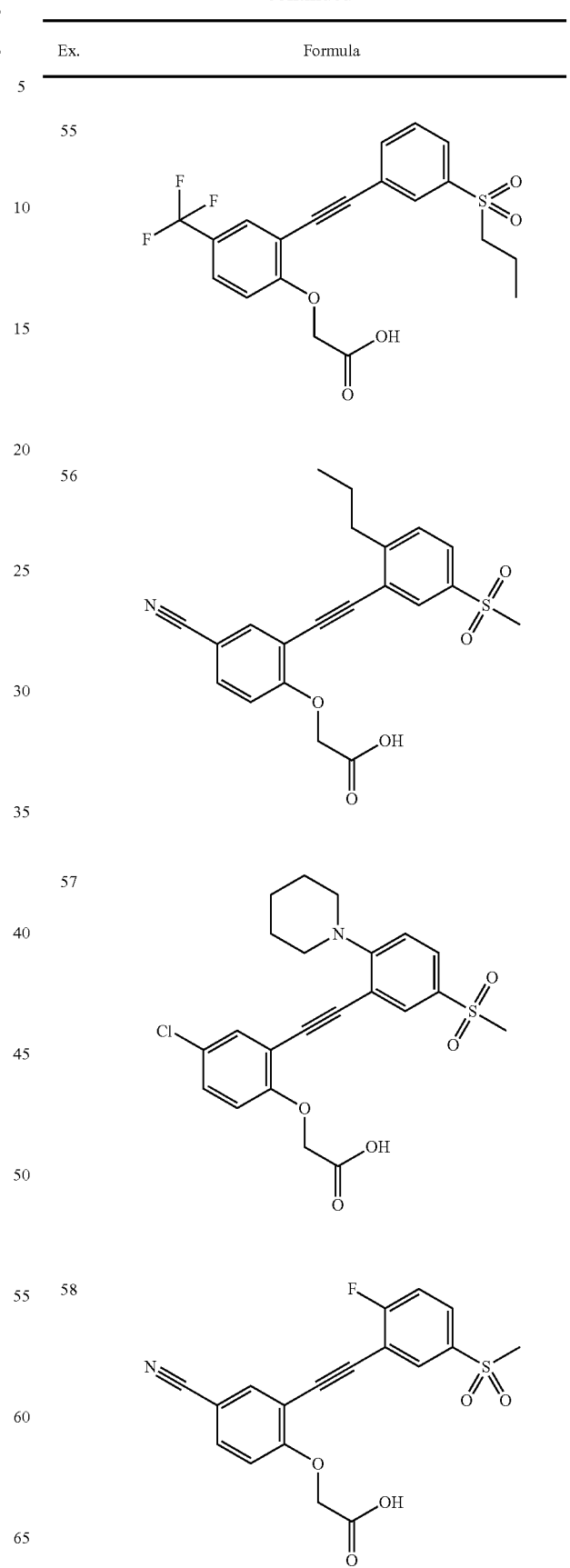

| Ex. | Formula |
|---|---|
| 59 | 4-chloro-2-((2-chloro-5-(methylsulfonyl)phenyl)ethynyl)phenoxyacetic acid |
| 60 | 4-chloro-2-((2-hydroxy-5-(methylsulfonyl)phenyl)ethynyl)phenoxyacetic acid |
| 61 | 4-cyano-2-((2-chloro-5-(methylsulfonyl)phenyl)ethynyl)phenoxyacetic acid |
| 62 | 4-cyano-2-((2-(piperidin-1-yl)-5-(methylsulfonyl)phenyl)ethynyl)phenoxyacetic acid |
| 63 | 4-cyano-2-((5-(ethylsulfonyl)-2-methylphenyl)ethynyl)phenoxyacetic acid |
| 64 | 4-cyano-2-((5-((2-hydroxyethyl)sulfonyl)-2-methylphenyl)ethynyl)phenoxyacetic acid |
| 65 | 4-cyano-2-((5-(isobutylsulfonyl)-2-methylphenyl)ethynyl)phenoxyacetic acid |
| 66 | 2-((6-methyl-3-((3-(propylsulfonyl)phenyl)ethynyl)pyridin-2-yl)oxy)acetic acid |
| 67 | 4-cyano-2-((5-(N,N-dimethylsulfamoyl)pyridin-3-yl)ethynyl)phenoxyacetic acid |

27
-continued
| Ex. | Formula |
|---|---|
| 68 | 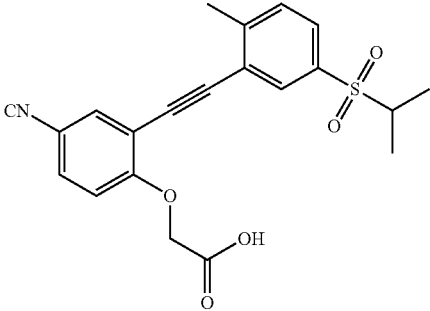 |
| 69 | 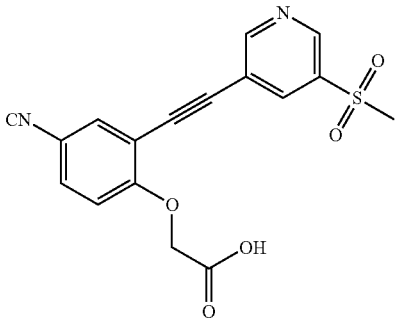 |
| 70 | 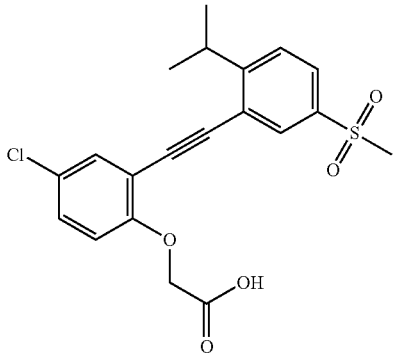 |
| 71 | 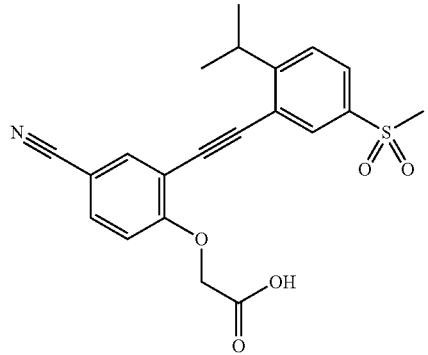 |
28
-continued
| Ex. | Formula |
|---|---|
| 72 | 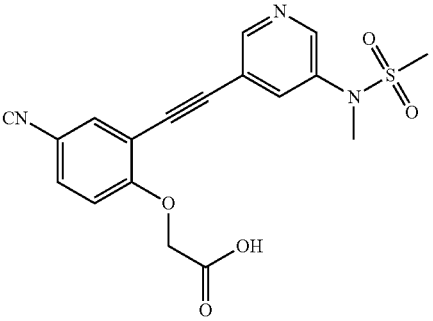 |
| 73 | 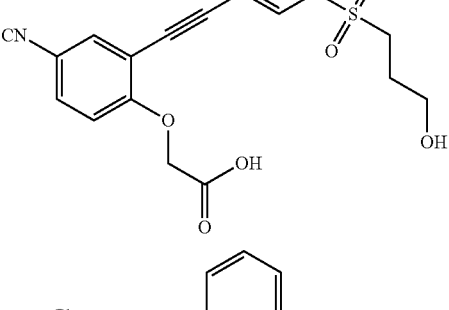 |
| 74 | 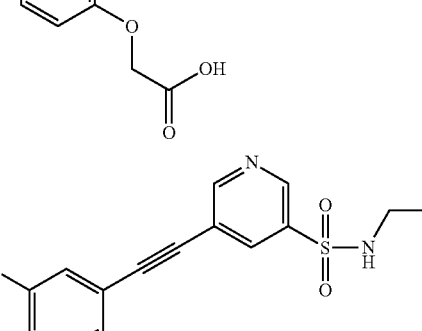 |
| 75 | 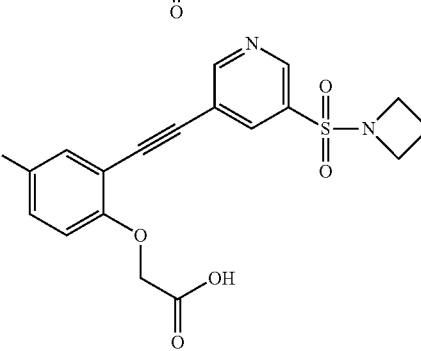 |
| 76 | 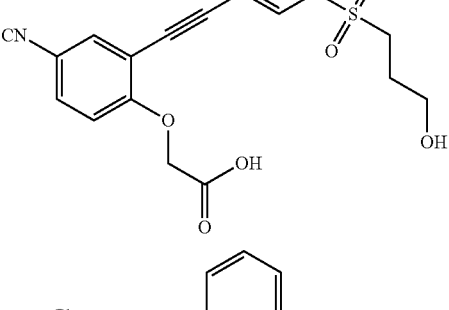 |

-continued
| Ex. | Formula |
|---|---|
| 77 | 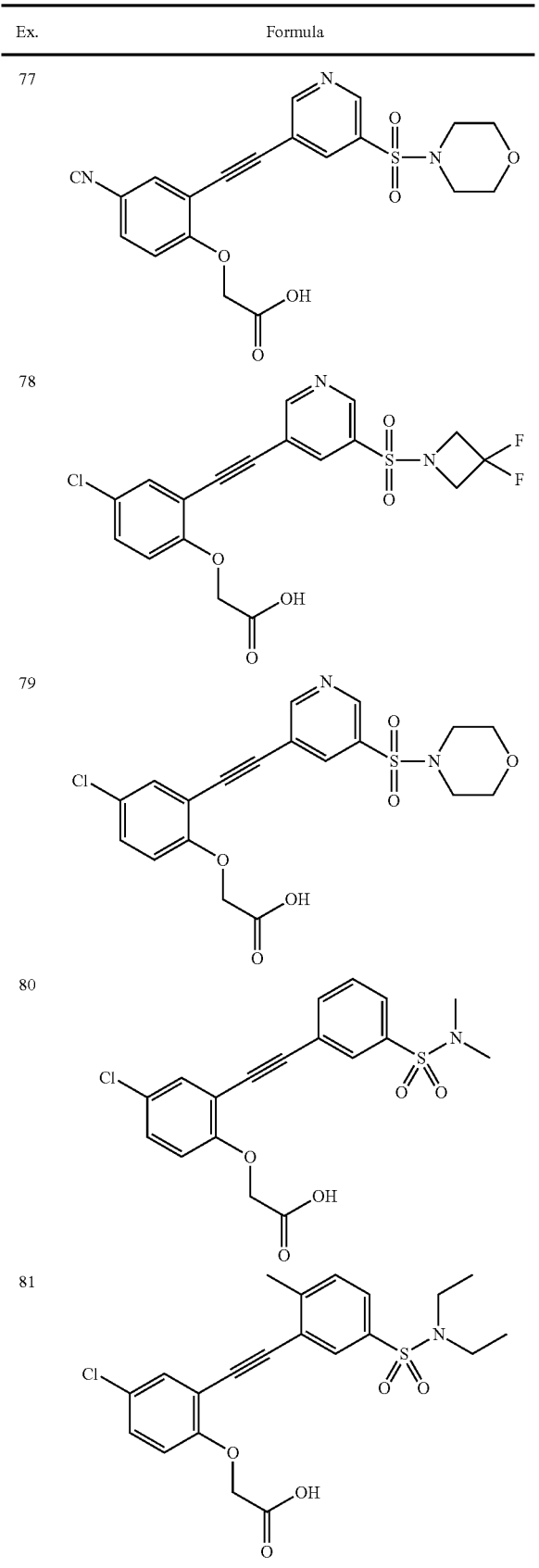 |
| 78 | |
| 79 | |
| 80 | |
| 81 | |
-continued
| Ex. | Formula |
|---|---|
| 82 |  |
| 83 | |
| 84 | |
| 85 | |
| 86 | |

-continued
| Ex. | Formula |
|---|---|
| 87 | 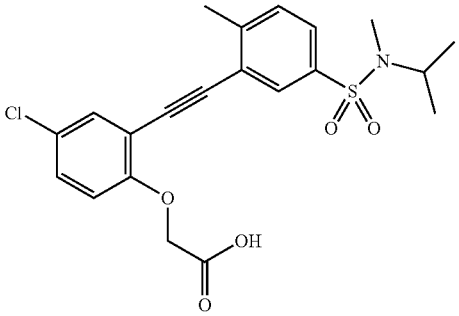 |
| 88 | 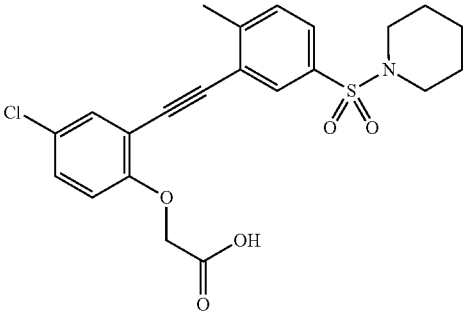 |
| 89 | 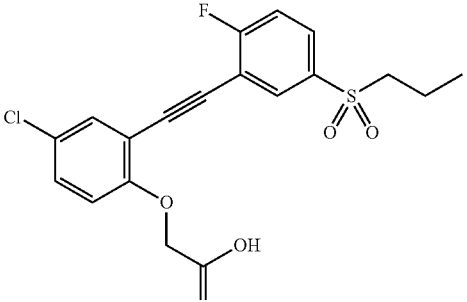 |
| 90 | 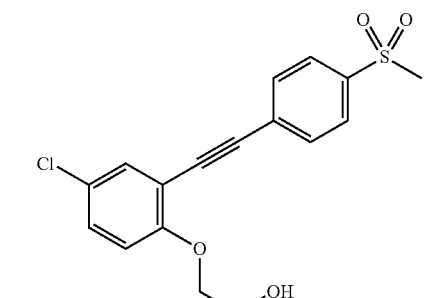 |
| 91 | 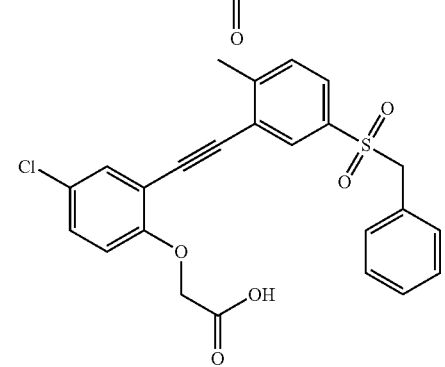 |
-continued
| Ex. | Formula |
|---|---|
| 92 | 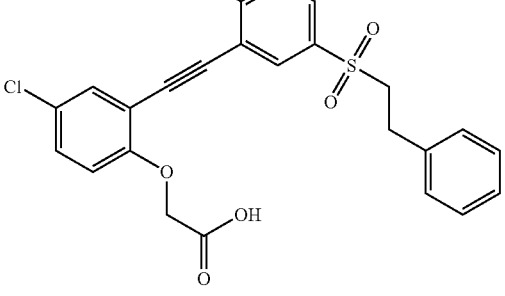 |
| 93 | 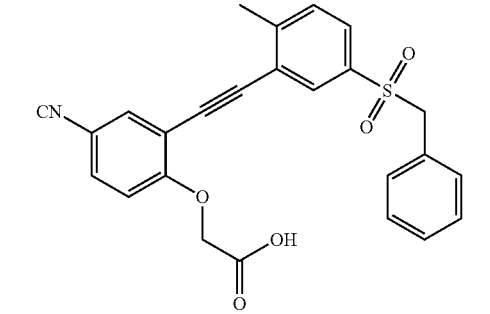 |
| 94 | 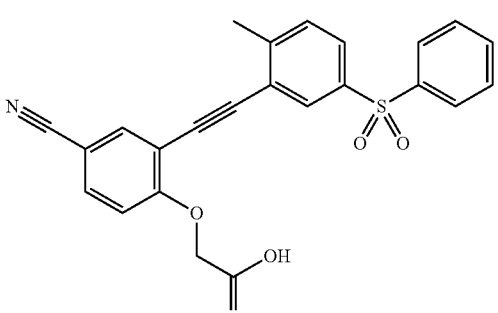 |
| 95 | 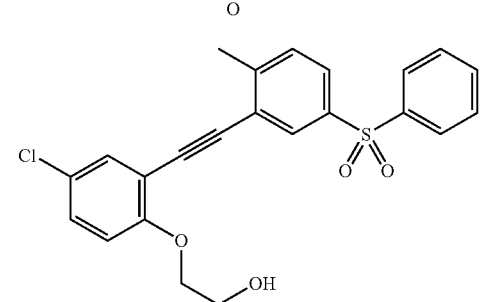 |
| 96 | 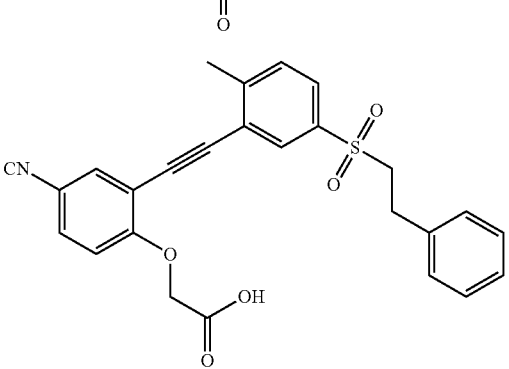 |

| Ex. | Formula |
|---|---|
| 97 | 4-chloro-2-[(4-fluoro-2-methyl-5-methylsulfonylphenyl)ethynyl]phenoxyacetic acid |
| 98 | {4-chloro-2-[(3-methylsulfonylmethylphenyl)ethynyl]phenoxy}acetic acid |
| 99 | {4-fluoro-2-[(3-propylsulfonylphenyl)ethynyl]phenoxy}acetic acid |
| 100 | {4-chloro-2-[(2-ethyl-5-methylsulfonylphenyl)ethynyl]phenoxy}acetic acid |

| Ex. | Formula |
|---|---|
| 101 | {4-chloro-2-[(4-chloro-3-propylsulfonylphenyl)ethynyl]phenoxy}acetic acid |
| 102 | {4-chloro-2-[(4-fluoro-3-isopropylsulfonylphenyl)ethynyl]phenoxy}acetic acid |
| 103 | {4-chloro-2-[(4-chloro-3-isopropylsulfonylphenyl)ethynyl]phenoxy}acetic acid |
| 104 | {4-chloro-2-[(3-ethylsulfonyl-4-fluorophenyl)ethynyl]phenoxy}acetic acid |

| Ex. | Formula |
|---|---|
| 105 | 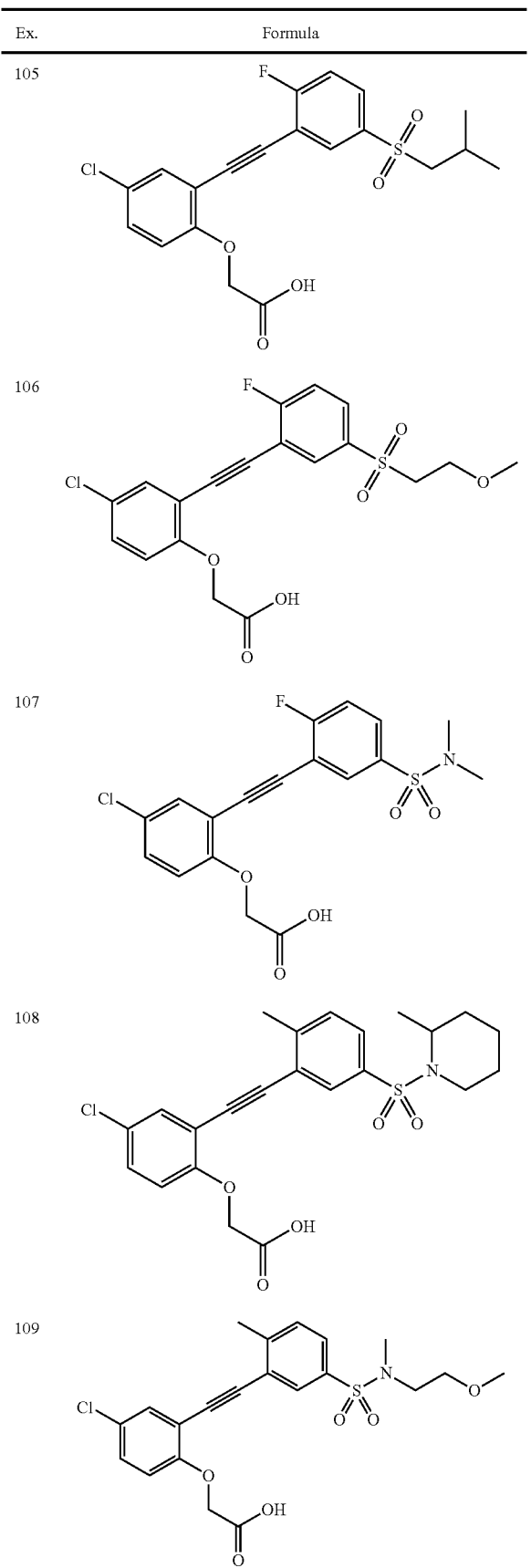 |
| 106 | |
| 107 | |
| 108 | |
| 109 | |
| Ex. | Formula |
|---|---|
| 110 | 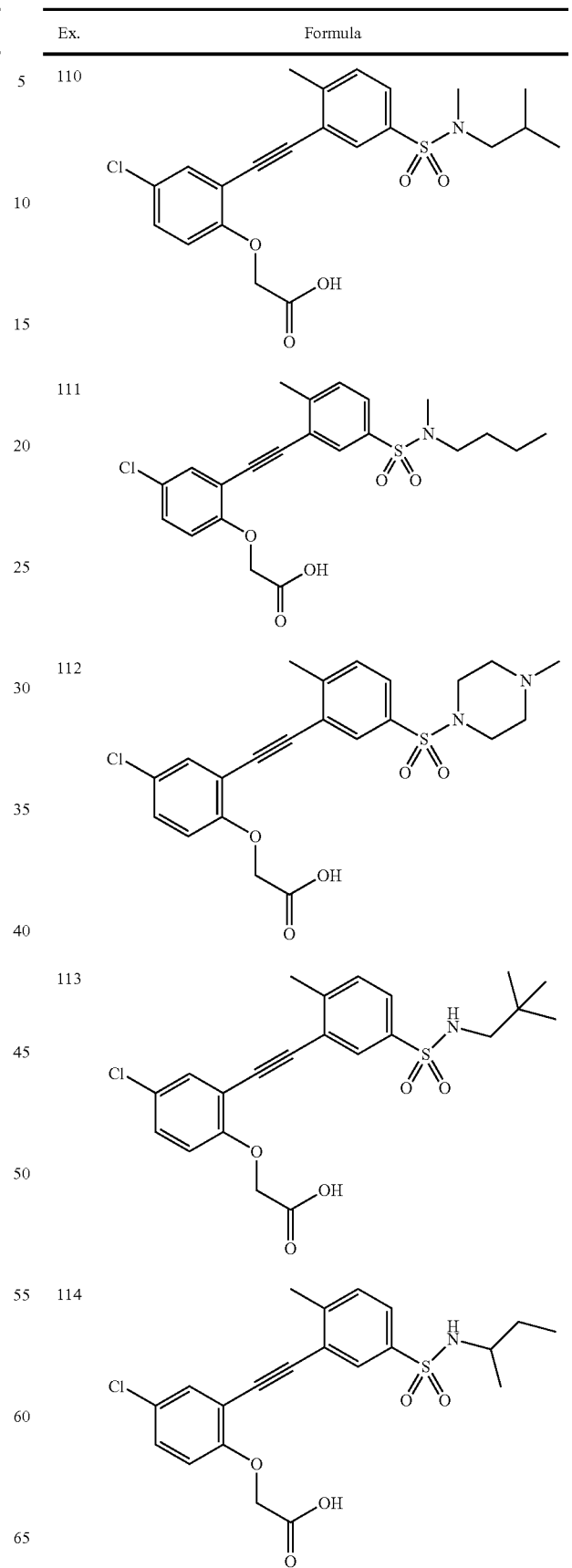 |
| 111 | |
| 112 | |
| 113 | |
| 114 | |

| Ex. | Formula |
|---|---|
| 115 | |
| 116 | |
| 117 | |
| 118 | |
| 119 | |
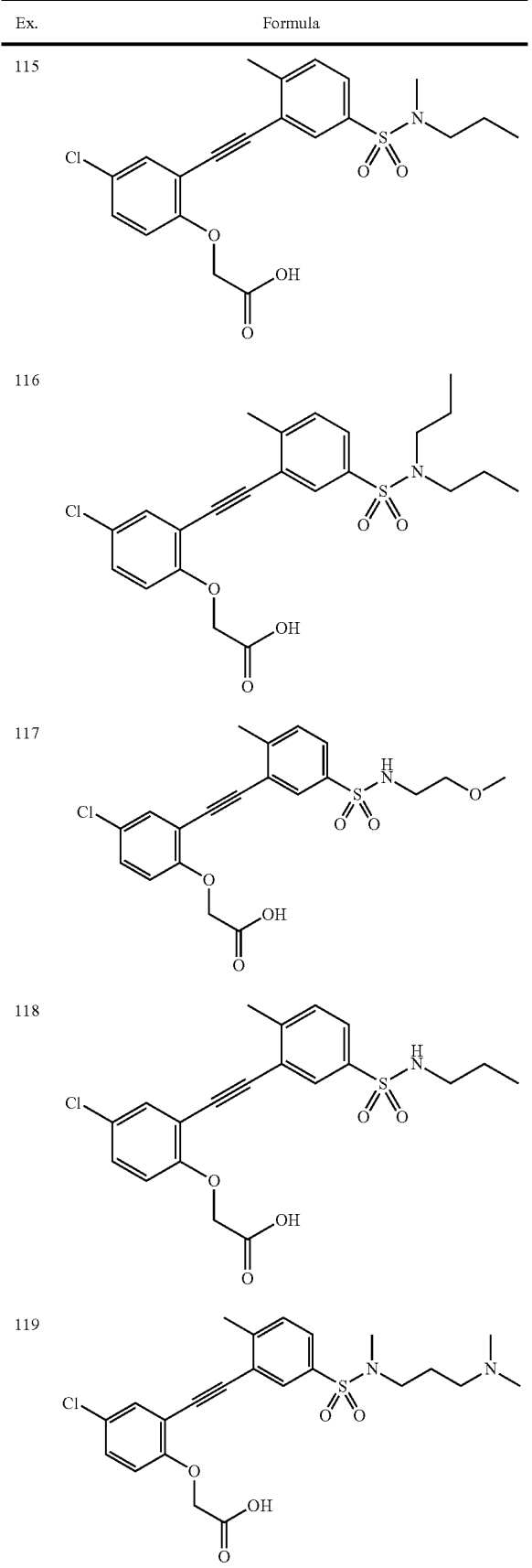
| Ex. | Formula |
|---|---|
| 120 | |
| 121 | |
| 122 | |
| 123 | |
| 124 | |
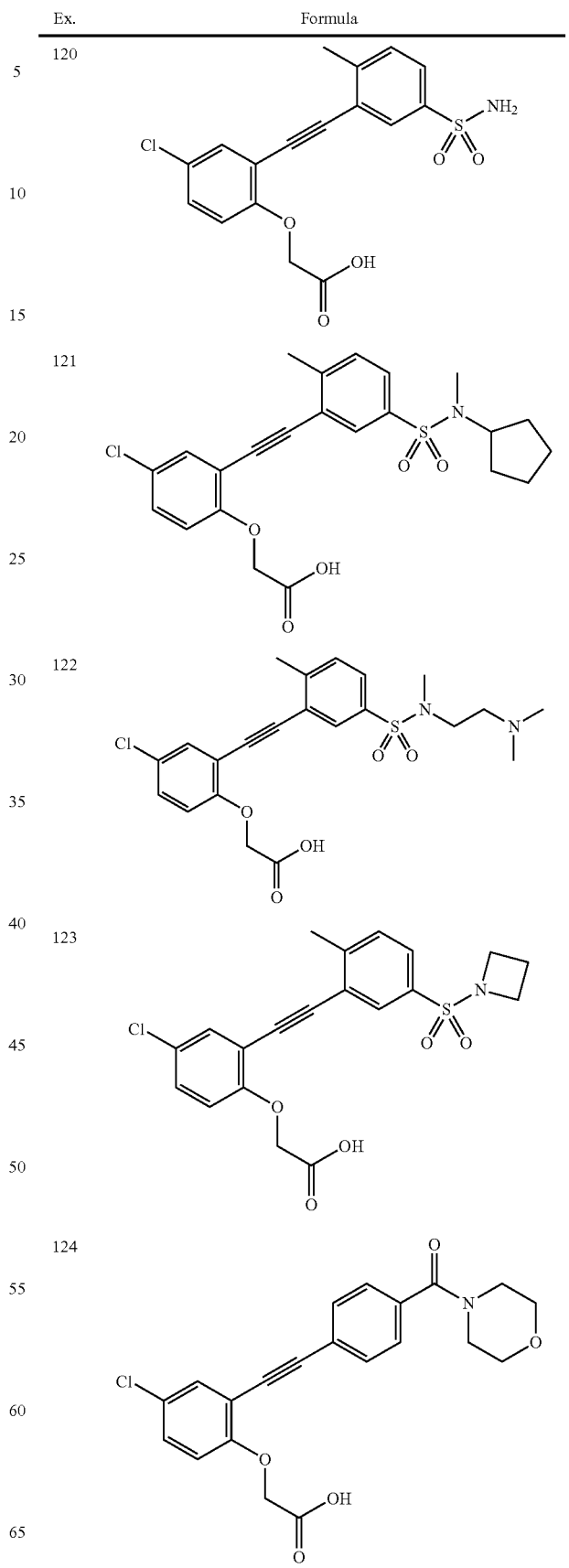

39
-continued
| Ex. | Formula |
|---|---|
| 125 | 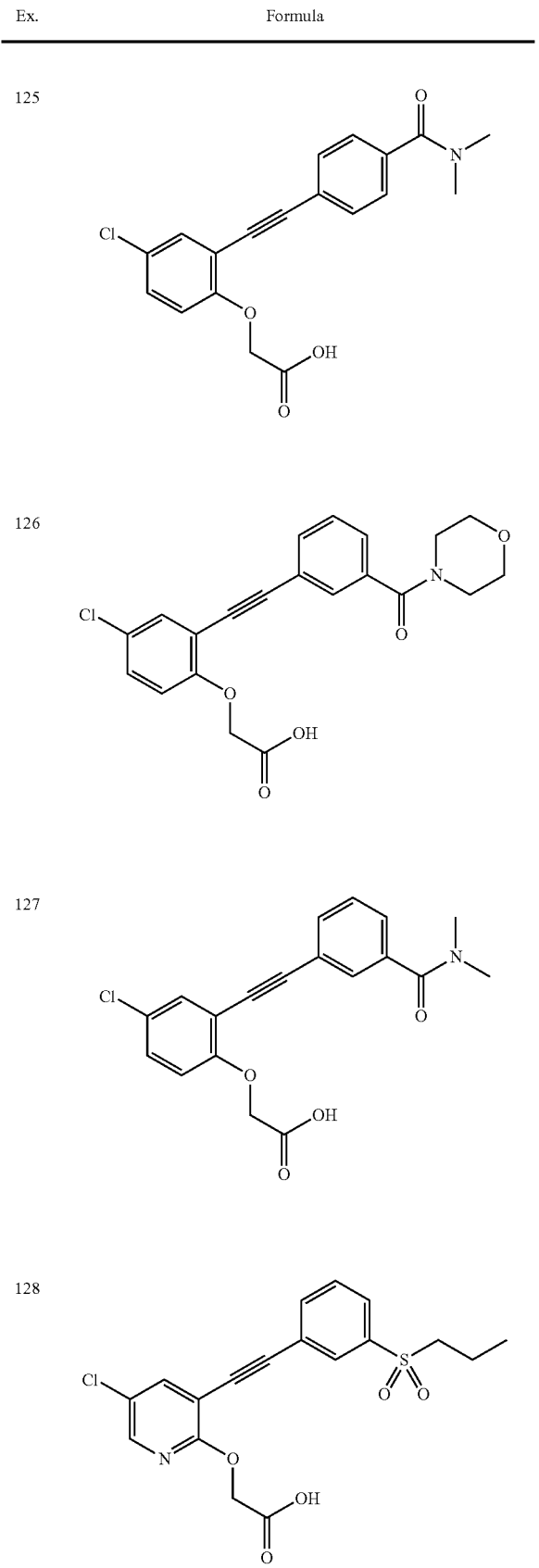 |
| 126 | |
| 127 | |
| 128 | |
40
-continued
| Ex. | Formula |
|---|---|
| 129 | 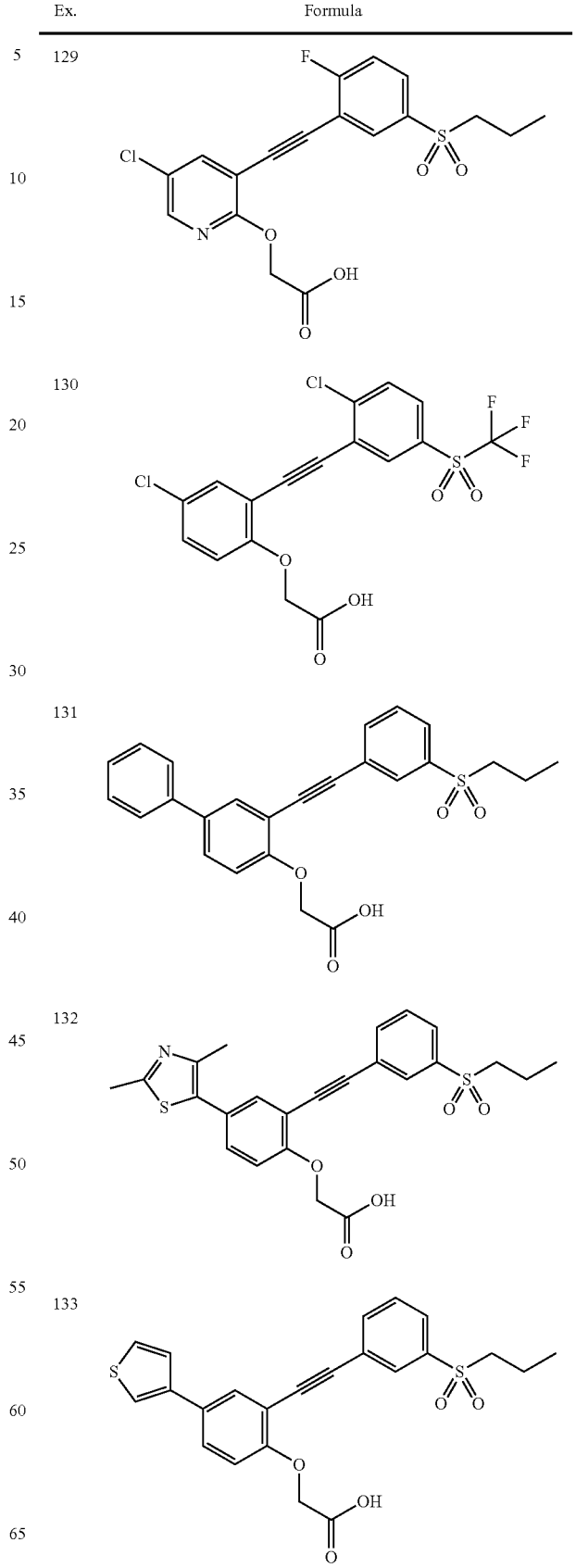 |
| 130 | |
| 131 | |
| 132 | |
| 133 | |

| Ex. | Formula |
|---|---|
| 134 | 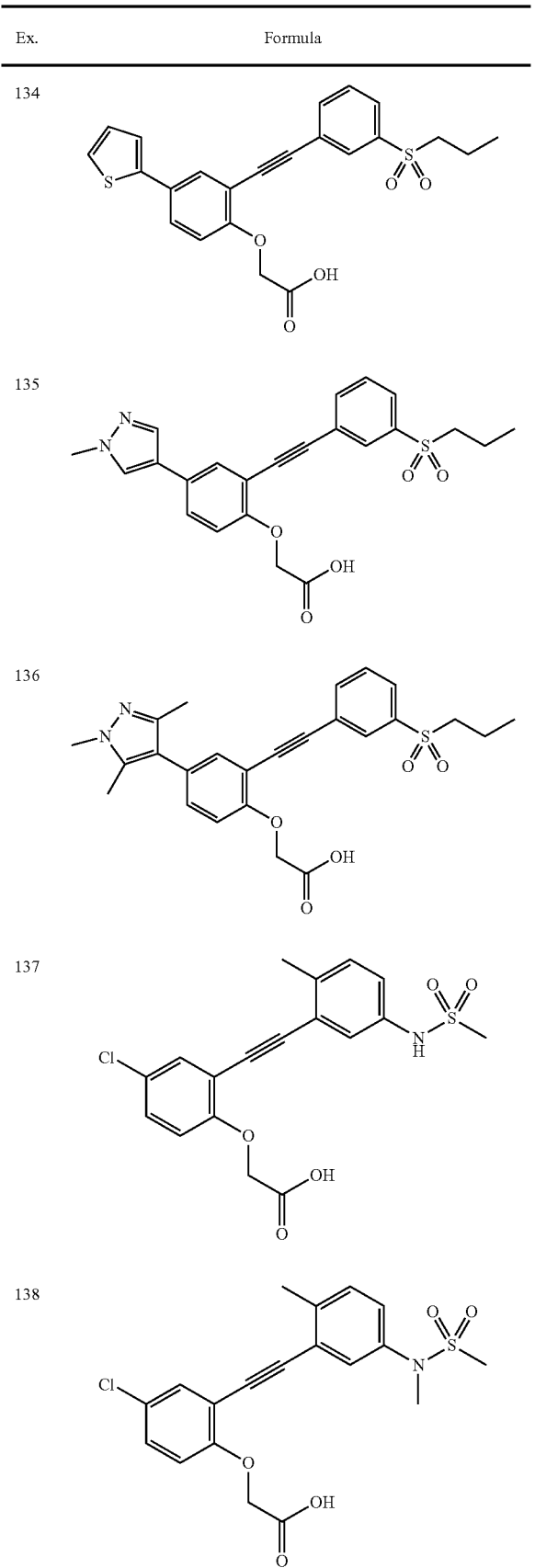 |
| 135 | |
| 136 | |
| 137 | |
| 138 | |
| Ex. | Formula |
|---|---|
| 139 | 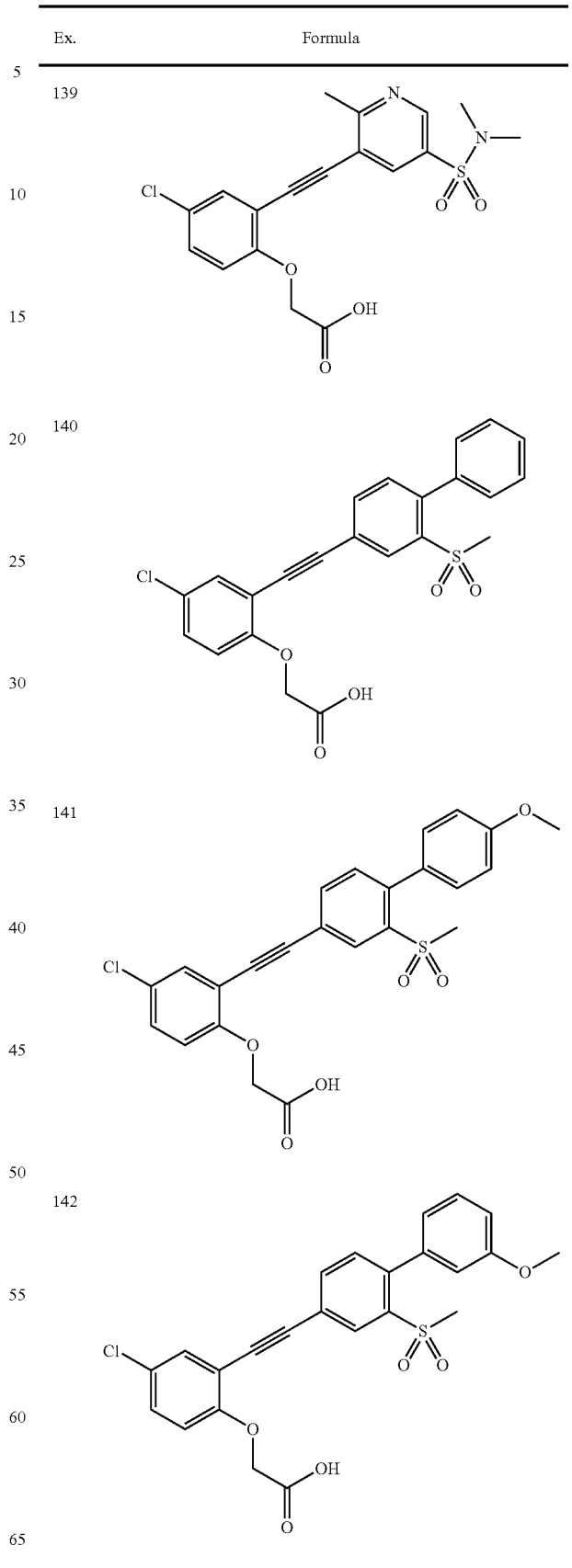 |
| 140 | |
| 141 | |
| 142 | |

| Ex. | Formula |
|---|---|
| 143 | 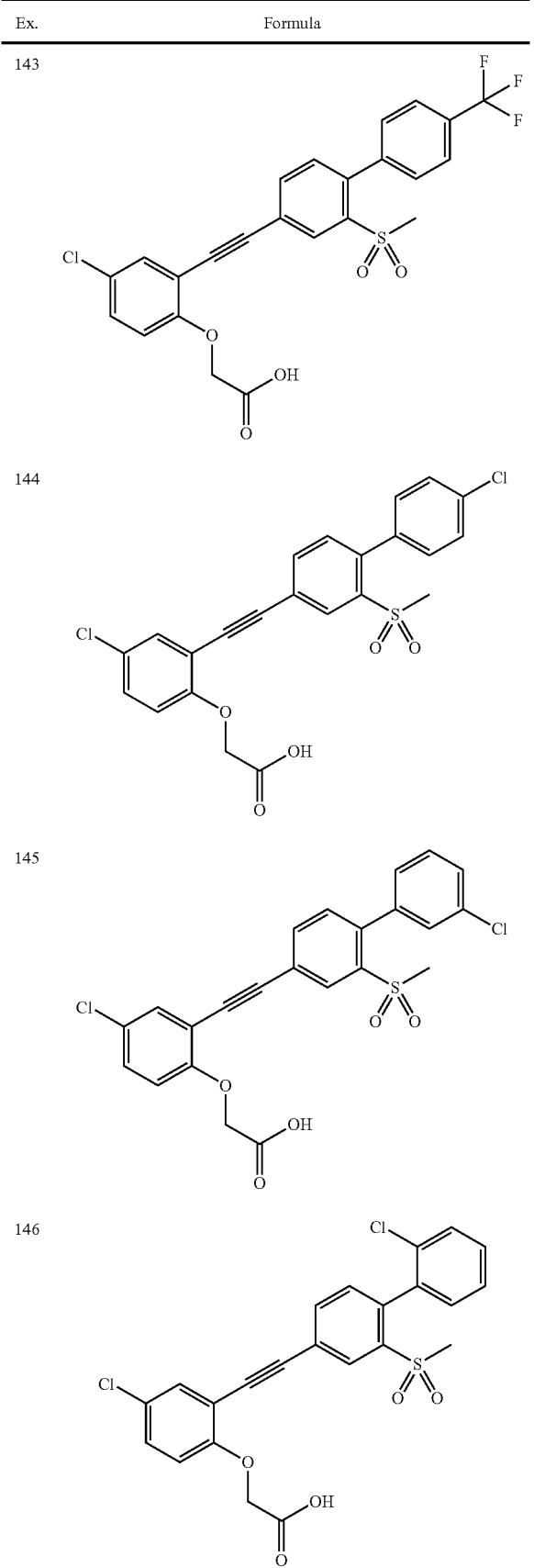 |
| 144 | |
| 145 | |
| 146 | |
| Ex. | Formula |
|---|---|
| 147 | 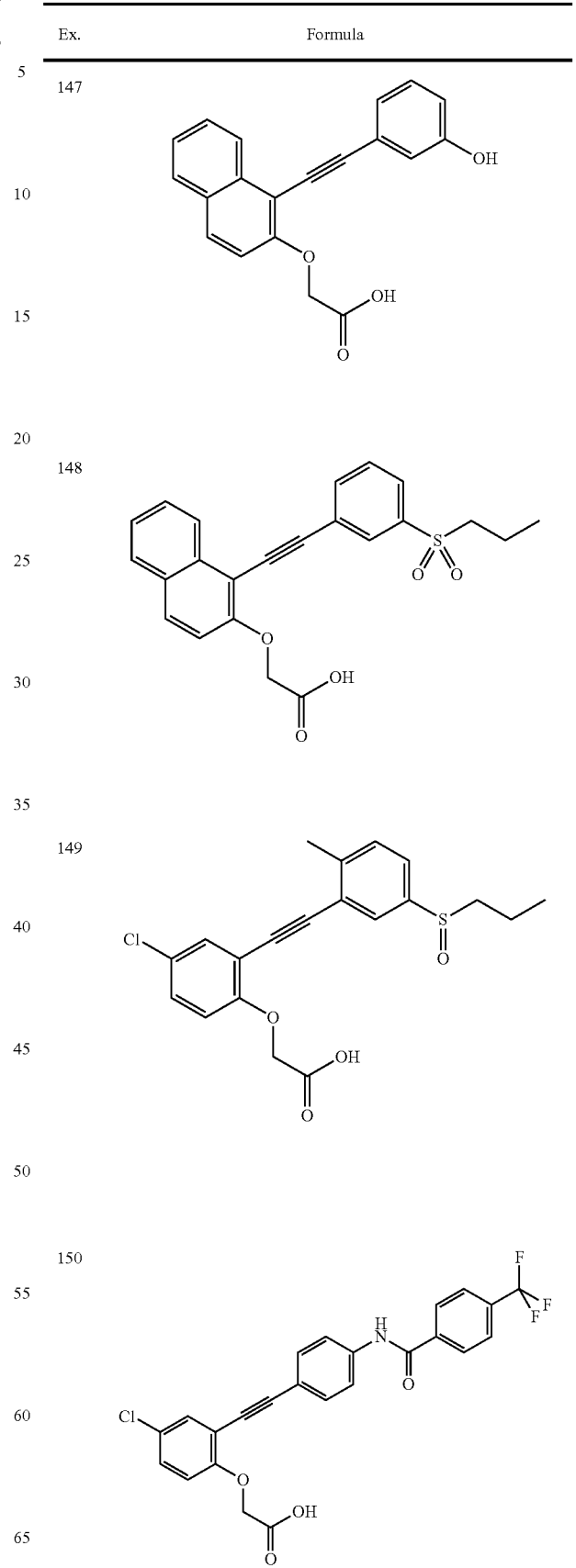 |
| 148 | |
| 149 | |
| 150 | |

45
-continued
| Ex. | Formula |
|---|---|
| 151 | 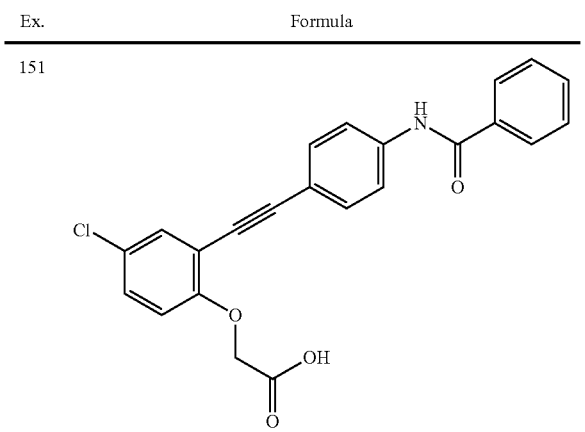 |
| 152 | 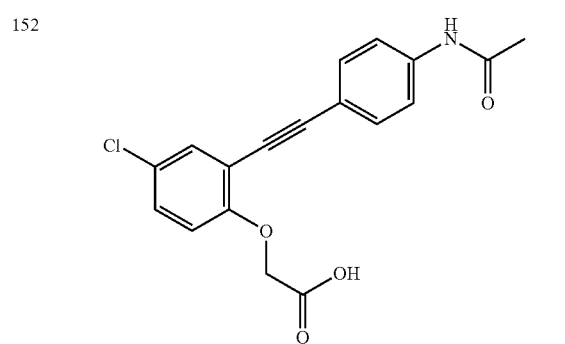 |
| 153 | 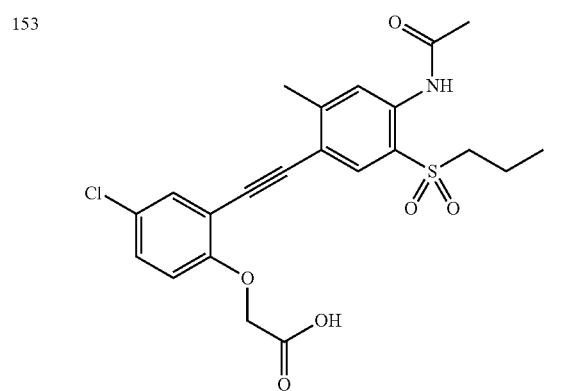 |
| 154 | 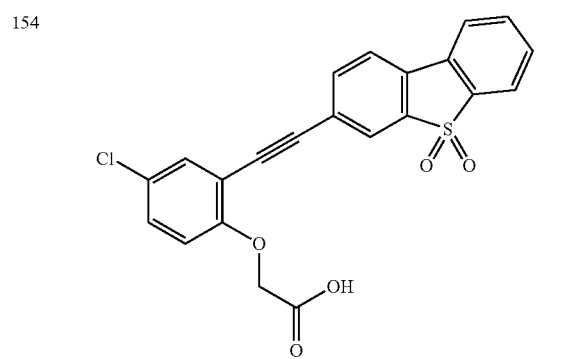 |
46
-continued
| Ex. | Formula |
|---|---|
| 155 | 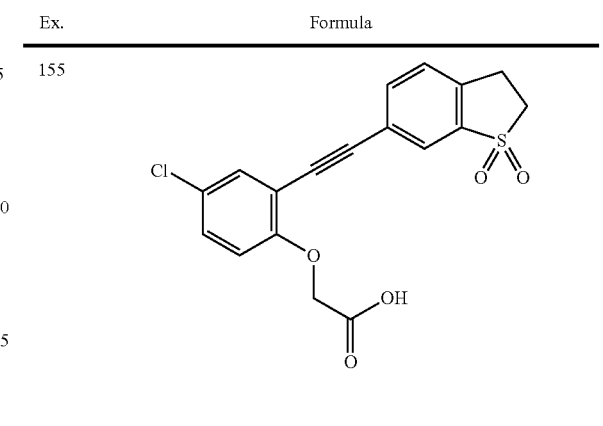 |
| 156 | 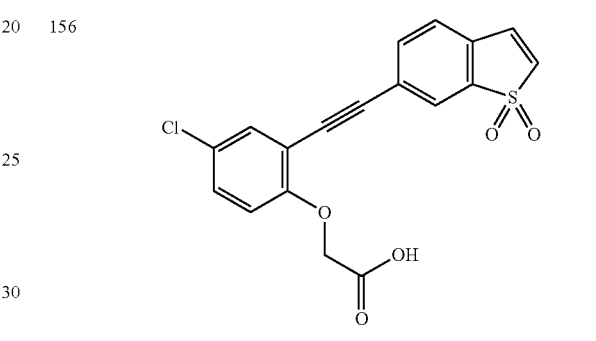 |
| 157 | 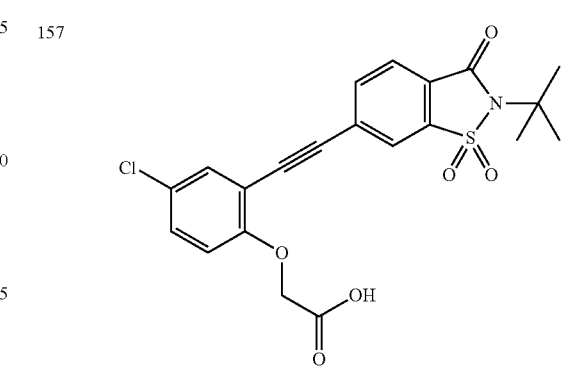 |
| 158 | 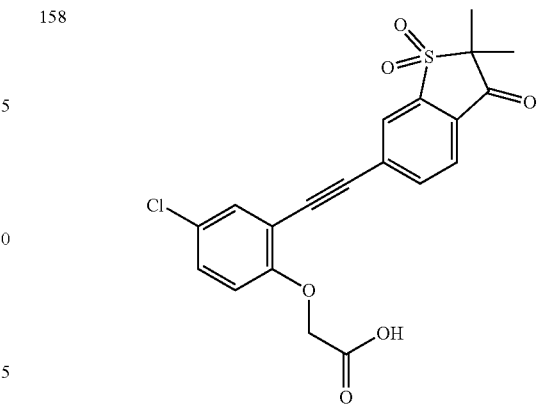 |

| Ex. | Formula |
|---|---|
| 159 | 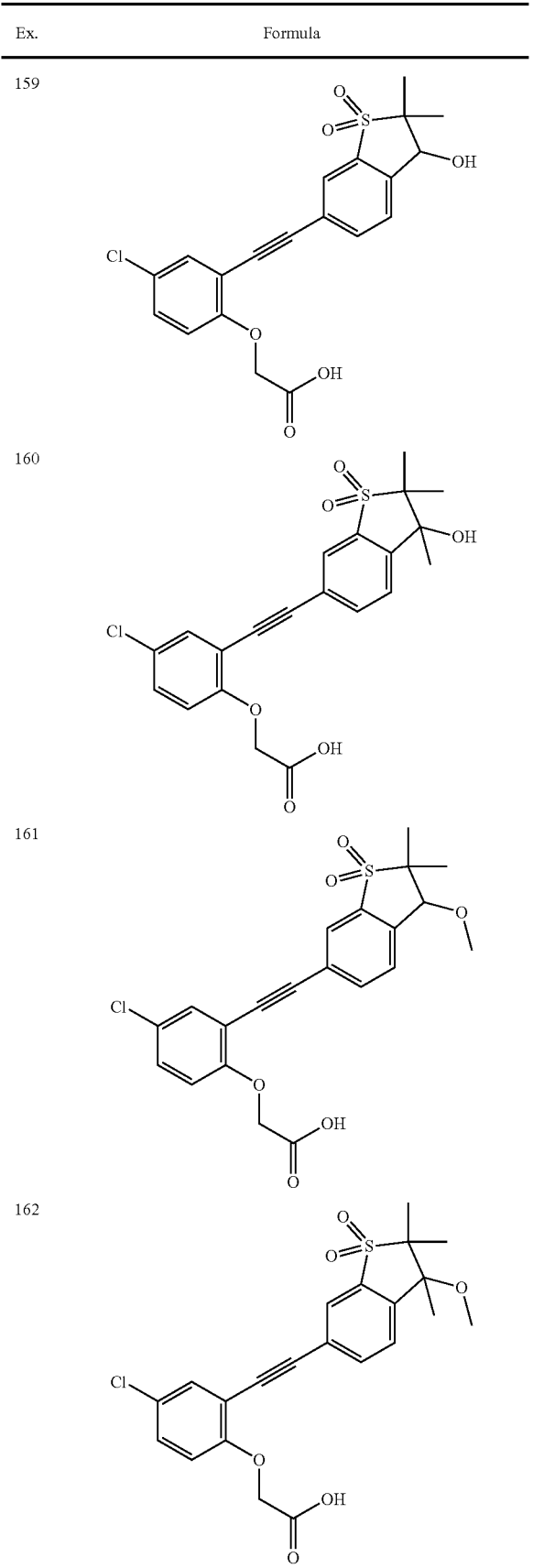 |
| 160 | |
| 161 | |
| 162 | |
| Ex. | Formula |
|---|---|
| 163 | 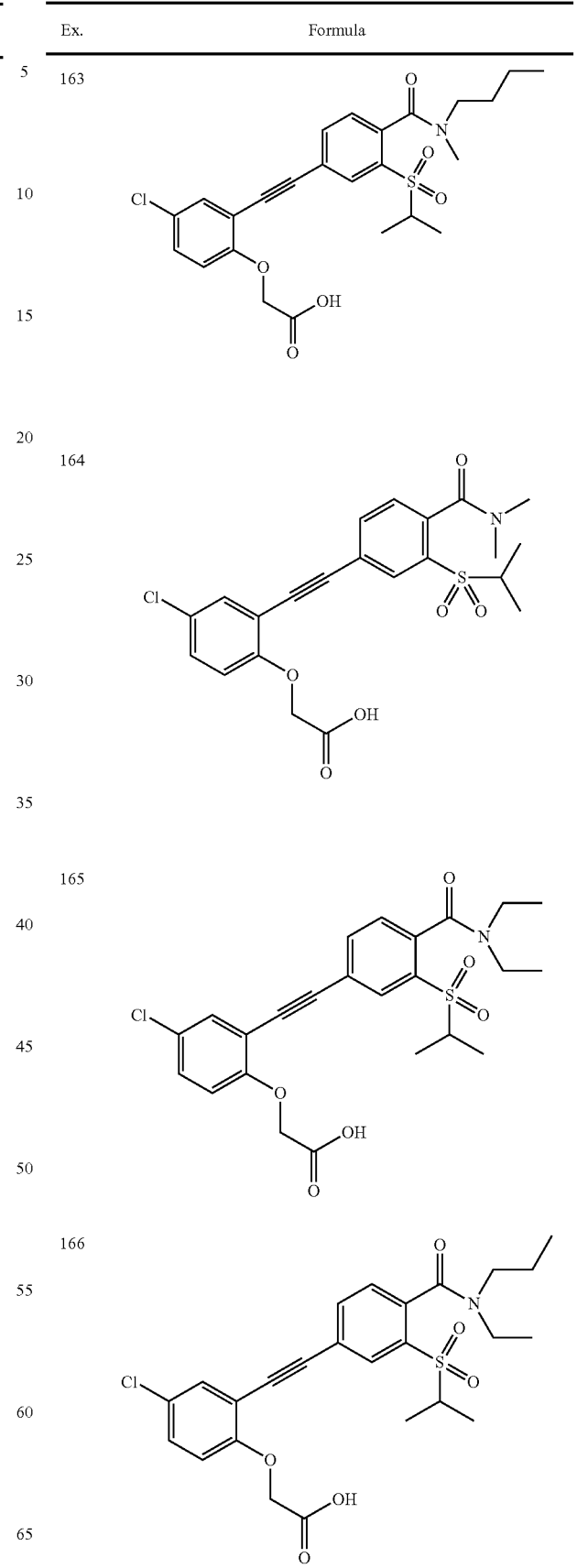 |
| 164 | |
| 165 | |
| 166 | |

| Ex. | Formula |
|---|---|
| 167 | 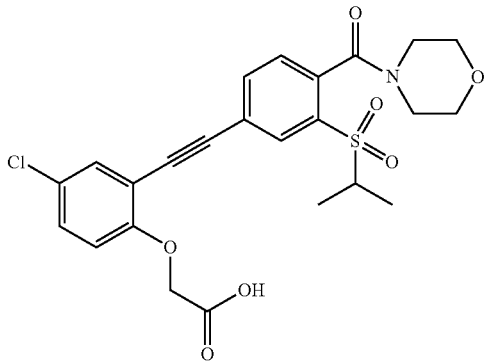 |
| 168 | 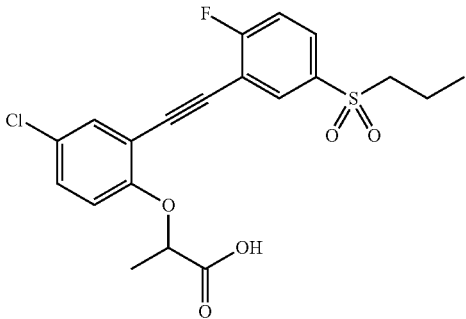 |
| 169 | 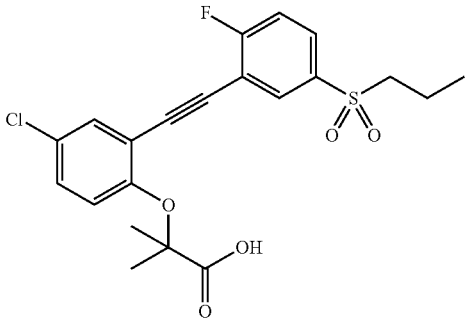 |
| 170 | 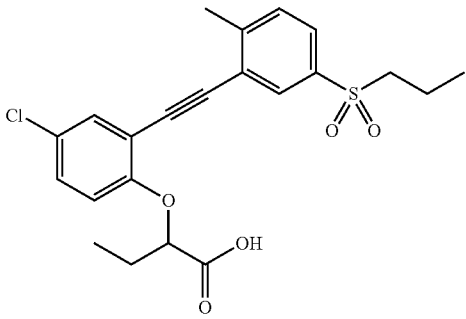 |
| 171 | 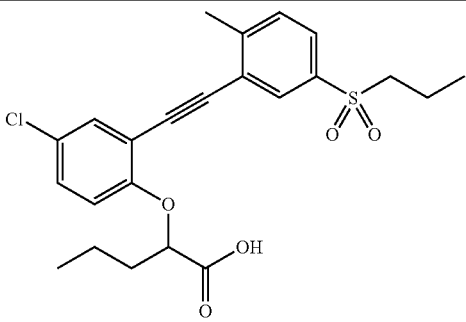 |
| 172 | 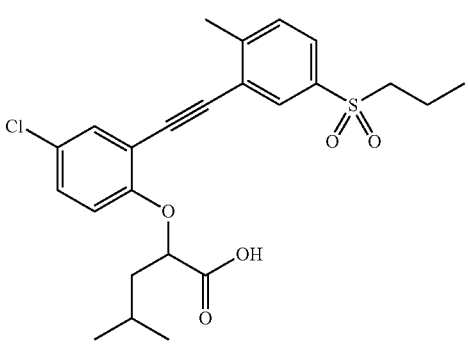 |
| 173 | 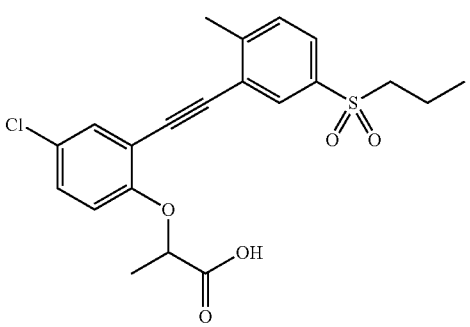 |

"Pharmaceutically acceptable cationic salts or complexes" is intended to define such salts as the alkali metal salts, (e.g. sodium and potassium), alkaline earth metal salts (e.g. calcium or magnesium), aluminium salts, ammonium salts and salts with organic amines such as with methylamine, dimethylamine, trimethylamine, ethylamine, triethylamine, morpholine, N-Me-D-glucamine, N,N'-bis(phenylmethyl)-1,2-ethanediamine, ethanolamine, diethanolamine, ethylenediamine, N-methylmorpholine, piperidine, benzathine (N,N'-dibenzylethylenediamine), choline, ethylene-diamine, meglumine (N-methylglucamine), benethamine (N-benzylphenethylamine), diethylamine, piperazine, thromethamine (2-amino-2-hydroxymethyl-1,3-propanediol), procaine as well as amines of formula —NR,R',R" wherein R, R', R" is independently hydrogen, alkyl or benzyl. Especially preferred salts are sodium and potassium salts.

"Pharmaceutically acceptable salts or complexes" refers to salts or complexes of the below-identified compounds of Formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disul-fonic acid, and poly-galacturonic acid. Said compounds can also be administered as pharmaceutically acceptable quaternary salts known by a person skilled in the art, which specifically include the quaternary ammonium salt of the Formula —NR, R',R"$^+$Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that, upon administration to the recipient, is capable of providing directly or indirectly, the activity disclosed herein.

The compounds of the present invention according to Formula (I) are useful in the treatment and/or prevention of diseases selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropathic pain, and other inflammatory diseases such as chronic obstructive pulmonary disease (COPD) rheumatoid arthritis, multiple sclerosis, osteoarthritis, and inflammatory bowel disease (IBD) such as ulcerative colitis and Crohn's disease.

In one aspect the compounds according to Formula (I) are suitable as modulators, notably as antagonists, of CRTH2. Therefore, the compounds of the present invention are also particularly useful for the treatment and/or prevention of disorders, which are mediated by CRTH2 activity. Said treatment involves the modulation of CRTH2, notably an inhibition of CRTH2 or an antagonizing effect of CRTH2 in mammals, and in particular in humans. The modulators of CRTH2 are selected from the group consisting of an antagonist, an inverse agonist, a partial agonist and an agonist of CRTH2.

In another embodiment, the modulators of CRTH2 are antagonists of CRTH2.

In one embodiment, the modulators of CRTH2 are inverse agonists of CRTH2.

In another embodiment, the modulators of CRTH2 are partial agonists of CRTH2.

In another embodiment, the modulators of CRTH2 are agonists of CRTH2.

The compounds according to Formula (I) are suitable for use as a medicament.

Compounds of Formula (I) include also their geometrical isomers, their optically active forms as enantiomers, diastereomers, its racemate forms and tautomers, as well as pharmaceutically acceptable salts thereof, wherein:

In a second aspect, the invention provides a pharmaceutical composition comprising a compound according to Formula (I), together with a pharmaceutically acceptable excipient or carrier.

In a third aspect, the invention provides the use of a compound according to formulae (I) for the preparation of a medicament for the treatment and/or prevention of a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis and other diseases with an inflammatory component such as chronic obstructive pulmonary disease (COPD), rheumatoid arthritis, osteoarthritis, and inflammatory bowel disease (IBD) such as ulcerative colitis and Crohn's disease and other diseases and disorders associated with CTRH2 activity.

In a fourth aspect, the invention provides a method for treating and/or preventing a patient suffering from a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropathic pain, and other inflammatory diseases such as chronic obstructive pulmonary disease (COPD), rheumatoid arthritis, multiple sclerosis, osteoarthritis, and inflammatory bowel disease (IBD) such as ulcerative colitis and Crohn's disease and other diseases and disorders associated with CTRH2 activity, by administering a compound according to Formula (I).

The term "preventing", as used herein, should be understood as partially or totally preventing, inhibiting, alleviating, or reversing one or more symptoms or cause(s) of allergic disease or inflammatory dermatitis.

In a fifth aspect, the invention provides the use of a compound of Formula (I) for the preparation of a pharmaceutical composition useful for a variety of therapies, including preventing and/or treating a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropathic pain, and other inflammatory diseases such as chronic obstructive pulmonary disease (COPD), rheumatoid arthritis, multiple sclerosis, osteoarthritis, and inflammatory bowel disease (IBD) such as ulcerative colitis and Crohn's disease and other diseases and disorders associated with CTRH2 activity.

The invention provides further the use of a compound of Formula (I) for preventing and/or treating a disease selected from allergic diseases such as allergic asthma, allergic rhinitis, allergic conjunctivitis, systemic anaphylaxis or hypersensitivity responses, and inflammatory dermatoses such as atopic dermatitis, eczema, allergic contact dermatitis, and urticaria, myositis, neurodegenerative disorders such as neuropathic pain, and other inflammatory diseases such as chronic obstructive pulmonary disease (COPD), rheumatoid arthritis, multiple sclerosis, osteoarthritis, and inflammatory bowel disease (IBD) such as ulcerative colitis and Crohn's disease and other diseases and disorders associated with CTRH2 activity.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

The compounds according to Formula (I) of the present invention are typically administered in form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the substituted methylene amide derivative according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate buffered saline or other injectable carriers known in the art. As above mentioned, substituted methylene amide derivatives of Formula (I) in such compositions is typically a minor component, frequently ranging between 0.05 to 10% by weight with the remainder being the injectable carrier and the like.

The above-described components for orally administered or injectable compositions are merely representative. Further materials as well as processing techniques and the like are set out in Part 5 of *Remington's Pharmaceutical Sciences, 20th Edition,* 2000, Marck Publishing Company, Easton, Pa., which is incorporated herein be reference. The compounds of this invention can also be administered in sustained release forms or from sustained release drug delivery systems. A description of representative sustained release materials can also be found in the incorporated materials in *Remington's Pharmaceutical Sciences*.

The compounds according to formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below: aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), µL (microliter), ACN (acetonitrile), BOC (tert-butoxy-carbonyl), CBZ (carbobenzoxy), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), $DMSO-d_6$ (deuterated dimethylsulfoxide), EDC (1-(3-dimethyl-amino-propyl)-3-ethylcarbodiimide), ESI (Electrospray ionization), EtOAc (ethyl acetate), $Et_2O$ (diethyl ether), EtOH (ethanol), FMOC (fluorenylmethyloxycarbonyl), HATU (dimethylamino-([1,2,3]triazolo[4,5-b]pyridin-3-yloxy)methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), Mtr. (4-Methoxy-2,3,6-trimethylbenzensulfonyl), $NaHCO_3$ (sodium bicarbonate), $NaBH_4$ (sodium borohydride), NMM (N-methyl morpholine), NMR (Nuclear Magnetic Resonance), POA (phenoxyacetate), PyBOP® (benzotriazole-1-yl-oxy-tris-pyrrolidino-phosphonium hexafluorophosphate), RT (room temperature), Rt (retention time), SPE (solid phase extraction), TBAF (tetrabutylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

"O-PG" denotes a protecting group, preferably for acyl groups, i.e an acyl-protecting group. O-PG denotes preferably an O-alkyl group like tert-butoxy, methoxyl, ethoxy or benzyloxy group.

The term "protecting group" is known in general terms and relates to groups which are suitable for protecting a functional group against chemical reactions, but are easy to remove after the desired chemical reaction has been carried out elsewhere in the molecule. The nature and size of the protecting groups are not crucial since they are removed again after the desired chemical reaction or reaction sequence; preference is given to groups having 1-20, in particular 1-10, carbon atoms.

In general, compounds according to Formula (I) of this invention can be prepared from readily available starting materials. If such starting materials are not commercially available they can be prepared by standard synthetic techniques. The following general methods and procedures described hereinafter in the examples can be employed to prepare compounds of Formula (I).

Depending on the nature of $R^1$, $R^x$, $R^y$, Q, m and n in formula (I), different synthetic strategies may be selected for the synthesis of compounds of Formula I. In the process illustrated in the following schemes $R^1$, $R^x$, $R^y$, Q, X, m and n are as defined in the description.

Generally, compounds of Formula (I), wherein $R^1$, $R^x$, $R^y$, Z, Q, m and n are defined as above, can be obtained in 2 steps as outlined in Scheme 1. The first step consists in coupling a compound of Formula (II), wherein $R^1$, $R^x$, $R^y$, Z, Q, m and n are defined as above, X denotes Cl, Br, I, preferably Br or I, or trifluoromethanesulfonyl and wherein PG denotes a protecting group such as tert-butyl, with an alkyne of Formula (III), wherein Q is defined as above. General protocols for such coupling are given below in the Examples, using conditions and methods well known to those skilled in the art to perform such coupling. The reaction can optionally be performed with an appropriate catalyst such as but not limited to dichlorobis(triphenylphosphine)palladium(II) or 1,1'-bis(diphenylphosphino)ferrocenedichloro palladium(II), Pd(OAc)$_2$, Pd$_2$(dba)$_3$, or Pd/C in the presence or absence of an additional ligand, such as but not limited to P(tBu)$_3$, P(oTol)$_3$, PPh$_3$, BINAP. Additionally, the reaction can optionally be performed in the presence of a suitable copper salt such as but not limited to copper (I) iodide, copper (I) bromide or copper (I) chloride. The reaction can be performed in the presence or absence of bases such as TEA, DIEA, NMM, piperidine, Cs$_2$CO$_3$, sodium phosphate, in the presence or absence of a suitable solvent such as THF, ACN, DMF, acetone at a temperature between about 20° C. to about 100° C., preferably at about 70° C., for a few hours, e.g. one hour to 24 h. For a list of conditions described for the coupling of an aryl alkyne with an aryl or heteroaryl triflate or halide, see also Rafael Chinchilla and Carmen Najera, *Chem. Rev.* 2007, 107, 874-892.

Conversion of compounds of Formula (IV) to give compounds of Formula (I) can be achieved using conditions and methods well known to those skilled in the art for the conversion of an ester to a carboxylic acid, such as but not limited to treatment with a base or an appropriate acid, such as trifluoroacetic acid or hydrochloric acid, in the presence of a suitable solvent such as DCM, dioxane, THF at a temperature between about 20° C. to about 100° C., preferably at about 20° C., for a few hours, e.g. one hour to 24 h.

Compounds of Formula (II), wherein R$^1$, R$^x$, R$^y$, Z, X, PG, m and n are defined as above, can be prepared by alkylation of a compound of Formula (V), wherein R$^1$, Z and X are defined as above, with a compound of Formula (VI), wherein R$^x$, R$^y$, X, PG, m and n are as defined above, as outlined in Scheme 2. The reaction can be performed in the presence of a suitable base, such as potassium carbonate, sodium carbonate, sodium hydroxide, potassium hydroxide, sodium tert-butoxide, in the presence of a suitable solvent such as DCM, dioxane, THF, in the presence or absence of water. The reaction can be carried out at a temperature between about 20° C. to about 100° C., preferably at about 20° C., for a few hours, e.g. one hour to 24 h. Alternatively, the Compounds of Formula (II) can be prepared by reaction of a compound of Formula (V) with an opportunely protected hydroxyalkyl carboxylic acid under Mitsunobu conditions, using conditions and methods well known to those skilled in the art such as in the presence of a phosphine, such as but not limited to triphenylphosphine, and an azadicarboxylate, such as but not limited to diisopropylazadicarboxylate.

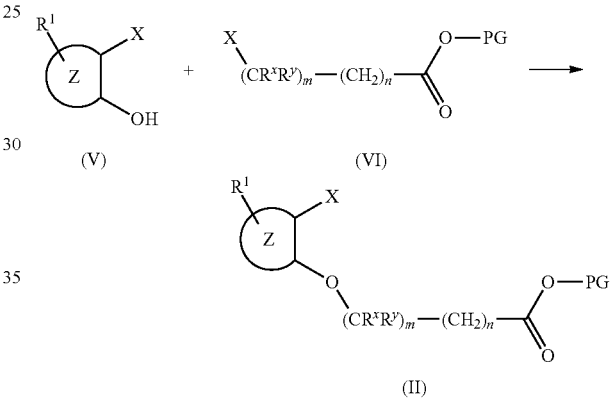

Scheme 2

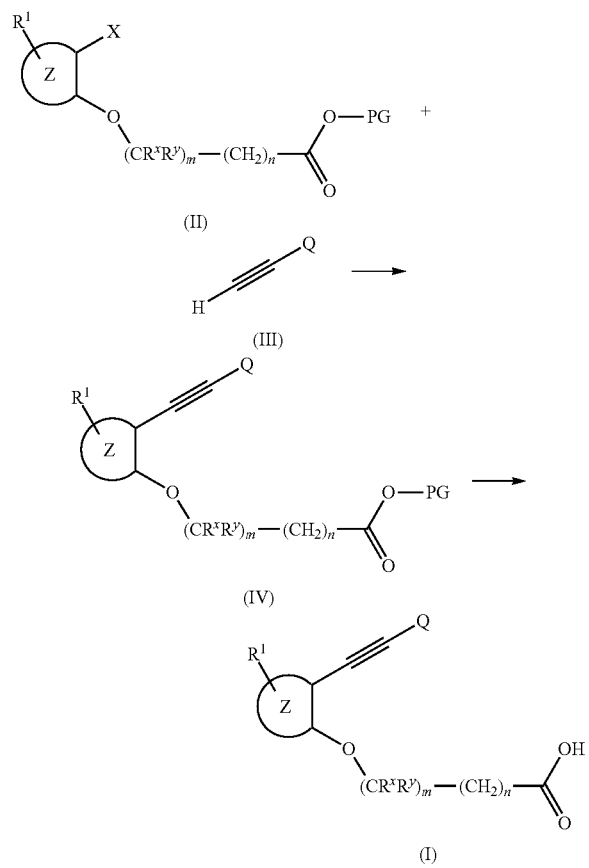

Scheme 1

Compounds of Formula (IV) wherein Q, Z, R$^1$, R$^x$, R$^y$, PG, m and n are as above defined can be obtained by coupling a compound of Formula (VII) wherein Z, R$^1$, R$^x$, R$^y$, PG, m and n are as above defined, with a compound of Formula (VIII) wherein Q is as above defined and wherein X denotes a triflate or an halide, preferably a bromide or an iodide, as outlined in Scheme 3. General protocols for such coupling are given below in the Examples, using conditions and methods well known to those skilled in the art to perform such coupling. This reaction is preferably performed with an appropriate catalyst such as but not limited to dichlorobis(triphenylphosphine)palladium(II) or 1,1'-bis(diphenylphosphino)ferrocenedichloro palladium(II), Pd(OAc)$_2$, Pd$_2$(dba)$_3$, Pd(Cl)$_2$ or Pd/C in the presence or absence of an additional ligand, such as but not limited to P(tBu)$_3$, P(oTol)$_3$, PPh$_3$, BINAP. The reaction can also be performed in the presence of a suitable copper salt such as but not limited to copper (I) iodide, copper (I) bromide or copper (I) chloride. The reaction can be performed in the presence or absence of bases such as TEA, DIEA, NMM, piperidine, Cs$_2$CO$_3$, sodium phosphate, in the presence or absence of a suitable solvent such as THF, ACN, DMF or acetone. This coupling reaction can be carried out at a temperature between about 20° C. to about 100° C., preferably at about 70° C., for a few hours, e.g. one hour to 24 h.

Scheme 3

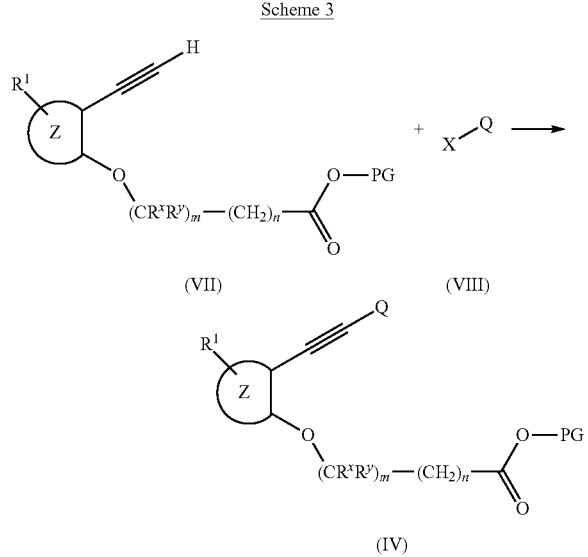

The method for preparing the compounds of Formula (IV) selected below:
tert-butyl{4-chloro-2-[(4-methylpyridin-3-yl)ethynyl]phenoxy}acetate
tert-butyl{4-chloro-2-{[3-(propylsulfonyl)phenyl]ethynyl}phenoxy)acetate
tert-butyl{4-chloro-2-[(5-cyano-2-fluorophenyl)ethynyl]phenoxy}acetate
tert-butyl{4-chloro-2-[(2-methylpyridin-3-yl)ethynyl]phenoxy}acetate
tert-butyl(4-chloro-2-{[2-fluoro-5-(hydroxymethyl)phenyl]ethynyl}phenoxy)acetate
tert-butyl(4-chloro-2-{[2-fluoro-4-(hydroxymethyl)phenyl]ethynyl}phenoxy)acetate
tert-butyl(4-chloro-2-{[2-fluoro-3-(hydroxymethyl)phenyl]ethynyl}phenoxy)acetate
tert-butyl(4-chloro-2-{[2-fluoro-5-(methoxymethyl)phenyl]ethynyl}phenoxy)acetate
tert-butyl{4-chloro-2-[(4-methyl-1-oxidopyridin-3-yl)ethynyl]phenoxy}acetate
tert-butyl(4-cyano-2-{[3-(propylsulfonyl)phenyl]ethynyl}phenoxy)acetate
tert-butyl(4-chloro-2-{[2-methyl-5-(methylsulfonyl)phenyl]ethynyl}phenoxy)acetate
tert-butyl(4-chloro-2-{[2-fluoro-4-(methoxymethyl)phenyl]ethynyl}phenoxy)acetate
tert-butyl(4-chloro-2-{[2-methyl-5-(propylsulfonyl)phenyl]ethynyl}phenoxy)acetate
tert-butyl{4-chloro-2-[(4-propylpyridin-3-yl)ethynyl]phenoxy}acetate
tert-butyl{4-chloro-2-[(4-isobutylpyridin-3-yl)ethynyl]phenoxy}acetate
tert-butyl{4-cyano-2-[(4-methylpyridin-3-yl)ethynyl]phenoxy}acetate
tert-butyl{2-[(2-chlorophenyl)ethynyl]phenoxy}acetate
tert-butyl(4-chloro-2-{[5-(methylsulfonyl)-2-propylphenyl]ethynyl}phenoxy)acetate
tert-butyl[2-{[3-(propylsulfonyl)phenyl]ethynyl}-4-(trifluoromethyl)phenoxy]acetate
tert-butyl(4-cyano-2-{[5-(methylsulfonyl)-2-propylphenyl]ethynyl}phenoxy)acetate
tert-butyl(4-chloro-2-{[5-(methylsulfonyl)-2-piperidin-1-ylphenyl]ethynyl}phenoxy)acetate
tert-butyl(4-cyano-2-{[2-fluoro-5-(methylsulfonyl)phenyl]ethynyl}phenoxy)acetate
tert-butyl(4-chloro-2-{[2-chloro-5-(methylsulfonyl)phenyl]ethynyl}phenoxy)acetate
tert-butyl(4-chloro-2-{[2-hydroxy-5-(methylsulfonyl)phenyl]ethynyl}phenoxy)acetate
tert-butyl(2-{[2-chloro-5-(methylsulfonyl)phenyl]ethynyl}-4-cyanophenoxy)acetate
tert-butyl(4-cyano-2-{[5-(methylsulfonyl)-2-piperidin-1-ylphenyl]ethynyl}phenoxy)acetate
tert-butyl[(6-methyl-2-{[3-(propylsulfonyl)phenyl]ethynyl}pyridin-3-yl)oxy]acetate
tert-butyl(4-chloro-2-{[2-isopropyl-5-(methylsulfonyl)phenyl]ethynyl}phenoxy)acetate
tert-butyl(4-cyano-2-{[2-isopropyl-5-(methylsulfonyl)phenyl]ethynyl}phenoxy)acetate
tert-butyl(3-chloro-2-{[3-(propylsulfonyl)phenyl]ethynyl}phenoxy)acetate
tert-butyl[4-chloro-2-({3-[(dimethylamino)sulfonyl]phenyl}ethynyl)phenoxy]acetate
tert-butyl[4-chloro-2-({5-[(diethylamino)sulfonyl]-2-methylphenyl]ethynyl)phenoxy}acetate
tert-butyl(4-chloro-2-{[2-methyl-5-(morpholiN-4-ylsulfonyl)phenyl]ethynyl}phenoxy)acetate
tert-butyl[4-chloro-2-({5-[(dimethylamino)sulfonyl]-2-methylphenyl]ethynyl)phenoxy}acetate
tert-butyl[4-chloro-2-({2-methyl-5-[(methylamino)sulfonyl]phenyl}ethynyl)phenoxy]acetate
tert-butyl[2-({5-[(tert-butylamino)sulfonyl]-2-methylphenyl}ethynyl)-4-chlorophenoxy]acetate
tert-butyl[4-chloro-2-({5-[(isopropylamino)sulfonyl]-2-methylphenyl]ethynyl)phenoxy}acetate
tert-butyl{4-chloro-2-[(5-{[isopropyl(methyl)amino]sulfonyl}-2-methylphenyl)ethynyl]phenoxy}acetate
tert-butyl(4-chloro-2-{[2-fluoro-5-(propylsulfonyl)phenyl]ethynyl}phenoxy)acetate
tert-butyl(4-chloro-2-{[4-(methylsulfonyl)phenyl]ethynyl}phenoxy)acetate
tert-butyl(4-cyano-2-{[2-methyl-5-(phenylsulfonyl)phenyl]ethynyl}phenoxy)acetate
tert-butyl(4-chloro-2-{[2-methyl-5-(phenylsulfonyl)phenyl]ethynyl}phenoxy)acetate
tert-butyl[4-chloro-2-{[4-fluoro-2-methyl-5-(methylsulfonyl)phenyl]ethynyl}phenoxy)acetate
tert-butyl[4-chloro-2-({3-[(methylsulfonyl)methyl]phenyl}ethynyl)phenoxy]acetate
tert-butyl(4-fluoro-2-{[3-(propylsulfonyl)phenyl]ethynyl}phenoxy)acetate
tert-butyl(4-chloro-2-{[2-ethyl-5-(methylsulfonyl)phenyl]ethynyl}phenoxy)acetate
tert-butyl(4-chloro-2-{[2-chloro-5-(propylsulfonyl)phenyl]ethynyl}phenoxy)acetate
tert-butyl(4-chloro-2-{[2-fluoro-5-(isopropylsulfonyl)phenyl]ethynyl}phenoxy)acetate
tert-butyl(4-chloro-2-{[2-chloro-5-(isopropylsulfonyl)phenyl]ethynyl}phenoxy)acetate
tert-butyl(4-chloro-2-{[5-(ethylsulfonyl)-2-fluorophenyl]ethynyl}phenoxy)acetate
tert-butyl(4-chloro-2-{[2-fluoro-5-(isobutylsulfonyl)phenyl]ethynyl}phenoxy)acetate
tert-butyl[4-chloro-2-({2-fluoro-5-[(2-methoxyethyl)sulfonyl]phenyl}ethynyl)phenoxy]acetate
tert-butyl(4-chloro-2-{[2-methyl-5-(piperidin-1-ylsulfonyl)phenyl]ethynyl}phenoxy)acetate
tert-butyl[4-chloro-2-({5-[(dimethylamino)sulfonyl]-2-fluorophenyl]ethynyl)phenoxy}acetate tert-butyl[4-chloro-2-({2-methyl-5-[(2-methylpiperidin-1-yl)sulfonyl]phenyl}ethynyl)phenoxy]acetate
tert-butyl{4-chloro-2-[(5-{[(2-methoxyethyl)(methyl)amino]sulfonyl}-2-methylphenyl)ethynyl]phenoxy}acetate
tert-butyl{4-chloro-2-[(5-{[isobutyl(methyl)amino]sulfonyl}-2-methylphenyl)ethynyl]phenoxy}acetate
tert-butyl{2-[(5-{[butyl(methyl)amino]sulfonyl}-2-methylphenyl)ethynyl]-4-chlorophenoxy}acetate
tert-butyl[4-chloro-2-({2-methyl-5-[(4-methylpiperaziN-1-yl)sulfonyl]phenyl}ethynyl)phenoxy]acetate
tert-butyl{4-chloro-2-[(5-{[(2,2-dimethylpropyl)amino]sulfonyl}-2-methylphenyl)ethynyl]phenoxy}acetate
tert-butyl[2-({5-[(sec-butylamino)sulfonyl]-2-methylphenyl}ethynyl)-4-chlorophenoxy]acetate
tert-butyl{4-chloro-2-[(2-methyl-5-{[methyl(propyl)amino]sulfonyl}phenyl)ethynyl]phenoxy}acetate tert-butyl[4-chloro-2-({5-[(dipropylamino)sulfonyl]-2-methylphenyl}ethynyl)phenoxy]acetate
tert-butyl{4-chloro-2-[(5-{[(2-methoxyethyl)amino]sulfonyl}-2-methylphenyl)ethynyl]phenoxy}acetate
tert-butyl[4-chloro-2-({2-methyl-5-[(propylamino)sulfonyl]phenyl}ethynyl)phenoxy]acetate
tert-butyl{4-chloro-2-[(5-{[[3-(dimethylamino)propyl](methyl)amino]sulfonyl}-2-methylphenyl)ethynyl]phenoxy}acetate
tert-butyl(2-{[5-(aminosulfonyl)-2-methylphenyl]ethynyl}-4-chlorophenoxy)acetate
tert-butyl{4-chloro-2-[(5-{[cyclopentyl(methyl)amino]sulfonyl}-2-methylphenyl)ethynyl]phenoxy}acetate
tert-butyl{4-chloro-2-[(5-{[[2-(dimethylamino)ethyl](methyl)amino]sulfonyl}-2-methylphenyl)ethynyl]phenoxy}acetate
tert-butyl(2-{[5-(azetidin-1-ylsulfonyl)-2-methylphenyl]ethynyl}-4-chlorophenoxy)acetate
tert-butyl(4-chloro-2-{[4-(morpholiN-4-ylcarbonyl)phenyl]ethynyl}phenoxy)acetate
tert-butyl[4-chloro-2-({4-[(dimethylamino)carbonyl]phenyl}ethynyl)phenoxy]acetate
tert-butyl(4-chloro-2-{[3-(morpholiN-4-ylcarbonyl)phenyl]ethynyl}phenoxy)acetate
tert-butyl[4-chloro-2-({3-[(dimethylamino)carbonyl]phenyl}ethynyl)phenoxy]acetate
tert-butyl[(5-chloro-3-{[3-(propylsulfonyl)phenyl]ethynyl}pyridin-2-yl)oxy]acetate
tert-butyl[(5-chloro-3-{[2-fluoro-5-(propylsulfonyl)phenyl]ethynyl}pyridin-2-yl)oxy]acetate
tert-butyl[4-chloro-2-({2-chloro-5-[(trifluoromethyl)sulfonyl]phenyl}ethynyl)phenoxy]acetate
tert-butyl(4-bromo-2-{[3-(propylsulfonyl)phenyl]ethynyl}phenoxy)acetate
tert-butyl(4-(2,4-dimethyl-1,3-thiazol-5-yl)-2-{[3-(propylsulfonyl)phenyl]ethynyl}phenoxy)acetate
tert-butyl[2-{[3-(propylsulfonyl)phenyl]ethynyl}-4-(2-thienyl)phenoxy]acetate
tert-butyl(4-(1-methyl-1H-pyrazol-4-yl)-2-{[3-(propylsulfonyl)phenyl]ethynyl}phenoxy)acetate
tert-butyl[2-{[3-(propylsulfonyl)phenyl]ethynyl}-4-(1,3,5-trimethyl-1H-pyrazol-4-yl)phenoxy]acetate
tert-butyl[4-chloro-2-({2-methyl-5-[(methylsulfonyl)amino]phenyl}ethynyl)phenoxy]acetate
tert-butyl[4-chloro-2-({2-methyl-5-[methyl(methylsulfonyl)amino]phenyl}ethynyl)phenoxy]acetate
tert-butyl[4-chloro-2-({5-[(dimethylamino)sulfonyl]-2-methylpyridin-3-yl}ethynyl)phenoxy]acetate
tert-butyl(4-chloro-2-{[2-(methylsulfonyl)biphenyl-4-yl]ethynyl}phenoxy)acetate
tert-butyl(4-chloro-2-{[4'-methoxy-2-(methylsulfonyl)biphenyl-4-yl]ethynyl}phenoxy)acetate
tert-butyl(4-chloro-2-{[3'-methoxy-2-(methylsulfonyl)biphenyl-4-yl]ethynyl}phenoxy)acetate
tert-butyl(4-chloro-2-{[2-(methylsulfonyl)-4'-(trifluoromethyl)biphenyl-4-yl]ethynyl}phenoxy)acetate
tert-butyl(4-chloro-2-{[4'-chloro-2-(methylsulfonyl)biphenyl-4-yl]ethynyl}phenoxy)acetate
tert-butyl(4-chloro-2-{[3'-chloro-2-(methylsulfonyl)biphenyl-4-yl]ethynyl}phenoxy)acetate
tert-butyl(4-chloro-2-{[2'-chloro-2-(methylsulfonyl)biphenyl-4-yl]ethynyl}phenoxy)acetate
tert-butyl[(1-{[3-(propylsulfonyl)phenyl]ethynyl}-2-naphthyl)oxy]acetate
methyl (4-chloro-2-{[2-methyl-5-(propylsulfinyl)phenyl]ethynyl}phenoxy)acetate
tert-butyl{4-chloro-2-[(4-{[4-(trifluoromethyl)benzoyl]amino}phenyl)ethynyl]phenoxy}acetate
tert-butyl(2-{[4-(benzoylamino)phenyl]ethynyl}-4-chlorophenoxy)acetate
tert-butyl(2-{[4-(acetylamino)phenyl]ethynyl}-4-chlorophenoxy)acetate
tert-butyl(2-{[4-(acetylamino)-2-methyl-5-(propylsulfonyl)phenyl]ethynyl}-4-chlorophenoxy)acetate
tert-butyl{4-chloro-2-[(5,5-dioxidodibenzo[b,d]thien-3-yl)ethynyl]phenoxy}acetate
tert-butyl{4-chloro-2-[(1,1-dioxido-2,3-dihydro-1-benzothien-6-yl)ethynyl]phenoxy}acetate
tert-butyl{4-chloro-2-[(1,1-dioxido-1-benzothien-6-yl)ethynyl]phenoxy}acetate
tert-butyl{4-chloro-2-[(2,2-dimethyl-1,1-dioxido-3-oxo-2,3-dihydro-1-benzothien-6-yl)ethynyl]phenoxy}acetate
tert-butyl{4-chloro-2-[(3-hydroxy-2,2-dimethyl-1,1-dioxido-2,3-dihydro-1-benzothien-6-yl)ethynyl]phenoxy}acetate
tert-butyl{4-chloro-2-[(3-hydroxy-2,2,3-trimethyl-1,1-dioxido-2,3-dihydro-1-benzothien-6-yl)ethynyl]phenoxy}acetate
tert-butyl{4-chloro-2-[(3-methoxy-2,2-dimethyl-1,1-dioxido-2,3-dihydro-1-benzothien-6-yl)ethynyl]phenoxy}acetate
tert-butyl{4-chloro-2-[(3-methoxy-2,2,3-trimethyl-1,1-dioxido-2,3-dihydro-1-benzothien-6-yl)ethynyl]phenoxy}acetate
tert-butyl(2-{[4-{[butyl(methyl)amino]carbonyl}-3-(isopropylsulfonyl)phenyl]ethynyl}-4-chlorophenoxy)acetate
tert-butyl(4-chloro-2-{[4-[(dimethylamino)carbonyl]-3-(isopropylsulfonyl)phenyl]ethynyl}phenoxy)acetate
tert-butyl(4-chloro-2-{[4-[(diethylamino)carbonyl]-3-(isopropylsulfonyl)phenyl]ethynyl}phenoxy)acetate
tert-butyl(4-chloro-2-{[4-{[ethyl(propyl)amino]carbonyl}-3-(isopropylsulfonyl)phenyl]ethynyl}phenoxy)acetate
tert-butyl(4-chloro-2-{[3-(isopropylsulfonyl)-4-(morpholiN-4-ylcarbonyl)phenyl]ethynyl}phenoxy)acetate
ethyl 2-(4-chloro-2-{[2-methyl-5-(propylsulfonyl)phenyl]ethynyl}phenoxy)butanoate
ethyl 2-(4-chloro-2-{[2-methyl-5-(propylsulfonyl)phenyl]ethynyl}phenoxy)pentanoate
ethyl 2-(4-chloro-2-{[2-methyl-5-(propylsulfonyl)phenyl]ethynyl}phenoxy)-4-methylpentanoate
is more particularly described in the examples.

Compounds of Formula (VII) wherein Z, $R^1$, $R^x$, $R^y$, PG, X, m and n are as above defined can be obtained in a 2-step protocol as outlined in Scheme 4. The first step consists in the coupling of a compound of Formula (II) wherein Z, $R^1$, $R^x$, $R^y$, PG, m and n are as above defined and wherein X is preferably Br, with trimethylsilylacetylene using conditions and methods well known to those skilled in the art. This reaction can be performed with or without a catalyst such as but not limited to dichlorobis(triphenylphosphine)palladium (II) or 1,1-bis(diphenylphosphino)ferrocenedichloro palladium(II), Pd(OAc)$_2$, Pd$_2$(dba)$_3$, or Pd/C in the presence or absence of an additional ligand, such as but not limited to P(tBu)$_3$, P(oTol)$_3$, PPh$_3$, BINAP. The reaction is preferably performed in the presence of a suitable copper salt such as but not limited to copper (I) iodide, copper (I) bromide or copper (I) chloride. The reaction can be performed in the presence or absence of bases such as TEA, DIEA, NMM, piperidine, in the presence or absence of a suitable solvent such as THF, ACN, DMF. The reaction can be carried out at a temperature between about 20° C. to about 100° C., preferably at about 70° C., for a few hours, e.g. one hour to 24 h. The second step consists in the removal of the trimethylsilyl protecting group, which can be accomplished by treatment with strong acids, or with potassium carbonate in methanol, or with a source of fluoride ions, such as but not limited to tetrabutylammonium fluoride or pyridinium fluoride, in the presence or absence of a suitable solvent such as THF, at a temperature between about 20° C. to about 100° C., preferably at about 70° C., for a few hours, e.g. one hour to 24 h.

well known to those skilled in the art to perform such coupling. This reaction can be performed by hydrogenolysis, with an appropriate catalyst such as but not limited to Pd/C, Pt/C, PtO$_2$, Ni Raney, in the presence of hydrogen gas or of a source of hydrogen gas such as cyclohexadiene or ammonium formate, in a suitable solvent such as MeOH, EtOH, EtOAc, THF, DMF. This coupling reaction can be carried out at a temperature between about 20° C. to about 100° C., preferably at about 20° C., for a few hours, e.g. one hour to 24 h. The reduction can also be carried out using a metal as reducing agent, such as iron or zinc, in the presence or absence of acetic acid, at a temperature between about 20° C. to about 100° C., preferably at about 20° C., for a few hours, e.g. one hour to 24 h.

The second step consists in the conversion of the compounds of Formula (Xb) to the corresponding compounds of Formula (VIII), using methods well known to those skilled in the art for the conversion of an aryl or hetaryl amine to an aryl or hetaryl halide (Sandmeyer reaction and variants thereof), such as using sodium nitrite or tert-butyl nitrite and CuBr, CuI, KI or another suitable source of bromine or iodine, in a suitable solvent, such as an aqueous HCl solution, at a temperature between about 20° C. to about 100° C., preferably at about 20° C., for a few hours, e.g. one hour to 24 h.

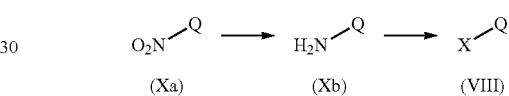

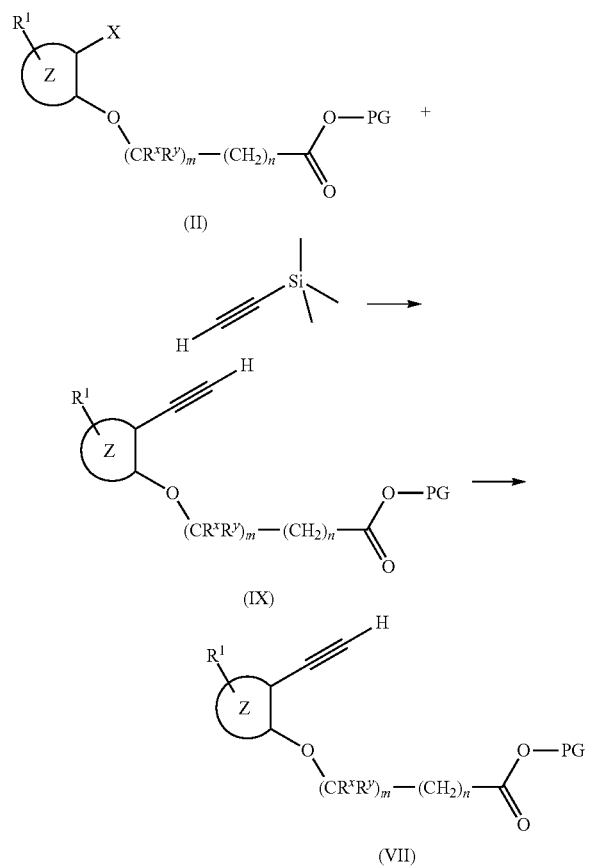

Compounds of Formula (VIII) wherein Q is as above defined and X represents a halogen, preferably bromine or iodine, can be obtained as shown in Scheme 5. The first step consists in the reduction of an aryl or hetaryl nitro compound of Formula (Xa). General protocols for such coupling are given below in the Examples, using conditions and methods Compounds of Formula (XV), wherein U is as above defined, R$^4$ is —CH$_2$-A wherein A is as defined above or T with p>0 and X represents an halogen or a triflate, can be obtained as shown in Scheme 6. An aromatic thiol of Formula (XI) can be alkylated with an alkyl halide of Formula (XII) in presence of a suitable base, such as but not limited to K$_2$CO$_3$, Cs$_2$CO$_3$, Na$_2$CO$_3$, NaOH, KOH, NaH, in a suitable solvent such as DMF, acetone, THF, in the presence of absence of water as a co-solvent, at a temperature between about 20° C. to about 100° C., preferably at about 20° C., for a few hours, e.g. one hour to 24 h.

The second step consists in the oxidation of the thioether group to a sulfone group, to give compounds of Formula (XIV), using oxidizing agents well known to those skilled in the art, such as but not limited to Oxone®, sodium periodate, hydrogen peroxide, 3-chloroperbenzoic acid, hydrogen peroxide in the presence of acetic acid, in a suitable solvent depending on the nature of the oxidant.

The third step consists in an aromatic bromination reaction, using a suitable source of bromine such as Br$_2$ or NBS, in the presence of a suitable solvent such as concentrated sulphuric acid, at a temperature between about 20° C. to about 100° C., preferably at about 20° C., for a few hours, e.g. one hour to 24 h.

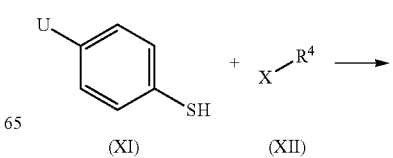

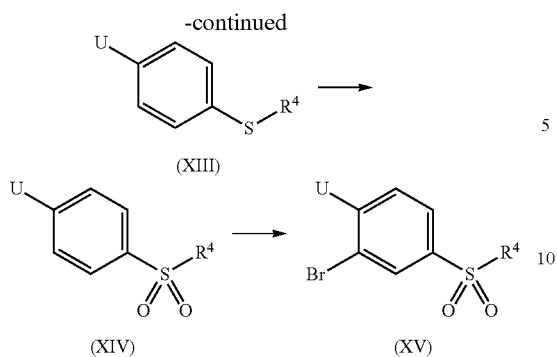

Alternatively, the compounds of Formula (XV), defined as above, can be obtained as shown in Scheme 7. Compounds of Formula (XVI) can be alkylated with a compound of Formula (XII), in presence of a suitable base, such as but not limited to $K_2CO_3$, $Cs_2CO_3$, $Na_2CO_3$, NaOH, KOH, NaH, in a suitable solvent such as DMF, acetone, THF, in the presence or absence of a water as a co-solvent, at a temperature between about 0° C. to about 100° C., preferably at about 20° C., for a few hours, e.g. one hour to 24 h.

The compounds of Formula (XV) could be obtained by oxidation, using oxidizing agents well known to those skilled in the art, such as but not limited to Oxone®, sodium periodate, hydrogen peroxide, m-chloroperbenzoic acid, hydrogen peroxide in the presence of acetic acid, in a suitable solvent depending on the nature of the oxidant.

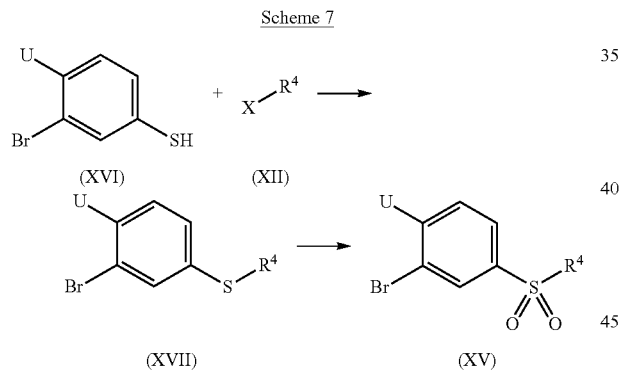

Compounds of Formula (XXIII), wherein U and $R^4$ are as above defined, can be prepared as shown in Scheme 8. A compound of Formula (XVIII), wherein U is as defined above, can be coupled with a compound of Formula (XIX), in the presence of a suitable base, such as $K_2CO_3$, $Cs_2CO_3$, $Na_2CO_3$, NaOH, KOH, NaH, in a suitable solvent such as DMF, acetone, THF, DMSO in the presence of absence of water as a co-solvent, at a temperature between about 20° C. to about 150° C., preferably at 20° C., for a few hours, e.g. one hour to 24 h. The compounds of Formula (XX) can be oxidized as described above, to yield the corresponding compounds of Formula (XXI).

The reduction of compounds of Formula (XXI) to afford compounds of Formula (XXII) can be performed by hydrogenolysis, with an appropriate catalyst such as but not limited to Pd/C, Pt/C, $PtO_2$, Ni raney, in the presence of hydrogen gas or of a source of hydrogen gas such as cyclohexadiene or ammonium formiate, in the a suitable solvent such as MeOH, EtOH, EtOAc, THF, DMF. This coupling reaction can be carried out at a temperature between about 20° C. to about 100° C., preferably at about 20° C., for a few hours, e.g. one hour to 24 h. The reduction can also be carried out using a metal as reducing agent, such as iron or zinc, in the presence or absence of acetic acid, at a temperature between about 20° C. to about 100° C., preferably at about 20° C., for a few hours, e.g. one hour to 24 h.

The last step consists in the conversion of the compounds of Formula (XXII) to the corresponding compounds of Formula (XXIII), using methods well known to those skilled in the art for the conversion of an aryl or hetaryl amine to an aryl or hetaryl halide (Sandmeyer reaction and variants thereof), such as using sodium nitrite or tert-butyl nitrite and CuBr, CuI, KI or another suitable source of bromine or iodine, in a suitable solvent, such as an aqueous HCl solution, at a temperature between about 20° C. to about 100° C., preferably at about 20° C., for a few hours, e.g. one hour to 24 h.

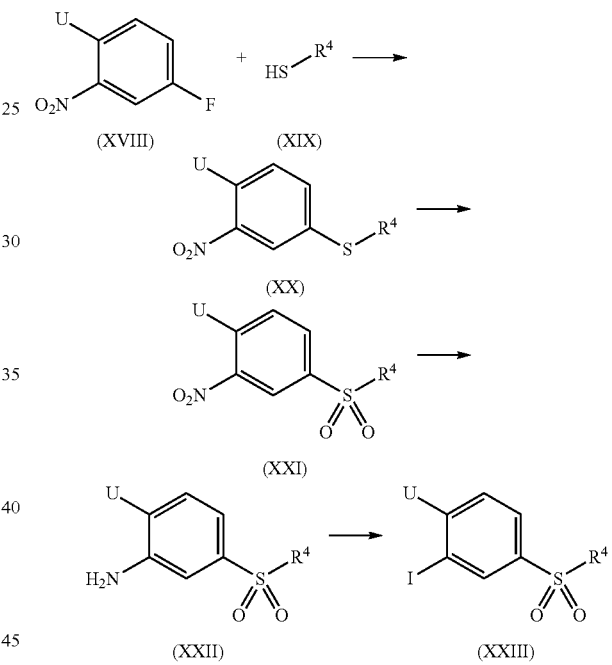

Compounds of Formula (IV), wherein Q, Z, $R^1$, $R^x$, $R^y$, PG, m and n are as defined above and $R^1$ is Ar or Het can be obtained as described in Scheme 9. Compounds of Formula (XXIV), wherein Z, $R^1$, $R^x$, $R^y$, PG, m and n are as defined above, and X and X' denote suitably selected halogens or a triflate group, with X being preferentially iodine and X' being preferentially bromine, can be coupled with compounds of Formula (III), wherein Q is as defined above.

General protocols for such coupling are given below in the Examples, using conditions and methods well known to those skilled in the art to perform such coupling. This reaction is preferably performed with an appropriate catalyst such as but not limited to dichlorobis(triphenylphosphine)palladium(II) or 1,1'-bis(diphenylphosphino)ferrocenedichloro palladium (II), $Pd(OAc)_2$, $Pd_2(dba)_3$, $Pd(Cl)_2$ or Pd/C in the presence or absence of an additional ligand, such as but not limited to $P(tBu)_3$, $P(oTol)_3$, $PPh_3$, BINAP. The reaction can also be performed in the presence of a suitable copper salt such as but not limited to copper (I) iodide, copper (I) bromide or copper (I) chloride. The reaction can be performed in the presence or absence of bases such as TEA, DIEA, NMM, piperidine, $Cs_2CO_3$, sodium phosphate, in the presence or absence of a suitable solvent such as THF, ACN, DMF or acetone. This coupling reaction can be carried out at a temperature between about 20° C. to about 100° C., preferably at about 70° C., for a few hours, e.g. one hour to 24 h.

Compounds of Formula (XXV) can be coupled with aryl or heteroaryl boronic acids of Formula (XXVI), wherein $R^1$ is Ar or Het, or the corresponding boronate esters. General protocols for such coupling are given below in the Examples, using conditions and methods well known to those skilled in the art to perform such coupling. This reaction is performed with an appropriate catalyst such as but not limited to dichlorobis(triphenylphosphine)palladium(II), $Pd(PPh_3)_4$ or 1,1'-bis(diphenylphosphino)ferrocenedichloro palladium(II), $Pd(OAc)_2$, $Pd_2(dba)_3$, $Pd(Cl)_2$ or Pd/C in the presence or absence of an additional ligand, such as but not limited to $P(tBu)_3$, $P(oTol)_3$, $PPh_3$, BINAP. The reaction is performed in the presence of a base such as $Cs_2CO_3$, $K_2CO_3$, CsF, in the presence of a suitable solvent such as THF, toluene or dioxane, in the presence or absence of water as a co-solvent. This coupling reaction can be carried out at a temperature between about 20° C. to about 150° C., preferably at about 120° C., for a few minutes to a few hours, possibly under microwave irradiation.

Scheme 9

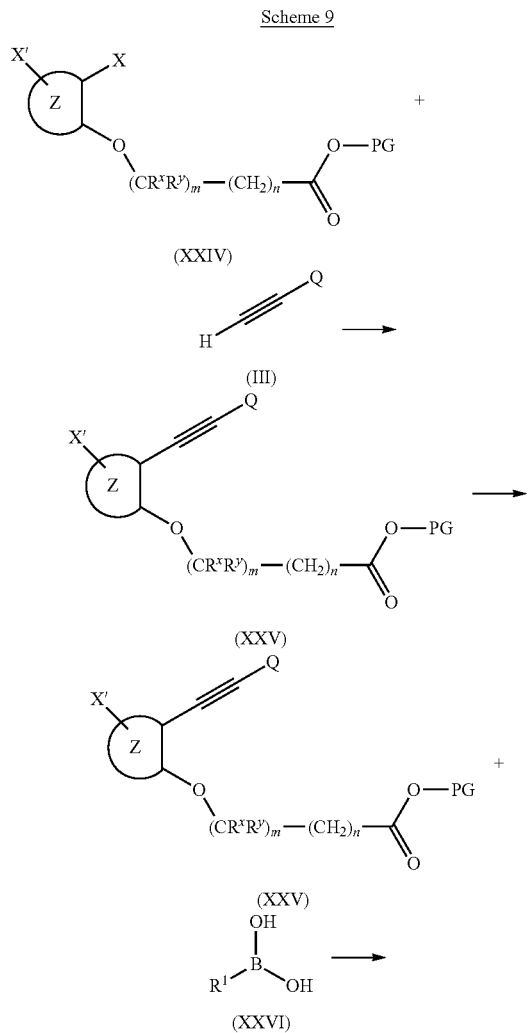

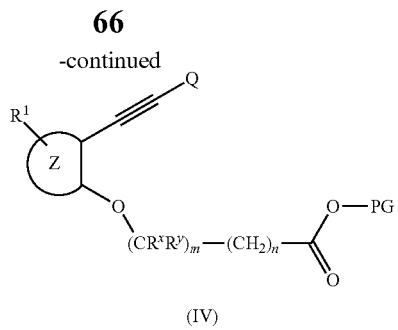

The above set out general synthetic methods may be modified to obtain compounds of Formula (I), since various suitable methods of preparation known by a person skilled in the art are available.

According to a further general process, compounds of Formula (I) can be converted to alternative compounds of Formula (I), employing suitable interconversion techniques well known by a person skilled in the art.

Suitable methods of preparation for the compounds and intermediates of the invention as known by a person skilled in the art should be used. In general, the synthesis pathways for any individual compound of Formula (I) will depend on the specific substitutents of each molecule and upon the ready availability of intermediates necessary; again such factors being appreciated by those of ordinary skill in the art.

General:

The HPLC data provided in the examples described below were obtained as followed.

Condition A: Column Waters Xbridge™ $C_8$ 50 mm×4.6 mm at a flow of 2 mL/min; 8 min gradient from 0.1% TFA in $H_2O$ to 0.07% TFA in $CH_3CN$.

Condition B: Column Waters ACQUITY UPLC® BEH $C_{18}$ 50 mm×2.1 mm 1.7 μm at a flow of 1 mL/min; 3 min gradient from 95% (10 mM $NH_4OAc$ in $H_2O$)/5% $CH_3CN$ to 100% $CH_3CN$.

Condition C: Column Waters ACQUITY UPLC® BEH $C_{18}$ 50 mm×2.1 mm 1.7 μm at a flow of 1 mL/min; 3 min gradient from 60% (10 mM $NH_4OAc$ in $H_2O$)/40% $CH_3CN$ to 100% $CH_3CN$.

Condition D: Column Waters ATLANTIS® $C_{18}$ 75 mm×4.6 mm, 5 μm at a flow of 0.8 mL/min; gradient from 0.1% TFA in $H_2O$ to $CH_3CN$.

Condition E: Column Grace Vidac GENESIS® $C_{18}$ 50 mm×4.6 mm 5 μm at a flow of 1.0 mL/min; gradient from 0.1% HCOOH in $H_2O$ to $CH_3CN$.

Condition F: Column Waters ATLANTIS $C_{18}$ 75 mm×4.6 mm, 5 μm at a flow of 1.0 mL/min; gradient from 0.1% HCOOH in $H_2O$ to $CH_3CN$.

UV detection (maxplot) for all conditions.

The MS data provided in the examples described below were obtained as followed:

Mass spectrum: LC/MS Waters ZMD (ESI) or a Waters Acquity SQD (ESI)

The NMR data provided in the examples described below were obtained as followed: $^1$H-NMR: Bruker DPX-300 MHz or a Bruker DPX 400 MHz.

The microwave chemistry was performed on a single mode microwave reactor Emrys™ Optimiser from Personal Chemistry Preparative HPLC purifications were performed with a mass directed autopurification Fractionlynx from Waters equipped with a Sunfire Prep C18 OBD column 19×100 mm 5 μm, unless otherwise reported. All HPLC purifications were performed with a gradient of ACN/H₂O or ACN/H₂O/HCOOH (0.1%).

The compounds of invention have been named according to the standards used in the program "ACD/Name Batch" from Advanced Chemistry Development Inc., ACD/Labs (7.00 Release). Product version: 7.10, build: Sep. 15, 2003.

Intermediate 1 tert-butyl(2-bromo-4-chlorophenoxy)acetate

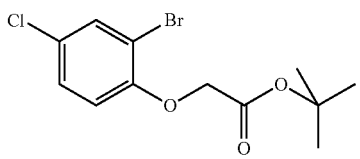

A solution of 2-bromo-4-chlorophenol (Aldrich; 13.11 g; 63.2 mmol) in acetone (100 mL) was treated with potassium carbonate (9.61 g; 69.5 mmol), stirred for 10 minutes then treated with tert-butyl bromoacetate (Aldrich; 9.34 mL; 63.2 mmol). The reaction mixture was stirred at 65° C. for 18 hours, then the mixture was filtered, the solid was washed with acetone and the filtrate was concentrated to dryness under vacuum to give the title compound as a yellow sticky solid (19.4 g, 95%).

$^1$H NMR (300 MHz, DMSO-$d_6$) δ [ppm] 7.68 (1H, d, J=2.6 Hz), 7.39 (1H, dd, J=9.0 Hz; J=2.6 Hz), 7.37 (1H, d, J=9.0 Hz), 4.80 (2H, s), 1.41 (9H, s). MS (ESI$^+$): 340.1 (M+NH$_4^+$). HPLC (Condition A): Rt 5.06 min (HPLC purity 96.8%).

Intermediate 2 tert-butyl{4-chloro-2-[(trimethylsilyl)ethynyl]phenoxy}acetate

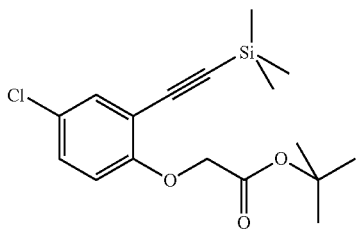

A solution of tert-butyl(2-bromo-4-chlorophenoxy)acetate (Intermediate 1; 19.40 g; 60.3 mmol) and 1,1'-bis(diphenylphosphino)ferrocenedichloro palladium(II) (2.65 g; 3.62 mmol) in THF (290 mL) was degassed during 2 minutes under nitrogen then triethylamine (12.5 mL; 91 mmol) and (trimethylsilyl)acetylene (Aldrich; 10.2 mL; 72.4 mmol) were added. The reaction mixture was stirred under nitrogen for 10 minutes before being treated with copper iodide (689 mg; 3.62 mmol) and triethlyamine (12.5 mL, 90.5 mmol) and stirred at 60° C. for 24 h. The reaction mixture was filtered through Celite and the cake of Celite was washed with EtOAc. The resulting filtrate was washed with HCl 1N and brine, dried over MgSO$_4$, filtered and concentrated to dryness affording a dark brown sticky solid, which was suspended in petroleum ether (350 mL). The resulting precipitate was filtered, washed with petroleum ether (2×150 mL) and the filtrated was concentrated to dryness affording the crude product (17.7 g, 87%) as a brown oil.

$^1$H NMR (300 MHz, DMSO-$d_6$) δ [ppm] 7.43 (1H, d, J=2.7 Hz), 7.38 (1H, dd, J=8.9, J=2.7 Hz), 6.92 (1H, d, J=8.9 Hz), 4.74 (s, 2H), 1.43 (s, 9H), 0.23 (s, 9H). MS (ESI$^+$): 356.2 (M+NH$_4^+$). HPLC (Condition A): Rt 6.32 min.

Intermediate 3 tert-butyl(4-chloro-2-ethynylphenoxy)acetate

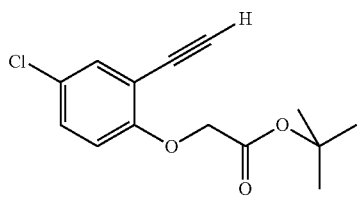

A solution of tert-butyl{4-chloro-2-[(trimethylsilyl)ethynyl]phenoxy}acetate (Intermediate 2, 17.70 g; 52.2 mmol) in THF (180 mL) was treated with tetrabutylammonium fluoride trihydrate (16.48 g; 52.2 mmol). The reaction mixture was stirred for 4 hours, then ethyl acetate (450 mL) was added and the organic phase was washed with water (750 mL) then with brine (750 mL), dried over MgSO$_4$, filtered and concentrated under vacuum to give a brown oily residue which was purified by flash chromatography (silica) eluting with cyclohexane containing increasing amounts of ethyl acetate. The title compound was obtained as a brown oil which solidified after prolonged standing.

$^1$H NMR (300 MHz, DMSO-$d_6$) δ [ppm] 7.47 (1H, d, J=2.7 Hz), 7.39 (1H, dd, J=9.0, J=2.7 Hz), 6.93 (1H, d, J=9.0 Hz), 4.77 (2H, s), 4.39 (1H, s), 1.42 (9H, s). MS (ESI$^+$): 267.1. HPLC (Condition A): Rt 4.79 min (HPLC purity 95.5%).

Intermediate 4

(2-bromo-4-chlorophenoxy)acetic acid

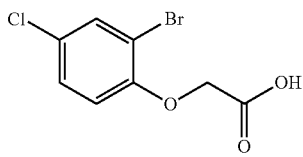

A cooled (0° C.) solution of tert-butyl(2-bromo-4-chlorophenoxy)acetate (1.00 g; 3.11 mmol) in DCM (22 mL) was treated with trifluoroacetic acid (2.38 mL; 31.1 mmol). The reaction mixture was stirred at room temperature for 5 hours, the solvents were removed under vacuum to give the title compound (825 mg, quant.).

$^1$H NMR (300 MHz, DMSO-$d_6$) δ [ppm] 13.16 (1H, s), 7.71 (1H, d, J=2.7 Hz), 7.39 (1H, dd, J=8.9, J=2.7 Hz), 7.03

(1H, d, J=8.9 Hz), 4.83 (2H, s). MS (ESI⁻): 264.9. HPLC (Condition A): Rt 3.56 min (HPLC purity 91.5%).

Intermediate 5

1-(Bromomethyl)-3-(propylsulfonyl)benzene

Step-1

1-Bromo-3-(propylthio)benzene

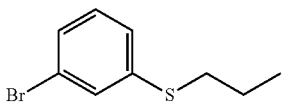

A solution of 3-bromobenzenethiol (5.00 g, 26.4 mmol) in anhydrous DMF (30 mL) was treated with $K_2CO_3$ (7.30 g, 52.8 mmol) followed by 1-bromopropane (3.90 g, 31.7 mmol) and the mixture was heated to about 50° C. under nitrogen for 12 h. The solvent was distilled out completely, and the residue was dissolved in DCM and washed with water and brine. The organic layer was dried over sodium sulphate and evaporated to afford 5.50 g (90%) of the title compound as pale yellow liquid.

¹H NMR (400 MHz, $CDCl_3$) δ [ppm] 7.44 (1H, s), 7.29-7.27 (1H, m), 7.24-7.21 (1H, m), 7.15-7.11 (1H, m), 2.90 (2H, t) 1.64-1.73 (2H, m), 1.04 (3H, t).

Step-2

1-(Bromomethyl)-3-(propylsulfonyl)benzene

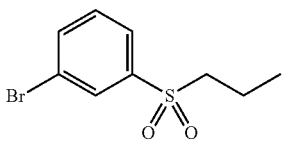

A solution of 1-bromo-3-(propylthio) benzene (5.50 g, 23.7 mmol) in DCM (75 mL) was treated with m-chloroperbenzoic acid (12.3 g, 71.3 mmol) and stirred at RT for 5 h. The solid formed was filtered off and the filtrate was washed with 10% solution of sodium bicarbonate, water and brine. The organic layer was dried over $Na_2SO_4$ and evaporated to afford 5.7 g (91%) of the title compound as yellow liquid.

¹H NMR (400 MHz, $CDCl_3$) δ [ppm] 8.05 (1H, s), 7.85-7.83 (1H, m), 7.80-7.77 (1H, m), 7.45 (1H, t), 3.10-3.06 (2H, m), 1.80-1.71 (2H, m), 1.02 (3H, t). HPLC (Condition D): Rt 3.54 min (HPLC purity 97.4%).

Intermediate 6

3-[(3-bromophenyl)sulfonyl]propan-1-ol

Step-1

3-[(3-Bromophenyl)thio]propan-1-ol

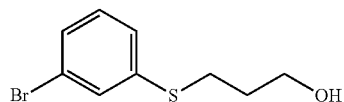

A solution of 3-bromobenzenethiol (5.00 g, 26.4 mmol) in anhydrous DMF (30 mL) was treated with $Cs_2CO_3$ (17.2 g, 52.9 mmol) followed by 3-bromopropan-1-ol (4.40 g, 31.6 mmol). The mixture was heated to 50° C. under nitrogen for 12 h. DMF was distilled out completely, and the residue was dissolved in DCM and washed with water, brine and dried over $Na_2SO_4$. The solvent was evaporated to afford 6.4 g (98%) of the title compound as pale yellow liquid.

¹H NMR (400 MHz, $CDCl_3$) δ [ppm] 7.46 (1H, s), 7.30-7.25 (2H, m), 7.16-7.12 (1H, m), 3.78 (2H, t), 3.07-2.99 (2H, m) 1.93-1.87 (2H, m). MS (ESI⁻): 247.1. HPLC (Condition E): Rt 3.36 min.

Step-2

3-[(3-bromophenyl)sulfonyl]propan-1-ol

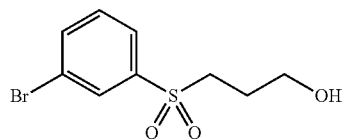

A solution of 3-[(3-bromophenyl)thio]propan-1-ol (7.00 g, 49.2 mmol) in DCM (75 mL) was treated with m-chloroperbenzoic acid (25.4 g, 148 mmol) and stirred at RT for 5 h. The solid formed was removed by filtration and the filtrate was washed with sodium-bicarbonate solution, water and brine. Organic layer was dried over $Na_2SO_4$ and evaporated to afford 6.7 g (93%) of the title compound as yellow semi-solid.

¹H NMR (400 MHz, $CDCl_3$) δ [ppm] 8.06 (1H, s), 7.85 (1H, dd), 7.79 (1H, dd), 7.46 (1H, dd), 3.76-3.73 (2H, m), 3.27-3.23 (2H, m), 2.02-1.97 (2H, m). MS (ESI⁺): 281.1. HPLC (Condition E): Rt 3.15 min (HPLC purity 99.3%).

Intermediate 7

2-[(3-Bromophenyl)sulfonyl]ethanol

Step-1

2-[(3-Bromophenyl)thio]ethanol

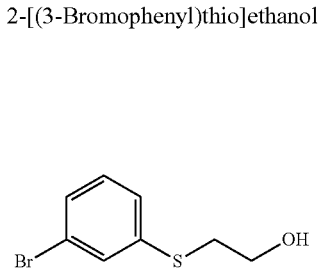

A solution of 3-bromobenzenethiol (5.00 g, 26.4 mmol) in anhydrous DMF (30 mL) was treated with $Cs_2CO_3$ (17.2 g, 52.8 mmol) and 2-bromoethanol (3.90 g, 31.7 mol) and heated to about 50° C. under nitrogen for 12 h. DMF was distilled out completely and the residue was dissolved in DCM and washed with water and brine. Organic layer was dried over $Na_2SO_4$, evaporated and purified by column chromatography (silica) to afford 5.5 g (90%) of the title compound as pale yellow solid.

$^1$H NMR (400 MHz, $CDCl_3$) δ [ppm] 7.53 (1H, s), 7.36 (1H, m), 7.34 (1H, m), 7.16 (1H, t), 3.78 (2H, t), 3.14 (2H, t). MS (ESI$^-$): 217.1. HPLC (Condition F): Rt 3.87 min (HPLC purity 99.8%).

Step-2

2-[(3-Bromophenyl)sulfonyl]ethanol

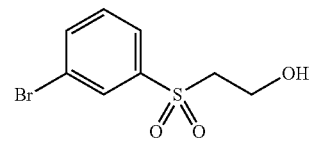

A solution of 2-[(3-bromophenyl)thio]ethanol (5.50 g, 23.5 mmol) in DCM (75 mL) was treated with m-chloroperbenzoic acid (12.2 g, 70.7 mmol) and stirred at RT for 5 h. The solid formed was filtered and washed with cold DCM and the filtrate was washed with 10% sodium hydroxide, water and brine. Organic layer was dried over $Na_2SO_4$, evaporated and passed through column chromatography using silica gel (60-120 mesh) to afford the title compound as off white solid.

$^1$H NMR (400 MHz, $CDCl_3$) δ [ppm] 8.04 (1H, s), 7.94-7.88 (2H, m), 7.61-7.53 (1H, m), 4.89 (1H, t), 3.70-3.66 (2H, m), 3.52 (2H, t). MS (ESI$^+$): 310.6. HPLC (Condition F): Rt 2.04 min (HPLC purity 95.6%).

Intermediate 8 tert-butyl(2-bromo-4-cyanophenoxy)acetate

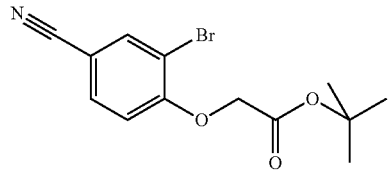

A solution of 3-bromo-4-hydroxybenzonitrile (Lancaster; 3.00 g; 15.2 mmol) in acetone (30 mL) was treated with potassium carbonate (2.30 g; 16.7 mmol), stirred for 10 minutes then treated with tert-butyl bromoacetate (2.24 mL; 15.2 mmol). The reaction mixture was stirred at 65° C. for 18 hours, then the mixture was filtered, the solid was washed with acetone and the filtrate was concentrated to dryness under vacuum to give the title compound as a yellow sticky solid (4.75 g, quant).

$^1$H NMR (300 MHz, DMSO-$d_6$) δ [ppm] 8.18 (1H, d, J=2.0 Hz), 7.84 (1H, dd, J=8.7, 2.0 Hz), 7.17 (1H, d, J=8.7 Hz), 4.95 (2H, s), 1.42 (9H, s).

Intermediate 9

(4-bromo-3-fluorophenyl)methanol

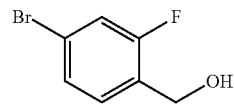

A cooled (0° C.) suspension of lithium aluminium hydride (88 mg; 2.3 mmol) in anhydrous THF (10 mL) was treated dropwise with a solution of methyl 4-bromo-3-fluorobenzoate (Combi-Blocks; 300 mg; 1.29 mmol) dissolved in anhydrous $Et_2O$ (10 mL), and the reaction mixture was stirred at RT for 2 days. The reaction mixture was treated with a saturated aqueous solution of sodium thiosulfate. The organic phase was separated, dried over $MgSO_4$, filtered and concentrated to dryness affording the title compound as a yellow liquid (247 mg, 94%).

$^1$H NMR (300 MHz, DMSO-$d_6$) δ [ppm] 7.64 (1H, dd, J=8.1, J=7.5 Hz), 7.28 (1H, m), 7.11 (1H, m), 5.40 (1H, t, J=5.8 Hz), 4.48 (2H, d, J=5.8 Hz). HPLC (Condition A): Rt 2.78 min (HPLC purity 90.2%).

Intermediate 10 tert-butyl(2-bromo-4-methyl phenoxy)acetate

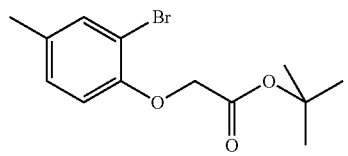

A solution of 2-bromo-4-methylphenol (Alfa; 3.00 g; 16.0 mmol) in acetone (30 mL) was treated with potassium carbonate (2.44 g; 17.6 mmol), stirred for 10 minutes then treated with tert-butyl bromoacetate (2.37 mL; 16.0 mmol). The reaction mixture was stirred at 65° C. for 18 hours, then the mixture was filtered, the solid was washed with acetone and the filtrate was concentrated to dryness under vacuum to give the title compound as a pale yellow liquid (4.8 g, 99%).

$^1$H NMR (300 MHz, DMSO-d$_6$) δ [ppm] 8.18 (1H, d, J=2.1 Hz), 7.84 (1H, dd, J=8.7, 2.1 Hz), 7.17 (1H, d, J=8.7 Hz), 4.95 (2H, s), 2.23 (3H, s), 1.42 (9H, s). MS (ESI$^+$): 320.1 (M+NH$_4^+$).

Intermediate 11

(3-bromo-2-fluorophenyl)methanol

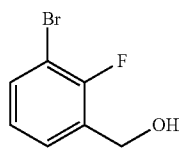

A cooled (0° C.) solution of 3-bromo-2-fluorobenzoic acid (Fluorochem; 500 mg; 2.28 mmol) in anhydrous THF (4 mL) was slowly treated with borane-tetrahydrofuran complex (3.42 mL; 1.00 M; 3.42 mmol) and the resulting solution was stirred at RT for 2 days. Borane-tetrahydrofuran complex (3.42 mL; 1.00 M; 3.42 mmol) was added and the reaction mixture was stirred at RT for a further 3 hours. The reaction was carefully quenched with water and the mixture was concentrated. The residue was dissolved in Et$_2$O, and the aqueous phase was saturated with K$_2$CO$_3$. The organic layer was separated and the aqueous phase was extracted with Et$_2$O. The combined organic phases were washed with water and brine, dried over MgSO$_4$ and concentrated to dryness affording the title compound as a colorless oil.

$^1$H NMR (300 MHz, DMSO-d$_6$) δ [ppm] 7.60 (1H, m), 7.45 (1H, m), 7.15 (1H, t, J=7.1 Hz), 5.42 (1H, s), 4.57 (2H, s). HPLC (Condition A): Rt 2.67 min (HPLC purity 97.6%).

Intermediate 12

3-bromo-4-(hex-1-en-1-yl)pyridine

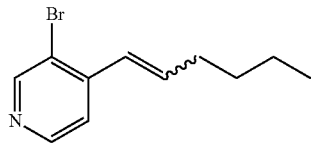

A cooled (0° C.) suspension of n-pentyl-triphenylphosphonium bromide (Acros; 1200 mg; 2.90 mmol) in anhydrous THF (20 mL) was slowly treated with a solution (1.6 M) of butyllithium in hexane (2 700 µL; 4.35 mmol). The mixture was stirred for 1 hour, then a solution of 3-bromo-4-pyridinecarboxaldehyde (Aldrich; 567 mg; 3.05 mmol) in anhydrous THF (10 mL) was added. After stirring for one hour, the reaction was quenched by addition of a saturated aqueous solution of ammonium chloride. After addition of EtOAc the phases were separated and the organic phase washed with brine, dried over MgSO$_4$ and concentrated under vacuum to afford a crude product, which was purified by column chromatography, eluting with cyclohexane containing increasing amounts of EtOAc to afford the title compound as a mixture of cis and trans isomers. MS (ESI$^-$): 240.1.

Intermediate 13

3-bromo-4-hexylpyridine

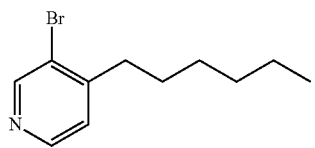

A mixture of 3-bromo-4-(hex-1-en-1-yl)pyridine (Intermediate 12; 360 mg; 1.50 mmol) and platinum dioxide (34 mg; 0.15 mmol) in EtOAc (35 mL) was hydrogenated at 7 atm for 1 hour in a PARR apparatus. The reaction mixture was filtered, evaporated and purified by flash column chromatography, eluting with cyclohexane containing increasing amounts of EtOAc, affording the title compound as a colorless liquid.

$^1$H NMR (300 MHz, DMSO-d$_6$) δ [ppm] 8.67 (1H, s), 8.45 (1H, d, J=5.0 Hz), 7.40 (1H, d, J=5.0 Hz), 2.70 (2H, t, J=7.8 Hz), 1.52-1.62 (2H, m), 1.28-1.34 (6H, m), 0.87 (3H, t, J=7.0 Hz). MS (ESI$^+$): 242.1. HPLC (Condition A): Rt 3.79 min (HPLC purity 98.0%).

Intermediate 14

3-bromo-4-fluorobenzyl methanesulfonate

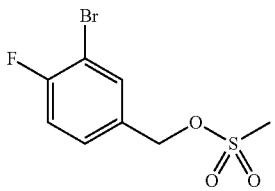

A cooled (−20° C.) solution of 3-bromo-4-fluorobenzyl alcohol (Oakwood; 500 mg; 2.44 mmol) and methanesulfonyl chloride (123 µL; 1.59 mmol) in DCM (5 mL) was treated with a solution of triethylamine (255 µL; 1.83 mmol) in DCM (2.5 mL). The reaction mixture was allowed to warm to RT and stirred for 30 minutes before being quenched with water. The phases were separated and the organic phase was washed with HCl (0.1N in water) and brine, dried over MgSO$_4$, filtered and concentrated to dryness affording a residue, which was purified by flash column chromatography), eluting with cyclohexane containing increasing amounts of EtOAc, to give the title compound as a colorless liquid.

$^1$H NMR (300 MHz, DMSO-d$_6$) δ [ppm] 7.84 (1H, dd, J=6.7, J=2.1 Hz), 7.54 (1H, ddd, J=8.7, J=4.9, J=2.1 Hz), 7.45 (1H, d, J=8.7 Hz), 5.25 (2H, s), 3.27 (3H, s).

Intermediate 15

2-bromo-1-fluoro-4-(methoxymethyl)benzene

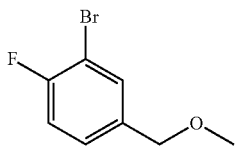

A solution of 3-bromo-4-fluorobenzyl methanesulfonate (Intermediate 14, 330 mg; 1.17 mmol) and 2,6-lutidine (176 µL; 1.52 mmol) in methanol (4 mL) was stirred for 16 hours at RT. Additional aliquots of 2,6-lutidine (176 µL; 1.52 mmol each) were added once a day for a total of three days, during which stirring was continued at RT. The mixture was taken up in Et$_2$O, washed with water, HCl (0.1N in water) and brine. The organic phase was dried over MgSO$_4$, filtered and concentrated with moderate vacuum and without heating affording the title compound as a pale yellow liquid.

$^1$H NMR (300 MHz, DMSO-d$_6$) δ [ppm] 7.66 (1H, d, J=7.3 Hz), 7.38 (2H, m), 4.41 (2H, s), 3.30 (3H, s).

Intermediate 16

2-methyl-5-(methylsulfonyl)aniline

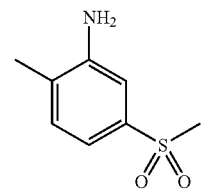

A mixture of 4-methylsulfonyl-2-nitrotoluene (Alfa; 4.00 g; 18.6 mmol) and platinum oxide (120 mg; 0.53 mmol) in EtOAc (200 mL) was hydrogenated in a PARR apparatus at 5 atm for 75 minutes. The mixture was filtered through a pad of celite and the solvent was evaporated to afford the title compound as a colorless oil (3.41 g, 99%).

$^1$H NMR (300 MHz, DMSO-d$_6$) δ [ppm] 7.16 (1H, d, J=7.8 Hz), 7.11 (1H, d, J=1.9 Hz), 6.95 (1H, dd, J=7.7, 1.9 Hz), 5.42 (2H, bs), 3.07 (3H, s), 2.12 (3H, s). MS (ESI$^+$): 186.1.

Intermediate 17

2-iodo-1-methyl-4-(methylsulfonyl)benzene

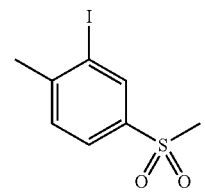

A cooled (0° C.) solution of 2-methyl-5-(methylsulfonyl)aniline (Intermediate 16; 556 mg; 3.00 mmol) in aqueous hydrogen chloride (5 M, 10 mL; 50 mmol) was treated with sodium nitrite (248 mg; 3.60 mmol) and the resulting mixture was stirred at 0° C. for 30 minutes, before being treated with a solution of potassium iodide (4.98 g; 30 mmol) in water (8 mL). The resulting mixture was stirred at RT for 1 hour, the EtOAc was added and the phases separated. The organic layer was washed twice with an aqueous, saturated sodium thiosulfate solution, then with brine, dried over MgSO$_4$ and concentrated to afford a residue which was purified by column chromatography, eluting with cyclohexane containing increasing amounts of EtOAc to afford the title compound (649 mg, 73%) as a colorless liquid.

¹H NMR (300 MHz, DMSO-d₆) δ [ppm] 8.28 (1H, d, J=2.0 Hz), 7.85 (1H, dd, J=8.0, 2.0 Hz), 7.60 (1H, d, J=8.0 Hz), 3.24 (3H, s), 2.47 (3H, s). HPLC (Condition A): Rt 3.23 min (HPLC purity 100%).

Intermediate 18

4-bromo-3-fluorobenzyl methanesulfonate

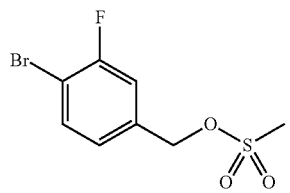

A cooled (0° C.) solution of (4-bromo-3-fluorophenyl)methanol (Intermediate 9; 299 mg; 1.46 mmol) and methanesulfonyl chloride (147 µL; 1.90 mmol) in DCM (3 mL) was treated slowly with a solution of triethylamine (305 µL; 2.19 mmol) in DCM (1.5 mL). The reaction mixture was allowed to warm to RT and stirred for 45 minutes before being quenched by addition of water. The organic phase was washed with HCl (0.1N in water) and brine, dried over MgSO₄, filtered and concentrated to dryness affording a residue, which was purified by flash column chromatography, eluting with cyclohexane containing increasing amounts of EtOAc to give the title compound as a colourless liquid.

¹H NMR (300 MHz, DMSO-d₆) δ [ppm] 7.77 (1H, dd, J=8.2, J=7.5 Hz), 7.48 (1H, dd, J=9.7, J=2.0 Hz), 7.26 (1H, dd, J=8.2, J=2.0 Hz), 5.26 (2H, s), 3.27 (3H, s).

Intermediate 19 tert-butyl{4-chloro-2-[(4-methylpyridin-3-yl)ethynyl]phenoxy}acetate

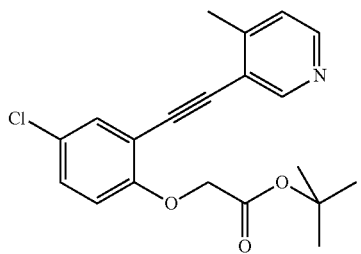

A mixture of 3-bromo-4-methylpyridine (Apollo; 355 mg; 2.06 mmol), tert-butyl(4-chloro-2-ethynylphenoxy)acetate (Intermediate 3, 500 mg; 1.87 mmol), dichlorobis(triphenylphosphine)palladium(II) (82 mg; 0.11 mmol), copper(I) iodide (21 mg; 0.11 mmol) was degassed during two minutes under nitrogen then THF (7.5 mL) and triethylamine (520 µL; 3.75 mmol) were added and reaction mixture was stirred at 60° C. for 16 hours. The solvents were removed under vacuum affording a dark brown residue, which was purified by flash column chromatography (silica), eluting with cyclohexane containing increasing amounts of EtOAc. The title compound was obtained as a dark brown sticky solid.

¹H NMR (300 MHz, DMSO-d₆) δ [ppm] 8.63 (1H, s), 8.44 (1H, d, J=5.0 Hz), 7.61 (1H, d, J=2.6 Hz), 7.44 (1H, dd, J=9.0, J=2.6 Hz), 7.38 (1H, d, J=5.0 Hz), 7.02 (1H, d, J=9.0 Hz), 4.81 (2H, s), 2.48 (3H, s), 1.43 (9H, s). MS (ESI⁺): 358.3. HPLC (Condition A): Rt 3.74 min (HPLC purity 99.8%).

Intermediate 20 tert-butyl{4-chloro-2-{[3-(propylsulfonyl)phenyl]ethynyl}phenoxy)acetate

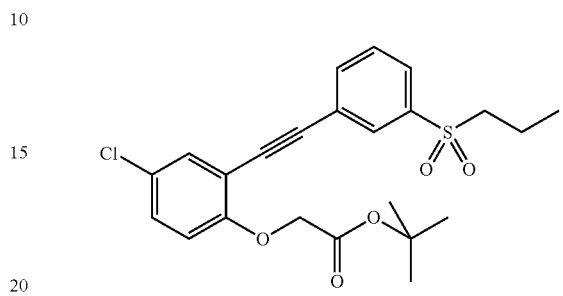

A mixture of 1-bromo-3-(propane-1-sulfonyl)-benzene (Intermediate 5; 493 mg, 1.87 mmol), tert-butyl(4-chloro-2-ethynylphenoxy)acetate (Intermediate 3, 500 mg; 1.87 mmol), dichlorobis(triphenylphosphine)palladium(II) (52 mg; 0.07 mmol) and piperidine (550 µL; 5.6 mmol) was heated at 70° C. for 18 hours. The reaction mixture was taken up in EtOAc, washed twice with citric acid (0.5 M aqueous solution) and once with brine. The organic phase was dried over MgSO₄, filtered and concentrated to dryness affording a crude, which was purified by flash column chromatography (silica), eluting with cyclohexane containing increasing amounts of EtOAc. The title compound was obtained as a dark orange sticky solid (640 mg, 76%).

¹H NMR (300 MHz, DMSO-d₆) δ [ppm] 8.04 (1H, t, J=1.7 Hz), 7.96-7.88 (2H, m), 7.75 (1H, t, J=7.8 Hz), 7.67 (1H, d, J=2.7 Hz), 7.47 (1H, dd, J=9.0, 2.7 Hz), 7.03 (1H, d, J=9.0 Hz), 4.84 (2H, s), 3.42-3.34 (2H, m), 1.66-1.51 (2H, m), 1.51-1.37 (9H, m), 0.94 (3H, t, J=7.4 Hz). MS (ESI⁺): 466.3 (M+NH₄⁺). HPLC (Condition A): Rt 5.48 min (HPLC purity 94.5%).

Intermediate 21 tert-butyl{4-chloro-2-[(5-cyano-2-fluorophenyl)ethynyl]phenoxy}acetate

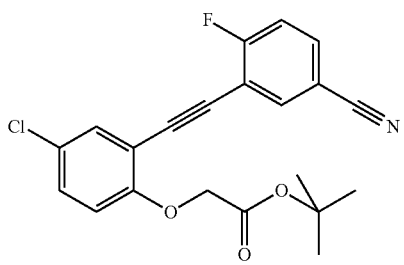

Following the general method as outlined in Intermediate 19, starting from tert-butyl(4-chloro-2-ethynylphenoxy)acetate (Intermediate 3) and 3-bromo-4-fluorobenzonitrile (ABCR), the title compound was obtained as a beige solid after purification by flash column chromatography (silica), eluting with cyclohexane containing increasing amounts of EtOAc ¹H NMR (300 MHz, DMSO-d₆) δ [ppm] 8.22 (1H, dd, J=6.7, J=2.3 Hz), 8.01 (1H, m), 7.58-7.64 (2H, m), 7.48 (1H, dd, J=9.0, J=2.7 Hz), 7.02 (1H, d, J=9.0 Hz), 4.82 (2H, s), 1.43 (9H, s). MS (ESI⁺): 403.2 (M+NH₄⁺). HPLC (Condition A): Rt 5.47 min (HPLC purity 99.4%).

Intermediate 22 tert-butyl{4-chloro-2-[(2-methylpyridin-3-yl)ethynyl]phenoxy}acetate

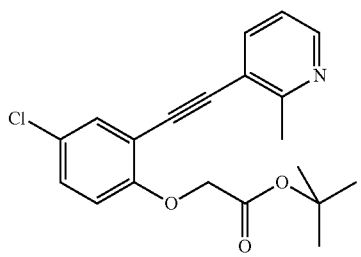

Following the general method as outlined in Intermediate 19, starting from tert-butyl(4-chloro-2-ethynylphenoxy)acetate (Intermediate 3) and 3-bromo-2-methylpyridine (Synchem-OHG), the title compound was obtained as a yellow sticky solid after purification by preparative HPLC.

MS (ESI⁺): 358.2. HPLC (Condition C): Rt 2.24 min (HPLC purity 100%).

Intermediate 23 tert-butyl(4-chloro-2-{[2-fluoro-5-(hydroxymethyl)phenyl]ethynyl}phenoxy)acetate

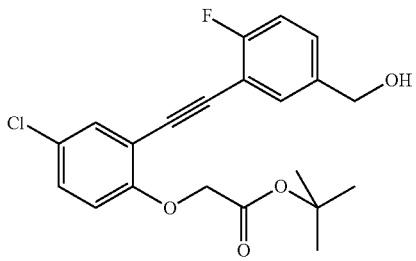

Following the general method as outlined in Intermediate 19, starting from tert-butyl(4-chloro-2-ethynylphenoxy)acetate (Intermediate 3) and 3-bromo-4-fluorobenzyl alcohol (Oakwood), the title compound was obtained as a dark brown sticky solid after purification by flash column chromatography (silica), eluting with cyclohexane containing increasing amounts of EtOAc.

MS (ESI⁺): 408.3 (M+NH₄⁺). HPLC (Condition A): Rt 7.81 min (HPLC purity 97.2%).

Intermediate 24 tert-butyl(4-chloro-2-{[2-fluoro-4-(hydroxymethyl)phenyl]ethynyl}phenoxy)acetate

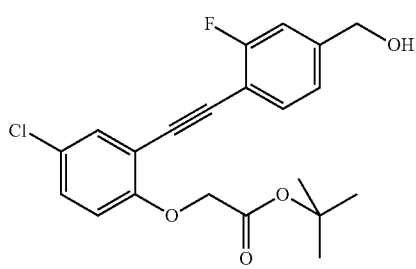

Following the general method as outlined in Intermediate 19, starting from tert-butyl(4-chloro-2-ethynylphenoxy)acetate (Intermediate 3) and (4-bromo-3-fluorophenyl)methanol (Intermediate 9), the title compound was obtained as a dark brown sticky solid after purification by flash column chromatography (silica), eluting with cyclohexane containing increasing amounts of EtOAc.

MS (ESI⁺): 408.3 (M+NH₄⁺). HPLC (Condition C): Rt 2.16 min (HPLC purity 100%).

Intermediate 25 tert-butyl(4-chloro-2-{[2-fluoro-3-(hydroxymethyl)phenyl]ethynyl}phenoxy)acetate

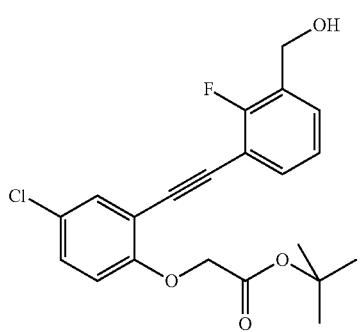

Following the general method as outlined in Intermediate 19, starting from tert-butyl(4-chloro-2-ethynylphenoxy)acetate (Intermediate 3) and (3-bromo-2-fluorophenyl)methanol (Intermediate 11), the title compound was obtained as a dark brown sticky solid after purification by flash column chromatography (silica), eluting with cyclohexane containing increasing amounts of EtOAc.

MS (ESI⁺): 408.3. HPLC (Condition C): Rt 1.62 min (HPLC purity 100%).

Intermediate 26 tert-butyl(4-chloro-2-{[2-fluoro-5-(methoxymethyl)phenyl]ethynyl}phenoxy)acetate

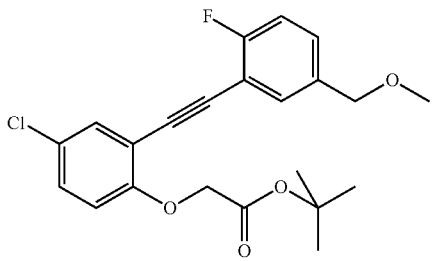

Following the general method as outlined in Intermediate 19, starting from tert-butyl(4-chloro-2-ethynylphenoxy)acetate (Intermediate 3) and 2-bromo-1-fluoro-4-(methoxymethyl)benzene (Intermediate 15), the title compound was obtained as a dark yellow sticky solid after purification by flash column chromatography (silica), eluting with cyclohexane containing increasing amounts of EtOAc.

MS (ESI+): 422.3.

Intermediate 27 tert-butyl{4-chloro-2-[(4-methyl-1-oxidopyridin-3-yl)ethynyl]phenoxy}acetate

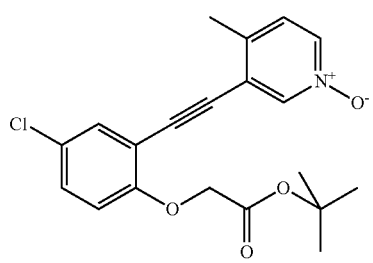

A solution of tert-butyl{4-chloro-2-[(4-methylpyridin-3-yl)ethynyl]phenoxy}acetate (Intermediate 19; 110 mg; 0.31 mmol) in DCM (5 mL) was treated with 3-chloroperbenzoic acid (91 mg; 0.37 mmol) and stirred at RT for 2 hours. The solvents were removed under vacuum, the residue was taken up in EtOAc and the organic phase washed with a saturated bicarbonate solution twice, then with brine. The organic layer was then dried over MgSO$_4$ and concentrated under vacuum to afford the title compound (110 mg, 96%) as a white solid.

$^1$H NMR (300 MHz, DMSO-d$_6$) δ [ppm] 8.26 (1H, d, J=1.9 Hz), 8.01 (1H, dd, J=6.6, 1.9 Hz), 7.41 (1H, d, J=2.6 Hz), 7.22 (1H, dd, J=8.9, 2.6 Hz), 7.06 (1H, d, J=6.6 Hz), 6.66 (1H, d, J=8.9 Hz), 4.53 (2H, s), 2.44 (3H, s), 1.41 (9H, s). MS (ESI+): 374.2. HPLC (Condition A): Rt 4.27 min (HPLC purity 92.2%).

Intermediate 28 tert-butyl(4-cyano-2-{[3-(propylsulfonyl)phenyl]ethynyl}phenoxy)acetate

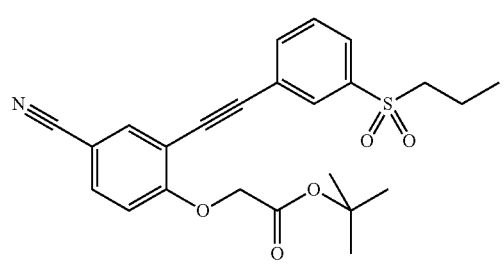

Following the general method as outlined in Intermediate 20, starting from (4-chloro-2-ethynyl-phenoxy)-acetic acid tert-butyl ester (Intermediate 8) and 1-bromo-3-(propane-1-sulfonyl)-benzene (Intermediate 5), the title compound was obtained as a colourless oil after purification by flash column chromatography (silica), eluting with cyclohexane containing increasing amounts of EtOAc.

$^1$H NMR (300 MHz, DMSO-d$_6$) δ [ppm] 8.11 (1H, d, J=2.1 Hz), 8.04 (1H, s), 7.98-7.85 (3H, m), 7.75 (1H, t, J=7.8 Hz), 7.19 (1H, d, J=8.8 Hz), 4.96 (2H, s), 3.38 (2H, m), 1.63-1.49 (2H, m), 1.44 (9H, s), 0.93 (3H, t, J=7.4 Hz). MS (ESI+): 457.3. HPLC (Condition A): Rt 4.95 min (HPLC purity 88.4%).

Intermediate 29 tert-butyl(4-chloro-2-{[2-methyl-5-(methylsulfonyl)phenyl]ethynyl}phenoxy)acetate

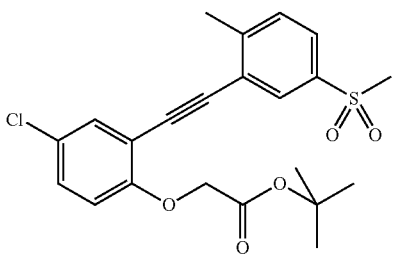

Following the general method as outlined in Intermediate 20, starting from (4-chloro-2-ethynyl-phenoxy)-acetic acid tert-butyl ester (Intermediate 3) and 2-iodo-1-methyl-4-(methylsulfonyl)benzene (Intermediate 17), the title compound was obtained as a colorless oil after purification by flash column chromatography (silica), eluting with cyclohexane containing increasing amounts of EtOAc.

$^1$H NMR (300 MHz, DMSO-d$_6$) δ [ppm] 8.01 (1H, d, J=2.0 Hz), 7.85 (1H, dd, J=8.0, 2.0 Hz), 7.65 (1H, d, J=2.7 Hz), 7.63 (1H, d, J=8.0 Hz), 7.46 (1H, dd, J=9.0, 2.7 Hz), 7.04 (1H, d, J=9.0 Hz), 4.83 (2H, s), 3.25 (3H, s), 2.58 (3H, s), 1.43 (9H, s). MS (ESI+): 452.3. HPLC (Condition A): Rt 5.23 min (HPLC purity 94.8%).

Intermediate 30 tert-butyl(4-chloro-2-{[2-fluoro-4-(methoxymethyl)phenyl]ethynyl}phenoxy)acetate

Step-1

1-bromo-2-fluoro-4-(methoxymethyl)benzene

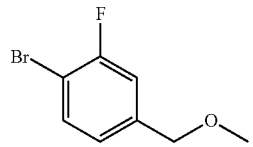

A solution of 4-bromo-3-fluorobenzyl methanesulfonate (Intermediate 18, 286 mg; 1.01 mmol) and 2,6-lutidine (234 µL; 2.0 mmol) in methanol (4 mL) was stirred for 16 hours at RT. Additional aliquots of 2,6-lutidine (234 µL; 2.0 mmol each) were added once a day for a total of three days, during which stirring was continued at RT. The mixture was taken up in Et$_2$O, washed with water, HCl (0.1N in water) and brine. The organic phase was dried over MgSO$_4$, filtered and concentrated with moderate vacuum and without heating affording the title compound in a mixture with ethyl ether.

HPLC (Condition C): Rt 1.34 min.

Step 2 tert-butyl(4-chloro-2-{[2-fluoro-4-(methoxymethyl)phenyl]ethynyl}phenoxy)acetate

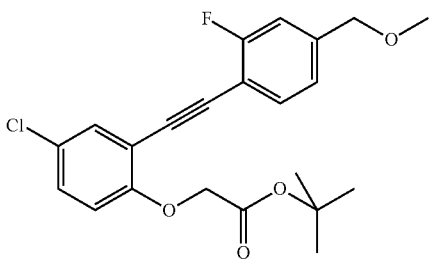

Following the general method as outlined in Intermediate 20, starting from (4-chloro-2-ethynyl-phenoxy)-acetic acid tert-butyl ester (Intermediate 3) and 1-bromo-2-fluoro-4-(methoxymethyl)benzene (obtained in Step 1), the title compound was obtained as a dark orange sticky solid after purification by flash column chromatography (silica), eluting with cyclohexane containing increasing amounts of EtOAc.

$^1$H NMR (300 MHz, DMSO-d$_6$) δ [ppm] 7.62 (1H, d, J=7.7 Hz), 7.59 (1H, d, J=2.6 Hz), 7.45 (1H, dd, J=9.0, J=2.6 Hz), 7.28 (1H, dd, J=10.3, J=1.4 Hz), 7.24 (1H, dd, J=8.0, J=1.4 Hz), 7.01 (1H, d, J=9.0 Hz), 4.82 (2H, s), 4.49 (2H, s), 3.34 (3H, s), 1.44 (9H, s). MS (ESI$^+$): 422.3 (M+NH$_4^+$). HPLC (Condition A): Rt 5.62 min.

Intermediate 31

5-bromo-N-(2-hydroxyethyl)pyridine-3-sulfonamide

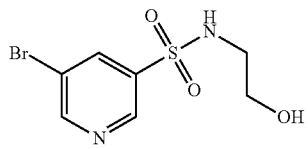

A cooled (0° C.) solution of 5-bromopyridine-3-sulfonyl chloride hydrochloride (3.00 g, 10.2 mmol) in DCM (50 ml) was slowly treated with triethylamine (4.3 ml) and stirred until a clear solution was obtained. This solution was treated dropwise with 2-hydroxyethylamine (0.68 g, 0.68 mL) and stirred at RT for 16 hours. The reaction mixture was washed successively with water and brine, the organic layer was dried with sodium sulfate and evaporated under reduced pressure. The crude product was purified by column chromatography (silica) eluting with 20% ethyl acetate in petroleum ether, to give the title compound.

$^1$H NMR (400 MHz, DMSO-d$_6$) δ [ppm] 8.97 (d, J=2.1 Hz, 1H), 8.91 (d, J=1.9 Hz, 1H), 8.37 (t, J=2.1 Hz, 1H), 7.99 (bs, 1H), 4.73 (t, J=5.4 Hz, 1H), 3.39-3.32 (m, 2H), 2.90-2.86 (m, 2H). HPLC (Condition A), Rt: 2.07 (purity: 93.7%). MS (ESI$^+$): 280.8.

The compounds in the table below were all prepared following the general method as outlined in Intermediate 31:

| Intermediate | Structure | Chemical name | $^1$H NMR 300 MHz, DMSO-d$_6$ δ [ppm] |
|---|---|---|---|
| 32 | 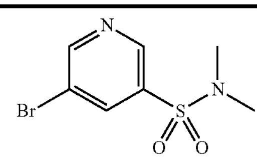 | 5-bromo-pyridine-3-sulfonic acid dimethylamide | 9.05 (d, J = 2.0 Hz, 1H), 8.90 (d, J = 2.0 Hz, 1H), 8.39 (t, J = 2.0 Hz, 1H), 2.69 (s, 6H) |
| 33 | 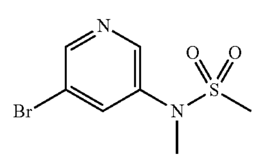 | N-(5-bromopyridin-3-yl)-N-methylmethanesulfonamide | 8.62-8.60 (m, 2H), 8.16 (t, J = 2.1 Hz, 1H), 3.28 (s, 3H), 3.05 (s, 3H) |

-continued

| Inter-mediate | Structure | Chemical name | 1H NMR 300 MHz, DMSO-d6) δ [ppm] |
|---|---|---|---|
| 34 | 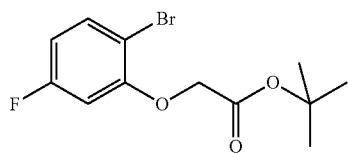 | 3-bromo-5-[(3,3-difluoroazetidin-1-yl)sulfonyl]pyridine | MS (ESI+): 313.8 |

Intermediate 35 tert-butyl(2-bromo-5-fluorophenoxy)acetate

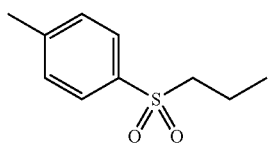

Following the general method as outlined in Intermediate 1, starting from 2-bromo-5-fluorophenol and tert-butyl bromoacetate (Aldrich), the title compound was obtained as a white solid in 95% yield.

$^1$H NMR (300 MHz, DMSO-d$_6$) δ [ppm] 7.62 (dd, J=6.3, J=8.8 Hz, 1H), 6.98 (dd, J=2.7, J=11.0 Hz, 1H), 6.80 (ddd, J=2.7; J=8.3, J=8.8 Hz, 1H), 4.83 (s, 2H), 1.42 (s, 9H). HPLC (Condition A) Purity 94.4%; Rt 4.7 min.

Intermediate 36

1-methyl-4-(propylsulfonyl)benzene

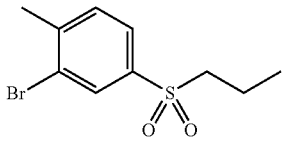

A cooled (0° C.) solution of 4-methylthiophenol (Aldrich; 20.0 g; 161 mmol) in MeOH (400 ml) was treated with a 5 N solution of NaOH in water (40 mL) and with 1-iodopropane (18.0 ml; 185 mmol). The reaction was stirred at 0° C. for 1 h then concentrated under reduced pressure. The concentrated solution was diluted with EtOAc then washed with brine. The organic phase was dried on MgSO$_4$, filtered and concentrated under reduced pressure to give a residue, which was dissolved in DCM (200 ml) and cooled to at 0° C. This solution was treated over 20 min with a suspension of 3-chloroperbenzoic acid (83.12 g; 337.2 mmol) in DCM (600 ml). The reaction suspension was stirred at 0° C. for 3 h then treated with a further portion of 3-chloroperbenzoic acid (18.86 g; 76.52 mmol) in DCM (150 ml). The reaction was warmed to RT and stirred for 16 h. The reaction solution was filtered and the filtrate reduced in volume under reduced pressure and diluted with EtOAc, then washed twice with a 1 N solution of NaOH in water and then brine. The organic phase was dried on MgSO$_4$, filtered and concentrated under reduced pressure to give the title compound (24.80 g, 78%) as an oil which solidified upon standing.

$^1$H NMR (300 MHz, DMSO-d$_6$) δ [ppm] 7.76 (d, J=8.1 Hz, 2H), 7.45 (d, J=8.1 Hz, 2H), 3.31-3.15 (m, 2H), 2.41 (s, 3H), 1.63-1.42 (m, 2H), 0.89 (t, J=7.4 Hz, 3H). HPLC (Condition A) Purity 95.4%; Rt 1.4 min.

Intermediate 37

2-bromo-1-methyl-4-(propylsulfonyl)benzene

A finely ground mixture of 1-methyl-4-(propylsulfonyl) benzene (Intermediate 36; 24.80 g; 0.13 mol) and N-bromosuccinimide (26.8 g; 0.15 mol) was treated with conc. sulfuric acid (115 ml; 2.15 mol). The reaction mixture was stirred for 16 h then treated with a further portion of N-bromosuccinimide (1.33 g; 0.01 mol). The reaction solution was stirred 1 h then carefully poured into 800 mL of crushed ice. The aqueous solution was extracted with 400 mL of AcOEt. The layers were separated and the organic phase was washed first with ca. 300 mL of brine, then twice with a 1N solution of NaOH in water and twice with brine. The organic phase was dried on MgSO$_4$, filtered and concentrated under reduced pressure to give the title compound (29.3 g, 85%) as a brown oil which solidified upon standing.

$^1$H NMR (300 MHz, DMSO-d$_6$) δ [ppm] 8.03 (d, J=1.9 Hz, 1H), 7.80 (dd, J=8.0, 1.9 Hz, 1H), 7.64 (d, J=8.0 Hz, 1H), 3.39-3.28 (m, 2H), 2.45 (s, 3H), 1.63-1.47 (m, 2H), 0.92 (t, J=7.4 Hz, 3H). HPLC (Condition A) Rt 3.8 min.

Intermediate 38 tert-butyl(4-chloro-2-{[2-methyl-5-(propylsulfonyl) phenyl]ethynyl}phenoxy)acetate

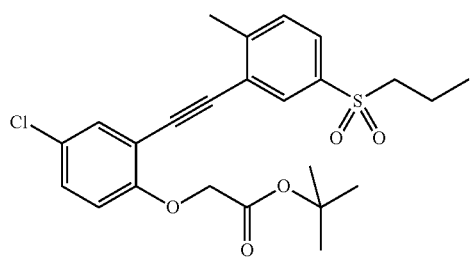

A mixture of 2-bromo-1-methyl-4-(propylsulfonyl)benzene (Intermediate 37; 14.86 g, 53.6 mmol), tert-butyl(4-chloro-2-ethynylphenoxy)acetate (Intermediate 3, 13.00 g;

48.7 mmol), dichlorobis(triphenylphosphine)palladium(II) (1.37 g; 1.95 mmol) and piperidine (14.5 mL) was heated at 70° C. for 18 hours. The reaction mixture was taken up in EtOAc, washed twice with ammonium chloride and once with brine. The organic phase was dried over MgSO$_4$, filtered and concentrated to dryness affording a crude, which was purified by flash column chromatography (silica), eluting with cyclohexane containing increasing amounts of EtOAc. The compound thus obtained as a brown sticky solid was recrystallized twice from EtOAc/petroleum ether to afford the title compound as a beige solid.

$^1$H NMR (300 MHz, DMSO-d$_6$) δ [ppm] 7.95 (1H, d, J=1.9 Hz), 7.80 (1H, dd, J=8.0 Hz, J=1.9 Hz), 7.65 (1H, d, J=2.7 Hz), 7.62 (1H, d, J=8.0 Hz), 7.45 (1H, dd, J=9.0 Hz, J=2.7 Hz), 7.04 (1H, d, J=9.0 Hz), 4.82 (2H, s), 3.31 (2H, m), 2.58 (3H, s), 1.55 (2H, sext., J=7.5 Hz), 1.43 (9H, s), 0.92 (3H, t, J=7.5 Hz). HPLC (Condition A) Purity 98.5%; Rt 5.8 min.

Intermediate 39

2-Trimethylsilylethynyl-1-methyl-4-(propylsulfonyl) benzene

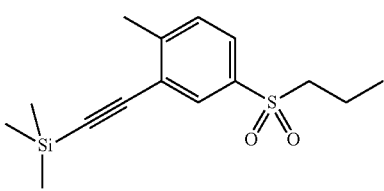

Following the general method as outlined in Intermediate 2, starting from 2-bromo-1-methyl-4-(propylsulfonyl)benzene (Intermediate 37) and trimethylsilylacetilene, the title compound was obtained as a brown liquid in 75% yield.

$^1$H NMR (300 MHz, DMSO-d$_6$) δ [ppm] 8.05 (s, 1H), 7.79 (d, 1H, J=8.0 Hz), 7.45 (d, 1H, J=8.0 Hz), 3.07 (t, 2H, J=8.0 Hz), 2.61 (s, 3H), 1.78-1.72 (m, 2H), 1.57 (s, 9H), 1.03-1.00 (t, 3H, J=7.4 Hz).

Intermediate 40

2-ethynyl-1-methyl-4-(propylsulfonyl) benzene

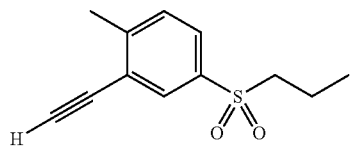

Following the general method as outlined in Intermediate 3, starting from 2-trimethylsilylethynyl-1-methyl-4-(propylsulfonyl)benzene (Intermediate 39), the title compound was obtained as a brown liquid after purification by column chromatography (silica) eluting with petroleum ether and ethyl acetate.

$^1$H NMR (300 MHz, DMSO-d$_6$) δ [ppm] 7.86 (s, 1H), 7.78 (d, 1H, J=8.1 Hz), 7.57 (d, 1H, J=8.1 Hz), 4.63 (s, 1H), 3.29 (t, 2H, J=8 Hz), 2.48 (s, 3H), 1.56-1.54 (m, 2H), 1.51 (t, 3H, J=7.6 Hz). MS (ESI$^+$): 223. HPLC (Condition A) Purity 99.7%; Rt 4.23 min.

Intermediate 41

1-(2-Trimethylsilyl-1-ethynyl)-3-(propylsulfonyl) benzene

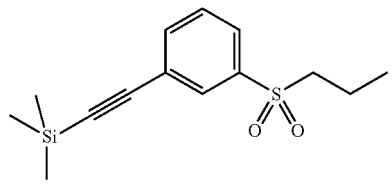

A solution of 1-bromo-3-(propylsulfonyl)benzene (Intermediate 5; 23 g, 88 mmol) in THF (450 ml) was treated with Pd(dppf)Cl$_2$ (3.9 g, 5.3 mmol), triethylamine (13.4 g, 132 mmol) and trimethylsilyl acetylene (8.64 g, 88 mmol). The reaction mixture was stirred at RT for 10 minutes, then cuprous iodide (1.0 g, 5.3 mmol) was added, the reaction mixture was heated at 60° C. for 24 h. The reaction mixture was filtered to remove the solid and the filtrate was concentrated under reduced pressure. The crude material was purified by column chromatography using petroleum ether and ethyl acetate (98:2) as a eluent to afford the title compound as a brown oil.

$^1$H NMR (300 MHz, DMSO-d$_6$) δ [ppm] 7.88 (2H, m), 7.79 (1H, t), 7.66 (1H, q), 3.34 (2H, m), 1.53 (2H, m), 0.92 (3H, t), 0.22 (9H, s).

Intermediate 42

1-Ethynyl-3-(propylsulfonyl)benzene

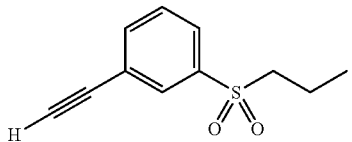

Following the general method as outlined in Intermediate 3, starting from 1-(2-trimethylsilyl-1-ethynyl)-3-(propylsulfonyl)benzene (Intermediate 41), the title compound was obtained as a brown liquid in 70% yield after purification by column chromatography (silica) eluting with petroleum ether and ethyl acetate.

$^1$H NMR (300 MHz, DMSO-d$_6$) δ [ppm] 7.89 (1H, t), 7.84 (1H, p), 7.67 (1H, t), 4.45 (1H, s), 3.33 (2H, p), 1.53 (2H, m), 0.90 (3H, t). MS (ESI$^+$): 208.8. HPLC (Condition A) Purity 98.6%; Rt 3.89 min.

Intermediate 43

3-Bromo-4-hydroxybenzonitrile

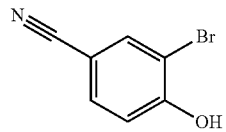

A solution of 4-cyanophenol (30.0 g, 252 mmol) in acetic acid (450 ml) was treated with N-bromosuccinimide (44.8 g, 252 mmol). The reaction mixture was stirred at RT for 18 h, filtered and the filtrate was concentrated under reduced pressure. The crude material was purified by column chromatography (silica) eluting with chloroform and methanol (99:1) to afford the title compound as a brown solid.

$^1$H NMR (300 MHz, DMSO-$d_6$) δ [ppm] 11.54 (1H, s), 8.04 (1H, d, J=2.0), 7.66 (1H, dd, J=2.0, J=8.5), 7.06 (1H, d, J=8.5).

Intermediate 44 tert-Butyl (2-bromo-4-cyanophenoxy)acetate

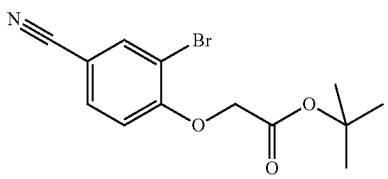

A solution of 3-bromo-4-hydroxybenzonitrile (Intermediate 43; 25.0 g, 126 mmol) in anhydrous acetone (400 ml) was treated with Potassium carbonate (20.8 g, 151 mmol) and dropwise with tert-butyl bromoacetate (24.5 g, 126 mmol). The reaction mixture was heated at 60° C. for 10 h. The reaction mixture was filtered and the filtrate was concentrated under reduced pressure. The crude material was purified by column chromatography (silica) eluting with petroleum ether and ethyl acetate (90:10) to afford the title compound as a brown solid.

$^1$H NMR (300 MHz, DMSO-$d_6$) δ [ppm] 8.16 (1H, d, J=2.1), 7.82 (1H, dd, J=2.1, J=8.6), 7.16 (1H, d, J=8.6), 4.93 (2H, s), 1.40 (9H, s).

Intermediate 45 tert-butyl{4-cyano-2-[(trimethylsilyl)ethynyl] phenoxy}acetate

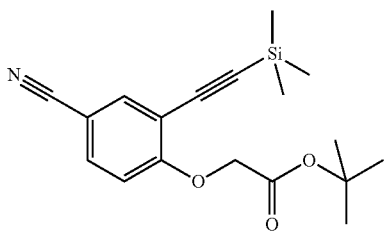

Following the general method as outlined in Intermediate 2, starting from tert-butyl(2-bromo-4-cyanophenoxy)acetate (Intermediate 44) and (trimethylsilyl)acetylene (Aldrich), the title compound was obtained as a dark brown sticky solid in 87% yield.

$^1$H NMR (300 MHz, DMSO-$d_6$) δ [ppm] 7.89 (1H, d, J=2.1 Hz), 7.81 (1H, dd, J=2.1 Hz, J=8.8 Hz), 7.09 (1H, d, J=8.8 Hz), 4.88 (2H, s), 1.42 (9H, s), 0.22 (9H, s).

Intermediate 46 tert-butyl(4-cyano-2-ethynyl phenoxy)acetate

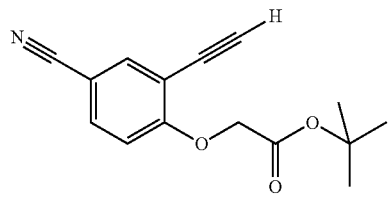

Following the general method as outlined in Intermediate 3, starting from tert-butyl{4-cyano-2-[(trimethylsilyl)ethynyl]phenoxy}acetate (Intermediate 45), the title compound was obtained as an oil in 72% yield.

$^1$H NMR (300 MHz, DMSO-$d_6$) δ [ppm] 7.93 (1H, d, J=2.1 Hz), 7.82 (1H, dd, J=2.1 Hz, J=8.8 Hz), 7.11 (1H, d, J=8.8 Hz), 4.89 (2H, s), 4.46 (1H, s), 1.41 (9H, s). MS (ESI$^+$): 199.7. HPLC (Condition A) Purity 98.0%; Rt 4.82 min.

Intermediate 47 tert-butyl[2-bromo-4-(trifluoromethyl)phenoxy]acetate

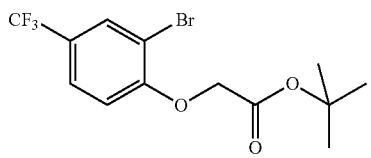

Following the general method as outlined in Intermediate 1, starting from 2-bromo-4-(trifluoromethyl)phenol and tert-butyl bromoacetate (Aldrich), the title compound was obtained as a dark orange sticky solid in quantitative yield.

$^1$H NMR (300 MHz, DMSO-$d_6$) δ [ppm] 7.99 (dd, J=0.6, J=2.2 Hz, 1H), 7.74 (ddd, J=0.6, J=2.2, J=8.6 Hz, 1H), 7.19 (d, J=8.6 Hz, 1H), 4.94 (s, 2H), 1.44 (s, 9H). HPLC (Condition A) Purity 92.3%; Rt 5.2 min.

Intermediate 48

3-bromo-4-[prop-1-en-1-yl]pyridine

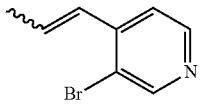

Following the general method as outlined in Intermediate 12, starting from 3-bromo-4-pyridinecarboxaldehyde (Aldrich) and ethyltriphenylphosphonium bromide, the title compound (mixture of cis and trans isomers) was obtained as a colorless liquid after purification by flash column chromatography, eluting with cyclohexane containing increasing amounts of EtOAc.

MS (ESI$^-$): 198.0

Intermediate 49

3-bromo-4-propylpyridine

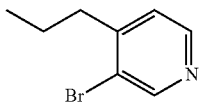

Following the general method as outlined in Intermediate 13, starting from 3-bromo-4-(prop-1-en-1-yl)pyridine (Intermediate 48), the title compound was obtained as a dark orange sticky solid in 79% yield after purification by flash column chromatography, eluting with cyclohexane containing increasing amounts of EtOAc.

$^1$H NMR (300 MHz, DMSO-d$_6$) δ [ppm] 8.68 (s, 1H), 8.46 (d, J=4.9 Hz, 1H), 7.40 (d, J=4.9 Hz, 1H), 2.69 (m, 2H), 1.62 (sext., J=7.5 Hz, 2H), 0.95 (t, J=7.5 Hz, 3H). HPLC (Condition A) Rt 1.8 min.

Intermediate 50 tert-butyl{4-chloro-2-[(4-propylpyridin-3-yl)ethynyl]phenoxy}acetate

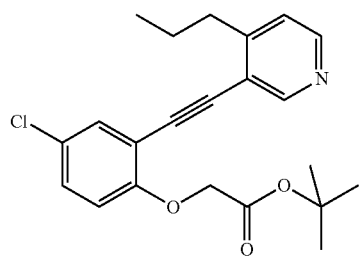

Following the general method as outlined in Intermediate 20, starting from (4-chloro-2-ethynyl-phenoxy)-acetic acid tert-butyl ester (Intermediate 3) and 3-bromo-4-propylpyridine (Intermediate 49), the title compound was obtained as a dark orange sticky solid after purification by flash column chromatography, eluting with cyclohexane containing increasing amounts of EtOAc.

MS (ESI$^+$): 386.3. HPLC (Condition A) Purity 94.1%; Rt 4.2 min.

Intermediate 51

3-bromo-4-(2-methylprop-1-en-1-yl)pyridine

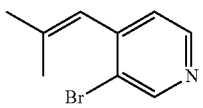

Following the general method as outlined in Intermediate 12, starting from 3-bromo-4-pyridinecarboxaldehyde (Aldrich) and isopropyltriphenylphosphonium iodide, the title compound was obtained as a yellow liquid after purification by flash column chromatography, eluting with cyclohexane containing increasing amounts of EtOAc.

$^1$H NMR (300 MHz, DMSO-d$_6$) δ [ppm] 8.73 (s, 1H), 8.50 (d, J=5.0 Hz, 1H), 7.36 (d, J=5.0 Hz, 1H), 6.21 (s, 1H), 1.96 (d, J=1.3 Hz, 3H), 1.80 (d, J=1.3 Hz, 3H). HPLC (Condition A) Purity 100.0%; Rt 1.9 min.

Intermediate 52

3-bromo-4-isobutylpyridine

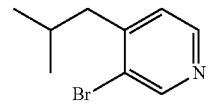

Following the general method as outlined in Intermediate 13, starting from 3-bromo-4-(2-methylprop-1-en-1-yl)pyridine (Intermediate 51), the title compound was obtained as a colorless liquid after purification by flash column chromatography, eluting with cyclohexane containing increasing amounts of EtOAc.

$^1$H NMR (300 MHz, DMSO-d$_6$) δ [ppm] 8.69 (s, 1H), 8.46 (d, J=4.9 Hz, 1H), 7.37 (d, J=4.9 Hz, 1H), 2.61 (d, J=7.3 Hz, 1H), 1.96 (m, 1H), 0.91 (d, J=6.6 Hz, 6H). HPLC (Condition A) Rt 2.3 min.

Intermediate 53 tert-butyl{4-chloro-2-[(4-isobutylpyridin-3-yl)ethynyl]phenoxy}acetate

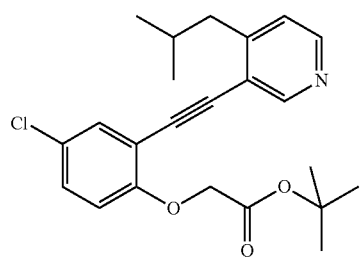

Following the general method as outlined in Intermediate 20, starting from (4-chloro-2-ethynyl-phenoxy)-acetic acid tert-butyl ester (Intermediate 3) and 3-bromo-4-isobutylpyridine (Intermediate 52), the title compound was obtained as a dark orange sticky solid after purification by preparative HPLC.

MS (ESI$^+$): 400.4. HPLC (Condition A) Purity 94.7%; Rt 4.4 min.

Intermediate 54 tert-butyl{4-cyano-2-[(4-methylpyridin-3-yl)ethynyl]phenoxy}acetate

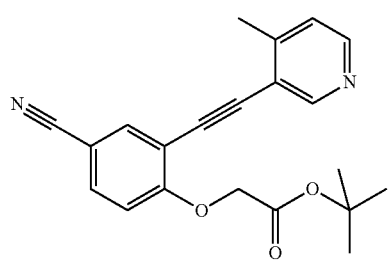

Following the general method as outlined in Intermediate 20, starting from tert-butyl(4-cyano-2-ethynylphenoxy)acetate (Intermediate 46) and 3-bromo-4-methylpyridine (53), the title compound was obtained as a dark orange sticky solid after purification by flash column chromatography, eluting with cyclohexane containing increasing amounts of EtOAc.

MS (ESI+): 349.3. HPLC (Condition A) Purity 88.7%; Rt 3.2 min.

Intermediate 55 tert-butyl(2-iodophenoxy)acetate

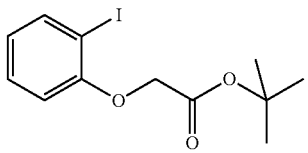

Following the general method as outlined in Intermediate 1, starting from 2-iodophenol and tert-butyl bromoacetate (Aldrich), the title compound was obtained as a yellow liquid in quantitative yield.

$^1$H NMR (300 MHz, DMSO-d$_6$) δ [ppm] 7.80 (dd, J=7.6, J=1.6 Hz, 1H), 7.35 (m, 1H), 6.88 (dd, 8.3, J=1.3 Hz, 1H), 6.79 (dd, J=7.6, J=1.3 Hz, 1H), 4.77 (s, 2H), 1.44 (s, 9H). HPLC (Condition A) Purity 97.8%; Rt 4.8 min.

Intermediate 56 tert-butyl{2-[(2-chlorophenyl)ethynyl]phenoxy}acetate

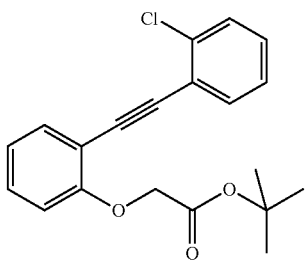

Following the general method as outlined in Intermediate 20, starting tert-butyl(2-iodophenoxy)acetate (Intermediate 55) and 2'-chlorophenyl acetylene (ABCR), the title compound was obtained as a dark orange sticky solid after purification by flash column chromatography, eluting with cyclohexane containing increasing amounts of EtOAc. HPLC (Condition A) Rt 5.5 min.

Intermediate 57

2-fluoro-5-(methylsulfonyl)aniline

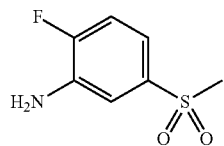

A mixture of 4-fluoro-3-nitrophenyl methyl sulfone (ABCR; 1.50 g; 6.84 mmol) and 10% Pd/C (100 mg) in MeOH (30 ml) was placed in a PARR reactor and treated with a pressure of 15 atm of hydrogen for 2 hours. The reaction mixture was filtered through Celite and the filtrate was concentrated to dryness affording the title compound (1.04 g, 80%).

$^1$H NMR (300 MHz, DMSO-d$_6$) δ [ppm] 7.31 (dd, J=2.4, J=8.4 Hz, 1H), 7.26 (dd, J=8.4, J=11.4 Hz, 1H), 7.05 (ddd, J=2.4, J=4.2, J=8.4 Hz, 1H), 5.75 (s, 2H), 3.14 (s, 3H).

Intermediate 58

1-fluoro-2-iodo-4-(methylsulfonyl)benzene

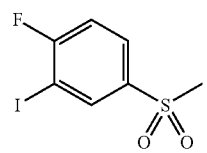

2-Fluoro-5-(methylsulfonyl)aniline (Intermediate 57; 500 mg; 2.64 mmol) was treated with a 5 N solution of hydrochloric acid in water (8.98 ml; 44.92 mmol) and the solution cooled to 0° C. The solution was treated with sodium nitrite (219 mg; 3.17 mmol) and stirred at 0° C. for 30 minutes, then treated with a solution of potassium iodide (4.39 g; 26.43 mmol) in water (8 mL) and stirred at RT for 1 hour. EtOAc was added, the phases were separated and the organic phase was washed with a saturated sodium thiosulfate solution twice, then with brine. The organic phase was dried on MgSO$_4$, filtered and concentrated under reduced pressure to give a residue which was purified by by flash column chromatography, eluting with cyclohexane containing increasing amounts of EtOAc. The title compound was obtained as a white solid.

$^1$H NMR (300 MHz, DMSO-d$_6$) δ [ppm] 8.37 (dd, J=5.8, J=2.3 Hz, 1H), 8.00 (ddd, J=2.3, J=4.8, J=8.6 Hz, 1H), 7.56 (dd, J=0.4, J=8.1 Hz, 1H), 3.30 (s, 3H).

Intermediate 59

4-(methylsulfonyl)-2-nitro-1-[(1E)-prop-1-en-1-yl]benzene

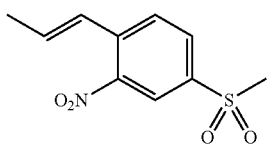

A mixture of 2-bromo-5-methylsulfonylnitrobenzene (1.50 g; 5.36 mmol), trans-propenylboronic acid (690 mg; 8.03 mmol), caesium fluoride (2.44 g; 16.1 mmol) and bis(triphenylphosphine)palladium(II) chloride (376 mg; 0.54 mmol) was degassed with nitrogen, then treated with dioxane (30 ml) and water (15 ml). The resulting reaction mixture was heated at 80° C. for 2 hours, taken up in EtOAc and washed with water and brine. The organic phase was dried on MgSO$_4$, filtered and concentrated under reduced pressure to give a residue which was purified by by flash column chromatography, eluting with cyclohexane containing increasing amounts of EtOAc. The title compound was obtained as an off-white solid (1.10 g, 85%).

$^1$H NMR (300 MHz, DMSO-d$_6$) δ [ppm] 8.40 (1H, d, J=1.9 Hz), 8.14 (1H, dd, J=8.3 Hz, J=1.9 Hz), 8.05 (1H, d, J=8.3 Hz), 6.68-6.59 (2H, m), 3.32 (3H, s), 1.95 (1H, dd, J=6.1 Hz, J=0.9 Hz).

Intermediate 60

5-(methylsulfonyl)-2-[(1E)-prop-1-en-1-yl]aniline

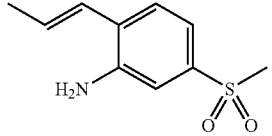

A solution of 4-(methylsulfonyl)-2-nitro-1-[(1E)-prop-1-en-1-yl]benzene (Intermediate 59; 1.10 g; 4.56 mmol) in AcOH (7 ml) was treated with powdered iron (3.82 g; 68.4 mmol) and the reaction mixture was stirred at 90° C. for 25 min. Further AcOH was added (20 mL), the solid was filtered off and rinsed with EtOAc. The solvents were removed under reduced pressure, the residue was taken up in EtOAc and washed with saturated NaHCO$_3$ solution twice the with brine. The organic phase was dried on MgSO$_4$, filtered and concentrated under reduced pressure to give the title compound as a brown oil (784 mg, 81%).

$^1$H NMR (300 MHz, DMSO-d$_6$) δ [ppm] 7.40 (1H, d, J=8.0 Hz), 7.13 (1H, d, J=2.0 Hz), 6.96 (1H, dd, J=8.0 Hz, J=2.0 Hz), 6.58 (1H, dd, J=5.5 Hz, J=1.6 Hz), 6.20 (1H, m), 5.60 (2H, s), 3.09 (3H, s), 1.88 (1H, dd, J=6.6 Hz, J=1.5 Hz).

Intermediate 61

5-(methylsulfonyl)-2-propylaniline

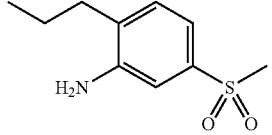

A mixture of 5-(methylsulfonyl)-2-[(1E)-prop-1-en-1-yl]aniline (Intermediate 60; 1.50 g; 6.84 mmol) and 10% Pd/C (196 mg) in MeOH (39 ml) was placed in a PARR reactor and treated with a pressure of 20 atm of hydrogen for 3 hours.

The reaction mixture was filtered through Celite and the filtrate was concentrated to dryness affording the title compound (600 g, 76%).

$^1$H NMR (300 MHz, DMSO-d$_6$) δ [ppm] 7.14-7.11 (2H, m), 6.96 (1H, dd, J=8.0 Hz, J=2.0 Hz), 5.42 (2H, s), 3.08 (3H, s), 2.50-2.40 (2H, m), 1.60-1.48 (2H, m), 0.93 (1H, t, J=7.3 Hz).

Intermediate 62

2-iodo-4-(methylsulfonyl)-1-propylbenzene

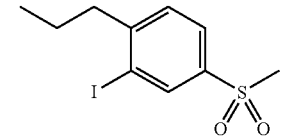

Following the general method as outlined in Intermediate 58, starting from 5-(methylsulfonyl)-2-propylaniline (Intermediate 61), the title compound was obtained as a yellow liquid after purification by flash column chromatography (silica), eluting with cyclohexane containing increasing amounts of EtOAc $^1$H NMR (300 MHz, DMSO-d$_6$) δ [ppm] 8.27 (1H, d, J=2.0 Hz), 7.87 (1H, dd, J=8.0 Hz, J=2.0 Hz), 7.55 (1H, d, J=8.0 Hz), 3.25 (3H, s), 2.74 (2H, m), 1.58 (2H, m), 0.96 (1H, t, J=7.3 Hz).

Intermediate 63 tert-butyl(4-chloro-2-{[5-(methylsulfonyl)-2-propylphenyl]ethynyl}phenoxy)acetate

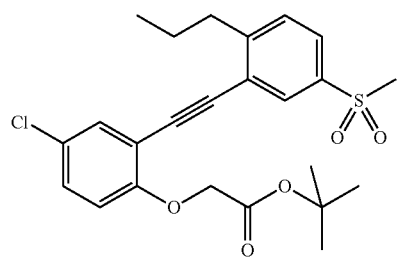

Following the general method as outlined in Intermediate 20, starting from (4-chloro-2-ethynyl-phenoxy)-acetic acid tert-butyl ester (Intermediate 3) and 2-iodo-4-(methylsulfonyl)-1-propylbenzene (Intermediate 62), the title compound was obtained as a white solid after purification by flash column chromatography (silica), eluting with cyclohexane containing increasing amounts of EtOAc $^1$H NMR (300 MHz, DMSO-d$_6$) δ [ppm] 8.01 (1H, d, J=1.5 Hz), 7.86 (1H, dd, J=8.0 Hz, J=1.5 Hz), 7.62-7.59 (2H, m), 7.45 (1H, dd, J=8.8 Hz, J=2.0 Hz), 7.05 (1H, d, J=8.8 Hz), 4.83 (2H, s), 3.26 (3H, s), 2.91 (2H, t, J=7.5 Hz), 1.68 (2H, sextet, J=7.5 Hz), 1.42 (9H, s), 0.94 (3H, t, J=7.5 Hz).

Intermediate 64

2-bromo-4-(isopropylsulfonyl)-1-methylbenzene

Step 1

3-bromo-4-methylbenzenethiol

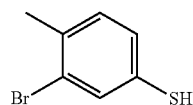

A cooled (−15° C.) solution of 3-bromo-4-methylaniline (ABCR; 2.0 g) in a 6N solution of HCl in water (30 mL) was treated drop-wise with a solution of sodium nitrite (1.78 g) in water (10 mL). The reaction mixture was stirred for 30 mins. The resulting clear solution was added dropwise to a stirred solution of O-ethyl xanthic acid potassium salt (6.1 g) in water (25 mL). The mixture was then heated to 80° C. for 15 minutes. The mixture was then cooled and extracted with diethyl ether twice. The solvents were evaporated under reduced pressure to give a residue, which was treated with a solution of KOH (6.1 g) in 95% ethanol (55 mL) and heated to reflux for 10 h. The reaction mixture was diluted with water and acidified with conc. HCl to pH 3 and extracted with diethyl ether. The organic layer was washed with water, brine and concentrated under reduced pressure. The crude product was purified by column chromatography (silica gel), eluting with petroleum ether. This product obtained was triturated with hexane to give the title compound (1.5 g, 70%) as an off-white solid.

Step 2

2-bromo-4-(isopropylthio)-1-methylbenzene

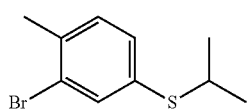

A stirred suspension of NaH (40 mg) in anhydrous DMF (5 mL) was treated with a solution of 3-bromo-4-methylbenzenethiol (200 mg) in anhydrous DMF (3 ml). The reaction mixture was stirred for 30 minutes at RT, then 2-iodo propane (0.14 ml) was added to the reaction mixture and the reaction mixture was heated to 55° C. for 3 hours. The reaction mixture was quenched with ice and extracted with diethylether. The organic layer was dried over sodium sulfate and concentrated under reduced pressure. The crude product was purified by flash chromatography (Silica gel), eluting with hexane, to give the title compounds.

Step 3

2-bromo-4-(isopropylsulfonyl)-1-methylbenzene

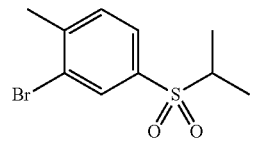

A cooled (0° C.) solution of 2-bromo-4-(isopropylthio)-1-methylbenzene (123 mg) in THF (10 ml) was treated with a solution of oxone (580 mg) in water (6 ml). The reaction mixture was stirred at RT for 16 hours. The reaction mixture was diluted with ethyl acetate and washed with water. The organic layer was dried over sodium sulfate and concentrated to give the title compound (120 mg, 92%).

$^1$H NMR (300 MHz, DMSO-$d_6$) δ [ppm] 7.55 (dd, J=8.4 Hz, J=2.8 Hz, 1H), 7.18 (dd, J=8.4 Hz, J=5.8 Hz, 1H), 7.09-7.04 (m, 1H), 2.86-2.83 (m, 1H), 2.49 (s, 3H), 1.34 (d, J=7.0 Hz, 3H), 1.13 (d, J=6.8 Hz, 3H). MS (ESI$^+$): 294.3 [M+NH4]$^+$. HPLC (Condition A) Purity 93.0%; Rt 5.42 min.

The compounds in the table below were all prepared following the general method as outlined in Intermediate 64:

| Int. | Structure | Chemical name | $^1$H NMR 400 MHz δ [ppm] |
|---|---|---|---|
| 65 | 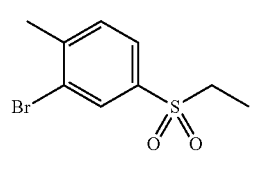 | 2-bromo-4-(ethylsulfonyl)-1-methylbenzene | 8.07 (d, J = 1.7 Hz, 1H), 7.74 (dd, J = 7.9 Hz, J = 1.9 Hz, 1H), 7.44 (d, J = 7.9 Hz, 1H), 3.76 (q, J = 7.4 Hz, 2H), 2.50 (s, 3H), 1.29 (t, J = 7.4 Hz, 3H). |
| 66 | 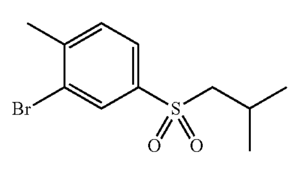 | 2-bromo-4-(isobutylsulfonyl)-1-methylbenzene | 8.07 (d, J = 1.7 Hz, 1H), 7.54 (dd, J = 7.9 Hz, J = 1.8 Hz, 1H), 7.42 (d, J = 7.9 Hz, 1H), 2.98 (d, J = 6.4 Hz, 2H), 2.49 (s, 3H), 2.28-2.21 (m, 1H), 1.08 (d, J = 6.7 Hz, 6H). |

| Int. | Structure | Chemical name | $^1$H NMR 400 MHz δ [ppm] |
|---|---|---|---|
| 67 | 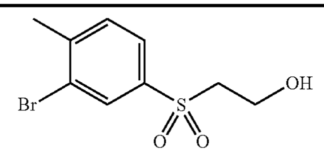 | 2-[(3-bromo-4-methylphenyl)sulfonyl]ethanol | 8.03 (d, J = 1.8 Hz, 1H), 7.79 (dd, J = 8.0 Hz, J = 1.8 Hz, 1H), 7.61 (d, J = 8 Hz, 1H), 4.88 (t, J = 5.4 Hz, 1H), 3.67 (m, 2H), 3.49 (t, J = 6.0 Hz, 2H), 2.43 (s, 3H). |
| 68 | 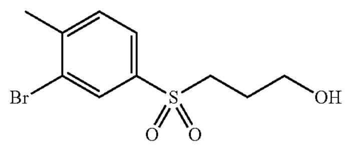 | 3-[(3-bromo-4-methylphenyl)sulfonyl]propan-1-ol | 8.08 (d, J = 1.7 Hz, 1H), 7.75 (dd, J = 7.9 Hz, J = 1.8 Hz, 1H), 7.44 (d, J = 7.9 Hz, 1H), 3.12 (q, J = 5.5 Hz, 2H), 3.27-3.22 (m, 2H), 2.50 (s, 3H), 2.03-1.96 (m, 2H), 1.60 (bs, 1H). |
| 69 | 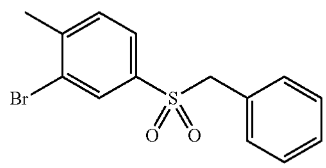 | 4-(benzylsulfonyl)-2-bromo-1-methylbenzene | 7.78 (d, J = 1.8 Hz, 1H), 7.43-7.40 (m, 2H), 7.36-7.28 (m, 3H), 7.13-7.10 (m, 2H), 4.31 (s, 2H), 2.46 (s, 3H). |
| 70 | 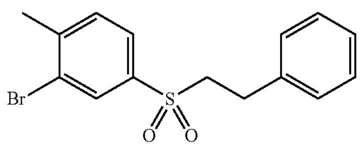 | 2-bromo-1-methyl-4-[(2-phenylethyl)sulfonyl]benzene | δ 8.08 (d, J = 1.8 Hz, 1H), 7.75 (dd, J = 7.9 Hz, J = 1.8 Hz, 1H), 7.43 (d, J = 8.0 Hz, 1H), 7.30-7.20 (m, 2H), 7.14-7.11 (m, 2H), 3.39-3.35 (m, 2H), 3.08-3.04 (m, 2H), 2.50 (s, 3H). |

Intermediate 71 tert-butyl[2-{[3-(propylsulfonyl)phenyl]ethynyl}-4-(trifluoromethyl)phenoxy]acetate

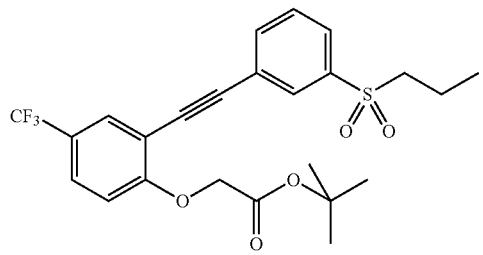

Following the general method as outlined in Intermediate 20, starting from tert-butyl[2-bromo-4-(trifluoromethyl)phenoxy]acetate (Intermediate 35) and 1-ethynyl-3-(propane-1-sulfonyl)-benzene (Intermediate 42), the title compound was obtained as a colorless oil after purification by flash column chromatography (silica), eluting with cyclohexane containing increasing amounts of EtOAc $^1$H NMR (300 MHz, DMSO-d$_6$) δ [ppm] 8.05 (1H, m), 7.97-7.90 (3H, m), 7.79-7.72 (2H, m), 7.18 (1H, d, J=8.8 Hz), 4.94 (2H, s), 3.40-3.34 (2H, m), 1.57 (2H, m), 1.45 (9H, s), 0.93 (3H, t, J=7.5 Hz).

Intermediate 72 tert-butyl(4-cyano-2-{[5-(methylsulfonyl)-2-propylphenyl]ethynyl}phenoxy)acetate

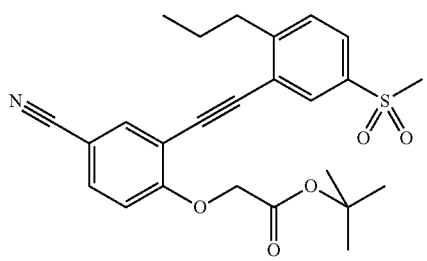

Following the general method as outlined in Intermediate 20, starting from (4-cyano-2-ethynyl-phenoxy)-acetic acid tert-butyl ester (Intermediate 46) and 2-iodo-4-(methylsulfonyl)-1-propylbenzene (Intermediate 62), the title compound was obtained after purification by flash column chromatography (silica), eluting with cyclohexane containing increasing amounts of EtOAc.

$^1$H NMR (300 MHz, DMSO-d$_6$) δ [ppm] 8.08 (1H, d, J=2.1 Hz), 8.02 (1H, d, J=2.1 Hz), 7.89-7.86 (2H, m), 7.62 (1H, d, J=8.1 Hz); 7.21 (1H, d, J=8.8 Hz), 4.96 (2H, s), 3.27 (3H, s), 2.92 (2H, t, J=7.5 Hz), 1.68 (2H, sext., J=7.5 Hz), 1.43 (9H, s), 0.94 (3H, t, J=7.5 Hz).

Intermediate 73

2-chloro-5-(methylsulfonyl)aniline

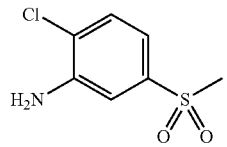

Following the general method as outlined in Intermediate 61, starting from 2-chloro-5-methylsulphonylnitrobenzene, the title compound was obtained as a dark green sticky solid in quantitative yield.

$^1$H NMR (300 MHz, DMSO-$d_6$) δ [ppm] 7.45 (d, J=8.2 Hz, 1H), 7.30 (d, J=2.1 Hz, 1H), 7.00 (dd, J=2.1, J=8.2 Hz, 1H), 5.94 (s, 2H), 3.14 (s, 3H). HPLC (Condition A) Rt 1.9 min.

Intermediate 74

1-chloro-2-iodo-4-(methylsulfonyl)benzene

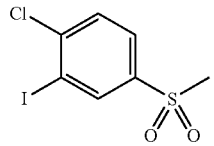

Following the general method as outlined in Intermediate 58, starting from 2-chloro-5-(methylsulfonyl)aniline (Intermediate 73), the title compound was obtained as a white solid after purification by flash column chromatography (silica), eluting with cyclohexane containing increasing amounts of EtOAc.

$^1$H NMR (300 MHz, DMSO-$d_6$) δ [ppm] 8.39 (d, J=2.1 Hz, 1H), 7.93 (dd, J=2.1, J=8.3 Hz, 1H), 7.85 (d, J=8.3 Hz, 1H), 3.29 (s, 3H). HPLC (Condition A) Rt 3.3 min.

Intermediate 75 tert-butyl(4-chloro-2-{[5-(methylsulfonyl)-2-piperidin-1-ylphenyl]ethynyl}phenoxy)acetate

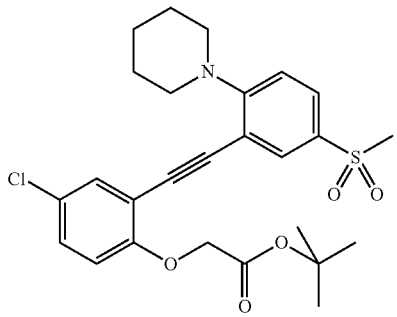

Following the general method as outlined in Intermediate 20, starting from (4-chloro-2-ethynyl-phenoxy)-acetic acid tert-butyl ester (Intermediate 3) and 1-chloro-2-iodo-4-(methylsulfonyl)benzene (Intermediate 74), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 7.91 (d, J=2.4 Hz, 1H), 7.76 (dd, J=2.4, J=8.8 Hz, 1H), 7.56 (d, J=2.7 Hz, 1H), 7.42 (dd, J=2.7, J=9.0 Hz, 1. HPLC (Condition A) Rt 5.8 min.

Intermediate 76

2-fluoro-5-(methylsulfonyl)aniline

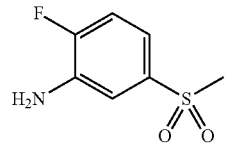

A mixture of 4-fluoro-3-nitrophenyl methyl sulfone (Acros; 1.00 g; 4.56 mmol) and PtO$_2$ (100 mg) in MeOH (150 ml) was placed in a PARR reactor and treated with a pressure of 20 atm of hydrogen for 3 hours. The reaction mixture was filtered through Celite and the filtrate was concentrated to dryness affording the title compound (964 mg) as a dark green oil.

$^1$H NMR (300 MHz, DMSO-$d_6$) δ [ppm] 7.31-7.20 (2H, m), 7.03 (ddd, J=8.4 Hz, J=4.3 Hz, J=2.4 Hz), 5.75 (s, 2H), 3.13 (s, 3H).

Intermediate 77

1-fluoro-2-iodo-4-(methylsulfonyl)benzene

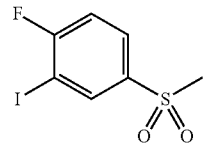

Following the general method as outlined in Intermediate 58, starting from 2-fluoro-5-(methylsulfonyl)aniline (Intermediate 76), the title compound was obtained as a white solid after purification by flash column chromatography (silica), eluting with cyclohexane containing increasing amounts of EtOAc. 2-Iodo-4-(methylsulfonyl)phenol was also isolated from the chromatography, and denominated as Intermediate 78.

$^1$H NMR (300 MHz, DMSO-$d_6$) δ [ppm] 8.37 (dd, J=5.8, J=2.3 Hz, 1H), 8.00 (ddd, J=2.3, J=4.8, J=8.6 Hz, 1H), 7.56 (dd, J=0.35, J=8.1 Hz, 1H), 3.30 (s, 3H)

Intermediate 78

2-iodo-4-(methylsulfonyl)phenol

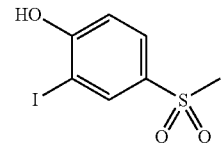

The title compound was isolated as a yellow solid during the preparation of Intermediate 77.

¹H NMR (300 MHz, DMSO-d₆) δ [ppm] 11.49 (s, 1H), 8.14 (d, J=2.3 Hz, 1H), 7.74 (dd, J=2.3, J=8.5 Hz, 1H), 7.03 (d, J=8.5 Hz, 1H), 3.16 (s, 3H)

Intermediate 79 tert-butyl(4-cyano-2-{[2-fluoro-5-(methylsulfonyl)phenyl]ethynyl}phenoxy)acetate

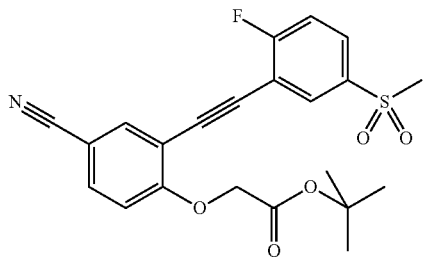

A suspension of (4-cyano-2-ethynyl-phenoxy)-acetic acid tert-butyl ester (Intermediate 46; 200 mg; 0.78 mmol), 1-fluoro-2-iodo-4-(methylsulfonyl)benzene (Intermediate 77; 233 mg; 0.78 mmol), 1,1'-bis(diphenylphosphino)ferrocenedichloro palladium(II) (34 mg; 0.05 mmol) and cuprous iodide (9 mg; 0.05 mmol) was degassed during 2 minutes under nitrogen then anhydrous THF (3 ml) and TEA (215 μl; 1.55 mmol) were added and the reaction mixture was stirred at 70° C. for 16 hours. The solvents were removed under reduced pressure and the residue was purified by flash column chromatography (silica), eluting with cyclohexane containing increasing amounts of EtOAc to give the title compound (260 mg, 78%) as a yellow sticky solid.

¹H NMR (300 MHz, DMSO-d₆) δ [ppm] 8.20 (dd, J=2.4, J=6.5 Hz, 1H), 8.11 (d, J=2.1 Hz, 1H), 8.02-8.07 (m, 1H), 7.91 (dd, J=2.1, J=9.0 Hz, 1H), 7.67 (t, J=9.0 Hz, 1H), 7.19 (d, J=9.0 Hz, 1H), 4.96 (s, 2H), 3.31 (s, 3H), 1.43 (s, 9H).

Intermediate 80 tert-butyl(4-chloro-2-{[2-chloro-5-(methylsulfonyl)phenyl]ethynyl}phenoxy)acetate

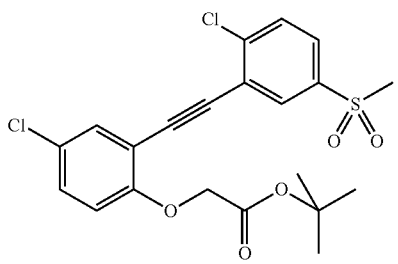

Following the general method as outlined in Intermediate 79, starting from (4-chloro-2-ethynyl-phenoxy)-acetic acid tert-butyl ester (Intermediate 3) and 1-chloro-2-iodo-4-(methylsulfonyl)benzene (Intermediate 74), the title compound was obtained after purification by flash column chromatography (silica), eluting with cyclohexane containing increasing amounts of EtOAc.

¹H NMR (300 MHz, DMSO-d₆) δ [ppm] 8.17 (d, J=2.1 Hz, 1H), 7.95 (dd, J=2.1, J=8.5 Hz, 1H), 7.90 (d, J=8.5 Hz, 1H), 7.64 (d, J=2.7 Hz, 1H), 7.49 (dd, J=2.7, J=9.0 Hz, 1H), 7.04 (d, J=9.0 Hz, 1H), 4.83 (s, 2H), 3.31 (s, 3H), 1.43 (s, 9H). HPLC (Condition A) Purity 99.2%; Rt 5.2 min.

Intermediate 81 tert-butyl(4-chloro-2-{[2-hydroxy-5-(methylsulfonyl)phenyl]ethynyl}phenoxy)acetate

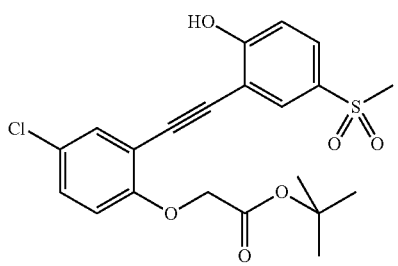

Following the general method as outlined in Intermediate 79, starting from (4-chloro-2-ethynyl-phenoxy)-acetic acid tert-butyl ester (Intermediate 3) and 2-iodo-4-(methylsulfonyl)phenol (Intermediate 78), the title compound was obtained after purification by flash column chromatography (silica), eluting with cyclohexane containing increasing amounts of EtOAc.

¹H NMR (300 MHz, DMSO-d₆) δ [ppm] 8.28 (m, 1H), 7.98 (d, J=2.7 Hz, 1H), 7.91-7.94 (m, 3H), 7.49 (dd, J=2.7, J=9.0 Hz, 1H), 7.21 (d, J=9.0 Hz, 1H), 4.94 (s, 2H), 3.27 (s, 3H), 1.50 (s, 9H). HPLC (Condition A) Purity 98.4%; Rt 5.12 min.

Intermediate 82 tert-butyl(2-{[2-chloro-5-(methylsulfonyl)phenyl]ethynyl}-4-cyanophenoxy)acetate

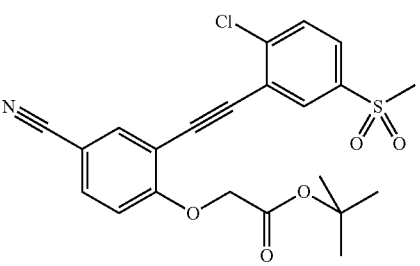

Following the general method as outlined in Intermediate 79, starting from (4-cyano-2-ethynyl-phenoxy)-acetic acid tert-butyl ester (Intermediate 46) and 1-chloro-2-iodo-4-(methylsulfonyl)benzene (Intermediate 74), the title compound was obtained as a yellow solid in 74% yield after purification by flash column chromatography (silica), eluting with cyclohexane containing increasing amounts of EtOAc.

¹H NMR (300 MHz, DMSO-d₆) δ [ppm] 8.18 (d, J=2.0 Hz, 1H), 8.11 (d, J=2.0 Hz, 1H), 7.96 (dd, J=2.0, J=8.6 Hz, 1H), 7.89-7.93 (m, 2H), 7.21 (d, J=8.6 Hz, 1H), 4.96 (s, 2H), 1.43

Intermediate 83 tert-butyl(4-cyano-2-{[5-(methylsulfonyl)-2-piperidin-1-ylphenyl]ethynyl}phenoxy)acetate

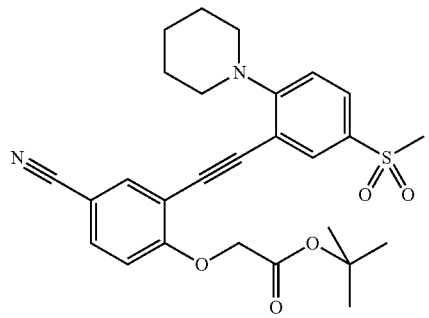

Following the general method as outlined in Intermediate 20, starting from (4-cyano-2-ethynyl-phenoxy)-acetic acid tert-butyl ester (Intermediate 46) and 1-chloro-2-iodo-4-(methylsulfonyl)benzene (Intermediate 74), the title compound was obtained as a yellow sticky solid after purification by flash column chromatography (silica), eluting with cyclohexane containing increasing amounts of EtOAc.

$^1$H NMR (300 MHz, DMSO-d$_6$) δ [ppm] 8.03 (d, J=2.1 Hz, 1H), 7.93 (d, J=2.4 Hz, 1H), 7.85 (dd, J=2.1, J=8.8 Hz, 1H), 7.77 (dd, J=2.4, J=8.8 Hz, 1H), 7.18 (d, J=8.8 Hz, 1H), 7.16 (d, J=8.8 Hz, 1H), 4.95 (s, 2H), 3.34 (m, 4H), 3.19 (s, 3H), 1.67 (m, 4H), 1.58 (m, 2H), 1.42 (s, 9H). HPLC (Condition A) Rt 5.12 min.

Intermediate 84 tert-Butyl[(2-bromo-6-methylpyridin-3-yl)oxy]acetate

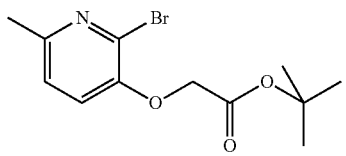

Following the general method as outlined in Intermediate 1, starting from 2-Bromo-6-methylpyridin-3-ol (Activate Scientific), the title compound was obtained in 79% yield as a yellow liquid after purification by flash column chromatography (silica), eluting with chloroform and methanol (98:2).

$^1$H NMR (300 MHz, DMSO-d$_6$) δ [ppm] 7.31 (1H, d), 7.21 (1H, d), 4.80 (2H, s), 2.36 (3H, s), 1.40 (9H, s). MS (ESI$^+$): 303.6. HPLC (Method D) Purity 97.0%; Rt 4.43 min.

Intermediate 85 tert-Butyl {[2-(trimethylsilyl-1-ethynyl)-6-methylpyridin-3-yl]oxy}acetate

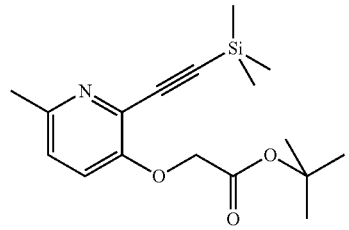

Following the general method as outlined in Intermediate 2, starting from tert-butyl[(2-bromo-6-methylpyridin-3-yl)oxy]acetate (Intermediate 84), the title compound was obtained as a brown oil after purification by flash column chromatography (silica), eluting with petroleum ether and ethyl acetate (98:2).

$^1$H NMR (300 MHz, DMSO-d$_6$) δ [ppm] 7.26 (1H, d), 7.20 (1H, d), 4.73 (2H, s), 2.35 (3H, s), 1.41 (9H, s), 0.22 (9H, s).

Intermediate 86 tert-Butyl [(2-ethynyl-6-methylpyridin-3-yl)oxy]acetate

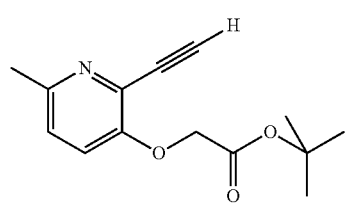

Following the general method as outlined in Intermediate 2, starting from tert-butyl{[2-(trimethylsilyl-1-ethynyl)-6-methylpyridin-3-yl]oxy}acetate (Intermediate 85), the title compound was obtained in 91% yield as a brown oil after purification by flash column chromatography (silica), eluting with petroleum ether and ethyl acetate (98:2).

$^1$H NMR (300 MHz, DMSO-d$_6$) δ [ppm] 7.28 (1H, d), 7.21 (1H, d), 4.78 (2H, s), 4.36 (1H, s), 2.35 (3H, s), 1.40 (9H, s). MS (ESI$^+$): 248.0. HPLC (Condition A) Purity 98.5%; Rt 3.03 min.

Intermediate 87 tert-butyl[(6-methyl-2-{[3-(propylsulfonyl)phenyl]ethynyl}pyridin-3-yl)oxy]acetate

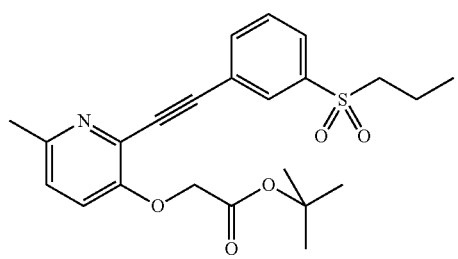

Following the general method as outlined in Intermediate 20, starting from (2-ethynyl-6-methyl-pyridin-3-yloxy)-acetic acid tert-butyl ester (Intermediate 86) and 1-bromo-3-

(propane-1-sulfonyl)-benzene (Intermediate 5), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 8.02 (t, J=1.5 Hz, 1H), 7.92-7.96 (m, 2H), 7.75 (t, J=7.8 Hz, 1H), 7.37 (d, J=8.7 Hz, 1H), 7.26 (d, J=8.7 Hz, 1H), 4.83 (s, 2H), 3.35-3.40 (m, 2H), 2.42 (s, 3H), 1.56 (sext., J=7.5 Hz, 2H), 1.43 (s, 9H), 0.93 (t, J=7.5 Hz, 3H). HPLC (Condition A) Purity 92.6%; Rt 3.93 min.

Intermediate 88

1-isopropenyl-4-(methylsulfonyl)-2-nitrobenzene

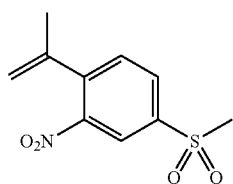

Following the general method as outlined in Intermediate 59, starting from 2-bromo-5-methylsulfonylnitrobenzene and isopropenylboronic acid pinacol ester, the title compound was obtained as a brown oil in quantitative yield after purification by flash column chromatography (silica), eluting with cyclohexane containing increasing amounts of EtOAc.

$^1$H NMR (300 MHz, DMSO-$d_6$) δ [ppm] 8.44 (1H, d, J=1.8 Hz) 8.20 (1H, dd, J=8.1 Hz, J=1.8 Hz), 7.78 (1H, d, J=8.1 Hz), 5.30 (1H, t, J=1.3 Hz), 5.30 (m, 1H), 5.00 (1H, s), 3.36 (3H, s), 2.08 (3H, s).

Intermediate 89

2-isopropenyl-5-(methylsulfonyl)aniline

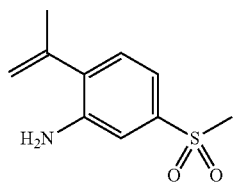

Following the general method as outlined in Intermediate 60, starting from 1-isopropenyl-4-(methylsulfonyl)-2-nitrobenzene (Intermediate 88), the title compound was obtained as an orange solid after purification by flash column chromatography (silica), eluting with cyclohexane containing increasing amounts of EtOAc.

$^1$H NMR (300 MHz, DMSO-$d_6$) δ [ppm] 7.18 (1H, d, J=1.9 Hz), 7.13 (1H, d, J=7.9 Hz), 7.00 (1H, dd, J=7.9 Hz, J=1.9 Hz), 5.37 (s, 2H), 5.29 (1H, m), 5.02 (1H, m), 3.10 (3H, s), 2.00 (3H, m).

Intermediate 90

2-isopropyl-5-(methylsulfonyl)aniline

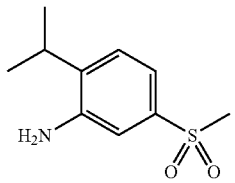

Following the general method as outlined in Intermediate 61, starting from 2-isopropenyl-5-(methylsulfonyl)aniline (Intermediate 89), the title compound was obtained as a green solid in 81% yield after purification by flash column chromatography (silica), eluting with cyclohexane containing increasing amounts of EtOAc.

$^1$H NMR (300 MHz, DMSO-$d_6$) δ [ppm] 7.22 (1H, d, J=8.0 Hz), 7.12 (1H, d, J=2.0 Hz), 7.00 (1H dd, J=8.0 Hz, J=2.0 Hz), 5.47 (2H, s), 3.07 (3H, s), 3.01 (1H, sept., J=6.7 Hz), 1.15 (6H, d, J=6.7 Hz)

Intermediate 91

2-iodo-1-isopropyl-4-(methylsulfonyl)benzene

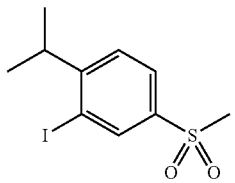

Following the general method as outlined in Intermediate 58, starting from 2-isopropyl-5-(methylsulfonyl)aniline (Intermediate 90), the title compound was obtained as a white solid after purification by flash column chromatography (silica), eluting with cyclohexane containing increasing amounts of EtOAc.

$^1$H NMR (300 MHz, DMSO-$d_6$) δ [ppm] 8.28 (1H, d, J=1.9 Hz), 7.90 (1H dd, J=8.2 Hz, J=1.9 Hz), 7.59 (1H d, J=8.2 Hz), 3.25 (3H, s), 3.18 (1H, sept., J=6.8 Hz), 1.21 (6H, d, J=6.8 Hz)

Intermediate 92 tert-butyl(4-chloro-2-{[2-isopropyl-5-(methylsulfonyl)phenyl]ethynyl}phenoxy)acetate

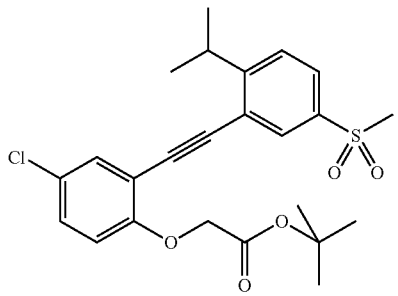

Following the general method as outlined in Intermediate 79, starting from (4-chloro-2-ethynyl-phenoxy)-acetic acid tert-butyl ester (Intermediate 3) and 2-iodo-1-isopropyl-4-

(methylsulfonyl)benzene (Intermediate 91), the title compound was obtained as a brown sticky solid after purification by flash column chromatography (silica), eluting with cyclohexane containing increasing amounts of EtOAc.

$^1$H NMR (300 MHz, DMSO-d$_6$) δ [ppm] 8.01 (1H, d, J=2.0 Hz), 7.90 (1H, dd, J=8.3 Hz, J=2.0 Hz), 7.67 (1H, d, J=8.3 Hz), 7.64 (1H, d, J=2.7 Hz), 7.45 (1H, dd, J=9.0 Hz, J=2.7 Hz), 7.06 (1H, d, J=9.0 Hz), 4.82 (2H, s), 3.65 (1H, sept., J=6.9 Hz), 3.26 (3H, s), 1.43 (9H, s), 1.28 (6H, d, J=6.9 Hz). HPLC (Condition A) Purity 92.4%; Rt 5.60 min.

Intermediate 93 tert-butyl(4-cyano-2-{[2-isopropyl-5-(methylsulfonyl)phenyl]ethynyl}phenoxy)acetate

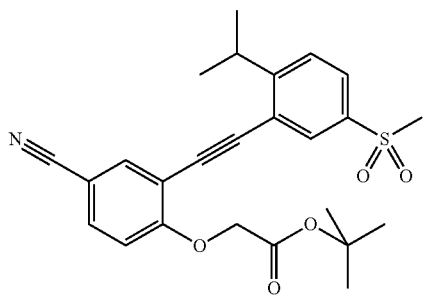

Following the general method as outlined in Intermediate 79, starting from (4-cyano-2-ethynyl-phenoxy)-acetic acid tert-butyl ester (Intermediate 46) and 2-iodo-1-isopropyl-4-(methylsulfonyl)benzene (Intermediate 91), the title compound was obtained as a brown solid in 74% yield after purification by flash column chromatography (silica), eluting with cyclohexane containing increasing amounts of EtOAc.

$^1$H NMR (300 MHz, DMSO-d$_6$) δ [ppm] 8.10 (1H, d, J=2.1 Hz), 8.02 (1H, d, J=2.1 Hz), 7.86-7.94 (2H, m), 7.67 (1H, d, J=8.3 Hz), 7.22 (1H, d, J=9.0 Hz) 4.95 (2H, s), 3.65 (1H, sept., J=7.0 Hz), 3.26 (3H, s), 1.43 (9H, s), 1.28 (6H, d, J=7.0 Hz). HPLC (Condition A) Rt 5.16 min.

Intermediate 94 tert-butyl(3-chloro-2-iodophenoxy)acetate

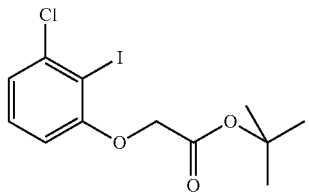

Following the general method as outlined in Intermediate 1, starting from 3-chloro-2-iodophenol (prepared as described in J. Org. Chem., 2005, 70, 6548-6551), the title compound was obtained as a white solid in 86% yield after purification by flash column chromatography (silica), eluting with cyclohexane containing increasing amounts of EtOAc.

$^1$H NMR (300 MHz, DMSO-d$_6$) δ [ppm] 7.34-7.30 (1H, m), 7.18-7.16 (1H, m), 6.80-6.77 (2H, d), 4.78 (2H, s), 1.40 (9H, s). MS (ESI$^+$): 310.8. HPLC (Condition A) Purity 98.9%; Rt 5.80 min.

Intermediate 95 tert-butyl(3-chloro-2-{[3-(propylsulfonyl)phenyl]ethynyl}phenoxy)acetate

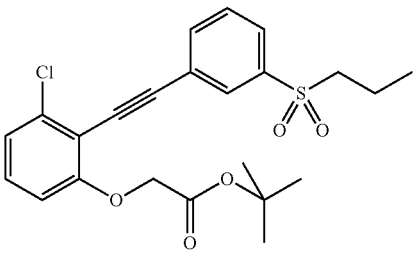

Following the general method as outlined in Intermediate 79, starting from (3-chloro-2-iodo-phenoxy)-acetic acid tert-butyl ester (Intermediate 94) and 1-ethynyl-3-(propane-1-sulfonyl)-benzene (Intermediate 42), the title compound was obtained a brown sticky solid after purification by flash column chromatography (silica), eluting with cyclohexane containing increasing amounts of EtOAc.

MS (ESI$^+$): 466.1 (M+NH$_4$)$^+$.

Intermediate 96 tert-butyl[4-chloro-2-({3-[(dimethylamino)sulfonyl]phenyl}ethynyl)phenoxy]acetate

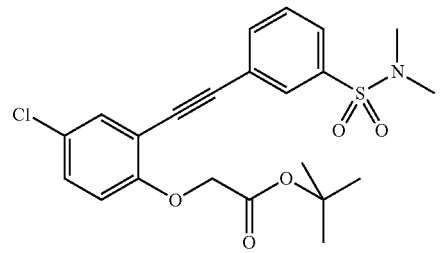

Following the general method as outlined in Intermediate 20, starting from (4-chloro-2-ethynyl-phenoxy)-acetic acid tert-butyl ester (Intermediate 3) and N,N-dimethyl 3-bromobenzenesulfonamide (Combiblocks), the title compound was obtained as a yellow oil after purification by flash column chromatography (silica), eluting with cyclohexane containing increasing amounts of EtOAc.

$^1$H NMR (300 MHz, DMSO-d$_6$) δ [ppm] 7.88-7.70 (4H, m), 7.66 (1H, d, J=2.7 Hz), 7.44 (1H, dd, J=9.0 Hz, J=2.7 Hz), 7.02 (1H, d, J=9.0 Hz), 4.82 (2H, s), 2.66 (6H, s), 1.44 (9H, s).

Intermediate 97 tert-butyl[4-chloro-2-({5-[(diethylamino)sulfonyl]-2-methylphenyl]ethynyl)phenoxy}acetate

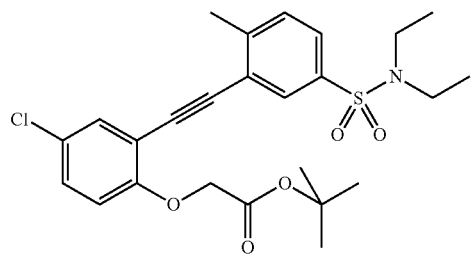

Following the general method as outlined in Intermediate 20, starting from (4-chloro-2-ethynyl-phenoxy)-acetic acid tert-butyl ester (Intermediate 3) and N,N-diethyl 3-bromobenzenesulfonamide (Combiblocks), the title compound was obtained as a yellow sticky solid in 72% yield after purification by flash column chromatography (silica), eluting with cyclohexane containing increasing amounts of EtOAc.

$^1$H NMR (300 MHz, DMSO-$d_6$) δ [ppm] 7.84 (1H, d, J=2.0 Hz), 7.71 (1H, dd, J=8.0 Hz, J=2.0 Hz), 7.66 (1H, d, J=2.7 Hz), 7.57 (1H, d, J=8.0 Hz), 7.44 (1H, dd, J=9.0 Hz, J=2.7 Hz), 7.03 (1H, d, J=9.0 Hz), 4.81 (2H, s), 3.18 (4H, q, J=7.1 Hz), 2.55 (3H, s), 1.43 (9H, s), 1.05 (6H, t, J=7.1 Hz). HPLC (Condition A) Purity 95.4%; Rt 6.23 min.

Intermediate 98 tert-butyl(4-chloro-2-{[2-methyl-5-(morpholin-4-ylsulfonyl)phenyl]ethynyl}phenoxy)acetate

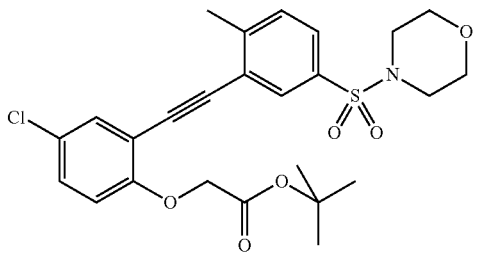

Following the general method as outlined in Intermediate 20, starting from (4-chloro-2-ethynyl-phenoxy)-acetic acid tert-butyl ester (Intermediate 3) and 1-(3-bromo-4-methylphenylsulfonyl)morpholine (Combiblocks), the title compound was obtained as a yellow sticky solid in 81% yield after purification by flash column chromatography (silica), eluting with cyclohexane containing increasing amounts of EtOAc.

$^1$H NMR (300 MHz, DMSO-$d_6$) δ [ppm] 7.80 (1H, d, J=1.5 Hz), 7.62-7.69 (3H, m), 7.45 (1H, dd, J=9.0 Hz, J=2.7 Hz), 7.04 (1H, d, J=9.0 Hz), 4.82 (2H, s), 3.64 (4H, m), 2.90 (4H, m), 2.59 (3H, s), 1.43 (9H, s). HPLC (Condition A) Purity 99.7%; Rt 5.73 min.

Intermediate 99 tert-butyl[4-chloro-2-({5-[(dimethylamino)sulfonyl]-2-methylphenyl]ethynyl)phenoxy}acetate

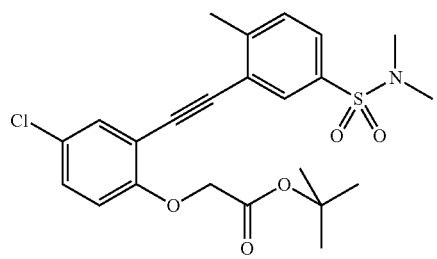

Following the general method as outlined in Intermediate 20, starting from (4-chloro-2-ethynyl-phenoxy)-acetic acid tert-butyl ester (Intermediate 3) and N,N-dimethyl 3-bromo-4-methylbenzenesulfonamide (Combiblocks), the title compound was obtained as an orange sticky solid after purification by flash column chromatography (silica), eluting with cyclohexane containing increasing amounts of EtOAc.

$^1$H NMR (300 MHz, DMSO-$d_6$) δ [ppm] 7.81 (1H, d, J=1.9 Hz), 7.60-7.69 (3H, m), 7.45 (1H, dd, J=9.0 Hz, J=2.7 Hz), 7.04 (1H, d, J=9.0 Hz), 4.81 (2H, s), 2.63 (6H, s), 2.57 (3H, s), 1.43 (9H, s). HPLC (Condition A) Purity 99.8%; Rt 5.84 min.

Intermediate 100 tert-butyl[4-chloro-2-({2-methyl-5-[(methylamino)sulfonyl]phenyl}ethynyl)phenoxy]acetate

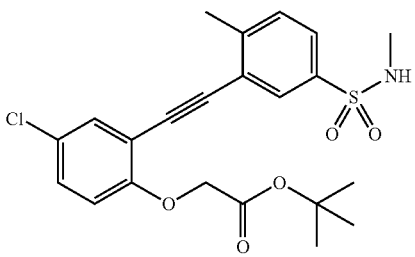

Following the general method as outlined in Intermediate 20, starting from (4-chloro-2-ethynyl-phenoxy)-acetic acid tert-butyl ester (Intermediate 3) and 3-bromo-N,4-dimethylbenzenesulfonamide (Combiblocks), the title compound was obtained as an orange sticky solid after purification by flash column chromatography (silica), eluting with cyclohexane containing increasing amounts of EtOAc.

$^1$H NMR (300 MHz, DMSO-$d_6$) δ [ppm] 7.85 (1H, d, J=2.0 Hz), 7.69 (1H, dd, J=8.0 Hz, J=2.0 Hz), 7.64 (1H, d, J=2.7 Hz), 7.57 (1H, d, J=8.0 Hz), 7.48 (1H, bs), 7.44 (1H, dd, J=9.0 Hz, J=2.7 Hz), 7.02 (1H, d, J=9.0 Hz), 4.82 (2H, s), 2.55 (3H, s), 2.42 (3H, s), 1.43 (9H, s). HPLC (Condition A) Purity 96.9%; Rt 5.19 min.

Intermediate 101 tert-butyl[2-({5-[(tert-butylamino)sulfonyl]-2-methylphenyl}ethynyl)-4-chlorophenoxy]acetate

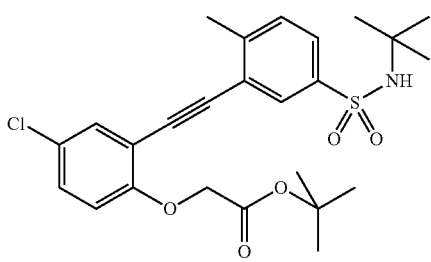

Following the general method as outlined in Intermediate 20, starting from (4-chloro-2-ethynyl-phenoxy)-acetic acid tert-butyl ester (Intermediate 3) and N-tert-butyl 3-bromo-4-methylbenzenesulfonamide (Combiblocks), the title compound was obtained as an orange sticky solid after purification by flash column chromatography (silica), eluting with cyclohexane containing increasing amounts of EtOAc.

$^1$H NMR (300 MHz, DMSO-$d_6$) δ [ppm] 7.89 (1H, d, J=1.9 Hz), 7.74 (1H, dd, J=8.0 Hz, J=1.9 Hz), 7.64 (1H, d, J=2.7 Hz), 7.56 (1H, s), 7.53 (1H, d, J=8.0 Hz), 7.44 (1H, dd, J=9.0 Hz, J=2.7 Hz), 7.03 (1H, d, J=9.0 Hz), 4.82 (2H, s), 2.54 (3H, s), 1.42 (9H, s), 1.10 (9H, s). HPLC (Condition A) Purity 95.3%; Rt 6.05 min.

Intermediate 102 tert-butyl[4-chloro-2-({5-[(isopropylamino)sulfonyl]-2-methylphenyl}ethynyl)phenoxy]acetate

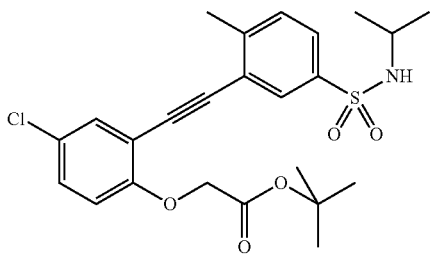

Following the general method as outlined in Intermediate 20, starting from (4-chloro-2-ethynyl-phenoxy)-acetic acid tert-butyl ester (Intermediate 3) and N-isopropyl 3-bromo-4-methylbenzenesulfonamide (Combiblocks), the title compound was obtained as an orange sticky solid after purification by flash column chromatography (silica), eluting with cyclohexane containing increasing amounts of EtOAc.

$^1$H NMR (300 MHz, DMSO-$d_6$) δ [ppm] 7.87 (1H, d, J=2.0 Hz), 7.71 (1H, dd, J=8.0 Hz, J=2.0 Hz), 7.64 (1H, d, J=2.7 Hz), 7.61 (1H, d, J=6.5 Hz), 7.55 (1H, d, J=8.0 Hz), 7.44 (1H, dd, J=9.0 Hz, J=2.7 Hz), 7.03 (1H, d, J=9.0 Hz), 4.82 (2H, s), 3.26 (1H, m), 2.55 (3H, s), 1.43 (9H, s), 0.95 (6H, d, J=6.5 Hz). HPLC (Condition A) Purity 94.7%; Rt 5.8 min.

Intermediate 103

3-bromo-N-isopropyl-N,4-dimethylbenzenesulfonamide

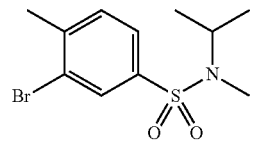

A solution of N-isopropyl 3-bromo-4-methylbenzenesulfonamide (Combiblocks; 200 mg; 0.68 mmol) in anhydrous DMF (4 mL) was treated with NaH (33 mg; 0.82 mmol) and stirred at RT for five minutes. The resulting mixture was treated with iodomethane (43 µl; 0.68 mmol) and the reaction mixture was stirred for 16 hours. The mixture was treated again with iodomethane (21 µl; 0.34 mmol) and the reaction mixture was stirred at RT for 24 hours. The mixture was quenched with an aqueous (5 N) solution of NaOH and extracted with EtOAc. The organic phase was washed with water and brine, dried over MgSO$_4$, concentrated and purified flash column chromatography (silica), eluting with cyclohexane containing increasing amounts of EtOAc affording the title compound as a colorless sticky solid.

$^1$H NMR (300 MHz, DMSO-$d_6$) δ [ppm] 7.89 (1H, d, J=1.9 Hz), 7.70 (1H, d, J=8.0 Hz, J=1.9 Hz), 7.59 (1H, d, J=8.0 Hz), 4.08 (1H, sept., J=6.7 Hz), 2.64 (3H, s), 2.43 (3H, s), 0.90 (6H, d, J=6.7 Hz). HPLC (Condition A) Purity 98.3%; Rt 4.4 min.

Intermediate 104 tert-butyl{4-chloro-2-[(5-{[isopropyl(methyl)amino]sulfonyl}-2-methylphenyl)ethynyl]phenoxy}acetate

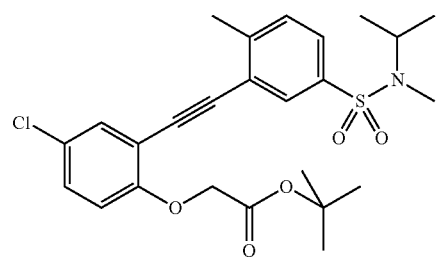

Following the general method as outlined in Intermediate 20, starting from (4-chloro-2-ethynyl-phenoxy)-acetic acid tert-butyl ester (Intermediate 3) and 3-bromo-N-isopropyl-N,4-dimethylbenzenesulfonamide (Intermediate 103), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 7.84 (1H, d, J=2.0 Hz), 7.71 (1H, dd, J=8.0 Hz, J=2.0 Hz), 7.66 (1H, d, J=2.7 Hz), 7.57 (1H, d, J=8.0 Hz), 7.44 (1H, dd, J=9.0 Hz, J=2.7 Hz), 7.04 (1H, d, J=9.0 Hz), 4.81 (2H, s), 4.09 (1H, sept., J=6.7 Hz), 2.66 (3H, s), 2.55 (3H, s), 1.43 (9H, s), 0.90 (6H, d, J=6.7 Hz). HPLC (Condition A) Purity 96.7%; Rt 6.2 min.

Intermediate 105

1-fluoro-4-(propylsulfonyl)benzene

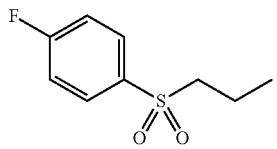

A cooled (0° C.) solution of 4-fluorothiophenol (Merck Kgaa; 2.00 g; 15.6 mmol) in MeOH (40 ml) was treated with a 5 N solution of NaOH in water (3.28 ml) and 1-iodopropane (1.67 ml; 17.2 mmol). The reaction mixture was stirred at RT for 1 hour, the mixture was concentrated under reduced pressure, the residue taken up in EtOAc and washed with brine, dried on MgSO$_4$, filtered and concentrated under reduced pressure. The intermediate thus obtained was dissolved in DCM (50 ml) and treated with 3-chloroperbenzoic acid (8.46 g; 34.33 mmol) and stirred at RT for 3 hours. The solvent was removed under reduced pressure, the residue taken up in EtOAc and washed with brine, dried on MgSO4, filtered and concentrated under reduced pressure to afford the title compound (2.75 g, 87%).

$^1$H NMR (300 MHz, DMSO-d$_6$) δ [ppm] 7.99-7.94 (2H, m), 7.55-7.47 (2H, m), 3.30 (2H, m), 1.55 (2H, m), 0.92 (3H, t, J=7.5 Hz).

Intermediate 106

2-bromo-1-fluoro-4-(propylsulfonyl)benzene

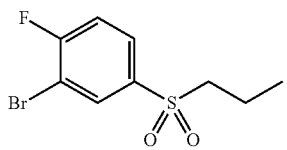

A suspension of 1-fluoro-4-(propylsulfonyl)benzene (Intermediate 105; 1.00 g; 4.94 mmol) in conc. sulfuric acid (3.97 ml; 74.2 mmol) was treated with N-bromosuccinimide (968 mg; 5.44 mmol) and stirred at RT for 6 hours. The reaction mixture was carefully poured on crushed ice, extracted with AcOEt and the organic phase was washed with a 0.1 N solution of NaOH in water twice, then with brine twice. The organic phase was dried on MgSO$_4$, filtered and concentrated under reduced pressure to give a residue, which was purified by flash column chromatography (silica), eluting with cyclohexane containing increasing amounts of EtOAc to give the title compound.

$^1$H NMR (300 MHz, DMSO-d$_6$) δ [ppm] 8.22 (1H, dd, J=6.3 Hz, J=2.3 Hz), 7.99 (1H, ddd, J=8.6 Hz, J=4.6 Hz, J=2.3 Hz), 7.67 (1H, t, J=8.6 Hz), 3.38 (2H, m), 1.56 (2H, m), 0.93 (3H, t, J=7.5 Hz).

Intermediate 107 tert-butyl(4-chloro-2-{[2-fluoro-5-(propylsulfonyl)phenyl]ethynyl}phenoxy)acetate

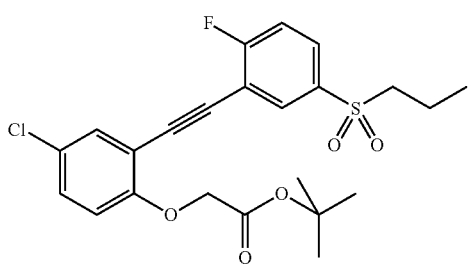

A mixture of 2-bromo-1-fluoro-4-(propylsulfonyl)benzene (Intermediate 106; 541 mg; 1.93 mmol), tert-butyl(4-chloro-2-ethynylphenoxy)acetate (Intermediate 467 mg; 1.75 mmol), dichlorobis(triphenylphosphine)palladium(II) (49 mg; 0.07 mmol) and TEA (728 µL; 5.2 mmol) was heated at 60° C. for 18 hours. The reaction mixture was taken up in EtOAc, washed twice with a sat. NH$_4$Cl aqueous solution and once with brine. The organic phase was dried over MgSO$_4$, filtered and concentrated to dryness affording a crude, which was purified by flash column chromatography (silica), eluting with cyclohexane containing increasing amounts of EtOAc. The title compound was obtained as a brown solid.

$^1$H NMR (300 MHz, DMSO-d$_6$) δ [ppm] 8.14 (1H, dd, J=6.5 Hz, J=2.4 Hz), 7.99 (1H, ddd, J=8.7 Hz, J=4.6 Hz, J=2.4 Hz), 7.69-7.63 (2H, m), 7.48 (1H, dd, J=9.0 Hz, J=2.7 Hz), 7.03 (1H, d, J=9.0 Hz), 4.83 (2H, s), 3.38 (2H, m), 1.58 (2H, m), 1.43 (9H, s), 0.93 (3H, t, J=7.5 Hz).

Intermediate 108

{[2-Fluoro-5-(propylsulfonyl)phenyl]ethynyl}trimethyl silane

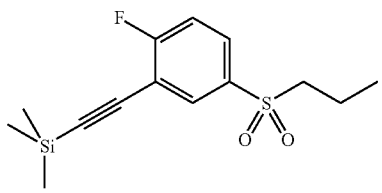

Following the general method as outlined in Intermediate 2, starting from 2-bromo-1-fluoro-4-(propylsulfonyl)benzene (Intermediate 106) and trimethylsilylacetilene, the title compound was obtained as a brown liquid in 97% yield.

$^1$H NMR (300 MHz, CDCl$_3$) δ [ppm] 8.03-8.01 (dd, 1H, J=2.3 Hz, 4.1 Hz), 7.85-7.81 (m, 1H), 7.24 (t, 1H, J=9.3 Hz), 3.06 (t, 2H, J=8 Hz), 1.77-1.69 (m, 2H), 1.02-0.99 (t, 3H, J=7.5 Hz), 0.28-0.27 (s, 9H).

Intermediate 109

2-Ethynyl-1-fluoro-4-(propylsulfonyl)benzene

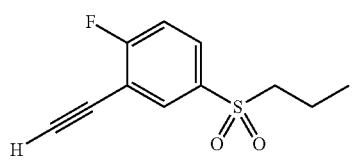

Following the general method as outlined in Intermediate 3, starting from {[2-Fluoro-5-(propylsulfonyl)phenyl]ethynyl}trimethyl silane (Intermediate 107), the title compound was obtained as a brown liquid after purification by column chromatography (silica) eluting with petroleum ether and ethyl acetate.

$^1$H NMR (300 MHz, DMSO-d$_6$) δ [ppm] 8.03 (dd, 1H, J=2.3 Hz, J=8.8 Hz), 7.98-7.94 (m, 1H), 7.60 (t, 1H, J=8.0 Hz), 4.74 (s, 1H), 3.34 (t, 2H, J=8.0 Hz), 1.56-1.49 (m, 2H), 0.90 (t, 3H, J=7.4 Hz). MS (ESI$^+$): 227.0. HPLC (Condition A) Purity 98.2%; Rt 4.07 min.

Intermediate 110 tert-butyl(4-chloro-2-{[4-(methylsulfonyl)phenyl]ethynyl}phenoxy)acetate

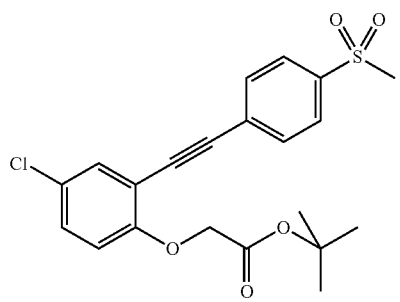

Following the general method as outlined in Intermediate 20, starting from (4-chloro-2-ethynyl-phenoxy)-acetic acid tert-butyl ester (Intermediate 3) and 4-bromophenyl methyl sulfone, the title compound was obtained as a brown sticky solid after purification by flash column chromatography (silica), eluting with cyclohexane containing increasing amounts of EtOAc.

$^1$H NMR (300 MHz, DMSO-d$_6$) δ [ppm] 7.98 (2H, d, J=8.6 Hz), 7.79 (2H, d, J=8.6 Hz), 7.64 (1H, d, J=2.7 Hz), 7.46 (1H, dd, J=9.0 Hz, J=2.7 Hz), 7.02 (1H, d, J=9.0 Hz), 4.83 (2H, s), 3.27 (3H, s), 1.43 (9H, s). HPLC (Condition A) Purity 98.9%; Rt 5.2 min.

Intermediate 111

1-methyl-2-nitro-4-(phenylthio)benzene

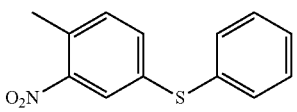

A mixture of 4-fluoro-2-nitrotoluene (ABCR; 120 µl; 0.97 mmol), thiophenol (120 µl; 1.16 mmol) and K$_2$CO$_3$ (267 mg; 1.93 mmol) in DMSO (3 ml) was placed in a microwave vial and submitted to microwave irradiation at 150° C. for 15 minutes. The reaction mixture was filtered, taken up in EtOAc and washed with water and brine. The organic phase was dried over MgSO$_4$, filtered, concentrated and purified by flash column chromatography (silica), eluting with cyclohexane containing increasing amounts of EtOAc affording the title compound as a yellow solid.

$^1$H NMR (300 MHz, DMSO-d$_6$) δ [ppm] 7.80 (1H, d, J=1.4 Hz), 7.50-7.51 (2H, m), 7.43-7.45 (5H, m), 2.47 (3H, s). HPLC (Condition A) Purity 91.6%; Rt 5.2 min.

Intermediate 112

1-methyl-2-nitro-4-(phenylsulfonyl)benzene

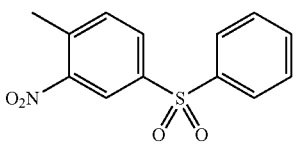

A solution of 1-methyl-2-nitro-4-(phenylthio)benzene (Intermediate 111; 745 mg; 3.04 mmol) in MeOH (11 ml) and water (11 ml) was treated with Oxone® (5.60 g; 9.11 mmol) and the reaction mixture was stirred at RT for 6 hours. Water was added and the reaction mixture was extracted 2 times with DCM. The combined organic extracts were dried over MgSO$_4$, filtered and concentrated to dryness affording the title compound as a beige solid (690 mg, 82%).

$^1$H NMR (300 MHz, DMSO-d$_6$) δ [ppm] 8.48 (1H, d, J=2.0 Hz), 8.18 (1H, dd, J=8.1 Hz, J=2.0 Hz), 8.01-8.05 (2H, m), 7.62-7.77 (4H, m), 2.56 (3H, s). HPLC (Condition A) Purity 91.3%; Rt 3.9 min.

Intermediate 113

2-methyl-5-(phenylsulfonyl)aniline

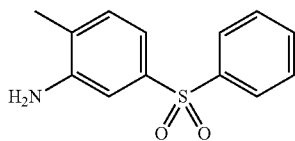

Following the general method as outlined in Intermediate 61 using MeOH and EtOAc as solvents, starting from 1-methyl-2-nitro-4-(phenylsulfonyl)benzene (Intermediate 112) and 4-bromophenyl methyl sulfone, the title compound was obtained as a beige solid in 94% yield.

$^1$H NMR (300 MHz, DMSO-$d_6$) δ [ppm] 7.83-7.86 (2H, m), 7.56-7.63 (3H, m), 7.10-7.13 (2H, m), 6.97 (1H, dd, J=7.8 Hz, J=2.0 Hz), 5.42 (2H, s), 2.06 (3H, s). HPLC (Condition A) Rt 2.8 min.

Intermediate 114

2-iodo-1-methyl-4-(phenylsulfonyl)benzene

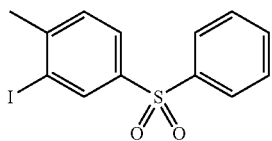

Following the general method as outlined in Intermediate 58, starting from 2-methyl-5-(phenylsulfonyl)aniline (Intermediate 113), the title compound was obtained as a white solid after purification by flash column chromatography (silica), eluting with cyclohexane containing increasing amounts of EtOAc affording the title compound as a yellow solid.

$^1$H NMR (300 MHz, DMSO-$d_6$) δ [ppm] 8.28 (1H, d, J=2.0 Hz), 7.96-7.99 (2H, m), 7.88 (1H, dd, J=8.0 Hz, J=2.0 Hz), 7.54-7.73 (4H, m), 2.41 (3H, s).

Intermediate 115 tert-butyl(4-cyano-2-{[2-methyl-5-(phenylsulfonyl)phenyl]ethynyl}phenoxy)acetate

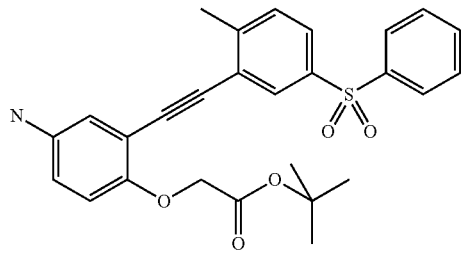

Following the general method as outlined in Intermediate 79, starting from (4-cyano-2-ethynyl-phenoxy)-acetic acid tert-butyl ester (Intermediate 46) and 2-iodo-1-methyl-4-(phenylsulfonyl)benzene (Intermediate 114), the title compound was obtained as a brown sticky solid in 89% yield.

$^1$H NMR (300 MHz, DMSO-$d_6$) δ [ppm] 8.11 (1H, d, J=2.0 Hz), 8.04 (1H, d, J=2.0 Hz), 7.97-8.02 (2H, m), 7.86-7.92 (2H, m), 7.58-7.73 (4H, m), 7.19 (1H, d, J=8.9 Hz), 4.94 (2H, s), 2.53 (3H, s), 1.43 (9H, s). HPLC (Condition A) Rt 5.5 min.

Intermediate 116 tert-butyl(4-chloro-2-{[2-methyl-5-(phenylsulfonyl)phenyl]ethynyl}phenoxy)acetate

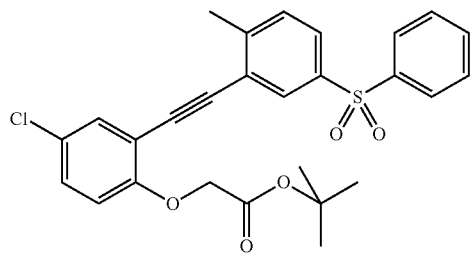

Following the general method as outlined in Intermediate 20, starting from (4-chloro-2-ethynyl-phenoxy)-acetic acid tert-butyl ester (Intermediate 3) and 2-iodo-1-methyl-4-(phenylsulfonyl)benzene (Intermediate 114), the title compound was obtained as a brown sticky solid in quantitative yield after purification by flash column chromatography (silica), eluting with cyclohexane containing increasing amounts of EtOAc.

$^1$H NMR (300 MHz, DMSO-$d_6$) δ [ppm] 7.97-8.03 (3H, m), 7.88 (1H, dd, J=8.1 Hz, J=2.0 Hz), 7.57-7.77 (5H, m), 7.45 (1H, dd, J=9.0 Hz, J=2.7 Hz), 7.03 (1H, d, J=9.0 Hz), 4.81 (2H, s), 2.52 (3H, s), 1.43 (9H, s). HPLC (Condition A) Rt 6.1 min.

Intermediate 117 tert-butyl(4-chloro-2-{[4-fluoro-2-methyl-5-(methylsulfonyl)phenyl]ethynyl}phenoxy)acetate

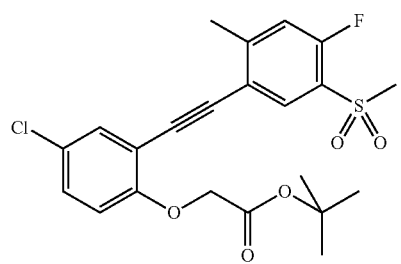

Following the general method as outlined in Intermediate 107, starting from (4-chloro-2-ethynyl-phenoxy)-acetic acid tert-butyl ester (Intermediate 3) and 1-bromo-4-fluoro-5-methanesulfonyl-2-methyl-benzene (Ger. Offen. 2000; DE 19919349), the title compound was obtained as a brown oil after purification by flash column chromatography (silica), eluting with cyclohexane containing increasing amounts of EtOAc.

$^1$H NMR (300 MHz, DMSO-$d_6$) δ [ppm] 7.89 (1H, d, J=7.2 Hz), 7.66 (1H, d, J=J=2.6 Hz), 7.59 (1H, d, J=11.1), 7.44 (1H, dd, J=9.0 Hz, J=2.6 Hz), 7.04 (1H, d, J=9.0 Hz), 4.82 (2H, s), 3.34 (3H, s), 2.58 (3H, s), 1.43 (9H, s).

Intermediate 118 tert-butyl[4-chloro-2-({3-[(methylsulfonyl)methyl]phenyl}ethynyl)phenoxy]acetate

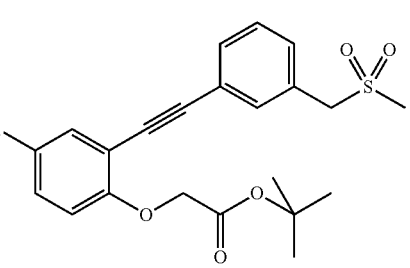

Following the general method as outlined in Intermediate 79, starting from (4-chloro-2-ethynyl-phenoxy)-acetic acid tert-butyl ester (Intermediate 3) and 3-bromobenzylmethylsulfone (Fluorochem), the title compound was obtained after purification by flash column chromatography (silica), eluting with cyclohexane containing increasing amounts of EtOAc.

$^1$H NMR (300 MHz, DMSO-d$_6$) δ [ppm] 7.54-7.60 (3H, m), 7.40-7.51 (3H, m), 6.98 (1H, d, J=9.0 Hz), 4.82 (2H, s), 2.93 (2H, s), 1.43 (9H, s). HPLC (Condition A) Purity 99.8%; Rt 5.1 min.

Intermediate 119 tert-butyl(2-bromo-4-fluorophenoxy)acetate

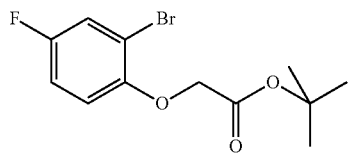

Following the general method as outlined in Intermediate 1, starting from 2-bromo-4-fluorophenol and tert-butyl bromoacetate, the title compound was obtained as a white solid in quantitative yield.

$^1$H NMR (300 MHz, DMSO-d$_6$) δ [ppm] 7.56 (1H, dd, J=8.2 Hz, J=3.1 Hz), 7.21 (1H, ddd, J=9.2 Hz, J=8.2 Hz, J=3.1 Hz), 7.02 (1H, dd, J=9.2 Hz, J=4.8 Hz), 4.77 (2H, s), 1.41 (9H, s). HPLC (Condition A) Purity 99.5%; Rt 4.9 min.

Intermediate 120 tert-butyl(4-fluoro-2-{[3-(propylsulfonyl)phenyl]ethynyl}phenoxy)acetate

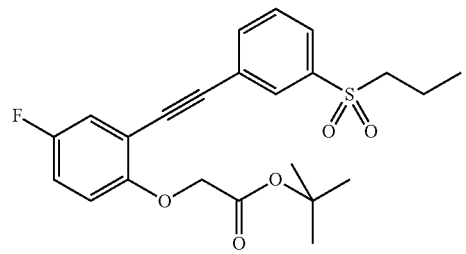

Following the general method as outlined in Intermediate 107, starting from tert-butyl(2-bromo-4-fluorophenoxy)acetate (Intermediate 119) and 1-ethynyl-3-(propane-1-sulfonyl)-benzene (Intermediate 42), the title compound was obtained as a yellow sticky solid after purification by flash column chromatography (silica), eluting with cyclohexane containing increasing amounts of EtOAc.

$^1$H NMR (300 MHz, DMSO-d$_6$) δ [ppm] 8.01 (1H, t, J=1.5 Hz), 7.87-7.94 (2H, m), 7.73 (1H, t, J=7.8 Hz), 7.45 (1H, dd, J=8.7 Hz, J=3.1 Hz), 7.26 (1H, m), 7.00 (1H, dd, J=9.4 Hz, J=4.5 Hz), 4.79 (2H, s), 3.36 (2H, m), 1.57 (2H, sext., J=7.5 Hz), 1.43 (9H, s), 0.93 (3H, t, J=7.5 Hz). HPLC (Condition A) Purity 91.0%; Rt 5.4 min.

Intermediate 121

4-(methylsulfonyl)-2-nitro-1-vinylbenzene

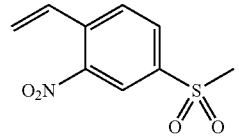

Following the general method as outlined in Intermediate 20, starting from 2-bromo-5-methylsulfonylnitrobenzene and vinylboronic acid pinacol ester, the title compound was obtained as a brown oil in quantitative yield.

HPLC (Condition A): Rt 3.04 min.

Intermediate 122

2-ethyl-5-(methylsulfonyl)aniline

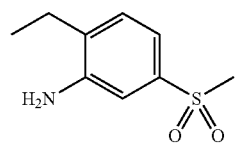

A solution of 4-(methylsulfonyl)-2-nitro-1-vinylbenzene (Intermediate 121; 3.60 g; 15.8 mmol) in AcOH (100 mL) was treated with a solution of iron (15.9 g; 285 mmol) in AcOH (20 ml) and the reaction mixture was stirred at 60° C.

for 1 h. EtOAc was added and the solution was filtered, the solvents removed under reduced pressure. The residue was taken up in EtOAc, washed with a sat. NaHCO₃ solution in water, then with brine. The organic layer was dried, filtered and concentrated to give the title compound.

MS (ESI⁻): 194.1

Intermediate 123

1-ethyl-2-iodo-4-(methylsulfonyl)benzene

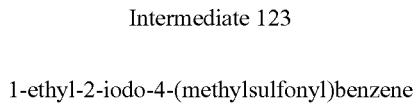

Following the general method as outlined in 58, starting from 2-ethyl-5-(methylsulfonyl)aniline (Intermediate 122), the title compound was obtained as a pink solid.

¹H NMR (300 MHz, DMSO-d₆) δ [ppm] 8.27 (1H, d, J=2.0 Hz), 7.88 (1H, dd, J=8.0 Hz, J=2.0 Hz), 7.58 (1H, d, J=2.0 Hz), 3.25 (3H, s), 2.77 (2H, q, J=7.5 Hz), 1.17 (3H, t, J=7.5 Hz). HPLC (Condition A) Purity 96.6%; Rt 3.8 min.

Intermediate 124 tert-butyl(4-chloro-2-{[2-ethyl-5-(methylsulfonyl)phenyl]ethynyl}phenoxy)acetate

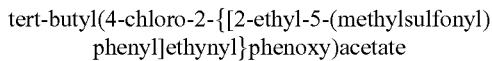

Following the general method as outlined in Intermediate 20, starting from (4-chloro-2-ethynyl-phenoxy)-acetic acid tert-butyl ester (Intermediate 3) and 1-ethyl-2-iodo-4-(methylsulfonyl)benzene (Intermediate 123), the title compound was obtained as an orange oil after purification by flash column chromatography (silica), eluting with cyclohexane containing increasing amounts of EtOAc.

¹H NMR (300 MHz, DMSO-d₆) δ [ppm] 8.01 (1H, d, J=2.0 Hz), 7.88 (1H, dd, J=8.0 Hz, J=2.0 Hz), 7.65-7.61 (2H, m), 7.45 (1H, dd, J=8.7 Hz, J=3.1 Hz), 7.04 (1H, d, J=9.0 Hz), 4.83 (2H, s), 3.26 (3H, s), 2.96 (2H, q, J=7.5 Hz), 1.26 (3H, t, J=7.5 Hz). MS (ESI⁻): 447.1. HPLC (Condition A) Purity 93.5%; Rt 5.6 min.

Intermediate 125

1-chloro-4-(propylsulfonyl)benzene

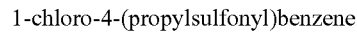
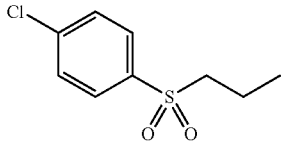

Following the general method as outlined in Intermediate 105, starting from 4-chlorothiophenol (Aldrich) and 1-iodopropane, the title compound was obtained as an oil which solidified upon standing in 82% yield after purification by flash column chromatography (silica), eluting with cyclohexane containing increasing amounts of EtOAc.

¹H NMR (300 MHz, DMSO-d₆) δ [ppm] 7.93-7.88 (2H, m), 7.76-7.72 (2H, m), 3.31 (2H, m), 1.57 (2H, m), 1.55 (9H, s), 0.91 (3H, t, J=7.4 Hz).

Intermediate 126

2-bromo-1-chloro-4-(propylsulfonyl)benzene

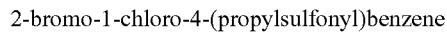
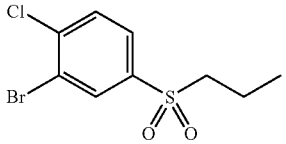

Following the general method as outlined in Intermediate 106, starting from 1-chloro-4-(propylsulfonyl)benzene (Intermediate 125), the title compound was obtained as an oil which solidified upon standing in 86% yield.

¹H NMR (300 MHz, DMSO-d₆) δ [ppm] 8.22 (1H, d, J=1.8 Hz), 7.95-7.87 (2H, m), 3.39 (2H, m), 1.57 (2H, m), 0.93 (3H, m).

Intermediate 127 tert-butyl(4-chloro-2-{[2-chloro-5-(propylsulfonyl)phenyl]ethynyl}phenoxy)acetate

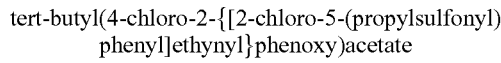
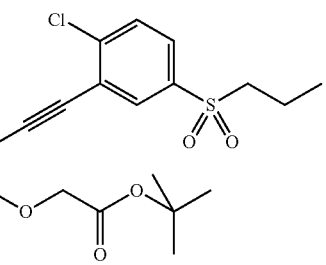

Following the general method as outlined in Intermediate 107, starting from (4-chloro-2-ethynyl-phenoxy)-acetic acid tert-butyl ester (Intermediate 3) and 2-bromo-1-chloro-4-(propylsulfonyl)benzene (Intermediate 126), the title compound was obtained as a colorless oil after purification by flash column chromatography (silica), eluting with cyclohexane containing increasing amounts of EtOAc.

$^1$H NMR (300 MHz, DMSO-d$_6$) δ [ppm] 8.13 (1H, t, J=1.3 Hz), 7.90 (2H, d, J=1.3 Hz), 7.65 (1H, d, J=2.7 Hz), 7.49 (1H, dd, J=9.0 Hz, J=2.7 Hz), 7.05 (1H, d, J=9.0 Hz), 4.84 (2H, s), 3.40 (2H, m), 1.57 (2H, m), 1.43 (9H, s), 0.93 (3H, t, J=7.4 Hz).

Intermediate 128

2-bromo-1-fluoro-4-(isopropylsulfonyl)benzene

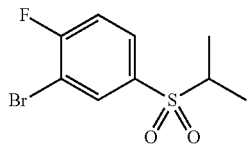

Step 1

1-fluoro-4-(isopropylthio)benzene

A cooled (0° C.) solution of p-thiocresol (5.0 mL; 46.8 mmol) in MeOH (100 ml) was treated with a 5 N solution of NaOH in water (9.8 ml; 49 mmol) and 2-iodopropane (5.2 ml; 52 mmol). The reaction mixture was stirred at RT for 4.5 hour, the mixture was concentrated under reduced pressure, the residue taken up in EtOAc and washed with brine, dried on MgSO$_4$, filtered and concentrated under reduced pressure to afford the title compound as a colorless oil (6.56 g, 82%).

Step 2

1-fluoro-4-(isopropylsulfonyl)benzene

1-Fluoro-4-(isopropylthio)benzene (6.56 g; 38.5 mmol) was dissolved in DCM (150 ml) and treated with 3-chloroperbenzoic acid (20.90 g; 84.77 mmol) and stirred at RT for 3 hours. The solvent was removed under reduced pressure, the residue taken up in EtOAc and washed with brine, dried on MgSO$_4$, filtered and concentrated under reduced pressure to afford the title compound as a white solid (6.88 g, 88%).

Step 3

2-bromo-1-fluoro-4-(isopropylsulfonyl)benzene

Following the general method as outlined in Intermediate 106, starting from 1-fluoro-4-(isopropylsulfonyl)benzene, the title compound was obtained as an oil which solidifies upon standing in 89% yield.

$^1$H NMR (300 MHz, DMSO-d$_6$) δ [ppm] 8.17 (1H, dd, J=6.4 Hz, J=2.2 Hz), 7.93 (1H, ddd, J=8.7 Hz, J=4.8 Hz, J=2.3 Hz), 7.68 (1H, d, J=8.7 Hz), 3.55 (2H, septet, J=6.8 Hz), 1.43 (9H, s), 1.17 (6H, d, J=6.8 Hz).

The compounds in the table below were all prepared following the general method as outlined in Intermediate 128:

| Int. | Structure | Chemical name | $^1$H NMR (DMSO-d$_6$; 400 MHz) δ [ppm] |
|---|---|---|---|
| 129 | 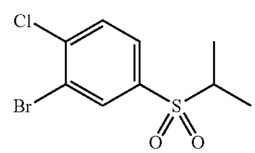 | 2-bromo-1-chloro-4-(isopropylsulfonyl)benzene | 8.18 (1H, d, J = 2.1 Hz), 7.95 (1H, d, J = 8.4 Hz), 7.86 (1H, dd, J = 8.4 Hz, J = 2.1 Hz), 3.58 (2H, septet, J = 6.8 Hz), 1.17 (6H, d, J = 6.8 Hz). |
| 130 | 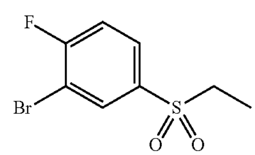 | 2-bromo-4-(ethylsulfonyl)-1-fluorobenzene | 8.21-8.19 (1H, dd, J = 2.2 Hz, J = 6.4 Hz), 7.96-7.92 (1H, m), 7.69-7.64 (1H, t, J = 8.64 Hz), 3.41-3.35 (2H, dd), 1.11-1.07 (3H, t). |
| 131 | 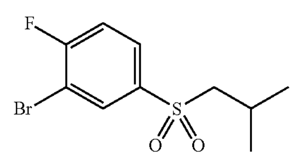 | 2-bromo-1-fluoro-4-(isobutylsulfonyl)benzene | 8.24-8.22 (1H, dd, J = 2.2 Hz, J = 6.4 Hz), 7.98-7.95 (1H, m), 7.68-7.64 (1H, t, J = 8.64 Hz), 3.32-3.30 (2H, d), 2.02 (1H, t), 0.97 (6H, t). |
| 132 | 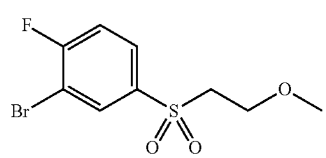 | 2-bromo-1-fluoro-4-[(2-methoxyethyl)sulfonyl]benzene | 8.21-8.19 (1H, dd, J = 2.2 Hz, J = 6.4 Hz), 7.95-7.91 (1H, m), 7.64 (1H, t, J = 8.7 Hz), 3.70-3.67 (2H, m), 3.63-3.59 (1H, m), 3.07 (3H, s). |

Intermediate 133 tert-butyl(4-chloro-2-{[2-fluoro-5-(isopropylsulfonyl)phenyl]ethynyl}phenoxy)acetate

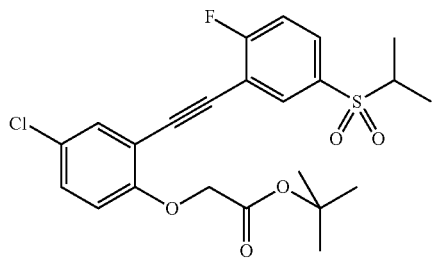

Following the general method as outlined in Intermediate 107, starting from (4-chloro-2-ethynyl-phenoxy)-acetic acid tert-butyl ester (Intermediate 3) and 2-bromo-1-fluoro-4-(isopropylsulfonyl)benzene (Intermediate 128), the title compound was obtained as a white solid after purification by flash column chromatography (silica), eluting with cyclohexane containing increasing amounts of EtOAc.

$^1$H NMR (300 MHz, DMSO-d$_6$) δ [ppm] 8.09 (1H, dd, J=6.5 Hz, J=2.4 Hz), 7.99 (1H, ddd, J=8.7 Hz, J=4.8 Hz, J=2.4 Hz), 7.70-7.64 (2H, m), 7.48 (1H, dd, J=9.0 Hz, J=2.7 Hz), 7.04 (1H, d, J=9.0 Hz), 4.83 (2H, s), 3.55 (2H, septet, J=6.8 Hz), 1.43 (9H, s), 1.19 (6H, d, J=6.8 Hz).

Intermediate 134 tert-butyl(4-chloro-2-{[2-chloro-5-(isopropylsulfonyl)phenyl]ethynyl}phenoxy)acetate

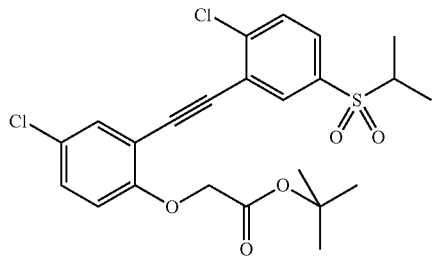

Following the general method as outlined in Intermediate 107, starting from (4-chloro-2-ethynyl-phenoxy)-acetic acid tert-butyl ester (Intermediate 3) and 2-bromo-1-chloro-4-(isopropylsulfonyl)benzene (Intermediate 129), the title compound was obtained as a white solid after purification by flash column chromatography (silica), eluting with cyclohexane containing increasing amounts of EtOAc.

$^1$H NMR (300 MHz, DMSO-d$_6$) δ [ppm] 8.09 (1H, d, J=1.9 Hz), 7.93-7.85 (2H, m), 7.66 (1H, d, J=2.7 Hz), 7.48 (1H, dd, J=9.0 Hz, J=2.7 Hz), 7.05 (1H, d, J=9.0 Hz), 4.83 (2H, s), 3.55 (2H, septet, J=6.8 Hz), 1.43 (9H, s), 1.19 (6H, d, J=6.8 Hz).

Intermediate 135 tert-butyl(4-chloro-2-{[5-(ethylsulfonyl)-2-fluorophenyl]ethynyl}phenoxy)acetate

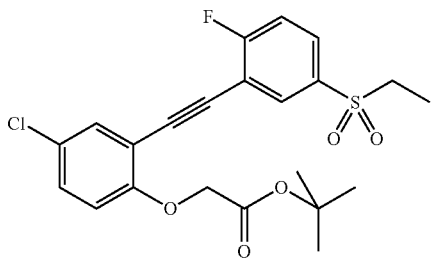

Following the general method as outlined in Intermediate 107, starting from (4-chloro-2-ethynyl-phenoxy)-acetic acid tert-butyl ester (Intermediate 3) and 2-bromo-4-ethanesulfonyl-1-fluoro-benzene (Intermediate 130), the title compound was obtained as a colorless oil in 86% yield after purification by flash column chromatography (silica), eluting with cyclohexane containing increasing amounts of EtOAc.

$^1$H NMR (300 MHz, DMSO-d$_6$) δ [ppm] 8.13 (dd, J=6.4, 2.3 Hz, 1H), 7.85 (ddd, J=7.1, 4.6, 2.4 Hz, 1H), 7.48 (d, J=2.6 Hz, 1H), 7.27 (m, 2H), 6.71 (d, J=8.9 Hz, 1H), 4.60 (s, 2H), 3.13 (t, J=7.5 Hz, 2H), 1.46 (s, 9H), 1.28 (t, J=7.4 Hz, 3H), (, H). HPLC (Condition A) Purity 95.8%; Rt 5.8 min.

Intermediate 136 tert-butyl(4-chloro-2-{[2-fluoro-5-(isobutylsulfonyl)phenyl]ethynyl}phenoxy)acetate

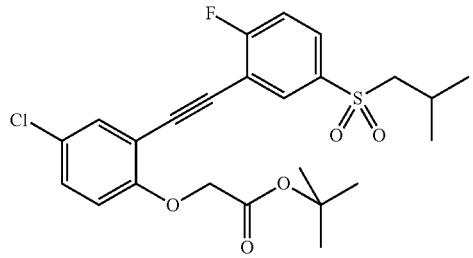

Following the general method as outlined in Intermediate 107, starting from (4-chloro-2-ethynyl-phenoxy)-acetic acid tert-butyl ester (Intermediate 3) and 2-Bromo-1-fluoro-4-(2-methyl-propane-1-sulfonyl)-benzene (Intermediate 131), the title compound was obtained as a colorless oil in 99% yield after purification by flash column chromatography (silica), eluting with cyclohexane containing increasing amounts of EtOAc.

$^1$H NMR (300 MHz, DMSO-d$_6$) δ [ppm] 8.12 (dd, J=6.4, 2.6 Hz, 1H), 7.85 (ddd, J=7.1, 4.8, 2.4 Hz, 1H), 7.48 (d, J=2.6 Hz, 1H), 7.27 (m, 2H), 6.72 (d, J=9.1 Hz, 1H), 4.61 (s, 2H), 2.99 (d, J=6.4 Hz, 2H), 2.24 (septet, J=6.8 Hz, 1H), 1.47 (s, 9H), 1.06 (d, J=6.9 Hz, 6H). HPLC (Condition A) Purity 100.0%; Rt 6.3 min.

Intermediate 137 tert-butyl[4-chloro-2-({2-fluoro-5-[(2-methoxyethyl)sulfonyl]phenyl}ethynyl)phenoxy]acetate

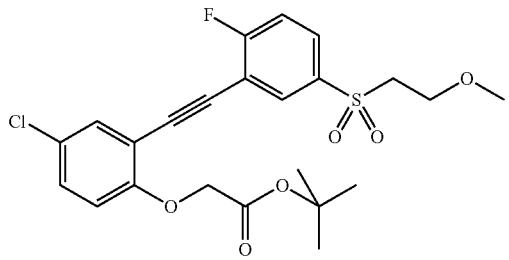

Following the general method as outlined in Intermediate 107, starting from (4-chloro-2-ethynyl-phenoxy)-acetic acid tert-butyl ester (Intermediate 3) and 2-Bromo-1-fluoro-4-(2-methoxy-ethanesulfonyl)-benzene (Intermediate 132), the title compound was obtained as a colorless oil in 80% yield after purification by flash column chromatography (silica), eluting with cyclohexane containing increasing amounts of EtOAc.

$^1$H NMR (300 MHz, DMSO-d$_6$) δ [ppm] 8.12 (dd, J=6.4, 2.4 Hz, 1H), 7.84 (ddd, J=7.1, 4.7, 2.4 Hz, 1H), 7.48 (d, J=2.6 Hz, 1H), 7.25 (m, 2H), 6.71 (d, J=8.9 Hz, 1H), 4.60 (s, 2H), 3.73 (t, J=6.1 Hz, 2H), 3.36 (t, J=6.2 Hz, 2H), 3.21 (t, 3H), 1.46 (s, 9H). $^1$H NMR (DMSO-d6) δ. HPLC (Condition A) Purity 99.0%; Rt 5.8 min.

Intermediate 138

3-bromo-4-fluoro-N,N-dimethylbenzenesulfonamide

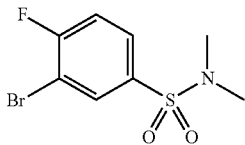

Step 1

4-fluoro-N,N-dimethylbenzenesulfonamide

A cooled (0° C.) solution of 4-fluorobenzenesulfonyl chloride (2.00 g; 10.3 mmol) in THF (40 ml) is treated with a 2 M solution of dimethylamine in THF (11.3 ml; 22.6 mmol) and stirred at 0° C. for 30 minutes. The solvents were removed under reduced pressure, the residue taken up in EtOAc, the organic phase was washed with a saturated solution of NH$_4$Cl twice and with water. The organic phase was dried on MgSO$_4$, filtered and the solvent removed under reduced pressure to afford the title compound (1.80 g, 86%).

Step 2

3-bromo-4-fluoro-N,N-dimethylbenzenesulfonamide

A solution of 4-fluoro-N,N-dimethylbenzenesulfonamide (1.80 g; 8.86 mmol) in conc. sulfuric acid (7 ml; 130 mmol) was treated with N-bromosuccinimide (1 730 mg; 9.74 mmol) and stirred at RT for 3 h. The reaction mixture was carefully poured on crushed ice, extracted with AcOEt and the organic phase was washed with a 0.1 N solution of NaOH in water twice, then with brine twice. The organic phase was dried on MgSO$_4$, filtered and concentrated under reduced pressure to give the title compound as a white solid (2.04 g, 82%).

$^1$H NMR (300 MHz, DMSO-d$_6$) δ [ppm] 8.04 (1H, dd, J=6.5 Hz, J=2.2 Hz), 7.83 (1H, ddd, J=8.7 Hz, J=4.6 Hz, J=2.3 Hz), 7.66 (1H, t, J=8.7 Hz), 2.65 (6H, s).

The compounds in the table below were all prepared following the general method as outlined in Intermediate 138:

| Int. | Structure | Chemical name | $^1$H NMR (CDCl$_3$, 400 MHz), δ [ppm] |
|---|---|---|---|
| 139 | 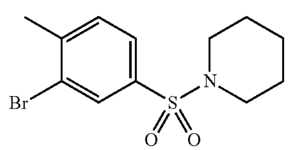 | 1-[(3-bromo-4-methylphenyl)sulfonyl]piperidine | 7.84 (1H, s), 7.64-7.63 (2H, m), 2.89 (1H, t, J = 5.5 Hz), 2.44 (3H, s), 1.54 (4H, m), 1.37 (2H, m). |
| 140 | 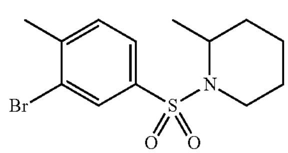 | 1-[(3-bromo-4-methylphenyl)sulfonyl]-2-methylpiperidine | 7.98 (s, 1H), 7.66-7.64 (d, 1H, J = 8 Hz), 7.35-7.33 (d, 1H, J = 8 Hz), 4.25-4.24 (s, 1H), 3.73-3.70 (m, 1H), 3.0-2.9 (t, 1H), 2.46 (s, 3H), 1.62-1.37 (m, 7H), 1.10-1.08 (bs, 3H) |
| 141 | 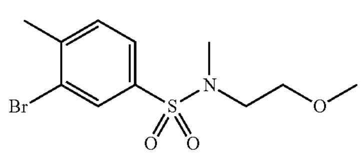 | 3-bromo-N-(2-methoxyethyl)-N,4-dimethylbenzenesulfonamide | 7.97-7.96 (s, 1H), 7.63-7.61 (d, 1H, J = 9.8 Hz), 7.38-7.36 (d, 1H, J = 8.0 Hz) 3.56-3.53 (t, 2H), 3.33 (s, 3H), 3.26-3.23 (t, 2H), 2.85 (s, 3H), 2.47 (s, 3H) |

| Int. | Structure | Chemical name | $^1$H NMR (CDCl$_3$, 400 MHz), δ [ppm] |
|---|---|---|---|
| 142 | 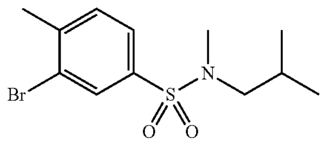 | 3-bromo-N-isobutyl-N,4-dimethylbenzenesulfonamide | 7.95-7.94 (s, 1H), 7.62-7.60 (d, 1H, J = 8.0 Hz), 7.39-7.37 (d, 1H, J = 8 Hz), 2.77-2.75 (d, 2H, J = 7.5 Hz), 2.72 (s, 3H), 2.47 (s, 3H), 1.90-1.83 (m, 1H), 0.96-0.94 (d, 6H, J = 6.6 Hz) |
| 143 | 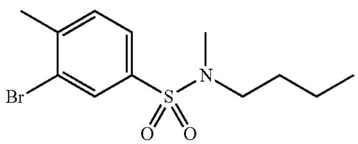 | 3-bromo-N-butyl-N,4-dimethylbenzenesulfonamide | 7.94 (s, 1H), 7.60 (d, 1H, J = 9.6 Hz), 7.37 (d, 1H, J = 8.0 Hz), 3.02-2.99 (t, 2H), 2.72 (s, 3H), 2.47 (s, 3H) 1.55-1.48 (m, 2H), 1.38-1.33 (m, 2H), 0.95-0.91 (t, 3H) |
| 144 | 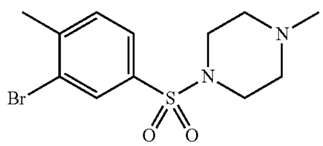 | 1-[(3-bromo-4-methylphenyl)sulfonyl]-4-methylpiperazine | 7.91-7.87 (s, 1H), 7.59-7.57 (d, 1H, J = 9.7 Hz), 7.40-7.38 (d, 1H, J = 7.9 Hz), 3.04 (bs, 4H), 2.50-2.47 (m, 7H), 2.28 (s, 3H) |
| 145 | 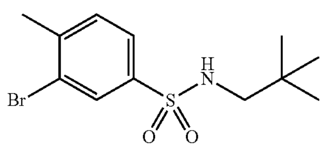 | 3-bromo-N-(2,2-dimethylpropyl)-4-methylbenzenesulfonamide | 8.03-8.02 (s, 1H), 7.69 (d, 1H, J = 9.8 Hz), 7.37 (d, 1H, J = 8.0 Hz), 4.65-4.61 (bs, 1H), 2.69 (d, 2H, J = 6.8 Hz), 0.89 (s, 9H). |
| 146 | 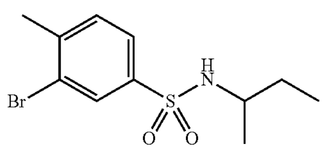 | 3-bromo-N-(sec-butyl)-4-methylbenzenesulfonamide | 8.05 (s, 1H) 7.71 (d, 1H, J = 9.8 Hz); 7.36 (s, 1H); 4.75 (bs, 1H) 3.29-3.22 (m, 1H); 2.46 (s, 3H), 1.45-1.38 (m, 2H); 1.04 (d, 3H, J = 6.5); 0.83-0.79 (t, 3H). |
| 147 | 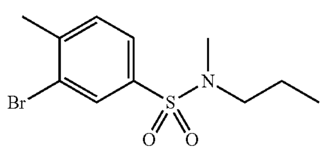 | 3-bromo-N,4-dimethyl-N-propylbenzenesulfonamide | 7.94 (s, 1H), 7.60 (d, 1H, J = 9.8 Hz), 7.37 (d, 1H, J = 8.0 Hz), 2.98-2.95 (t, 2H), 2.73 (s, 3H), 2.4 (s, 3H), 1.59-1.53 (m, 2H), 0.94-0.91 (t, 3H) |
| 148 | 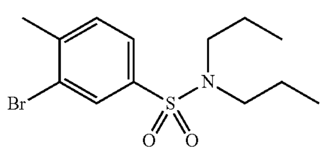 | 3-bromo-4-methyl-N,N-dipropylbenzenesulfonamide | 7.97 (s, 1H), 7.63 (d, 1H, J = 9.8 Hz), 7.35 (d, 1H, J = 8.0 Hz), 3.09-3.06 (t, 4H), 2.4 (s, 3H), 1.59-1.53 (m, 4H), 0.9-0.8 (t, 6H) |
| 149 | 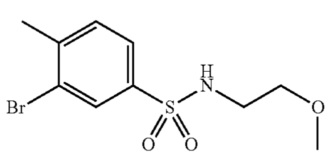 | 3-bromo-N-(2-methoxyethyl)-4-methylbenzenesulfonamide | 8.02 (s, 1H), 7.7 (d, 1H, J = 9.8 Hz), 7.37 (d, 1H, J = 8.0 Hz), 4.9 (bs, 1H), 3.43-3.41 (t, 2H), 3.29 (s, 3H), 3.15-3.11 (t, 2H), 2.47 (s, 3H) |
| 150 | 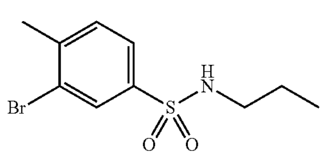 | 3-bromo-4-methyl-N-propylbenzenesulfonamide | 8.04 (s, 1H), 7.70 (d, 1H, J = 9.8 Hz), 7.38 (d, 1H, J = 8.0 Hz), 4.53-4.50 (m, 1H), 2.96-2.91 (m, 2H), 2.47 (s, 3H), 1.54-1.48 (m, 2H), 0.91-0.87 (m, 3H) |
| 151 | 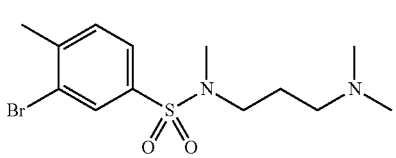 | 3-bromo-N-[3-(dimethylamino)propyl]-N,4-dimethylbenzenesulfonamide | 7.92 (s, 1H), 7.62 (d, 1H, J = 9.8 Hz), 7.41 (d, 1H, J = 8.0 Hz), 3.16-3.10 (m, 4H), 2.8 (s, 3H), 2.78 (s, 6H), 2.48 (s, 3H), 2.19-2.15 (m, 2H) |

-continued

| Int. | Structure | Chemical name | $^1$H NMR (CDCl$_3$, 400 MHz), δ [ppm] |
|---|---|---|---|
| 152 | 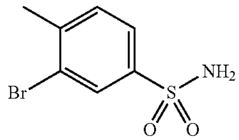 | 3-bromo-4-methylbenzenesulfonamide | 7.96 (s, 1H), 7.70 (d, 1H, J = 8.0 Hz), 7.54 (d, 1H, J = 8.0 Hz), 7.44 (s, 2H), 2.40 (s, 3H) |
| 153 | 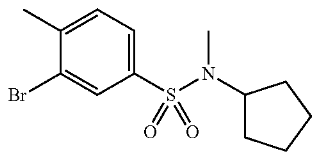 | 3-bromo-N-cyclopentyl-N,4-dimethylbenzenesulfonamide | 7.96 (s, 1H), 7.63 (d, 1H, J = 9.8 Hz), 7.36 (d, 1H, J = 7.8 Hz), 4.39-4.30 (m, 1H), 2.72 (s, 3H), 2.47 (s, 3H). |
| 154 | 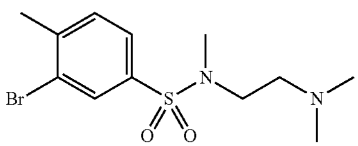 | bromo-N-[2-(dimethylamino)ethyl]-N,4-dimethylbenzenesulfonamide | 7.98 (s, 1H), 7.62 (d, 1H, J = 9.8 Hz), 7.38 (d, 1H, J = 8 Hz), 3.15-3.12 (t, 2H), 2.8 (s, 3H), 2.51-2.47 (t, 2H), 2.26 (s, 6H) |
| 155 | 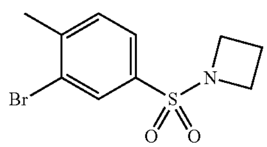 | 1-[(3-bromo-4-methylphenyl)sulfonyl]azetidine | 8.02 (s, 1H), 7.68 (d, 1H, J = 9.7 Hz), 7.44 (d, 1H, J = 7.9 Hz), 3.82-3.78 (t, 4H), 2.51 (s, 3H), 2.15-2.07 (m, 2H) |

Intermediate 156 tert-butyl(4-chloro-2-{[2-methyl-5-(piperidin-1-yl-sulfonyl)phenyl]ethynyl}phenoxy)acetate

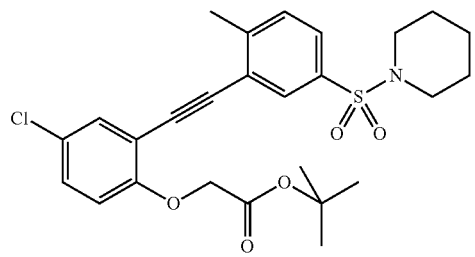

Following the general method as outlined in Intermediate 20, starting from (4-chloro-2-ethynyl-phenoxy)-acetic acid tert-butyl ester (Intermediate 3) and 1-[(3-bromo-4-methylphenyl)sulfonyl]piperidine (Intermediate 139), the title compound was obtained as a yellow solid after purification by flash column chromatography (silica), eluting with cyclohexane containing increasing amounts of EtOAc.

$^1$H NMR (300 MHz, DMSO-d$_6$) δ [ppm] 7.78 (1H, d, J=1.8 Hz), 7.67-7.59 (3H, m), 7.45 (1H, dd, J=9.0 Hz, J=2.7 Hz), 7.04 (1H, d, J=9.0 Hz), 4.81 (2H, s), 2.91 (4H, m), 2.57 (3H, s); 1.55 (4H, m), 1.43 (9H, s), 1.40 (2H, m).

Intermediate 157 tert-butyl[4-chloro-2-({5-[(dimethylamino)sulfonyl]-2-fluorophenyl]ethynyl)phenoxy}acetate

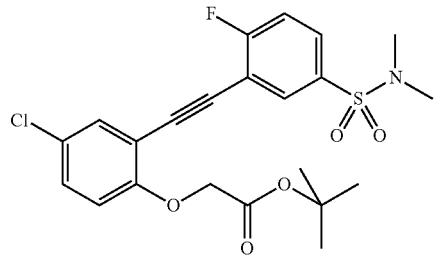

Following the general method as outlined in Intermediate 107, starting from (4-chloro-2-ethynyl-phenoxy)-acetic acid tert-butyl ester (Intermediate 3) and 3-bromo-4-fluoro-N,N-dimethylbenzenesulfonamide (Intermediate 138), the title compound was obtained as a colorless oil after purification by flash column chromatography (silica), eluting with cyclohexane containing increasing amounts of EtOAc.

$^1$H NMR (300 MHz, DMSO-d$_6$) δ [ppm] 7.99 (1H, dd, J=6.5 Hz, J=2.4 Hz), 7.85 (1H, ddd, J=8.7 Hz, J=4.8 Hz, J=2.4 Hz), 7.67-7.61 (2H, m), 7.48 (1H, dd, J=9.0 Hz, J=2.7 Hz), 7.04 (1H, d, J=9.0 Hz), 4.82 (2H, s), 2.67 (6H, s).

Intermediate 158 tert-butyl[4-chloro-2-({2-methyl-5-[(2-methylpiperidin-1-yl)sulfonyl]phenyl}ethynyl)phenoxy]acetate

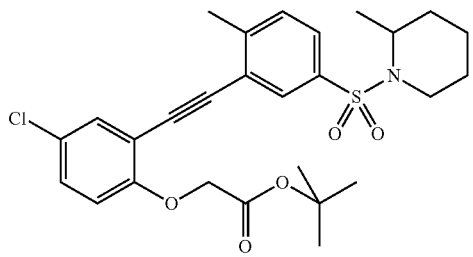

Following the general method as outlined in Intermediate 20, starting from (4-chloro-2-ethynyl-phenoxy)-acetic acid tert-butyl ester (Intermediate 3) and 1-(3-bromo-4-methyl-benzenesulfonyl)-2-methyl-piperidine (Intermediate 140), the title compound was obtained as a yellow sticky solid after purification by flash column chromatography (silica), eluting with cyclohexane containing increasing amounts of EtOAc.

$^1$H NMR (300 MHz, DMSO-d$_6$) δ [ppm] 7.85 (1H, d, J=2.0 Hz), 7.72 (1H, dd, J=8.1 Hz, J=2.0 Hz), 7.66 (1H, d, J=2.7 Hz), 7.56 (1H, d, J=8.1 Hz), 7.44 (1H, dd, J=9.0 Hz, J=2.7 Hz), 7.04 (1H, d, J=9.0 Hz), 4.81 (2H, s), 4.14 (1H, m), 3.63 (1H, m), 2.98 (1H, dt, J=13.0 Hz, J=2.5 Hz), 2.55 (3H, s), 1.40-1.56 (14H, m), 1.21 (1H, m), 1.00 (3H, d, J=6.9 Hz). HPLC (Condition A) Purity 99.6%; Rt 6.4 min.

Intermediate 159 tert-butyl{4-chloro-2-[(5-{[(2-methoxyethyl)(methyl)amino]sulfonyl}-2-methylphenyl)ethynyl]phenoxy}acetate

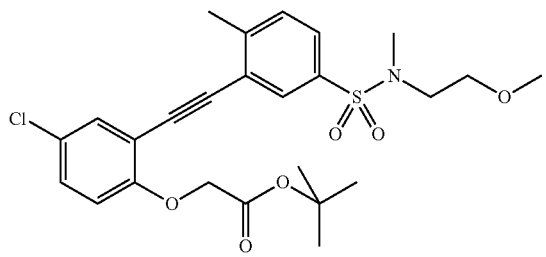

Following the general method as outlined in Intermediate 20, starting from (4-chloro-2-ethynyl-phenoxy)-acetic acid tert-butyl ester (Intermediate 3) and 3-bromo-N-(2-methoxyethyl)-4,N-dimethyl-benzenesulfonamide (Intermediate 141), the title compound was obtained as a yellow sticky solid after purification by flash column chromatography (silica), eluting with cyclohexane containing increasing amounts of EtOAc.

$^1$H NMR (300 MHz, DMSO-d$_6$) δ [ppm] 7.84 (1H, d, J=1.9 Hz), 7.70 (1H, dd, J=8.1 Hz, J=1.9 Hz), 7.66 (1H, d, J=2.7 Hz), 7.58 (1H, d, J=8.1 Hz), 7.45 (1H, dd, J=9.0 Hz, J=2.7 Hz), 7.03 (1H, d, J=9.0 Hz), 4.81 (2H, s), 3.45 (2H, t, J=5.3 Hz), 3.22 (3H, s), 3.17 (2H, t, J=5.3 Hz), 2.73 (3H, s), 2.56 (3H, s), 1.43 (9H, s). HPLC (Condition A) Purity 97.1%; Rt 5.8 min.

Intermediate 160 tert-butyl{4-chloro-2-[(5-{[isobutyl(methyl)amino]sulfonyl}-2-methylphenyl)ethynyl]phenoxy}acetate

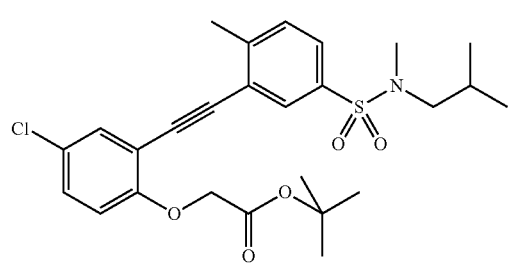

Following the general method as outlined in Intermediate 20, starting from (4-chloro-2-ethynyl-phenoxy)-acetic acid tert-butyl ester (Intermediate 3) and 3-bromo-N-isobutyl-4,N,dimethyl-benzenesulfonamide (Intermediate 142), the title compound was obtained as a yellow sticky solid after purification by flash column chromatography (silica), eluting with cyclohexane containing increasing amounts of EtOAc.

$^1$H NMR (300 MHz, DMSO-d$_6$) δ [ppm] 7.81 (1H, d, J=2.0 Hz), 7.68 (1H, dd, J=8.0 Hz, J=2.0 Hz), 7.67 (1H, d, J=2.7 Hz), 7.59 (1H, d, J=8.0 Hz), 7.45 (1H, dd, J=9.0 Hz, J=2.7 Hz), 7.03 (1H, d, J=9.0 Hz), 4.81 (2H, s), 2.71 (2H, d, J=7.4 Hz), 2.66 (3H, s), 2.56 (3H, s), 1.84 (1H, m), 1.43 (9H, s), 0.87 (6H, d, J=6.6 Hz). HPLC (Condition A) Purity 100.0%; Rt 6.4 min.

Intermediate 161 tert-butyl{2-[(5-{[butyl(methyl)amino]sulfonyl}-2-methylphenyl)ethynyl]-4-chlorophenoxy}acetate

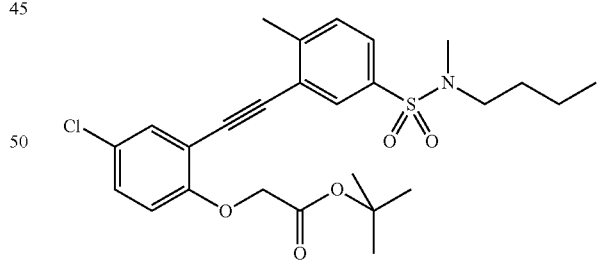

Following the general method as outlined in Intermediate 20, starting from (4-chloro-2-ethynyl-phenoxy)-acetic acid tert-butyl ester (Intermediate 3) and 3-bromo-N-butyl-4,N,dimethyl-benzenesulfonamide (Intermediate 143), the title compound was obtained as a yellow sticky solid after purification by flash column chromatography (silica), eluting with cyclohexane containing increasing amounts of EtOAc.

$^1$H NMR (300 MHz, DMSO-d$_6$) δ [ppm] 7.82 (1H, d, J=1.9 Hz), 7.69 (1H, dd, J=8.1 Hz, J=1.9 Hz), 7.66 (1H, d, J=2.7 Hz), 7.59 (1H, d, J=8.1 Hz), 7.45 (1H, dd, J=9.0 Hz, J=2.7 Hz), 7.04 (1H, d, J=9.0 Hz), 4.81 (2H, s), 2.95 (2H, t, J=7.0

Hz), 2.66 (3H, s), 2.56 (3H, s), 1.45 (2H, m), 1.43 (9H, s), 1.28 (2H, m), 0.88 (3H, t, J=7.3 Hz). HPLC (Condition A) Purity 95.6%; Rt 6.4 min.

Intermediate 162 tert-butyl[4-chloro-2-({2-methyl-5-[(4-methylpiperazin-1-yl)sulfonyl]phenyl}ethynyl)phenoxy]acetate

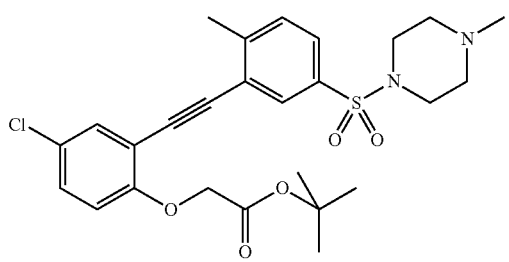

Following the general method as outlined in Intermediate 20, starting from (4-chloro-2-ethynyl-phenoxy)-acetic acid tert-butyl ester (Intermediate 3) and 1-(3-bromo-4-methyl-benzenesulfonyl)-4-methyl-piperazine (Intermediate 144), the title compound was obtained after purification by flash column chromatography (silica), eluting with cyclohexane containing increasing amounts of EtOAc.

$^1$H NMR (300 MHz, DMSO-$d_6$) δ [ppm] 7.79 (1H, d, J=1.6 Hz), 7.63-7.67 (3H, m), 7.45 (1H, dd, J=9.0 Hz, J=2.7 Hz), 7.04 (1H, d, J=9.0 Hz), 4.81 (2H, s), 2.91 (4H, m), 2.58 (3H, s), 2.36 (4H, m), 2.13 (3H, s), 1.43 (9H, s). HPLC (Condition A) Purity 94.4%; Rt 4.2 min.

Intermediate 163 tert-butyl{4-chloro-2-[(5-{[(2,2-dimethylpropyl)amino]sulfonyl}-2-methylphenyl)ethynyl]phenoxy}acetate

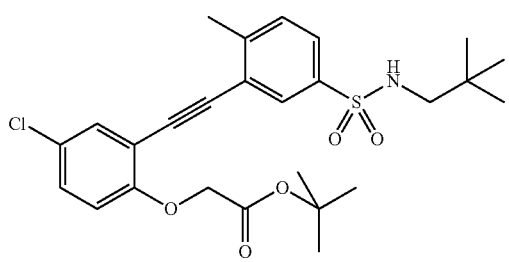

Following the general method as outlined in Intermediate 20, starting from (4-chloro-2-ethynyl-phenoxy)-acetic acid tert-butyl ester (Intermediate 3) and 3-bromo-N-(2,2-dimethyl-propyl)-4-methyl-benzenesulfonamide (Intermediate 145), the title compound was obtained after purification by flash column chromatography (silica), eluting with cyclohexane containing increasing amounts of EtOAc.

$^1$H NMR (300 MHz, DMSO-$d_6$) δ [ppm] 7.87 (1H, d, J=2.0 Hz), 7.70 (1H, dd, J=8.0 Hz, J=2.0 Hz), 7.64 (1H, d, J=2.7 Hz), 7.53-7.61 (2H, m), 7.44 (1H, dd, J=9.0 Hz; J=2.7 Hz), 7.03 (1H, d, J=9.0 Hz), 4.82 (2H, s), 2.54 (3H, s), 1.42 (9H, s), 0.83 (9H, s) (3 remaining protons, probably hidden under the signal of DMSO). HPLC (Condition A) Purity 94.0%; Rt 5.7 min.

Intermediate 164 tert-butyl[2-({5-[(sec-butylamino)sulfonyl]-2-methylphenyl}ethynyl)-4-chlorophenoxy]acetate

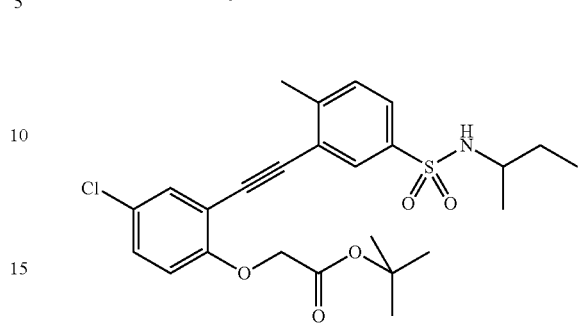

Following the general method as outlined in Intermediate 20, starting from (4-chloro-2-ethynyl-phenoxy)-acetic acid tert-butyl ester (Intermediate 3) and 3-bromo-N-sec-butyl-4-methyl-benzenesulfonamide (Intermediate 146), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 7.87 (1H, d, J=2.0 Hz), 7.71 (1H, dd, J=8.0 Hz, J=2.0 Hz), 7.65 (1H, d, J=2.7 Hz), 7.53-7.57 (2H, m), 7.44 (1H, dd, J=9.0 Hz, J=2.7 Hz), 7.03 (1H, d, J=9.0 Hz), 4.82 (2H, s), 3.05 (1H, m), 2.54 (3H, s), 1.42 (9H, s), 1.30 (2H, quint., J=7.0 Hz), 0.87 (3H, d, J=6.6 Hz), 0.72 (3H, t, J=7.0 Hz). HPLC (Condition A) Purity 92.2%; Rt 5.7 min.

Intermediate 165 tert-butyl{4-chloro-2-[(2-methyl-5-{[methyl(propyl)amino]sulfonyl}phenyl)ethynyl]phenoxy}acetate

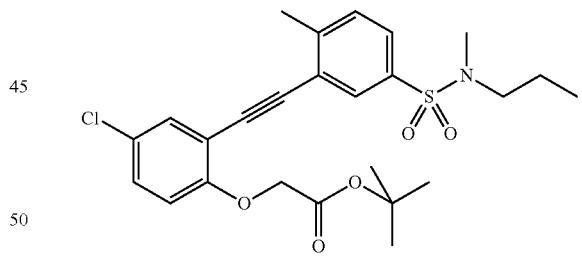

Following the general method as outlined in Intermediate 20, starting from (4-chloro-2-ethynyl-phenoxy)-acetic acid tert-butyl ester (Intermediate 3) and 3-bromo-4,N-dimethyl-N,propyl-benzenesulfonamide (Intermediate 147), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 7.82 (1H, d, J=2.0 Hz), 7.69 (1H, dd, J=8.1 Hz, J=2.0 Hz), 7.66 (1H, d, J=2.7 Hz), 7.59 (1H, d, J=8.1 Hz), 7.45 (1H, dd, J=9.0 Hz, J=2.7 Hz), 7.04 (1H, d, J=9.0 Hz), 4.81 (2H, s), 2.92 (2H, t, J=7.2 Hz), 2.67 (3H, s), 2.56 (3H, s), 1.48 (2H, sext., J=7.2 Hz), 1.43 (9H, s), 0.85 (3H, t, J=7.2 Hz). HPLC (Condition A) Purity 98.4%; Rt 5.9 min.

Intermediate 166 tert-butyl[4-chloro-2-({5-[(dipropylamino)sulfonyl]-2-methylphenyl]ethynyl)phenoxy}acetate

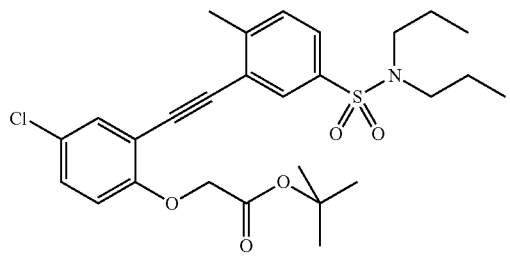

Following the general method as outlined in Intermediate 20, starting from (4-chloro-2-ethynyl-phenoxy)-acetic acid tert-butyl ester (Intermediate 3) and 3-bromo-4-methyl-N,N-dipropyl-benzenesulfonamide (Intermediate 148), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 7.84 (1H, d, J=2.0 Hz), 7.72 (1H, dd, J=8.1 Hz, J=2.0 Hz), 7.66 (1H, d, J=2.7 Hz), 7.56 (1H, d, J=8.1 Hz), 7.44 (1H, dd, J=9.0 Hz, J=2.7 Hz), 7.03 (1H, d, J=9.0 Hz), 4.81 (2H, s), 3.04 (4H, m), 2.55 (3H, s), 1.46 (4H, m), 1.43 (9H, s), 0.82 (6H, t, J=7.4 Hz). HPLC (Condition A) Purity 97.8%; Rt 6.3 min.

Intermediate 167 tert-butyl{4-chloro-2-[(5-{[(2-methoxyethyl)amino]sulfonyl}-2-methylphenyl)ethynyl]phenoxy}acetate

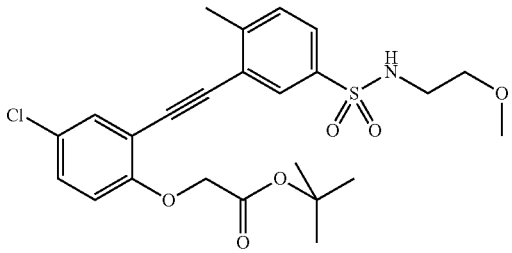

Following the general method as outlined in Intermediate 20, starting from (4-chloro-2-ethynyl-phenoxy)-acetic acid tert-butyl ester (Intermediate 3) and 3-bromo-N-(2-methoxyethyl)-4-methyl-benzenesulfonamide (Intermediate 149), the title compound was obtained as a orange sticky solid after purification by flash column chromatography (silica), eluting with cyclohexane containing increasing amounts of EtOAc.

$^1$H NMR (300 MHz, DMSO-$d_6$) δ [ppm] 7.87 (1H, d, J=2.0 Hz), 7.77 (1H, t, J=5.8 Hz), 7.70 (1H, dd, J=8.0 Hz, J=2.0 Hz), 7.64 (1H, d, J=2.7 Hz), 7.55 (1H, d, J=8.0 Hz), 7.44 (1H, dd, J=9.0 Hz, J=2.7 Hz), 7.03 (1H, d, J=9.0 Hz), 4.82 (2H, s), 3.30 (2H, t, J=5.8 Hz), 3.16 (3H, s), 2.91 (2H, q, J=5.8 Hz), 2.55 (3H, s), 1.42 (9H, s). HPLC (Condition A) Purity 97.2%; Rt 5.4 min.

Intermediate 168 tert-butyl[4-chloro-2-({2-methyl-5-[(propylamino)sulfonyl]phenyl}ethynyl)phenoxy]acetate

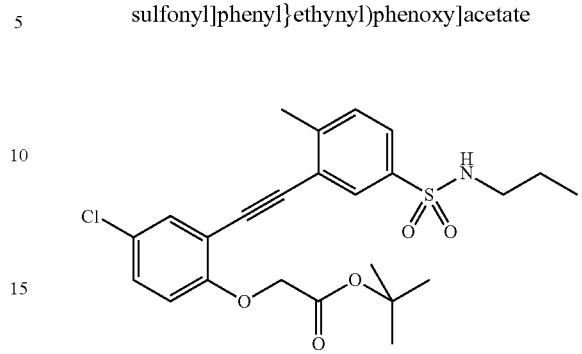

Following the general method as outlined in Intermediate 20, starting from (4-chloro-2-ethynyl-phenoxy)-acetic acid tert-butyl ester (Intermediate 3) and 3-bromo-4-methyl-N-propyl-benzenesulfonamide (Intermediate 150), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 7.85 (1H, d, J=2.0 Hz), 7.69 (1H, dd, J=8.1 Hz, J=2.0 Hz), 7.64 (1H, d, J=2.7 Hz), 7.61 (1H, bs), 7.56 (1H, d, J=8.1 Hz), 7.45 (1H, dd, J=9.0 Hz, J=2.7 Hz), 7.03 (1H, d, J=9.0 Hz), 4.82 (2H, s), 2.70 (2H, t, J=6.9 Hz), 2.55 (3H, s), 1.43 (9H, s), 1.37 (2H, m), 0.79 (3H, t, J=7.3 Hz). HPLC (Condition A) Purity 95.4%; Rt 5.8 min.

Intermediate 169 tert-butyl{4-chloro-2-[(5-{[[3-(dimethylamino)propyl](methyl)amino]sulfonyl}-2-methylphenyl)ethynyl]phenoxy}acetate

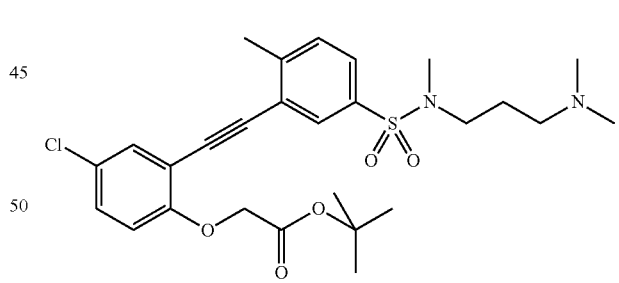

Following the general method as outlined in Intermediate 20, starting from (4-chloro-2-ethynyl-phenoxy)-acetic acid tert-butyl ester (Intermediate 3) and 3-bromo-N-(3-dimethylamino-propyl)-4,N-dimethyl-benzenesulfonamide (Intermediate 151), the title compound was obtained after purification by preparative HPLC.

$^1$H NMR (300 MHz, DMSO-$d_6$) δ [ppm] 7.84 (1H, d, J=2.0 Hz), 7.71 (1H, dd, J=8.1 Hz, J=2.0 Hz), 7.65 (1H, d, J=2.7 Hz), 7.61 (1H, d, J=8.1 Hz), 7.45 (1H, dd, J=9.0 Hz, J=2.7 Hz), 7.04 (1H, d, J=9.0 Hz), 4.82 (2H, s), 3.00-3.05 (4H, m), 2.73 (6H, s), 2.70 (3H, s), 2.57 (3H, s), 1.84-1.93 (2H, m), 1.43 (9H, s). HPLC (Condition A) Purity 98.5%; Rt 5.0 min.

Intermediate 170 tert-butyl(2-{[5-(aminosulfonyl)-2-methylphenyl]ethynyl}-4-chlorophenoxy)acetate

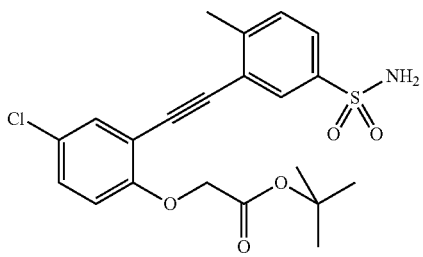

Following the general method as outlined in Intermediate 20, starting from (4-chloro-2-ethynyl-phenoxy)-acetic acid tert-butyl ester (Intermediate 3) and 3-bromo-4-methylbenzenesulfonamide (Intermediate 152), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 7.90 (1H, d, J=2.0 Hz), 7.73 (1H, dd, J=8.0 Hz, J=2.0 Hz), 7.63 (1H, d, J=2.7 Hz), 7.53 (1H, d, J=8.0 Hz), 7.44 (1H, dd, J=9.0 Hz, J=2.7 Hz), 7.40 (2H, bs), 7.02 (1H, d, J=9.0 Hz), 4.82 (2H, s), 2.54 (3H, s), 1.43 (9H, s). HPLC (Condition A) Purity 93.1%; Rt 5.0 min.

Intermediate 171 tert-butyl{4-chloro-2-[(5-{[cyclopentyl(methyl)amino]sulfonyl}-2-methylphenyl)ethynyl]phenoxy}acetate

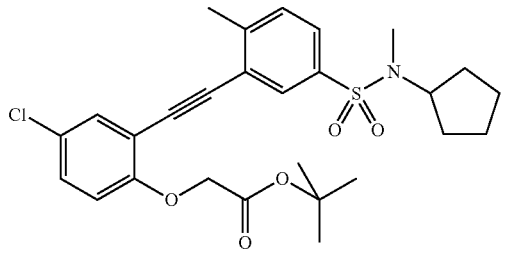

Following the general method as outlined in Intermediate 20, starting from (4-chloro-2-ethynyl-phenoxy)-acetic acid tert-butyl ester (Intermediate 3) and 3-bromo-N-cyclopentyl-4,N-dimethyl-benzenesulfonamide (Intermediate 153), the title compound was obtained as a orange sticky solid after purification by flash column chromatography (silica), eluting with cyclohexane containing increasing amounts of EtOAc.

$^1$H NMR (300 MHz, DMSO-$d_6$) δ [ppm] 7.84 (1H, d, J=2.0 Hz), 7.71 (1H, dd, J=8.0 Hz, J=2.0 Hz), 7.66 (1H, d, J=2.7 Hz), 7.57 (1H, d, J=8.0 Hz), 7.45 (1H, dd, J=9.0 Hz, J=2.7 Hz), 7.04 (1H, d, J=9.0 Hz), 4.81 (2H, s), 4.25 (1H, quint., J=7.7 Hz), 2.66 (3H, s), 2.56 (3H, s), 1.31-1.53 (17H, m). HPLC (Condition A) Purity 87.7%; Rt 6.1 min.

Intermediate 172 tert-butyl{4-chloro-2-[(5-{[[2-(dimethylamino)ethyl](methyl)amino]sulfonyl}-2-methylphenyl)ethynyl]phenoxy}acetate

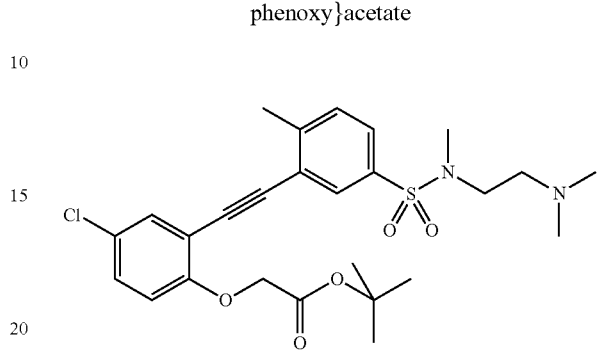

Following the general method as outlined in Intermediate 20, starting from (4-chloro-2-ethynyl-phenoxy)-acetic acid tert-butyl ester (Intermediate 3) and 3-bromo-N-(2-dimethylamino-ethyl)-4,N-dimethyl-benzenesulfonamide (Intermediate 154), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 7.85 (1H, d, J=2.0 Hz), 7.71 (1H, dd, J=8.0 Hz, J=2.0 Hz), 7.663 (1H, d, J=2.7 Hz), 7.58 (1H, d, J=8.0 Hz), 7.45 (1H, dd, J=9.0 Hz, J=2.7 Hz), 7.04 (1H, d, J=9.0 Hz), 4.81 (2H, s), 3.07 (2H, t, J=6.6 Hz), 2.72 (3H, s), 2.56 (3H, s), 2.37 (2H, t, J=6.6 Hz), 2.13 (6H, s), 1.43 (9H, s). HPLC (Condition A) Purity 95.2%; Rt 4.2 min.

Intermediate 173 tert-butyl(2-{[5-(azetidin-1-ylsulfonyl)-2-methylphenyl]ethynyl}-4-chlorophenoxy)acetate

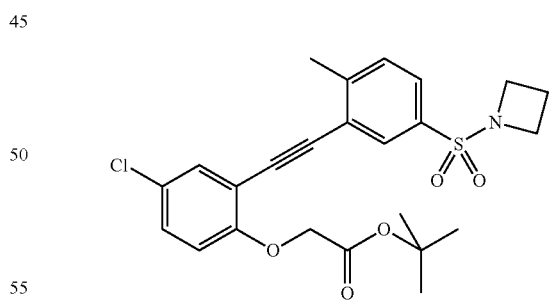

Following the general method as outlined in Intermediate 20, starting from (4-chloro-2-ethynyl-phenoxy)-acetic acid tert-butyl ester (Intermediate 3) and 1-(3-bromo-4-methylbenzenesulfonyl)-azetidine (Intermediate 155), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 7.85 (1H, d, J=2.0 Hz), 7.73 (1H, dd, J=8.0 Hz, J=2.0 Hz), 7.65-7.68 (2H, m), 7.45 (1H, dd, J=9.0 Hz, J=2.7 Hz), 7.03 (1H, d, J=9.0 Hz), 4.82 (2H, s), 3.69 (4H, t, J=7.7 Hz), 2.60 (3H, s), 2.01 (2H, quint., J=7.7 Hz), 1.43 (9H, s). HPLC (Condition A) Purity 96.9%; Rt 5.6 min.

Intermediate 174

4-(4-bromobenzoyl)morpholine

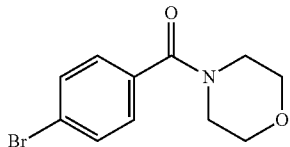

A cooled (0° C.) solution of 4-bromobenzoyl chloride (250 mg; 1.14 mmol) in THF (5 ml) was treated with a 2 M solution of morpholine in THF (219 µl; 2.51 mmol). The reaction mixture was allowed to warm to RT and stirred for 2 days, diluted with EtOAc and washed with a saturated NH$_4$Cl solution in water. The organic phase was dried over MgSO$_4$, filtered and concentrated to dryness affording the title compound as a pink solid (307 mg, quantitative yield).

$^1$H NMR (300 MHz, DMSO-d$_6$) δ [ppm] 7.65 (2H, d, J=8.5 Hz), 7.37 (2H, d, J=8.5 Hz), 3.59 (6H, bs), 3.33 (2H, bs). HPLC (Condition A) Purity 94.2%; Rt 2.6 min.

Intermediate 175 tert-butyl(4-chloro-2-{[4-(morpholin-4-ylcarbonyl)phenyl]ethynyl}phenoxy)acetate

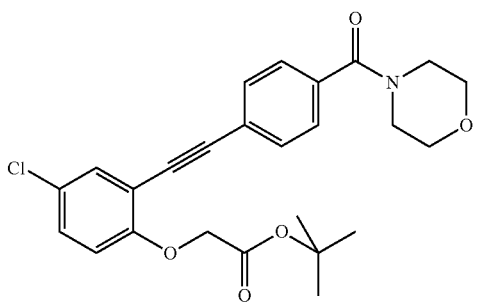

Following the general method as outlined in Intermediate 20, starting from (4-chloro-2-ethynyl-phenoxy)-acetic acid tert-butyl ester (Intermediate 3) and 4-(4-bromobenzoyl)morpholine (Intermediate 174), the title compound was obtained as a brown sticky solid after purification by flash column chromatography (silica), eluting with cyclohexane containing increasing amounts of EtOAc.

$^1$H NMR (300 MHz, DMSO-d$_6$) δ [ppm] 7.59-7.62 (3H, m), 7.41-7.49 (3H, m), 7.00 (1H, d, J=9.0 Hz), 4.81 (2H, s), 3.60 (6H, bs), 1.43 (9H, s) (2 remaining protons, probably hidden under the signal of water). HPLC (Condition A) Purity 98.4%; Rt 5.0 min.

Intermediate 176

4-bromo-N,N-dimethylbenzamide

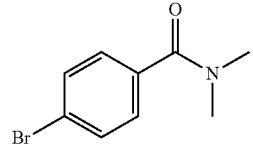

Following the general method as outlined in Intermediate 174, starting from 4-bromobenzoyl chloride and dimethylamine, the title compound was obtained as a pink solid in 93% yield.

$^1$H NMR (300 MHz, DMSO-d$_6$) δ [ppm] 7.63 (2H, d, J=8.5 Hz), 7.36 (2H, d, J=8.5 Hz), 2.97 (3H, s), 2.89 (3H, s). HPLC (Condition A) Purity 91.3%; Rt 2.7 min.

Intermediate 177 tert-butyl[4-chloro-2-({4-[(dimethylamino)carbonyl]phenyl}ethynyl)phenoxy]acetate

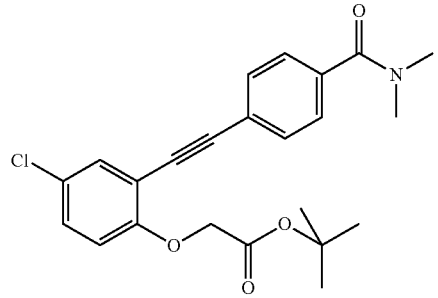

Following the general method as outlined in Intermediate 20, starting from (4-chloro-2-ethynyl-phenoxy)-acetic acid tert-butyl ester (Intermediate 3) and 4-bromo-N,N-dimethylbenzamide (Intermediate 176), the title compound was obtained as a brown sticky solid after purification by flash column chromatography (silica), eluting with cyclohexane containing increasing amounts of EtOAc.

$^1$H NMR (300 MHz, DMSO-d$_6$) δ [ppm] 7.57-7.60 (3H, m), 7.41-7.47 (3H, m), 6.99 (1H, d, J=9.0 Hz), 4.81 (2H, s), 2.99 (3H, s), 2.91 (3H, s), 1.43 (9H, s). HPLC (Condition A) Purity 99.5%; Rt 5.0 min.

Intermediate 178

4-(3-bromobenzoyl)morpholine

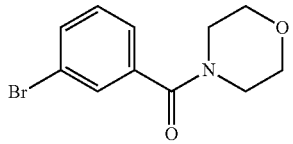

Following the general method as outlined in Intermediate 174, starting from 3-bromobenzoyl chloride and morpholine, the title compound was obtained as a colorless sticky solid in 71% yield.

$^1$H NMR (300 MHz, DMSO-d$_6$) δ [ppm] 7.66 (1H, m), 7.61 (1H, m), 7.41 (2H, m), 3.60 (6H, bs), 3.32 (2H, bs). HPLC (Condition A) Purity 96.4%; Rt 2.6 min.

Intermediate 179 tert-butyl(4-chloro-2-{[3-(morpholin-4-ylcarbonyl)phenyl]ethynyl}phenoxy)acetate

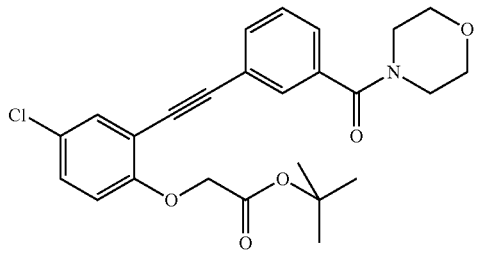

Following the general method as outlined in Intermediate 20, starting from (4-chloro-2-ethynyl-phenoxy)-acetic acid tert-butyl ester (Intermediate 3) and 4-(3-bromobenzoyl)morpholine (Intermediate 178), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 7.40-7.63 (6H, m), 7.00 (1H, d, J=9.0 Hz), 4.81 (2H, s), 3.61 (6H, bs), 1.43 (9H, s) (2 remaining protons, probably hidden under the signal of water). HPLC (Condition A) Purity 96.6%; Rt 4.8 min.

Intermediate 180

3-bromo-N,N-dimethylbenzamide

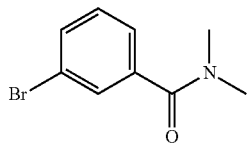

Following the general method as outlined in Intermediate 174, starting from 3-bromobenzoyl chloride and dimethylamine, the title compound was obtained as a orange sticky solid in 85% yield.

$^1$H NMR (300 MHz, DMSO-$d_6$) δ [ppm] 7.64 (1H, m), 7.58 (1H, m), 7.36-7.43 (2H, m), 2.97 (3H, s), 2.88 (3H, s). HPLC (Condition A) Purity 98.2%; Rt 2.6 min.

Intermediate 181 tert-butyl[4-chloro-2-({3-[(dimethylamino)carbonyl]phenyl}ethynyl)phenoxy]acetate

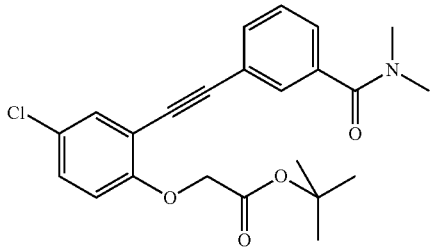

Following the general method as outlined in Intermediate 20, starting from (4-chloro-2-ethynyl-phenoxy)-acetic acid tert-butyl ester (Intermediate 3) and 3-bromo-N,N-dimethylbenzamide (Intermediate 180), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 7.37-7.61 (6H, m), 6.99 (1H, d, J=9.0 Hz), 4.81 (2H, s), 2.99 (3H, s), 2.92 (3H, s), 1.43 (9H, s). HPLC (Condition A) Purity 99.0%; Rt 5.5 min.

Intermediate 182 tert-butyl[(3-bromo-5-chloropyridin-2-yl)oxy]acetate

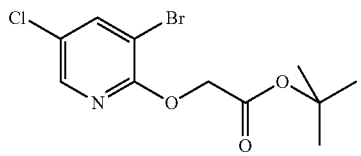

A solution of 2-tert-butyl glycolate (437 mg; 3.31 mmol) in anhydrous THF (5 mL) was treated with NaH (159 mg; 3.97 mmol) and stirred at RT for 10 minutes before treating with a solution of 3-bromo-2,5-dichloropyridine (Matrix; 500 mg; 2.20 mmol) in anhydrous THF (5 mL). The resulting reaction mixture was stirred for 22 hours. The reaction mixture was treated with a solution of 2-tert-butyl glycolate (437 mg; 3.31 mmol) in THF (2 ml), then with NaH (159 mg; 3.97 mmol) and the reaction mixture was stirred for 16 h. The reaction was quenched with tBuOH, the solvent removed under reduced pressure affording a brown solid, which was purified by flash column chromatography (silica), eluting with cyclohexane containing increasing amounts of EtOAc, affording the title compound as a yellow sticky solid.

$^1$H NMR (300 MHz, DMSO-$d_6$) δ [ppm] 8.33 (1H, d, J=2.3 Hz), 8.21 (1H, d, J=2.3 Hz), 4.86 (2H, s), 1.38 (9H, s). HPLC (Condition A) Rt 5.1 min.

Intermediate 183 tert-butyl[(5-chloro-3-{[3-(propylsulfonyl)phenyl]ethynyl}pyridin-2-yl)oxy]acetate

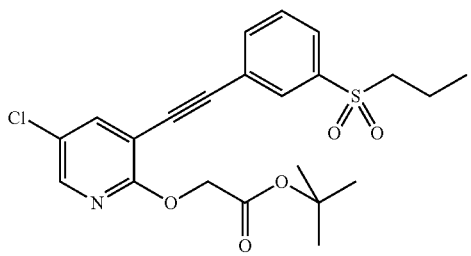

A mixture of tert-butyl[(3-bromo-5-chloropyridin-2-yl)oxy]acetate (Intermediate 182; 160 mg; 0.50 mmol), 1-ethynyl-3-(propane-1-sulfonyl)-benzene (Intermediate 42; 155 mg; 0.74 mmol), bis(triphenylphosphine)palladium (II) chloride (10 mg; 0.01 mmol) and triphenylphosphine (26 mg; 0.10 mmol) is treated with cuprous iodide (3 mg; 0.01 mmol) and TEA (1.10 ml) and heated at 90° C. in a sealed vessel for 15 hours. The mixture was diluted with EtOAc and washed with a saturated NH$_4$Cl solution and brine. The organic phase was dried over MgSO$_4$, concentrated to dryness under reduced pressure affording a sticky solid, which was purified by column chromatography (silica), eluting with cyclohexane containing increasing amounts of EtOAc, affording the title compound as a yellow sticky solid $^1$H NMR (300 MHz, DMSO-d$_6$) δ [ppm] 8.26 (1H, d, J=2.6 Hz), 8.24 (1H, d, J=2.6 Hz), 8.04 (1H, t, J=1.5 Hz), 7.96 (1H, dt, J=7.8 Hz, J=1.5 Hz), 7.92 (1H, dt, J=7.8 Hz, J=1.5 Hz), 7.75 (1H, t, J=7.8 Hz), 4.89 (2H, s), 3.37 (2H, m), 1.56 (2H, sext., J=7.6 Hz), 1.40 (9H, s), 0.92 (3H, t, J=7.6 Hz). HPLC (Condition A) Purity 98.4%; Rt 5.6 min.

Intermediate 184 tert-butyl[(5-chloro-3-{[2-fluoro-5-(propylsulfonyl)phenyl]ethynyl}pyridin-2-yl)oxy]acetate

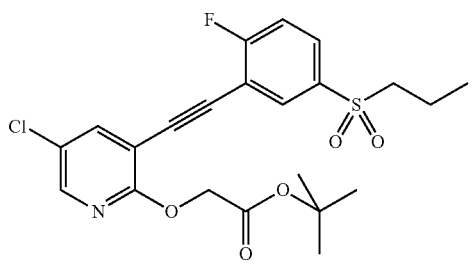

Following the general method as outlined in Intermediate 182, starting from tert-butyl[(3-bromo-5-chloropyridin-2-yl)oxy]acetate (Intermediate 183) and 2-ethynyl-1-fluoro-4-(propane-1-sulfonyl)-benzene (Intermediate 109), the title compound was obtained as a yellow sticky solid after purification by flash column chromatography (silica), eluting with cyclohexane containing increasing amounts of EtOAc.

$^1$H NMR (300 MHz, DMSO-d$_6$) δ [ppm] 8.29 (1H, d, J=2.5 Hz), 8.254 (1H, d, J=2.5 Hz), 8.15 (1H, dd, J=6.4 Hz, J=2.2 Hz), 8.02 (1H, m), 7.68 (1H, t, J=9.0 Hz), 4.89 (2H, s), 3.397 (2H, m), 1.57 (2H, sext., J=7.4 Hz), 1.40 (9H, s), 0.93 (3H, t, J=7.4 Hz). HPLC (Condition A) Purity 97.0%; Rt 5.4 min.

Intermediate 185

2-chloro-5-[(trifluoromethyl)sulfonyl]aniline

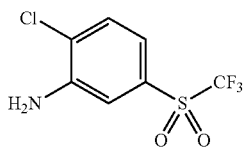

Following the general method as outlined in Intermediate 76, starting from 1-chloro-2-nitro-4-[(trifluoromethyl)sulfonyl]benzene (MDA), the title compound was obtained as a brown solid in quantitative yield.

$^1$H NMR (300 MHz, DMSO-d$_6$) δ [ppm] 7.65 (1H, d, J=8.3 Hz), 7.47 (1H, d, J=2.2 Hz), 7.16 (1H, dd, J=8.3 Hz, J=2.2 Hz), 6.29 (2H, s). HPLC (Condition A) Purity 92.2%; Rt 3.9 min.

Intermediate 186

1-chloro-2-iodo-4-[(trifluoromethyl)sulfonyl]benzene

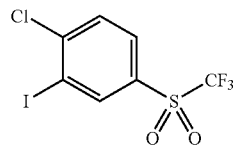

Following the general method as outlined in Intermediate 58, starting from 2-chloro-5-[(trifluoromethyl)sulfonyl]aniline (Intermediate 185), the title compound was obtained as a beige solid after purification by flash column chromatography (silica), eluting with cyclohexane containing increasing amounts of EtOAc.

$^1$H NMR (300 MHz, DMSO-d$_6$) δ [ppm] 8.53 (1H, d, J=2.2 Hz), 8.15 (1H, dd, J=8.5 Hz, J=2.2 Hz), 8.03 (1H, d, J=8.5 Hz). HPLC (Condition A) Rt 5.0 min.

Intermediate 187 tert-butyl[4-chloro-2-({2-chloro-5-[(trifluoromethyl)sulfonyl]phenyl}ethynyl)phenoxy]acetate

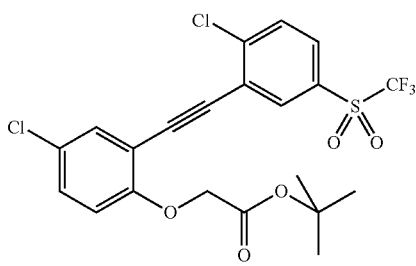

Following the general method as outlined in Intermediate 79, starting from (4-chloro-2-ethynyl-phenoxy)-acetic acid tert-butyl ester (Intermediate 3) and 1-chloro-2-iodo-4-[(trifluoromethyl)sulfonyl]benzene (Intermediate 186), the title compound was obtained as a white solid in 72% yield after purification by flash column chromatography (silica), eluting with cyclohexane containing increasing amounts of EtOAc.

$^1$H NMR (300 MHz, DMSO-d$_6$) δ [ppm] 8.39 (1H, d, J=2.2 Hz), 8.16 (1H, dd, J=8.6 Hz, J=2.2 Hz), 8.08 (1H, d, J=8.6 Hz), 7.70 (1H, d, J=2.7 Hz), 7.50 (1H, dd, J=9.0 Hz, J=2.0 Hz), 7.06 (1H, d, J=9.0 Hz), 4.83 (2H, s), 1.43 (9H, s). HPLC (Condition A) Purity 100.0%; Rt 6.1 min.

Intermediate 188 tert-butyl[(3-bromobiphenyl-4-yl)oxy]acetate

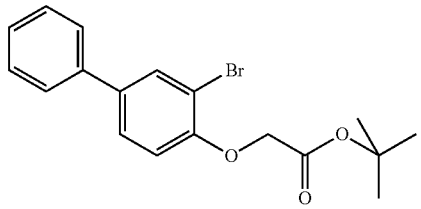

Following the general method as outlined in Intermediate 1, starting from 3-bromo[1,1'-biphenyl]-4-ol and tert-butyl bromoacetate (Matrix), the title compound was obtained as a colorless sticky solid after purification by flash column chromatography (silica), eluting with cyclohexane containing increasing amounts of EtOAc.

$^1$H NMR (300 MHz, DMSO-$d_6$) δ [ppm] 7.88 (1H, d, J=2.3 Hz), 7.61-7.66 (3H, m), 7.41-7.47 (2H, m), 7.34 (1H, m), 7.06 (1H, d, J=8.7 Hz), 4.83 (2H, s), 1.44 (9H, s). HPLC (Condition A) Purity 94.2%; Rt 5.6 min.

Intermediate 189

4-Bromo-2-iodophenol

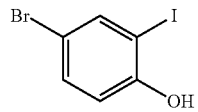

A solution of 4-bromophenol (35.0 g, 145 mmol) in acetic acid (250 ml) was treated with N-iodosuccinimide (32.5 g, 145 mmol) at RT. The reaction mixture was stirred at RT for 18 h. The reaction mixture was filtered to remove the solid and the filtrate was concentrated under reduced pressure. The crude material was purified by column chromatography (silica) eluting with 1% methanol in chloroform to afford the title compound as a brown liquid.

$^1$H NMR (300 MHz, DMSO-$d_6$) δ [ppm] 10.59 (1H, s), 7.78 (1H, s), 7.35 (1H, d), 6.82 (1H, d). MS (ESI$^+$): 296.6. HPLC (Method D) Purity 99.3%; Rt 3.81 min.

Intermediate 190 tert-Butyl (4-bromo-2-iodophenoxy)acetate

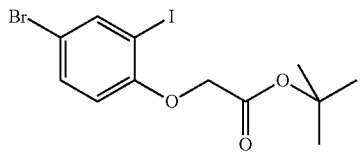

Following the general method as outlined in Intermediate 1, starting from 4-bromo-2-iodophenol (Intermediate 189), the title compound was obtained as a brown oil after purification by flash column chromatography (silica), eluting with 2% methanol in chloroform.

$^1$H NMR (300 MHz, DMSO-$d_6$) δ [ppm] 7.92 (1H, t), 7.51 (1H, p), 6.83 (1H, d), 4.76 (2H, s), 1.40 (9H, s). MS (ESI$^+$): 355.0. HPLC (Condition A) Purity 96.7%; Rt 6.03 min.

Intermediate 191 tert-butyl(4-bromo-2-{[3-(propylsulfonyl)phenyl]ethynyl}phenoxy)acetate

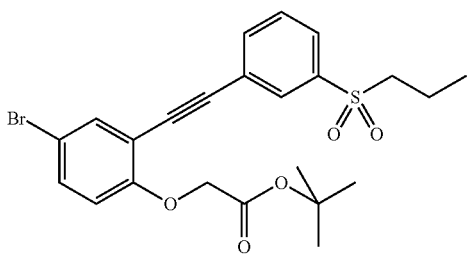

Following the general method as outlined in Intermediate 20, starting from (4-bromo-2-iodo-phenoxy)-acetic acid tert-butyl ester (Intermediate 190) and 1-ethynyl-3-(propane-1-sulfonyl)-benzene (Intermediate 42), the title compound was obtained as a yellow sticky solid after purification by flash column chromatography (silica), eluting with cyclohexane containing increasing amounts of EtOAc.

$^1$H NMR (300 MHz, DMSO-$d_6$) δ [ppm] 8.02 (1H, t, J=1.6 Hz), 7.84-7.94 (2H, m), 7.77 (1H, d, J=2.5 Hz), 7.73 (1H, t, J=7.8 Hz), 7.57 (1H, dd, J=9.0 Hz, J=2.5 Hz), 6.96 (1H, d, J=9.0 Hz), 4.82 (2H, s), 3.36 (2H, m); 1.57 (2H, sext., J=7.6 Hz), 1.73 (9H, s), 0.92 (3H, t, J=7.6 Hz). HPLC (Condition A) Purity 100.0%; Rt 5.4 min.

Intermediate 192 tert-butyl(4-(2,4-dimethyl-1,3-thiazol-5-yl)-2-{[3-(propylsulfonyl)phenyl]ethynyl}phenoxy)acetate

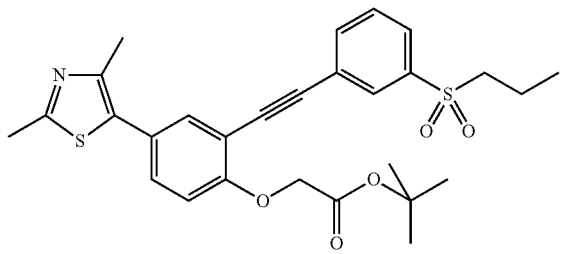

A solution of tert-butyl(4-bromo-2-{[3-(propylsulfonyl)phenyl]ethynyl}phenoxy)acetate (Intermediate 191; 100 mg; 0.20 mmol), 2,4-dimethyl-5-(4,4,5,5-tetramethyl-1,3,2-dioxaborolan-2-yl)-1,3-thiazole (73 mg; 0.30 mmol) was placed in a microwave vial and treated with caesium fluoride (93 mg; 0.61 mmol) and bis(triphenylphosphine)palladium (II) chloride (14 mg; 0.02 mmol). The tube was sealed and degased with N$_2$ before adding dioxane (2 ml) and water (1 ml). The resulting reaction mixture was irradiated in a microwave reactor at 120° C. for 10 minutes. The reaction mixture was taken up in EtOAc and washed with water and brine. The organic phase was dried over MgSO$_4$, filtered, concentrated and purified by flash column chromatography (silica), eluting with cyclohexane containing increasing amounts of EtOAc affording the title compound as a brown sticky solid (78 mg, 73%).

$^1$H NMR (300 MHz, DMSO-$d_6$) δ [ppm] 8.02 (1H, t, J=1.5 Hz), 7.89-7.93 (2H, m), 7.73 (1H, t, J=7.8 Hz), 7.60 (1H, d, J=2.4 Hz), 7.46 (1H, dd, J=8.8 Hz), 7.05 (1H, d, J=7.8 Hz), 4.86 (2H, s), 3.36 (2H, m), 2.62 (3H, s), 2.36 (3H, s), 1.57 (2H, sext., J=7.5 Hz), 1.45 (9H, s), 0.93 (3H, t, J=7.5 Hz). HPLC (Condition A) Purity 97.7%; Rt 4.5 min.

Intermediate 193 tert-butyl[1-{[3-(propylsulfonyl)phenyl]ethynyl}-4-(2-thienyl)phenoxy]acetate

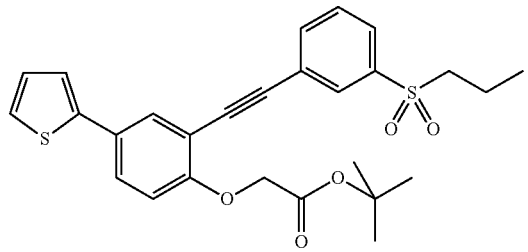

Following the general method as outlined in Intermediate 192, starting from tert-butyl(4-bromo-2-{[3-(propylsulfonyl)phenyl]ethynyl}phenoxy)acetate (Intermediate 191) and 2-(4,4,5,5-tetramethyl-1,3,2-dioxaborolan-2-yl)thiophene, the title compound was obtained as a yellow sticky solid in 99% yield after purification by flash column chromatography (silica), eluting with cyclohexane containing increasing amounts of EtOAc.

$^1$H NMR (300 MHz, DMSO-$d_6$) δ [ppm] 8.04 (1H, t, J=1.5 Hz), 7.90-7.94 (2H, m), 7.85 (1H, d, J=2.4 Hz), 7.74 (1H, t, J=7.8 Hz), 7.67 (1H, dd, J=8.8 Hz, J=2.4 Hz), 7.50-7.53 (2H, m), 7.13 (1H, dd, J=8.8 Hz), 7.03 (1H, d, J=8.8 Hz), 4.84 (2H, s), 3.37 (2H, m), 1.58 (2H, sext., J=7.5 Hz), 1.45 (9H, s), 0.93 (3H, t, J=7.5 Hz). HPLC (Condition A) Purity 99.2%; Rt 5.8 min.

Intermediate 194 tert-butyl(4-(1-methyl-1H-pyrazol-4-yl)-2-{[3-(propylsulfonyl)phenyl]ethynyl}phenoxy)acetate

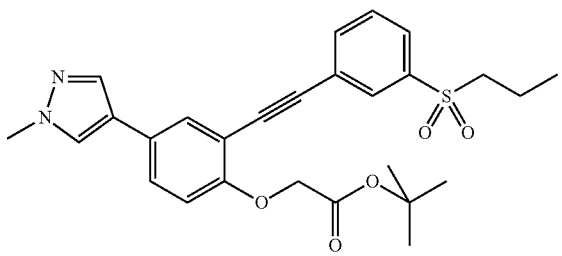

Following the general method as outlined in Intermediate 192, starting from tert-butyl(4-bromo-2-{[3-(propylsulfonyl)phenyl]ethynyl}phenoxy)acetate (Intermediate 191) and 1-methyl-1H-pyrazole-4-boronic acid, pinacol ester, the title compound was obtained as a yellow sticky solid in 79% yield after purification by flash column chromatography (silica), eluting with cyclohexane containing increasing amounts of EtOAc.

$^1$H NMR (300 MHz, DMSO-$d_6$) δ [ppm] 8.13 (1H, s), 8.01 (1H, t, J=1.5 Hz), 7.90 (2H, m), 7.86 (1H, s), 7.77 (1H, d, J=2.4 Hz), 7.73 (1H, t, J=7.8 Hz), 7.58 (1H, dd, J=8.7 Hz, J=2.4 Hz), 6.96 (1H, d, J=8.7 Hz), 4.80 (2H, s), 3.85 (3H, s), 3.37 (2H, m), 1.57 (2H, sext., J=7.5 Hz), 1.44 (9H, s), 0.93 (3H, t, J=7.5 Hz). HPLC (Condition A) Purity 98.9%; Rt 4.7 min.

Intermediate 195 tert-butyl[2-{[3-(propylsulfonyl)phenyl]ethynyl}-4-(1,3,5-trimethyl-1H-pyrazol-4-yl)phenoxy]acetate

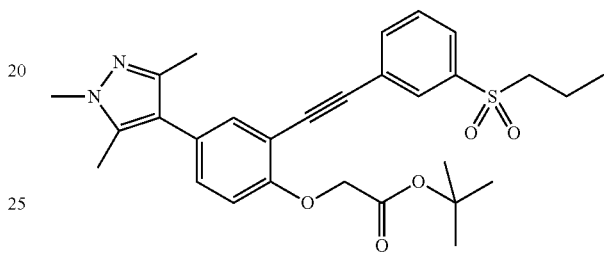

Following the general method as outlined in Intermediate 192, starting from tert-butyl(4-bromo-2-{[3-(propylsulfonyl)phenyl]ethynyl}phenoxy)acetate (Intermediate 191) and 1,3,5-trimethyl-1H-pyrazole-4-boronic acid, pinacol ester, the title compound was obtained as a black sticky solid after purification by flash column chromatography (silica), eluting with cyclohexane containing increasing amounts of EtOAc.

$^1$H NMR (300 MHz, DMSO-$d_6$) δ [ppm] 8.01 (1H, t, J=1.5 Hz), 7.80-7.92 (2H, m), 7.72 (1H, t, J=7.8 Hz), 7.39 (1H, d, J=2.2 Hz), 7.26 (1H, dd, J=8.6 Hz, J=2.2 Hz), 7.00 (1H, d, J=8.6 Hz), 4.82 (2H, s), 3.69 (3H, s), 3.37 (2H, m), 2.20 (3H, s), 2.11 (3H, s), 1.57 (2H, sext., J=7.5 Hz), 1.45 (9H, s), 0.93 (3H, t, J=7.5 Hz). HPLC (Condition A) Purity 99.2%; Rt 4.4 min.

Intermediate 196 tert-butyl[4-chloro-2-({2-methyl-5-[(methylsulfonyl)amino]phenyl}ethynyl)phenoxy]acetate

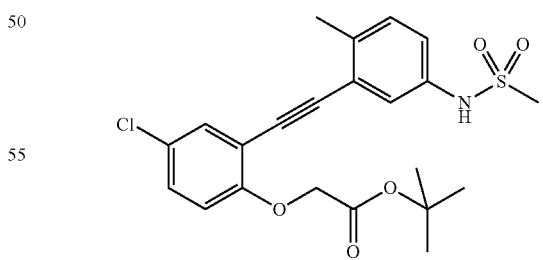

Step 1

N-(3-bromo-4-methylphenyl)methanesulfonamide

A cooled (0° C.) solution of 3-bromo-4-methylaniline (ABCR; 1.00 g; 5.37 mmol) in pyridine (20 ml) was treated with methanesulfonyl chloride (500 µl; 6.45 mmol). The reaction mixture was allowed to warm to RT and stirred for 1 hour, then EtOAc was added and the organic layer was washed with a 1N aqueous solution of HCl. The organic layer was dried over MgSO₄, filtered and concentrated to dryness to give the title compound as a brown solid (1.42 g, quantitative).

$^1$H NMR (300 MHz, DMSO-$d_6$) δ [ppm] 9.81 (1H, s), 7.40 (1H, d, J=2.1 Hz), 7.31 (1H, d, J=8.3 Hz), 7.13 (1H, d, J=8.3 Hz, J=2.1 Hz), 2.99 (3H, s), 2.29 (3H, s)

Step 2 tert-butyl[4-chloro-2-({2-methyl-5-[(methylsulfonyl) amino]phenyl}ethynyl)phenoxy]acetate Following the general method as outlined in Intermediate 20, starting from (4-chloro-2-ethynyl-phenoxy)-acetic acid tert-butyl ester (Intermediate 3) and N-(3-bromo-4-methylphenyl)methanesulfonamide, the title compound was obtained after purification by flash column chromatography (silica), eluting with cyclohexane containing increasing amounts of EtOAc.

$^1$H NMR (300 MHz, DMSO-$d_6$) δ [ppm] 9.73 (1H, bs), 7.59 (1H, d, J=2.7 Hz), 7.41 (1H, dd, J=9.0 Hz, J=2.7 Hz), 7.28-7.31 (2H, m), 7.16 (1H, dd, J=8.2 Hz, J=2.3 Hz), 7.00 (1H, d, J=9.0 Hz), 4.80 (2H, s), 2.97 (3H, s), 2.41 (3H, s), 1.42 (9H, s). HPLC (Condition A) Rt 5.3 min.

Intermediate 197

N-(3-bromo-4-methylphenyl)-N-methylmethanesulfonamide

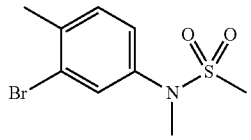

A solution of N-(3-bromo-4-methylphenyl)methanesulfonamide (Intermediate 196, step 1; 710 mg; 2.69 mmol) in anhydrous DMF (14 mL) was treated with NaH (129 mg; 3.23 mmol) followed after 5 minutes by treatment with iodomethane (200 µl; 3.23 mmol). The reaction mixture was stirred for 16 hours, then quenched with a 5 N solution of NaOH in water. The reaction mixture was stirred for few minutes and extracted with EtOAc. The organic phase was washed with water and brine, dried over MgSO₄ and concentrated to dryness affording the title compound as a brown sticky solid (730 mg, 98%).

$^1$H NMR (300 MHz, DMSO-$d_6$) δ [ppm] 7.63 (1H, d, J=2.1 Hz), 7.39 (1H, d, J=8.3 Hz), 7.33 (1H, dd, J=8.3 Hz, J=2.1 Hz), 3.22 (3H, s), 2.95 (3H, s), 2.33 (3H, s). HPLC (Condition A) Purity 98.9%; Rt 3.8 min.

Intermediate 198 tert-butyl[4-chloro-2-({2-methyl-5-[methyl(methylsulfonyl)amino]phenyl}ethynyl)phenoxy]acetate

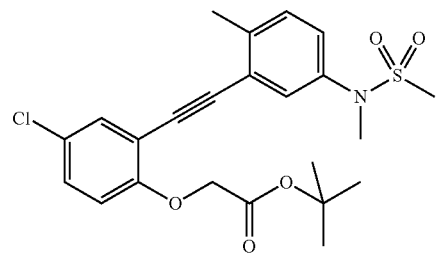

Following the general method as outlined in Intermediate 20, starting from (4-chloro-2-ethynyl-phenoxy)-acetic acid tert-butyl ester (Intermediate 3) and N-(3-bromo-4-methylphenyl)-N-methylmethanesulfonamide (Intermediate 197), the title compound was obtained after purification by flash column chromatography (silica), eluting with cyclohexane containing increasing amounts of EtOAc.

$^1$H NMR (300 MHz, DMSO-$d_6$) δ [ppm] 7.59 (1H, d, J=2.7 Hz), 7.52 (1H, t, J=1.2 Hz), 7.42 (1H, dd, J=9.0 Hz, J=2.7 Hz), 7.36 (2H, m), 7.01 (1H, d, J=9.0 Hz), 4.80 (2H, s), 3.24 (3H, s), 2.95 (3H, s), 2.46 (3H, s), 1.43 (9H, s). HPLC (Condition A) Purity 94.9%; Rt 5.6 min.

Intermediate 199

5-bromo-N,N,6-trimethylpyridine-3-sulfonamide

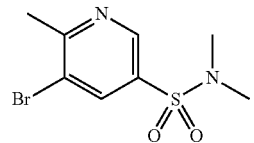

Step 1

5-bromo-6-chloropyridine-3-sulfonyl chloride

A cooled (0° C.) solution of 6-amino-5-bromopyridine-3-sulfonic acid (12.65 g; 50.00 mmol) in HCl (60 ml; 5 N solution in water) was treated carefully with a solution of sodium nitrite (3.80 g; 55.0 mmol) in water (15 ml) and stirred at 0° C. for 1 hour. The solvents were evaporated and the residue was dried under high vacuum for 2 days, then treated with phosphorus pentachloride (15.00 g; 72 mmol) and phosphorus oxide chloride (0.50 ml; 5.5 mmol). The solid mixture was heated at 125° C. to give a refluxing solution. After heating at 75° C. for 3 hours, the solution was cooled and carefully poured on crushed ice. EtOAc was added and the phases separated. The organic phase was washed with brine, dried on MgSO₄, filtered and concentrated under reduced pressure to give the title compound as a brown oil (14.91 g, quantitative yield), which was used without purification.

Step 2

5-bromo-6-chloro-N,N-dimethylpyridine-3-sulfonamide

A cooled (0° C.) solution of 5-bromo-6-chloropyridine-3-sulfonyl chloride (2.00 g; 6.87 mmol) in DCM (20 mL) was treated first with triethylamine (1.06 ml; 7.56 mmol) then with a 5.6 M solution of dimethylamine in EtOH (1.35 ml; 7.56 mmol). The reaction was stirred at 0° C. for 1.5 hours then brine was added and the phases separated. The organic phase was washed with brine, dried on $MgSO_4$, filtered and concentrated under reduced pressure to give a residue which was purified by flash column chromatography (silica), eluting with cyclohexane containing increasing amounts of EtOAc to give the title compound as a colorless oil.

Step 3 diethyl {3-bromo-5-[(dimethylamino)sulfonyl]pyridin-2-yl}malonate

A solution of 5-bromo-6-chloro-N,N-dimethylpyridine-3-sulfonamide (400 mg; 1.34 mmol) and diethyl malonate (204 µl; 1.34 mmol) in anhydrous THF (2 ml) was added to a suspension of sodium hydride (53 mg; 1.34 mmol) in anhydrous THF (2 ml). The resulting mixture was stirred for 48 hours, then quenched by careful addition of a saturated solution of $NH_4Cl$ in water. EtOAc was added and the phases separated. The organic phase was washed with brine, dried on $MgSO_4$, filtered and concentrated under reduced pressure to give a residue which was purified by flash column chromatography (silica), eluting with cyclohexane containing increasing amounts of EtOAc to give the title compound as a colorless oil.

Step 4

5-bromo-N,N,6-trimethylpyridine-3-sulfonamide

Diethyl {3-bromo-5-[(dimethylamino)sulfonyl]pyridin-2-yl}malonate (222 mg; 0.52 mmol) was treated with a 5 N solution of HCl in water (11 ml) and the resulting solution was refluxed for 6 h. The solvent was removed under reduced pressure, and the solid residue was carefully quenched with a saturated $Na_2CO_3$ solution in water. The resulting suspension was extracted with AcOEt. The organic phase was washed with brine, dried on $MgSO_4$, filtered and concentrated under reduced pressure to give the title compound as a white solid (125 mg; 86% yield).

$^1$H NMR (300 MHz, DMSO-$d_6$) δ [ppm] 8.78 (1H, d, J=2.0 Hz), 8.31 (1H, d, J=2.0 Hz), 2.70 (3H, s), 2.69 (6H, s).

Intermediate 200 tert-butyl[4-chloro-2-({5-[(dimethylamino)sulfonyl]-2-methylpyridin-3-yl}ethynyl)phenoxy]acetate

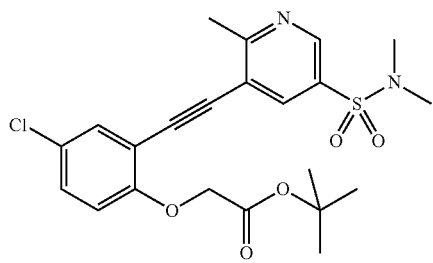

Following the general method as outlined in Intermediate 79, starting from (4-chloro-2-ethynyl-phenoxy)-acetic acid tert-butyl ester (Intermediate 3) and N-(4-bromophenyl)-4-(trifluoromethyl)benzamide (Intermediate 199), the title compound was obtained after purification by flash column chromatography (silica), eluting with cyclohexane containing increasing amounts of EtOAc.

$^1$H NMR (300 MHz, DMSO-$d_6$) δ [ppm] 8.77 (1H, d, J=2.2 Hz), 8.18 (1H, d, J=2.2 Hz), 7.70 (1H, d, J=2.7 Hz), 7.48 (1H, dd, J=9.0 Hz, J=2.7 Hz), 7.08 (1H, d, J=9.0 Hz), 4.83 (2H, s), 2.79 (3H, s), 2.69 (6H, s), 1.44 (9H, s).

Intermediate 201

1-iodo-2-(methylsulfonyl)benzene

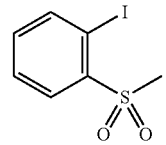

A cooled (0° C.) solution of 2-iodothioanisole (2.00 g; 8.00 mmol) in DCM (40 ml) was treated carefully with 3-chloroperbenzoic acid (3.94 g; 17.59 mmol) and the reaction mixture was stirred at RT for 20 hours. DCM was added and the reaction mixture was washed twice with NaOH 0.1N and twice with brine. The organic phase was dried over $MgSO_4$, filtered, concentrated and purified by flash chromatography (silica), eluting with cyclohexane containing increasing amounts of EtOAc to give the title compound as a white solid.

$^1$H NMR (300 MHz, DMSO-$d_6$) δ [ppm] 8.20 (1H, dd, J=7.8 Hz, J=1.5 Hz), 8.09 (1H, dd, J=7.8 Hz, J=1.5 Hz), 7.67 (1H, dt, J=7.8 Hz, J=1.5 Hz), 7.40 (1H, dt, J=7.8 Hz, J=1.5 Hz), 3.33 (3H, s). HPLC (Condition A) Rt 2.6 min.

Intermediate 202

4-bromo-1-iodo-2-(methylsulfonyl)benzene

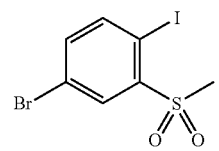

A suspension of 1-iodo-2-(methylsulfonyl)benzene (Intermediate 201; 1.45 g; 5.14 mmol) in conc. $H_2SO_4$ (4 mL) was treated with N-bromosuccinimide (1.01 g; 5.65 mmol) and the resulting mixture was stirred for 4 h. The reaction mixture was carefully poured on crushed ice and extracted with EtOAc. The organic phase was washed twice with NaOH 0.1 N and brine, dried over $MgSO_4$, filtered and concentrated to dryness affording the title compound as a white solid (1.6 g, 86%).

$^1$H NMR (300 MHz, DMSO-d$_6$) δ [ppm] 8.11 (1H, d, J=8.3 Hz), 8.10 (1H, d, J=2.4 Hz), 7.63 (1H, dd, J=8.3 Hz, J=2.4 Hz), 3.38 (3H, s). HPLC (Condition A) Purity 90.1%; Rt 3.5 min.

Intermediate 203

4-bromo-2-(methylsulfonyl)biphenyl

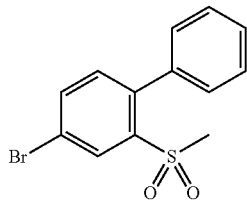

A solution of 4-bromo-1-iodo-2-(methylsulfonyl)benzene (Intermediate 202; 200 mg; 0.55 mmol), phenylboronic acid (68 mg; 0.55 mmol;) was placed in a microwave vial and treated with caesium fluoride (252 mg; 1.66 mmol) and bis(triphenylphosphine)palladium(II) chloride (39 mg; 0.06 mmol). The tube was sealed and degased with N$_2$ before adding dioxane (3 ml) and water (1.5 ml). The resulting reaction mixture was irradiated in a microwave reactor at 110° C. for 20 minutes. The reaction mixture was taken up in EtOAc and washed with water and brine. The organic phase was dried over MgSO$_4$, filtered, concentrated and purified by flash column chromatography (silica), eluting with cyclohexane containing increasing amounts of EtOAc affording the title compound as an orange sticky solid.

$^1$H NMR (300 MHz, DMSO-d$_6$) δ [ppm] 8.17 (1H, dd, J=2.2 Hz), 7.98 (1H, dd, J=8.2 Hz, J=2.2 Hz), 7.36-7.47 (6H, m), 2.86 (3H, s). HPLC (Condition A) Purity 90.7%; Rt 4.2 min.

Intermediate 204 tert-butyl(4-chloro-2-{[2-(methylsulfonyl)biphenyl-4-yl]ethynyl}phenoxy)acetate

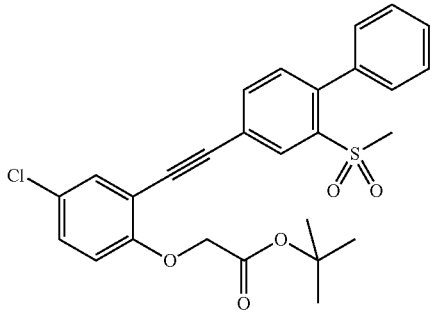

Following the general method as outlined in Intermediate 107, starting from (4-chloro-2-ethynyl-phenoxy)-acetic acid tert-butyl ester (Intermediate 3) and 4-bromo-2-(methylsulfonyl)biphenyl (Intermediate 203), the title compound was obtained as a brown sticky solid after purification by flash column chromatography (silica), eluting with cyclohexane containing increasing amounts of EtOAc.

$^1$H NMR (300 MHz, DMSO-d$_6$) δ [ppm] 8.43 (1H, d, J=1.7 Hz), 7.82 (1H, dd, J=7.9 Hz, J=1.7 Hz), 7.53 (1H, d, J=2.6 Hz), 7.46-7.49 (5H, m), 7.39 (1H, d, J=7.9 Hz), 7.28 (1H, dd, J=8.8 Hz, J=2.6 Hz), 6.75 (1H, d, J=8.8 Hz), 4.66 (2H, s), 2.66 (3H, s), 1.51 (9H, s). HPLC (Condition A) Purity 91.9%; Rt 5.8 min.

Intermediate 205

4-bromo-4'-methoxy-2-(methylsulfonyl)biphenyl

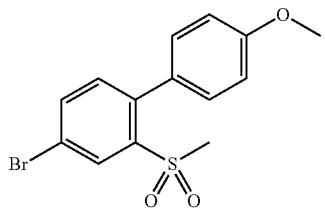

Following the general method as outlined in Intermediate 203, starting from 4-bromo-1-iodo-2-(methylsulfonyl)benzene (Intermediate 202) and 4-methoxyphenylboronic acid, the title compound was obtained as a brown solid in 73% yield after purification by flash column chromatography (silica), eluting with cyclohexane containing increasing amounts of EtOAc.

$^1$H NMR (300 MHz, DMSO-d$_6$) δ [ppm] 8.14 (1H, dd, J=2.1 Hz), 7.95 (1H, dd, J=8.1 Hz, J=2.1 Hz), 7.32-7.36 (3H, m), 7.02 (2H, d, J=8.8 Hz), 3.81 (3H, s), 2.83 (3H, s). HPLC (Condition A) Rt 4.1 min.

Intermediate 206 tert-butyl(4-chloro-2-{[4'-methoxy-2-(methylsulfonyl)biphenyl-4-yl]ethynyl}phenoxy)acetate

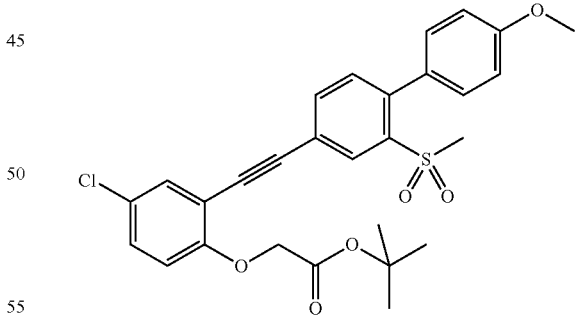

Following the general method as outlined in Intermediate 107, starting from (4-chloro-2-ethynyl-phenoxy)-acetic acid tert-butyl ester (Intermediate 3) and 4-bromo-4'-methoxy-2-(methylsulfonyl)biphenyl (Intermediate 205), the title compound was obtained as a brown sticky solid in 72% yield after purification by flash column chromatography (silica), eluting with cyclohexane containing increasing amounts of EtOAc.

$^1$H NMR (300 MHz, DMSO-d$_6$) δ [ppm] 8.17 (1H, d, J=1.7 Hz), 7.87 (1H, dd, J=7.9 Hz, J=1.9 Hz), 7.68 (1H, d, J=2.7 Hz), 7.44-7.48 (2H, m), 7.38 (2H, d, J=8.7 Hz), 7.00-7.05

(3H, m), 4.84 (2H, s), 3.82 (3H, s), 2.84 (3H, s), 1.44 (9H, s). HPLC (Condition A) Rt 5.8 min.

Intermediate 207

4-bromo-3'-methoxy-2-(methylsulfonyl)biphenyl

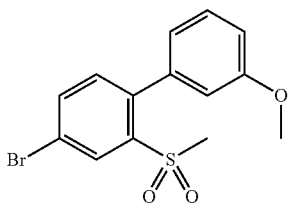

Following the general method as outlined in Intermediate 203, starting from 4-bromo-1-iodo-2-(methylsulfonyl)benzene (Intermediate 202) and 3-methoxyphenylboronic acid, the title compound was obtained as a brown sticky solid in 74% yield after purification by flash column chromatography (silica), eluting with cyclohexane containing increasing amounts of EtOAc.

$^1$H NMR (300 MHz, DMSO-$d_6$) δ [ppm] 8.16 (1H, dd, J=2.1 Hz), 7.97 (1H, dd, J=8.1 Hz, J=2.1 Hz), 7.34-7.40 (2H, m), 6.95-7.05 (3H, m), 3.77 (3H, s), 2.88 (3H, s). HPLC (Condition A) Rt 4.3 min.

Intermediate 208 tert-butyl(4-chloro-2-{[3'-methoxy-2-(methylsulfonyl)biphenyl-4-yl]ethynyl}phenoxy)acetate

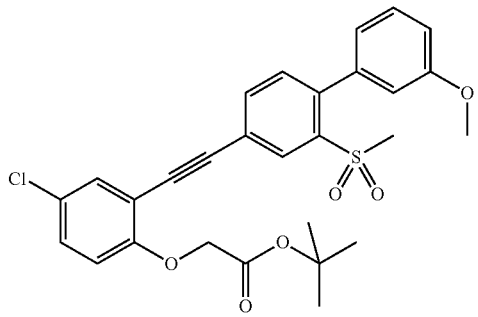

Following the general method as outlined in Intermediate 107, starting from (4-chloro-2-ethynyl-phenoxy)-acetic acid tert-butyl ester (Intermediate 3) and 4-bromo-3'-methoxy-2-(methylsulfonyl)biphenyl (Intermediate 207), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.17 (1H, d, J=1.7 Hz), 7.87 (1H, dd, J=7.9 Hz, J=1.9 Hz), 7.68 (1H, d, J=2.7 Hz), 7.44-7.48 (2H, m), 7.38 (2H, d, J=8.7 Hz), 7.00-7.05 (3H, m), 4.84 (2H, s), 3.82 (3H, s), 2.84 (3H, s), 1.44 (9H, s). HPLC (Condition A) Rt 6.3 min.

Intermediate 209

4-bromo-2-(methylsulfonyl)-4'-(trifluoromethyl)biphenyl

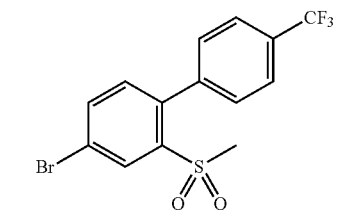

Following the general method as outlined in Intermediate 203, starting from 4-bromo-1-iodo-2-(methylsulfonyl)benzene (Intermediate 202) and 4-trifluorophenylboronic acid, the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.20 (1H, dd, J=2.1 Hz), 8.02 (1H, dd, J=8.1 Hz, J=2.1 Hz), 7.81 (2H, d, J=8.1 Hz), 7.62 (2H, d, J=8.1 Hz), 7.40 (1H, d, J=8.1 Hz), 3.02 (3H, s). HPLC (Condition A) Rt 5.3 min.

Intermediate 210 tert-butyl(4-chloro-2-{[2-(methylsulfonyl)-4'-(trifluoromethyl)biphenyl-4-yl]ethynyl}phenoxy)acetate

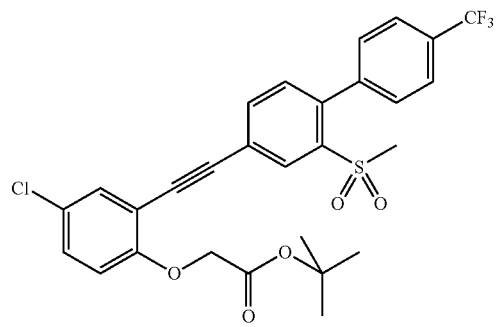

Following the general method as outlined in Intermediate 107, starting from (4-chloro-2-ethynyl-phenoxy)-acetic acid tert-butyl ester (Intermediate 3) and 4-bromo-2-(methylsulfonyl)-4'-(trifluoromethyl)biphenyl (Intermediate 209), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.21 (1H, d, J=1.7 Hz), 7.92 (1H, dd, J=8.0 Hz, J=1.7 Hz), 7.83 (1H, d, J=8.0 Hz), 7.69 (1H, d, J=2.7 Hz), 7.67 (2H, d, J=8.0 Hz), 7.51 (2H, d, J=8.0 Hz), 7.47 (1H, dd, J=9.0 Hz, J=2.7 Hz), 7.03 (1H, d, J=9.0 Hz), 4.84 (2H, s), 3.02 (3H, s), 1.44 (9H, s). HPLC (Condition A) Purity 92.2%; Rt 6.6 min.

Intermediate 211

4-bromo-4'-chloro-2-(methylsulfonyl)biphenyl

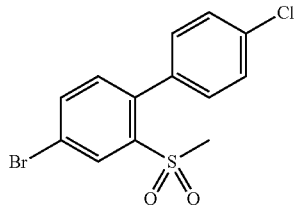

Following the general method as outlined in Intermediate 203, starting from 4-bromo-1-iodo-2-(methylsulfonyl)benzene (Intermediate 202) and 4-chlorophenylboronic acid, the title compound was obtained as a beige solid after purification by flash column chromatography (silica), eluting with cyclohexane containing increasing amounts of EtOAc.

$^1$H NMR (300 MHz, DMSO-$d_6$) δ [ppm] 8.17 (1H, dd, J=2.1 Hz), 7.99 (1H, dd, J=8.2 Hz, J=2.1 Hz), 7.52 (2H, d, J=8.6 Hz), 7.42 (2H, d, J=8.6 Hz), 7.37 (1H, d, J=8.2 Hz), 2.96 (3H, s). HPLC (Condition A) Rt 4.6 min.

Intermediate 212 tert-butyl(4-chloro-2-{[4'-chloro-2-(methylsulfonyl)biphenyl-4-yl]ethynyl}phenoxy)acetate

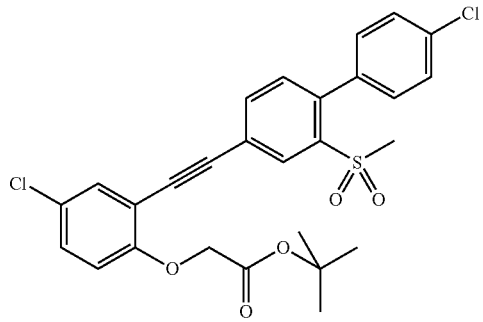

Following the general method as outlined in Intermediate 107, starting from (4-chloro-2-ethynyl-phenoxy)-acetic acid tert-butyl ester (Intermediate 3) and 4-bromo-4'-chloro-2-(methylsulfonyl)biphenyl (Intermediate 211), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.19 (1H, d, J=1.8 Hz), 7.90 (1H, dd, J=8.0 Hz, J=1.8 Hz), 7.68 (1H, d, J=2.7 Hz), 7.54 (2H, d, J=8.6 Hz), 7.44-7.50 (4H, m), 7.01 (1H, d, J=9.0 Hz), 4.84 (2H, s), 2.97 (3H, s), 1.44 (9H, s). HPLC (Condition A) Rt 5.8 min.

Intermediate 213

4-bromo-3'-chloro-2-(methylsulfonyl)biphenyl

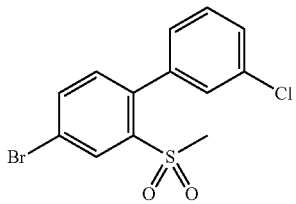

Following the general method as outlined in Intermediate 203, starting from 4-bromo-1-iodo-2-(methylsulfonyl)benzene (Intermediate 202) and 3-chlorophenylboronic acid, the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.18 (1H, dd, J=2.0 Hz), 7.99 (1H, dd, J=8.0 Hz, J=2.0 Hz), 7.45-7.55 (3H, m), 7.34-7.40 (2H, m), 2.98 (3H, s). HPLC (Condition A) Purity 90.6%; Rt 4.6 min.

Intermediate 214 tert-butyl(4-chloro-2-{[3'-chloro-2-(methylsulfonyl)biphenyl-4-yl]ethynyl}phenoxy)acetate

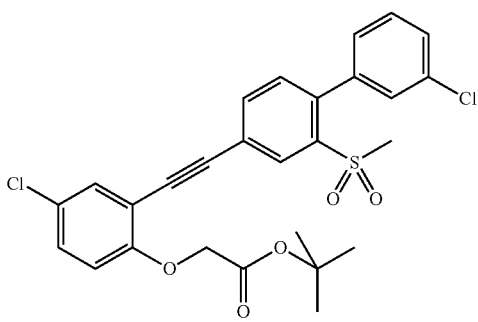

Following the general method as outlined in Intermediate 107, starting from (4-chloro-2-ethynyl-phenoxy)-acetic acid tert-butyl ester (Intermediate 3) and 4-bromo-3'-chloro-2-(methylsulfonyl)biphenyl (Intermediate 213), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.19 (1H, d, J=1.7 Hz), 7.90 (1H, dd, J=8.0 Hz, J=1.7 Hz), 7.68 (1H, d, J=2.7 Hz), 7.44-7.568 (5H, m), 7.40 (1H, dt, J=7.0 Hz, J=1.7 Hz), 7.01 (1H, d, J=9.0 Hz), 4.84 (2H, s), 2.98 (3H, s), 1.44 (9H, s). HPLC (Condition A) Purity 93.7%; Rt 6.1 min.

Intermediate 215

4-bromo-2'-chloro-2-(methylsulfonyl)biphenyl

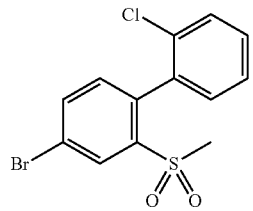

Following the general method as outlined in Intermediate 203, starting from 4-bromo-1-iodo-2-(methylsulfonyl)benzene (Intermediate 202) and 2-chlorophenylboronic acid, the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.20 (1H, dd, J=2.2 Hz), 8.01 (1H, dd, J=8.2 Hz, J=2.2 Hz), 7.56 (1H, m), 7.38-7.50 (3H, m), 7.34 (1H, d, J=8.2 Hz), 3.04 (3H, s). HPLC (Condition A) Purity 98.4%; Rt 4.4 min.

Intermediate 216 tert-butyl(4-chloro-2-{[2'-chloro-2-(methylsulfonyl)biphenyl-4-yl]ethynyl}phenoxy)acetate

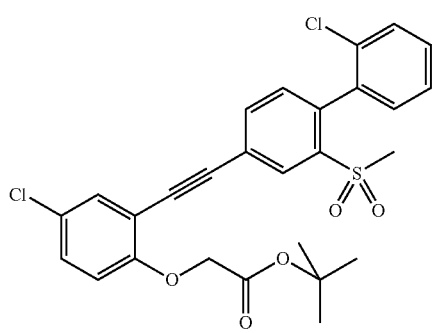

Following the general method as outlined in Intermediate 107, starting from (4-chloro-2-ethynyl-phenoxy)-acetic acid tert-butyl ester (Intermediate 3) and 4-bromo-2'-chloro-2-(methylsulfonyl)biphenyl (Intermediate 215), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 8.20 (1H, d, J=1.6 Hz), 7.92 (1H, dd, J=7.9 Hz, J=1.6 Hz), 7.68 (1H, d, J=2.7 Hz), 7.57 (1H, m), 7.40-7.51 (5H, m), 7.02 (1H, d, J=9.0 Hz), 4.85 (2H, s), 3.04 (3H, s), 1.44 (9H, s). HPLC (Condition A) Purity 96.5%; Rt 5.9 min.

Intermediate 217 tert-Butyl[(1-bromo-2-naphthyl)oxy]acetate

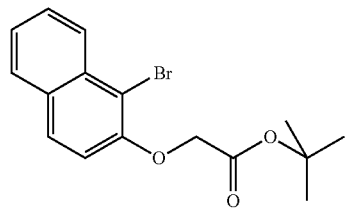

Following the general method as outlined in Intermediate 1, starting from 1-bromo-2-naphthol, the title compound was obtained as an off-white solid in 98% yield after purification by flash column chromatography (silica), eluting with petroleum ether and EtOAc (95:5).

$^1$H NMR (300 MHz, DMSO-$d_6$) δ [ppm] 8.10 (1H, d), 7.94 (2H, m), 7.61 (1H, m), 7.45 (1H, m), 7.38 (1H, d), 4.94 (2H, s), 1.42 (9H, S). MS (ESI$^+$): 279.0. HPLC (Condition A) Purity 98.0%; Rt 5.85 min.

Intermediate 218 tert-butyl[(1-{[3-(propylsulfonyl)phenyl]ethynyl}-2-naphthyl)oxy]acetate

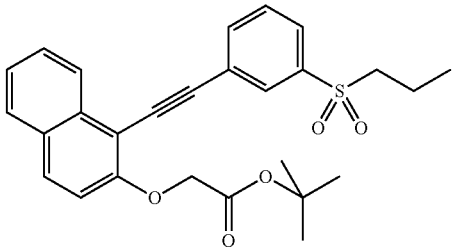

A mixture of (1-bromo-naphthalen-2-yloxy)-acetic acid tert-butyl ester (Intermediate 217; 500 mg; 1.48 mmol), 1-ethynyl-3-(propane-1-sulfonyl)-benzene (618 mg; 2.97 mmol) and PPh3 (39 mg; 0.15 mmol) in water (4.40 ml) and Acetone (5.6 ml) was treated with palladium(II) chloride (13 mg; 0.07 mmol) and piperidine (295 µl; 2.97 mmol) and heated at 60° C. for 2 days. The reaction mixture was extracted with EtOAc, the organic phase was dried over MgSO$_4$ and concentrated under reduced pressure. The resulting residue was purified by flash column chromatography (silica), eluting with cyclohexane containing increasing amounts of EtOAc to give the title compound as a yellow sticky solid.

$^1$H NMR (300 MHz, DMSO-$d_6$) δ [ppm] 8.29 (1H, d, J=8.2 Hz), 8.12 (1H, t, J=1.5 Hz), 8.01-8.04 (2H, m), 7.92-7.96 (2H, m), 7.76 (1H, t, J=7.7 Hz), 7.66 (1H, ddd, J=8.2 Hz, J=7.0 Hz, J=1.5 Hz), 7.48 (1H, ddd, J=8.2 Hz, J=7.0 Hz, J=1.5 Hz), 7.36 (1H, d, J=9.2 Hz), 4.99 (2H, s), 3.40 (2H, m), 1.60 (2H, sext., J=7.5 Hz), 1.44 (9H, s), 0.94 (3H, t, J=7.5 Hz). HPLC (Condition A) Purity 94.7%; Rt 5.4 min.

Intermediate 219

2-bromo-1-methyl-4-(propylsulfinyl)benzene

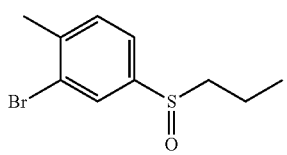

A solution of 3-bromo-4-methyl-benzenethiol (1.27 g; 6.25 mmol) in anhydrous DMF (12.5 ml) was treated with sodium hydride (300 mg; 7.5 mmol). Then reaction mixture was stirred at RT for 15 minutes, then the treated with 1-iodopropane (0.73 ml; 7.5 mmol). The reaction was stirred for 24 hours, before being quenched by dropwise addition of water. EtOAc was added and the layers separated. The organic layer was washed with brine, dried on MgSO4, filtered and concentrated under reduced pressure. The residue was dissolved in MeOH (13 mL), cooled to 0° C. and treated with a 0.5 M solution of sodium (meta)periodate in water (12.5 ml; 6.24 mmol). After stirring for 24 hours at RT, EtOAc and water were added and the phases separated and the organic phase was dried over $MgSO_4$ and concentrated under reduced pressure. The resulting residue was purified by flash column chromatography (silica), eluting with cyclohexane containing increasing amounts of EtOAc to give the title compound as a yellow sticky solid.

$^1$H NMR (300 MHz, DMSO-$d_6$) δ [ppm] 8.28 (1H, s), 8.00 (2H, m), 3.40-3.15 (2H, m), 2.91 (3H, s), 2.28-1.96 (2H, m), 1.48 (3H, t, J=7.4 Hz).

Intermediate 220 methyl (4-chloro-2-ethynylphenoxy)acetate

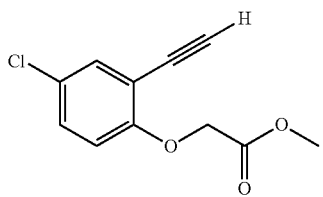

A solution of (4-chloro-2-ethynyl-phenoxy)-acetic acid tert-butyl ester (Intermediate 3; 500 mg; 1.87 mmol) in MeOH (10 ml) was treated with an 1.25 N solution of HCl in methanol (1.5 ml). The solution was heated at 60° C. for 24 hours. The solvents were removed under reduced pressure to give the title compound as an oil which solidifies upon standing (445 mg, quantitative yield).

$^1$H NMR (300 MHz, DMSO-$d_6$) δ [ppm] 7.47 (1H, d, J=2.7 Hz), 7.38 (1H, dd, J=9.0 Hz, J=2.7 Hz), 6.98 (1H, d, J=9.0 Hz), 4.91 (2H, s), 4.40 (1H, s), 3.68 (3H, s).

Intermediate 221 methyl (4-chloro-2-{[2-methyl-5-(propylsulfinyl)phenyl]ethynyl}phenoxy)acetate

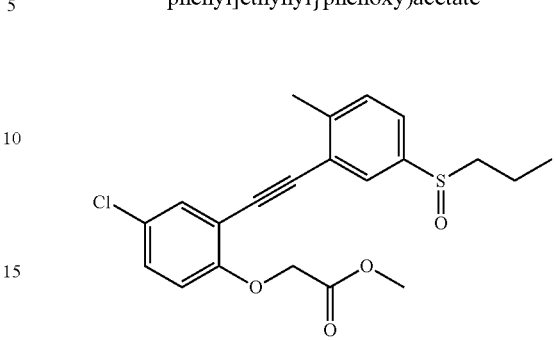

Following the general method as outlined in Intermediate 107, starting from methyl (4-chloro-2-ethynylphenoxy)acetate (Intermediate 220) and 2-bromo-1-methyl-4-(propylsulfinyl)benzene (Intermediate 219), the title compound was obtained as a yellow oil after purification by flash column chromatography (silica), eluting with cyclohexane containing increasing amounts of EtOAc.

$^1$H NMR (300 MHz, DMSO-$d_6$) δ [ppm] 7.75 (1H, d, J=1.6 Hz), 7.63-7.52 (3H, m), 7.43 (1H, dd, J=9.0 Hz, J=2.7 Hz), 7.08 (1H, d, J=9.0 Hz), 4.96 (2H, s), 3.72 (3H, s), 2.94 (1H, m), 2.78 (1H, m), 2.54 (3H, s), 1.64 (1H, m), 1.47 (1H, m), 0.97 (3H, t, J=7.4 Hz).

Intermediate 222 tert-butyl{2-[(4-aminophenyl)ethynyl]-4-chlorophenoxy}acetate

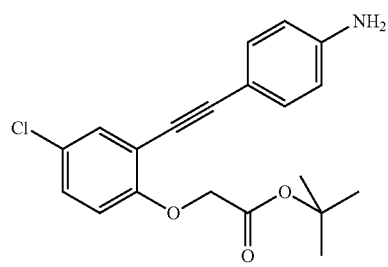

A mixture of (4-chloro-2-ethynyl-phenoxy)-acetic acid tert-butyl ester (Intermediate 3; 800 mg; 3.00 mmol), 4-iodoaniline (788 mg; 3.60 mmol) and dichlorobis(triphenylphosphine)palladium(II) (526 mg; 0.75 mmol) in anhydrous THF (20 mL) was treated with cuprous iodide (29 mg; 0.15 mmol), then the mixture was degassed with $N_2$ for 10 minutes, then treated with triethylamine (5.0 ml; 36 mmol). The mixture was stirred for 18 hours at RT, then EtOAc and water were added, the phases separated and the organic phase was dried over $MgSO_4$ and concentrated under reduced pressure. The resulting residue was purified by flash column chromatography (silica), eluting with cyclohexane containing increasing amounts of EtOAc to give the title compound.

$^1$H NMR (300 MHz, DMSO-$d_6$) δ [ppm] 7.44 (1H, d, J=2.6 Hz), 7.38 (1H, dd, J=9.0 Hz, J=2.7 Hz), 7.18 (2H, d, J=8.5

Hz), 6.92 (1H, d, J=9.0 Hz), 6.56 (2H, d, J=8.5 Hz), 5.60 (2H, bs), 4.77 (2H, s), 1.44 (9H, s).

Intermediate 223 tert-butyl{4-chloro-2-[(4-{[4-(trifluoromethyl)benzoyl]amino}phenyl)ethynyl]phenoxy}acetate

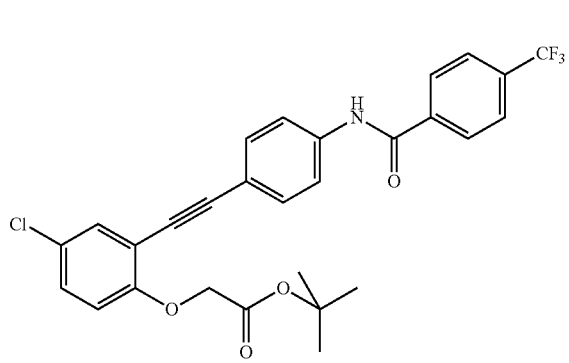

A solution of tert-butyl{2-[(4-aminophenyl)ethynyl]-4-chlorophenoxy}acetate (Intermediate 222; 72 mg; 0.20 mmol) and triethylamine (83 μl; 0.60 mmol) in DCM (2 ml) was treated with 4-(trifluoromethyl)-benzoyl chloride (30 μl; 0.20 mmol). After stirring at RT for 1 hour, the reaction was quenched with a saturated aqueous ammonia solution (1 mL). EtOAc and a saturated NH₄Cl solution in water were added, the phases separated and the organic phase was dried over MgSO₄ and concentrated under reduced pressure. The resulting residue was purified by flash column chromatography (silica), eluting with cyclohexane containing increasing amounts of EtOAc to give the title compound.

MS (ESI⁺): 547.2 [M+NH₄]⁺. HPLC (Condition A): Rt 5.88 min (HPLC purity>99%).

Intermediate 224 tert-butyl(2-{[4-(benzoylamino)phenyl]ethynyl}-4-chlorophenoxy)acetate

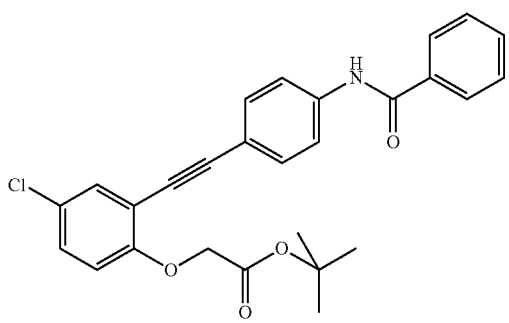

Following the general method as outlined in Intermediate 223, starting from tert-butyl{2-[(4-aminophenyl)ethynyl]-4-chlorophenoxy}acetate (Intermediate 222) and benzoyl chloride, the title compound was obtained after purification by flash column chromatography (silica), eluting with cyclohexane containing increasing amounts of EtOAc.

MS (ESI⁺): 479.2 [M+NH₄]⁺. HPLC (Condition A): Rt 5.48 min (HPLC purity 99.1%).

Intermediate 225 tert-butyl(2-{[4-(acetylamino)phenyl]ethynyl}-4-chlorophenoxy)acetate

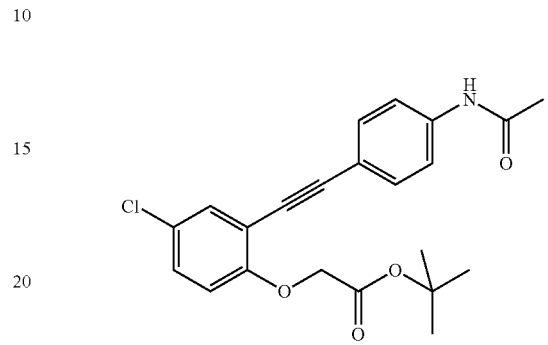

Following the general method as outlined in Intermediate 223, starting from tert-butyl{2-[(4-aminophenyl)ethynyl]-4-chlorophenoxy}acetate (Intermediate 222) and acetyl chloride, the title compound was obtained in 91% yield after purification by flash column chromatography (silica), eluting with cyclohexane containing increasing amounts of EtOAc.

¹H NMR (300 MHz, DMSO-d₆) δ [ppm] 10.15 (1H, s), 7.64 (2H, d, J=8.7 Hz), 7.54 (1H, d, J=2.7 Hz), 7.47 (2H, d, J=8.7 Hz), 7.38 (1H, dd, J=9.0 Hz, J=2.7 Hz), 6.96 (1H, d, J=9.0 Hz), 4.80 (2H, s), 2.07 (3H, s), 1.44 (9H, s).

Intermediate 226

4-Methyl-2-nitro-1-(propylthio)benzene

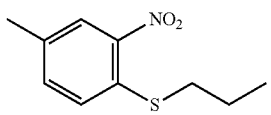

A solution of 4-chloro-3-nitro-toluene (25 g, 145 mmol) in anhydrous DMF (200 ml) was treated with K₂CO₃ (40.29 g, 291 mmol) and 1-propane thiol (12.2 g, 160 mmol). The reaction mixture was heated to 70° C. for 12 h. The reaction mixture was filtered, the filtrate was concentrated under reduced pressure, diluted water and extracted with ethyl acetate (200 ml). The organic layer was washed with brine, dried over sodium sulphate and evaporated under reduced pressure, to give a crude which was purified by column chromatography (silica) using petroleum ether/ethyl acetate as eluent to afford the title compound (28 g, 91%) as a pale yellow solid.

¹H NMR (300 MHz, DMSO-d₆) δ [ppm] 8.01 (s, 1H), 7.37-7.35 (d, 2H, J=10 Hz), 7.29-7.27 (dd, 1H, J=9.6 Hz), 2.96-2.89 (m, 2H), 2.40 (s, 3H), 1.81-1.17 (m, 2H), 1.11 (s, 1H).

Intermediate 227

4-Methyl-2-nitro-1-(propylsulfonyl) benzene

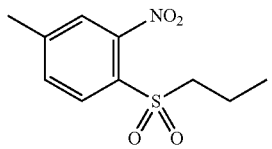

A cooled (0° C.) solution of 4-methyl-2-nitro-1-(propylthio) benzene (Intermediate 226; 15 g, 70 mmol) in anhydrous DCM (200 ml) was treated with a solution of 3-chloroperbenzoic acid (60%) (51.0 g, 177,mol) in DCM (300 ml). The reaction mixture was stirred at 0° C. for 3 h, then at RT for 16 h. The reaction mixture was filtered and the filtrate was extracted with ethyl acetate. The organic layer was washed with 1N NaOH (200 ml), water (200 ml), brine and dried over sodium sulphate and evaporated under reduced pressure. The crude product was purified by column chromatography (silica) using petroleum ether/ethyl acetate as eluent to afford the title compound as a pale yellow liquid.

$^1$H NMR (300 MHz, CDCl$_3$) δ [ppm] 8.01-7.99 (dd, 1H), 7.62 (s, 1H), 7.56-7.54 (dd, 1H), 3.53-3.49 (m, 2H), 2.53 (s, 3H), 1.89-1.80 (m, 2H), 1.09 (s, 3H)

Intermediate 228

5-Methyl-2-(propylsulfonyl)aniline

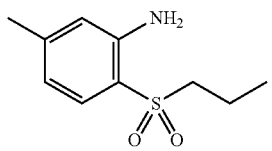

A solution of 4-methyl-2-nitro-1-(propylsulfonyl)benzene (Intermediate 227; 11 g, 45 mmol) in methanol (150 ml) was treated with Pd/C (1.1 g) and the reaction mixture was stirred under 3 Kg/cm$^2$ pressure of hydrogen at RT for 5 h. The catalyst was filtered through celite and the solvent was removed under reduced pressure to afford the title compound (9 g, 94%) as pale yellow liquid.

$^1$H NMR (300 MHz, DMSO-d$_6$) δ [ppm] 7.35-7.33 (dd, 1H), 6.65 (s, 1H), 6.51-6.49 (dd, 1H), 5.94 (brs, 2H), 3.13-3.10 (m, 2H), 2.20 (s, 3H), 1.55-1.49 (m, 2H), 0.90-0.85 (t, 3H). MS (ESI$^+$): 214.2. HPLC (Method D) Purity 99.8%; Rt 3.34 min.

Intermediate 229

N-[5-Methyl-2-(propylsulfonyl)phenyl]acetamide

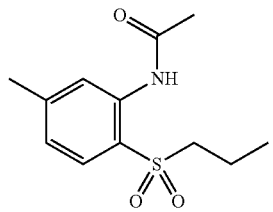

A solution of 5-methyl-2-(propylsulfonyl) aniline (Intermediate 228; 6.0 g, 28 mmol) in DCM (100 ml) was added N-methyl morpholine (4.3 g, 42.1 mmol) and Acetyl chloride (2.4 g, 31 mmol). The reaction mixture was stirred at RT for 12 h. The reaction mixture was diluted with water (200 ml), the organic layer was washed with brine solution and dried over sodium sulphate and evaporated. The crude product was purified by column chromatography (silica) using petroleum ether/ethyl acetate as eluent to afford the title compound (5.0 g, 70%) as a white solid.

$^1$H NMR (300 MHz, DMSO-d$_6$) δ [ppm] 9.53 (brs, 1H), 7.84 (s, 1H), 7.72-7.70 (dd, 1H, J=8.12 Hz), 7.21-7.19 (dd, 1H, J=7.96 Hz), 3.28-3.24 (m, 2H), 2.36 (s, 3H), 2.10 (s, 3H), 1.54-1.48 (m, 2H), 0.9-0.86 (t, 3H, J=14.84 Hz). MS (ESI$^+$): 256. HPLC (Condition A) Purity 99.1%; Rt 3.36 min.

Intermediate 230

N-[4-Bromo-5-methyl-2-(propylsulfonyl)phenyl] acetamide

A mixture of N-[5-methyl-2-(propylsulfonyl)phenyl]acetamide (Intermediate 229; 5.0 g, 20 mmol) in conc. sulphuric acid (25 ml) was treated in portions with N-bromosuccinamide (3.8 g, 22 mmol). Reaction mixture was stirred at RT for 18 hrs, carefully quenched on ice and extracted to DCM (100 ml). The organic layer was washed with water and brine, dried over sodium sulphate and concentrated. The crude product was purified by column chromatography (silica) eluting with petroleum ether/ethyl acetate to afford the title compound as a white solid.

$^1$H NMR (300 MHz, DMSO-d$_6$) δ [ppm] 9.54 (brs, 1H), 7.98 (s, 1H), 7.91 (s, 1H), 3.37-3.33 (m, 2H), 2.40 (s, 3H), 2.10 (s, 3H), 1.59-1.5 (m, 2H), 0.92-0.89 (t, 3H, J=14.76 Hz). MS (ESI$^+$): 334. HPLC (Condition A) Purity 97%; Rt 4.35 min.

Intermediate 231 tert-butyl(2-{[4-(acetylamino)-2-methyl-5-(propyl-sulfonyl)phenyl]ethynyl}-4-chlorophenoxy)acetate

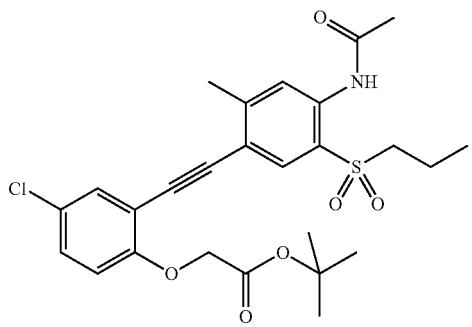

Following the general method as outlined in Intermediate 107, starting from (4-chloro-2-ethynyl-phenoxy)-acetic acid tert-butyl ester (Intermediate 3) and N-[4-Bromo-5-methyl-2-(propane-1-sulfonyl)-phenyl]-acetamide (Intermediate 230), the title compound was obtained as a brown sticky solid after purification by flash column chromatography (silica), eluting with cyclohexane containing increasing amounts of EtOAc.

$^1$H NMR (300 MHz, DMSO-d$_6$) δ [ppm] 9.62 (1H, s), 8.11 (1H, s), 7.89 (1H, s), 7.64 (1H, d, J=2.7 Hz), 7.43 (1H, dd, J=9.0 Hz, J=2.7 Hz), 7.02 (1H, d, J=9.0 Hz), 4.81 (2H, s), 3.38 (2H, m), 2.54 (3H, s), 2.15 (3H, s), 1.57 (2H, sext., J=7.5 Hz), 1.43 (9H, s), 0.92 (3H, t, J=7.5 Hz). HPLC (Condition A) Purity 100.0%; Rt 6.1 min.

Intermediate 232

3-iododibenzo[b,d]thiophene 5,5-dioxide

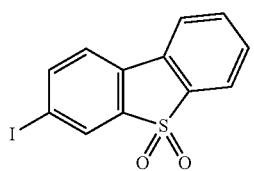

Following the general method as outlined in Intermediate 58, starting from 5,5-dioxidodibenzo[b,d]thien-3-ylamine (Zerenex), the title compound was obtained as a beige solid after purification by flash column chromatography (silica), eluting with cyclohexane containing increasing amounts of EtOAc.

$^1$H NMR (300 MHz, DMSO-d$_6$) δ [ppm] 8.40 (1H, d, J=1.5 Hz), 8.21 (1H, d, J=7.6 Hz), 8.18 (1H, dd, J=8.3 Hz, J=1.5 Hz), 7.97-8.01 (2H, m), 7.81 (1H, dt, J=7.6 Hz, J=1.0 Hz), 7.69 (1H, dt, J=7.6 Hz, J=1.0 Hz). HPLC (Condition A) Purity 91.5%; Rt 4.1 min.

Intermediate 233 tert-butyl{4-chloro-2-[(5,5-dioxidodibenzo[b,d]thien-3-yl)ethynyl]phenoxy}acetate

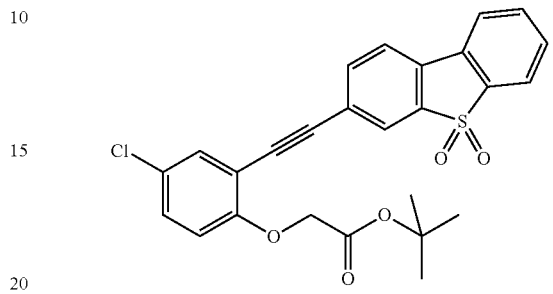

Following the general method as outlined in Intermediate 79, starting from (4-chloro-2-ethynyl-phenoxy)-acetic acid tert-butyl ester (Intermediate 3) 3-iododibenzo[b,d]thiophene 5,5-dioxide (Intermediate 232), the title compound was obtained as a pink solid after purification by flash column chromatography (silica), eluting with cyclohexane containing increasing amounts of EtOAc.

$^1$H NMR (300 MHz, DMSO-d$_6$) δ [ppm] 8.28 (1H, d, J=8.0 Hz), 8.25 (1H, d, J=7.6 Hz), 8.18 (1H, d, J=1.5 Hz), 8.02 (1H, d, J=7.6 Hz), 7.94 (1H, dd, J=8.0 Hz, J=1.5 Hz), 7.84 (1H, dt, J=7.6 Hz, J=1.0 Hz), 7.65 (1H, dt, J=7.6 Hz, J=1.0 Hz), 7.47 (1H, dd, J=9.0 Hz, J=2.7 Hz), 7.02 (1H, d, J=9.0 Hz), 4.84 (2H, s), 1.44 (9H, s). HPLC (Condition A) Purity 99.0%; Rt 5.7 min.

Intermediate 234

6-iodo-2,3-dihydro-1-benzothiophene 1,1-dioxide

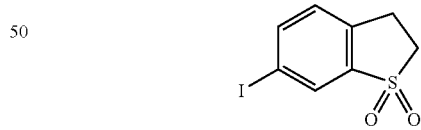

Following the general method as outlined in Intermediate 58, starting from 1,1-dioxido-2,3-dihydro-1-benzothien-6-ylamine (Intermediate 233), the title compound was obtained as a beige solid after purification by flash column chromatography (silica), eluting with cyclohexane containing increasing amounts of EtOAc.

$^1$H NMR (300 MHz, DMSO-d$_6$) δ [ppm] 8.08 (1H, d, J=1.5 Hz), 7.99 (1H, dd, J=8.1 Hz, J=1.5 Hz), 7.36 (1H, d, J=8.1 Hz), 3.60 (2H, t, J=6.9 Hz), 3.29 (2H, t, J=6.9 Hz). HPLC (Condition A) Purity 98.2%; Rt 2.9 min.

Intermediate 235 tert-butyl{4-chloro-2-[(1,1-dioxido-2,3-dihydro-1-benzothien-6-yl)ethynyl]phenoxy}acetate

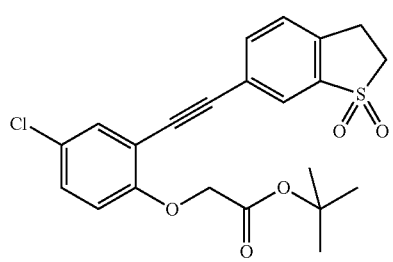

Following the general method as outlined in Intermediate 20, starting from (4-chloro-2-ethynyl-phenoxy)-acetic acid tert-butyl ester (Intermediate 3) and 6-iodo-2,3-dihydro-1-benzothiophene 1,1-dioxide (Intermediate 234), the title compound was obtained as a beige solid after purification by flash column chromatography (silica), eluting with cyclohexane containing increasing amounts of EtOAc.

$^1$H NMR (300 MHz, DMSO-d$_6$) δ [ppm] 7.90 (1H, d, J=1.5 Hz), 7.79 (1H, dd, J=8.0 Hz, J=1.5 Hz), 7.61-7.64 (2H, m), 7.44 (1H, dd, J=9.0 Hz, J=2.7 Hz), 7.00 (1H, d, J=9.0 Hz), 4.82 (2H, s), 3.64 (2H, m), 3.40 (2H, t, J=6.8 Hz), 1.43 (9H, s). HPLC (Condition A) Purity 96.6%; Rt 5.1 min.

Intermediate 236

6-iodo-1-benzothiophene 1,1-dioxide

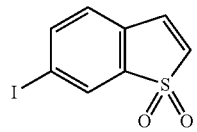

Following the general method as outlined in Intermediate 58, starting from 6-amino-1,1-dioxobenzo[β]thiophene, the title compound was obtained as a beige solid after purification by flash column chromatography (silica), eluting with cyclohexane containing increasing amounts of EtOAc.

$^1$H NMR (300 MHz, DMSO-d$_6$) δ [ppm] 8.25 (1H, m), 8.07 (1H, dd, J=7.9 Hz, J=1.6 Hz), 7.601 (1H, dd, J=6.9 Hz, J=1.0 Hz), 7.38 (1H, d, J=7.9 Hz), 7.34 (1H, d, J=6.9 Hz). HPLC (Condition A) Purity 97.4%; Rt 3.0 min.

Intermediate 237 tert-butyl{4-chloro-2-[(1,1-dioxido-1-benzothien-6-yl)ethynyl]phenoxy}acetate

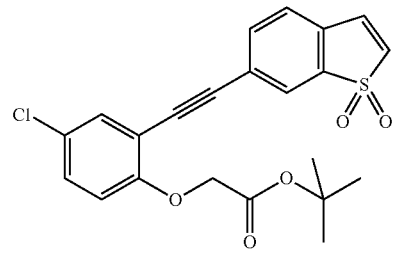

Following the general method as outlined in Intermediate 107, starting from (4-chloro-2-ethynyl-phenoxy)-acetic acid tert-butyl ester (Intermediate 3) and 6-iodo-1-benzothiophene 1,1-dioxide (Intermediate 236), the title compound was obtained as a yellow solid after purification by flash column chromatography (silica), eluting with cyclohexane containing increasing amounts of EtOAc.

$^1$H NMR (300 MHz, DMSO-d$_6$) δ [ppm] 8.03 (1H, m), 7.82 (1H, dd, J=7.8 Hz, J=1.5 Hz), 7.63-7.70 (3H, m), 7.49 (1H, d, J=6.7 Hz), 7.46 (1H, dd, J=9.0 Hz, J=2.7 Hz), 7.01 (1H, d, J=9.0 Hz), 4.83 (2H, s), 1.44 (9H, s). HPLC (Condition A) Purity 97.6%; Rt 5.7 min.

Intermediate 238

(4-chloro-2-ethynylphenoxy)acetic acid

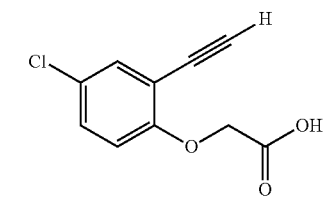

A solution of (4-chloro-2-ethynyl-phenoxy)-acetic acid tert-butyl ester (Intermediate 3; 500 mg; 1.87 mmol) in DCM (2.5 ml) was treated with a 4 N solution of HCl in dioxane (14 ml; 56 mmol) and stirred overnight. The solvents were removed under reduced pressure, to give the title compound.

$^1$H NMR (300 MHz, DMSO-d$_6$) δ [ppm] 13.0 (1H, bs), 7.34-7.24 (2H, m), 6.82 (1H, d, J=9.0 Hz), 4.66 (2H, s), 4.25 (1H, s).

Intermediate 239 methyl 4-bromo-2-(methylsulfonyl)benzoate

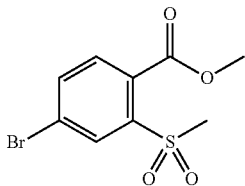

A suspension of 4-bromo-2-(methylsulphonyl)benzoic acid (5.00 g; 17.9 mmol) in MeOH (100 ml) was treated with conc. sulphuric acid and the resulting mixture was heated at reflux for 5 days. The mixture was concentrated under reduced pressure, the residue was dissolved in EtOAc then washed with water, twice with NaHCO$_3$ (sat) then with brine, dried on MgSO$_4$, filtered and concentrated to give the title compound as a yellow solid (4.00 g, 72%).

$^1$H NMR (300 MHz, DMSO-d$_6$) δ [ppm] 8.14 (1H, d, J=1.9 Hz), 8.08 (1H, d, J=1.9 Hz, 8.1 Hz), 7.73 (1H, d, J=8.1 Hz), 3.86 (3H, s), 3.42 (3H, s). HPLC (Condition A): Rt 3.54 min (HPLC purity 95.5%).

Intermediate 240

6-bromo-1-benzothiophen-3(2H)-one 1,1-dioxide

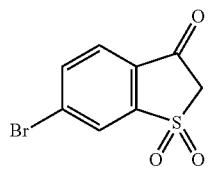

A solution of methyl 4-bromo-2-(methylsulfonyl)benzoate (Intermediate 239; 4.00 g; 13.6 mmol) in anhydrous THF (60 ml) was treated with NaH (595 mg; 13.6 mmol) and stirred at RT for 1.5 h. The reaction was quenched with water. AcOEt and a 1N solution of HCl in water were added and the phases were separated. The organic phase was washed with brine, dried on MgSO$_4$, filtered and concentrated to give the title compound as a yellow solid (3.63 g).

$^1$H NMR (300 MHz, DMSO-d$_6$) δ [ppm] 8.55 (1H, d, J=1.7 Hz), 8.15 (1H, d, J=1.7 Hz, 8.2 Hz), 7.93 (1H, d, J=8.2 Hz), 4.62 (2H, s). MS (ESI$^-$): 261.0. HPLC (Condition A): Rt 2.56 min.

Intermediate 241

6-bromo-2,2-dimethyl-1-benzothiophen-3(2H)-one 1,1-dioxide

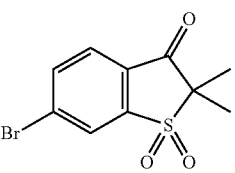

A solution of 6-bromo-1-benzothiophen-3(2H)-one 1,1-dioxide (Intermediate 240; 1.00 g; 3.83 mmol) in anhydrous DMF (4 mL) was treated with sodium hydride (337 mg; 8.43 mmol) and stirred for 1 h. The resulting mixture was treated with iodomethane (715 µl; 11.5 mmol) and stirred for 15 min. The reaction was quenched with water, then partitioned between AcOEt and brine. The organic phase was washed with brine, dried on MgSO$_4$, filtered and concentrated to give a residue which was purified by flash column chromatography (silica), eluting with cyclohexane containing increasing amounts of EtOAc. The title compound was obtained as an orange oil. Methyl 4-bromo-2-(isopropylsulfonyl)benzoate was also isolated and denominated as Intermediate 242.

$^1$H NMR (300 MHz, DMSO-d$_6$) δ [ppm] 8.64-858 (1H, m), 8.22-8.12 (1H, m), 8.0-7.94 (1H, m), 1.50 (6H, s). HPLC (Condition A): Rt 3.65 min (HPLC purity 100%).

Intermediate 242

Methyl 4-bromo-2-(isopropylsulfonyl)benzoate

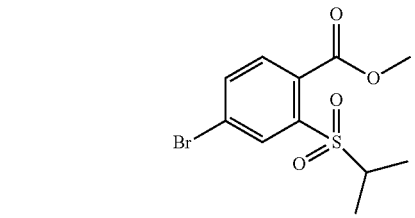

The title compound was isolated by column chromatography during the synthesis of Intermediate 241.

$^1$H NMR (300 MHz, DMSO-d$_6$) δ [ppm] 8.12-8.04 (2H, m), 7.74 (1H, d, J=8 Hz), 3.85 (3H, s), 3.81 (1H, m), 1.24 (3H, s), 1.22 (3H, s). MS (ESI$^+$): 321.0. HPLC (Condition A): Rt 3.78 min.

Intermediate 243 tert-butyl{4-chloro-2-[(2,2-dimethyl-1,1-dioxido-3-oxo-2,3-dihydro-1-benzothien-6-yl)ethynyl]phenoxy}acetate

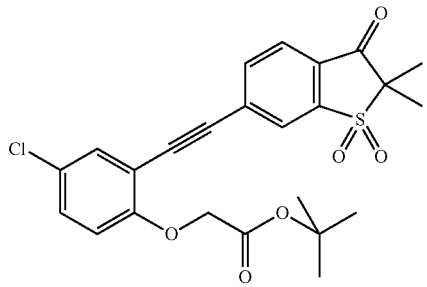

Following the general method as outlined in Intermediate 107, starting from (4-chloro-2-ethynyl-phenoxy)-acetic acid tert-butyl ester (Intermediate 3) and 6-bromo-2,2-dimethyl-1-benzothiophen-3(2H)-one 1,1-dioxide (Intermediate 241), the title compound was obtained in 91% yield after purification by flash column chromatography (silica), eluting with cyclohexane containing increasing amounts of EtOAc.

$^1$H NMR (300 MHz, DMSO-d$_6$) δ [ppm] 8.42-8.40 (1H, m), 8.11 (1H, dd, J=0.6 Hz, 8.1 Hz), 8.05 (1H, m, J=1.3 Hz, 8.1 Hz), 7.71 (1H, d, J=2.7 Hz), 7.51 (1H, dd, J=2.7 Hz, 9 Hz) 7.05 (1H, d, J=9. Hz), 4.85 (2H, s), 1.52 (6H, s), 1.44 (9H, s). MS (ESI$^+$): 492 [M+NH4]$^+$. HPLC (Condition A): Rt 5.73 min (purity 99%).

Intermediate 244

6-bromo-2,2-dimethyl-2,3-dihydro-1-benzothiophene-3-ol 1,1-dioxide

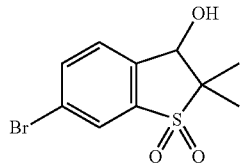

A cooled (0° C.) solution of 6-bromo-2,2-dimethyl-1-benzothiophen-3(2H)-one 1,1-dioxide (Intermediate 241; 652 mg; 2.25 mmol) in MeOH (15 ml) and DCM (7 ml) was treated with NaBH$_4$ (43 mg; 1.13 mmol) portionwise. The resulting solution was stirred at RT for 1.5 h, before being cooled to 0° C. and carefully quenched with water. The mixture was concentrated under reduced pressure, water was added to the residue and the aqueous phase was extracted three times with DCM. The combined organic phases were washed with brine, dried with MgSO$_4$, filtered and concentrated to dryness to give the title compound as a white solid (637 mg, 97%).

$^1$H NMR (300 MHz, DMSO-d$_6$) δ [ppm] 8.12 (1H, d, J=1.8 Hz), 7.99 (1H, dd, J=1.8 Hz, 8.1 Hz), 7.65 (1H, d, J=8.1 Hz), 6.62 (1H, s), 4.95 (1H, s), 1.47 (3H, s), 1.19 (3H, s). MS (ESI$^+$): 308.0 [M+NH$_4$]$^+$. HPLC (Condition A): Rt 3.30 min (purity 97%).

Intermediate 245 tert-butyl{4-chloro-2-[(3-hydroxy-2,2-dimethyl-1,1-dioxido-2,3-dihydro-1-benzothien-6-yl)ethynyl]phenoxy}acetate

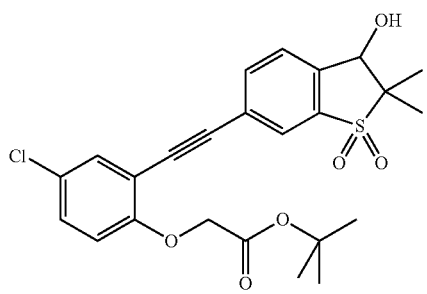

Following the general method as outlined in Intermediate 107, starting from (4-chloro-2-ethynyl-phenoxy)-acetic acid tert-butyl ester (Intermediate 3) and 6-bromo-2,2-dimethyl-2,3-dihydro-1-benzothiophene-3-ol 1,1-dioxide (Intermediate 244), the title compound was obtained after purification by flash column chromatography (silica), eluting with cyclohexane containing increasing amounts of EtOAc.

$^1$H NMR (300 MHz, DMSO-d$_6$) δ [ppm] 7.94 (1H, m), 7.86 (1H, dd, J=1.4 Hz, 7.9 Hz), 7.69 (1H, m), 7.63 (1H, d, J=2.7 Hz) 7.05 (1H, dd, J=7.9 Hz, 2.7 Hz), 7.00 (1H, d, J=8.9 Hz), 4.96 (1H, s), 4.82 (2H, s), 1.43 (9H, s), 1.39 (3H, s) 1.13 (3H, s). MS (ESI$^+$): 594 [M+NH$_4$]$^+$. HPLC (Condition A): Rt 5.09 min (HPLC purity 95%).

Intermediate 246

6-bromo-2,2,3-trimethyl-2,3-dihydro-1-benzothiophene-3-ol 1,1-dioxide

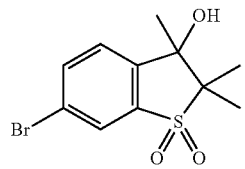

A cooled (0° C.) solution of 6-bromo-2,2-dimethyl-1-benzothiophen-3(2H)-one 1,1-dioxide (Intermediate 241; 750 mg; 2.59 mmol) in anhydrous Et$_2$O (22.5 ml) was treated carefully with a 3 M solution of methylmagnesium bromide in Et$_2$O (2.6 ml; 7.8 mmol). The white solution was stirred at RT for 1.5 before being quenched with a saturated solution of NH$_4$Cl in water. The phases were separated and the aqueous phase was extracted with Et$_2$O. The combined organic phases were washed with water and brine, dried over anhydrous magnesium sulfate and concentrated to dryness to afford the title compound as a white solid (767 mg, 97%).

$^1$H NMR (300 MHz, DMSO-d$_6$) δ [ppm] 8.02 (1H, d, J=1.9 Hz), 7.93 (1H, dd, J=1.9 Hz, 8.1 Hz), 7.64 (1H, d, J=8.1 Hz),

Intermediate 247 tert-butyl{4-chloro-2-[(3-hydroxy-2,2,3-trimethyl-1,1-dioxido-2,3-dihydro-1-benzothien-6-yl)ethynyl]phenoxy}acetate

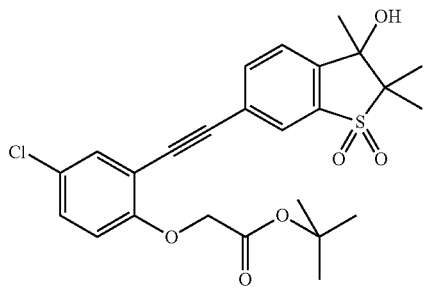

Following the general method as outlined in Intermediate 107, starting from (4-chloro-2-ethynyl-phenoxy)-acetic acid tert-butyl ester (Intermediate 3) and 6-bromo-2,2,3-trimethyl-2,3-dihydro-1-benzothiophene-3-ol 1,1-dioxide (Intermediate 246), the title compound was obtained as a white foam after purification by flash column chromatography (silica), eluting with cyclohexane containing increasing amounts of EtOAc.

$^1$H NMR (300 MHz, DMSO-$d_6$) δ [ppm] 7.92 (1H, m), 7.87 (1H, dd, J=1.6 Hz, 8 Hz), 7.75 (1H, d, J=8 Hz), 7.65 (1H, d, J=2.7 Hz) 7.44 (1H, dd, J=9 Hz, 2.7 Hz), 7.01 (1H, d, J=9 Hz), 6.13 (1H, brs), 4.82 (2H, s), 1.47 (3H, s), 1.43 (9H, s) 1.34 (3H, s), 1.20 (3H, s). MS (ESI$^+$): 508.4 [M+NH$_4$]$^+$. HPLC (Condition A): Rt 5.20 min.

Intermediate 248

6-bromo-2,2-dimethyl-1,1-dioxido-2,3-dihydro-1-benzothien-3-yl methyl ether

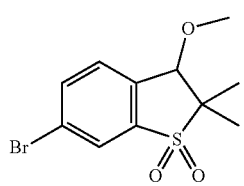

A cooled (0° C.) suspension of NaH (20.61 mg; 0.52 mmol; 1.00 eq.) in dry DMF was carefully treated with solution of 6-bromo-2,2-dimethyl-2,3-dihydro-1-benzothiophene-3-ol 1,1-dioxide (Intermediate 244; 150 mg; 0.52 mmol) in anhydrous DMF. The reaction mixture was stirred at RT for 4 min then treated with a 3 M solution of iodomethane (240 µl; 0.72 mmol). The mixture was stirred at RT for 2.5 h, then quenched with water. EtOAc was added, the phases were separated and the aqueous phase was extracted with EtOAc. The combined organic phases were washed with brine, dried over anhydrous magnesium sulfate and concentrated to dryness to afford a residue, which was purified by flash column chromatography (silica), eluting with cyclohexane containing increasing amounts of EtOAc. The title compound was obtained as a white solid.

$^1$H NMR (300 MHz, DMSO-$d_6$) δ [ppm] 8.11 (1H, d, J=1.8 Hz), 7.94 (1H, dd, J=1.8 Hz, 8 Hz), 7.65 (1H, d, J=8 Hz), 4.69 (1H, s), 3.52 (3H, s), 1.40 (3H, s) 1.27 (3H, s). HPLC (Condition A): Rt 3.64 min.

Intermediate 249 tert-butyl{4-chloro-2-[(3-methoxy-2,2-dimethyl-1,1-dioxido-2,3-dihydro-1-benzothien-6-yl)ethynyl]phenoxy}acetate

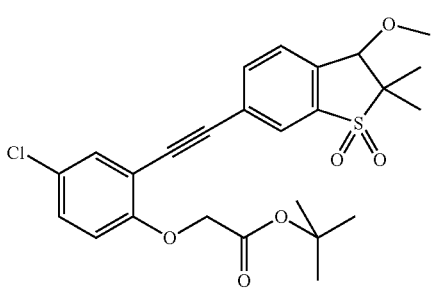

Following the general method as outlined in Intermediate 107, starting from (4-chloro-2-ethynyl-phenoxy)-acetic acid tert-butyl ester (Intermediate 3) and 6-bromo-2,2-dimethyl-1,1-dioxido-2,3-dihydro-1-benzothien-3-yl methyl ether (Intermediate 248), the title compound was obtained after purification by flash column chromatography (silica), eluting with cyclohexane containing increasing amounts of EtOAc.

$^1$H NMR (300 MHz, DMSO-$d_6$) δ [ppm] 7.98 (1H, m), 7.87 (1H, dd, J=1.6 Hz, 8 Hz), 7.76 (1H, d, J=8 Hz), 7.63 (1H, d, J=2.7 Hz) 7.45 (1H, dd, J=9 Hz, 2.7 Hz), 7.00 (1H, d, J=9 Hz), 4.81 (2H, s), 4.76 (1H, s), 3.56 (3H, s), 1.43 (9H, s) 1.39 (6H, s). MS (ESI$^+$): 508.4 [M+NH$_4$]$^+$. HPLC (Condition A): Rt 5.61 min.

Intermediate 250

6-bromo-2,2,3-trimethyl-1,1-dioxido-2,3-dihydro-1-benzothien-3-yl methyl ether

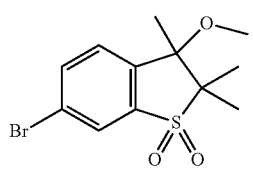

Following the general method as outlined in Intermediate 248, starting from 6-bromo-2,2,3-trimethyl-2,3-dihydro-1-benzothiophene-3-ol 1,1-dioxide (Intermediate 246), the title compound was obtained.

¹H NMR (300 MHz, DMSO-d₆) δ [ppm] 8.10 (1H, d, J=1.9 Hz), 7.95 (1H, dd, J=1.9 Hz, 8.1 Hz), 7.72 (1H, d, J=8.1 Hz), 3.95 (3H, s), 1.53 (3H, s) 1.35 (3H, s), 1.24 (3H, s). HPLC (Condition A): Rt 3.64 min.

Intermediate 251 tert-butyl{4-chloro-2-[(3-methoxy-2,2,3-trimethyl-1,1-dioxido-2,3-dihydro-1-benzothien-6-yl)ethynyl]phenoxy}acetate

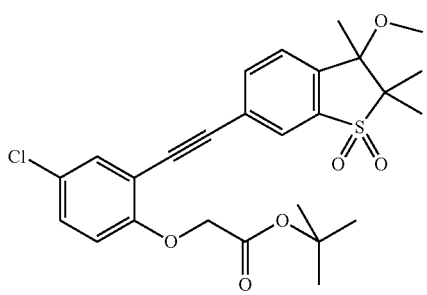

Following the general method as outlined in Intermediate 107, starting from (4-chloro-2-ethynyl-phenoxy)-acetic acid tert-butyl ester (Intermediate 3) and 6-bromo-2,2,3-trimethyl-1,1-dioxido-2,3-dihydro-1-benzothien-3-yl methyl ether (Intermediate 250), the title compound was obtained after purification by flash column chromatography (silica), eluting with cyclohexane containing increasing amounts of EtOAc.

¹H NMR (300 MHz, DMSO-d₆) δ [ppm] 7.98 (1H, m), 7.88 (1H, dd, J=1.5 Hz, 8 Hz), 7.83 (1H, d, J=8 Hz), 7.64 (1H, d, J=2.7 Hz) 7.45 (1H, dd, J=9 Hz, 2.7 Hz), 7.01 (1H, d, J=9 Hz), 4.82 (2H, s), 3.06 (3H, s), 1.56 (3H, s), 1.43 (9H, s) 1.36 (3H, s), 1.25 (3H, s). HPLC (Condition A): Rt 5.65 min (HPLC purity 97%).

Intermediate 252

4-bromo-2-(isopropylsulfonyl)benzoic acid

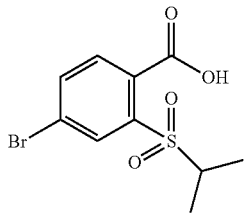

A solution of methyl 4-bromo-2-(isopropylsulfonyl)benzoate (Intermediate 242; 516 mg; 1.61 mmol) in THF (10 ml) was treated with a 5 N solution of NaOH in water (4 mL) and the reaction mixture was heated at 60° C. for 1 day. The reaction mixture was acidified with aqueous HCl and the reaction mixture was extracted 3 times with EtOAc. The combined organic phases were dried over MgSO4, filtered and concentrated to dryness affording the title compound as a pale yellow solid (386 mg; 78%).

¹H NMR (300 MHz, DMSO-d₆) δ [ppm] 12.50 (1H, bs), 8.05 (1H, dd, J=8.1 Hz, J=2.0 Hz), 8.01 (1H, d, J=2.0 Hz), 7.73 (1H, dd, J=8.1 Hz), 3.96 (1H, sext., J=6.9 Hz), 1.22 (6H, d, J=6.9 Hz). HPLC (Condition A) Purity 97.8%; Rt 3.1 min.

Intermediate 253

4-bromo-N-butyl-2-(isopropylsulfonyl)-N-methyl-benzamide

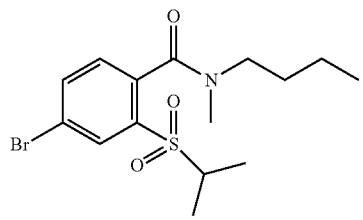

A solution of 4-bromo-2-(isopropylsulfonyl)benzoic acid (Intermediate 242; 260 mg; 0.85 mmol), N-methylbuthylamine (200 μl; 1.69 mmol) and TEA (352 μl; 2.54 mmol) in DMF (10 ml) was treated with polymer-supported Mukaiyama reagent (1.35 g; 1.69 mmol) and the reaction mixture was stirred for 18 hours. The reaction mixture was filtered and the polymer was washed with DCM. The filtrate was washed twice with a sat. NaHCO₃ solution and twice with brine. The organic phase was dried over MgSO₄, filtered and concentrated to dryness to afford the title compound as a pink solid.

MS (ESI⁺): 378.0. HPLC (Condition A) Purity 90.6%; Rt 4.2 min.

Intermediate 254 tert-butyl(2-{[4-{[butyl(methyl)amino]carbonyl}-3-(isopropylsulfonyl)phenyl]ethynyl}-4-chlorophenoxy)acetate

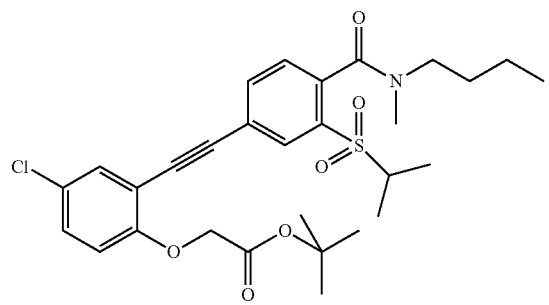

Following the general method as outlined in Intermediate 107, starting from (4-chloro-2-ethynyl-phenoxy)-acetic acid tert-butyl ester (Intermediate 3) and 4-bromo-N-butyl-2-(isopropylsulfonyl)-N-methylbenzamide (Intermediate 253), the title compound was obtained.

MS (ESI⁺): 562.0. HPLC (Condition A) Purity 94.4%; Rt 5.9 min.

Intermediate 255

4-bromo-2-(isopropylsulfonyl)-N,N-dimethylbenzamide

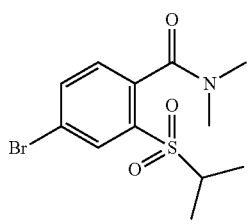

Following the general method as outlined in Intermediate 253, starting from 4-bromo-2-(isopropylsulfonyl)benzoic acid (Intermediate 242) and dimethylamine, the title compound was obtained as a pink solid after purification by flash column chromatography (silica), eluting with cyclohexane containing increasing amounts of EtOAc.

$^1$H NMR (300 MHz, DMSO-$d_6$) δ [ppm] 8.04 (1H, dd, J=8.0 Hz, J=2.0 Hz), 7.99 (1H, d, J=2.0 Hz), 7.48 (1H, d, J=8.0 Hz), 3.71 (1H, sept., J=7.0 Hz), 2.96 (3H, s), 2.71 (3H, s), 1.27 (3H, m), 1.04 (3H, m). HPLC (Condition A) Purity 99.4%; Rt 3.0 min.

Intermediate 256 tert-butyl(4-chloro-2-{[4-[(dimethylamino)carbonyl]-3-(isopropylsulfonyl)phenyl]ethynyl}phenoxy)acetate

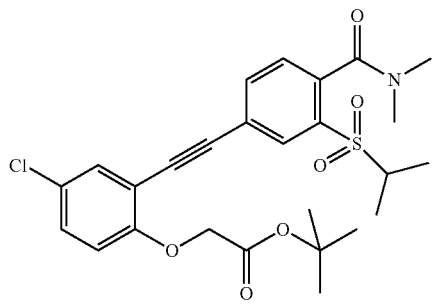

Following the general method as outlined in Intermediate 107, starting from (4-chloro-2-ethynyl-phenoxy)-acetic acid tert-butyl ester (Intermediate 3) and 4-bromo-2-(isopropylsulfonyl)-N,N-dimethylbenzamide (Intermediate 255), the title compound was obtained as brown sticky solid after purification by flash column chromatography (silica), eluting with cyclohexane containing increasing amounts of EtOAc.

$^1$H NMR (300 MHz, DMSO-$d_6$) δ [ppm] 7.99 (1H, d, J=1.7 Hz), 7.93 (1H, dd, J=8.0 Hz, J=1.7 Hz), 7.68 (1H, d, J=2.7 Hz), 7.57 (1H, d, J=8.0 Hz), 7.46 (1H, dd, J=9.0 Hz, J=2.7 Hz), 7.01 (1H, d, J=9.0 Hz), 4.82 (2H, s), 3.72 (1H, sept., J=6.8 Hz), 2.98 (3H, s), 2.73 (3H, s), 1.43 (9H, s), 1.28 (3H, m), 1.05 (3H, m). HPLC (Condition A) Rt 5.2 min.

Intermediate 257

4-bromo-N,N-diethyl-2-(isopropylsulfonyl)benzamide

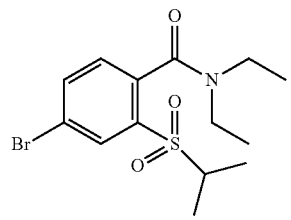

Following the general method as outlined in Intermediate 253, starting from 4-bromo-2-(isopropylsulfonyl)benzoic acid (Intermediate 242) and diethylamine, the title compound was obtained as a pink solid in 81% yield.

$^1$H NMR (300 MHz, DMSO-$d_6$) δ [ppm] 8.02 (1H, dd, J=8.0 Hz, J=2.0 Hz), 7.98 (1H, d, J=2.0 Hz), 7.48 (1H, d, J=8.0 Hz), 3.74 (1H, sept., J=6.9 Hz), 3.57 (1H, m), 3.25 (1H, m), 2.92-3.09 (2H, m), 1.28 (3H, d, J=6.9 Hz), 1.12 (3H, t, J=7.1 Hz), 1.03 (3H, d, J=6.9 Hz), 1.01 (3H, t, J=7.1 Hz). HPLC (Condition A) Purity 95.1%; Rt 4.2 min.

Intermediate 258 tert-butyl(4-chloro-2-{[4-[(diethylamino)carbonyl]-3-(isopropylsulfonyl)phenyl]ethynyl}phenoxy)acetate

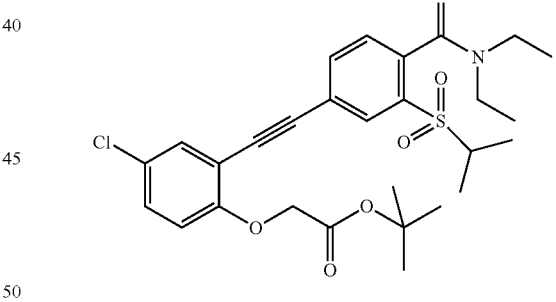

Following the general method as outlined in Intermediate 107, starting from (4-chloro-2-ethynyl-phenoxy)-acetic acid tert-butyl ester (Intermediate 3) and 4-bromo-N,N-diethyl-2-(isopropylsulfonyl)benzamide (Intermediate 257), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 7.99 (1H, d, J=1.7 Hz), 7.92 (1H, dd, J=7.9 Hz, J=1.7 Hz), 7.68 (1H, d, J=2.7 Hz), 7.58 (1H, d, J=7.9 Hz), 7.46 (1H, dd, J=9.0 Hz, J=2.7 Hz), 7.02 (1H, d, J=9.0 Hz), 4.83 (2H, s), 3.75 (1H, sept., J=6.9 Hz), 3.57 (1H, m), 3.28 (1H, m), 3.01 (2H, m), 1.43 (9H, s), 1.29 (3H, d, J=6.9 Hz), 1.14 (3H, t, J=7.0 Hz), 1.05 (3H, d, J=6.9 Hz), 1.03 (3H, t, J=7.0 Hz). HPLC (Condition A) Purity 97.6%; Rt 5.6 min.

Intermediate 259

4-bromo-N-ethyl-2-(isopropylsulfonyl)-N-propyl-benzamide

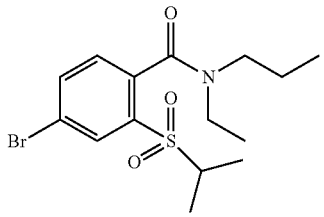

Following the general method as outlined in Intermediate 253, starting from 4-bromo-2-(isopropylsulfonyl)benzoic acid (Intermediate 242) and N-ethyl-N-propylamine, the title compound was obtained as a pink solid in 80% yield.

$^1$H NMR (300 MHz, DMSO-$d_6$) δ [ppm] 8.03 (1H, m), 7.99 (1H, m), 7.47 (0.5H, d, J=8.0 Hz), 7.45 (0.5H, d, J=8.0 Hz), 3.72 (1H, m), 3.60 (0.5H, m), 3.38-3.47 (0.5H, m), 3.19-3.30 (1H, m), 2.97-3.11 (1H, m), 2.91-2.97 (0.5H, m), 2.77-2.85 (0.5H, m), 1.42-1.64 (2H, m), 1.27 (3H, d, J=7.0 Hz), 1.12 (1.5H, t, J=7.0 Hz), 0.98-1.04 (4.5H, m), 0.91 (1.5H, t, J=7.5 Hz), 0.67 (1.5H, t, J=7.5 Hz). HPLC (Condition A) Purity 95.0%; Rt 4.2 min.

Intermediate 260 tert-butyl(4-chloro-2-{[4-{[ethyl(propyl)amino]carbonyl}-3-(isopropylsulfonyl)phenyl]ethynyl}phenoxy)acetate

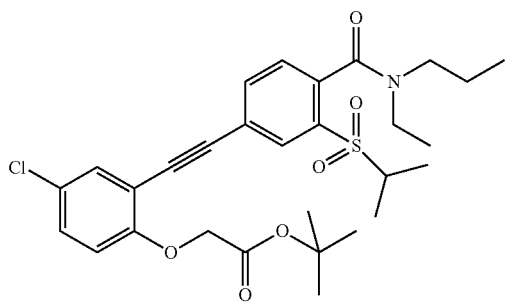

Following the general method as outlined in Intermediate 107, starting from (4-chloro-2-ethynyl-phenoxy)-acetic acid tert-butyl ester (Intermediate 3) and 4-bromo-N-ethyl-2-(isopropylsulfonyl)-N-propylbenzamide (Intermediate 259), the title compound was obtained as a brown sticky solid after purification by flash column chromatography (silica), eluting with cyclohexane containing increasing amounts of EtOAc.

$^1$H NMR (300 MHz, DMSO-$d_6$) δ [ppm] 7.99 (1H, m), 7.92 (1H, dd, J=7.9 Hz, J=1.6 Hz), 7.68 (1H, d, J=2.7 Hz), 7.57 (1H, m), 7.46 (1H, dd, J=9.0 Hz, J=2.7 Hz), 7.02 (1H, d, J=9.0 Hz), 4.83 (2H, s), 3.74 (1H, m), 3.60 (0.5H, m), 3.38-3.47 (0.5H, m), 3.21-3.30 (1H, m), 2.76-3.13 (2H, m), 1.50-1.65 (2H, m), 1.43 (9H, s), 1.29 (3H, d, J=7.0 Hz), 1.15 (1.5H, t, J=7.0 Hz), 1.00-1.06 (4.5H, m), 0.93 (1.5H, t, J=7.4 Hz), 0.69 (1.5H, t, J=7.4 Hz). HPLC (Condition A) Purity 93.6%; Rt 5.9 min.

Intermediate 261

4-[4-bromo-2-(isopropylsulfonyl)benzoyl]morpholine

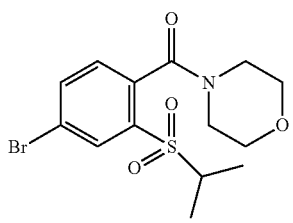

Following the general method as outlined in Intermediate 253, starting from 4-bromo-2-(isopropylsulfonyl)benzoic acid (Intermediate 242) and morpholine, the title compound was obtained as a pink solid.

$^1$H NMR (300 MHz, DMSO-$d_6$) δ [ppm] 8.04 (1H, dd, J=8.0 Hz, J=2.0 Hz), 8.01 (1H, d, J=2.0 Hz), 7.52 (1H, d, J=8.0 Hz), 3.46-3.76 (7H, m), 2.98-3.18 (2H, m), 1.28 (3H, d, J=6.8 Hz), 1.05 (3H, d, J=6.8 Hz). HPLC (Condition A) Purity 98.4%; Rt 3.0 min.

Intermediate 262 tert-butyl(4-chloro-2-{[3-(isopropylsulfonyl)-4-(morpholin-4-ylcarbonyl)phenyl]ethynyl}phenoxy)acetate

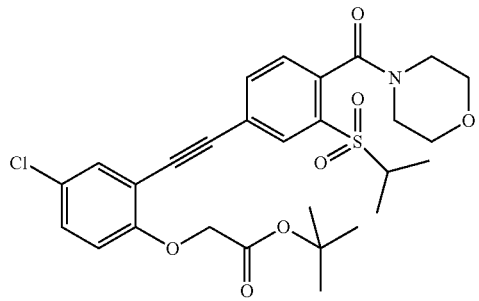

Following the general method as outlined in Intermediate 107, starting from (4-chloro-2-ethynyl-phenoxy)-acetic acid tert-butyl ester (Intermediate 3) and 4-[4-bromo-2-(isopropylsulfonyl)benzoyl]morpholine (Intermediate 261), the title compound was obtained.

HPLC (Condition A) Rt 3.5 min.

Intermediate 263 methyl 2-(2-bromo-4-chlorophenoxy)propanoate

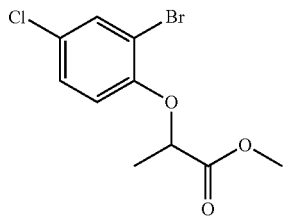

A mixture of 2-bromo-4-chlorophenol (250 mg; 1.21 mmol) and methyl-2-bromopropionate (VWR; 135 μL, 1.21 mmol) in DME (5 mL) was treated with $K_2CO_3$ (250 mg, 1.81 mmol) and refluxed for 18 hours. The reaction mixture was filtered, the filtrate was concentrated and purified by flash column chromatography (silica), eluting with heptane containing increasing amounts of EtOAc. The title compound was obtained as a yellow liquid (306 mg; 87%).

$^1$H NMR (300 MHz, DMSO-$d_6$) δ [ppm] 7.71 (1H, d, J=2.6 Hz), 7.38 (1H, dd, J=9.0 Hz, J=2.6 Hz), 6.99 (1H, d, J=9.0 Hz), 5.10 (1H, q, J=6.8 Hz), 3.68 (3H, s), 1.54 (3H, d, J=6.8 Hz). HPLC (Condition A) Purity 98.8%; Rt 4.6 min.

Intermediate 264 ethyl 2-(2-bromo-4-chlorophenoxy)-2-methylpropanoate

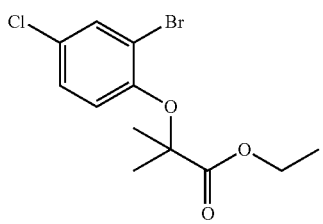

A mixture of 2-bromo-4-chlorophenol (250 mg; 1.21 mmol) and ethyl-2-bromoisobutyrate (450 μl; 3.0 mmol) in DMF (5 mL) was treated with $K_2CO_3$ (250 mg, 1.81 mmol) and heated at 120° C. for 4.5 hours. Water was added and the reaction mixture was extracted 3 times with EtOAc. The combined organic phases were dried over $MgSO_4$, filtered, concentrated and purified by flash column chromatography (silica), eluting with heptane containing increasing amounts of EtOAc. The title compound was obtained as a yellow sticky solid (320 mg; 83%).

$^1$H NMR (300 MHz, DMSO-$d_6$) δ [ppm] 7.73 (1H, d, J=2.6 Hz), 7.37 (1H, dd, J=9.0 Hz, J=2.6 Hz), 6.85 (1H, d, J=9.0 Hz), 4.18 (2H, q, J=7.1 Hz), 1.55 (6H, s), 1.17 (3H, t, J=7.1 Hz). HPLC (Condition A) Purity 99.4%; Rt 5.3 min.

Intermediate 265

2-bromo-4-chloro-1-(methoxymethoxy)benzene

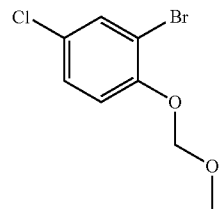

A solution of 2-bromo-4-chlorophenol (3.00 g; 14.5 mmol) in DCM (20 ml) was treated with chloromethyl methyl ether (1.3 ml; 17 mmol) DIEA (3.3 ml; 19 mmol) for 18 hours. The solvents were evaporated, the residue was taken up in EtOAc, washed with sat. NH4Cl solution and brine, dried over $MgSO_4$, filtered and the solvent removed under reduced pressure to afford the title compound as a colorless oil (3.27 g, 90%).

$^1$H NMR (300 MHz, DMSO-$d_6$) δ [ppm] 7.70 (1H, d, J=2.6 Hz), 7.41 (1H, dd, J=9.0 Hz, J=2.6 Hz), 7.23 (1H, d, J=9.0 Hz), 5.29 (2H, s), 3.40 (3H, s).

Intermediate 266

3-{[5-chloro-2-(methoxymethoxy)phenyl]ethynyl}-4-methylphenyl propyl sulfone

Following the general method as outlined in Intermediate 183, starting from 2-bromo-4-chloro-1-(methoxymethoxy) benzene (Intermediate 265) and 2-ethynyl-1-methyl-4-(propane-1-sulfonyl)-benzene (Intermediate 40), the title compound was obtained as a white solid in 70% yield after purification by flash column chromatography (silica), eluting with cyclohexane containing increasing amounts of EtOAc.

$^1$H NMR (300 MHz, DMSO-$d_6$) δ [ppm] 7.94 (1H, d, J=2.0 Hz), 7.80 (1H, dd, J=8.0 Hz, J=2.0 Hz), 7.67 (1H, d, J=2.7 Hz), 7.63 (1H, d, J=8.0 Hz), 7.47 (1H, dd, J=9.0 Hz, J=2.7 Hz), 7.24 (1H, d, J=9.0 Hz), 5.34 (2H, s), 3.43 (3H, s), 3.31 (2H, m), 2.58 (3H, s), 1.55 (2H, sext., J=7.5 Hz), 0.92 (3H, t, J=7.5 Hz). HPLC (Condition A) Purity 100.0%; Rt 5.3 min.

Intermediate 267

4-chloro-2-{[2-methyl-5-(propylsulfonyl)phenyl]ethynyl}phenol

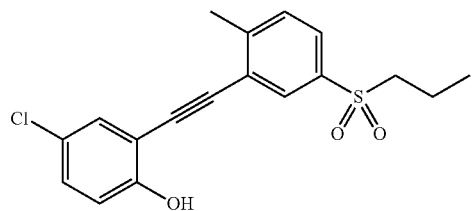

3-{[5-Chloro-2-(methoxymethoxy)phenyl]ethynyl}-4-methylphenyl propyl sulfone (Intermediate 266; 1.09 g; 2.77 mmol) was treated with a 4 N solution hydrogen chloride in 1,4-dioxane (21 ml) and stirred at RT for 7 hours. The reaction mixture was concentrated to dryness under reduced pressure to afford the title compound as a beige solid (884 mg; 91%).

$^1$H NMR (300 MHz, DMSO-$d_6$) δ [ppm] 10.48 (1H, s), 7.94 (1H, d, J=2.0 Hz), 7.78 (1H, dd, J=8.0 Hz, J=2.0 Hz), 7.61 (1H, d, J=8.0 Hz), 7.51 (1H, d, J=2.7 Hz), 7.30 (1H, dd, J=9.0 Hz, J=2.7 Hz), 6.94 (1H, d, J=9.0 Hz), 3.32 (2H, m), 2.57 (3H, s), 1.55 (2H, sext., J=7.5 Hz), 0.91 (3H, t, J=7.5 Hz). HPLC (Condition A) Purity 99.8%; Rt 4.8 min.

Intermediate 268 ethyl 2-(4-chloro-2-{[2-methyl-5-(propylsulfonyl)phenyl]ethynyl}phenoxy)butanoate

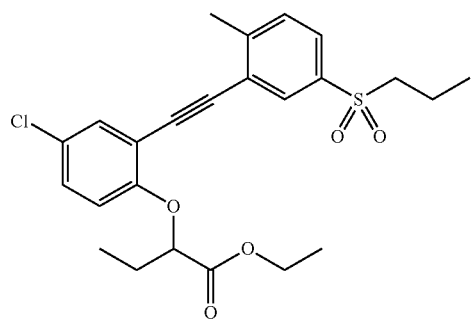

A mixture of 4-chloro-2-{[2-methyl-5-(propylsulfonyl)phenyl]ethynyl}phenol (Intermediate 267; 110 mg; 0.32 mmol) and ethyl 2-bromobutyrate (50 µl; 0.35 mmol) in DME (2 mL) was treated with $K_2CO_3$ (250 mg, 1.81 mmol) and refluxed for 18 hours. Water was added and the reaction mixture was extracted with EtOAc. The organic phase was dried over $MgSO_4$, filtered, concentrated and purified by flash column chromatography (silica), eluting with heptane containing increasing amounts of EtOAc. The title compound was obtained as a colorless sticky solid which was not further purified before use.

HPLC (Condition A) Rt 5.2 min.

Intermediate 269 ethyl 2-(4-chloro-2-{[2-methyl-5-(propylsulfonyl)phenyl]ethynyl}phenoxy)pentanoate

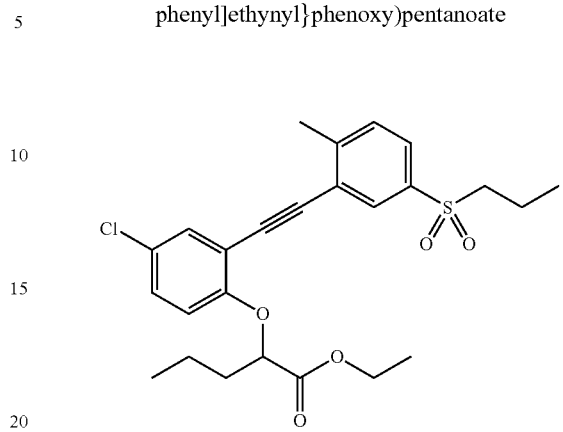

Following the general method as outlined in Intermediate 268, starting from 4-chloro-2-{[2-methyl-5-(propylsulfonyl)phenyl]ethynyl}phenol (Intermediate 267) and ethyl 2-bromovalerate, the title compound was obtained as a colorless sticky solid.

MS (ESI$^+$): 494.3 (M+NH$_4$)$^+$. HPLC (Condition A) Rt 5.7 min.

Intermediate 270 ethyl 2-(4-chloro-2-{[2-methyl-5-(propylsulfonyl)phenyl]ethynyl}phenoxy)-4-methylpentanoate

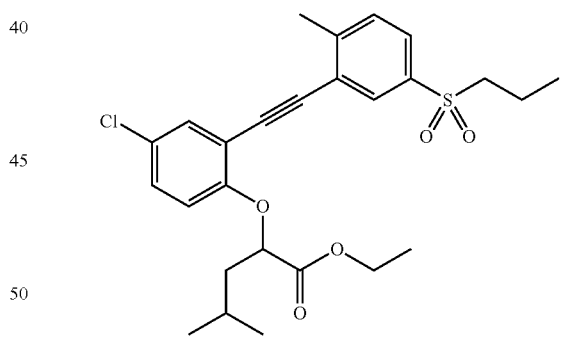

Following the general method as outlined in Intermediate 268, starting from 4-chloro-2-{[2-methyl-5-(propylsulfonyl)phenyl]ethynyl}phenol (Intermediate 267) and 2-bromo-4-methyl-pentanoic acid ethyl ester, the title compound was obtained as a colorless sticky solid in 81% yield.

$^1$H NMR (300 MHz, DMSO-$d_6$) δ [ppm] 7.93 (1H, d, J=2.0 Hz), 7.80 (1H, dd, J=8.0 Hz, J=2.0 Hz), 7.67 (1H, d, J=2.7 Hz), 7.62 (1H, d, J=8.0 Hz), 7.43 (1H, dd, J=9.0 Hz, J=2.7 Hz), 6.98 (1H, d, J=9.0 Hz), 5.00 (1H, dd, J=8.7 Hz, J=4.0 Hz), 4.16 (2H, m), 3.30 (2H, m), 2.58 (3H, s), 1.84-1.95 (2H, m), 1.70-1.79 (1H, m), 1.54 (2H, sext., J=7.5 Hz), 1.17 (3H, t, J=7.0 Hz), 0.89-0.96 (9H, s). HPLC (Condition A) Rt 6.2 min.

EXAMPLE 1

[4-chloro-2-(phenylethynyl)phenoxy]acetic acid

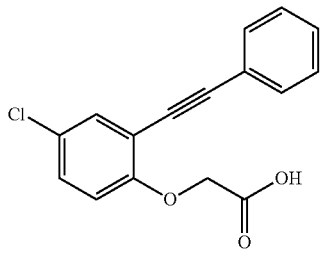

A solution of tert-butyl(2-bromo-4-chlorophenoxy)acetate (350 mg; 1.09 mmol) and phenylacetylene (Aldrich; 122 mg; 1.20 mmol) in degassed, anhydrous ACN (2.80 mL) was treated with dichlorobis(triphenylphosphine)palladium(II) (38 mg; 0.05 mmol), copper(I) iodide (10 mg; 0.05 mmol) and triethylamine (0.45 mL; 3.26 mmol). The reaction mixture was heated at 50° C. under stirring for 16 hours. The solvent was evaporated, the residue dissolved in DCM (4 mL) and TFA (1 mL) was added. After stirring for 45 minutes, the solvents were removed under vacuum and the crude product purified by preparative HPLC. The title compound was obtained as a brown solid.

$^1$H NMR (300 MHz, DMSO-$d_6$) δ [ppm] 13.17 (1H, s), 7.57-7.52 (3H, m), 7.46-7.38 (4H, m), 6.99 (1H, d, J=9.0 Hz), 4.82 (2H, s). MS (ESI$^-$): 285.1. HPLC (Condition A): Rt 4.61 min (HPLC purity 98.3%).

EXAMPLE 2

{4-chloro-2-[(4-chlorophenyl)ethynyl]phenoxy}acetic acid

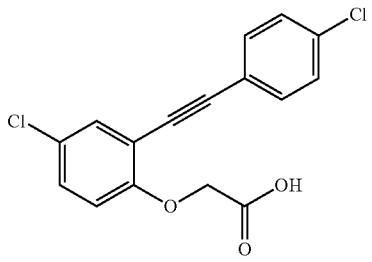

Following the general method as outlined in Example 1, starting from tert-butyl(2-bromo-4-chlorophenoxy)acetate (Intermediate 1) and 4-chlorophenylacetylene (Apollo), the title compound was obtained as a beige solid after purification by preparative HPLC $^1$H NMR (300 MHz, DMSO-$d_6$) δ [ppm] 13.17 (1H, bs), 7.59-7.48 (5H, m), 7.42 (1H, dd, J=9.0, 2.7 Hz), 7.00 (1H, d, J=9.0 Hz), 4.83 (2H, s). MS (ESI$^-$): 319.0. HPLC (Condition A): Rt 4.79 min (HPLC purity 98.7%).

EXAMPLE 3

{4-chloro-2-[(3-chlorophenyl)ethynyl]phenoxy}acetic acid

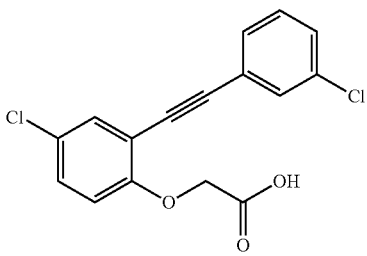

Following the general method as outlined in Example 1, starting from tert-butyl(2-bromo-4-chlorophenoxy)acetate (Intermediate 1) and 3-chloro-1-ethynylbenzene (Aldrich), the title compound was obtained as a brown solid after purification by preparative HPLC.

$^1$H NMR (300 MHz, DMSO-$d_6$) δ [ppm] 13.19 (1H, s), 7.62 (1H, m), 7.58 (1H, d, J=2.7 Hz), 7.45-7.54 (3H, m), 7.42 (1H, dd, J=9.1, J=2.7 Hz), 7.01 (d, J=9.1 Hz, 1H), 4.83 (2H, s). MS (ESI$^-$): 319.0. HPLC (Condition A): Rt 4.91 min (HPLC purity 100%).

EXAMPLE 4

{4-chloro-2-[(2-chlorophenyl)ethynyl]phenoxy}acetic acid

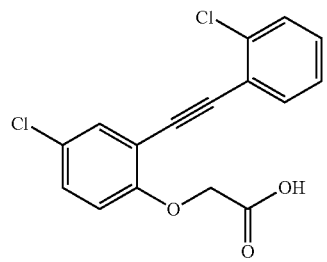

Following the general method as outlined in Example 1, starting from tert-butyl(2-bromo-4-chlorophenoxy)acetate (Intermediate 1) and 1-chlorophenylacetylene (ABCR), the title compound was obtained as a beige solid after purification by preparative HPLC.

$^1$H NMR (300 MHz, DMSO-$d_6$) δ [ppm] 13.21 (1H, s), 7.66 (1H, dd, J=7.3, J=2.5 Hz), 7.60 (1H, dd, J=7.3, J=1.5 Hz), 7.55 (1H, d, J=2.5 Hz), 7.37-7.48 (3H, m), 7.02 (1H, d, J=9.0 Hz), 4.83 (2H, s). MS (ESI$^-$): 319.0. HPLC (Condition A): Rt 4.54 min (HPLC purity 99.8%).

EXAMPLE 5

{4-chloro-2-[(2-fluorophenyl)ethynyl]phenoxy}acetic acid

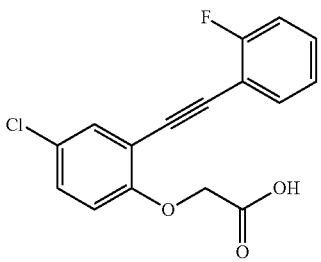

A solution of tert-butyl(2-bromo-4-chlorophenoxy)acetate (Intermediate 1; 350 mg; 1.09 mmol) and 1-fluorophenylacetylene (Aldrich, 135 µL; 1.20 mmol) in degassed, anhydrous CH$_3$CN (2.80 mL) was treated with dichlorobis(triphenylphosphine)palladium(II) (38 mg; 0.05 mmol), copper(I) iodide (10 mg; 0.05 mmol) and triethylamine (0.45 mL; 3.26 mmol). The reaction mixture was heated at 50° C. under stirring for 16 hours. The solvent was evaporated and the residue purified by column chromatography (silica), eluting with cyclohexane containing increasing amounts of EtOAc. The purified ester intermediate was dissolved in DCM (6 mL) and an HCl solution (4 N in dioxane, 2.7 mL) was added. After stirring for 16 hours, the solvents were removed under vacuum and the crude product purified by preparative HPLC. The title compound was obtained as a light brown solid.

$^1$H NMR (300 MHz, DMSO-d$_6$) δ [ppm] 7.63 (1H, td, J=7.5, 1.8 Hz), 7.57 (1H, d, J=2.6 Hz), 7.55-7.23 (4H, m), 7.01 (1H, d, J=9.0 Hz), 4.83 (2H, s). MS (ESI$^-$): 303.1. HPLC (Condition A): Rt 4.42 min (HPLC purity 98.3%).

EXAMPLE 6

{4-chloro-2-[(2-methoxyphenyl)ethynyl]phenoxy}acetic acid

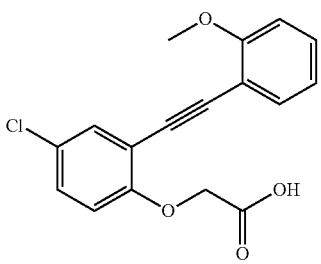

A solution of (2-bromo-4-chlorophenoxy)acetic acid (200 mg; 0.75 mmol, Intermediate 4) and 2-ethynylanisole (Aldrich, 107 µL; 0.83 mmol) in anhydrous, degassed ACN (2 mL) was treated with dichlorobis(triphenylphosphine)palladium (II) (38 mg; 0.05 mmol) followed after 5 minutes by copper iodide (10 mg; 0.05 mmol) and triethylamine (0.45 mL; 3.3 mmol). The reaction mixture was heated at 50° C. under stirring for 16 hours. The solvents were removed under vacuum, the residue was then taken up in EtOAc and washed with HCl (1N aqueous solution), the organic phase was washed with water (750 mL) then with brine (750 mL), dried over MgSO$_4$, filtered and concentrated under vacuum to give a brown oily residue which was purified by preparative HPLC to afford the title compound as a brown oil.

MS (ESI$^-$): 315.1. HPLC (Condition A): Rt 4.27 min (HPLC purity 100%).

EXAMPLE 7

(4-chloro-2-{[3-(trifluoromethyl)phenyl]ethynyl}phenoxy)acetic acid

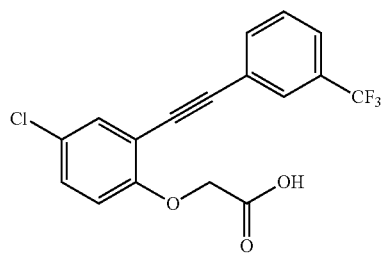

Following the general method as outlined in Example 6, starting from (2-bromo-4-chlorophenoxy)acetic acid (Intermediate 4) and 3-ethynyl-□.□.□-trifluorotoluene (Aldrich), using degassed, anhydrous DMF as solvent, the title compound was obtained as a brown sticky solid after purification by preparative HPLC.

$^1$H NMR (300 MHz, DMSO-d$_6$) δ [ppm] 13.16 (1H, bs), 7.91 (1H, s), 7.85 (1H, d, J=7.8 Hz), 7.80 (1H, d, J=7.8 Hz), 7.69 (1H, t, J=7.8 Hz), 7.63 (1H, d, J=2.7 Hz), 7.44 (1H, dd, J=9.0, 2.7 Hz), 7.02 (1H, d, J=9.0 Hz), 4.84 (2H, s). MS (ESI$^-$): 353.1. HPLC (Condition A): Rt 5.12 min (HPLC purity 96.1%).

EXAMPLE 8

{4-chloro-2-[(2,4-difluorophenyl)ethynyl]phenoxy}acetic acid

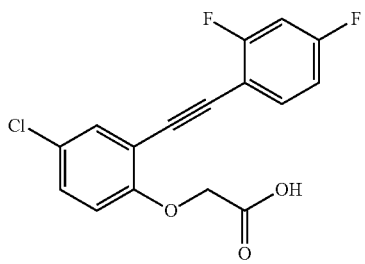

A solution of tert-butyl(2-bromo-4-chlorophenoxy)acetate (350 mg; 1.09 mmol) and 1-ethynyl-2,4-difluorobenzene (Aldrich, 165 mg; 1.20 mmol) in degassed, anhydrous CH$_3$CN (2.80 mL) was treated with dichlorobis(triphenylphosphine)palladium(II) (38 mg; 0.05 mmol), copper(I) iodide (10 mg; 0.05 mmol) and triethylamine (0.45 mL; 3.26 mmol). The reaction mixture was heated at 50° C. under stirring for 16 hours. The solvent was evaporated and the residue dissolved in DCM (1 mL) and an HCl solution (4 N in dioxane, 2.7 mL) was added. After stirring for 16 hours, the solvents were removed under vacuum and the crude product purified by preparative HPLC. The title compound was obtained as an off-white solid.

¹H NMR (300 MHz, DMSO-d₆) δ [ppm] 13.17 (1H, s), 7.70 (1H, td, J=8.5, 6.5 Hz), 7.57 (1H, d, J=2.7 Hz), 7.49-7.40 (2H, m), 7.24-7.16 (1H, m), 7.01 (1H, d, J=9.0 Hz), 4.83 (2H, s). MS (ESI⁻): 321.1. HPLC (Condition A): Rt 4.50 min (HPLC purity 100%).

EXAMPLE 9

(4-chloro-2-{[2-(trifluoromethyl)phenyl]ethynyl}phenoxy)acetic acid

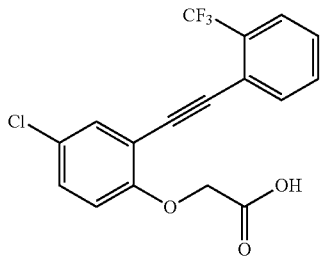

Following the general method as outlined in Example 8, starting from tert-butyl(2-bromo-4-chlorophenoxy)acetate (Intermediate 1) and 2-ethynyl-α.α.α-trifluorotoluene (Aldrich), the title compound was obtained as a beige solid after purification by preparative HPLC.

¹H NMR (300 MHz, DMSO-d₆) δ [ppm] 13.2 (1H, bs), 7.86-7.69 (3H, m), 7.63 (1H, t, J=7.5 Hz), 7.49-7.42 (2H, m), 7.03 (1H, d, J=8.8 Hz), 4.82 (2H, s). MS (ESI⁻): 353.1. HPLC (Condition A): Rt 4.75 min (HPLC purity 95.9%).

EXAMPLE 10

{4-chloro-2-[(5-chloro-2-thienyl)ethynyl]phenoxy}acetic acid

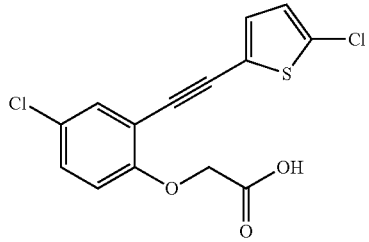

A mixture of 2-bromo-5-chlorothiophene (Aldrich, 163 mg; 0.82 mmol), tert-butyl(4-chloro-2-ethynylphenoxy)acetate (Intermediate 3, 200 mg; 0.75 mmol), dichlorobis(triphenylphosphine)palladium(II) (33 mg; 0.04 mmol), copper(I) iodide (8.6 mg; 0.04 mmol) was degassed during two minutes under nitrogen then THF (3 mL) and triethylamine (208 µL; 1.50 mmol) were added and reaction mixture was stirred at 60° C. for 16 hours. The solvent was evaporated and the residue was treated with an HCl solution (4 N in dioxane, 3.7 mL). After stirring for 16 hours, the solvents were removed under vacuum and the crude product purified by preparative HPLC. The title compound was obtained as a brown sticky solid.

¹H NMR (300 MHz, DMSO-d₆) δ [ppm] 13.2 (1H, bs), 7.57 (1H, d, J=2.7 Hz), 7.43 (1H, dd, J=9.0, 2.7 Hz), 7.31 (1H, d, J=4.0 Hz), 7.19 (1H, d, J=4.0 Hz), 7.00 (1H, d, J=9.0 Hz), 4.82 (2H, s). MS (ESI⁺): 325.0. HPLC (Condition A): Rt 5.35 min (HPLC purity 96.4%).

EXAMPLE 11

{4-chloro-2-[(1-methyl-1H-imidazol-2-yl)ethynyl]phenoxy}acetic acid

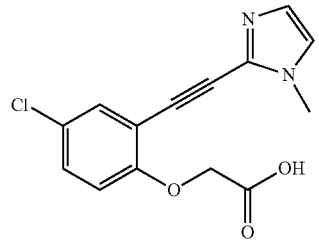

Following the general method as outlined in Example 10, starting from tert-butyl(4-chloro-2-ethynylphenoxy)acetate (Intermediate 3) and 2-bromo-1-methyl-1H-imidazole (Aldrich), the title compound was obtained as an off-white solid after purification by preparative HPLC.

¹H NMR (300 MHz, DMSO-d₆) δ [ppm] 13.2 (1H, bs), 7.73 (1H, d, J=2.7 Hz), 7.68 (1H, d, J=1.6 Hz), 7.55 (1H, dd, J=9.0, 2.7 Hz), 7.49 (1H, H, d, J=1.6 Hz), 7.12 (1H, d, J=9.0 Hz), 4.89 (2H, s), 3.92-3.89 (3H, s). MS (ESI⁺): 291.1. HPLC (Condition A): Rt 2.16 min (HPLC purity 98.2%).

EXAMPLE 12

[4-chloro-2-(pyridin-4-ylethynyl)phenoxy]acetic acid

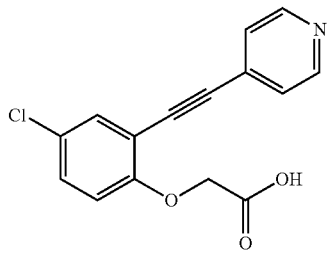

Following the general method as outlined in Example 10, starting from tert-butyl(4-chloro-2-ethynylphenoxy)acetate (Intermediate 3) and 4-bromopyridine hydrochloride (Fluka), the title compound was obtained as a yellow solid after purification by precipitation in dioxane.

¹H NMR (300 MHz, DMSO-d₆) δ [ppm] 13.2 (1H, bs), 8.66-8.62 (2H, m), 7.64 (1H, d, J=2.7 Hz), 7.53-7.44 (3H, m), 7.04 (1H, d, J=9.0 Hz), 4.86 (2H, s). MS (ESI⁺): 288.0. HPLC (Condition A): Rt 2.37 min (HPLC purity 97.5%).

EXAMPLE 13

[4-chloro-2-(pyridin-2-ylethynyl)phenoxy]acetic acid

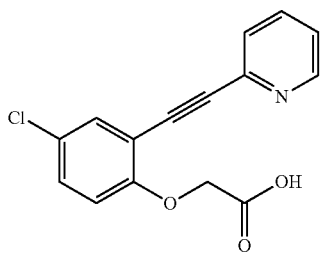

Following the general method as outlined in Example 10, starting from tert-butyl(4-chloro-2-ethynylphenoxy)acetate (Intermediate 3) and 2-bromopyridine (Acros), the title compound was obtained as a beige powder after purification by precipitation in acetonitrile.

$^1$H NMR (300 MHz, DMSO-$d_6$) δ [ppm] 13.18 (1H, s), 8.62 (1H, ddd, J=4.9, 1.8, 1.0 Hz), 7.87 (1H, td, J=7.7, 1.8 Hz), 7.66-7.61 (2H, m), 7.48-7.39 (2H, m), 7.02 (1H, d, J=9.0 Hz), 4.86 (2H, s). MS (ESI$^+$): 288.1. HPLC (Condition A): Rt 2.53 min (HPLC purity 98.4%).

EXAMPLE 14

[4-chloro-2-(pyridin-3-ylethynyl)phenoxy]acetic acid

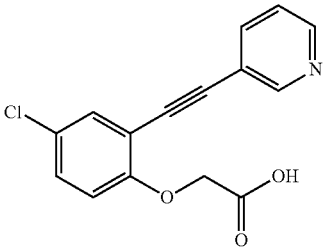

Following the general method as outlined in Example 10, starting from tert-butyl(4-chloro-2-ethynylphenoxy)acetate (Intermediate 3) and 3-bromopyridine (Fluka), the title compound was obtained as an off-white solid after purification by preparative HPLC.

$^1$H NMR (300 MHz, DMSO-$d_6$) δ [ppm] 13.17 (1H, s), 8.75 (1H, d, J=2.1 Hz), 8.61 (1H, dd, J=4.9, 1.8 Hz), 7.97 (1H, dt, J=7.9, 1.8 Hz), 7.61 (1H, d, J=2.7 Hz), 7.52-7.42 (2 H, m), 7.02 (1H, d, J=9.0 Hz), 4.85 (2H, s). MS (ESI$^+$): 288.0. HPLC (Condition A): Rt 2.56 min (HPLC purity 98.1%).

EXAMPLE 15

{4-chloro-2-[(4-methylpyridin-3-yl)ethynyl]phenoxy}acetic acid

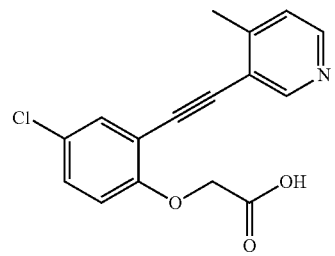

A solution of tert-butyl{4-chloro-2-[(4-methylpyridin-3-yl)ethynyl]phenoxy}acetate (Intermediate 19, 138 mg; 0.39 mmol) in DCM (1.4 mL) was treated with an HCl solution (4 N in dioxane, 2.7 mL). After stirring for 20 hours, the solvents were removed under vacuum to afford the title compound as a beige solid (107 mg, 82%).

$^1$H NMR (300 MHz, DMSO-$d_6$) δ [ppm] 8.91 (1H, s), 8.68 (1H, s), 7.86-7.72 (1H, m), 7.65 (1H, d, J=2.7 Hz), 7.49 (1H, dd, J=9.0, 2.7 Hz), 7.08 (1H, d, J=9.0 Hz), 4.86 (2 H, s), 2.64 (3H, s). MS (ESI$^+$): 302.2. HPLC (Condition A): Rt 2.53 min (HPLC purity 99.6%).

EXAMPLE 16

[4-chloro-2-({5-[(ethylamino)sulfonyl]-2-methylphenyl}ethynyl)phenoxy]acetic acid

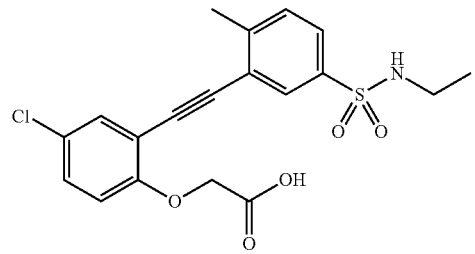

Following the general method as outlined in Example 10, starting from tert-butyl(4-chloro-2-ethynylphenoxy)acetate (Intermediate 3) and N-ethyl 3-bromo-4-methylbenzenesulfonamide (Combi-Blocks), the title compound was obtained as a beige solid after purification by preparative HPLC.

$^1$H NMR (300 MHz, DMSO-$d_6$) δ [ppm] 13.15 (1H, s), 7.85 (1H, d, J=2.0 Hz), 7.69 (1H, dd, J=8.0, J=2.0 Hz), 7.63 (1H, d, J=2.7 Hz), 7.54-7.60 (2H, m), 7.44 (1H, dd, J=9.0, J=2.7 Hz), 7.04 (1H, d, J=9.0 Hz), 4.84 (2H, s), 2.78 (2H, qd, J=7.1, J=5.7 Hz), 2.55 (3H, s), 0.97 (3H, t, J=7.1 Hz). MS (ESI$^+$): 408.2. HPLC (Condition A): Rt 4.31 min (HPLC purity 99.6%).

EXAMPLE 17

(4-chloro-2-{[3-(propylsulfonyl)phenyl]ethynyl}phenoxy)acetic acid

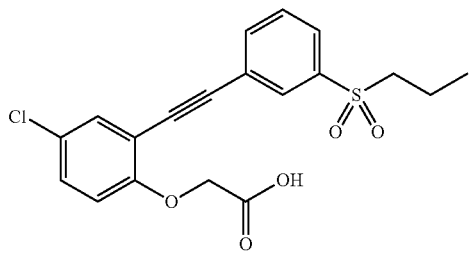

Following the general method as outlined in Example 15, starting from tert-butyl{4-chloro-2-{[3-(propylsulfonyl)phenyl]ethynyl}phenoxy)acetate (Intermediate 20), the title compound was obtained as a beige solid after purification by preparative HPLC.

$^1$H NMR (300 MHz, DMSO-d$_6$) δ [ppm] 13.17 (1H, s), 8.01 (1H, t, J=1.6 Hz), 7.88-7.94 (2H, m), 7.73 (1H, t, J=7.6 Hz), 7.64 (1H, d, J=2.7 Hz), 7.44 (1H, dd, J=9.0, J=2.7 Hz), 7.02 (1H, d, J=9.0 Hz), 4.83 (2H, s), 3.34-3.39 (2H, m), 1.57 (2H, sext., J=7.6 Hz), 0.93 (3H, t, J=7.6 Hz). MS (ESI$^-$): 391.3. HPLC (Condition A): Rt 4.27 min (HPLC purity 99.8%).

EXAMPLE 18

(4-chloro-2-{[3-(methylsulfonyl)phenyl]ethynyl}phenoxy)acetic acid

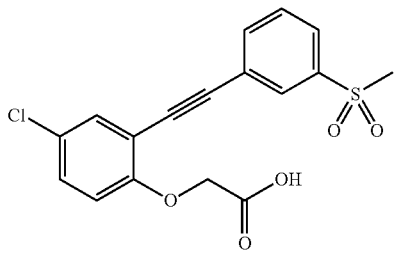

Following the general method as outlined in Example 10, starting from tert-butyl(4-chloro-2-ethynylphenoxy)acetate (Intermediate 3) and 3-bromophenylmethylsulfone (Asymchem), the title compound was obtained as a beige solid after purification by preparative HPLC.

$^1$H NMR (300 MHz, DMSO-d$_6$) δ [ppm] 13.21 (1H, s), 8.06 (1H, t, J=1.6 Hz), 7.96 (1H, dt, J=7.8, J=1.6 Hz), 7.88 (1H, dt, J=7.8, J=1.6 Hz), 7.72 (1H, t, J=7.8 Hz), 7.63 (1H, d, J=2.6 Hz), 7.44 (1H, dd, J=9.0, J=2.6 Hz), 7.01 (1H, d, J=9.0 Hz), 4.84 (2H, s), 3.29 (1H, s). MS (ESI$^-$): 363.2. HPLC (Condition A): Rt 3.81 min (HPLC purity 99.2%).

EXAMPLE 19

[4-chloro-2-({3-[(3-hydroxypropyl)sulfonyl]phenyl}ethynyl)phenoxy]acetic acid

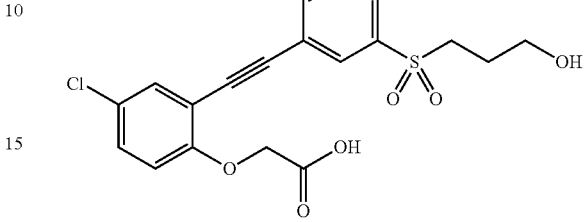

Following the general method as outlined in Example 10, starting from tert-butyl(4-chloro-2-ethynylphenoxy)acetate (Intermediate 3) and 3-(3-bromo-benzenesulfonyl)-propan-1-ol (Intermediate 6), the title compound was obtained as a brown solid after purification by preparative HPLC.

$^1$H NMR (300 MHz, DMSO-d$_6$) δ [ppm] 13.21 (1H, s), 8.01 (1H, t, J=1.6 Hz), 7.92 (2H, m), 7.74 (1H, t, J=7.8 Hz), 7.65 (1H, d, J=2.6 Hz), 7.44 (1H, dd, J=9.0, J=2.6 Hz), 7.01 (1H, d, J=9.0 Hz), 4.85 (2H, s), 4.66 (1H, s), 3.36-3.43 (4H, m), 1.68 (2H, m). MS (ESI$^+$): 409.2. HPLC (Condition A): Rt 3.60 min (HPLC purity 93.7%).

EXAMPLE 20

[4-chloro-2-({3-[(2-hydroxyethyl)sulfonyl]phenyl}ethynyl)phenoxy]acetic acid

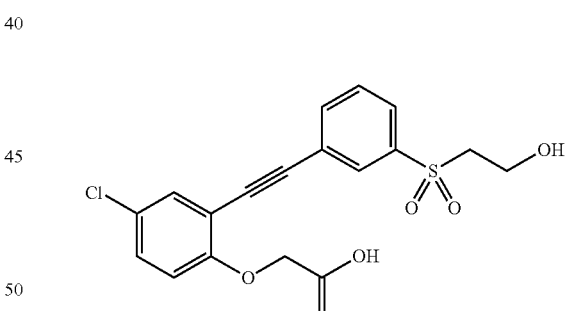

Following the general method as outlined in Example 10, starting from tert-butyl(4-chloro-2-ethynylphenoxy)acetate (Intermediate 3) and 2-(3-bromo-benzenesulfonyl)-ethanol (Intermediate 7), the title compound was obtained as a beige solid after purification by preparative HPLC.

$^1$H NMR (300 MHz, DMSO-d$_6$) δ [ppm] 13.28 (1H, s), 8.00 (1H, t, J=1.6 Hz), 7.90 (1H, dt, J=7.8, J=1.6 Hz), 7.85 (1H, dt, J=7.8, J=1.6 Hz), 7.68 (1H, t, J=7.8 Hz), 7.61 (1H, d, J=2.7 Hz), 7.41 (1H, dd, 9.0, J=2.7 Hz), 6.99 (1H, d, J=9.0 Hz), 4.85 (1H, bs), 4.83 (2H, s), 3.67 (2H, t, J=6.1 Hz), 3.51 (2H, t, J=6.1 Hz). MS (ESI$^-$): 393.2. HPLC (Condition A): Rt 3.46 min (HPLC purity 97.9%).

EXAMPLE 21

{4-chloro-2-[(5-cyano-2-fluorophenyl)ethynyl]phenoxy}acetic acid

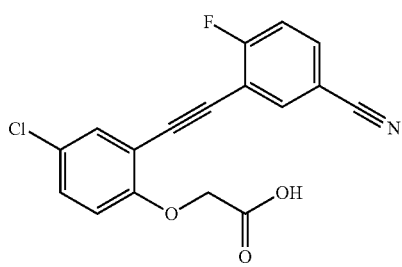

Following the general method as outlined in Example 15, starting from tert-butyl{4-chloro-2-[(5-cyano-2-fluorophenyl)ethynyl]phenoxy}acetate (Intermediate 21), the title compound was obtained as a white solid (119 mg, 99%).

$^1$H NMR (300 MHz, DMSO-d$_6$) δ [ppm] 13.20 (1H, s), 8.22 (1H, dd, J=6.6, J=2.2 Hz), 7.99-8.04 (1H, m), 7.58-7.65 (2H, m), 7.47 (1H, dd, J=9.0, J=2.7 Hz), 7.03 (1H, d, J=9.0 Hz), 4.85 (2H, s). MS (ESI⁻): 328.1. HPLC (Condition A): Rt 4.26 min (HPLC purity 97.1%).

EXAMPLE 22

{4-chloro-2-[(2-methylpyridin-3-yl)ethynyl]phenoxy}acetic acid

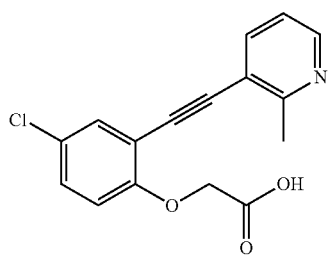

Following the general method as outlined in Example 15, starting from tert-butyl{4-chloro-2-[(2-methylpyridin-3-yl)ethynyl]phenoxy}acetate (Intermediate 22), the title compound was obtained as a dark brown solid (37.6 quant).

$^1$H NMR (300 MHz, DMSO-d$_6$) δ [ppm] 13.32 (1H, s), 8.65 (1H, d, J=5.1 Hz), 8.29 (1H, d, J=7.9 Hz), 7.65-7.70 (2H, m), 7.48 (1H, dd, J=9.0, J=2.8 Hz), 7.07 (1H, d, J=9.0 Hz), 4.85 (2H, s), 2.81 (3H, s). MS (ESI⁺): 302.1. HPLC (Condition A): Rt 2.56 min (HPLC purity 93.4%).

EXAMPLE 23

{2-[(2-chlorophenyl)ethynyl]-4-cyanophenoxy}acetic acid

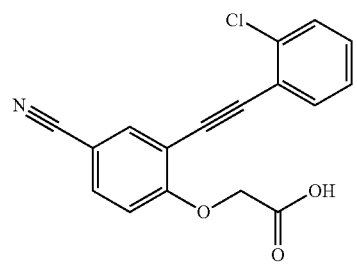

Following the general method as outlined in Example 8, starting from tert-butyl(2-bromo-4-cyanophenoxy)acetate (Intermediate 8) and 2-bromochlorobenzene (Aldrich), the title compound was obtained as a white solid after purification by preparative HPLC.

$^1$H NMR (300 MHz, DMSO-d$_6$) δ [ppm] 13.3 (1H, bs), 8.02 (1H, d, J=2.2 Hz), 7.87 (1H, dd, J=8.8, 2.2 Hz), 7.68 (1H, dd, J=7.3, 2.1 Hz), 7.61 (1H, dd, J=7.7, 1.6 Hz), 7.51-7.39 (2H, m), 7.19 (1H, d, J=8.8 Hz), 4.95 (2H, s). MS (ESI⁻): 310.1. HPLC (Condition A): Rt 4.19 min (HPLC purity 98.0%).

EXAMPLE 24

{4-chloro-2-[(2,4-dimethyl-1,3-thiazol-5-yl)ethynyl]phenoxy}acetic acid

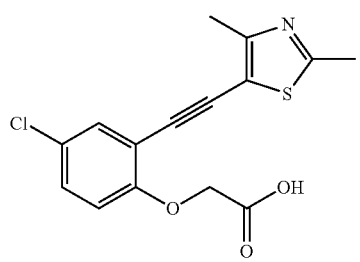

Following the general method as outlined in Example 8, starting from tert-butyl(4-chloro-2-ethynylphenoxy)acetate (Intermediate 3) and 5-bromo-2,4-dimethyl-1,3-thiazole (Acros), the title compound was obtained as a white solid after purification by preparative HPLC.

$^1$H NMR (300 MHz, DMSO-d$_6$) δ [ppm] 13.2 (1H, bs), 7.57 (1H, d, J=2.7 Hz), 7.41 (1H, dd, J=9.0, 2.7 Hz), 7.01 (1H, d, J=9.0 Hz), 4.80 (2H, s), 2.64 (3H, s), 2.45 (3H, s). MS (ESI⁺): 322.1. HPLC (Condition A): Rt 3.85 min (HPLC purity 94.7%).

EXAMPLE 25

(4-chloro-2-{[2-fluoro-5-(hydroxymethyl)phenyl]ethynyl}phenoxy)acetic acid

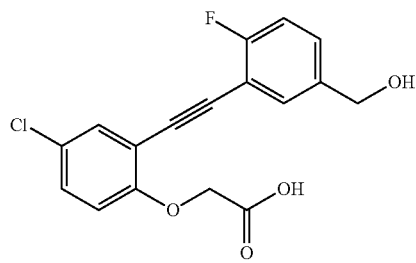

Following the general method as outlined in Example 15, starting from tert-butyl(4-chloro-2-{[2-fluoro-5-(hydroxymethyl)phenyl]ethynyl}phenoxy)acetate (Intermediate 23), the title compound was obtained as a beige solid after purification by preparative HPLC.

$^1$H NMR (300 MHz, DMSO-$d_6$) δ [ppm] 13.2 (1H, s), 7.55 (1H, d, J=2.6 Hz), 7.54 (1H, dd, J=5.1, J=2.2 Hz), 7.42 (1H, dd, J=9.0, J=2.6 Hz), 7.40 (1H, ddd, J=8.7, J=5.1, J=2.2 Hz), 7.29 (1H, t, J=5.7 Hz), 6.99 (1H, d, J=9.0 Hz), 5.31 (1H, bs), 4.81 (2H, s), 4.50 (2H, s). MS (ESI$^-$): 333.2. HPLC (Condition A): Rt 3.83 min (HPLC purity 99.2%).

EXAMPLE 26

(4-chloro-2-{[2-fluoro-4-(hydroxymethyl)phenyl]ethynyl}phenoxy)acetic acid

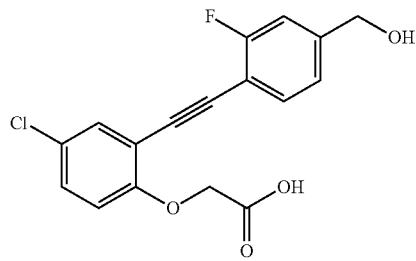

Following the general method as outlined in Example 15, starting from tert-butyl(4-chloro-2-{[2-fluoro-4-(hydroxymethyl)phenyl]ethynyl}phenoxy)acetate (Intermediate 24), the title compound was obtained as a white solid after purification by preparative HPLC.

$^1$H NMR (300 MHz, DMSO-$d_6$) δ [ppm] 13.2 (1H, s), 7.57 (1H, d, J=7.8 Hz), 7.54 (1H, d, J=2.6 Hz), 7.42 (1H, dd, J=9.0, J=2.6 Hz), 7.24 (1H, d, J=10.7 Hz), 7.20 (1H, d, J=7.8 Hz), 6.98 (1H, d, J=9.0 Hz), 5.43 (1H, s), 4.80 (2H, s), 4.55 (2H, s). MS (ESI$^-$): 333.2. HPLC (Condition A): Rt 3.73 min (HPLC purity 99.7%).

EXAMPLE 27

{2-[(2-chlorophenyl)ethynyl]-4-methylphenoxy}acetic acid

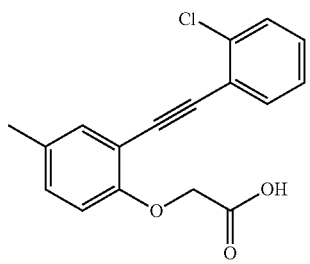

Following the general method as outlined in Example 8, starting from tert-butyl(2-bromo-4-methylphenoxy)acetate (Intermediate 10) and 2'-chlorophenyl acetylene (ABCR), the title compound was obtained as a brown solid after purification by preparative HPLC.

MS (ESI$^-$): 299.1. HPLC (Condition B): Rt 1.31 min (HPLC purity 97.5%).

EXAMPLE 28

(4-chloro-2-{[2-fluoro-3-(hydroxymethyl)phenyl]ethynyl}phenoxy)acetic acid

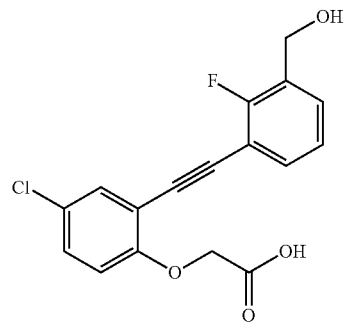

Following the general method as outlined in Example 15, starting from tert-butyl(4-chloro-2-{[2-fluoro-3-(hydroxymethyl)phenyl]ethynyl}phenoxy)acetate (Intermediate 25), the title compound was obtained as a white solid after purification by preparative HPLC.

$^1$H NMR (300 MHz, DMSO-$d_6$) δ [ppm] 7.47-7.54 (3H, m), 7.41 (1H, dd, J=9.0, J=2.7 Hz), 7.25 (1H, t, J=7.6 Hz), 6.97 (1H, d, J=9.0 Hz), 5.37 (1H, bs), 4.75 (2H, s), 4.58 (2H, s). MS (ESI$^-$): 333.1. HPLC (Condition A): Rt 3.70 min (HPLC purity 98.8%).

EXAMPLE 29

{4-chloro-2-[(4-hexylpyridin-3-yl)ethynyl]phenoxy}acetic acid

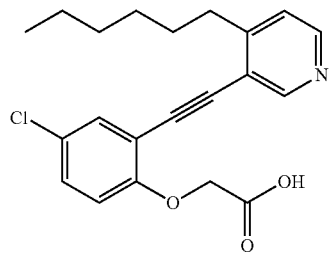

Following the general method as outlined in Example 8, starting from tert-butyl(4-chloro-2-ethynylphenoxy)acetate (Intermediate 3) and 3-bromo-4-hexylpyridine (Intermediate 13), the title compound was obtained as a beige solid after purification by preparative HPLC.

$^1$H NMR (300 MHz, DMSO-d$_6$) δ [ppm] 13.2 (1H, bs), 8.64 (1H, s), 8.46 (1H, d, J=5.1 Hz), 7.56 (1H, d, J=2.7 Hz), 7.44 (1H, d, J=9.0, J=2.7 Hz), 7.36 (1H, d, J=5.1 Hz), 7.03 (1H, d, J=9.0 Hz), 4.81 (2H, s), 2.83 (2H, m), 1.62 (2H, m), 1.27 (6H, m), 0.82 (3H, t, J=7.2 Hz). MS (ESI$^+$): 372.3. HPLC (Condition A): Rt 3.85 min (HPLC purity 96.7%).

EXAMPLE 30

(4-chloro-2-{[2-fluoro-5-(methoxymethyl)phenyl]ethynyl}phenoxy)acetic acid

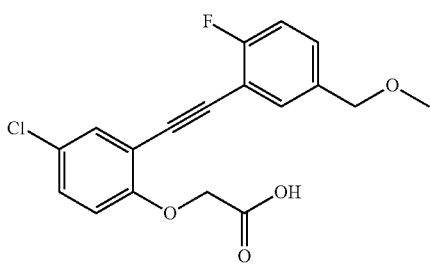

Following the general method as outlined in Example 15, starting from tert-butyl(4-chloro-2-{[2-fluoro-5-(methoxymethyl)phenyl]ethynyl}phenoxy)acetate (Intermediate 26), the title compound was obtained as a beige solid after purification by preparative HPLC.

$^1$H NMR (300 MHz, DMSO-d$_6$) δ [ppm] 13.2 (1H, bs), 7.56-7.59 (2H, m), 7.41-7.47 (2H, m), 7.34 (1H, m), 7.01 (1H, d, J=9.0 Hz), 4.84 (2H, s), 4.43 (2H, s), 3.32 (3H, s). MS (ESI$^-$): 347.2. HPLC (Condition A): Rt 4.37 min (HPLC purity 96.0%).

EXAMPLE 31

{4-chloro-2-[(4-methyl-1-oxidopyridin-3-yl)ethynyl]phenoxy}acetic acid

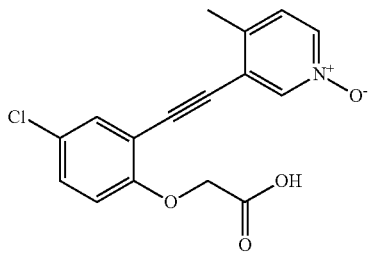

Following the general method as outlined in Example 15, starting from tert-butyl{4-chloro-2-[(4-methyl-1-oxidopyridin-3-yl)ethynyl]phenoxy}acetate (Intermediate 27), the title compound was obtained as a white solid after precipitation from the reaction mixture.

$^1$H NMR (300 MHz, DMSO-d$_6$) δ [ppm] 8.57 (1H, d, J=2.0 Hz), 8.37 (1H, dd, J=6.6, 2.0 Hz), 7.64 (1H, d, J=2.7 Hz), 7.56 (1H, d, J=6.6 Hz), 7.49 (1H, dd, J=9.0, 2.7 Hz), 7.08 (1H, d, J=9.0 Hz), 4.85 (2H, s), 2.50 (3H, s). MS (ESI$^+$): 318.1. HPLC (Condition A): Rt 2.96 min (HPLC purity 97.7%).

EXAMPLE 32

(4-cyano-2-{[3-(propylsulfonyl)phenyl]ethynyl}phenoxy)acetic acid

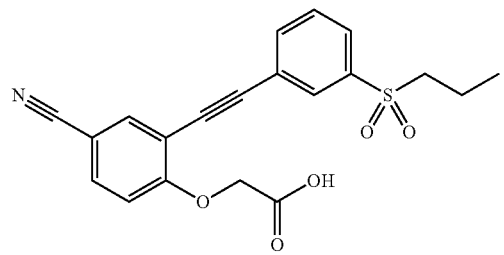

Following the general method as outlined in Example 15, starting from tert-butyl(4-cyano-2-{[3-(propylsulfonyl)phenyl]ethynyl}phenoxy)acetate (Intermediate 28), the title compound was obtained as a white solid after purification by preparative HPLC.

$^1$H NMR (300 MHz, DMSO-d$_6$) δ [ppm] 13.3 (1H, bs), 8.10 (1H, d, J=2.2 Hz), 8.03 (1H, t, J=1.7 Hz), 7.96-7.85 (3H, m), 7.75 (1H, t, J=7.8 Hz), 7.19 (1H, d, J=8.9 Hz), 4.96 (2H, s), 3.41-3.33 (2H, m), 1.62-1.51 (2H, m), 0.97-0.89 (3H, t, J=7.4). MS (ESI$^-$): 382.3. HPLC (Condition A): Rt 3.75 min (HPLC purity 99.5%).

EXAMPLE 33

(4-chloro-2-{[2-methyl-5-(methylsulfonyl)phenyl]ethynyl}phenoxy)acetic acid

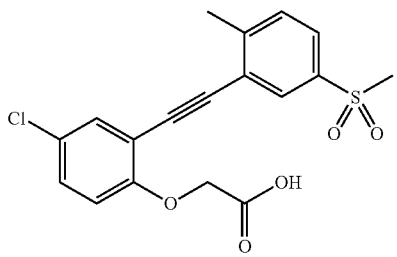

Following the general method as outlined in Example 15, starting from tert-butyl(4-chloro-2-{[2-methyl-5-(methylsulfonyl)phenyl]ethynyl}phenoxy)acetate (Intermediate 29), the title compound was obtained as a light brown solid (150.2 mg, 91%).

$^1$H NMR (300 MHz, DMSO-$d_6$) δ [ppm] 13.2 (1H, bs), 8.00 (1H, d, J=2.0 Hz), 7.84 (1H, dd, J=8.0, 2.0 Hz), 7.65 (1H, d, J=2.7 Hz), 7.62 (1H, d, J=8.0 Hz), 7.45 (1H, dd, J=9.0, 2.7 Hz), 7.05 (1H, d, J=9.0 Hz), 4.85 (2H, s), 3.25 (3H, s), 2.58 (3H, s). MS (ESI$^-$) δ 377.2. HPLC (Condition A): Rt 4.00 min (HPLC purity 93.4%).

EXAMPLE 34

(4-chloro-2-{[2-fluoro-4-(methoxymethyl)phenyl]ethynyl}phenoxy)acetic acid

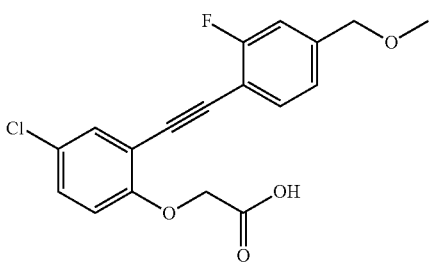

Following the general method as outlined in Example 15, starting from tert-butyl(4-chloro-2-{[2-fluoro-4-(methoxymethyl)phenyl]ethynyl}phenoxy)acetate (Intermediate 30), the title compound was obtained as a beige solid after purification by preparative HPLC.

$^1$H NMR (300 MHz, DMSO-$d_6$) δ [ppm] 13.25 (1H, s), 7.62 (1H, t, J=7.6 Hz), 7.58 (1H, d, J=2.7 Hz), 7.44 (1H, dd, J=9.0, 2.7 Hz), 7.29 (1H, d, J=10.5 Hz), 7.24 (1H, m), 7.02 (1H, d, J=9.0 Hz), 4.83 (2H, s), 4.49 (2H, s), 3.3 (3H). MS (ESI$^+$): 347.2. HPLC (Condition A): Rt 4.40 min (HPLC purity 99.9%).

EXAMPLE 35

[4-chloro-2-({5-[(dimethylamino)sulfonyl]pyridin-3-yl}ethynyl)phenoxy]acetic acid

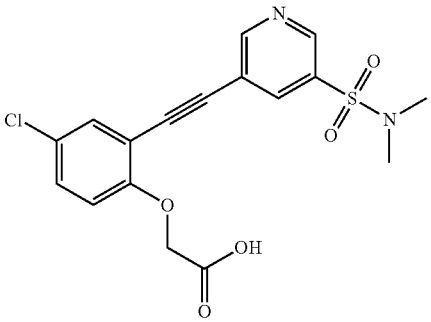

Step 1 tert-butyl[4-chloro-2-({5-[(dimethylamino)sulfonyl]pyridin-3-yl}ethynyl)phenoxy]acetate A solution of tert-butyl(4-chloro-2-ethynyl phenoxy)acetate (Intermediate 3; 250 mg, 0.93 mmol), 5-bromo-pyridine-3-sulfonic acid dimethylamide (Intermediate 32; 270 mg, 1.03 mmol) and triethylamine (0.25 ml, 1.86 mmol) in anhydrous THF was degassed for 20 min with argon, then treated with 1,1'-bis(diphenylphosphino)ferrocenedichloro palladium(II) (45 mg) and cuprous iodide (11 mg) and heated to 65° C. for 5 h. The reaction mixture was concentrated under reduced pressure and the residue was purified by flash column chromatography (silica), eluting with petroleum ether and ethylacetate (85:15) to give the tert-butyl ester intermediate as a brown sticky solid.

Step 2

[4-chloro-2-({5-[(dimethylamino)sulfonyl]pyridin-3-yl}ethynyl)phenoxy]acetic acid Following the general method as outlined in Example 15, starting from tert-butyl[4-chloro-2-({5-[(dimethylamino)sulfonyl]pyridin-3-yl}ethynyl)phenoxy]acetate, the title compound was obtained as a white solid after precipitation from the reaction mixture.

$^1$H NMR (300 MHz, DMSO-$d_6$) δ [ppm] 13.17 (bs, 1H), 9.01 (d, J=1.9 Hz, 1H), 8.91 (d, J=2.1 Hz, 1H), 8.26 (d, J=2.1 Hz, 1H), 7.67 (d, J=2.6 Hz, 1H), 7.47 (dd, J=8.9 Hz, J=2.6 Hz, 1H), 7.04 (d, J=9.0 Hz, 1H), 4.85 (s, 2H), 2.70 (s, 6H). MS (ESI$^+$): 393.0. HPLC (Condition A): Rt 4.40 min (HPLC purity 98.2%).

EXAMPLE 36

(4-chloro-2-{[5-(methylsulfonyl)pyridin-3-yl]ethynyl}phenoxy)acetic acid

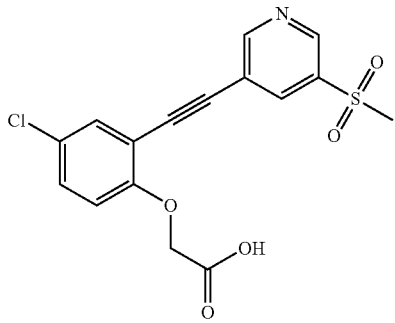

Following the general method as outlined in Example 35, starting from tert-butyl(4-chloro-2-ethynyl phenoxy)acetate (Intermediate 3) and 5-bromo-3-methylsulfonylpyridine (Combiblocks), the title compound was obtained as a white solid after purification by flash column chromatography (silica).

$^1$H NMR (300 MHz, DMSO-$d_6$) δ [ppm] 9.06-9.04 (m, 2H) 8.45 (t, J=2.0 Hz, 1H), 7.66 (d, J=2.7 Hz, 1H), 7.47 (dd, J=9.0 Hz, J=2.7 Hz, 1H), 7.04 (d, J=9.0 Hz, 1H), 4.85 (s, 2H) 3.39 (s, 3H). MS (ESI$^+$): 363.9. HPLC (Condition A): Rt 3.93 min (HPLC purity 98.9%).

EXAMPLE 37

{2-[(2-chlorophenyl)ethynyl]-5-fluorophenoxy}acetic acid

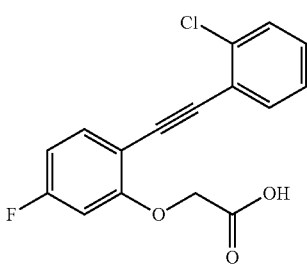

A solution of tert-butyl(2-bromo-5-fluorophenoxy)acetate (Intermediate 35; 305 mg; 1.00 mmol) and 2'-chlorophenyl acetylene (137 mg; 1.00 mmol) in piperidine (300 μl; 3.00 mmol) was treated with dichlorobis(triphenylphosphine)palladium(II) (28 mg; 0.04 mmol) and heated at 70° C. The reaction mixture was taken up in EtOAc, washed twice with citric acid (0.5 M aqueous solution) and once with brine. The organic phase was dried over MgSO$_4$, filtered and concentrated to dryness affording a crude, which was purified by flash column chromatography (silica), eluting with cyclohexane containing increasing amounts of EtOAc. The partially purified intermediate was dissolved in a solution of HCl in dioxane (4N, 3 mL). After stirring for 16 hours, the solvents were removed under vacuum and the crude product purified by preparative HPLC. The title compound was obtained as a red oil.

MS (ESI$^-$): 303.2. HPLC (Condition A): Rt 4.48 min.

EXAMPLE 38

(4-chloro-2-{[2-methyl-5-(propylsulfonyl)phenyl]ethynyl}phenoxy)acetic acid

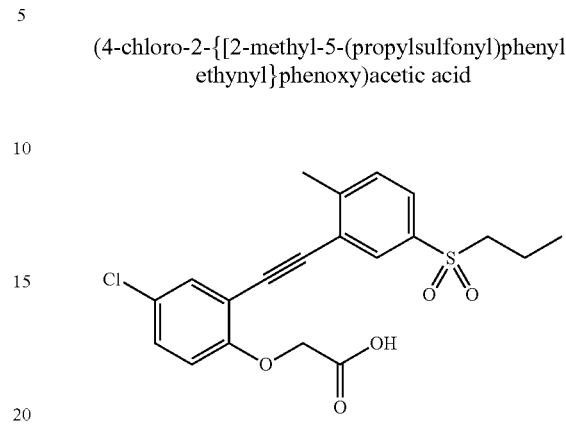

Following the general method as outlined in Example 15, starting from tert-butyl(4-chloro-2-{[2-methyl-5-(propylsulfonyl)phenyl]ethynyl}phenoxy)acetate (Intermediate 38), the title compound was obtained as a white solid in 82% yield after recrystallization from acetonitrile.

$^1$H NMR (300 MHz, DMSO-$d_6$) δ [ppm] 13.17 (1H, bs), 7.95 (1H, t, J=2.0 Hz), 7.80 (1H, dd, J=8.0 Hz, J=2.0 Hz), 7.65 (1H, d, J=2.7 Hz), 7.62 (1H, d, J=8.0 Hz), 7.45 (1H, dd, J=9.0 Hz, J=2.7 Hz), 7.04 (1H, d, J=9.0 Hz), 4.84 (2H, s), 3.32 (2H, m), 2.58 (3H, s), 1.55 (2H, sext., J=7.5 Hz), 0.92 (3H, t, J=7.5 Hz). MS (ESI$^-$): 405.2. HPLC (Condition A): Rt 4.61 min (HPLC purity 98.6%).

EXAMPLE 39

[4-chloro-2-({5-[(methylsulfonyl)amino]pyridin-3-yl}ethynyl)phenoxy]acetic acid

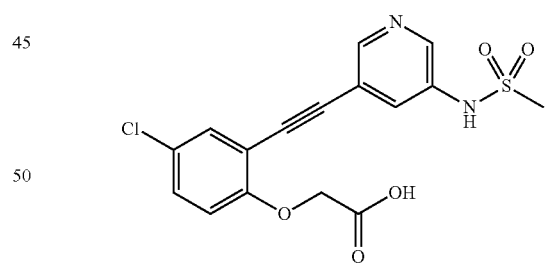

Following the general method as outlined in Example 35, starting from tert-butyl(4-chloro-2-ethynyl phenoxy)acetate (Intermediate 3) and N-(5-bromopyridin-3-yl)methanesulfonamide (prepared according to the method described in WO2008141065), the title compound was obtained as a beige solid after purification.

$^1$H NMR (300 MHz, DMSO-$d_6$) δ [ppm] 10.24 (s, 1H), 8.47 (d, J=1.6 Hz, 1H), 8.43-8.40 (m, 1H), 7.70 (d, J=2.3 Hz, 1H), 7.63 (d, J=2.6 Hz, 1H), 7.44 (dd, J=8.9 Hz, J=2.6 Hz, 1H), 7.00 (d, J=9.0 Hz, 1H), 4.84 (s, 2H), 3.12 (s, 3H). MS (ESI$^+$): 381.0. HPLC (Condition A): Rt 3.66 min (HPLC purity 95.4%).

EXAMPLE 40

(4-cyano-2-{[2-methyl-5-(propylsulfonyl)phenyl]ethynyl}phenoxy)acetic acid

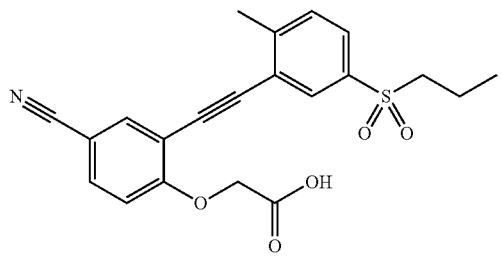

Following the general method as outlined in Example 37, starting from 2-bromo-1-methyl-4-(propylsulfonyl)benzene (Intermediate 37) and tert-butyl(4-cyano-2-ethynylphenoxy)acetate (Intermediate 46), the title compound was obtained as a white solid after purification by preparative HPLC.

$^1$H NMR (300 MHz, DMSO-$d_6$) δ [ppm] 13.2 (1H, bs), 8.11 (1H, d, J=2.0 Hz), 7.95 (1H, d, J=2.0 Hz), 7.87 (1H, dd, J=8.8 Hz, J=2.0 Hz), 7.81 (1H, dd, J=8.0 Hz, J=2.0 Hz), 7.61 (1H, d, J=8.0 Hz), 7.21 (1H, d, J=8.8 Hz), 4.96 (2H, s), 3.32 (2H, m), 2.59 (3H, s), 1.55 (2H, m), 0.94 (3H, t, J=7.5 Hz). MS (ESI$^-$): 396.3. HPLC (Condition A): Rt 4.04 min (HPLC purity 99.7%).

EXAMPLE 41

[2-[(2-chlorophenyl)ethynyl]-4-(trifluoromethyl)phenoxy]acetic acid

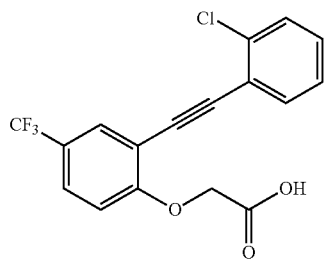

Following the general method as outlined in Example 37, starting from tert-butyl[2-bromo-4-(trifluoromethyl)phenoxy]acetate (Intermediate 47) and 2'-chlorophenyl acetylene (ABCR), the title compound was obtained as a white solid after purification by preparative HPLC.

$^1$H NMR (300 MHz, DMSO-$d_6$) δ [ppm] 13.2 (1H, bs), 7.84 (1H, d, J=2.0 Hz), 7.77 (1H, dd, J=9.0 Hz, J=2.0 Hz), 7.07 (1H, m), 7.61 (1H, m), 7.50-7.39 (2H, m), 7.20 (1H, d, J=8.8 Hz), 4.94 (2H, s). MS (ESI$^-$): 353.2. HPLC (Condition A): Rt 4.80 min (HPLC purity 98.3%).

EXAMPLE 42

{4-chloro-2-[(4-propylpyridin-3-yl)ethynyl]phenoxy}acetic acid

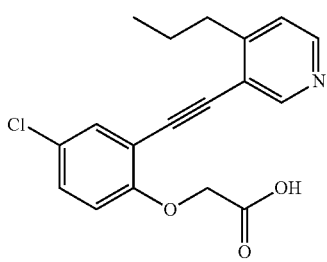

Following the general method as outlined in Example 15, starting from tert-butyl{4-chloro-2-[(4-propylpyridin-3-yl)ethynyl]phenoxy}acetate (Intermediate 50), the title compound was obtained as a white solid after purification by preparative HPLC.

$^1$H NMR (300 MHz, DMSO-$d_6$) δ [ppm] 8.66 (s, 1H), 8.48 (d, J=5.1 Hz, 1H), 7.59 (d, J=2.7 Hz, 1H), 7.45 (dd, J=2.7, J=9.0 Hz, 1H), 7.38 (d, J=5.1 Hz, 1H), 7.05 (d, J=9.0 Hz, 1H), 4.82 (s, 2H), 2.83 (t, J=7.5 Hz, 2H), 1.69 (sext. J=7.5 Hz, 2H), 0.94 (t, J=7.5 Hz, 3H). MS (ESI$^-$): 328.2. HPLC (Condition A): Rt 3.06 min (HPLC purity 97.2%).

EXAMPLE 43

{4-chloro-2-[(4-isobutylpyridin-3-yl)ethynyl]phenoxy}acetic acid

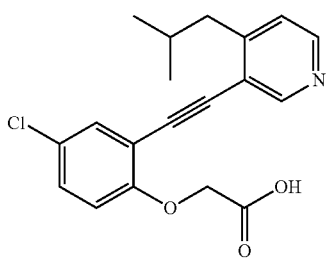

Following the general method as outlined in Example 15, starting from tert-butyl{4-chloro-2-[(4-isobutylpyridin-3-yl)ethynyl]phenoxy}acetate (Intermediate 53), the title compound was obtained as a beige solid after purification by preparative HPLC.

$^1$H NMR (300 MHz, DMSO-$d_6$) δ [ppm] 8.68 (s, 1H), 8.48 (d, J=5.1 Hz, 1H), 7.58 (d, J=2.7 Hz, 1H), 7.45 (dd, J=2.7, J=9.0 Hz, 1H), 7.34 (d, J=5.1 Hz, 1H), 7.05 (d, J=9.0 Hz, 1H), 4.83 (s, 2H), 2.74 (d, J=6.8 Hz, 2H), 2.05 (sept., J=6.8 Hz, 1H), 0.91 (d, J=6.8 Hz, 6H). MS (ESI$^-$): 342.2. HPLC (Condition A): Rt 3.84 min (HPLC purity 99.7).

EXAMPLE 44

{4-cyano-2-[(4-methylpyridin-3-yl)ethynyl]phenoxy}acetic acid

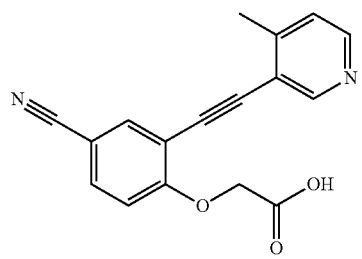

Following the general method as outlined in Example 15, starting from tert-butyl{4-cyano-2-[(4-methylpyridin-3-yl)ethynyl]phenoxy}acetate (Intermediate 54), the title compound was obtained as a beige solid after purification by preparative HPLC.

$^1$H NMR (300 MHz, DMSO-$d_6$) δ [ppm] 13.26 (bs, 1H), 8.71 (s, 1H), 8.51 (d, J=5.1 Hz, 1H), 8.09 (d, J=2.1 Hz, 1H), 7.89 (dd, J=2.1, J=8.8 Hz, 1H), 7.48 (d, J=5.1 Hz, 1H), 7.23 (d, J=8.8 Hz, 1H), 4.98 (s, 2H), 2.54 (s, 3H). MS (ESI$^-$): 291.2 (Condition A): Rt 1.99 (HPLC purity 98.0%).

EXAMPLE 45

{2-[(2-chlorophenyl)ethynyl]phenoxy}acetic acid

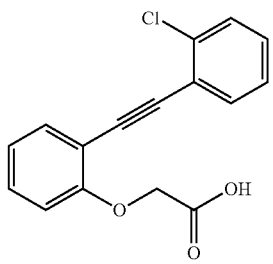

Following the general method as outlined in Example 15, starting from tert-butyl{2-[(2-chlorophenyl)ethynyl]phenoxy}acetate (Intermediate 56), the title compound was obtained as a beige solid after purification by preparative HPLC.

$^1$H NMR (300 MHz, DMSO-$d_6$) δ [ppm] 13.14 (bs, 1H), 7.67 (m, 1H), 7.61 (m, 1H), 7.53 (d, J=1.6, J=7.5 Hz, 1H), 7.48-7.37 (m, 3H), 7.06-6.97 (m, 2H), 4.82 (s, 2H). MS (ESI$^-$): 285.1. HPLC (Condition A): Rt 4.18 min (HPLC purity 98.8%).

EXAMPLE 46

{4-chloro-2-[(5-{[(2-hydroxyethyl)amino]sulfonyl}pyridin-3-yl)ethynyl]phenoxy}acetic acid

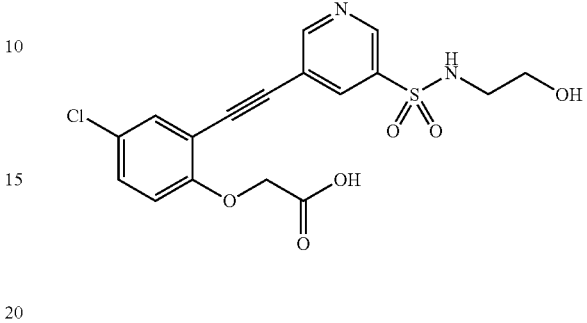

Following the general method as outlined in Example 37, starting from tert-butyl(4-chloro-2-ethynyl phenoxy)acetate (Intermediate 3) and 5-bromo-N-(2-hydroxyethyl)pyridine-3-sulfonamide (Intermediate 31), the title compound was obtained as an off-white solid.

$^1$H NMR (300 MHz, DMSO-$d_6$) δ [ppm] 8.95 (d, J=2.2 Hz, 1H), 8.91 (d, J=2.0 Hz, 1H), 8.31 (d, J=1.8 Hz, 1H), 8.02 (bs, 1H), 7.64 (d, J=2.6 Hz, 1H), 7.44 (dd, J=9.0 Hz, J=2.6 Hz, 1H), 6.98 (d, J=9.0 Hz, 1H), 4.71 (s, 2H), 3.39-3.36 (m, 2H), 2.99 (bs, 1H), 2.90-2.88 (m, 2H). MS (ESI$^+$): 410.8. HPLC (Condition A): Rt 3.73 min (HPLC purity 93.5%).

EXAMPLE 47

[4-chloro-2-({5-[methyl(methylsulfonyl)amino]pyridin-3-yl}ethynyl)phenoxy]acetic acid

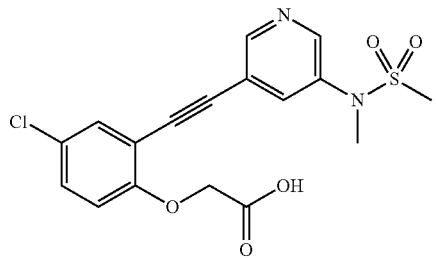

Following the general method as outlined in Example 37, starting from tert-butyl(4-chloro-2-ethynyl phenoxy)acetate (Intermediate 3) and N-(5-bromopyridin-3-yl)-N-methylmethanesulfonamide (Intermediate 33), the title compound was obtained as an off-white solid.

$^1$H NMR (300 MHz, DMSO-$d_6$) δ [ppm] 8.64-8.62 (m, 2H), 8.03 (t, J=6.9 Hz, 1H), 7.61 (d, J=2.6 Hz, 1H), 7.44 (dd, J=8.9 Hz, J=2.6 Hz, 1H), 7.01 (d, J=9.0 Hz, 1H), 4.83 (s, 2H), 3.32 (s, 3H), 3.05 (s, 3H). MS (ESI$^+$): 395.0. HPLC (Condition A): Rt 4.93 min (HPLC purity 99.0%).

EXAMPLE 48

(4-chloro-2-{[2-fluoro-5-(methylsulfonyl)phenyl]ethynyl}phenoxy)acetic acid

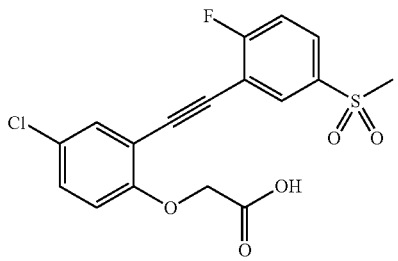

A mixture of (4-chloro-2-ethynyl-phenoxy)-acetic acid tert-butyl ester (Intermediate 3, 164 mg; 0.61 mmol), 1-fluoro-2-iodo-4-(methylsulfonyl)benzene (Intermediate 58, 184 mg; 0.61 mmol), 1,1'-bis(diphenylphosphino)ferrocenedichloro palladium(ii) (27 mg; 0.04 mmol) and cuprous iodide (7 mg; 0.04 mmol) was degassed during two minutes under nitrogen then anhydrous THF (3 mL) and triethylamine (170 µL; 1.23 mmol) were added and reaction mixture was stirred at 60° C. for 60 hours. The solvent was evaporated and the residue was treated with an HCl solution (4 N in dioxane, 3.7 mL). After stirring for 16 hours, the solvents were removed under vacuum and the crude product purified by preparative HPLC. The title compound was obtained as a brown solid.

$^1$H NMR (300 MHz, DMSO-$d_6$) δ [ppm] 13.25 (bs, 1H), 8.18 (dd, J=2.4, J=6.5 Hz, 1H), 8.03 (m, 1H), 7.69-7.63 (m, 2H), 7.47 (dd, J=2.7, J=9.0 Hz, 1H), 7.03 (d, J=9.0 Hz, 1H), 4.85 (s, 2H), 3.31 (s, 3H). MS (ESI$^-$): 381.2. HPLC (Condition A): Rt 3.89 min (HPLC purity 96.7%).

EXAMPLE 49

(4-chloro-2-{[5-(methylsulfonyl)-2-propylphenyl]ethynyl}phenoxy)acetic acid

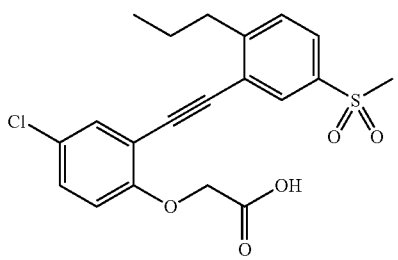

Following the general method as outlined in Example 15, starting from tert-butyl(4-chloro-2-{[5-(methylsulfonyl)-2-propylphenyl]ethynyl}phenoxy)acetate (Intermediate 63), the title compound was obtained as a white solid in 87% yield after slurrying in diethyl ether.

$^1$H NMR (300 MHz, DMSO-$d_6$) δ [ppm] 13.18 (1H, bs), 8.01 (1H, d, J=1.5 Hz), 7.86 (1H, dd, J=8.0 Hz, J=1.5 Hz), 7.62-7.59 (2H, m), 7.45 (1H, dd, J=8.8 Hz, J=2.0 Hz), 7.05 (1H, d, J=8.8 Hz), 4.85 (2H, s), 3.26 (3H, s), 2.91 (2H, t, J=7.5 Hz), 1.68 (2H, sextet, J=7.5 Hz), 0.94 (3H, t, J=7.5 Hz). MS (ESI$^-$): 405.3. HPLC (Condition A): Rt 4.60 min (HPLC purity 98.8%).

EXAMPLE 50

(4-chloro-2-{[5-(ethylsulfonyl)-2-methylphenyl]ethynyl}phenoxy)acetic acid

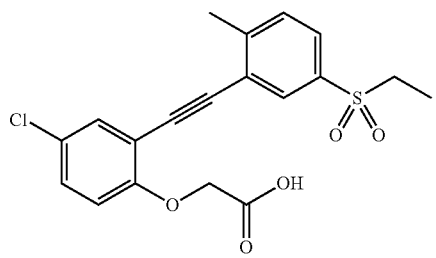

Following the general method as outlined in Example 37, starting from tert-butyl(4-chloro-2-ethynyl phenoxy)acetate (Intermediate 3) and 2-bromo-4-(ethylsulfonyl)-1-methylbenzene (Intermediate 65), the title compound was obtained as a brown oil.

$^1$H NMR (300 MHz, DMSO-$d_6$) δ [ppm] 7.93 (s, 1H), 7.92-7.76 (m, 1H), 7.62-7.58 (m, 2H), 7.38 (dd, J=9.0 Hz, J=2.4 Hz, 1H), 6.91 (d, J=9.0 Hz, 1H), 4.53 (s, 2H), 3.34 (m, 2H), 2.57 (s, 3H), 1.08 (t, J=7.3 Hz, 3H). MS (ESI$^+$): 392.8. HPLC (Condition A): Rt 4.77 min (HPLC purity 96.0%).

EXAMPLE 51

(4-chloro-2-{[5-(isopropylsulfonyl)-2-methylphenyl]ethynyl}phenoxy)acetic acid

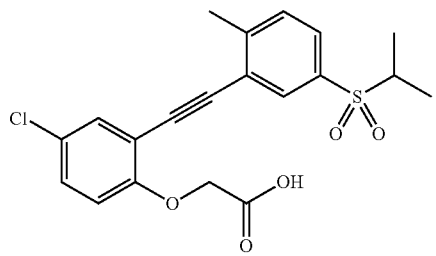

Following the general method as outlined in Example 37, starting from tert-butyl(4-chloro-2-ethynyl phenoxy)acetate (Intermediate 3) and 2-bromo-4-(isopropylsulfonyl)-1-methylbenzene (Intermediate 64), the title compound was obtained as a yellow solid.

$^1$H NMR (300 MHz, DMSO-$d_6$) δ [ppm] 13.15 (s, 1H), 7.89 (d, J=1.8 Hz, 1H), 7.60 (dd, J=8.0 Hz, J=1.8 Hz, 1H), 7.65-7.61 (m, 2H), 7.43 (dd, J=9.0 Hz, J=2.6 Hz, 1H), 7.03 (d, J=9.0 Hz, 1H), 4.83 (s, 2H), 3.46 (septet, J=6.8 Hz, 1H), 2.57 (s, 3H), 1.12 (d, J=6.8 Hz, 6H). MS (ESI$^-$): 407.0. HPLC (Condition A): Rt 4.98 min (HPLC purity 92.3%).

EXAMPLE 52

[4-chloro-2-({5-[(2-hydroxyethyl)sulfonyl]-2-methylphenyl}ethynyl)phenoxy]acetic acid

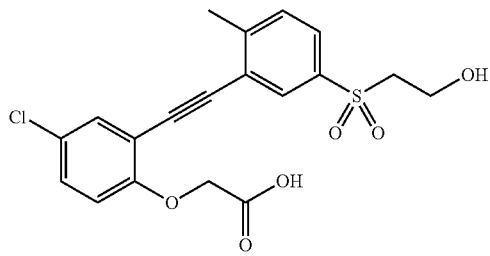

Following the general method as outlined in Example 37, starting from tert-butyl(4-chloro-2-ethynyl phenoxy)acetate (Intermediate 3) and 2-[(3-bromo-4-methylphenyl)sulfonyl]ethanol (Intermediate 67), the title compound was obtained as a yellow solid.

$^1$H NMR (300 MHz, DMSO-$d_6$) δ [ppm] 13.15 (s, 1H), 7.94 (d, J=2.0 Hz, 1H), 7.79 (dd, J=8.0 Hz, J=2.0 Hz, 1H), 7.64 (d, J=2.6 Hz, 1H), 7.59 (d, J=8.0 Hz, 1H), 7.43 (dd, J=9.0 Hz, J=2.6 Hz, 1H), 7.03 (d, J=9.0 Hz, 1H), 4.83 (s, 2H), 3.67 (m, 2H), 3.48 (t, J=6.0 Hz, 2H), 2.56 (s, 3H). MS (ESI$^+$): 408.8. HPLC (Condition A): Rt 4.17 min (HPLC purity 96.4%).

EXAMPLE 53

(4-chloro-2-{[5-(isobutylsulfonyl)-2-methylphenyl]ethynyl}phenoxy)acetic acid

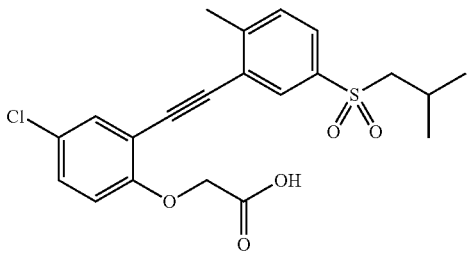

Following the general method as outlined in Example 37, starting from tert-butyl(4-chloro-2-ethynyl phenoxy)acetate (Intermediate 3) and 2-bromo-4-(isobutylsulfonyl)-1-methylbenzene (Intermediate 66), the title compound was obtained as a yellow solid.

$^1$H NMR (300 MHz, DMSO-$d_6$) δ [ppm] 7.95 (s, 1H), 7.80 (d, J=8.0 Hz, 1H), 7.63-7.60 (m, 2H), 7.43 (dd, J=9.0 Hz, J=2.6 Hz, 1H), 7.01 (d, J=9.0 Hz, 1H), 4.79 (s, 2H), 3.25 (d, J=6.4 Hz, 2H), 2.57 (s, 3H), 2.03-1.96 (m, 1H), 0.96 (d, J=6.7 Hz, 6H). MS (ESI$^+$): 420.0. HPLC (Condition A): Rt 5.33 min (HPLC purity 97.6%).

EXAMPLE 54

[4-chloro-2-({5-[(3-hydroxypropyl)sulfonyl]-2-methylphenyl}ethynyl)phenoxy]acetic acid

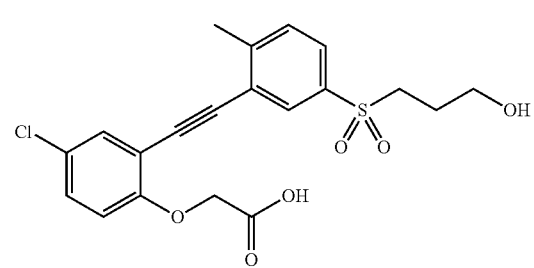

Following the general method as outlined in Example 37, starting from tert-butyl(4-chloro-2-ethynyl phenoxy)acetate (Intermediate 3) and 3-[(3-bromo-4-methylphenyl)sulfonyl]propan-1-ol (Intermediate 68), the title compound was obtained as a yellow solid.

$^1$H NMR (300 MHz, DMSO-$d_6$) δ [ppm] 7.93 (d, J=2.0 Hz, 1H), 7.79 (dd, J=8.0 Hz, J=2.0 Hz, 1H), 7.64-7.61 (m, 2H), 7.43 (dd, J=9.0 Hz, J=2.6 Hz, 1H), 7.02 (d, J=9.0 Hz, 1H), 4.80 (s, 2H), 3.39 (t, J=6.2 Hz, 2H), 3.35-3.31 (m, 2H), 2.57 (s, 3H), 1.65 (d, J=7.9 Hz, 2H). MS (ESI$^-$): 422.0. HPLC (Condition A): Rt 4.27 min (HPLC purity 97.2%).

EXAMPLE 55

[2-{[3-(propylsulfonyl)phenyl]ethynyl}-4-(trifluoromethyl)phenoxy]acetic acid

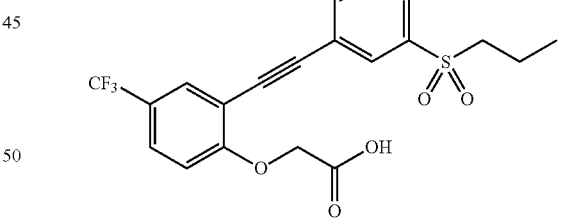

Following the general method as outlined in Example 15, starting from tert-butyl[2-{[3-(propylsulfonyl)phenyl]ethynyl}-4-(trifluoromethyl)phenoxy]acetate (Intermediate 71), the title compound was obtained as a yellow solid after slurrying in diethyl ether.

$^1$H NMR (300 MHz, DMSO-$d_6$) δ [ppm] 13.2 (1H, bs), 8.05 (1H, m), 7.96-7.91 (3H, m), 7.78-7.71 (2H, m), 7.20 (1H, d, J=8.8 Hz), 4.97 (2H, s), 3.40-3.34 (2H, m), 1.57 (2H, m), 0.93 (3H, t, J=7.5 Hz). MS (ESI$^-$): 425.2. HPLC (Condition A): Rt 4.45 min (HPLC purity 96.2%).

EXAMPLE 56

(4-cyano-2-{[5-(methylsulfonyl)-2-propylphenyl]ethynyl}phenoxy)acetic acid

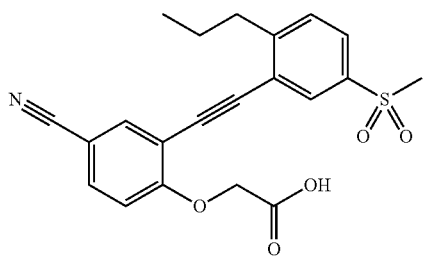

Following the general method as outlined in Example 15, starting from tert-butyl(4-cyano-2-{[5-(methylsulfonyl)-2-propylphenyl]ethynyl}phenoxy)acetate (Intermediate 72), the title compound was obtained as a pink solid after purification by preparative HPLC.

$^1$H NMR (300 MHz, DMSO-$d_6$) δ [ppm] 13.31 (s, 1H), 8.08 (d, J=2.1 Hz, 1H), 8.02 (d, J=2.1 Hz, 1H), 7.85-7.89 (m, 2H), 7.61 (d, J=8.1 Hz, 1H); 7.21 (d, J=8.8 Hz, 1H), 4.97 (s, 2H), 3.26 (s, 3H), 2.92 (t, J=7.5 Hz, 2H), 1.69 (sext., J=7.5 Hz, 2H), 0.94 (t, J=7.5 Hz, 3H). MS (ESI$^-$): 396.2. HPLC (Condition A): Rt 3.94 min (HPLC purity 97.9%).

EXAMPLE 57

(4-chloro-2-{[5-(methylsulfonyl)-2-piperidin-1-ylphenyl]ethynyl}phenoxy)acetic acid

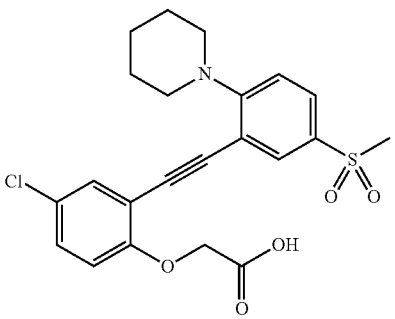

Following the general method as outlined in Example 15, starting from tert-butyl (4-chloro-2-{[5-(methylsulfonyl)-2-piperidin-1-ylphenyl]ethynyl}phenoxy)acetate (Intermediate 75), the title compound was obtained as a white solid after filtration from the reaction mixture.

$^1$H NMR (300 MHz, DMSO-$d_6$) δ [ppm] 7.91 (d, J=2.4 Hz, 1H), 7.76 (dd, J=2.4, J=8.8 Hz, 1H), 7.56 (d, J=2.7 Hz, 1H), 7.41 (dd, J=2.7, J=9.0 Hz, 1H), 7.14 (d, J=8.8 Hz, 1H), 7.01 (d, J=9.0 Hz, 1H), 4.83 (s, 2H), 3.35 (m, 4H), 3.18 (s, 3H), 1.68 (m, 4H), 1.59 (m, 2H). MS (ESI$^-$): 446.3. HPLC (Condition A): Rt 4.48 min (HPLC purity 98.0%).

EXAMPLE 58

(4-cyano-2-{[2-fluoro-5-(methylsulfonyl)phenyl]ethynyl}phenoxy)acetic acid

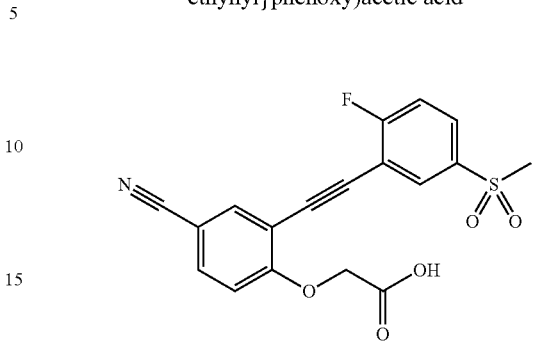

Following the general method as outlined in Example 15, starting from tert-butyl(4-cyano-2-{[2-fluoro-5-(methylsulfonyl)phenyl]ethynyl}phenoxy)acetate (Intermediate 79), the title compound was obtained as a grey solid after purification by preparative HPLC.

$^1$H NMR (300 MHz, DMSO-$d_6$) δ [ppm] 13.30 (bs, 1H), 8.18 (dd, J=2.2, J=6.5 Hz, 1H), 8.09 (d, J=2.2 Hz, 1H), 8.04 (m, 1H), 7.89 (dd, J=2.2, J=8.8 Hz, 1H), 7.66 (t, J=9.0 Hz, 1H), 7.20 (d, J=8.8 Hz, 1H), 4.97 (s, 2H), 3.31 (s, 1H). MS (ESI$^-$): 372.2. HPLC (Condition A): Rt 3.41 min (HPLC purity 94.1%).

EXAMPLE 59

(4-chloro-2-{[2-chloro-5-(methylsulfonyl)phenyl]ethynyl}phenoxy)acetic acid

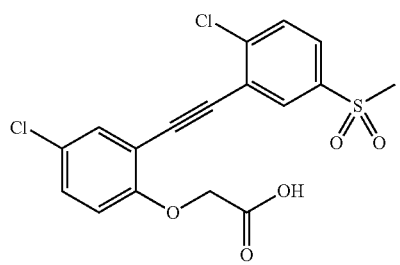

Following the general method as outlined in Example 15, starting from tert-butyl(4-chloro-2-{[2-chloro-5-(methylsulfonyl)phenyl]ethynyl}phenoxy)acetate (Intermediate 80), the title compound was obtained as a beige solid after purification by preparative HPLC.

$^1$H NMR (300 MHz, DMSO-$d_6$) δ [ppm] 13.17 (s, 1H), 8.17 (d, J=2.0 Hz, 1H), 7.94 (dd, J=2.0, J=8.4 Hz, 1H), 7.90 (d, J=8.4 Hz, 1H), 7.64 (d, J=2.7 Hz, 1H), 7.47 (dd, J=2.7, J=9.0 Hz, 1H), 7.05 (d, J=9.0 Hz, 1H), 4.85 (s, 2H) (3 remaining protons, probably hidden under the signal of water). MS (ESI$^-$): 397.2. HPLC (Condition A): Rt 4.10 min (HPLC purity 96.8%).

EXAMPLE 60

(4-chloro-2-{[2-hydroxy-5-(methylsulfonyl)phenyl]ethynyl}phenoxy)acetic acid

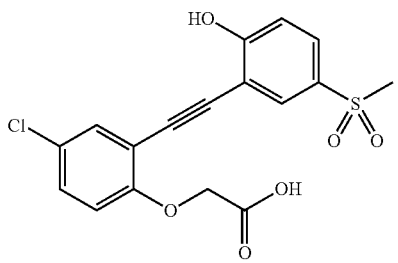

Following the general method as outlined in Example 15, starting from tert-butyl(4-chloro-2-{[2-hydroxy-5-(methylsulfonyl)phenyl]ethynyl}phenoxy)acetate (Intermediate 81), the title compound was obtained as a beige solid after precipitation from the reaction mixture.

$^1$H NMR (300 MHz, DMSO-d$_6$) δ [ppm] 13.30 (bs, 1H), 8.27 (t, J=1.1 Hz, 1H), 7.97 (d, J=2.7 Hz, 1H), 7.94-7.91 (m, 3H), 7.48 (dd, J=2.7, J=9.0 Hz, 1H), 7.20 (d, J=9.0 Hz, 1H), 4.96 (s, 2H), 3.26 (s, 3H). MS (ESI$^-$): 379.1. HPLC (Condition A): Rt 3.96 min (HPLC purity 100%).

EXAMPLE 61

(2-{[2-chloro-5-(methylsulfonyl)phenyl]ethynyl}-4-cyanophenoxy)acetic acid

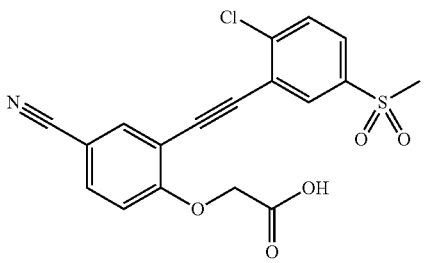

Following the general method as outlined in Example 15, starting from tert-butyl(2-{[2-chloro-5-(methylsulfonyl)phenyl]ethynyl}-4-cyanophenoxy)acetate (Intermediate 82), the title compound was obtained as a beige solid after purification by preparative HPLC.

$^1$H NMR (300 MHz, DMSO-d$_6$) δ [ppm] 13.28 (bs, 1H), 8.18 (d, J=2.1 Hz, 1H), 8.10 (d, J=2.1 Hz, 1H), 7.96 (dd, J=2.1, J=8.6 Hz, 1H), 7.88-7.92 (m, 2H), 7.22 (d, J=8.6 Hz, 1H), 4.98 (sm 2H) (3 remaining protons, probably hidden under the signal of water). MS (ESI$^-$): 388.1. HPLC (Condition A): Rt 3.66 min (HPLC purity 97.7%).

EXAMPLE 62

(4-cyano-2-{[5-(methylsulfonyl)-2-piperidin-1-ylphenyl]ethynyl}phenoxy)acetic acid

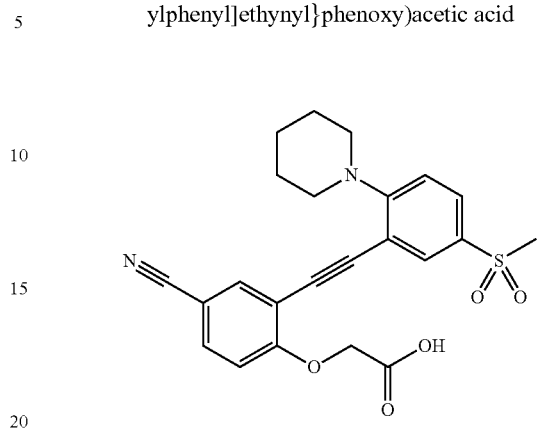

Following the general method as outlined in Example 15, starting from tert-butyl(4-cyano-2-{[5-(methylsulfonyl)-2-piperidin-1-ylphenyl]ethynyl}phenoxy)acetate (Intermediate 83), the title compound was obtained as a beige solid after purification by preparative HPLC followed by trituration in diethyl ether.

$^1$H NMR (300 MHz, DMSO-d$_6$) δ [ppm] 8.01 (d, J=2.1 Hz, 1H), 7.92 (d, J=2.3 Hz, 1H), 7.83 (dd, J=2.1, J=8.7 Hz, 1H), 7.76 (dd, J=2.3, J=8.7 Hz, 1H), 7.16 (2d, J=8.7 Hz, 2H), 4.89 (s, 2H), 3.18 (s, 3H), 1.67 (m, 4H), 1.58 (m, 2H) (4 remaining protons, probably hidden under the signal of water). MS (ESI$^-$): 437.2. HPLC (Condition A): Rt 4.11 min (HPLC purity 95.2%).

EXAMPLE 63

(4-cyano-2-{[5-(ethylsulfonyl)-2-methylphenyl]ethynyl}phenoxy)acetic acid

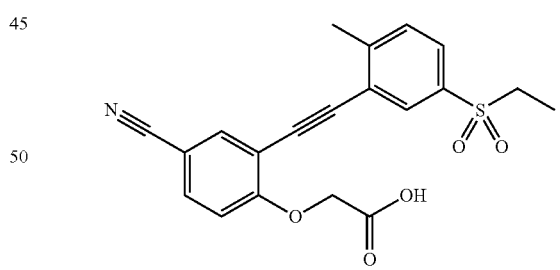

Following the general method as outlined in Example 37, starting from tert-butyl(4-cyano-2-ethynyl phenoxy)acetate (Intermediate 46) and 2-ethynyl-1-methyl-4-(propylsulfonyl)benzene (Intermediate 40), the title compound was obtained as a yellow solid.

$^1$H NMR (300 MHz, DMSO-d$_6$) δ [ppm] 13.26 (bs, 1H), 8.10 (s, 1H), 7.94 (d, J=1.8 Hz, 1H), 7.87 (dd, J=8.0 Hz, J=1.9 Hz, 1H), 7.80 (dd, J=8.1 Hz, J=2.0 Hz, 1H), 7.63 (d, J=8.1 Hz, 1H), 7.20 (d, J=8.0 Hz, 1H), 4.96 (s, 2H), 3.33 (q, J=7.4 Hz, 2H), 1.07 (t, J=7.4 Hz, 3H). MS (ESI$^+$): 383.8. HPLC (Condition A): Rt 4.15 min.

EXAMPLE 64

[4-cyano-2-({5-[(2-hydroxyethyl)sulfonyl]-2-methylphenyl}ethynyl)phenoxy]acetic acid

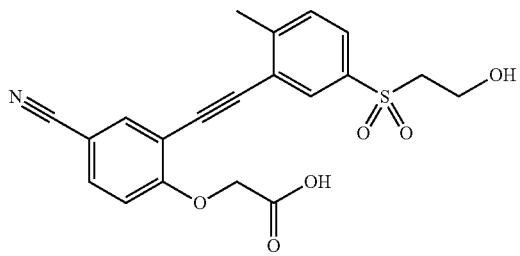

Following the general method as outlined in Example 37, starting from tert-butyl(4-cyano-2-ethynyl phenoxy)acetate (Intermediate 46) and 2-[(3-bromo-4-methylphenyl)sulfonyl]ethanol (Intermediate 67), the title compound was obtained as a yellow solid.

$^1$H NMR (300 MHz, DMSO-$d_6$) δ [ppm] 13.36 (bs, 1H), 8.10 (d, J=2.0 Hz, 1H), 7.95 (d, J=1.8 Hz, 1H), 7.87-7.79 (m, 2H), 7.60 (d, J=8.1 Hz, 1H), 7.19 (d, J=8.8 Hz, 1H), 4.94 (s, 2H), 3.67 (t, J=6.2 Hz, 2H), 3.48 (d, J=6.8 Hz, 2H), 2.57 (s, 3H). MS (ESI$^+$): 400.0. HPLC (Condition A): Rt 3.56 min (HPLC purity 97.7%).

EXAMPLE 65

(4-cyano-2-{[5-(isobutylsulfonyl)-2-methylphenyl]ethynyl}phenoxy)acetic acid

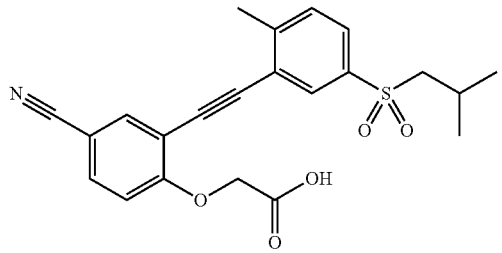

Following the general method as outlined in Example 37, starting from tert-butyl(4-cyano-2-ethynyl phenoxy)acetate (Intermediate 46) and 2-bromo-4-(isobutylsulfonyl)-1-methylbenzene (Intermediate 66), the title compound was obtained as a yellow solid.

$^1$H NMR (300 MHz, DMSO-$d_6$) δ [ppm] 8.10 (d, J=1.9 Hz, 1H), 7.96 (s, 1H), 7.87-7.81 (m, 2H), 7.62 (d, J=8.2 Hz, 1H), 7.20 (d, J=8.6 Hz, 1H), 4.95 (s, 2H), 3.25 (d, J=6.4 Hz, 2H), 2.57 (s, 3H), 2.03-1.98 (m, 1H), 0.96 (d, J=6.7 Hz, 6H). MS (ESI$^-$): 412.0. HPLC (Condition A): Rt 4.74 min (HPLC purity 98.8%).

EXAMPLE 66

[(6-methyl-2-{[3-(propylsulfonyl)phenyl]ethynyl}pyridin-3-yl)oxy]acetic acid

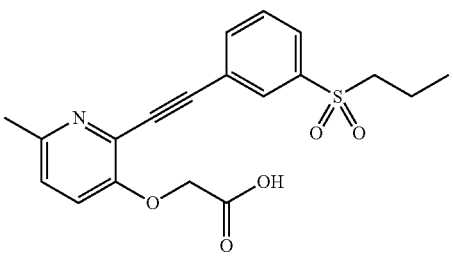

Following the general method as outlined in Example 15, starting from tert-butyl[(6-methyl-2-{[3-(propylsulfonyl)phenyl]ethynyl}pyridin-3-yl)oxy]acetate (Intermediate 87), the title compound was obtained as a beige solid after purification by preparative HPLC followed by precipitation from DMSO/acetonitrile.

$^1$H NMR (300 MHz, DMSO-$d_6$) δ [ppm] 13.30 (bs, 1H), 8.18 (dd, J=2.2, J=6.5 Hz, 1H), 8.09 (d, J=2.2 Hz, 1H), 8.04 (m, 1H), 7.89 (dd, J=2.2, J=8.8 Hz, 1H), 7.66 (t, J=9.0 Hz, 1H), 7.20 (d, J=8.8 Hz, 1H), 4.97 (s, 2H), 3.31 (s, 1H). HPLC (Condition A): Rt 2.38 min (HPLC purity 96.9%).

EXAMPLE 67

[4-cyano-2-({5-[(dimethylamino)sulfonyl]pyridin-3-yl}ethynyl)phenoxy]acetic acid

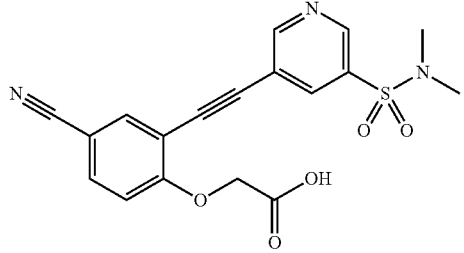

Following the general method as outlined in Example 37, starting from tert-butyl(4-cyano-2-ethynyl phenoxy)acetate (Intermediate 46) and 5-bromo-pyridine-3-sulfonic acid dimethylamide (Intermediate 32), the title compound was obtained as a yellow solid.

$^1$H NMR (300 MHz, DMSO-$d_6$) δ [ppm] 13.30 (s, 1H), 9.03 (d, J=1.8 Hz, 1H), 8.93 (d, J=2.1 Hz, 1H), 8.28 (t, J=1.9 Hz, 1H), 8.12 (d, J=2.1 Hz, 1H), 7.89 (dd, J=8.8 Hz, J=2.0 Hz, 1H), 7.21 (d, J=8.8 Hz, 1H), 4.97 (s, 2H), 2.70 (s, 6H). MS (ESI$^-$): 386.0. HPLC (Condition A): Rt 3.75 min (HPLC purity 93.2%).

EXAMPLE 68

(4-cyano-2-{[5-(isopropylsulfonyl)-2-methylphenyl]ethynyl}phenoxy)acetic acid

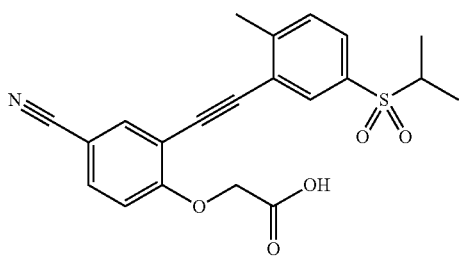

Following the general method as outlined in Example 37, starting from tert-butyl(4-cyano-2-ethynyl phenoxy)acetate (Intermediate 46) and 2-bromo-4-(isopropylsulfonyl)-1-methylbenzene (Intermediate 64), the title compound was obtained as a yellow solid.

$^1$H NMR (300 MHz, DMSO-$d_6$) δ [ppm] 13.26 (bs, 1H), 8.11 (d, J=2.1 Hz, 1H), 7.90-7.78 (m, 2H), 7.77 (t, J=1.8 Hz, 1H), 7.63 (d, J=8.24 Hz, 1H), 7.20 (d, J=8.8 Hz, 1H), 4.96 (s, 2H), 3.50-3.42 (m, 1H), 2.66 (s, 3H), 1.16 (d, J=6.8 Hz, 6H). MS (ESI$^+$): 398.0. HPLC (Condition A): Rt 4.35 min (HPLC purity 98.5%).

EXAMPLE 69

(4-cyano-2-{[5-(methylsulfonyl)pyridin-3-yl]ethynyl]phenoxy)acetic acid

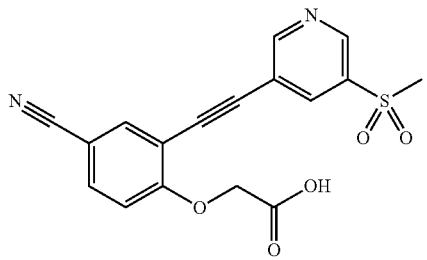

Following the general method as outlined in Example 37, starting from tert-butyl(4-cyano-2-ethynyl phenoxy)acetate (Intermediate 46) and 5-bromo-3-methylsulfonylpyridine (Combiblocks), the title compound was obtained as a yellow solid.

$^1$H NMR (300 MHz, DMSO-$d_6$) δ [ppm] 9.07-9.05 (m, 2H), 8.46 (t, J=2.1 Hz, 1H), 8.11 (d, J=2.0 Hz, 1H), 7.90 (dd, J=8.8 Hz, J=2.1 Hz, 1H), 7.21 (d, J=2.1 Hz, 1H), 4.98 (s, 2H), 3.39 (s, 3H). MS (ESI$^+$): 357.0. HPLC (Condition A): Rt 3.27 min (HPLC purity 93.9%).

EXAMPLE 70

(4-chloro-2-{[2-isopropyl-5-(methylsulfonyl)phenyl]ethynyl}phenoxy)acetic acid

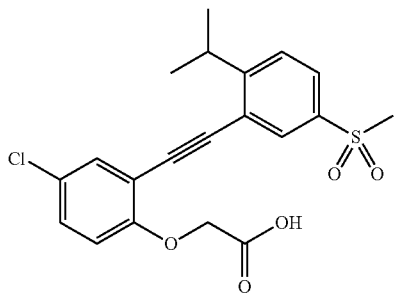

Following the general method as outlined in Example 15, starting from tert-butyl(4-chloro-2-{[2-isopropyl-5-(methylsulfonyl)phenyl]ethynyl}phenoxy)acetate (Intermediate 92), the title compound was obtained as a white solid after purification by preparative HPLC.

$^1$H NMR (300 MHz, DMSO-$d_6$) δ [ppm] 13.18 (1H, bs), 8.01 (1H, d, J=2.0 Hz), 7.90 (1H, dd, J=8.3 Hz, J=2.0 Hz), 7.67 (1H, d, J=8.3 Hz), 7.63 (1H, d, J=2.7 Hz), 7.44 (1H, dd, J=9.0 Hz, J=2.7 Hz), 7.05 (1H, d, J=9.0 Hz), 4.83 (2H, s), 3.65 (1H, sept., J=6.9 Hz), 3.26 (3H, s), 1.28 (6H, d, J=6.9 Hz). MS (ESI$^-$): 405.2. HPLC (Condition A): Rt 4.43 min (HPLC purity 99.8%).

EXAMPLE 71

(4-cyano-2-{[2-isopropyl-5-(methylsulfonyl)phenyl]ethynyl}phenoxy)acetic acid

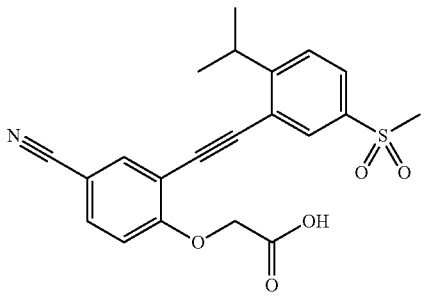

Following the general method as outlined in Example 15, starting from tert-butyl(4-cyano-2-{[2-isopropyl-5-(methylsulfonyl)phenyl]ethynyl}phenoxy)acetate (Intermediate 94), the title compound was obtained as a beige solid after purification by preparative HPLC.

$^1$H NMR (300 MHz, DMSO-$d_6$) δ [ppm] 13.31 (1H, bs), 8.10 (1H, d, J=2.1 Hz), 8.01 (1H, d, J=2.0 Hz), 7.91 (1H, dd, J=8.3 Hz, J=2.0 Hz), 7.87 (1H, dd, J=8.7 Hz, J=2.1 Hz), 7.68 (1H, d, J=8.3 Hz), 7.21 (1H, d, J=8.7 Hz), 4.95 (2H, s), 3.65 (1H, sept., J=6.9 Hz), 3.26 (3H, s), 1.28 (6H, d, J=6.9 Hz). MS (ESI$^-$): 396.3. HPLC (Condition A): Rt 3.93 min (HPLC purity 97.3%).

EXAMPLE 72

[4-cyano-2-({5-[methyl(methylsulfonyl)amino]pyridin-3-yl}ethynyl)phenoxy]acetic acid

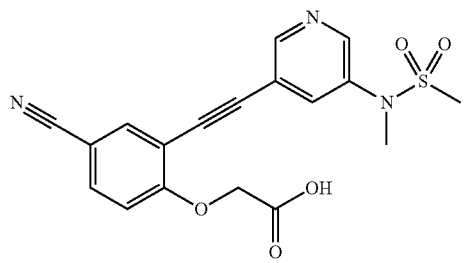

Following the general method as outlined in Example 35, starting from tert-butyl(4-cyano-2-ethynyl phenoxy)acetate (Intermediate 46) and N-(5-bromopyridin-3-yl)-N-methyl-methanesulfonamide (Intermediate 33), the title compound was obtained as an off-white solid.

$^1$H NMR (300 MHz, DMSO-$d_6$) δ [ppm] 8.64-8.62 (m, 2H), 8.06 (d, J=1.8 Hz, 1H), 7.99 (d, J=2.0 Hz, 1H), 7.81 (d, J=8.9 Hz, 1H), 6.97 (d, J=8.9 Hz, 1H), 4.48 (s, 2H), 3.33 (s, 3H), 3.05 (s, 3H). MS (ESI$^+$): 385.0. HPLC (Condition A): Rt 3.35 min (HPLC purity 95.6%).

EXAMPLE 73

[4-cyano-2-({5-[(3-hydroxypropyl)sulfonyl]-2-methylphenyl}ethynyl)phenoxy]acetic acid

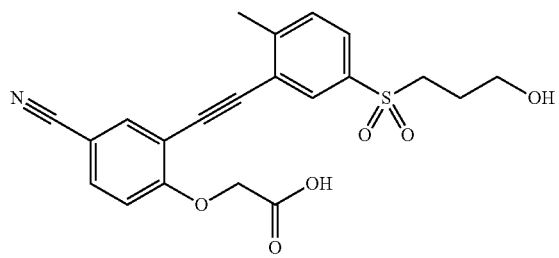

Following the general method as outlined in Example 37, starting from tert-butyl(4-cyano-2-ethynyl phenoxy)acetate (Intermediate 46) and 3-[(3-bromo-4-methylphenyl)sulfonyl]propan-1-ol (Intermediate 68), the title compound was obtained as an off-white solid.

$^1$H NMR (300 MHz, DMSO-$d_6$) δ [ppm] 8.02 (d, J=1.8 Hz, 1H), 7.93 (d, J=1.6 Hz, 1H), 7.80-7.78 (m, 2H), 7.62 (d, J=8.0 Hz, 1H), 6.97 (d, J=8.8 Hz, 1H), 4.46 (s, 2H), 4.10 (s, 1H), 3.41-3.36 (m, 2H), 3.16-3.15 (m, 2H), 1.69-1.62 (m, 2H). MS (ESI$^-$): 414.0. HPLC (Condition A): Rt 3.67 min (HPLC purity 95.4%).

EXAMPLE 74

(3-chloro-2-{[3-(propylsulfonyl)phenyl]ethynyl}phenoxy)acetic acid

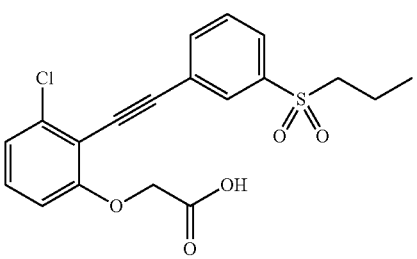

Following the general method as outlined in Example 15, starting from tert-butyl(3-chloro-2-{[3-(propylsulfonyl)phenyl]ethynyl}phenoxy)acetate (Intermediate 95), the title compound was obtained as a dark brown sticky solid after purification by preparative HPLC.

$^1$H NMR (300 MHz, DMSO-$d_6$) δ [ppm] 13.28 (1H, bs), 7.97-7.89 (3H, m), 7.74 (1H, t, J=7.8 Hz), 7.39 (1H, t, J=8.3 Hz), 7.20 (1H, d, 7.8 Hz), 6.99 (1H, d, J=8.3 Hz), 4.86 (2H, s), 3.38 (2H, m), 1.56 (2H, sext., J=7.5 Hz), 0.93 (3H, t, J=7.5 Hz). MS (ESI$^-$): 391.1. HPLC (Condition A): Rt 4.29 min (HPLC purity 98.8%).

EXAMPLE 75

{4-cyano-2-[(5-{[(2-hydroxyethyl)amino]sulfonyl}pyridin-3-yl)ethynyl]phenoxy}acetic acid

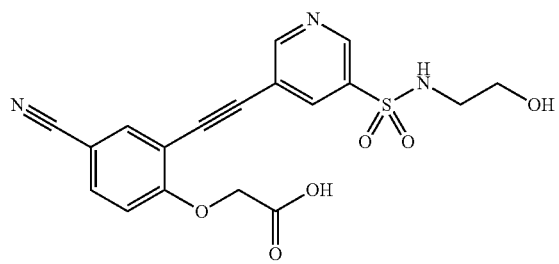

Following the general method as outlined in Example 37, starting from tert-butyl(4-cyano-2-ethynyl phenoxy)acetate (Intermediate 46) and 5-bromo-N-(2-hydroxyethyl)pyridine-3-sulfonamide (Intermediate 31), the title compound was obtained as a yellow solid.

$^1$H NMR (300 MHz, DMSO-$d_6$) δ [ppm] 13.30 (bs, 1H), 8.95 (dd, J=11.7 Hz, J=1.9 Hz, 1H), 8.29 (t, J=2.0 Hz, 1H), 8.11 (d, J=2.1 Hz, 1H), 7.98 (d, J=5.8 Hz, 1H), 7.89 (dd, J=8.7 Hz, J=2.1 Hz, 1H), 7.20 (d, J=8.8 Hz, 1H), 5.02 (s, 2H), 3.39-3.33 (m, 2H), 2.91-2.87 (m, 2H). MS (ESI$^+$): 401.9. HPLC (Condition A): Rt 3.05 min (HPLC purity 91.6%).

EXAMPLE 76

[4-cyano-2-({5-[(3,3-difluoroazetidin-1-yl)sulfonyl]pyridin-3-yl}ethynyl)phenoxy]acetic acid

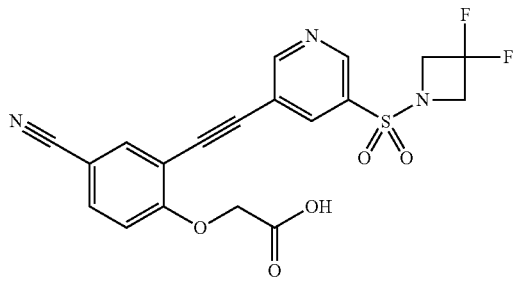

Following the general method as outlined in Example 35, starting from tert-butyl(4-cyano-2-ethynyl phenoxy)acetate (Intermediate 46) and 3-bromo-5-[(3,3-difluoroazetidin-1-yl)sulfonyl]pyridine (Intermediate 34), the title compound was obtained as an off-white solid.

$^1$H NMR (300 MHz, DMSO-$d_6$) δ [ppm] 9.10-9.08 (m, 2H), 8.47 (s, 1H), 8.10 (s, 1H), 7.89 (d, J=8.7 Hz, 1H), 7.18 (d, J=8.7 Hz, 1H), 4.91 (s, 2H), 4.45 (t, J=13.7 Hz, 4H). MS (ESI$^+$): 435.8. HPLC (Condition A): Rt 4.19 min (HPLC purity 95.3%).

EXAMPLE 77

(4-cyano-2-{[5-(morpholin-4-ylsulfonyl)pyridin-3-yl]ethynyl}phenoxy)acetic acid

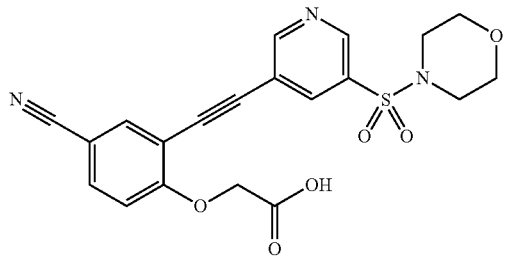

Following the general method as outlined in Example 35, starting from tert-butyl(4-cyano-2-ethynyl phenoxy)acetate (Intermediate 46) and 4-[(5-bromopyridin-3-yl)sulfonyl]morpholine (Apollo), the title compound was obtained as an off-white solid.

$^1$H NMR (300 MHz, DMSO-$d_6$) δ [ppm] 9.05 (d, J=1.6 Hz, 1H), 8.90 (d, J=2.0 Hz, 1H), 8.25 (dd, J=2.0 Hz, J=1.6 Hz, 1H), 8.04 (d, J=2.0 Hz, 1H), 7.82 (dd, J=9.0 Hz, J=2.0 Hz, 1H), 6.97 (d, J=9.0 Hz, 1H), 4.47 (s, 2H), 3.65-3.57 (m, 4H), 3.01-2.99 (m, 4H). MS (ESI$^-$): 427.8. HPLC (Condition A): Rt 3.77 min (HPLC purity 98.4%).

EXAMPLE 78

[4-chloro-2-({5-[(3,3-difluoroazetidin-1-yl)sulfonyl]pyridin-3-yl}ethynyl)phenoxy]acetic acid

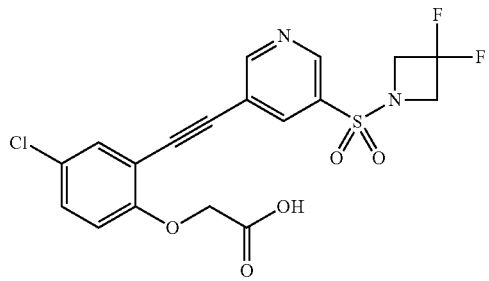

Following the general method as outlined in Example 35, starting from tert-butyl(4-chloro-2-ethynyl phenoxy)acetate (Intermediate 3) and 3-bromo-5-[(3,3-difluoroazetidin-1-yl)sulfonyl]pyridine (Intermediate 34), the title compound was obtained as an off-white solid.

$^1$H NMR (300 MHz, DMSO-$d_6$) δ [ppm] 9.09-9.07 (m, 2H), 8.45 (t, J=1.8 Hz, 1H), 7.67 (d, J=2.6 Hz, 1H), 7.48 (dd, J=9.0 Hz, J=2.6 Hz, 1H), 7.04 (d, J=9.0 Hz, 1H), 4.86 (s, 2H), 4.44 (t, J=12.7 Hz, 4H). MS (ESI$^+$): 442.8. HPLC (Condition A): Rt 4.77 min (HPLC purity 98.0%).

EXAMPLE 79

(4-chloro-2-{[5-(morpholin-4-ylsulfonyl)pyridin-3-yl]ethynyl}phenoxy)acetic acid

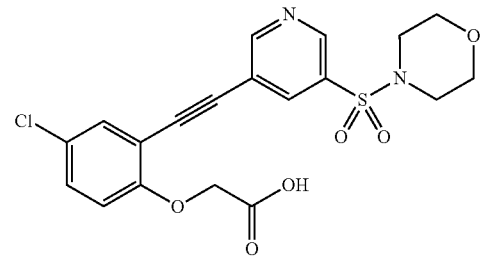

Following the general method as outlined in Example 35, starting from tert-butyl(4-chloro-2-ethynyl phenoxy)acetate (Intermediate 3) and 4-[(5-bromopyridin-3-yl)sulfonyl]morpholine (Apollo), the title compound was obtained as an off-white solid.

$^1$H NMR (300 MHz, DMSO-$d_6$) δ [ppm] 9.04 (d, J=2.0 Hz, 1H), 8.90 (d, J=2.0 Hz, 1H), 8.25 (t, J=2.0 Hz, 1H), 7.67 (d, J=2.6 Hz, 1H), 7.47 (dd, J=9.0 Hz, J=2.6 Hz, 1H), 7.04 (d, J=9.0 Hz, 1H), 4.85 (s, 2H), 3.64 (t, J=4.7 Hz, 4H), 3.00 (t, J=4.7 Hz, 4H). MS (ESI$^+$): 435.0. HPLC (Condition A): Rt 4.36 min (HPLC purity 98.4%).

EXAMPLE 80

[4-chloro-2-({3-[(dimethylamino)sulfonyl]phenyl}ethynyl)phenoxy]acetic acid

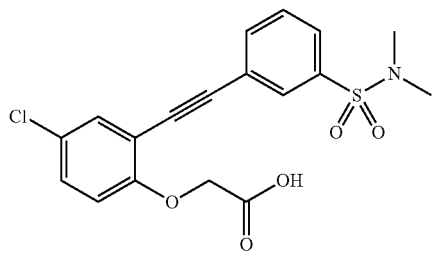

Following the general method as outlined in Example 15, starting from tert-butyl[4-chloro-2-({3-[(dimethylamino)sulfonyl]phenyl}ethynyl)phenoxy]acetate (Intermediate 96), the title compound was obtained as an off-white solid in 93% yield.

$^1$H NMR (300 MHz, DMSO-d$_6$) δ [ppm] 13.16 (1H, bs), 7.89-7.60 (4H, m), 7.66 (1H, d, J=2.7 Hz), 7.44 (1H, dd, J=9.0 Hz, J=2.7 Hz), 7.03 (1H, d, J=9.0 Hz), 4.85 (2H, s), 2.66 (6H, s). MS (ESI⁻): 392.1. HPLC (Condition A): Rt 4.40 min (HPLC purity 96.5%).

EXAMPLE 81

[4-chloro-2-({5-[(diethylamino)sulfonyl]-2-methylphenyl}ethynyl)phenoxy]acetic acid

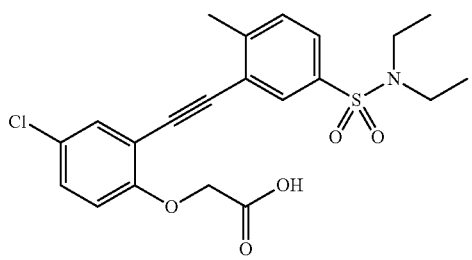

Following the general method as outlined in Example 15, starting from tert-butyl[4-chloro-2-({5-[(diethylamino)sulfonyl]-2-methylphenyl}ethynyl)phenoxy]acetate (Intermediate 97), the title compound was obtained as a white solid after purification by preparative HPLC.

$^1$H NMR (300 MHz, DMSO-d$_6$) δ [ppm] 13.16 (1H, bs), 7.84 (1H, d, J=2.0 Hz), 7.71 (1H, dd, J=8.1 Hz, J=2.0 Hz), 7.66 (1H, d, J=2.7 Hz), 7.57 (1H, d, J=8.1 Hz), 7.44 (1H, dd, J=9.0 Hz, J=2.7 Hz), 7.04 (1H, d, J=9.0 Hz), 4.82 (2H, s), 3.17 (4H, q, J=7.1 Hz), 2.56 (3H, s), 1.05 (6H, t, J=7.1 Hz). MS (ESI⁻): 434.1. HPLC (Condition A): Rt 4.80 min (HPLC purity 99.2%).

EXAMPLE 82

(4-chloro-2-{[2-methyl-5-(morpholin-4-ylsulfonyl)phenyl]ethynyl}phenoxy)acetic acid

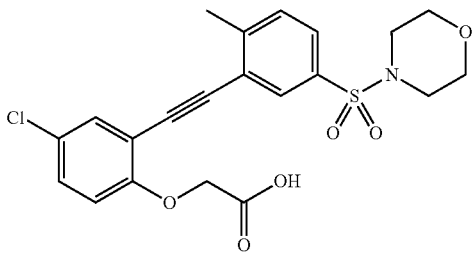

Following the general method as outlined in Example 15, starting from tert-butyl(4-chloro-2-{[2-methyl-5-(morpholin-4-ylsulfonyl)phenyl]ethynyl}phenoxy)acetate (Intermediate 98), the title compound was obtained as a white solid after purification by preparative HPLC.

$^1$H NMR (300 MHz, DMSO-d$_6$) δ [ppm] 13.16 (1H, bs), 7.79 (1H, d, J=1.5 Hz), 7.68-7.61 (3H, m), 7.44 (1H, dd, J=9.0 Hz, J=2.7 Hz), 7.04 (1H, d, J=9.0 Hz), 4.83 (2H, s), 3.64 (4H, m), 2.89 (4H, m), 2.59 (3H, s). MS (ESI⁻): 448.1. HPLC (Condition A): Rt 4.46 min (HPLC purity 98.9%).

EXAMPLE 83

[4-chloro-2-({5-[(dimethylamino)sulfonyl]-2-methylphenyl}ethynyl)phenoxy]acetic acid

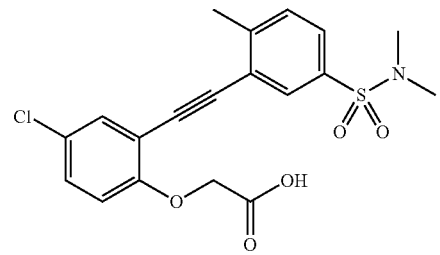

Following the general method as outlined in Example 15, starting from tert-butyl[4-chloro-2-({5-[(dimethylamino)sulfonyl]-2-methylphenyl}ethynyl)phenoxy]acetate (Intermediate 99), the title compound was obtained as a white solid after purification by preparative HPLC.

$^1$H NMR (300 MHz, DMSO-d$_6$) δ [ppm] 13.15 (1H, bs), 7.80 (1H, d, J=1.8 Hz), 7.69-7.60 (3H, m), 7.44 (1H, dd, J=9.0 Hz, J=2.7 Hz), 7.04 (1H, d, J=9.0 Hz), 4.83 (2H, s), 2.63 (6H, s), 2.58 (3H, s). MS (ESI⁻): 406.1. HPLC (Condition A): Rt 4.55 min (HPLC purity 97.1%).

EXAMPLE 84

[4-chloro-2-({2-methyl-5-[(methylamino)sulfonyl]phenyl}ethynyl)phenoxy]acetic acid

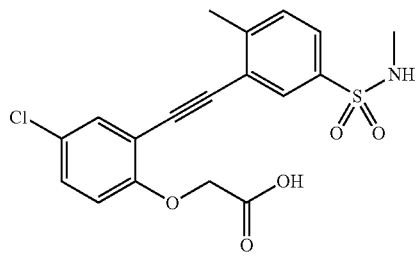

Following the general method as outlined in Example 15, starting from tert-butyl[4-chloro-2-({2-methyl-5-[(methylamino)sulfonyl]phenyl}ethynyl)phenoxy]acetate (Intermediate 100), the title compound was obtained as a beige solid after purification by preparative HPLC.

$^1$H NMR (300 MHz, DMSO-$d_6$) δ [ppm] 13.19 (1H, bs), 7.85 (1H, d, J=2.0 Hz), 7.68 (1H, dd, J=8.0 Hz, J=2.0 Hz), 7.64 (1H, d, J=2.7 Hz), 7.57 (1H, d, J=8.0 Hz), 7.50 (1H, q, J=5.0 Hz), 7.45 (1H, dd, J=9.0 Hz, J=2.7 Hz), 7.03 (1H, d, J=9.0 Hz), 4.82 (2H, s), 2.55 (3H, s), 2.41 (3H, d, J=5.0 Hz). MS (ESI$^-$): 392.1. HPLC (Condition A): Rt 4.05 min (HPLC purity 99.3%).

EXAMPLE 85

[2-({5-[(tert-butylamino)sulfonyl]-2-methylphenyl}ethynyl)-4-chlorophenoxy]acetic acid

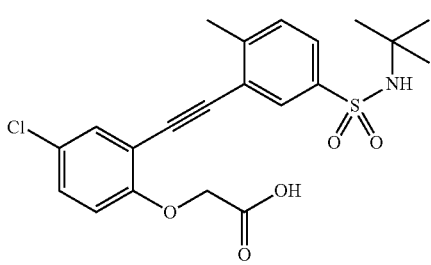

Following the general method as outlined in Example 15, starting from tert-butyl[2-({5-[(tert-butylamino)sulfonyl]-2-methylphenyl}ethynyl)-4-chlorophenoxy]acetate (Intermediate 101), the title compound was obtained as a beige solid after purification by preparative HPLC.

$^1$H NMR (300 MHz, DMSO-$d_6$) δ [ppm] 13.17 (1H, bs), 7.90 (1H, d, J=2.0 Hz), 7.74 (1H, dd, J=8.0 Hz, J=2.0 Hz), 7.64 (1H, d, J=2.7 Hz), 7.57 (1H, s), 7.53 (1H, d, J=8.0 Hz), 7.43 (1H, dd, J=9.0 Hz, J=2.7 Hz), 7.03 (1H, d, J=9.0 Hz), 4.82 (2H, s), 2.54 (3H, s); 1.10 (9H, s). MS (ESI$^-$): 434.2. HPLC (Condition A): Rt 4.86 min (HPLC purity 96.7%).

EXAMPLE 86

[4-chloro-2-({5-[(isopropylamino)sulfonyl]-2-methylphenyl}ethynyl)phenoxy]acetic acid

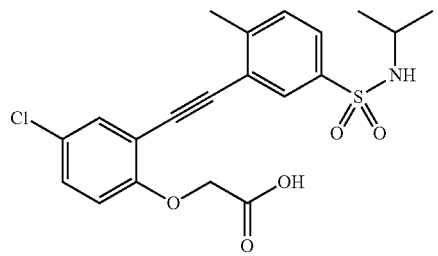

Following the general method as outlined in Example 15, starting from tert-butyl[4-chloro-2-({5-[(isopropylamino)sulfonyl]-2-methylphenyl}ethynyl)phenoxy}acetate (Intermediate 102), the title compound was obtained as a beige solid after purification by preparative HPLC.

$^1$H NMR (300 MHz, DMSO-$d_6$) δ [ppm] 13.17 (1H, bs), 7.87 (1H, d, J=2.0 Hz), 7.71 (1H, dd, J=8.0 Hz, J=2.0 Hz), 7.64 (1H, d, J=2.7 Hz), 7.61 (1H, d, J=7.0 Hz), 7.54 (1H, d, J=8.0 Hz), 7.43 (1H, dd, J=9.0 Hz, J=2.7 Hz), 7.03 (1H, d, J=9.0 Hz), 4.83 (2H, s), 3.25 (1H, m), 2.55 (3H, s), 0.95 (6H, d, J=6.6 Hz). MS (ESI$^-$): 420.2. HPLC (Condition A): Rt 4.64 min (HPLC purity 98.4%). HPLC (max plot) 98.4%; Rt 4.64 min.

EXAMPLE 87

{4-chloro-2-[(5-{[isopropyl(methyl)amino]sulfonyl}-2-methylphenyl)ethynyl]phenoxy}acetic acid

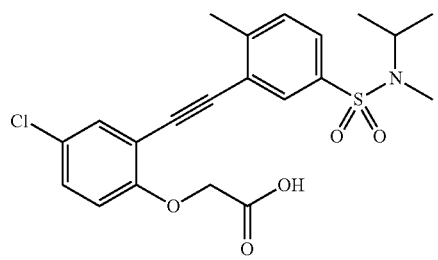

Following the general method as outlined in Example 15, starting from tert-butyl{4-chloro-2-[(5-{[isopropyl(methyl)amino]sulfonyl}-2-methylphenyl)ethynyl]phenoxy}acetate (Intermediate 104), the title compound was obtained as a beige solid after purification by preparative HPLC.

$^1$H NMR (300 MHz, DMSO-$d_6$) δ [ppm] 13.16 (1H, bs), 7.83 (1H, d, J=2.0 Hz), 7.71 (1H, dd, J=8.1 Hz, J=2.0 Hz), 7.66 (1H, d, J=2.7 Hz), 7.57 (1H, d, J=8.1 Hz), 7.44 (1H, dd, J=9.0 Hz, J=2.7 Hz), 7.04 (1H, d, J=9.0 Hz), 4.83 (2H, s), 4.09 (1H, septet., J=6.7 Hz), 2.66 (3H, s); 2.56 (3H, s), 0.91 (6H, d, J=6.7 Hz). MS (ESI$^-$): 434.1. HPLC (Condition A): Rt 4.99 min (HPLC purity 98.6%).

EXAMPLE 88

(4-chloro-2-{[2-methyl-5-(piperidin-1-ylsulfonyl)phenyl]ethynyl}phenoxy)acetic acid

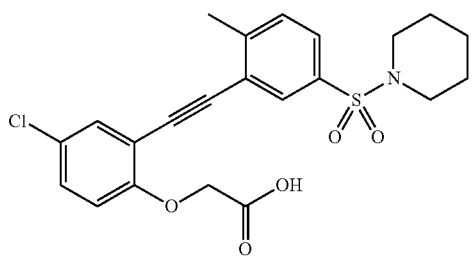

Following the general method as outlined in Example 15, starting from tert-butyl(4-chloro-2-{[2-methyl-5-(piperidin-1-ylsulfonyl)phenyl]ethynyl}phenoxy)acetate (Intermediate 156), the title compound was obtained as an off-white solid in 89% yield.

$^1$H NMR (300 MHz, DMSO-d$_6$) δ [ppm] 13.06 (1H, bs), 7.68 (1H, d, J=1.8 Hz), 7.59-7.50 (3H, m), 7.35 (1H, dd, J=9.0 Hz, J=2.7 Hz), 6.96 (1H, d, J=9.0 Hz), 4.75 (2H, s), 2.81 (4H, m), 2.49 (3H, s); 1.46 (4H, m), 1.28 (2H, m). MS (ESI$^-$): 446.1. HPLC (Condition A): Rt 4.88 min (HPLC purity 96.8%).

EXAMPLE 89

(4-chloro-2-{[2-fluoro-5-(propylsulfonyl)phenyl]ethynyl}phenoxy)acetic acid

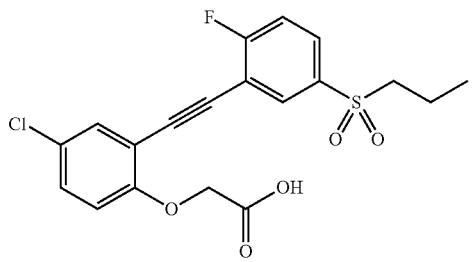

Following the general method as outlined in Example 15, starting from tert-butyl(4-chloro-2-{[2-fluoro-5-(propylsulfonyl)phenyl]ethynyl}phenoxy)acetate (Intermediate 107), the title compound was obtained as a beige solid in 97% yield.

$^1$H NMR (300 MHz, DMSO-d$_6$) δ [ppm] 13.18 (1H, bs), 8.13 (1H, dd, J=6.5 Hz, J=2.4 Hz), 7.95 (1H, ddd, J=8.7 Hz, J=4.6 Hz, J=2.4 Hz), 7.68-7.62 (2H, m), 7.47 (1H, dd, J=9.0 Hz, J=2.7 Hz), 7.04 (1H, d, J=9.0 Hz), 4.86 (2H, s), 3.38 (2H, m), 1.58 (2H, m), 0.93 (3H, t, J=7.5 Hz). MS (ESI$^-$): 409.1. HPLC (Condition A): Rt 4.48 min (HPLC purity 96.1%).

EXAMPLE 90

(4-chloro-2-{[4-(methylsulfonyl)phenyl]ethynyl}phenoxy)acetic acid

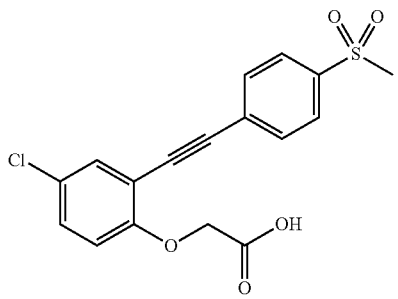

Following the general method as outlined in Example 15, starting from tert-butyl(4-chloro-2-{[4-(methylsulfonyl)phenyl]ethynyl}phenoxy)acetate (Intermediate 110), the title compound was obtained as a white solid after purification by preparative HPLC.

$^1$H NMR (300 MHz, DMSO-d$_6$) δ [ppm] 13.20 (1H, bs), 77.98 (2H, d, J=8.5 Hz), 7.80 (2H, d, J=8.5 Hz), 7.63 (1H, d, J=2.7 Hz), 7.45 (1H, dd, J=9.0 Hz, J=2.7 Hz), 7.02 (1H, d, J=9.0 Hz), 4.84 (2H, s), 3.27 (3H, s). MS (ESI$^-$): 363.0. HPLC (Condition A): Rt 3.91 min (HPLC purity 100%).

EXAMPLE 91

(2-{[5-(benzylsulfonyl)-2-methylphenyl]ethynyl}-4-chlorophenoxy)acetic acid

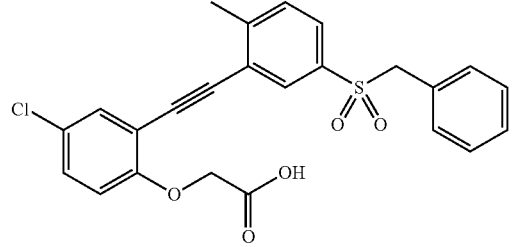

Following the general method as outlined in Example 37, starting from tert-butyl(4-chloro-2-ethynyl phenoxy)acetate (Intermediate 3) and 4-(benzylsulfonyl)-2-bromo-1-methylbenzene (Intermediate 69), the title compound was obtained as a yellow solid.

$^1$H NMR (300 MHz, DMSO-d$_6$) δ [ppm] 13.15 (bs, 1H), 7.80 (s, 1H), 7.62 (d, J=2.6 Hz, 1H), 7.54-7.53 (m, 2H), 7.45 (s, 1H), 7.31-7.30 (m, 3H), 7.18 (d, J=5.0 Hz, 2H), 7.03 (d, J=9.2 Hz, 1H), 4.83 (s, 2H), 4.71 (s, 2H), 2.55 (s, 3H). MS (ESI$^+$): 455.0. HPLC (Condition A): Rt 5.29 min (HPLC purity 97.2%).

EXAMPLE 92

[4-chloro-2-({2-methyl-5-[(2-phenylethyl)sulfonyl]phenyl}ethynyl)phenoxy]acetic acid

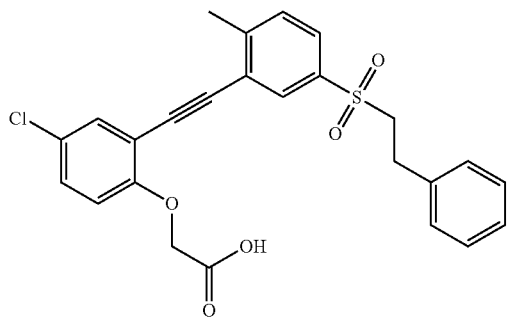

Following the general method as outlined in Example 37, starting from tert-butyl(4-chloro-2-ethynyl phenoxy)acetate (Intermediate 3) and 2-bromo-1-methyl-4-[(2-phenylethyl)sulfonyl]benzene (Intermediate 70), the title compound was obtained as a yellow solid.

$^1$H NMR (300 MHz, DMSO-d$_6$) δ [ppm] 13.16 (s, 1H), 7.97 (s, 1H), 7.82 (d, J=8.0 Hz, 1H), 7.61 (t, J=9.1 Hz, 1H), 7.44 (d, J=8.4 Hz, 1H), 7.24-7.17 (m, 5H), 7.04 (d, J=9.0 Hz, 1H), 4.84 (s, 2H), 3.68 (t, J=8.0 Hz, 2H), 2.88 (t, J=8.0 Hz, 2H), 2.57 (s, 3H). MS (ESI$^+$): 467.0. HPLC (Condition A): Rt 5.53 min (HPLC purity 97.0%).

EXAMPLE 93

(2-{[5-(benzylsulfonyl)-2-methylphenyl]ethynyl}-4-cyanophenoxy)acetic acid

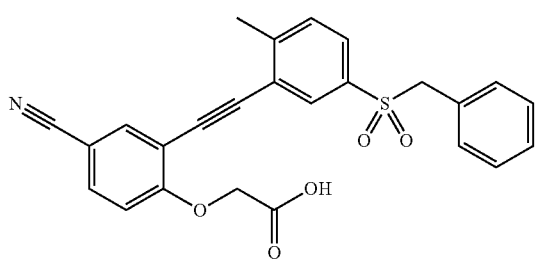

Following the general method as outlined in Example 37, starting from tert-butyl(4-cyano-2-ethynyl phenoxy)acetate (Intermediate 46) and 4-(benzylsulfonyl)-2-bromo-1-methylbenzene (Intermediate 69), the title compound was obtained as a yellow solid.

$^1$H NMR (300 MHz, DMSO-d$_6$) δ [ppm] 13.36 (bs, 1H), 8.08 (d, J=2.0 Hz, 1H), 7.86 (dd, J=8.7 Hz, J=2.1 Hz, 1H), 7.81 (d, J=1.6 Hz, 1H), 7.58-7.52 (m, 2H), 7.31-7.28 (m, 3H), 7.20-7.16 (m, 3H), 4.94 (s, 2H), 4.71 (s, 2H), 2.55 (s, 3H). MS (ESI$^+$): 446.0. HPLC (Condition A): Rt 4.77 min (HPLC purity 98.9%).

EXAMPLE 94

(4-cyano-2-{[2-methyl-5-(phenylsulfonyl)phenyl]ethynyl}phenoxy)acetic acid

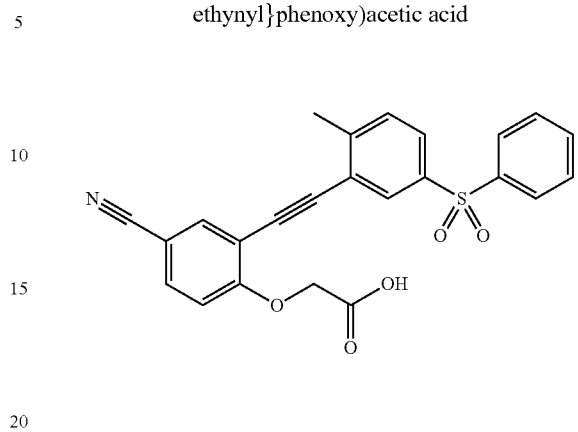

Following the general method as outlined in Example 15, starting from tert-butyl(4-cyano-2-{[2-methyl-5-(phenylsulfonyl)phenyl]ethynyl}phenoxy)acetate (Intermediate 115), the title compound was obtained as a brown solid after purification by preparative HPLC.

$^1$H NMR (300 MHz, DMSO-d$_6$) δ [ppm] 13.36 (1H, bs), 8.10 (1H, d, J=2.1 Hz), 7.97-8.02 (3H, m), 7.84-7.90 (2H, m), 7.57-7.73 (4H, m), 7.19 (1H, d, J=8.9 Hz), 4.93 (2H, s), 2.53 (3H, s). MS (ESI$^-$): 430.2. HPLC (Condition A): Rt 4.24 min (HPLC purity 99.6%).

EXAMPLE 95

(4-chloro-2-{[2-methyl-5-(phenylsulfonyl)phenyl]ethynyl}phenoxy)acetic acid

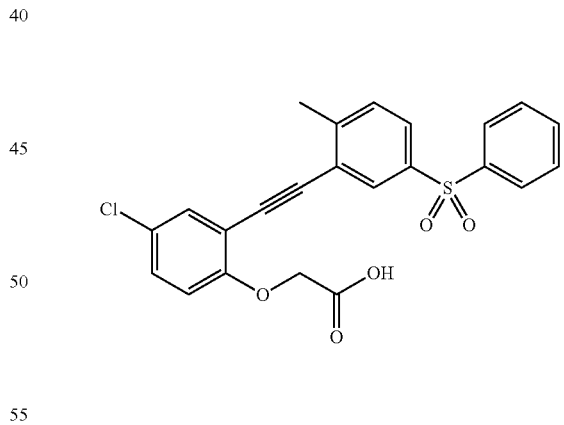

Following the general method as outlined in Example 15, starting from tert-butyl(4-chloro-2-{[2-methyl-5-(phenylsulfonyl)phenyl]ethynyl}phenoxy)acetate (Intermediate 116), the title compound was obtained as a brown solid after purification by preparative HPLC.

$^1$H NMR (300 MHz, DMSO-d$_6$) δ [ppm] 13.26 (1H, bs), 7.97-8.02 (3H, m), 7.87 (1H, dd, J=8.0 Hz, J=2.0 Hz), 7.56-7.73 (5H, m), 7.43 (1H, dd, J=9.0 Hz, J=2.7 Hz), 7.03 (1H, d, J=9.0 Hz), 4.79 (2H, s), 2.52 (3H, s). MS (ESI$^-$): 439.2. HPLC (Condition A): Rt 4.90 min (HPLC purity 98.4%).

EXAMPLE 96

[4-cyano-2-({2-methyl-5-[(2-phenylethyl)sulfonyl]phenyl}ethynyl)phenoxy]acetic acid

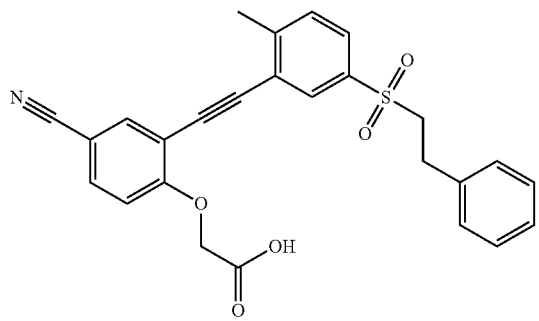

Following the general method as outlined in Example 37, starting from tert-butyl(4-cyano-2-ethynyl phenoxy)acetate (Intermediate 46) and 2-bromo-1-methyl-4-[(2-phenylethyl)sulfonyl]benzene (Intermediate 70), the title compound was obtained as a yellow solid.

$^1$H NMR (300 MHz, DMSO-d$_6$) δ [ppm] 8.05 (s, 1H), 7.97 (s, 1H) 7.83 (d, J=6.6 Hz, 2H), 7.60 (d, J=8.2 Hz, 1H), 7.26-7.17 (m, 5H), 7.08 (d, J=9.0 Hz, 1H), 4.71 (s, 2H), 3.69 (d, J=7.9 Hz, 2H), 2.88 (d, J=7.9 Hz, 2H), 2.57 (s, 3H). MS (ESI$^+$): 460.0. HPLC (Condition A): Rt 5.03 min (HPLC purity 98.3%).

EXAMPLE 97

(4-chloro-2-{[4-fluoro-2-methyl-5-(methylsulfonyl)phenyl]ethynyl}phenoxy)acetic acid

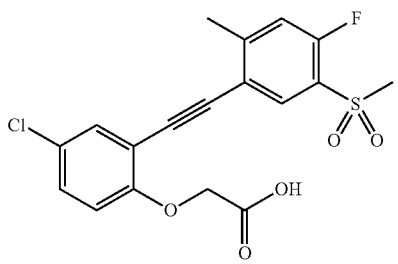

Following the general method as outlined in Example 15, starting from tert-butyl(4-chloro-2-{[4-fluoro-2-methyl-5-(methylsulfonyl)phenyl]ethynyl}phenoxy)acetate (Intermediate 117), the title compound was obtained as a white solid after purification by preparative HPLC.

$^1$H NMR (300 MHz, DMSO-d$_6$) δ [ppm] 13.17 (1H, bs), 7.89 (1H, d, J=7.2 Hz), 7.66 (1H, d, J=J=2.6 Hz), 7.59 (1H, d, J=11.1), 7.44 (1H, dd, J=9.0 Hz, J=2.6 Hz), 7.04 (1H, d, J=9.0 Hz), 4.83 (2H, s), 3.34 (3H, s), 2.58 (3H, s). MS (ESI$^-$): 395.0. HPLC (Condition A): Rt 4.28 min (HPLC purity 97.4%).

EXAMPLE 98

[4-chloro-2-({3-[(methylsulfonyl)methyl]phenyl}ethynyl)phenoxy]acetic acid

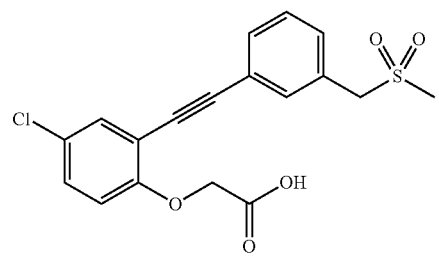

Following the general method as outlined in Example 15, starting from tert-butyl[4-chloro-2-({3-[(methylsulfonyl)methyl]phenyl}ethynyl)phenoxy]acetate (Intermediate 118), the title compound was obtained as a beige solid.

$^1$H NMR (300 MHz, DMSO-d$_6$) δ [ppm] 13.16 (1H, bs), 7.55-7.59 (3H, m), 7.46-7.48 (2H, m), 7.41 (1H, dd, J=9.0 Hz, J=2.7 Hz), 7.00 (1H, d, J=9.0 Hz), 4.84 (2H, s), 4.54 (2H, s), 2.93 (3H, s). MS (ESI$^-$): 377.0. HPLC (Condition A): Rt 3.82 min (HPLC purity 94.8%).

EXAMPLE 99

(4-fluoro-2-{[3-(propylsulfonyl)phenyl]ethynyl}phenoxy)acetic acid

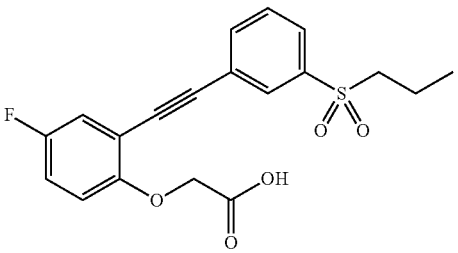

Following the general method as outlined in Example 15, starting from tert-butyl(4-fluoro-2-{[3-(propylsulfonyl)phenyl]ethynyl}phenoxy)acetate (Intermediate 119), the title compound was obtained as an orange sticky solid.

$^1$H NMR (300 MHz, DMSO-d$_6$) δ [ppm] 13.12 (1H, bs), 8.00 (1H, t, J=1.5 Hz), 7.91 (2H, m), 7.73 (1H, t, J=7.8 Hz), 7.45 (1H, dd, J=8.7 Hz, J=3.1 Hz), 7.26 (1H, m), 7.00 (1H, dd, J=9.3 Hz, J=4.4 Hz), 4.82 (2H, s), 3.37 (2H, m), 1.57 (2H, sext., J=7.5 Hz), 0.92 (3H, t, J=7.5 Hz). MS (ESI$^-$): 375.1. HPLC (Condition A): Rt 3.95 min (HPLC purity 95.4%).

EXAMPLE 100

(4-chloro-2-{[2-ethyl-5-(methylsulfonyl)phenyl]ethynyl}phenoxy)acetic acid

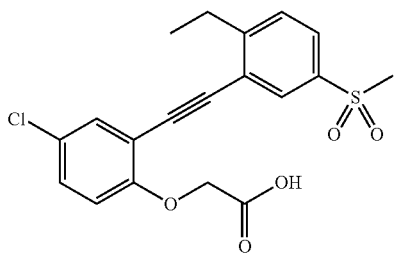

Following the general method as outlined in Example 15, starting from tert-butyl(4-chloro-2-{[2-ethyl-5-(methylsulfonyl)phenyl]ethynyl}phenoxy)acetate (Intermediate 124), the title compound was obtained as a pale pink solid after precipitation from pentane.

$^1$H NMR (300 MHz, DMSO-$d_6$) δ [ppm] 13.16 (1H, bs), 8.00 (1H, d, J=2.0 Hz), 7.88 (1H, dd, J=8.0 Hz, J=2.0 Hz), 7.65-7.61 (2H, m), 7.45 (1H, dd, J=9.0 Hz, J=2.7 Hz), 7.06 (1H, d, J=9.0 Hz), 4.85 (2H, s), 3.26 (3H, s), 2.96 (2H, q, J=7.5 Hz), 1.26 (3H, t, J=7.5 Hz). MS (ESI$^-$): 392.9. HPLC (Condition A): Rt 4.39 min (HPLC purity 97.7%).

EXAMPLE 101

(4-chloro-2-{[2-chloro-5-(propylsulfonyl)phenyl]ethynyl}phenoxy)acetic acid

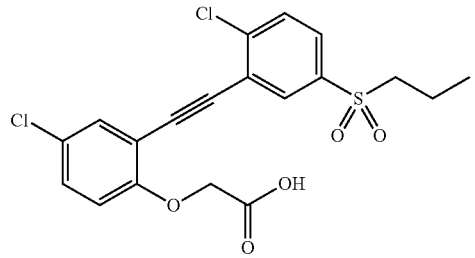

Following the general method as outlined in Example 15, starting from tert-butyl(4-chloro-2-{[2-chloro-5-(propylsulfonyl)phenyl]ethynyl}phenoxy)acetate (Intermediate 127), the title compound was obtained as a white solid after purification by preparative HPLC.

$^1$H NMR (300 MHz, DMSO-$d_6$) δ [ppm] 13.20 (1H, bs), 8.12 (1H, t, J=1.3 Hz), 7.90 (2H, d, J=1.3 Hz), 7.65 (1H, d, J=2.7 Hz), 7.48 (1H, dd, J=9.0 Hz, J=2.7 Hz), 7.05 (1H, d, J=9.0 Hz), 4.85 (2H, s), 3.40 (2H, m), 1.58 (2H, m), 0.93 (3H, t, J=7.5 Hz). MS (ESI$^-$): 425.0. HPLC (Condition A): Rt 4.51 min (HPLC purity 100%).

EXAMPLE 102

(4-chloro-2-{[2-fluoro-5-(isopropylsulfonyl)phenyl]ethynyl}phenoxy)acetic acid

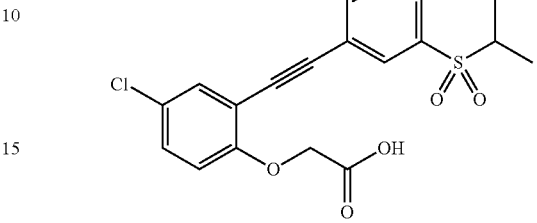

Following the general method as outlined in Example 15, starting from tert-butyl(4-chloro-2-{[2-fluoro-5-(isopropylsulfonyl)phenyl]ethynyl}phenoxy)acetate (Intermediate 133), the title compound was obtained as a white solid after purification by preparative HPLC.

$^1$H NMR (300 MHz, DMSO-$d_6$) δ [ppm] 13.20 (1H, bs), 8.08 (1H, dd, J=6.5 Hz, J=2.4 Hz), 7.95 (1H, ddd, J=8.7 Hz, J=4.6 Hz, J=2.4 Hz), 7.70-7.64 (2H, m), 7.47 (1H, dd, J=9.0 Hz, J=2.7 Hz), 7.03 (1H, d, J=9.0 Hz), 4.85 (2H, s), 3.55 (2H, septet, J=6.8 Hz), 1.18 (6H, d, J=6.8 Hz). MS (ESI$^-$): 409.0. HPLC (Condition A): Rt 4.34 min (HPLC purity 98.3%).

EXAMPLE 103

(4-chloro-2-{[2-chloro-5-(isopropylsulfonyl)phenyl]ethynyl}phenoxy)acetic acid

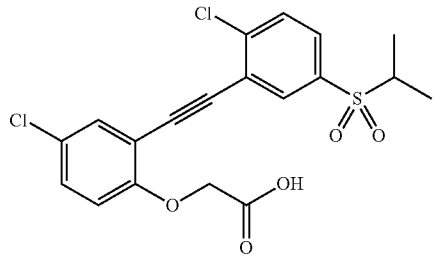

Following the general method as outlined in Example 15, starting from tert-butyl(4-chloro-2-{[2-chloro-5-(isopropylsulfonyl)phenyl]ethynyl}phenoxy)acetate (Intermediate 134), the title compound was obtained as a white solid after purification by preparative HPLC.

$^1$H NMR (300 MHz, DMSO-$d_6$) δ [ppm] 13.19 (1H, bs), 8.07 (1H, d, J=1.9 Hz), 7.93-7.85 (2H, m), 7.66 (1H, d, J=2.7 Hz), 7.48 (1H, dd, J=9.0 Hz, J=2.7 Hz), 7.05 (1H, d, J=9.0 Hz), 4.85 (2H, s), 3.57 (2H, septet, J=6.8 Hz), 1.19 (6H, d, J=6.8 Hz). MS (ESI$^-$): 424.9. HPLC (Condition A): Rt 4.57 min (HPLC purity 99.6%).

EXAMPLE 104

(4-chloro-2-{[5-(ethylsulfonyl)-2-fluorophenyl]ethynyl}phenoxy)acetic acid

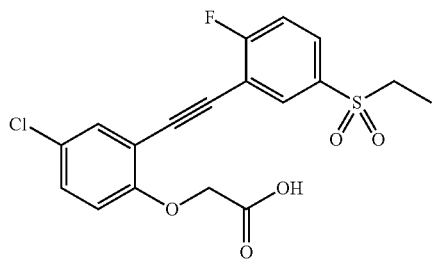

Following the general method as outlined in Example 15, starting from tert-butyl[4-chloro-2-({2-fluoro-5-[(2-methoxyethyl)sulfonyl]phenyl}ethynyl)phenoxy]acetate (Intermediate 135), the title compound was obtained as a white solid after precipitation from DCM/pentane.

$^1$H NMR (300 MHz, DMSO-$d_6$) δ [ppm] 13.18 (brs, 1H), 8.11 (dd, J=2.3, J=6.6 Hz, 1H), 7.98 (ddd, J=2.3, J=4.9, J=7.3 Hz, 1H), 7.63 (m, 2H), 7.45 (dd, J=2.6, J=9.1 Hz, 1H), 7.02 (d, J=9.5 Hz, 1H), 4.84 (d, 2H), 3.39 (q, J=7.5 Hz, 2H), 1.11 (t, J=7.2 Hz, 3H). m.p.=165-169° C. MS (ESI$^-$): 395.1. HPLC (Condition A): Rt 4.22 min (HPLC purity 96.7%).

EXAMPLE 105

(4-chloro-2-{[2-fluoro-5-(isobutylsulfonyl)phenyl]ethynyl}phenoxy)acetic acid

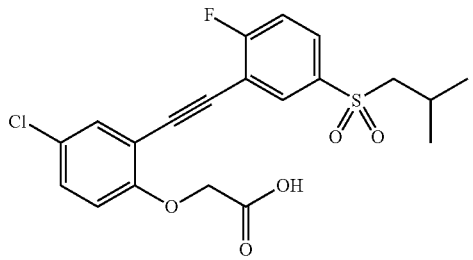

Following the general method as outlined in Example 15, starting from tert-butyl[4-chloro-2-({2-fluoro-5-[(2-methoxyethyl)sulfonyl]phenyl}ethynyl)phenoxy]acetate (Intermediate 136), the title compound was obtained as a white solid after purification by preparative HPLC.

$^1$H NMR (300 MHz, DMSO-$d_6$) δ [ppm] 13.2 (brs, 1H), 8.14 (dd, J=2.3, J=6.4 Hz, 1H), 8.00 (ddd, J=2.5, J=4.8, J=7.5 Hz, 1H), 7.63 (m, 2H), 7.46 (dd, J=2.7, J=9.1 Hz, 1H), 7.02 (d, J=9.1 Hz, 1H), 4.84 (s, 2H), 3.30 (m, 2H), 2.02 (septet, J=6.6 Hz, 1H), 0.98 (d, 6H). m.p.=141-143° C. MS (ESI$^-$): 423.2. HPLC (Condition A): Rt 5.18 min (HPLC purity 100%).

EXAMPLE 106

[4-chloro-2-({2-fluoro-5-[(2-methoxyethyl)sulfonyl]phenyl}ethynyl)phenoxy]acetic acid

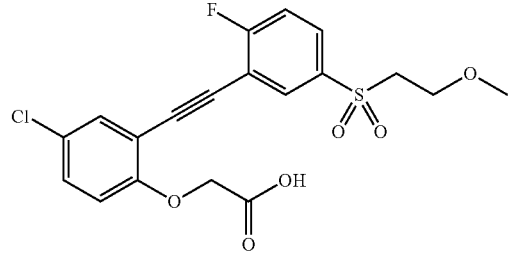

Following the general method as outlined in Example 15, starting from tert-butyl[4-chloro-2-({2-fluoro-5-[(2-methoxyethyl)sulfonyl]phenyl}ethynyl)phenoxy]acetate (Intermediate 137), the title compound was obtained as a white solid after purification by preparative HPLC followed by crystallization from DCM/hexane.

$^1$H NMR (300 MHz, DMSO-$d_6$) δ [ppm] 13.2 (brs, 1H), 8.11 (dd, 1H), 7.96 (ddd, J=2.5, J=4.9, J=7.4 Hz, 1H), 7.63 (m, 2H), 7.46 (dd, J=2.7, J=9.01 Hz, 1H), 7.02 (d, J=9.1 Hz, 1H), 4.84 (s, 2H), 3.65 (m, 4H), 3.08 (s, 3H). m.p.=125-128° C. MS (ESI$^-$): 425.2. HPLC (Condition A): Rt 4.62 min (HPLC purity 100%).

EXAMPLE 107

[4-chloro-2-({5-[(dimethylamino)sulfonyl]-2-fluorophenyl}ethynyl)phenoxy]acetic acid

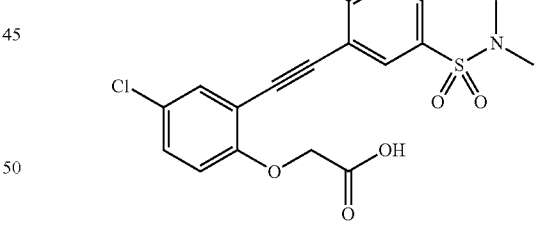

Following the general method as outlined in Example 15, starting from tert-butyl[4-chloro-2-({5-[(dimethylamino)sulfonyl]-2-fluorophenyl]ethynyl)phenoxy}acetate (Intermediate 157), the title compound was obtained as a white solid after purification by preparative HPLC.

$^1$H NMR (300 MHz, DMSO-$d_6$) δ [ppm] 13.18 (1H, bs), 7.97 (1H, dd, J=6.5 Hz, J=2.4 Hz), 7.86 (1H, ddd, J=8.7 Hz, J=4.6 Hz, J=2.4 Hz), 7.67-7.61 (2H, m), 7.47 (1H, dd, J=9.0 Hz, J=2.7 Hz), 7.04 (1H, d, J=9.0 Hz), 4.85 (2H, s), 2.66 (6H, s). MS (ESI$^-$): 410.0. HPLC (Condition A): Rt 4.27 min (HPLC purity 99.7%).

EXAMPLE 108

[4-chloro-2-({2-methyl-5-[(2-methylpiperidin-1-yl)sulfonyl]phenyl}ethynyl)-phenoxy]acetic acid

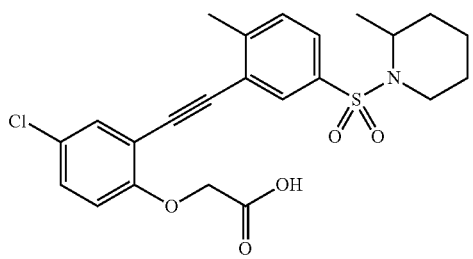

Following the general method as outlined in Example 15, starting from tert-butyl[4-chloro-2-({2-methyl-5-[(2-methylpiperidin-1-yl)sulfonyl]phenyl}ethynyl)phenoxy]acetate (Intermediate 158), the title compound was obtained as a white solid after purification by preparative HPLC.

$^1$H NMR (300 MHz, DMSO-$d_6$) δ [ppm] 13.17 (1H, bs), 7.84 (1H, d, J=2.0 Hz), 7.71 (1H, dd, J=8.1 Hz, J=2.0 Hz), 7.66 (1H, d, J=2.7 Hz), 7.56 (1H, d, J=8.1 Hz), 7.44 (1H, dd, J=9.0 Hz, J=2.7 Hz), 7.03 (1H, d, J=9.0 Hz), 4.82 (2H, s), 4.13 (1H, m), 3.63 (1H, m), 2.98 (1H, dt, J=13.0 Hz, J=2.0 Hz), 2.55 (3H, s), 1.40-4.56 (5H, m), 1.20 (1H, m), 1.00 (3H, d, J=6.9 Hz). MS (ESI$^-$): 460.1. HPLC (Condition A): Rt 5.19 min (HPLC purity 99.6%).

EXAMPLE 109

{4-chloro-2-[(5-{[(2-methoxyethyl)(methyl)amino]sulfonyl}-2-methylphenyl)ethynyl]phenoxy}acetic acid

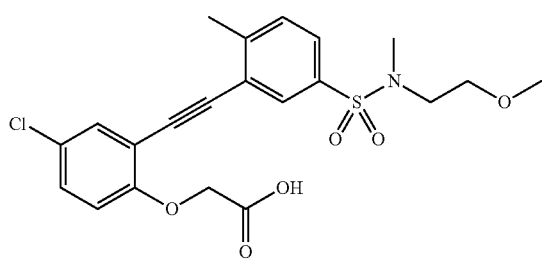

Following the general method as outlined in Example 15, starting from tert-butyl{4-chloro-2-[(5-{[(2-methoxyethyl)(methyl)amino]sulfonyl}-2-methylphenyl)ethynyl]phenoxy}acetate (Intermediate 159), the title compound was obtained as a pink solid after purification by preparative HPLC.

$^1$H NMR (300 MHz, DMSO-$d_6$) δ [ppm] 13.17 (1H, bs), 7.83 (1H, d, J=2.0 Hz), 7.70 (1H, dd, J=8.1 Hz, J=2.0 Hz), 7.66 (1H, d, J=2.7 Hz), 7.58 (1H, d, J=8.1 Hz), 7.44 (1H, dd, J=9.0 Hz, J=2.7 Hz), 7.04 (1H, d, J=9.0 Hz), 4.83 (2H, s), 3.45 (2H, t, J=5.5 Hz), 3.22 (3H, s), 3.17 (2H, t, J=5.5 Hz), 2.73 (3H, s), 2.56 (3H, s). MS (ESI$^-$): 450.1. HPLC (Condition A): Rt 4.39 min (HPLC purity 100%).

EXAMPLE 110

{4-chloro-2-[(5-{[isobutyl(methyl)amino]sulfonyl}-2-methylphenyl)ethynyl]phenoxy}acetic acid

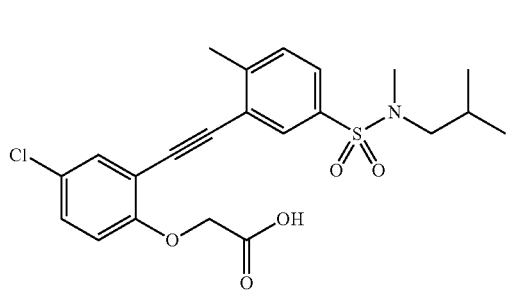

Following the general method as outlined in Example 15, starting from tert-butyl{4-chloro-2-[(5-{[isobutyl(methyl)amino]sulfonyl}-2-methylphenyl)ethynyl]phenoxy}acetate (Intermediate 160), the title compound was obtained as a beige solid in 77% yield after trituration in pentane/diethyl ether.

$^1$H NMR (300 MHz, DMSO-$d_6$) δ [ppm] 13.14 (1H, bs), 7.81 (1H, d, J=2.0 Hz), 7.69 (1H, dd, J=8.0 Hz, J=2.0 Hz), 7.66 (1H, d, J=2.7 Hz), 7.58 (1H, d, J=8.0 Hz), 7.44 (1H, dd, J=9.0 Hz, J=2.7 Hz), 7.04 (1H, d, J=9.0 Hz), 4.83 (2H, s), 2.71 (2H, d, J=7.4 Hz), 2.66 (3H, s), 2.56 (3H, s), 1.83 (1H, m), 0.87 (6H, d, J=6.7 Hz). MS (ESI$^-$): 448.1. HPLC (Condition A): Rt 5.03 min (HPLC purity 92.2%).

EXAMPLE 111

{2-[(5-{[butyl(methyl)amino]sulfonyl}-2-methylphenyl)ethynyl]-4-chlorophenoxy}acetic acid

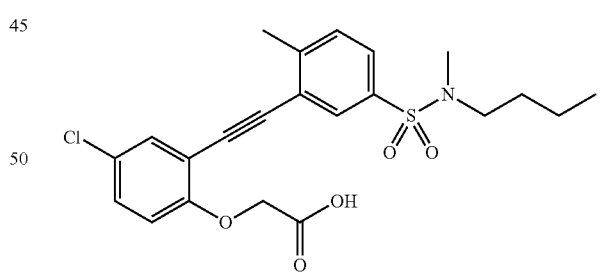

Following the general method as outlined in Example 15, starting from tert-butyl{2-[(5-{[butyl(methyl)amino]sulfonyl}-2-methylphenyl)ethynyl]-4-chlorophenoxy}acetate (Intermediate 161), the title compound was obtained as a beige solid in 96% yield after trituration in diethyl ether/pentane.

$^1$H NMR (300 MHz, DMSO-$d_6$) δ [ppm] 13.15 (1H, bs), 7.81 (1H, d, J=2.0 Hz), 7.68 (1H, dd, J=8.0 Hz, J=2.0 Hz), 7.66 (1H, d, J=2.7 Hz), 7.58 (1H, d, J=8.0 Hz), 7.44 (1H, dd, J=9.0 Hz, J=2.7 Hz), 7.04 (1H, d, J=9.0 Hz), 4.83 (2H, s), 2.95 (2H, t, J=7.0 Hz), 2.66 (3H, s), 2.56 (3H, s), 1.45 (2H, m), 1.27

(2H, m), 0.88 (3H, d, J=7.3 Hz). MS (ESI⁻): 448.1. HPLC (Condition A): Rt 5.06 min (HPLC purity 94.6%).

EXAMPLE 112

[4-chloro-2-({2-methyl-5-[(4-methylpiperazin-1-yl)sulfonyl]phenyl}ethynyl)phenoxy]acetic acid

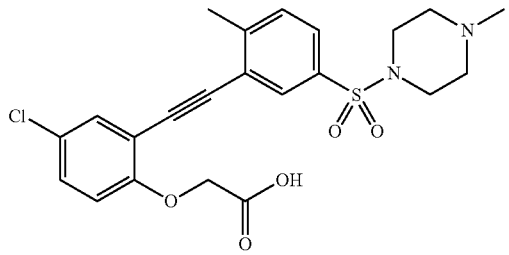

Following the general method as outlined in Example 15, starting from tert-butyl[4-chloro-2-({2-methyl-5-[(4-methylpiperazin-1-yl)sulfonyl]phenyl}ethynyl)phenoxy]acetate (Intermediate 162), the title compound was obtained as a white solid after filtration from the reaction mixture.

¹H NMR (300 MHz, DMSO-d₆) δ [ppm] 7.84 (1H, d, J=1.7 Hz), 7.65-7.73 (3H, m), 7.45 (1H, dd, J=9.0 Hz, J=2.7 Hz), 7.05 (1H, d, J=9.0 Hz), 4.84 (2H, s), 3.79 (2H, bs), 3.36 (4H, bs), 3.19 (2H, bs), 2.74 (3H, s), 2.60 (3H, s). MS (ESI⁻): 461.0. HPLC (Condition A): Rt 3.31 min (HPLC purity 99.7%).

EXAMPLE 113

{4-chloro-2-[(5-{[(2,2-dimethylpropyl)amino]sulfonyl}-2-methylphenyl)ethynyl]phenoxy}acetic acid

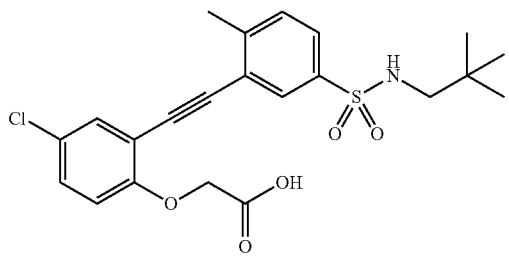

Following the general method as outlined in Example 15, starting from tert-butyl{4-chloro-2-[(5-{[(2,2-dimethylpropyl)amino]sulfonyl}-2-methylphenyl)ethynyl]phenoxy}acetate (Intermediate 163), the title compound was obtained as a white solid after purification by preparative HPLC.

¹H NMR (300 MHz, DMSO-d₆) δ [ppm] 13.14 (1H, bs), 7.88 (1H, d, J=1.9 Hz), 7.70 (1H, dd, J=8.0 Hz, J=1.9 Hz), 7.63 (1H, d, J=2.7 Hz), 7.53-7.61 (2H, m), 7.44 (1H, dd, J=9.0 Hz, J=2.7 Hz), 7.03 (1H, d, J=9.0 Hz), 4.83 (2H, s), 2.54 (3H, s), 0.83 (9H, s)+2H under the signal of DMSO. MS (ESI⁻): 448.0. HPLC (Condition A): Rt 5.14 min (HPLC purity 98.6%).

EXAMPLE 114

[2-({5-[(sec-butylamino)sulfonyl]-2-methylphenyl}ethynyl)-4-chlorophenoxy]acetic acid

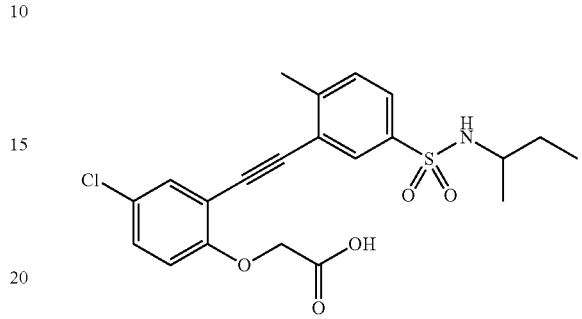

Following the general method as outlined in Example 15, starting from tert-butyl[2-({5-[(sec-butylamino)sulfonyl]-2-methylphenyl}ethynyl)-4-chlorophenoxy]acetate (Intermediate 164), the title compound was obtained as a white solid after purification by preparative HPLC.

¹H NMR (300 MHz, DMSO-d₆) δ [ppm] 13.18 (1H, bs), 7.87 (1H, d, J=2.0 Hz), 7.71 (1H, dd, J=8.0 Hz, J=2.0 Hz), 7.65 (1H, d, J=2.7 Hz), 7.53-7.58 (2H, m), 7.44 (1H, dd, J=9.0 Hz, J=2.7 Hz), 7.04 (1H, d, J=9.0 Hz), 4.84 (2H, s), 3.07 (1H, m), 2.55 (3H, s), 1.31 (2H, quint., J=7.2 Hz), 0.88 (3H, d, J=6.7 Hz), 0.72 (3H, t, J=7.2 Hz). MS (ESI⁻): 434.2. HPLC (Condition A): Rt 4.82 min (HPLC purity 99.3%).

EXAMPLE 115

{4-chloro-2-[(2-methyl-5-{[methyl(propyl)amino]sulfonyl}phenyl)ethynyl]phenoxy}acetic acid

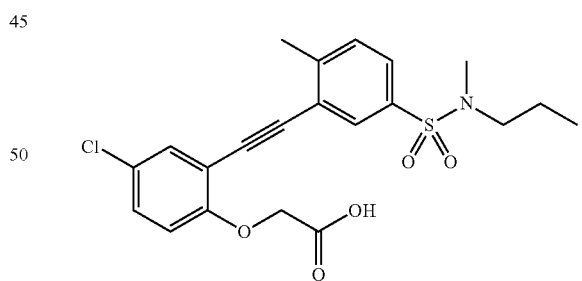

Following the general method as outlined in Example 15, starting from tert-butyl{4-chloro-2-[(2-methyl-5-{[methyl(propyl)amino]sulfonyl}phenyl)ethynyl]phenoxy}acetate (Intermediate 165), the title compound was obtained in 80% yield as a beige solid.

¹H NMR (300 MHz, DMSO-d₆) δ [ppm] 13.14 (1H, bs), 7.81 (1H, d, J=2.0 Hz), 7.69 (1H, d, J0 8.0 Hz, J=2.0 Hz), 7.67 (1H, d, J=2.7 Hz), 7.59 (1H, d, J=8.0 Hz), 7.44 (1H, dd, J=9.0 Hz, J=2.7 Hz), 7.04 (1H, d, J=9.0 Hz), 4.84 (2H, s), 2.92 (2H, m), 2.67 (3H, s), 2.57 (3H, s), 1.49 (2H, sext., J=7.3 Hz), 0.85

(3H, t, J=7.3 Hz). MS (ESI−): 434.2. HPLC (Condition A): Rt 4.82 min (HPLC purity 97.6%).

EXAMPLE 116

[4-chloro-2-({5-[(dipropylamino)sulfonyl]-2-methylphenyl}ethynyl)phenoxy]acetic acid

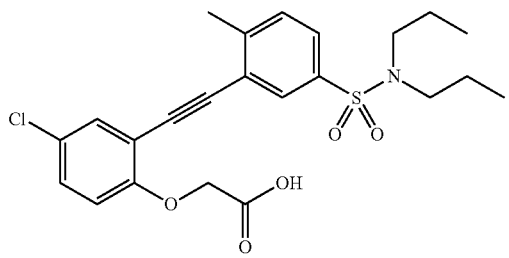

Following the general method as outlined in Example 15, starting from tert-butyl[4-chloro-2-({5-[(dipropylamino)sulfonyl]-2-methylphenyl]ethynyl)phenoxy}acetate (Intermediate 166), the title compound was obtained as a grey solid after purification by preparative HPLC.

$^1$H NMR (300 MHz, DMSO-d$_6$) δ [ppm] 13.17 (1H, bs), 7.83 (1H, d, J=2.0 Hz), 7.71 (1H, d, J=8.1 Hz, J=2.0 Hz), 7.66 (1H, d, J=2.7 Hz), 7.56 (1H, d, J=8.1 Hz), 7.44 (1H, dd, J=9.0 Hz, J=2.7 Hz), 7.04 (1H, d, J=9.0 Hz), 4.83 (2H, s), 3.04 (4H, m), 2.55 (3H, s), 1.47 (4H, sext., J=7. Hz), 0.82 (6H, t, J=7.3 Hz). MS (ESI−): 462.1. HPLC (Condition A): Rt 5.22 min (HPLC purity 100%).

EXAMPLE 117

{4-chloro-2-[(5-{[(2-methoxyethyl)amino]sulfonyl}-2-methylphenyl)ethynyl]phenoxy}acetic acid

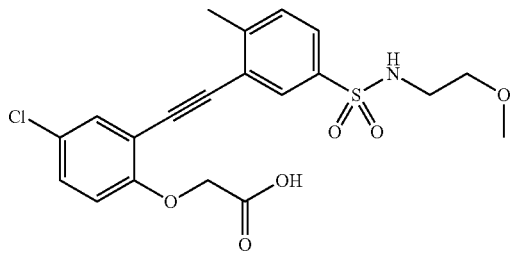

Following the general method as outlined in Example 15, starting from tert-butyl{4-chloro-2-[(5-{[(2-methoxyethyl)amino]sulfonyl}-2-methylphenyl)ethynyl]phenoxy}acetate (Intermediate 167), the title compound was obtained as a white solid in 99% yield after purification by preparative HPLC.

$^1$H NMR (300 MHz, DMSO-d$_6$) δ [ppm] 13.17 (1H, bs), 7.87 (1H, d, J=2.0 Hz), 7.77 (1H, t, J=5.9 Hz), 7.70 (1H, dd, J=8.1 Hz, J=2.0 Hz), 7.63 (1H, d, J=2.7 Hz), 7.55 (1H, d, J=8.1 Hz), 7.44 (1H, d, J=9.0 Hz, J=2.7 Hz), 7.03 (1H, d, J=9.0 Hz), 4.83 (2H, s), 3.30 (2H, t, J=5.7 Hz), 3.16 (3H, s), 2.91 (2H, q, J=5.7 Hz), 2.55 (3H, s). MS (ESI−): 436.0.

EXAMPLE 118

[4-chloro-2-({2-methyl-5-[(propylamino)sulfonyl]phenyl}ethynyl)phenoxy]acetic acid

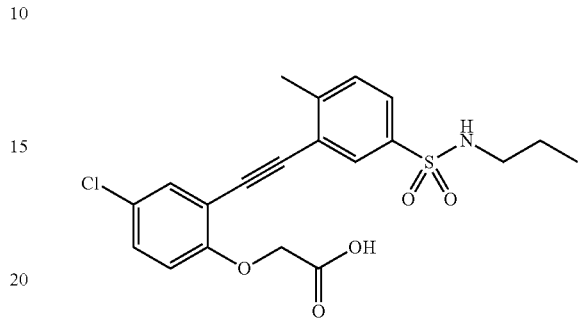

Following the general method as outlined in Example 15, starting from tert-butyl[4-chloro-2-({2-methyl-5-[(propylamino)sulfonyl]phenyl}ethynyl)phenoxy]acetate (Intermediate 168), the title compound was obtained as a white solid after purification by preparative HPLC.

$^1$H NMR (300 MHz, DMSO-d$_6$) δ [ppm] 13.17 (1H, bs), 7.85 (1H, t, J=2.0 Hz), 7.69 (1H, dd, J=8.0 Hz, J=2.0 Hz), 7.64 (1H, d, J=2.7 Hz), 7.61 (1H, t, J=5.8 Hz), 7.56 (1H, d, J=8.0 Hz), 7.44 (1H, dd, J=9.0 Hz, J=2.7 Hz), 7.04 (1H, d, J=9.0 Hz), 4.84 (2H, s), 2.69 (2H, m), 2.55 (3H, s), 1.37 (2H, sext., J=7.3 Hz), 0.79 (3H, t, J=7.3 Hz). MS (ESI−): 420.0. HPLC (Condition A): Rt 4.68 min (HPLC purity 98.8%).

EXAMPLE 119

{4-chloro-2-[(5-{[[3-(dimethylamino)propyl](methyl)amino]sulfonyl}-2-methylphenyl)ethynyl]phenoxy}acetic acid

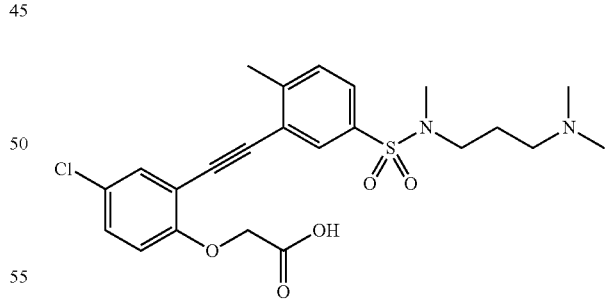

Following the general method as outlined in Example 15, starting from tert-butyl{4-chloro-2-[(5-{[[3-(dimethylamino)propyl](methyl)amino]sulfonyl}-2-methylphenyl)ethynyl]phenoxy}acetate (Intermediate 169), the title compound was obtained as a white solid in quantitative yield.

$^1$H NMR (300 MHz, DMSO-d$_6$) δ [ppm] 7.83 (1H, d, J=1.9 Hz), 7.71 (1H, dd, J=8.0 Hz, J=1.9 Hz), 7.65 (1H, d, J=2.7 Hz), 7.61 (1H, d, J=8.0 Hz), 7.45 (1H, dd, =9.0 Hz, J=2.7 Hz), 7.04 (1H, d, J=9.0 Hz), 4.83 (2H, s), 3.04 (4H, m), 2.75 (6H, s), 2.70 (3H, s), 2.57 (3H, s), 1.89 (2H, m). MS (ESI⁻): 477.2. HPLC (Condition A): Rt 3.57 min (HPLC purity 98.8%).

EXAMPLE 120

(2-{[5-(aminosulfonyl)-2-methylphenyl]ethynyl}-4-chlorophenoxy)acetic acid

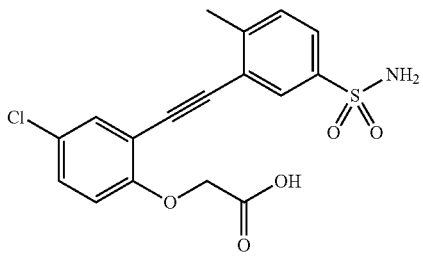

Following the general method as outlined in Example 15, starting from tert-butyl(2-{[5-(aminosulfonyl)-2-methylphenyl]ethynyl}-4-chlorophenoxy)acetate (Intermediate 170), the title compound was obtained as a white solid after purification by preparative HPLC.

¹H NMR (300 MHz, DMSO-$d_6$) δ [ppm] 13.18 (1H, bs), 7.91 (1H, s), 7.72 (1H, d, J=8.0 Hz), 7.63 (1H, d, J=2.7 Hz), 7.53 (1H, d, J=8.0 Hz), 7.44 (1H, d, J=9.0 Hz, J=2.7 Hz), 7.40 (2H, bs), 7.04 (1H, d, J=9.0 Hz), 4.83 (2H, s), 2.54 (3H, s). MS (ESI⁻): 378.0. HPLC (Condition A): Rt 3.69 min (HPLC purity 99.2%).

EXAMPLE 121

{4-chloro-2-[(5-{[cyclopentyl(methyl)amino]sulfonyl}-2-methylphenyl)ethynyl]phenoxy}acetic acid

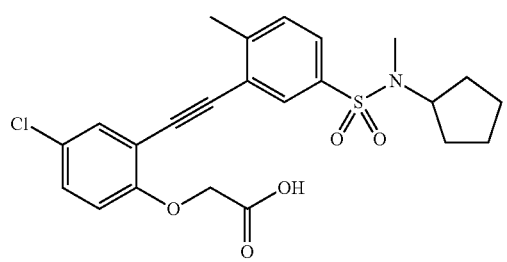

Following the general method as outlined in Example 15, starting from tert-butyl{4-chloro-2-[(5-{[cyclopentyl(methyl)amino]sulfonyl}-2-methylphenyl)ethynyl]phenoxy}acetate (Intermediate 171), the title compound was obtained as a beige solid after purification by preparative HPLC.

¹H NMR (300 MHz, DMSO-$d_6$) δ [ppm] 13.17 (1H, bs), 7.83 (1H, t, J=2.0 Hz), 7.71 (1H, dd, J=8.0 Hz, J=2.0 Hz), 7.66 (1H, d, J=2.7 Hz), 7.57 (1H, d, J=8.0 Hz), 7.44 (1H, dd, J=9.0 Hz, J=2.7 Hz), 7.04 (1H, d, J=9.0 Hz), 4.83 (2H, s), 4.25 (1H, quint., J=7.7 Hz), 2.65 (3H, s), 2.56 (3H, s), 1.30-1.53 (8H, m). MS (ESI⁻): 460.2. HPLC (Condition A): Rt 5.27 min (HPLC purity 97.9%).

EXAMPLE 122

{4-chloro-2-[(5-{[[2-(dimethylamino)ethyl](methyl)amino]sulfonyl}-2-methylphenyl)ethynyl]phenoxy}acetic acid

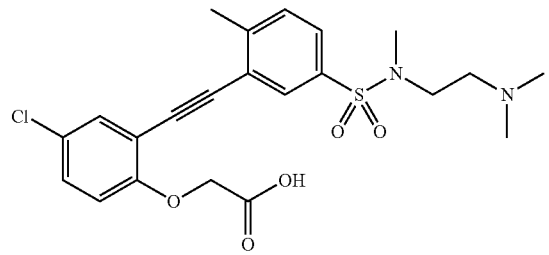

Following the general method as outlined in Example 15, starting tert-butyl{4-chloro-2-[(5-{[[2-(dimethylamino)ethyl](methyl)amino]sulfonyl}-2-methylphenyl)ethynyl]phenoxy}acetate (Intermediate 172), the title compound was obtained as a beige solid after purification by preparative HPLC.

¹H NMR (300 MHz, DMSO-$d_6$) δ [ppm] 7.95 (1H, t, J=2.0 Hz), 7.69 (1H, dd, J=8.0 Hz, J=2.0 Hz), 7.58-7.61 (2H, m), 7.42 (1H, dd, J=9.0 Hz, J=2.7 Hz), 7.05 (1H, d, J=9.0 Hz), 4.54 (2H, s), 3.23 (2H, m), 2.83 (2H, m), 2.69 (3H, s), 2.56 (3H, s), 2.43 (6H, s). MS (ESI⁻): 463.0. HPLC (Condition A): Rt 3.47 min (HPLC purity 99.1%).

EXAMPLE 123

(2-{[5-(azetidin-1-ylsulfonyl)-2-methylphenyl]ethynyl}-4-chlorophenoxy)acetic acid

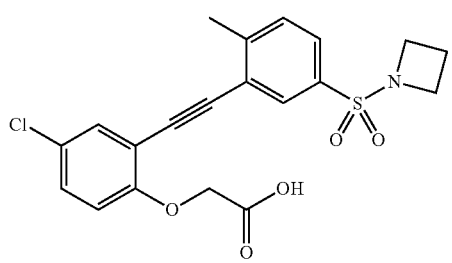

Following the general method as outlined in Example 15, starting from tert-butyl(2-{[5-(azetidin-1-ylsulfonyl)-2-methylphenyl]ethynyl}-4-chlorophenoxy)acetate (Intermediate 173), the title compound was obtained in 70% yield as a pink solid after purification by preparative HPLC.

¹H NMR (300 MHz, DMSO-$d_6$) δ [ppm] 13.15 (1H, bs), 7.84 (1H, d, J=2.0 Hz), 7.73 (1H, dd, J=8.0 Hz, J=2.0 Hz), 7.65-7.68 (2H, m), 7.44 (1H, dd, J=9.0 Hz, J=2.7 Hz), 7.05 (1H, d, J=9.0 Hz), 4.84 (2H, s), 3.69 (4H, t, J=7.7 Hz), 2.60

(3H, s), 2.01 (2H, quint., J=7.7 Hz). MS (ESI⁻): 418.0. HPLC (Condition A): Rt 4.54 min (HPLC purity 98.8%).

EXAMPLE 124

(4-chloro-2-{[4-(morpholin-4-ylcarbonyl)phenyl]ethynyl}phenoxy)acetic acid

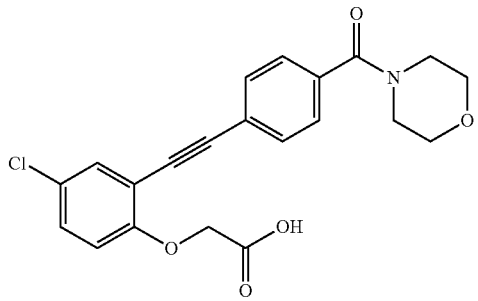

Following the general method as outlined in Example 15, starting from tert-butyl(4-chloro-2-{[4-(morpholin-4-ylcarbonyl)phenyl]ethynyl}phenoxy)acetate (Intermediate 175), the title compound was obtained as a beige solid after purification by preparative HPLC.

¹H NMR (300 MHz, DMSO-d₆) δ [ppm] 13.09 (1H, bs), 7.61 (2H, d, J=8.2 Hz), 7.58 (1H, d, J=2.7 Hz), 7.47 (2H, d, J=8.2 Hz), 7.42 (1H, dd, J=9.0 Hz, J=2.7 Hz), 6.99 (1H, d, J=9.0 Hz), 4.80 (2H, s), 3.60 (6H, bs) (2 remaining protons, probably hidden under the signal of water). MS (ESI⁻): 398.1. HPLC (Condition A): Rt 3.75 (HPLC purity 96.2%).

EXAMPLE 125

[4-chloro-2-({4-[(dimethylamino)carbonyl]phenyl}ethynyl)phenoxy]acetic acid

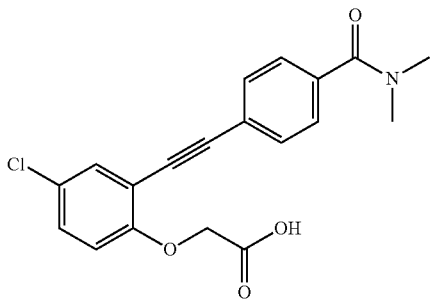

Following the general method as outlined in Example 15, starting from tert-butyl[4-chloro-2-({4-[(dimethylamino)carbonyl]phenyl}ethynyl)phenoxy]acetate (Intermediate 177), the title compound was obtained in 84% yield as a beige solid.

¹H NMR (300 MHz, DMSO-d₆) δ [ppm] 13.15 (1H, bs), 7.58-7.61 (3H, m), 7.40-7.47 (3H, m), 7.01 (1H, d, J=9.0 Hz), 4.84 (2H, s), 2.99 (3H, s), 2.92 (3H, s). MS (ESI⁻): 356.1. HPLC (Condition A): Rt 4.21 min (HPLC purity 95.8%).

EXAMPLE 126

(4-chloro-2-{[3-(morpholin-4-ylcarbonyl)phenyl]ethynyl}phenoxy)acetic acid

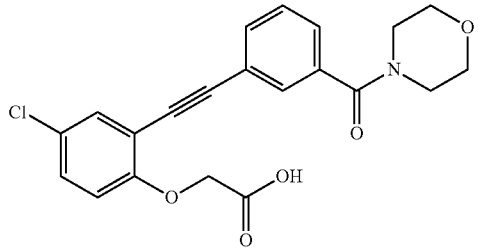

Following the general method as outlined in Example 15, starting from tert-butyl(4-chloro-2-{[3-(morpholin-4-ylcarbonyl)phenyl]ethynyl}phenoxy)acetate (Intermediate 179), the title compound was obtained as a beige solid after purification by preparative HPLC.

¹H NMR (300 MHz, DMSO-d₆) δ [ppm] 13.20 (1H, bs), 7.40-7.64 (6H, m), 7.00 (1H, d, J=9.0 Hz), 4.81 (2H, s), 3.61 (6H, bs) (2 remaining protons, probably hidden under the signal of water). MS (ESI⁻): 398.1. HPLC (Condition A): Rt 3.73 min (HPLC purity 97.3%).

EXAMPLE 127

[4-chloro-2-({3-[(dimethylamino)carbonyl]phenyl}ethynyl)phenoxy]acetic acid

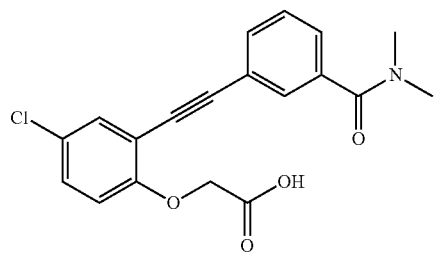

Following the general method as outlined in Example 15, starting from tert-butyl[4-chloro-2-({3-[(dimethylamino)carbonyl]phenyl}ethynyl)phenoxy]acetate (Intermediate 181), the title compound was obtained as a white solid after purification preparative HPLC.

¹H NMR (300 MHz, DMSO-d₆) δ [ppm] 13.17 (1H, bs), 7.39-7.62 (6H, m), 6.99 (1H, d, J=9.0 Hz), 4.82 (2H, s), 2.99 (3H, s), 2.92 (3H, s). MS (ESI⁻): 356.0. HPLC (Condition A): Rt 3.78 min (HPLC purity 100%).

EXAMPLE 128

[(5-chloro-3-{[3-(propylsulfonyl)phenyl]ethynyl}pyridin-2-yl)oxy]acetic acid

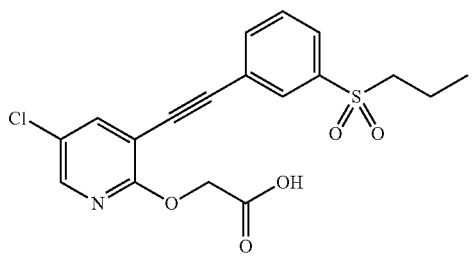

Following the general method as outlined in Example 15, starting from tert-butyl[(5-chloro-3-{[3-(propylsulfonyl)phenyl]ethynyl}pyridin-2-yl)oxy]acetate (Intermediate 183), the title compound was obtained as a beige solid.

$^1$H NMR (300 MHz, DMSO-$d_6$) δ [ppm] 13.02 (1H, bs), 8.27 (1H, d, J=2.6 Hz), 8.22 (1H, d, J=2.6 Hz), 8.04 (1H, t, J=1.5 Hz), 7.90-7.98 (2H, m), 7.75 (1H, t, J=7.8 Hz), 4.93 (2H, s), 3.38 (2H, m), 1.57 (2H, sext., J=7.5 Hz), 0.93 (3H, t, J=7.5 Hz). MS (ESI$^-$): 392.0. HPLC (Condition A): Rt 4.07 min (HPLC purity 91.7%).

EXAMPLE 129

[(5-chloro-3-{[2-fluoro-5-(propylsulfonyl)phenyl]ethynyl}pyridin-2-yl)oxy]acetic acid

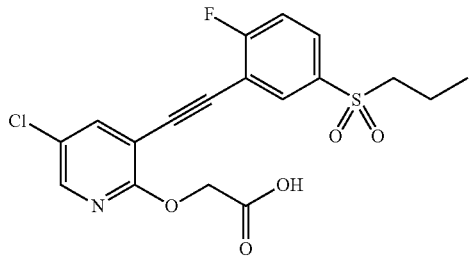

Following the general method as outlined in Example 15, starting from tert-butyl[(5-chloro-3-{[2-fluoro-5-(propylsulfonyl)phenyl]ethynyl}pyridin-2-yl)oxy]acetate (Intermediate 184), the title compound was obtained in 80% yield as a beige solid.

$^1$H NMR (300 MHz, DMSO-$d_6$) δ [ppm] 13.04 (1H, bs), 8.30 (1H, d, J=2.5 Hz), 8.24 (1H, d, J=2.5 Hz), 8.15 (1H, dd, J=6.6 Hz, J=2.0 Hz), 8.02 (1H, m), 7.68 (1H, t, J=9.0 Hz), 4.94 (2H, s), 3.39 (2H, m), 1.57 (2H, sext., J=7.5 Hz), 0.93 (3H, t, J=7.5 Hz). MS (ESI$^-$): 410.1. HPLC (Condition A): Rt 4.20 min (HPLC purity 97.9%).

EXAMPLE 130

[4-chloro-2-({2-chloro-5-[(trifluoromethyl)sulfonyl]phenyl}ethynyl)phenoxy]acetic acid

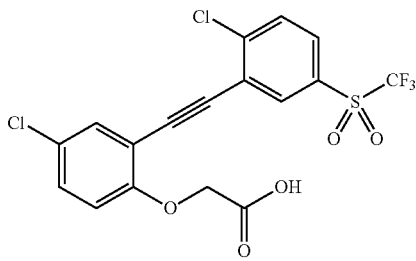

Following the general method as outlined in Example 15, starting from tert-butyl[4-chloro-2-({2-chloro-5-[(trifluoromethyl)sulfonyl]phenyl}ethynyl)phenoxy]acetate (Intermediate 187), the title compound was obtained as a white solid in 75% yield after purification by preparative HPLC.

$^1$H NMR (300 MHz, DMSO-$d_6$) δ [ppm] 13.19 (1H, bs), 8.36 (1H, d, J=2.2 Hz), 8.15 (1H, dd, J=8.6 Hz, J=2.2 Hz), 8.08 (1H, d, J=8.6 Hz), 7.70 (1H, d, J=2.7 Hz), 7.50 (1H, d, J=9.0 Hz, J=2.7 Hz), 7.06 (1H, d, J=9.0 Hz), 4.85 (2H, s). MS (ESI$^-$): 450.8. HPLC (Condition A): Rt 5.01 min (HPLC purity 100%).

EXAMPLE 131

[(3-{[3-(Propylsulfonyl)phenyl]ethynyl}biphenyl-4-yl)oxy]acetic acid

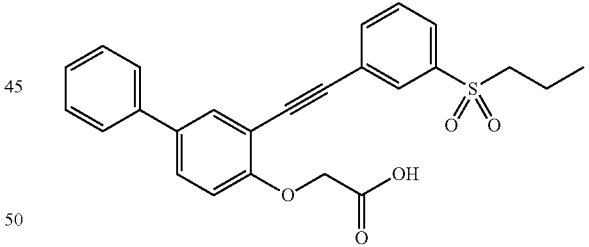

Following the general method as outlined in Example 37, starting from tert-butyl[(3-bromobiphenyl-4-yl)oxy]acetate (Intermediate 188) and 1-ethynyl-3-(propane-1-sulfonyl)-benzene (Intermediate 42), the title compound was obtained as a beige solid after purification by preparative HPLC.

$^1$H NMR (300 MHz, DMSO-$d_6$) δ [ppm] 13.20 (1H, bs), 8.02 (1H, t, J=1.6 Hz), 7.92 (1H, m), 7.90 (1H, d, J=1.6 Hz), 7.86 (1H, d, J=2.3 Hz), 7.66-7.75 (4H, m), 7.43-7.48 (2H, m), 7.35 (1H, dt, J=7.3 Hz, J=2.3 Hz), 7.06 (1H, d, J=8.8 Hz), 4.86 (2H, s), 3.36-3.40 (2H, m), 1.57 (2H, sext., J=7.6 Hz), 0.93 (3H, t, J=7.6 Hz). MS (ESI$^-$): 433.1. HPLC (Condition A): Rt 5.20 min (HPLC purity 91.8%).

EXAMPLE 132

(4-(2,4-dimethyl-1,3-thiazol-5-yl)-2-{[3-(propylsulfonyl)phenyl]ethynyl}phenoxy)acetic acid

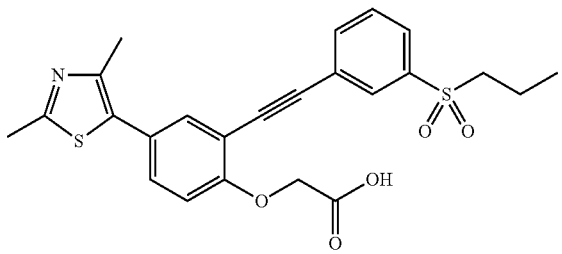

Following the general method as outlined in Example 15, starting from tert-butyl(4-(2,4-dimethyl-1,3-thiazol-5-yl)-2-{[3-(propylsulfonyl)phenyl]ethynyl}phenoxy)acetate (Intermediate 192), the title compound was obtained as a white solid yield after purification by preparative HPLC.

$^1$H NMR (300 MHz, DMSO-$d_6$) δ [ppm] 13.34 (1H, bs), 8.01 (1H, t, J=1.5 Hz), 7.89-7.93 (2H, m), 7.72 (1H, t, J=7.8 Hz), 7.60 (1H, d, J=2.3 Hz), 7.45 (1H, dd, J=8.8 Hz, J=2.3 Hz), 7.06 (1H, d, J=8.8 Hz), 4.86 (2H, s), 3.37 (2H, m), 2.62 (3H, s), 2.36 (3H, s), 1.57 (2H, sext., J=7.6 Hz), 0.93 (3H, t, J=7.6 Hz). MS (ESI$^-$): 468.0. HPLC (Condition A): Rt 3.43 min (HPLC purity 100%).

EXAMPLE 133

[2-{[3-(propylsulfonyl)phenyl]ethynyl}-4-(3-thienyl)phenoxy]acetic acid

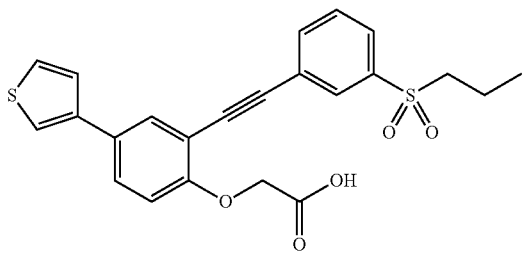

A mixture of tert-butyl (4-bromo-2-{[3-(propylsulfonyl)phenyl]ethynyl}phenoxy)acetate (Intermediate 191, 200 mg; 0.41 mmol), 3-thienylboronic acid (78 mg; 0.61 mmol), caesium fluoride (185 mg; 1.22 mmol) and bis(triphenylphosphine)palladium(II) chloride (28 mg; 0.04 mmol) was placed in a microwave tube. The tube was sealed and degased with nitrogen before adding dioxane (4 ml) and water (2 ml). The reaction mixture was heated at 150° C. for 15 minutes in a microwave reaction system. The reaction mixture was taken up in EtOAc and washed with water and brine. The organic phase was dried over MgSO$_4$, filtered and concentrated. The residue was dissolved in DCM (1.00 ml), treated with a 4 N solution of HCl in dioxane (2.0 ml) and stirred for 1 day. The solvents were removed under reduced pressure and the residue purified by preparative HPLC to give the title compound as a white solid.

$^1$H NMR (300 MHz, DMSO-$d_6$) δ [ppm] 13.17 (1H, bs), 8.01 (1H, t, J=1.5 Hz), 7.86-7.93 (4H, m), 7.70-7.77 (2H, m), 7.64 (1H, dd, J=5.0 Hz, J=2.9 Hz), 7.58 (1H, dd, J=5.0 Hz, J=1.0 Hz), 7.02 (1H, d, J=8.6 Hz), 4.85 (2H, s), 3.37 (2H, m), 1.57 (2H, sext., J=7.5 Hz), 0.93 (3H, t, J=7.5 Hz). MS (ESI$^-$): 439.0. HPLC (Condition A): Rt 4.66 min (HPLC purity 97.3%).

EXAMPLE 134

[2-{[3-(propylsulfonyl)phenyl]ethynyl}-4-(2-thienyl)phenoxy]acetic acid

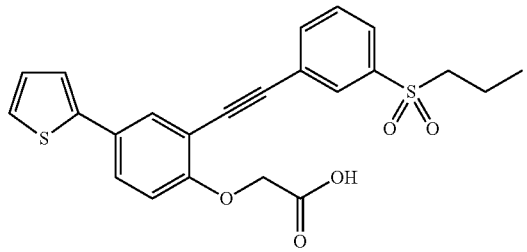

Following the general method as outlined in Example 15, starting from tert-butyl[2-{[3-(propylsulfonyl)phenyl]ethynyl}-4-(2-thienyl)phenoxy]acetate (Intermediate 193), the title compound was obtained as a white solid after purification by preparative HPLC.

$^1$H NMR (300 MHz, DMSO-$d_6$) δ [ppm] 13.19 (1H, bs), 8.03 (1H, t, J=1.5 Hz), 7.92 (2H, dd, J=7.8 Hz, J=1.5 Hz), 7.84 (1H, d, J=8.7 Hz, J=2.4 Hz), 7.73 (1H, t, J=7.8 Hz), 7.67 (1H, dd, J=2.4 Hz), 7.52 (1H, dd, J=5.1 Hz, J=1.1 Hz), 7.50 (1H, dd, J=3.6 Hz, J0 1.1 Hz), 7.13 (1H, dd, J=5.1 Hz, J=3.6 Hz), 7.04 (1H, d, J=8.7 Hz), 4.87 (2H, s), 3.37 (2H, m), 1.57 (2H, sext., J=7.5 Hz), 0.93 (3H, t, J=7.5 Hz). MS (ESI$^-$): 439.0. HPLC (Condition A): Rt 4.66 min (HPLC purity 99.7%).

EXAMPLE 135

(4-(1-methyl-1H-pyrazol-4-yl)-2-{[3-(propylsulfonyl)phenyl]ethynyl}phenoxy)acetic acid

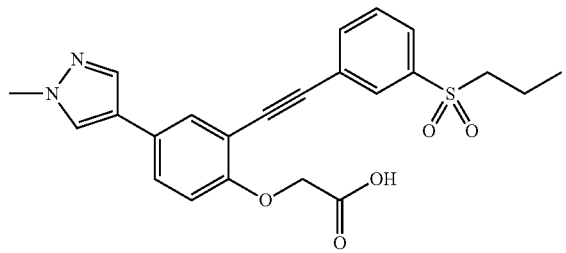

Following the general method as outlined in Example 15, starting from tert-butyl(4-(1-methyl-1H-pyrazol-4-yl)-2-{[3-(propylsulfonyl)phenyl]ethynyl}phenoxy)acetate (Intermediate 194), the title compound was obtained as a white solid in 81% yield.

$^1$H NMR (300 MHz, DMSO-$d_6$) δ [ppm] 8.13 (1H, bs), 7.99 (1H, t, J=1.5 Hz), 7.87-7.93 (2H, m), 7.86 (1H, s), 7.76 (1H, d, J=2.3 Hz), 7.73 (1H, t, J=7.8 Hz), 7.57 (1H, dd, J=8.7 Hz, J=2.3 Hz), 6.97 (1H, d, J=8.7 Hz), 4.83 (2H, s), 3.85 (3H, s), 3.37 (2H, m), 1.57 (2H, sext., J=7.5 Hz), 0.93 (3H, t, J=7.5 Hz). MS (ESI⁻): 437.1. HPLC (Condition A): Rt 3.71 min (HPLC purity 99.3%).

EXAMPLE 136

[2-{[3-(Propylsulfonyl)phenyl]ethynyl}-4-(1,3,5-trimethyl-1H-pyrazol-4-yl)phenoxy]acetic acid

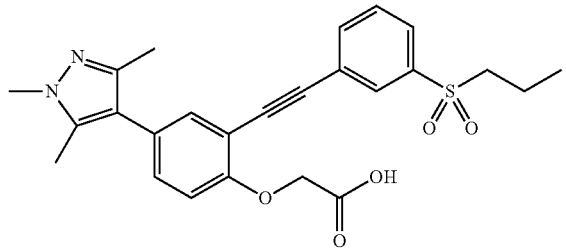

Following the general method as outlined in Example 15, starting from tert-butyl[2-{[3-(propylsulfonyl)phenyl]ethynyl}-4-(1,3,5-trimethyl-1H-pyrazol-4-yl)phenoxy]acetate (Intermediate 195), the title compound was obtained as a white solid in 79% yield.

¹H NMR (300 MHz, DMSO-d₆) δ [ppm] 7.99 (1H, t, J=7.7 Hz), 7.88-7.92 (2H, m), 7.72 (1H, t, J=7.7 Hz), 7.39 (1H, d, J=2.2 Hz), 7.26 (1H, dd, J=8.7 Hz, J=2.2 Hz), 7.01 (1H, d, J=8.7 Hz), 4.86 (2H, s), 3.71 (3H, s), 3.36 (2H, m), 2.21 (3H, s), 2.12 (3H, s), 1.57 (2H, sext., J=7.5 Hz), 0.93 (3H, t, J=7.5 Hz). MS (ESI⁻): 465.1. HPLC (Condition A): Rt 3.32 min (HPLC purity 95.2%).

EXAMPLE 137

[4-chloro-2-({2-methyl-5-[(methylsulfonyl)amino]phenyl}ethynyl)phenoxy]acetic acid

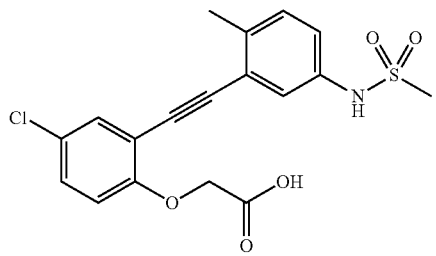

Following the general method as outlined in Example 15, starting from tert-butyl[4-chloro-2-({2-methyl-5-[(methylsulfonyl)amino]phenyl}ethynyl)phenoxy]acetate (Intermediate 196), the title compound was obtained as a pink solid after purification by preparative HPLC.

¹H NMR (300 MHz, DMSO-d₆) δ [ppm] 13.18 (1H, bs), 9.73 (1H, s), 7.58 (1H, d, J=2.7 Hz), 7.40 (1H, dd, J=9.0 Hz, J=2.7 Hz), 7.28-7.30 (2H, m), 7.16 (1H, dd, J=8.2, J=2.3 Hz), 7.00 (1H, d, J=9.0 Hz), 4.81 (2H, s), 2.98 (3H, s), 2.42 (3H, s).

MS (ESI⁻): 392.0. HPLC (Condition A): Rt 4.17 min (HPLC purity 99.9%).

EXAMPLE 138

[4-chloro-2-({2-methyl-5-[methyl(methylsulfonyl)amino]phenyl}ethynyl)phenoxy]acetic acid

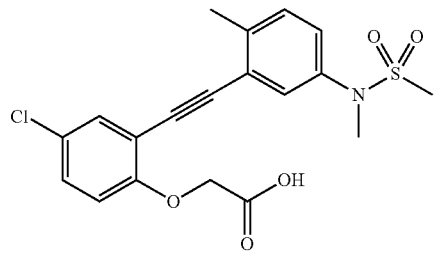

Following the general method as outlined in Example 15, starting from tert-butyl[4-chloro-2-({2-methyl-5-[methyl(methylsulfonyl)amino]phenyl}ethynyl)phenoxy]acetate (Intermediate 196), the title compound was obtained as a white solid after purification by preparative HPLC.

¹H NMR (300 MHz, DMSO-d₆) δ [ppm] 13.17 (1H, bs), 7.58 (1H, d, J=2.7 Hz), 7.52 (1H, m), 7.42 (1H, dd, J=9.0 Hz, J=2.7 Hz), 7.36 (2H, m), 7.02 (1H, d, J=9.0 Hz), 4.82 (2H, s), 3.24 (3H, s), 2.95 (3H, s), 2.46 (3H, s). MS (ESI⁻): 406.0. HPLC (Condition A): Rt 4.23 min (HPLC purity 99.8%).

EXAMPLE 139

[4-chloro-2-({5-[(dimethylamino)sulfonyl]-2-methylpyridin-3-yl}ethynyl)phenoxy]acetic acid

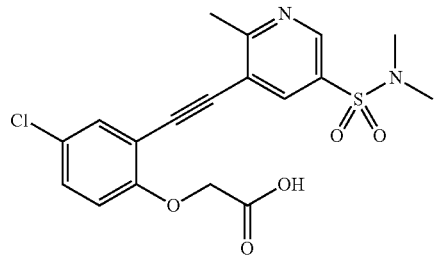

Following the general method as outlined in Example 15, starting from tert-butyl[4-chloro-2-({5-[(dimethylamino)sulfonyl]-2-methylpyridin-3-yl}ethynyl)phenoxy]acetate (Intermediate 200) at a temperature of 80° C., the title compound was obtained as a white solid after filtration from the reaction mixture.

¹H NMR (300 MHz, DMSO-d₆) δ [ppm] 13.4 (1H, bs), 8.77 (1H, d, J=2.2 Hz), 8.18 (1H, d, J=2.2 Hz), 7.70 (1H, d, J=2.7 Hz), 7.48 (1H, dd, J=9.0 Hz, J=2.7 Hz), 7.08 (1H, d, J=9.0 Hz), 4.85 (2H, s), 2.79 (3H, s), 2.69 (6H, s). MS (ESI⁻): 407.1. HPLC (Condition A): Rt 3.93 min (HPLC purity 99.1%).

EXAMPLE 140

(4-chloro-2-{[2-(methylsulfonyl)biphenyl-4-yl]ethynyl}phenoxy)acetic acid

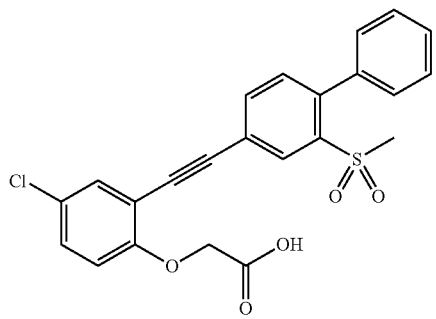

Following the general method as outlined in Example 15, starting from tert-butyl(4-chloro-2-{[2-(methylsulfonyl)biphenyl-4-yl]ethynyl}phenoxy)acetate (Intermediate 204), the title compound was obtained as a white solid after purification by preparative HPLC.

$^1$H NMR (300 MHz, DMSO-$d_6$) δ [ppm] 13.23 (1H, bs), 8.18 (1H, d, J=1.8 Hz), 7.89 (1H, dd, J=7.9 Hz, J=1.8 Hz), 7.68 (1H, d, J=2.7 Hz), 7.43 (7H, m), 7.02 (1H, d, J=9.0 Hz), 4.84 (2H, s), 2.88 (3H, s). MS (ESI$^-$): 439.2. HPLC (Condition A): Rt 4.78 min (HPLC purity 98.8%).

EXAMPLE 141

(4-chloro-2-{[4'-methoxy-2-(methylsulfonyl)biphenyl-4-yl]ethynyl}phenoxy)acetic acid

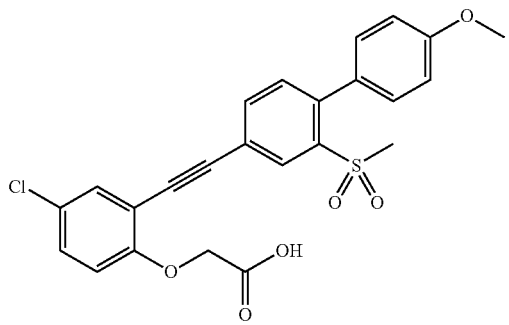

Following the general method as outlined in Example 15, starting from tert-butyl(4-chloro-2-{[4'-methoxy-2-(methylsulfonyl)biphenyl-4-yl]ethynyl}phenoxy)acetate (Intermediate 206), the title compound was obtained as a beige solid after purification by preparative HPLC.

$^1$H NMR (300 MHz, DMSO-$d_6$) δ [ppm] 13.21 (1H, bs), 8.17 (1H, d, J=1.8 Hz), 7.87 (1H, dd, J=8.0 Hz, J=1.8 Hz), 7.67 (1H, d, J=2.7 Hz), 7.43-7.47 (2H, m), 7.38 (2H, d, J=8.7 Hz), 7.00-7.05 (3H, m), 4.85 (2H, s), 3.82 (3H, s), 2.85 (3H, s). MS (ESI$^-$): 469.1. HPLC (Condition A): Rt 4.76 min (HPLC purity 95.7%).

EXAMPLE 142

(4-chloro-2-{[3-methoxy-2-(methylsulfonyl)biphenyl-4-yl]ethynyl}phenoxy)acetic acid

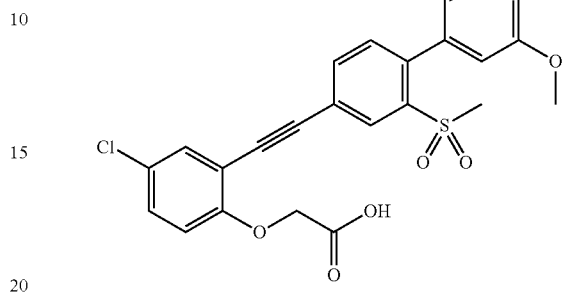

Following the general method as outlined in Example 15, starting from tert-butyl(4-chloro-2-{[3'-methoxy-2-(methylsulfonyl)biphenyl-4-yl]ethynyl}phenoxy)acetate (Intermediate 208), the title compound was obtained as a white solid after purification by preparative HPLC.

$^1$H NMR (300 MHz, DMSO-$d_6$) δ [ppm] 8.17 (1H, d, J=1.8 Hz), 7.89 (1H, dd, J=8.0 Hz, J=1.8 Hz), 7.66 (1H, d, J=2.7 Hz), 7.48 (1H, d, J=8.0 Hz), 7.36-7.45 (2H, m), 6.96-7.06 (4H, m), 4.74 (2H, s), 3.79 (3H, s), 2.90 (3H, s). MS (ESI$^-$): 469.2. HPLC (Condition A): Rt 4.78 min (HPLC purity 99.0%).

EXAMPLE 143

(4-chloro-2-{[2-(methylsulfonyl)-4'-(trifluoromethyl)biphenyl-4-yl]ethynyl}phenoxy)acetic acid

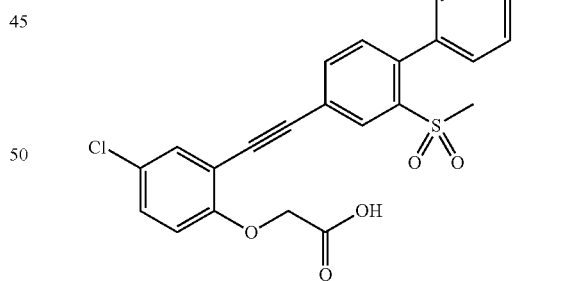

Following the general method as outlined in Example 15, starting from tert-butyl(4-chloro-2-{[2-(methylsulfonyl)-4'-(trifluoromethyl)biphenyl-4-yl]ethynyl}phenoxy)acetate (Intermediate 210), the title compound was obtained as a beige solid in 70% yield after purification by preparative HPLC.

$^1$H NMR (300 MHz, DMSO-$d_6$) δ [ppm] 13.21 (1H, bs), 8.21 (1H, d, J=1.7 Hz), 7.93 (1H, dd, J=7.9 Hz, J=1.7 Hz), 7.83 (2H, d, J=8.1 Hz), 7.65-7.68 (3H, m), 7.51 (1H, d, J=7.9 Hz), 7.46 (1H, dd, J=9.0 Hz, J=2.7 Hz), 7.02 (1H, d, J=9.0

Hz), 4.85 (2H, s), 3.03 (3H, s). MS (ESI⁻): 507.2. HPLC (Condition A): Rt 5.23 min (HPLC purity 98.2%).

EXAMPLE 144

(4-chloro-2-{[4'-chloro-2-(methylsulfonyl)biphenyl-4-yl]ethynyl}phenoxy)acetic acid

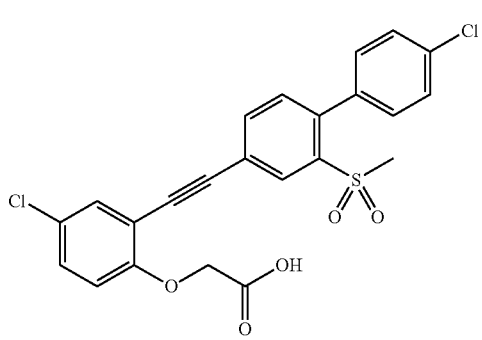

Following the general method as outlined in Example 15, starting from tert-butyl(4-chloro-2-{[4'-chloro-2-(methylsulfonyl)biphenyl-4-yl]ethynyl}phenoxy)acetate (Intermediate 212), the title compound was obtained as a beige solid in 55% yield after purification by preparative HPLC.

$^1$H NMR (300 MHz, DMSO-d$_6$) δ [ppm] 13.22 (1H, bs), 8.181 (1H, d, J=1.7 Hz), 7.90 (1H, dd, J=7.9 Hz, J=1.7 Hz), 7.67 (1H, d, J=2.7 Hz), 7.531 (2H, d, J=8.6 Hz), 7.43-7.49 (4H, m), 7.02 (1H, d, J=9.0 Hz), 4.85 (2H, s), 2.97 (3H, s). MS (ESI⁻): 473.1. HPLC (Condition A): Rt 5.07 min (HPLC purity 97.7%).

EXAMPLE 145

(4-chloro-2-{[3'-chloro-2-(methylsulfonyl)biphenyl-4-yl]ethynyl}phenoxy)acetic acid

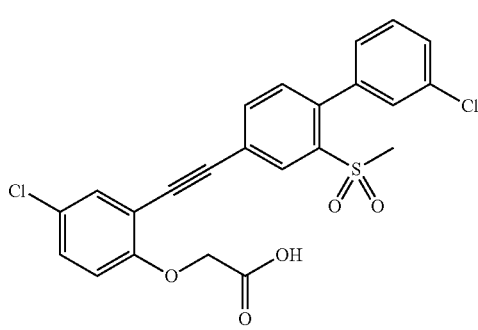

Following the general method as outlined in Example 15, starting from tert-butyl(4-chloro-2-{[3'-chloro-2-(methylsulfonyl)biphenyl-4-yl]ethynyl}phenoxy)acetate (Intermediate 214), the title compound was obtained as a beige solid after purification by preparative HPLC.

$^1$H NMR (300 MHz, DMSO-d$_6$) δ [ppm] 13.21 (1H, bs), 8.18 (1H, d, J=1.8 Hz), 7.90 (1H, dd, J=7.9 Hz, J=1.8 Hz), 7.68 (1H, d, J=2.7 Hz), 7.44-7.56 (5H, m), 7.40 (1H, dt, J=7.1 Hz, J=1.6 Hz), 7.03 (1H, d, J=9.0 Hz), 4.85 (2H, s), 2.99 (3H, s). MS (ESI⁻): 473.2. HPLC (Condition A): Rt 5.04 min (HPLC purity 100%).

EXAMPLE 146

(4-chloro-2-{[2'-chloro-2-(methylsulfonyl)biphenyl-4-yl]ethynyl}phenoxy)acetic acid

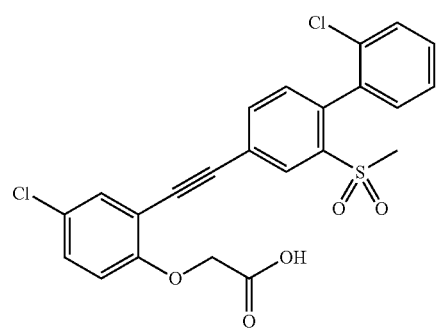

Following the general method as outlined in Example 15, starting from tert-butyl(4-chloro-2-{[2'-chloro-2-(methylsulfonyl)biphenyl-4-yl]ethynyl}phenoxy)acetate (Intermediate 216), the title compound was obtained as a white solid after purification by preparative HPLC.

$^1$H NMR (300 MHz, DMSO-d$_6$) δ [ppm] 13.22 (1H, bs), 8.20 (1H, d, J=1.6 Hz), 7.92 (1H, dd, J=7.9 Hz, J=1.6 Hz), 7.67 (1H, d, J=2.7 Hz), 7.57 (1H, m), 7.39-7.50 (5H, m), 7.03 (1H, d, J=9.0 Hz), 4.86 (2H, s), 3.04 (3H, s). MS (ESI⁻): 473.1 HPLC (Condition A): Rt 4.89 min (HPLC purity 100%).

EXAMPLE 147

({1-[(3-hydroxyphenyl)ethynyl]-2-naphthyl}oxy)acetic acid

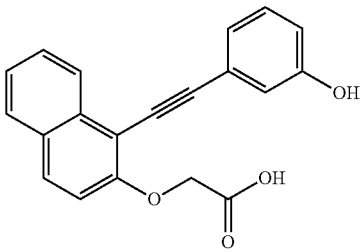

A mixture of (1-bromo-naphthalen-2-yloxy)-acetic acid tert-butyl ester (Intermediate 217, 125 mg; 0.37 mmol), 3-hydroxyphenylacetylene (53 mg; 0.44 mmol), palladium(II) chloride (3.3 mg; 0.02 mmol), triphenylphosphine (10 mg; 0.04 mmol) and piperidine (73 µl; 0.74 mmol) in distilled water (1.1 ml) and Acetone (1.4 ml) was stirred overnight at 60° C. The reaction mixture was extracted by EtOAc and the organic phases was dried over MgSO$_4$, concentrated to dryness and purified by preparative HPLC. The intermediate obtained was diluted in DCM (1 ml) and treated with a 4 M solution of HCl in dioxane (930 µl). After stirring overnight, the reaction mixture was concentrated to dryness and purified by preparative HPLC to afford the title compound as a beige solid.

¹H NMR (300 MHz, DMSO-d₆) δ [ppm] 13.04 (1H, bs), 9.23 (1H, bS), 8.02 (1H, d, J=9.2 Hz), 7.91 (1H, d, J=8.1 Hz), 7.74 (1H, d, J=8.1 Hz), 7.45-7.50 (1H, m), 7.36-7.40 (2H, m), 7.23 (1H, s), 6.81 (1H, t, J=8.1 Hz); 6.38-6.48 (2H, m), 4.86 (1H, d, J=16.8 Hz), 4.77 (1H, d, J=16.8 Hz). MS (ESI⁺): 319.0. HPLC (Condition A): Rt 4.13 min (HPLC purity 96.7%).

EXAMPLE 148

[(1-{[3-(propylsulfonyl)phenyl]ethynyl}-2-naphthyl)oxy]acetic acid

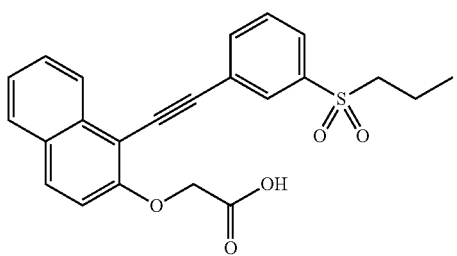

A solution of tert-butyl[(1-{[3-(propylsulfonyl)phenyl]ethynyl}-2-naphthyl)oxy]acetate (Intermediate 218, 60 mg; 0.13 mmol) in DCM (1.2 mL) was treated with trifluoroacetic acid (98 µl; 0.65 mmol). After stirring for 1 hour, the solvents were removed under vacuum to afford a residue, which was purified by preparative HPLC to give the title compound as a beige solid.

¹H NMR (300 MHz, DMSO-d₆) δ [ppm] 13.18 (1H, bs), 8.29 (1H, d, J=8.0 Hz), 8.10 (1H, t, J=1.5 Hz), 8.00-8.04 (2H, m), 7.91-7.96 (2H, m), 7.76 (1H, t, J=8.0 Hz), 7.63-7.68 (1H, m), 7.45-7.50 (1H, m), 7.39 (1H, d, J=9.2 Hz), 5.01 (2H, s), 3.40 (2H, m), 1.60 (2H, sext., J=7.6 Hz), 0.94 (3H, t, J=7.6 Hz). MS (ESI⁻): 407.1. HPLC (Condition A): Rt 4.88 min.

EXAMPLE 149

(4-chloro-2-{[2-methyl-5-(propylsulfinyl)phenyl]ethynyl}phenoxy)acetic acid

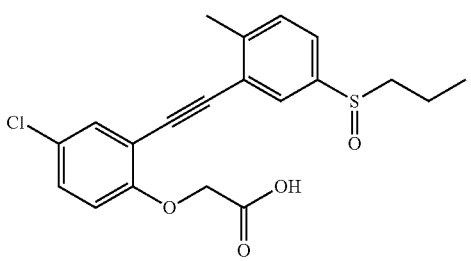

A solution of methyl (4-chloro-2-{[2-methyl-5-(propylsulfinyl)phenyl]ethynyl}phenoxy)acetate (Intermediate 221, 125 mg; 0.31 mmol) in MeOH (5 ml) was treated with a 1M solution of sodium hydroxide in water (0.93 ml; 0.93 mmol). After stirring for 3 hours, the solvent was removed under reduced pressure, the residue was taken up in AcOEt and extracted with 0.1N HCl. The organic phase was dried on MgSO₄ and concentrated to give a residue which was triturated in diethyl ether, to afford the title compound as a pale yellow solid (101 mg, 83%).

¹H NMR (300 MHz, DMSO-d₆) δ [ppm] 13.2 (1H, bs), 7.73 (1H, d, J=1.6 Hz), 7.62-7.52 (3H, m), 7.43 (1H, dd, J=9.0 Hz, J=2.7 Hz), 7.03 (1H, d, J=9.0 Hz), 4.83 (2H, s), 2.96 (1H, m), 2.77 (1H, m), 2.54 (3H, s), 1.65 (1H, m), 1.46 (1H, m), 0.97 (3H, t, J=7.4 Hz). MS (ESI⁻): 389.1. HPLC (Condition A): Rt 4.15 min (HPLC purity 98.8%).

EXAMPLE 150

{4-chloro-2-[(4-{[4-(trifluoromethyl)benzoyl]amino}phenyl)ethynyl]phenoxy}acetic acid

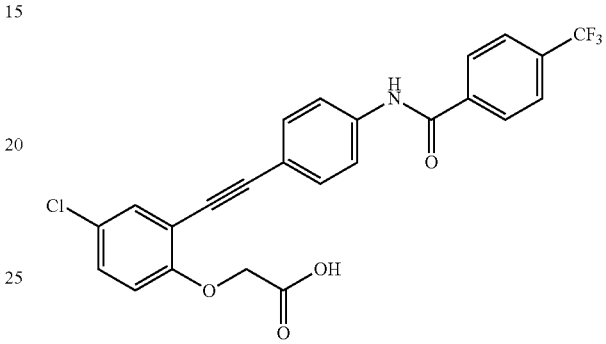

Following the general method as outlined in Example 15, starting from tert-butyl[4-chloro-2-({5-[(dimethylamino)sulfonyl]-2-methylpyridin-3-yl}ethynyl)phenoxy]acetate (Intermediate 223), the title compound was obtained as a white solid after purification by preparative HPLC.

MS (ESI⁻): 472.1. HPLC (Condition A): Rt 4.92 min (HPLC purity 99.4%).

EXAMPLE 151

(2-{[4-(benzoylamino)phenyl]ethynyl}-4-chlorophenoxy)acetic acid

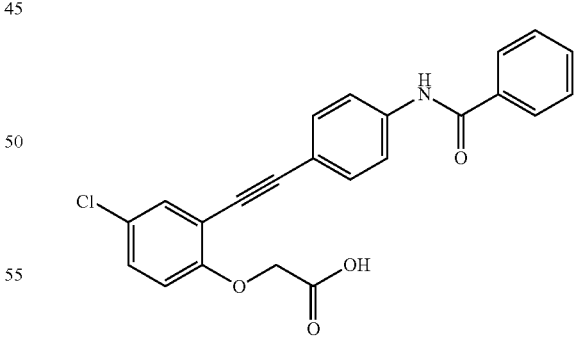

Following the general method as outlined in Example 148, starting from tert-butyl(2-{[4-(benzoylamino)phenyl]ethynyl}-4-chlorophenoxy)acetate (Intermediate 224), the title compound was obtained as a white solid after purification by preparative HPLC.

¹H NMR (300 MHz, DMSO-d₆) δ [ppm] 13.2 (1H, bs), 10.46 (1H, s), 7.98-7.95 (2H, m), 7.90-7.85 (2H, m), 7.65-7.52 (6H, m), 7.38 (1H, dd, J=9.0 Hz, J=2.6 Hz), 6.98 (1H, d, J=9.0 Hz), 4.81 (2H, s). MS (ESI⁻): 404.1. HPLC (Condition A): Rt 4.42 min (HPLC purity 99.7%).

EXAMPLE 152

(2-{[4-(acetylamino)phenyl]ethynyl}-4-chlorophenoxy)acetic acid

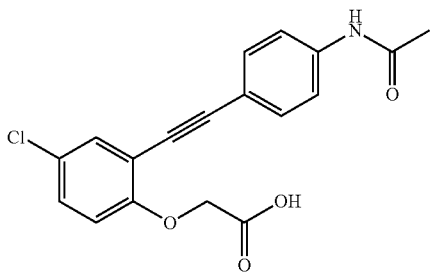

Following the general method as outlined in Example 148, starting from tert-butyl(2-{[4-(acetylamino)phenyl]ethynyl}-4-chlorophenoxy)acetate (Intermediate 225), the title compound was obtained as a white solid after purification by preparative HPLC.

$^1$H NMR (300 MHz, DMSO-d$_6$) δ [ppm] 13.15 (1H, bs), 10.15 (1H, s), 7.64 (2H, d, J=8.7 Hz), 7.52 (1H, d, J=2.7 Hz), 7.47 (2H, d, J=8.7 Hz), 7.38 (1H, dd, J=9.0 Hz, J=2.7 Hz), 6.98 (1H, d, J=9.0 Hz), 4.82 (2H, s), 2.07 (3H, s). MS (ESI⁻): 342.1. HPLC (Condition A): Rt 3.65 min (HPLC purity 99.9%).

EXAMPLE 153

(2-{[4-(acetylamino)-2-methyl-5-(propylsulfonyl)phenyl]ethynyl}-4-chlorophenoxy)acetic acid

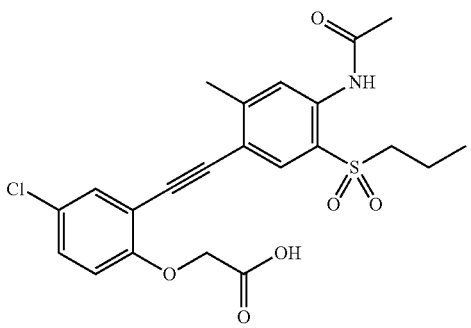

Following the general method as outlined in Example 15, starting from tert-butyl(2-{[4-(acetylamino)-2-methyl-5-(propylsulfonyl)phenyl]ethynyl}-4-chlorophenoxy)acetate (Intermediate 231), the title compound was obtained as a white solid after purification by preparative HPLC.

$^1$H NMR (300 MHz, DMSO-d$_6$) δ [ppm] 13.20 (1H, bs), 9.62 (1H, s), 8.12 (1H, s), 7.89 (1H, s), 7.64 (1H, d, J=2.7 Hz), 7.42 (1H, dd, J=9.0 Hz, J=2.7 Hz), 7.02 (1H, d, J=9.0 Hz), 4.823 (2H, s), 3.37 (2H, m), 2.54 (3H, s), 2.15 (3H, s), 1.57 (2H, sext., J=7.5 Hz), 0.93 (3H, t, J=7.5 Hz). MS (ESI⁻): 462.2. HPLC (Condition A): Rt 4.51 min (HPLC purity 97.9%).

EXAMPLE 154

{4-chloro-2-[(5,5-dioxidodibenzo[b,d]thien-3-yl)ethynyl]phenoxy}acetic acid

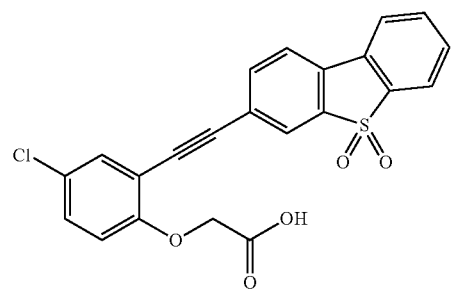

Following the general method as outlined in Example 15, starting from tert-butyl{4-chloro-2-[(5,5-dioxidodibenzo[b,d]thien-3-yl)ethynyl]phenoxy}acetate (Intermediate 233), the title compound was obtained as a beige solid in 73% yield after purification by preparative HPLC.

$^1$H NMR (300 MHz, DMSO-d$_6$) δ [ppm] 13.21 (1H, bs), 8.27 (2H, m), 8.17 (1H, d, J=1.4 Hz), 8.03 (1H, d, J=7.6 Hz), 7.95 (1H, dd, J=8.0 Hz, J=1.4 Hz), 7.84 (1H, dt, J=7.6 Hz, J=1.0 Hz), 7.69 (1H, dt, J=7.6 Hz, J=1.0 Hz), 7.65 (1H, d, J=2.7 Hz), 7.46 (1H, dd, J=9.0 Hz, J=2.7 Hz), 7.04 (1H, d, J=9.0 Hz), 4.86 (2H, s). MS (ESI⁻): 423.0. HPLC (Condition A): Rt 4.56 min (HPLC purity 100%).

EXAMPLE 155

{4-chloro-2-[(1,1-dioxido-2,3-dihydro-1-benzothien-6-yl)ethynyl]phenoxy}acetic acid

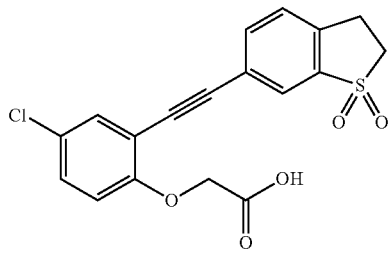

Following the general method as outlined in Example 15, starting from tert-butyl{4-chloro-2-[(1,1-dioxido-2,3-dihydro-1-benzothien-6-yl)ethynyl]phenoxy}acetate (Intermediate 235), the title compound was obtained as a beige solid in 93% yield after trituration in DCM/pentane.

$^1$H NMR (300 MHz, DMSO-d$_6$) δ [ppm] 13.17 (1H, bs), 7.90 (1H, m), 7.80 (1H, dd, J=8.0 Hz, J=1.5 Hz), 7.60-7.63 (2H, m), 7.43 (1H, dd, J=9.0 Hz, J=2.7 Hz), 7.02 (1H, d, J=9.0

Hz), 4.84 (2H, s), 3.65 (2H, t, J=6.8 Hz), 3.40 (2H, t, J=6.8 Hz). MS (ESI⁻): 375.0. HPLC (Condition A): Rt 3.89 min (HPLC purity 97.8%).

EXAMPLE 156

{4-chloro-2-[(1,1-dioxido-1-benzothien-6-yl)ethynyl]phenoxy}acetic acid

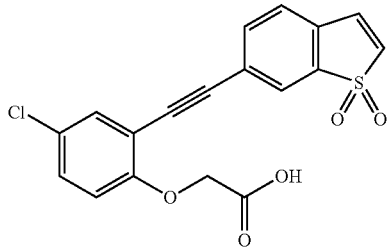

Following the general method as outlined in Example 15, starting from tert-butyl{4-chloro-2-[(1,1-dioxido-1-benzothien-6-yl)ethynyl]phenoxy}acetate (Intermediate 237), the title compound was obtained as a beige solid in 82% yield.

¹H NMR (300 MHz, DMSO-d₆) δ [ppm] 13.19 (1H, bs), 8.04 (1H, m), 7.83 (1H, dd, J=7.9 Hz, J=1.4 Hz), 7.65-7.70 (2H, m), 7.63 (1H, d, J=2.7 Hz), 7.49 (1H, d, J=7.0 Hz), 7.45 (1H, dd, J=9.0 Hz, J=2.7 Hz), 7.03 (1H, d, J=9.0 Hz), 4.85 (2H, s). MS (ESI⁻): 373.0. HPLC (Condition A): Rt 4.03 min (HPLC purity 94.8%).

EXAMPLE 157

{2-[(2-tert-butyl-1,1-dioxido-3-oxo-2,3-dihydro-1,2-benzisothiazol-6-yl)ethynyl]-4-chlorophenoxy}acetic acid

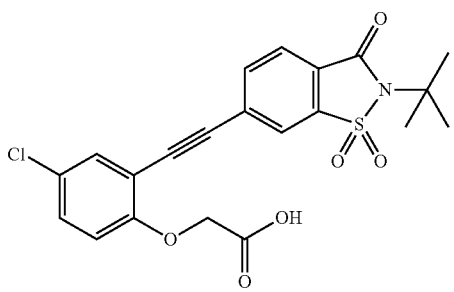

A mixture of (4-chloro-2-ethynylphenoxy)acetic acid (Intermediate 238; 211 mg; 1.00 mmol), 6-bromo-2-tert-butyl-1,2-benzisothiazol-3(2H)-one-1,1-dioxide (prepared as described in *Tetrahedron*, 2006, 62, 7902-7910, 382 mg; 1.20 mmol), dichlorobis(triphenylphosphine)palladium(II) (70 mg; 0.10 mmol) and cuprous iodide (9.5 mg; 0.05 mmol) in anhydrous THF (4 ml) was degassed for 10 minutes then treated with triethylamine (1.00 ml; 7.21 mmol) and the mixture stirred at 60° C. for 16 h. EtOAc was added and the organic phase washed with a sat. NH₄Cl solution then brine. The organic phase was dried on MgSO₄, filtered and concentrated under reduced pressure to give a residue which was purified by preparative HPLC to afford the title compound as a white solid.

¹H NMR (300 MHz, DMSO-d₆) δ [ppm] 13.2 (1H, bs), 8.42 (1H, t, J=0.9 Hz), 8.09-8.02 (2H, m), 7.67 (1H, d, J=2.7 Hz), 7.48 (1H, dd, J=9.0 Hz, J=2.7 Hz), 7.06 (1H, d, J=9.0 Hz), 4.87 (2H, s), 1.70 (9H, s). MS (ESI⁻): 446.1. HPLC (Condition A): Rt 4.86 min (HPLC purity 96.6%).

EXAMPLE 158

{4-chloro-2-[(2,2-dimethyl-1,1-dioxido-3-oxo-2,3-dihydro-1-benzothien-6-yl)ethynyl]phenoxy}acetic acid

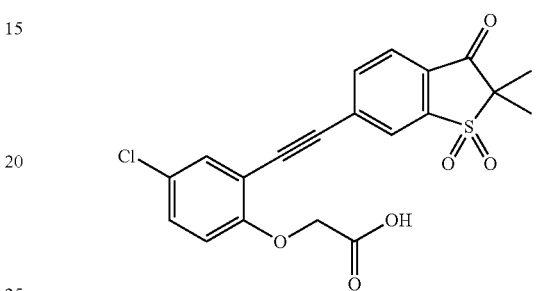

Following the general method as outlined in Example 15, starting from tert-butyl{4-chloro-2-[(2,2-dimethyl-1,1-dioxido-3-oxo-2,3-dihydro-1-benzothien-6-yl)ethynyl]phenoxy}acetate (Intermediate 243), the title compound was obtained as a yellow solid in 97% yield.

¹H NMR (300 MHz, DMSO-d₆) δ [ppm] 13.2 (brs, 1H), 8.38 (m, 1H), 8.11-8.03 (m, 2H), 7.69 (d, J=2.7 Hz, 1H), 7.49 (dd, J=9-2.7 Hz, 1H), 7.06 (d, J=9 Hz, 1H), 4.87 (s, 2H), 1.52 (s, 6H). MS (ESI⁻): 417.1. HPLC (Condition A): Rt 4.53 min (HPLC purity 95.6%).

EXAMPLE 159

{4-chloro-2-[(3-hydroxy-2,2-dimethyl-1,1-dioxido-2,3-dihydro-1-benzothien-6-yl)ethynyl]phenoxy}acetic acid

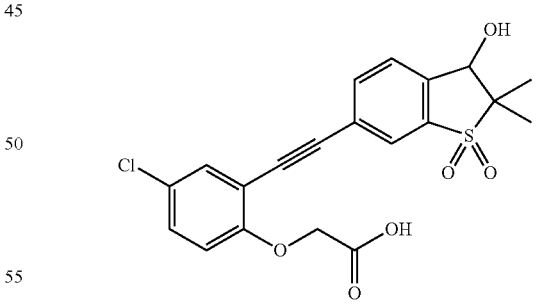

Following the general method as outlined in Example 15, starting from tert-butyl{4-chloro-2-[(3-hydroxy-2,2-dimethyl-1,1-dioxido-2,3-dihydro-1-benzothien-6-yl)ethynyl]phenoxy}acetate (Intermediate 245), the title compound was obtained as a beige solid after purification by preparative HPLC.

¹H NMR (300 MHz, DMSO-d₆) δ [ppm] 13.2 (brs, 1H), 7.94 (m, 1H), 7.86 (dd, J=8-1.5 Hz, 1H), 7.69 (d, J=8 Hz, 1H), 7.62 (d, J=2.7 Hz, 1H), 7.44 (dd, J=2.7-9 Hz, 1H), 7.01 (d, J=9 Hz, 1H), 6.58 (brs, 1H), 4.96 (s, 1H), 4.82 (s, 2H), 1.42 (s, 3H), 1.13 (s, 3H). MS (ESI⁻): 419.2. HPLC (Condition A): Rt 3.89 min (HPLC purity 99.8%).

EXAMPLE 160

{4-chloro-2-[(3-hydroxy-2,2,3-trimethyl-1,1-dioxido-2,3-dihydro-1-benzothien-6-yl)ethynyl]phenoxy}acetic acid

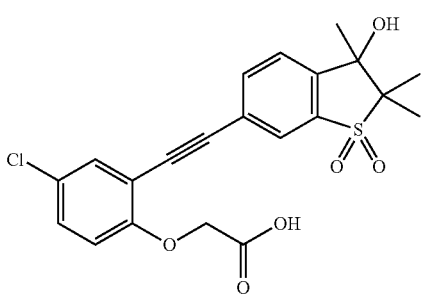

Following the general method as outlined in Example 15, starting from tert-butyl{4-chloro-2-[(3-hydroxy-2,2,3-trimethyl-1,1-dioxido-2,3-dihydro-1-benzothien-6-yl)ethynyl]phenoxy}acetate (Intermediate 247), the title compound was obtained as a yellow solid after purification by preparative HPLC and precipitation from pentane.

¹H NMR (300 MHz, DMSO-d₆) δ [ppm] 13.24-13.18 (brs, 1H), 7.95-7.82 (m, 2H), 7.75 (d, J=8.0, 1H), 7.62 (d, J=2.7, 1H), 7.44 (dd, J=9.0, 2.7, 1H), 7.02 (d, J=9.0, 1H), 6.12 (brs, 1H), 4.83 (s, 2H), 1.48 (s, 3H), 1.34 (s, 3H), 1.21 (s, 3H). MS (ESI⁻): 433.2. HPLC (Condition A): Rt 3.98 min (HPLC purity 100%).

EXAMPLE 161

{4-chloro-2-[(3-methoxy-2,2-dimethyl-1,1-dioxido-2,3-dihydro-1-benzothien-6-yl)ethynyl]phenoxy}acetic acid

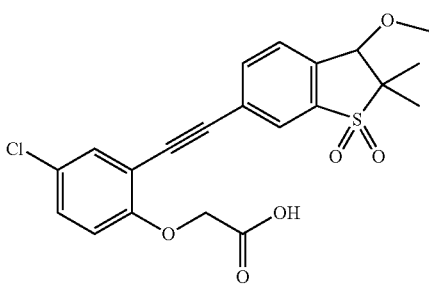

Following the general method as outlined in Example 15, starting from tert-butyl{4-chloro-2-[(3-methoxy-2,2-dimethyl-1,1-dioxido-2,3-dihydro-1-benzothien-6-yl)ethynyl]phenoxy}acetate (Intermediate 249), the title compound was obtained as a yellow solid after preparative HPLC.

¹H NMR (300 MHz, DMSO-d₆) δ [ppm] 7.97 (brs, 1H), 7.87 (dd, J=1.3, 7.8 Hz, 1H), 7.74 (d, J=8.1 Hz, 1H), 7.61 (d, J=2.8 Hz, 1H), 7.43 (dd, J=2.8, 8.9 Hz, 1H), 7.00 (d, J=8.9 Hz, 1H), 4.80 (s, 2H), 4.76 (s, 1H), 3.56 (s, 3H), 1.42 (s, 3H), 1.27 (s, 3H). MS (ESI⁻): 433.2. HPLC (Condition A): Rt 4.84 min (HPLC purity 100%).

EXAMPLE 162

{4-chloro-2-[(3-methoxy-2,2,3-trimethyl-1,1-dioxido-2,3-dihydro-1-benzothien-6-yl)ethynyl]phenoxy}acetic acid

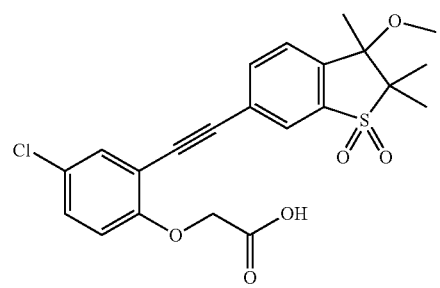

Following the general method as outlined in Example 15, starting from tert-butyl{4-chloro-2-[(3-methoxy-2,2,3-trimethyl-1,1-dioxido-2,3-dihydro-1-benzothien-6-yl)ethynyl]phenoxy}acetate (Intermediate 251), the title compound was obtained as a white solid after purification by preparative HPLC.

¹H NMR (300 MHz, DMSO-d₆) δ [ppm] 13.01 (brs, 1H), 7.97 (d, J=1.2 Hz, 1H), 7.87 (dd, J=1.4, J=8.0 Hz, 1H), 7.82 (d, J=8.1 Hz, 1H), 7.62 (d, J=2.6 Hz, 1H), 7.43 (dd, J=2.6, J=8.9 Hz, 1H), 7.02 (d, J=9.1 Hz, 1H), 4.84 (s, 2H), 3.06 (s, 3H), 1.55 (s, 3H), 1.34 (s, 3H), 1.24 (s, 3H). MS (ESI⁻): 447.2. HPLC (Condition A): Rt 4.91 min (HPLC purity 99.7%). m.p.=80-95° C.

EXAMPLE 163

(2-{[4-{[butyl(methyl)amino]carbonyl}-3-(isopropylsulfonyl)phenyl]ethynyl}-4-chlorophenoxy)acetic acid

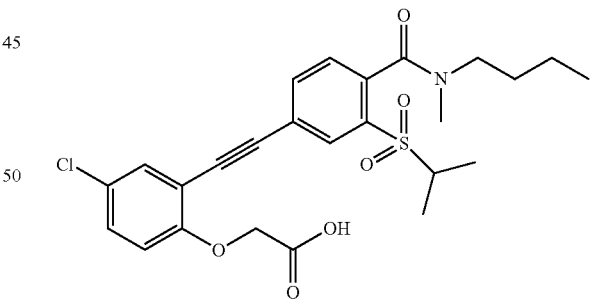

Following the general method as outlined in Example 15, starting from tert-butyl(2-{[4-{[butyl(methyl)amino]carbonyl}-3-(isopropylsulfonyl)phenyl]ethynyl}-4-chlorophenoxy)acetate (Intermediate 254), the title compound was obtained as a white solid after purification by preparative HPLC.

¹H NMR (300 MHz, DMSO-d₆) δ [ppm] 13.20 (1H, bs), 7.98 (1H, m), 7.93 (1H, J=7.9 Hz, J=1.6 Hz), 7.68 (1H, d, J=2.7 Hz), 7.55 (1H, m), 7.45 (1H, dd, J=9.0 Hz, J=2.7 Hz), 7.02 (1H, d, J=9.0 Hz), 4.85 (2H, s), 3.75 (1H, sept., J=6.9 Hz), 3.43 (1.3H, m), 2.95 (0.7H, m), 2.95 (1.2H, s), 2.72 (1.8H, s), 1.05-1.59 (10H, m), 0.93 (1.8H, t, J=7.3 Hz), 0.74

(1.2H, t, J=7.3 Hz) (high-temperature NMR experiment gave evidence of presence of rotamers). MS (ESI−): 504.2. HPLC (Condition A): HPLC purity 99.0%.

EXAMPLE 164

(4-chloro-2-{[4-[(dimethylamino)carbonyl]-3-(isopropylsulfonyl)phenyl]ethynyl}phenoxy)acetic acid

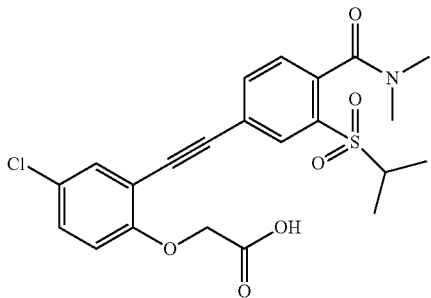

Following the general method as outlined in Example 15, starting from tert-butyl(4-chloro-2-{[4-[(dimethylamino)carbonyl]-3-(isopropylsulfonyl)phenyl]ethynyl}phenoxy)acetate (Intermediate 256), the title compound was obtained as a beige solid after purification by preparative HPLC.

$^1$H NMR (300 MHz, DMSO-$d_6$) δ [ppm] 13.20 (1H, bs), 7.98 (1H, d, J=1.6 Hz), 7.93 (1H, dd, J=7.8 Hz; J=1.6 Hz), 7.68 (1H, d, J=2.7 Hz), 7.57 (1H, d, J=7.8 Hz), 7.45 (1H, dd, J=9.0 Hz, J=2.7 Hz), 7.01 (1H, d, J=9.0 Hz), 4.83 (2H, s), 3.72 (1H, sept., J=6.9 Hz), 2.98 (3H, s), 2.73 (3H, s), 1.29 (3H, m), 1.05 (3H, m). MS (ESI−): 432.2. HPLC (Condition A): Rt 3.95 min (HPLC purity 100%). CHN analysis: [$C_{22}H_{22}NO_6ClS$+0.15 $CH_2Cl_2$+0.5 $H_2O$] Calculated: C, 54.78%; H, 4.85%; N, 2.87%. Found: C, 54.73%; H, 4.88%; N, 2.98%.

EXAMPLE 165

(4-chloro-2-{[4-[(diethylamino)carbonyl]-3-(isopropylsulfonyl)phenyl]ethynyl}phenoxy)acetic acid

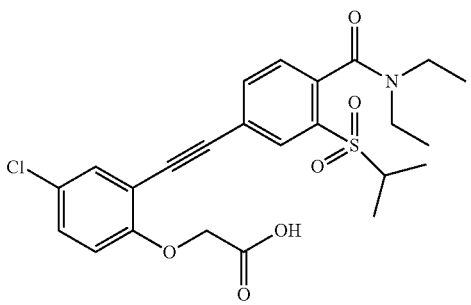

Following the general method as outlined in Example 15, starting from tert-butyl(4-chloro-2-{[4-[(diethylamino)carbonyl]-3-(isopropylsulfonyl)phenyl]ethynyl}phenoxy)acetate (Intermediate 258), the title compound was obtained as a white solid in 76% yield after purification by preparative HPLC.

$^1$H NMR (300 MHz, DMSO-$d_6$) δ [ppm] 13.19 (1H, bs), 7.97 (1H, d, J=1.6 Hz), 7.92 (1H, dd, J=7.8 Hz, J=1.6 Hz), 7.68 (1H, d, J=2.7 Hz), 7.57 (1H, d, J=7.8 Hz), 7.45 (1H, dd, J=9.0 Hz, J=2.7 Hz), 7.02 (1H, d, J=9.0 Hz), 4.84 (2H, s), 3.75 (1H, sept., J=6.9 Hz), 3.58 (1H, m), 3.30 (1H, m), 2.94-3.12 (2H, m), 1.29 (3H, d, J=6.9 Hz), 1.14 (3H, t, J=7.1 Hz), 1.05 (3H, d, J=6.9 Hz), 1.03 (3H, t, J=7.1 Hz). MS (ESI−): 490.3. HPLC (Condition A): Rt 4.88 min (HPLC purity 99.9%). CHN analysis: [$C_{24}H_{26}NO_6ClS$+0.5$H_2O$] Calculated: C, 57.31%; H, 5.43%; N, 2.77%. Found: C, 57.27%; H, 5.32%; N, 3.00%.

EXAMPLE 166

(4-chloro-2-{[4-{[ethyl(propyl)amino]carbonyl}-3-(isopropylsulfonyl)phenyl]ethynyl}phenoxy)acetic acid

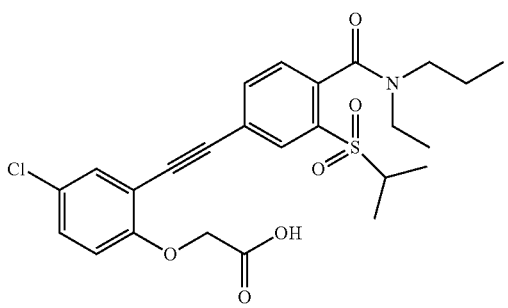

Following the general method as outlined in Example 15, starting from tert-butyl(4-chloro-2-{[4-{[ethyl(propyl)amino]carbonyl}-3-(isopropylsulfonyl)phenyl]ethynyl}phenoxy)acetate (Intermediate 260), the title compound was obtained as a beige solid after purification by preparative HPLC.

$^1$H NMR (300 MHz, DMSO-$d_6$) δ [ppm] 13.27 (1H, bs), 7.97 (1H, m), 7.94 (1H, dd, J=7.8 Hz, J=1.6 Hz), 7.68 (1H, d, J=2.7 Hz), 7.56 (1H, m), 7.45 (1H, dd, J=9.0 Hz, J=2.7 Hz), 7.01 (1H, d, J=9.0 Hz), 4.85 (2H, s), 3.73 (1H, m), 3.59 (0.5H, m), 3.44 (0.5H, m), 3.26 (1H, m), 2.79-3.13 (2H, m), 1.40-1.65 (2H, m), 1.28 (3H, d, J=7.0 Hz), 1.13 (1.5H, t, J=7.0 Hz), 1.04 (3H, d, J=7.0 Hz), 1.02 (1.5H, t, J=7.0 Hz), 0.93 (1.5H, t, J=7.0 Hz), 0.69 (1.5H, t, J=7.0 Hz). (high-temperature NMR experiment gave evidence of presence of rotamers) MS (ESI−): 504.3. HPLC (Condition A): Rt 4.72 min (HPLC purity 99.3%). CHN analysis: [$C_{25}H_{28}NO_6ClS$+0.2$H_2O$] Calculated: C, 58.70%; H, 5.60%; N, 2.76%. Found: C, 58.49%; H, 5.35%; N, 2.85%.

EXAMPLE 167

(4-chloro-2-{[3-(isopropylsulfonyl)-4-(morpholin-4-ylcarbonyl)phenyl]ethynyl}phenoxy)acetic acid

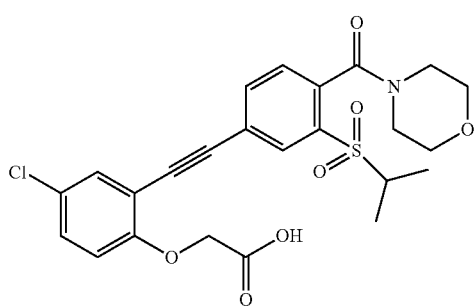

Following the general method as outlined in Example 15, starting from tert-butyl(4-chloro-2-{[3-(isopropylsulfonyl)-4-(morpholin-4-ylcarbonyl)phenyl]ethynyl}phenoxy)acetate (Intermediate 262), the title compound was obtained as a beige solid after purification by preparative HPLC.

$^{1}$H NMR (300 MHz, DMSO-d$_{6}$) δ [ppm] 13.25 (1H, bs), 7.98 (1H, d, J=1.6 Hz), 7.94 (1H, dd, J=7.8 Hz, J=1.6 Hz), 7.68 (1H, d, J=2.7 Hz), 7.61 (1H, d, J=7.8 Hz), 7.45 (1H, dd, J=9.0 Hz, J=2.7 Hz), 7.01 (1H, d, J=9.0 Hz), 4.83 (2H, s), 3.53-3.77 (6H, m), 3.02-3.21 (2H, m), 1.30 (3H, d, J=6.8 Hz), 1.07 (3H, d, J=6.8 Hz) (1 remaining proton, probably hidden under the signal of water). MS (ESI$^{-}$): 504.2. HPLC (Condition A): Rt 3.96 min (HPLC purity 99.7%).

EXAMPLE 168

2-(4-chloro-2-{[2-fluoro-5-(propylsulfonyl)phenyl]ethynyl}phenoxy)propanoic acid

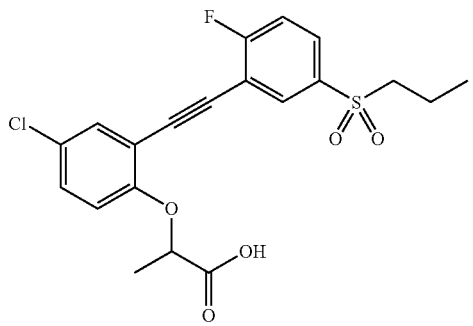

A solution of methyl 2-(2-bromo-4-chlorophenoxy)propanoate (Intermediate 263 ; 130 mg; 0.44 mmol), 2-ethynyl-1-fluoro-4-(propane-1-sulfonyl)-benzene (Intermediate 109 ; 110 mg; 0.49 mmol), bis(triphenylphosphine)palladium (II) chloride (9.3 mg; 0.01 mmol), triphenylphosphine (23.2 mg; 0.09 mmol) and cuprous iodide (2.5 mg; 0.01 mmol) in TEA (985 µl) was degassed with nitrogen. The reaction mixture was heated overnight at 80° C., diluted with EtOAc and washed with sat. ammonium chloride solution and brine. The organic phase was dried over MgSO$_{4}$, filtered and concentrated to dryness affording a dark brown sticky solid, which was purified by flash column chromatography (silica), eluting with cyclohexane containing increasing amounts of EtOAc. The intermediate thus obtained was dissolved in a mixture of dioxane (2.6 ml) and water (2.6 ml) and treated with a 4 N solution of HCl in dioxane (1.33 ml). After heating at 100° C. for 16 hours, water was added and the reaction mixture was extracted 3 times with EtOAC. The organic phase was dried over MgSO$_{4}$, filtered and concentrated to dryness affording a yellow sticky solid, which was triturated in diethylether/pentane to afford the title compound as a white solid.

$^{1}$H NMR (300 MHz, DMSO-d$_{6}$) δ [ppm] 13.27 (1H, bs), 8.10 (1H, dd, J=6.5 Hz, J=2.3 Hz), 7.98 (1H, m), 7.63-7.69 (2H, m), 7.47 (1H, dd, J=9.0 Hz, J=2.7 Hz), 6.95 (1H, d, J=9.0 Hz), 4.96 (1H, q, J=6.8 Hz), 3.38 (2H, m), 1.50-1.63 (5H, m), 0.93 (3H, t, J=7.5 Hz). MS (ESI$^{-}$): 423.1. HPLC (Condition A): Rt 4.66 min (HPLC purity 91.9%).

EXAMPLE 169

2-(4-chloro-2-{[2-fluoro-5-(propylsulfonyl)phenyl]ethynyl}phenoxy)-2-methylpropanoic acid

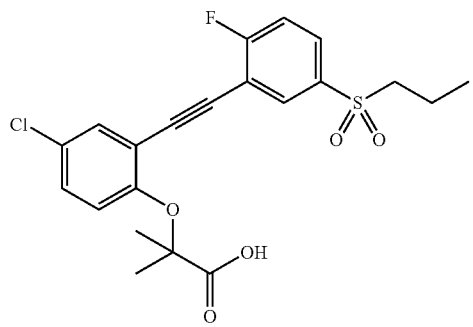

Following the general method as outlined in Example 168, starting from 2-(2-bromo-4-chlorophenoxy)-2-methylpropanoate (Intermediate 264), and 2-ethynyl-1-fluoro-4-(propane-1-sulfonyl)-benzene (Intermediate 109) the title compound was obtained as a brown sticky solid after purification by preparative HPLC.

$^{1}$H NMR (300 MHz, DMSO-d$_{6}$) δ [ppm] 13.41 (1H, bs), 8.11 (1H, dd, J=6.5 Hz, J=2.4 Hz), 7.98 (1H, ddd, J=8.8 Hz, J=4.7 Hz, J=2.4 Hz), 7.63-7.69 (2H, m), 7.457 (1H, dd, J=9.0 Hz, J=2.7 Hz), 6.91 (1H, d, J=9.0 Hz), 3.37 (2H, m), 1.51-1.60 (8H, m), 0.93 (3H, t, J=7.4 Hz). MS (ESI$^{-}$): 437.1. HPLC (Condition A): Rt 4.81 min (HPLC purity 98.9%).

EXAMPLE 170

2-(4-chloro-2-{[2-methyl-5-(propylsulfonyl)phenyl]ethynyl}phenoxy)butanoic acid

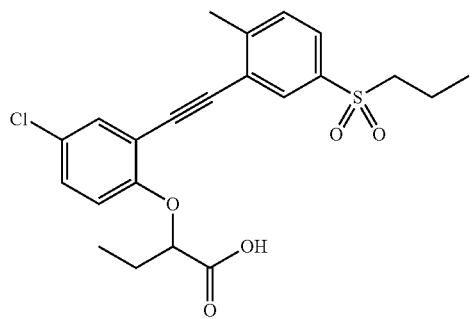

A solution of ethyl 2-(4-chloro-2-{[2-methyl-5-(propylsulfonyl)phenyl]ethynyl}phenoxy)butanoate (Intermediate 268; 100 mg; 0.11 mmol) in EtOH (1 ml) was treated with a 1M solution of sodium hydroxide in water (0.16 ml; 0.16 mmol). After stirring at 70° C. for 45 minutes, a 1 N solution of HCl in water (65 µl) was added, the solvents removed under reduced pressure and the residue purified by preparative HPLC to afford the title compound as a beige solid.

$^{1}$H NMR (300 MHz, DMSO-d$_{6}$) δ [ppm] 7.94 (1H, d, J=2.0 Hz), 7.80 (1H, dd, J=8.0 Hz, J=2.0 Hz), 7.65 (1H, d, J=2.7 Hz), 7.62 (1H, d, J=8.0 Hz), 7.42 (1H, dd, J=9.0 Hz, J=2.0 Hz), 6.92 (1H, d, J=9.0 Hz), 4.78 (1H, t, J=5.7 Hz), 2.58 (3H, s), 1.94 (2H, m), 1.54 (2H, sext., J=7.5 Hz), 1.04 (3H, t, J=7.5

Hz), 0.91 (3H, t, J=7.5 Hz) (2 remaining protons, probably hidden under the peak of water). MS (ESI−): 433.2. HPLC (Condition A): Rt 4.98 min (HPLC purity 98.4%).

EXAMPLE 171

2-(4-chloro-2-{[2-methyl-5-(propylsulfonyl)phenyl]ethynyl}phenoxy)pentanoic acid

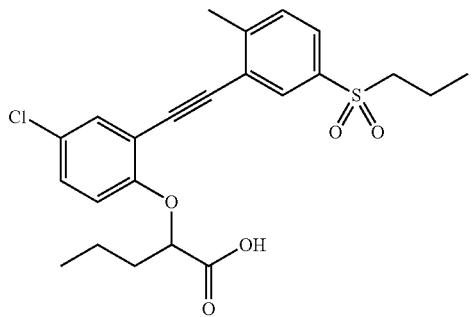

Following the general method as outlined in Example 170, starting from ethyl 2-(4-chloro-2-{[2-methyl-5-(propylsulfonyl)phenyl]ethynyl}phenoxy)pentanoate (Intermediate 269), the title compound was obtained as a white solid after purification by preparative HPLC.

$^1$H NMR (300 MHz, DMSO-d$_6$) δ [ppm] 13.28 (1H, bs), 7.94 (1H, d, J=2.0 Hz), 7.80 (1H, dd, J=8.0 Hz, J=2.0 Hz), 7.65 (1H, d, J=2.7 Hz), 7.63 (1H, d, J=8.0 Hz), 7.43 (1H, dd, J=9.0 Hz, J=2.7 Hz), 6.92 (1H, d, J=9.0 Hz), 4.85 (1H, t, J=5.8 Hz), 3.30 (2H, m), 2.58 (3H, s), 1.86-1.94 (2H, m), 1.49-1.63 (4H, m), 0.89-0.95 (6H, m). MS (ESI−): 447.2. HPLC (Condition A): Rt 5.69 min (HPLC purity 99.7%).

EXAMPLE 172

2-(4-chloro-2-{[2-methyl-5-(propylsulfonyl)phenyl]ethynyl}phenoxy)-4-methylpentanoic acid

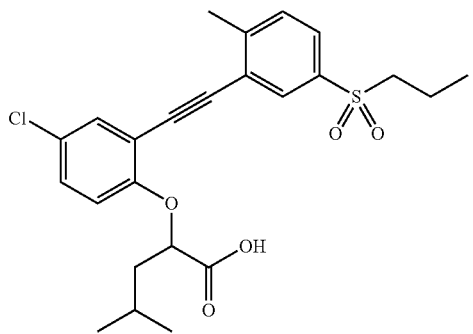

Following the general method as outlined in Example 170, starting from ethyl 2-(4-chloro-2-{[2-methyl-5-(propylsulfonyl)phenyl]ethynyl}phenoxy)-4-methylpentanoate (Intermediate 270), the title compound was obtained as a beige solid after purification by preparative HPLC.

$^1$H NMR (300 MHz, DMSO-d$_6$) δ [ppm] 13.25 (1H, bs), 7.93 (1H, d, J=2.0 Hz), 7.80 (1H, dd, J=8.0 Hz, J=2.0 Hz), 7.66 (1H, d, J=2.7 Hz), 7.63 (1H, d, J=8.0 Hz), 7.44 (1H, dd, J=9.0 Hz, J=2.7 Hz), 6.96 (1H, d, J=9.0 Hz), 4.86 (1H, dd, J=9.0 Hz, J=3.7 Hz), 3.29 (2H, m), 2.58 (3H, s), 1.84-1.99 (2H, m), 1.66-1.77 (1H, m), 1.54 (2H, sext., J=7.5 Hz), 0.89-0.97 (9H, m). MS (ESI−): 461.2. HPLC (Condition A): Rt 5.42 min (HPLC purity 98.5%).

EXAMPLE 173

2-(4-chloro-2-{[2-methyl-5-(propylsulfonyl)phenyl]ethynyl}phenoxy)propanoic acid

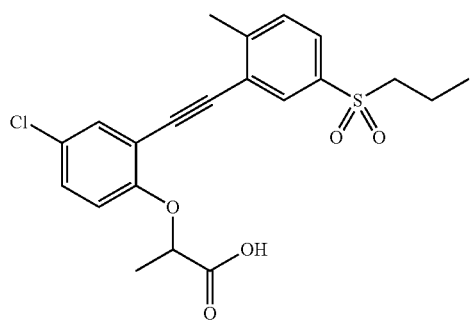

A solution of 4-chloro-2-{[2-methyl-5-(propylsulfonyl)phenyl]ethynyl}phenol (150 mg; 0.43 mmol) and methyl-2-bromopropionate (53 µl; 0.47 mmol) in DME (3 ml) was treated with K$_2$CO$_3$ (89 mg, 69 mmol) and heated at 70° C. for 4.5 hours. The reaction mixture was filtered and the filtrate was concentrated affording a sticky solid, which was dissolved in MeOH (1.5 ml) and treated with a 1 N solution of NaOH in water (129 µl) and the mixture heated for 1 hour at 70° C. A 5 N solution of HCl in water (52 µl) was added and the solvents removed under reduced pressure, to give a residue which was purified by preparative HPLC to give the title compound as a white solid.

$^1$H NMR (300 MHz, DMSO-d$_6$) δ [ppm] 13.26 (1H, bs), 7.95 (1H, d, J=2.0 Hz), 7.80 (1H, dd, J=8.0 Hz, J=2.0 Hz), 7.65 (1H, d, J=2.7 Hz), 7.63 (1H, d, J=8.0 Hz), 7.44 (1H, dd, J=9.0 Hz, J=2.7 Hz), 6.95 (1H, d, J=9.0 Hz), 4.98 (1H, q, J=6.7 Hz), 3.32 (2H, m), 2.59 (3H, s), 1.49-1.62 (5H, m), 0.92 (3H, t, J=7.5 Hz). MS (ESI−): 418.9. HPLC (Condition A): Rt 5.23 min (HPLC purity 98.6%).

EXAMPLE 174

Preparation of hCRTH2-CHO Expressing Cell Membranes

Adherent CHO cells expressing hCRTH2 (Euroscreen, Belgium) were cultured in 225 cm$^2$ cell culture flasks (Corning, USA) in 30 ml of medium. After two rinses of phosphate buffered saline (PBS), cells were harvested in 10 ml of PBS containing 1 mM EDTA, centrifuged at 500×g for 5 min at 4° C. and frozen at −80° C. The pellet was re-suspended in 50 mM Tris-HCl, pH 7.4, 2 mM EDTA, 250 mM Sucrose, containing protease inhibitor cocktail tablets, (Complete EDTA-free, Roche, Germany) and incubated 30 min at 4° C. Cells were disrupted by nitrogen cavitation (Parr Instruments, USA) at 4° C. (800 p.s.i. for 30 min), and centrifuged at 500×g for 10 min at 4° C. Pellet containing nuclei and cellular debris was discarded and supernatant was centrifuged 60 min at 4° C. at 45000×g. Membrane pellet was re-suspended in storage buffer (10 mM HEPES/KOH pH 7.4, 1 mM EDTA, 250 mM sucrose, protease inhibitor cocktail tablets) using Dounce homogenization and frozen in liquid nitrogen, and stored at −80° C.

EXAMPLE 175

Radioligand Binding Assay

The compounds of the present invention inhibit the binding of PGD2 to its receptor CRTH2. The inhibitory activity can be investigated by a radioligand binding Scintillation Proximity Assay (SPA) (Sawyer et al., Br. J. Pharmocol 2002, 137, 1163-72). The SPA radioligand binding assay was performed at room temperature in binding buffer (10 mM HEPES/KOH pH 7.4, 10 mM $MnCl_2$, with protease inhibitor cocktail tablets), containing 1.5 nM [$^3$H]$PGD_2$ (Perkin Elmer), 10-50 µg/ml of hCRTH2-CHO cell membrane protein and 2 mg/ml of Wheat-germ agglutinin Sintillation Proximity Assay beads (RPNQ0001, GE-Healthcare) in a final volume of 100 µl in 96 well plates (Corning, USA). Non-specific binding was determined in the presence of 10 µM $PGD_2$ (Cayman, USA). Competing Compounds of Formula (I) were diluted in dimethylsulphoxide so that the total volume of dimethylsulfoxide was kept constant at 1% dimethylsulphoxide ($Me_2SO$). Serial dilutions of 100 µM to 100 pM were prepared and 10 µl each of the compounds of Formula (I) stock solutions were added to the binding assay reagents and incubated for 90 min with agitation at room temperature. Binding activity was determined by using a 1450 Micro-beta scintillation counter (Wallac, UK).

In one embodiment, the compounds of Formula (I) of the present invention inhibit CRTH2 at a concentration of <5 µM. In another embodiment, the compounds of Formula (I) of the present invention inhibit CRTH2 at a concentration of <1 µM. In a preferred embodiment, the compounds of Formula (I) of the present invention inhibit CRTH2 at a concentration of <0.1 µM.

Results:

| Example | Formula | IC50 binding (µM) |
|---|---|---|
| 1 | | 0.076 |
| 2 | | 0.091 |
| 3 | | 0.026 |
| 4 | | 0.015 |

-continued

| Example | Formula | IC50 binding (μM) |
|---|---|---|
| 5 | 2-[4-chloro-2-[(2-fluorophenyl)ethynyl]phenoxy]acetic acid | 0.056 |
| 6 | 2-[4-chloro-2-[(2-methoxyphenyl)ethynyl]phenoxy]acetic acid | 0.229 |
| 7 | 2-[4-chloro-2-[[3-(trifluoromethyl)phenyl]ethynyl]phenoxy]acetic acid | 0.111 |
| 8 | 2-[4-chloro-2-[(2,4-difluorophenyl)ethynyl]phenoxy]acetic acid | 0.123 |
| 9 | 2-[4-chloro-2-[[2-(trifluoromethyl)phenyl]ethynyl]phenoxy]acetic acid | 0.030 |
| 10 | 2-[4-chloro-2-[(5-chlorothiophen-2-yl)ethynyl]phenoxy]acetic acid | 0.267 |

-continued
| Example | Formula | IC50 binding (μM) |
|---|---|---|
| 11 | 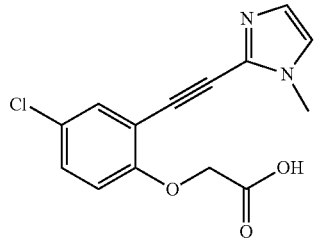 | 1.765 |
| 12 | 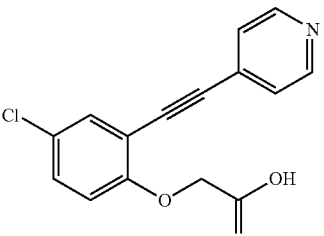 | 0.811 |
| 13 | 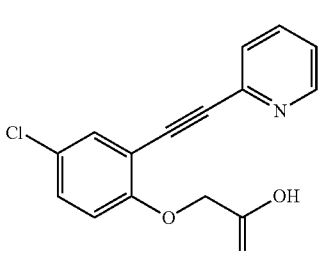 | 1.445 |
| 14 | 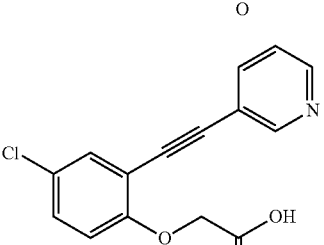 | 0.146 |
| 15 | 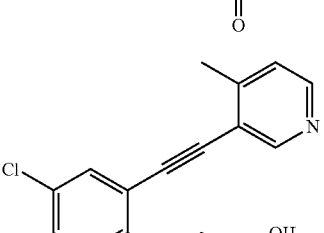 | 0.030 |
| 16 | 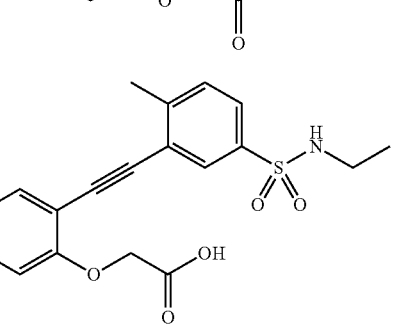 | 0.006 |

-continued

| Example | Formula | IC50 binding (μM) |
|---|---|---|
| 17 | | 0.010 |
| 18 | | 0.019 |
| 19 | | 0.036 |
| 20 | | 0.012 |
| 21 | | 0.046 |

-continued

| Example | Formula | IC50 binding (μM) |
|---|---|---|
| 22 | | 0.175 |
| 23 | | 0.030 |
| 24 | | 0.102 |
| 25 | | 0.089 |
| 26 | | 0.028 |

-continued
| Example | Formula | IC50 binding (μM) |
|---|---|---|
| 27 | 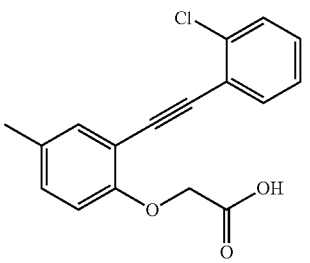 | 0.346 |
| 28 | 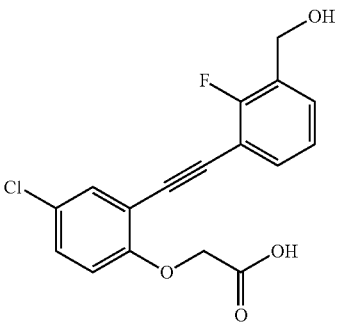 | 0.048 |
| 29 | 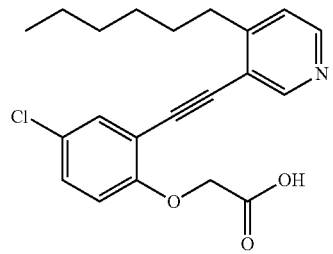 | 0.051 |
| 30 | 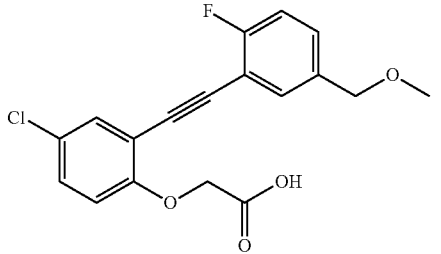 | 0.085 |
| 31 | 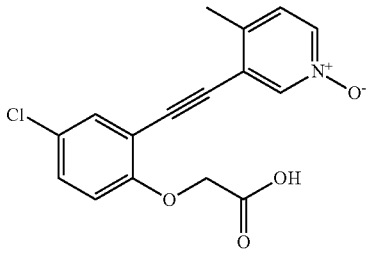 | 0.019 |

-continued

| Ex-ample | Formula | IC50 binding (μM) |
|---|---|---|
| 32 | | 0.025 |
| 33 | | 0.009 |
| 34 | | 0.026 |
| 35 | | 0.055 |
| 36 | | 0.075 |

-continued

| Example | Formula | IC50 binding (μM) |
|---|---|---|
| 37 | | 5.94 |
| 38 | | 0.005 |
| 39 | | 0.023 |
| 40 | | 0.009 |

-continued
| Example | Formula | IC50 binding (μM) |
|---|---|---|
| 41 | 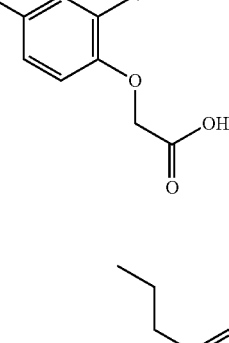 | 0.015 |
| 42 | 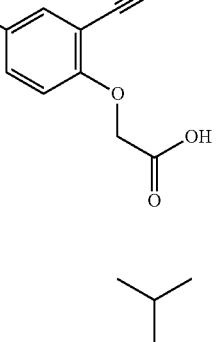 | 0.005 |
| 43 | 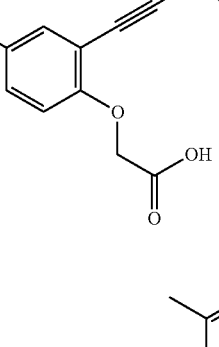 | 0.006 |
| 44 | 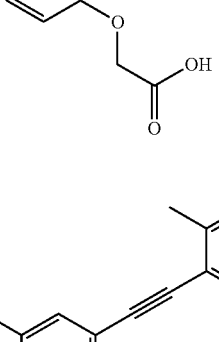 | 0.06 |

-continued

| Example | Formula | IC50 binding (μM) |
|---|---|---|
| 45 | | 0.958 |
| 46 | | 0.323 |
| 47 | | 0.34 |
| 48 | | 0.009 |

| Example | Formula | IC50 binding (μM) |
|---|---|---|
| 49 | | 0.011 |
| 50 | | 0.011 |
| 51 | | 0.008 |
| 52 | | 0.025 |

-continued

| Example | Formula | IC50 binding (μM) |
|---|---|---|
| 53 | | 0.005 |
| 54 | | 0.01 |
| 55 | | 0.013 |
| 56 | | 0.03 |

| Example | Formula | IC50 binding (μM) |
|---|---|---|
| 57 | 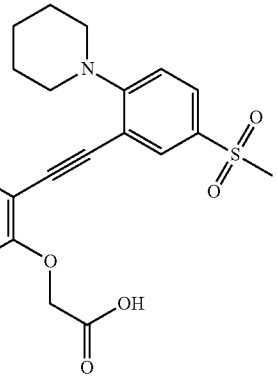 | 0.28 |
| 58 | 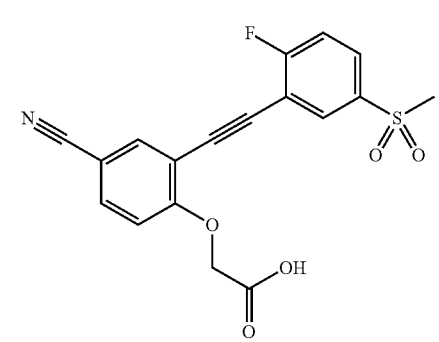 | 0.014 |
| 59 | 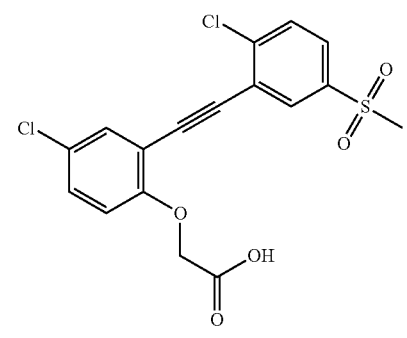 | 0.006 |
| 60 | 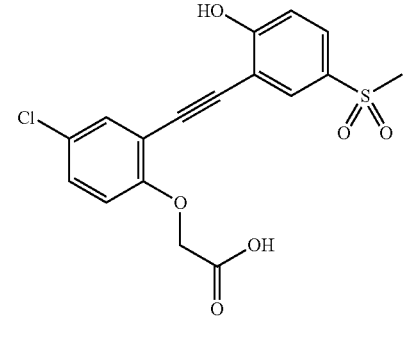 | 0.296 |

-continued

| Example | Formula | IC50 binding (μM) |
|---|---|---|
| 61 | | 0.008 |
| 62 | | 0.202 |
| 63 | | 0.033 |
| 64 | | 0.136 |

-continued

| Example | Formula | IC50 binding (μM) |
|---|---|---|
| 65 | | 0.009 |
| 66 | | 0.193 |
| 67 | | 0.086 |
| 68 | | 0.012 |

| Example | Formula | IC50 binding (μM) |
|---|---|---|
| 69 | | 0.186 |
| 70 | | 0.007 |
| 71 | | 0.016 |
| 72 | | 0.364 |

-continued

| Example | Formula | IC50 binding (μM) |
|---|---|---|
| 73 | | 0.057 |
| 74 | | 0.07 |
| 75 | | 0.372 |
| 76 | | 0.171 |

-continued

| Example | Formula | IC50 binding (μM) |
|---------|---------|-------------------|
| 77 | | 0.36 |
| 78 | | 0.04 |
| 79 | | 0.052 |
| 80 | | 0.019 |

-continued

| Example | Formula | IC50 binding (µM) |
|---|---|---|
| 81 | | 0.005 |
| 82 | | 0.005 |
| 83 | | 0.007 |
| 84 | | 0.013 |

-continued
| Example | Formula | IC50 binding (μM) |
|---|---|---|
| 85 | 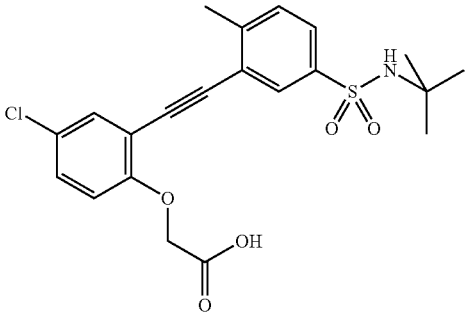 | 0.007 |
| 86 | 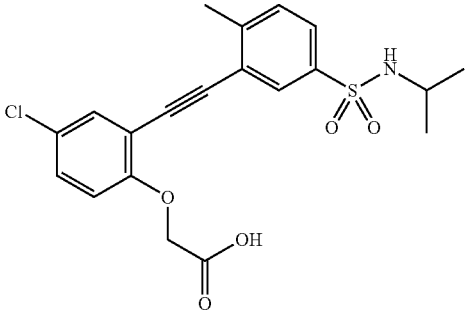 | 0.005 |
| 87 | 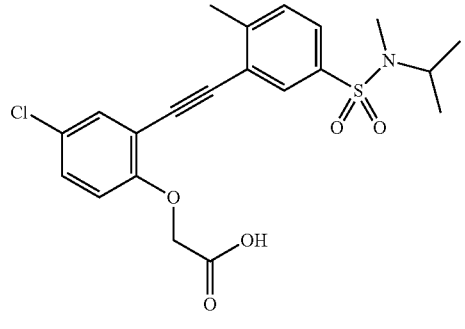 | 0.006 |
| 88 | 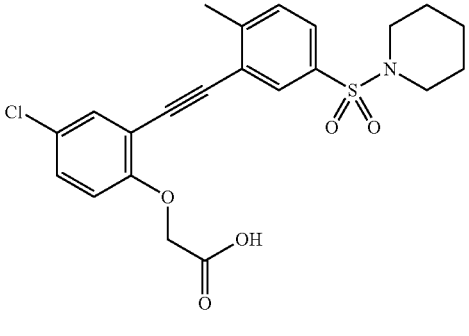 | 0.007 |

-continued
| Example | Formula | IC50 binding (μM) |
|---|---|---|
| 89 | 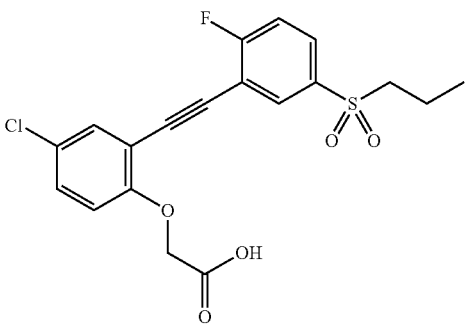 | 0.006 |
| 90 | 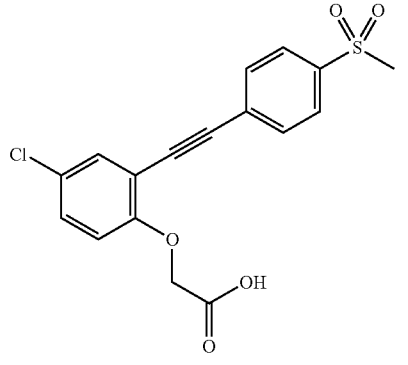 | 0.154 |
| 91 | 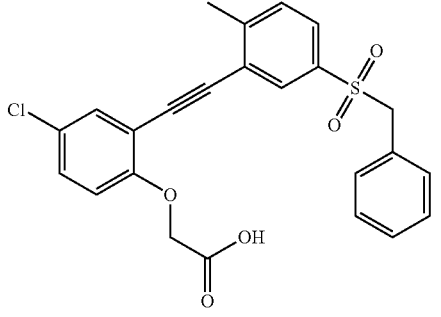 | 0.007 |
| 92 | 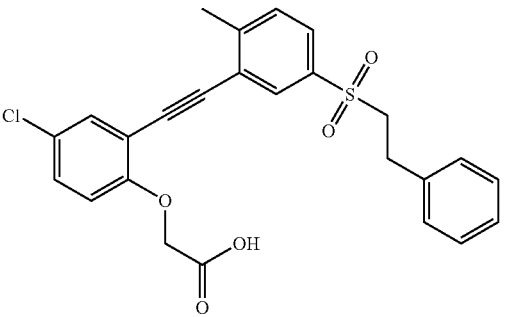 | 0.009 |

-continued

| Example | Formula | IC50 binding (μM) |
|---------|---------|-------------------|
| 93 | | 0.013 |
| 94 | | 0.011 |
| 95 | | 0.009 |
| 96 | | 0.007 |

-continued
| Example | Formula | IC50 binding (μM) |
|---|---|---|
| 97 | 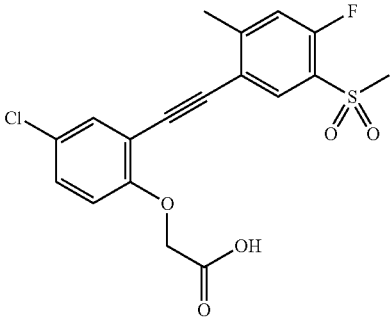 | 0.008 |
| 98 | 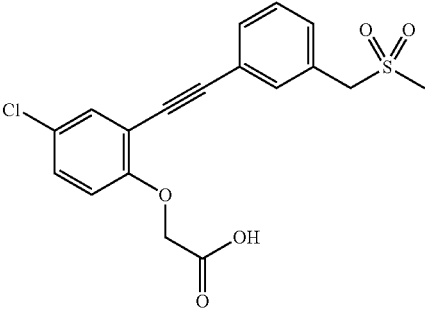 | 0.060 |
| 99 | 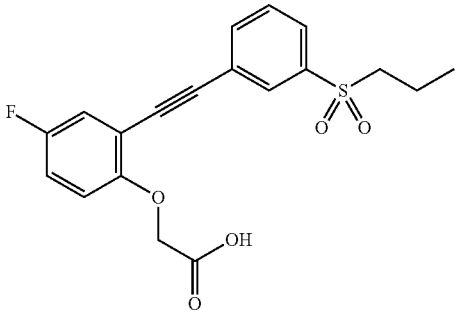 | 0.079 |
| 100 | 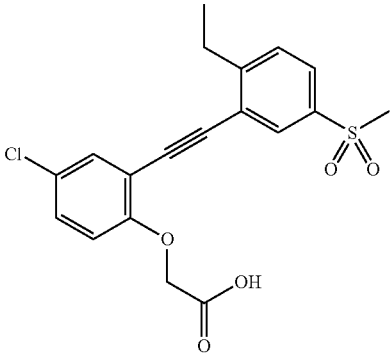 | 0.003 |

-continued

| Example | Formula | IC50 binding (μM) |
|---|---|---|
| 101 | | 0.003 |
| 102 | | 0.005 |
| 103 | | 0.004 |
| 104 | | 0.003 |

-continued

| Example | Formula | IC50 binding (μM) |
|---|---|---|
| 105 | | 0.002 |
| 106 | | 0.002 |
| 107 | | 0.004 |
| 108 | | 0.002 |

-continued

| Example | Formula | IC50 binding (μM) |
|---|---|---|
| 109 | | 0.005 |
| 110 | | 0.005 |
| 111 | | 0.006 |
| 112 | | 0.027 |

-continued
| Example | Formula | IC50 binding (μM) |
|---|---|---|
| 113 | 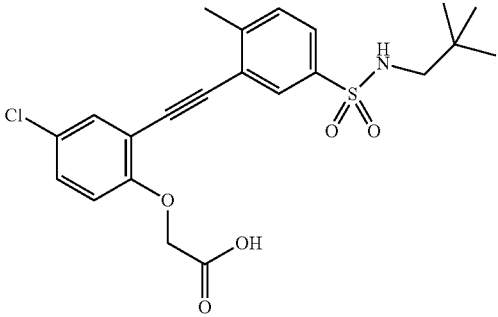 | 0.002 |
| 114 | 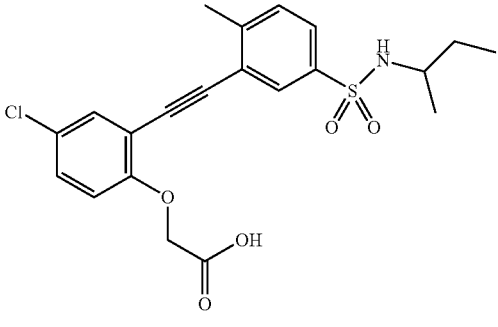 | 0.003 |
| 115 | 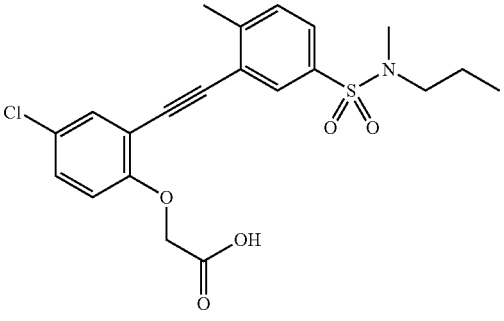 | 0.005 |
| 116 | 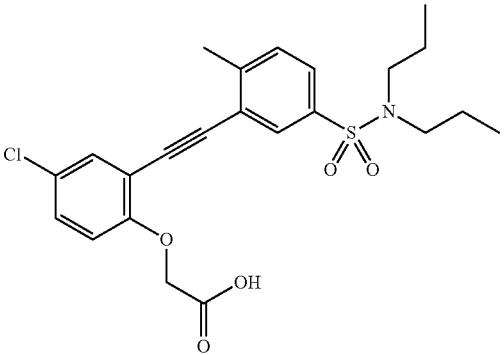 | 0.008 |

-continued
| Example | Formula | IC50 binding (μM) |
|---|---|---|
| 117 | 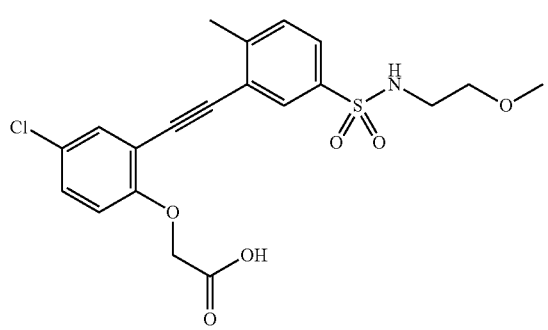 | 0.005 |
| 118 | 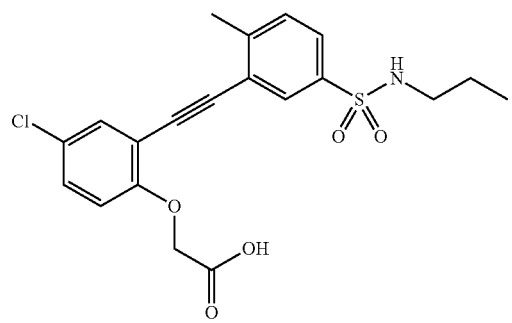 | 0.004 |
| 119 | 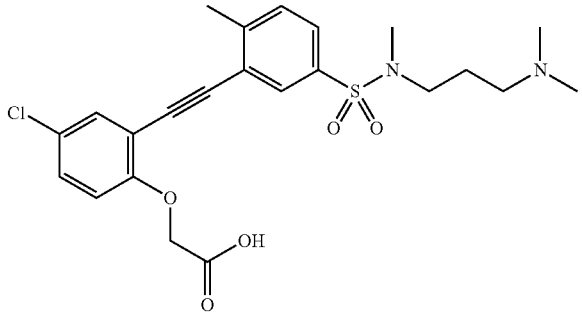 | 0.369 |
| 120 | 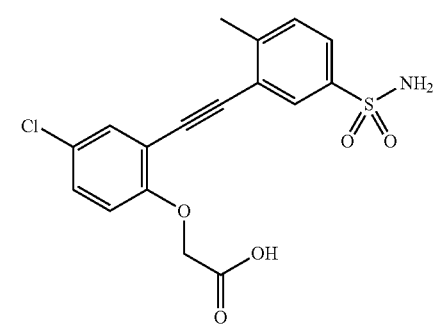 | 0.025 |

-continued

| Example | Formula | IC50 binding (μM) |
|---|---|---|
| 121 | | 0.008 |
| 122 | | 0.452 |
| 123 | | 0.005 |
| 124 | | 0.106 |

-continued

| Example | Formula | IC50 binding (μM) |
|---|---|---|
| 125 | | 0.057 |
| 126 | | 0.060 |
| 127 | | 0.068 |
| 128 | | 0.063 |

| Example | Formula | IC50 binding (μM) |
|---|---|---|
| 129 | | 0.010 |
| 130 | | 0.009 |
| 131 | | 0.024 |
| 132 | | 0.068 |

-continued
| Example | Formula | IC50 binding (μM) |
|---|---|---|
| 133 | 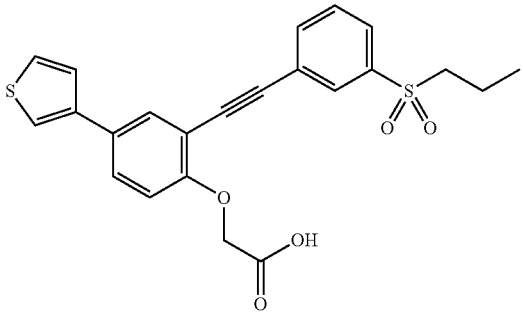 | 0.023 |
| 134 | 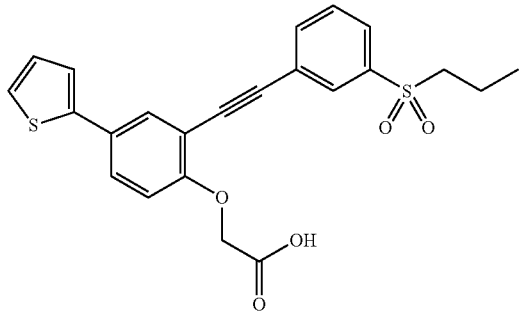 | 0.015 |
| 135 | 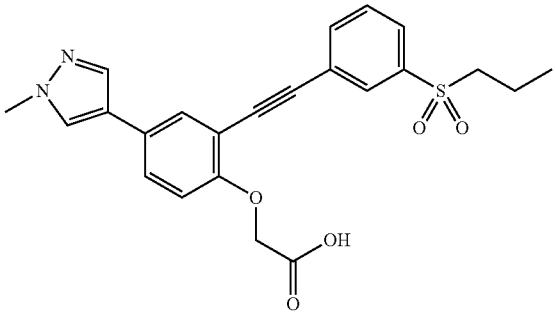 | 0.530 |
| 136 | 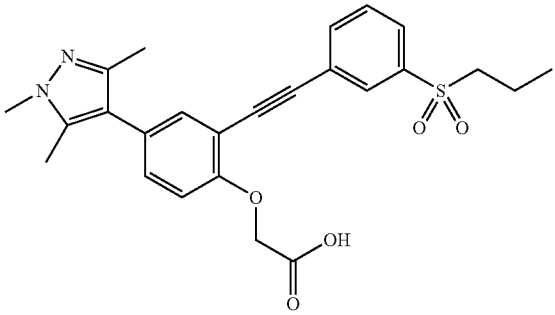 | 0.360 |

-continued

| Example | Formula | IC50 binding (μM) |
| --- | --- | --- |
| 137 | | 0.070 |
| 138 | | 0.150 |
| 139 | | 0.051 |
| 140 | | 0.006 |

| Example | Formula | IC50 binding (μM) |
|---|---|---|
| 141 | 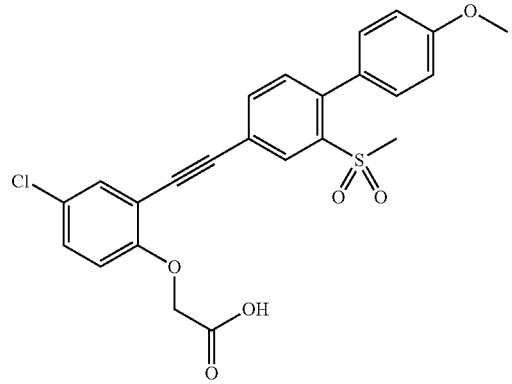 | 0.008 |
| 142 | 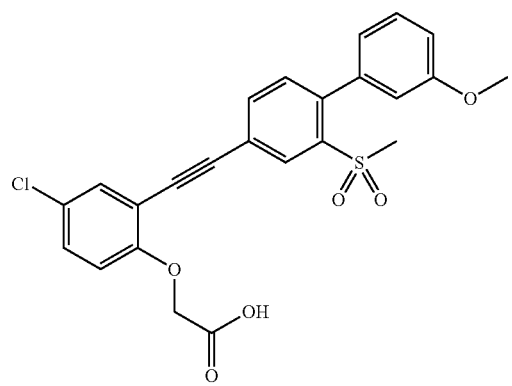 | 0.009 |
| 143 | 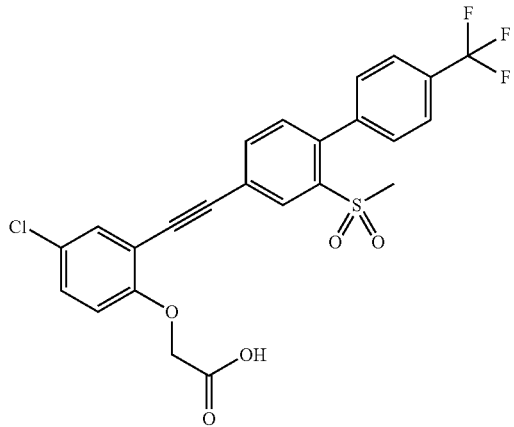 | 0.050 |

-continued

| Example | Formula | IC50 binding (μM) |
|---|---|---|
| 144 | | 0.017 |
| 145 | | 0.019 |
| 146 | | 0.004 |
| 147 | | 0.102 |

| Example | Formula | IC50 binding (μM) |
|---|---|---|
| 148 | 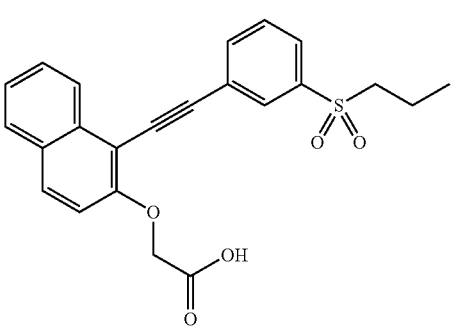 | 0.056 |
| 149 | 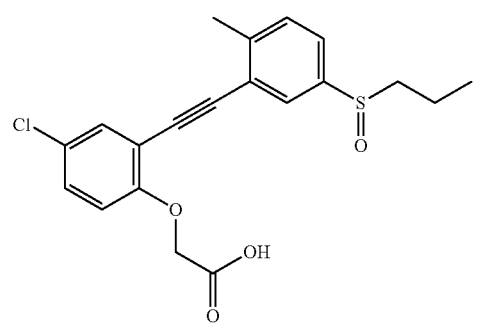 | 0.011 |
| 150 | 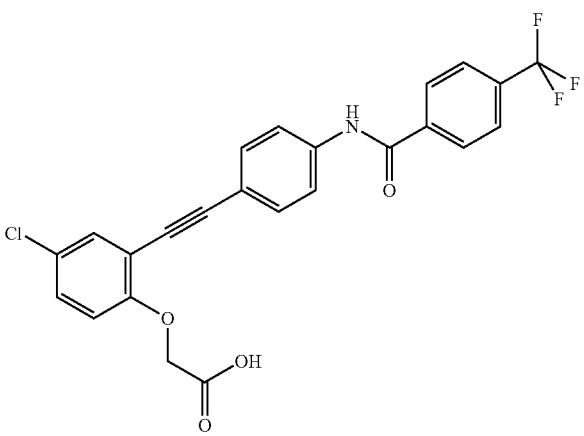 | 0.267 |
| 151 | 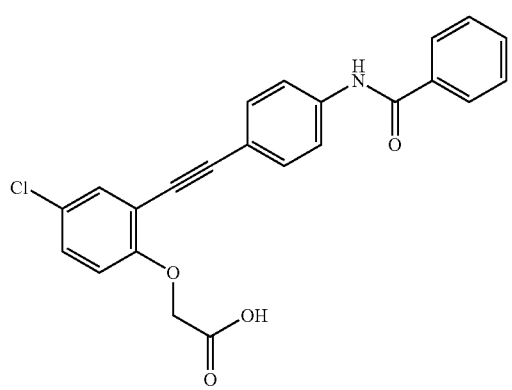 | 0.028 |

-continued

| Example | Formula | IC50 binding (μM) |
|---|---|---|
| 152 | | 0.028 |
| 153 | | 0.001 |
| 154 | | 0.014 |
| 155 | | 0.029 |

-continued

| Example | Formula | IC50 binding (μM) |
|---|---|---|
| 156 | | 0.032 |
| 157 | | 0.017 |
| 158 | | 0.034 |
| 159 | | 0.037 |

-continued

| Example | Formula | IC50 binding (μM) |
|---|---|---|
| 160 | | 0.032 |
| 161 | | 0.024 |
| 162 | | 0.029 |

-continued

| Example | Formula | IC50 binding (μM) |
|---|---|---|
| 163 | | 0.032 |
| 164 | | 0.075 |
| 165 | | 0.053 |
| 166 | | 0.043 |

-continued

| Example | Formula | IC50 binding (μM) |
|---|---|---|
| 167 | | 0.100 |
| 168 | | 0.003 |
| 169 | | 0.287 |
| 170 | | 0.035 |

| Example | Formula | IC50 binding (μM) |
|---|---|---|
| 171 | [structure: 4-chlorophenyl-O-CH(propyl)-COOH linked via alkyne to methylphenyl-SO2-propyl] | 0.066 |
| 172 | [structure: 4-chlorophenyl-O-CH(isobutyl)-COOH linked via alkyne to methylphenyl-SO2-propyl] | 0.060 |
| 173 | [structure: 4-chlorophenyl-O-CH(methyl)-COOH linked via alkyne to methylphenyl-SO2-propyl] | 0.001 |

EXAMPLE 176

[$^{35}$S]GTPγS Binding Assay

The [$^{35}$S]GTPγS assay measures the increase in guanine nucleotide exchange at G-proteins in cell membranes, resulting from agonist (PGD2) binding to CRTH2. This process can be monitored in vitro by incubating cell membranes containing G-proteins and CRTH2 with GDP and [$^{35}$S]GTPγS, a radiolabeled, hydrolysis-resistant analogue of GTP (see, Harrison et al., Life Sciences 74, 489-508, 2003). The addition of a Compounds of Formula (I) results in binding to CRTH2 and thus in an inhibition of agonist binding, which can be monitored as inhibition of the stimulation of GTP/GDP exchange.

Briefly, Compounds of Formula (I) are incubated in 96-well scintillating white polystyrene plates (Perkin Elmer, USA) in a final volume of 200 μl containing 20 mM HEPES/KOH pH 7.4, 3 mM MgCl$_2$, 10 μg/ml Saponin, 5 μM GDP, 75 mM NaCl and 2% of dimethylsulphoxide (DMSO). Reaction is triggered by the addition of 5-10 μg of CHO-CRTH2 cell membranes and 0.15 nM [$^{35}$S]GTPγS. After 60 min incubation at 30° C., reaction is stopped by centrifugation at 700×g, at 4° C. for 10 minutes and supernatant is removed. The radioactivity coming from the [$^{35}$S]GTPγS bound on centrifuged cell membranes is recorded using a 1450 Micro-beta scintillation counter. For IC50 determination, increasing concentrations of compounds are incubated in presence of a fixed concentration of PGD2 (EC$_{80}$). For EC$_{50}$ measurements, compounds are incubated without addition of PGD2. Basal [$^{35}$S]GTPγS activity is determined without addition of any ligands or compounds. 100% [$^{35}$S]GTPγS activity is measured by the addition of 1 μM of PGD2.

In one embodiment, the compounds of Formula (I) of the present invention are antagonists of CRTH2. The results of selected examples are reported in the Table below.

Results:

| Example | IC$_{50}$ (μM) |
|---|---|
| 3 | 0.105 |
| 4 | 0.037 |
| 20 | 0.288 |

-continued

| Example | IC$_{50}$ (μM) |
|---|---|
| 26 | 0.140 |
| 32 | 0.185 |
| 35 | 0.126 |
| 38 | 0.006 |
| 40 | 0.039 |
| 42 | 0.010 |
| 48 | 0.015 |
| 56 | 0.049 |
| 58 | 0.034 |
| 59 | 0.006 |
| 95 | 0.010 |
| 102 | 0.004 |
| 140 | 0.037 |
| 168 | 0.009 |
| 173 | 0.007 |

In another embodiment, the compounds of Formula (I) of the present invention are partial agonists of CRTH2. For example the compound of Example 44 gave an Emax of 13% (100% being the activity measured by the addition of 1 μM of PGD2), with an EC$_{50}$ of 0.040 μM.

In another embodiment, the compounds of Formula (I) of the present invention are inverse agonists of CRTH2. The results of representative examples are reported in the Table below (100% of Emax being the activity measured by the addition of 1 μM of PGD2).
Results:

| Example | EMax |
|---|---|
| 95 | −17% |
| 154 | −17% |
| 107 | −13% |
| 168 | −13% |
| 152 | −13% |
| 140 | −11% |

EXAMPLE 177

Cellular Dielectric Spectroscopy

Cellular Dielectric Spectroscopy (CDS) is a label-free technology based on the measurement of complex impedance changes (delta Z or dZ). Impedance (Z) is related to the ratio of voltage to current as described by Ohm's law (Z=V/I). In order to measure the changes in impedance that occur in response to receptor stimulation, mammalian cells are seeded onto a custom 96-well microliter plate that contains electrodes at the bottom of each well. Key contributors to the impedance measurements are changes in cell-substrate adherence, changes in cell shape and volume, and changes in cell-cell interactions. These factors individually or collectively affect the flow of current, influencing the magnitude and characteristics of the signal measured. G-protein coupled receptors ligand-induced activity can be measured using this technology and specific G protein coupling can be identified. Activities of reference agonist and antagonist molecules of CRTH2 have been measured using this assay and similar results were obtained compared to different functional assays.

CHO-CRTH2 cells are cultured in HAM's F12 (Lonza, Switzerland) supplemented with 10% foetal calf serum (PAA, Australia) and 400 μg/ml Geneticin. 100000 cells/well are seeded in standard 96W Microplates (MDS Analytical Technologies) and incubated at 37° C. in 5% CO$_2$ for 24 hours. Cells are washed twice with 135 μl of cell key buffer (Hank's Balanced Salt Solution 1× (HBSS) (Invitrogen) supplemented with 10 mM HEPES pH 7.4 in presence of 1% DMSO). For EC$_{50}$ determination. 15 μl of increasing concentration of Compounds of Formula (I) diluted in cell key buffer are added to the cells and agonist activity is then recorded for 25 minutes. For IC$_{50}$ determination, 16.6 μl of a fixed concentration of PGD2 (EC80) diluted in cell key buffer is added to the cells-compounds mixture, and antagonist activity is measured during 25 minutes. Results are expressed as the amplitude between the highest and the lowest signal produced (max-min). Basal and maximum activities are measured, respectively in absence or presence of PGD2 (EC$_{80}$).

In one embodiment, the compounds of Formula (I) of the present invention are antagonists of CRTH2. The results of representative examples are reported in the Table below.
Results:

| Example | IC$_{50}$(μM) |
|---|---|
| 15 | 0.074 |
| 17 | 0.022 |
| 35 | 0.023 |
| 38 | 0.032 |
| 42 | 0.025 |
| 43 | 0.269 |
| 48 | 0.009 |
| 53 | 0.050 |
| 54 | 0.037 |
| 56 | 0.053 |
| 59 | 0.014 |
| 67 | 0.034 |
| 70 | 0.021 |
| 71 | 0.015 |
| 86 | 0.118 |
| 87 | 0.083 |
| 89 | 0.029 |
| 95 | 0.084 |
| 100 | 0.023 |
| 101 | 0.038 |
| 102 | 0.016 |
| 103 | 0.044 |
| 107 | 0.023 |

In another embodiment, the compounds of Formula (I) of the present invention are partial agonists of CRTH2. The results of representative examples are reported in the Table below.
Results:

| Example | EC$_{50}$(μM) | EMax |
|---|---|---|
| 15 | 0.053 | 46% |
| 44 | 0.115 | 59% |
| 48 | 0.001 | 12% |
| 55 | 0.024 | 62% |
| 58 | 0.006 | 32% |
| 131 | 0.074 | 68% |

EXAMPLE 178

PGD2-Induced Eosinophil Cell Shape Assay in Human Whole Blood

The Compounds of Formula (I) were diluted in dimethylsulphoxide so that the total volume of dimethylsulfoxide was kept constant at 2% dimethylsulphoxide (Me$_2$SO). Serial dilutions of 200 μM to 0.09 μM were prepared. Samples of 90 μl of human blood from healthy volunteers (Centre de Transfusion Sanguine de Genève) were pre-incubated in polypropylene Falcon tubes (BD 352063) for 20 minutes in a water bath at 37° C. with 10 μl of diluted compounds. For CRTH2 activation, 100 μl PGD2 (Cayman 12010) at 20 nM was added (10 nM final) to each tube and cells were maintained at 37° C. For negative control cells were treated with PBS. After 10 minutes, cell activation was stopped with 120 μl Formaldehyde 10% (4% final, Fluka 41650) and cells were rested for 10 minutes at room temperature. Fixed cells were transferred into polypropylene tubes and then treated for 1 hour in a water bath at 37° C. with 2 ml of Triton-Surfact-Amps X-100 (Pierce 28314) at 0.166% (0.13% Triton final). After several washes with PBS (red cells lysed progressively during washes, two washes are necessary), cells were analyzed by flow cytometry on a FACSCalibur. In one embodiment, the compounds of Formula (I) of the present invention are capable of blocking the cell shape change of eosinophils induced by PGD2 in Whole Blood. The results of representative examples are reported in the Table below.

Results:

| Example | $IC_{50}$(μM) |
| --- | --- |
| 17 | 0.150 |
| 26 | 0.679 |
| 33 | 0.064 |
| 35 | 0.289 |
| 38 | 0.081 |
| 48 | 0.095 |
| 49 | 1.190 |
| 58 | 0.095 |
| 65 | 0.123 |
| 83 | 0.077 |
| 89 | 0.023 |
| 100 | 0.100 |
| 101 | 0.023 |
| 102 | 0.091 |
| 103 | 0.067 |
| 107 | 0.023 |
| 109 | 0.077 |
| 117 | 0.088 |

EXAMPLE 179

In Vivo Pharmacokinetic Evaluation in Rat and Mouse

In order to study the pharmacokinetic (PK) profile of test compounds in vivo, Sprague Dawley male rats or C57BL/6 female mice were dosed intravenously or after oral gavage. For both species, test compounds were dosed in solution at 1 mg/kg for i.v. route (10% ethanol, 10% N,N-dimethylacetamide, 30% propylene glycol, 50% water, v/v) and in suspension at 5 mg/kg (0.5% carboxymethylcellulose suspension, containing 0.25% Tween 20 in water) for oral gavage. PK profile in rat was obtained from 3 animals per dosing route and mouse PK profile was determined from 3 animals for each time points. The volume of administration was 2 mL/kg for i.v. dosing in both species and either 5 mL/kg (rat) or 10 mL/kg (mouse) for oral gavage. Blood samples (100 μL/time point) were collected at 0.083 (5 min), 0.25, 0.5, 1, 4, 7 and 24 hours post-dose for i.v. dosing, and at 0.5, 1, 4, 7 and 24 h for oral dosing, into heparin-Li+ containing tubes. For rats, all blood samples were collected trough a catheter in the carotid artery (placed in the artery the day before the experiment), under light isoflurane anesthesia, and stored on ice until centrifugation and plasma isolation. For mouse, blood samples were collected from intracardiac puncture at sacrifice at each time point and processed as described above for the rat. Plasma samples were stored frozen until analysis (−20° C. to −70° C.). For bioanalysis, samples were processed by protein precipitation (acetonitrile, formic acid 0.1%, addition of 3 volumes) after addition of one internal standard and analysed using a sensitive and selective LC/MS/MS method. An aliquot of the resulting supernatant was subject to LC/MS/MS analysis using a reverse phase column (Waters Xterra, C8, (3.5 μm particle size, 2.1×50 mm) and a short gradient (1 min) from (Solvent A) 85% water, 15% acetonitrile and 0.1% formic acid to (Solvent B) 90% acetonitrile, 10% water and 0.1% formic acid followed by isocratic conditions of Solvent B for 3.5 min at 0.4 mL/min. Column effluent was monitored using a Sciex API 4000 triple quadrupole mass spectrometer with a Turbo V electrospray ion source. Unknown concentrations of test compounds were determined using a calibration curve ranging from 1 to 3000 ng/mL.

Pharmacokinetic Profile in Mice of Representative Compounds

| Compound | Clearance iv (1 mg/Kg) (L/Kg/h) | AUC po (5 mg/Kg) (h*ng/ml) | Oral bioavailability |
| --- | --- | --- | --- |
| Example 17 | 0.3 | 5768 | 37% |
| Example 35 | 0.8 | 6213 | 95% |
| Example 38 | 1.0 | 3685 | 80% |
| Example 89 | 0.4 | 6752 | 63% |
| Example 101 | 1.0 | 5795 | 110% |
| Example 102 | 0.35 | 18691 | 130% |
| Example 103 | 0.7 | 4889 | 64% |
| Example 107 | 0.6 | 4880 | 58% |
| Example 154 | 0.1 | 30942 | 57% |

Pharmacokinetic Profile in Rat of a Representative Compound

| | Clearance iv (1 mg/Kg) (L/Kg/h) | AUC po (5 mg/Kg) (h*ng/ml) | Oral bioavailability |
| --- | --- | --- | --- |
| Example 17 | 0.4 | 3695 | 28% |

EXAMPLE 180

OVA-Induced Lung Eosinophilia in Mice

BALB/c mice (6-8 weeks old) were immunized with ovalbumin (10 μg i.p) on day 0 and 7. In order to elicit a local inflammatory response in the lung, mice were challenged between day's 15-17 with a nebulised solution of ovalbumin (10 μg/ml; De Vilibiss Ultraneb 2000, once daily for 30 min during the 3 days). On each separate day between 15 and 17 each animal received via oral gavage the test compound, at t−1 h and t+7 h with respect to OVA exposure at t=0 h. Eight hours after the final OVA challenge, bronchoalveolar lavage (BAL) was then carried out. Total cell numbers in the BAL fluid samples were measured using a haemocytometer. Cytospin smears of the BAL fluid samples were prepared by centrifugation at 1200 rpm for 2 min at room temperature and stained using a DiffQuik stain system (Dade Behring) for differential cell counts. Compounds of Formula (I) of the present invention were tested at 3, 10 and 30 mg/Kg. Selected compounds showed a significant decrease of cell numbers in BALF. For example the compounds of Examples 38 and 89 showed the % inhibition of total cells and eosinophils as showed in the table below.

| Compound | Dose (mg/kg) | % inhibition total cells (mean ± s.e.m.) | % inhibition eosinophils (mean ± s.e.m.) |
| --- | --- | --- | --- |
| Dexamethasone | 1 | 88 ± 11 | 90 ± 10 |
| | 3 | 21 ± 13 | 29 ± 14 |
| Example 38 | 10 | 42 ± 14 | 54 ± 16 |
| | 30 | 67 ± 8 | 81 ± 7 |
| | 3 | 12 ± 15 | 19 ± 18 |
| Example 89 | 10 | 19 ± 8 | 27 ± 10 |
| | 30 | 44 ± 10 | 55 ± 11 |

EXAMPLE 181

FITC 1 Week Model

Fluorescein isothiocyanate (FITC) induced contact hypersensitivity (CHS) is a commonly used model for atopic dermatitis (AD). The hapten FITC is a small molecule that is able to elicit an immune response only when attached to a larger carrier such as a protein. It is reactive towards e-amino groups (lysine). The immune response to FITC sensitization and challenge is Th2 cytokine driven (IL-4, IL-5, IL-6, IL-10 and IL-13) and associated with elevated serum IgE levels. The skin inflammation at the site of the challenge is characterized by edema and eosinophil infiltrations.

Female 9 week old Balb/C mice were sensitized on days 0 and 1 with 0.5% FITC in acetone/dibuthylphtalate (A/DBP). One group (sham) was sensitized with A/DBP alone. On day 6 all the mice including the sham group were challenged on the right ear (inner and outer surface) with 0.5% FITC in A/DBP. The mice were treated with the compounds via oral gavage 1 h before and 7 h after the challenge. The baseline ear thickness was measured before the challenge and 24 h after the challenge. At the end of the experiment (24 h after the challenge) the mice were sacrificed. Serum and plasma samples were taken. The challenged ear was excised and stored at −80° C. Compounds of Formula (I) of the present invention were tested at 3, 10 and 30 mg/Kg. Selected compounds showed a significative decrease of ear swelling. For example the compounds of Examples 38, 89 and 154 showed the % inhibition of ear swelling as showed in the table below.

| Compound | dose (mg/kg) | % inhibition (mean ± s.e.m.) |
| --- | --- | --- |
| | 30 | 52 ± 12 |
| Example 38 | 10 | 56 ± 12 |
| | 3 | 23 ± 16 |
| | 30 | 48 ± 11 |
| Example 89 | 10 | 54 ± 16 |
| | 3 | 36 ± 19 |
| | 30 | 54 ± 17 |
| Example 154 | 10 | 49 ± 9 |
| | 3 | 41 ± 9 |

EXAMPLE 182

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:
1. A compound of Formula (I)

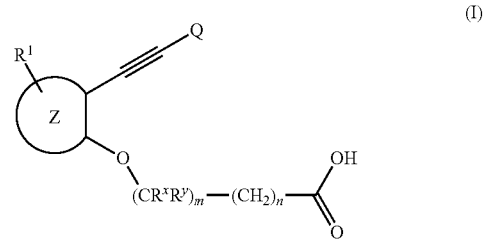

wherein:
$R^1$ is H, Hal, A, CN, $NO_2$, OA, $CF_3$, $OCF_3$, Ar or Het,
Q is Ar, Het,
n is 0, 1, 2, 3, or 4,
m is 0, 1 or 2 wherein n+m is not 0,
Z is phenyl, naphthyl or pyridinyl,
A is branched or linear alkyl having 1 to 12 C-atoms, wherein one or more, preferably 1 to 7 H-atoms may be replaced by Hal, $OR^3$, CN or $N(R^3)_2$ and wherein one or more, preferably 1 to 7 non-adjacent $CH_2$-groups may be replaced by O, $NR^3$ or S and/or by CH=CH— or —C≡C— groups, or denotes cycloalkyl or cycloalkylalkylen having 3 to 7 ring C atoms,
Hal is F, Cl, Br or I,
Ar denotes a monocyclic or bicyclic, unsaturated or aromatic carbocyclic ring having 6 to 14 carbon atoms which may be unsubstituted or monosubstituted, disubstituted or trisubstituted or tetrasubstituted by Hal, A, —$CH_2$OA, —$CH_2SO_2$A, —$CH_2OR^3$, —$OR^3$, $CF_3$, —$N(R^3)_2$, $NO_2$, —CN, —$NR^3$COA, —$NR^3$COAr', —$NR^3SO_2$A, —$COR^3$, $CON(R^3)_2$, COHet, —$SO_2$N$(R^3)_2$, —SOA, —$SO_2$A, Het, or by $SO_2$T, SOT, or Ar',
T denotes —$(CH_2)_p$—Ar' or —$(CH_2)_p$-Het',
p is 0, 1, 2, 3 or 4,
Ar' denotes a monocyclic or bicyclic, aromatic carbocyclic ring having 6 to 14 carbon atoms which may be unsubstituted or monosubstituted, disubstituted or trisubstituted by Hal, A, —$CH_2$OA, —$CH_2OR^3$, —$OR^3$, —$CF_3$, or —$OCF_3$, Het' denotes a monocyclic or bicyclic, saturated, unsaturated or aromatic heterocyclic ring, having 1 to 4 N, O and/or S atoms, which may be unsubstituted or monosubstituted, disubstituted or trisubstituted by Hal, A, $CH_2OA$, $OR^3$, $CF_3$, or $OCF_3$, Het denotes a monocyclic or bicyclic or tricyclic, saturated, unsaturated or aromatic heterocyclic ring, having 1 to 4 N, O, S atoms, and/or 1 $SO_2$ and/or CO groups and/or NO groups, which may be unsubstituted or monosubstituted, disubstituted or trisubstituted or tetrasubstituted by Hal, A, $CH_2OA$, $OR^3$, $CF_3$, $OCF_3$, $N(R^3)_2$, $NO_2$, CN, $NR^3COA$, $NR^3SO_2A$, $COR^3$, $SO_2N(R^3)_2$, SOA, $SO_2A$, or $SO_2T$, $R^3$ is H or A, $R^x$, $R^y$ independently denote H, a linear or branched alkyl having 1 to 8 carbon atoms optionally substituted with OH, Hal, CN, or $R^x$ and $R^y$ together form a carbocyclic ring having 3 to 7 carbon atoms, optionally substituted by OH, Hal, or CN;

and esters, geometrical isomers, optically active enantiomers, racemates or tautomers thereof.

2. The compound according to claim 1, wherein the compound is of Formula (Z),

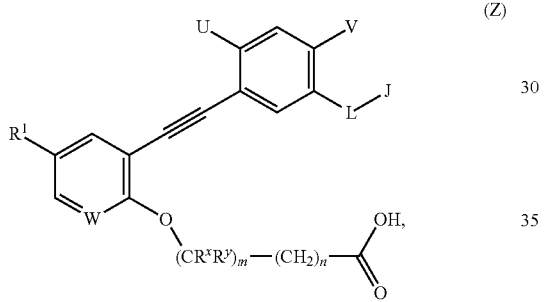

wherein $R^1$, $R^x$, $R^y$, m and n are as defined in claim 1,

L denotes $SO_2$, SO, or O,

W denotes C or N,

U denotes H, Hal, $R^Z$,

V denotes H, Ar', $R^Z$, $COR^Z$, or $CONHR^Z$, and if linked to J also —CO—, —$CONR^Z$, or an arylen, J denotes $R^Z$, $NHR^Z$, $N(R^Z)_2$, or $(CH_2)_sAr'$, wherein s is 0 or 1; and if linked to V also —$NR^Z$, or $(CH_2)_sAr''$; or when L is O, J also denotes H, and wherein J and V may be linked to each other to form a ring, $R^Z$ denotes a linear or branched alkyl or alkenyl having 1 to 6 carbon atoms, optionally substituted by OH, or $OCH_3$, Ar'' denotes an arylen which may be further substituted by 1 or 2 groups selected from $OR^3$, Hal, or $CF_3$, wherein $R^3$ is as defined in claim 1.

3. The compound according to claim 1, wherein Q is selected from the following groups:

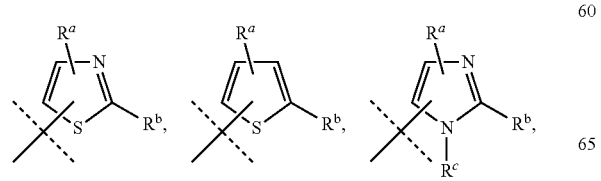

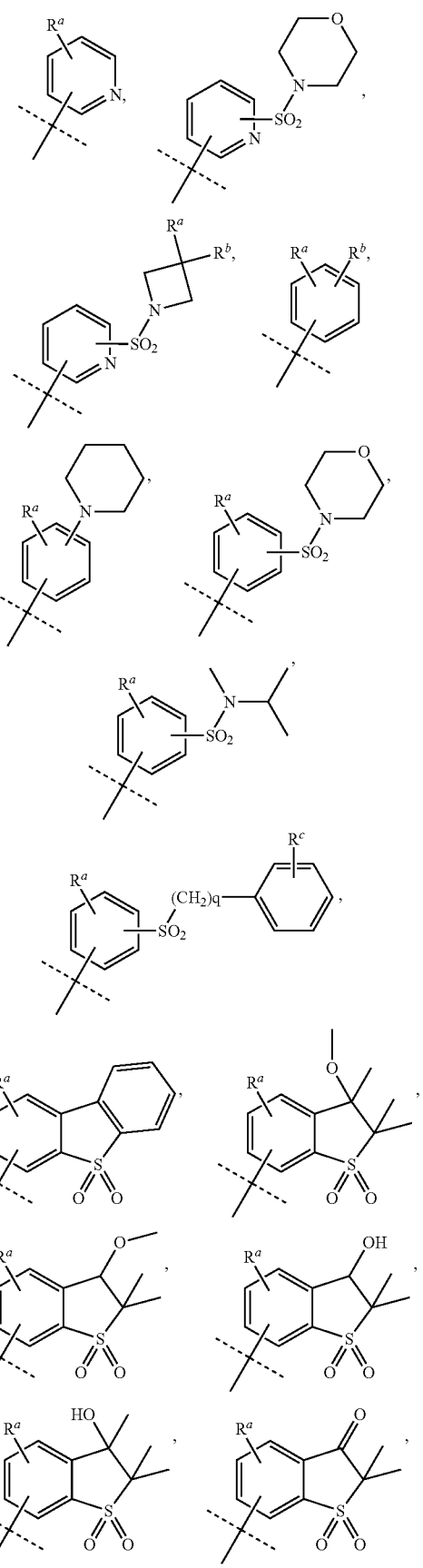

-continued

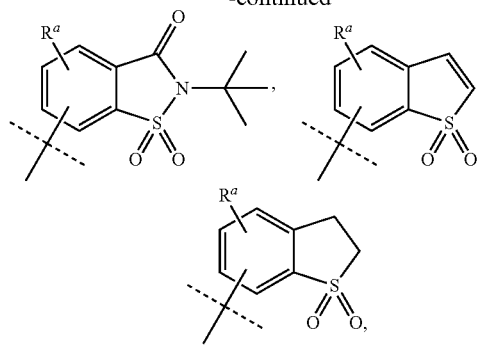

wherein $R^a$ and $R^b$ independently from one another denotes an alkyl group having 1 to 6 carbon atoms, H, Hal, CN, OH, $CF_3$, —OMe, —OEt, $(CH_2)_qCH_3$, —$(CH_2)_q(CH)(CH_3)_2$, $SO_2NH(CH_2)_qCH_3$, —$SO_2NH(CH_2)_qC(CH_3)_3$, —$SO_2N(C_2H_5)_2$, —$SO_2N(CH_3)_2$, —$SO_2(CH_2)_qCH_3$, —$SO_2(CH)(CH_3)_2$, —$SO_2(CH_2)_qCH(CH_3)_2$, —$SO_2NH(CH_2)_qOH$, —$SO_2(CH_2)_qOH$, —$SO_2NH(CH_2)_qO(CH_2)_qCH_3$, —$SO_2(CH_2)_qO(CH_2)_qCH_3$, $N(CH_3)$—$SO_2$—$(CH_2)_qCH_3$, —Ar', —$(CH_2)Ar'$, or $SO_2T$, wherein q denotes 0, 1, 2, 3 or 4, and wherein $R^c$ denotes H, Me, or Et.

4. The compound according to claim 1, wherein $R^1$ denotes one of the following groups: H, Cl, F, CN, —$CH_3$, —$CF_3$, a phenyl group optionally substituted by an alkyl having 1 to 6 carbon atoms,

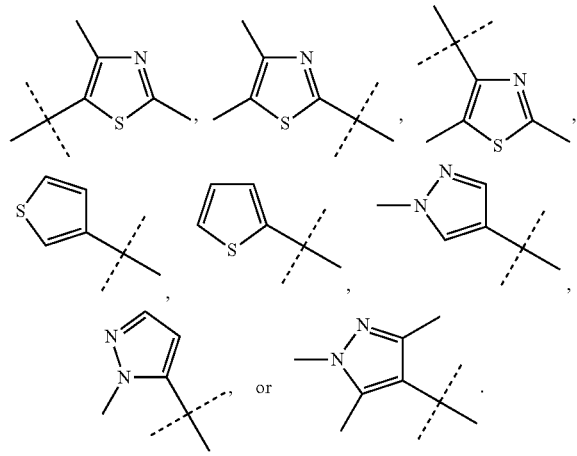

5. The compound according to claim 1, said compound being selected from:

| Ex. | Formula |
|---|---|
| 1 | 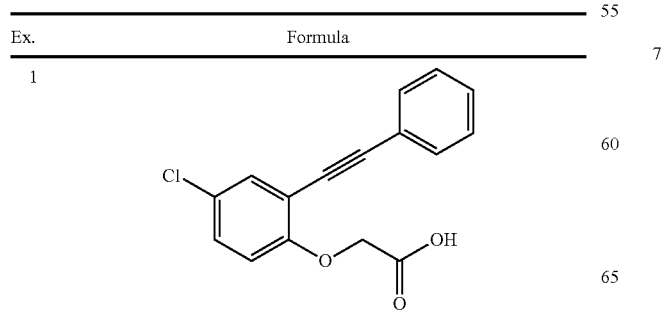 |

-continued

| Ex. | Formula |
|---|---|
| 2 | 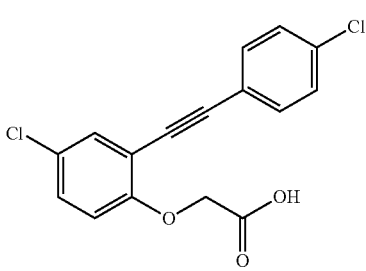 |
| 3 | 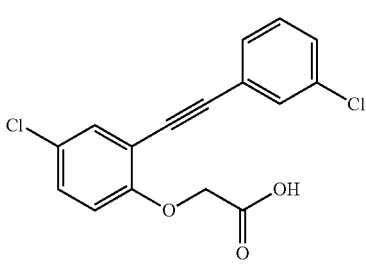 |
| 4 | 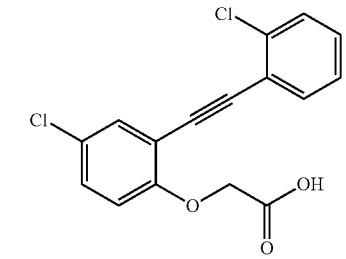 |
| 5 | 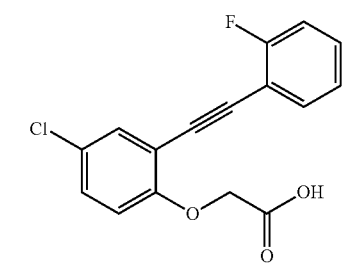 |
| 6 | 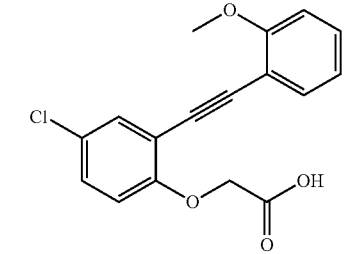 |
| 7 | 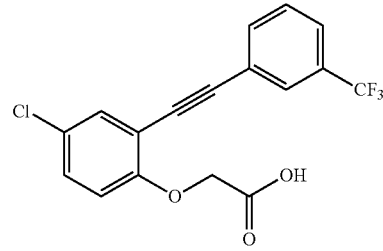 |

-continued

| Ex. | Formula |
|---|---|
| 8 | 2-(4-chloro-2-((2,4-difluorophenyl)ethynyl)phenoxy)acetic acid |
| 9 | 2-(4-chloro-2-((2-(trifluoromethyl)phenyl)ethynyl)phenoxy)acetic acid |
| 10 | 2-(4-chloro-2-((5-chlorothiophen-2-yl)ethynyl)phenoxy)acetic acid |
| 11 | 2-(4-chloro-2-((1-methyl-1H-imidazol-2-yl)ethynyl)phenoxy)acetic acid |
| 12 | 2-(4-chloro-2-(pyridin-4-ylethynyl)phenoxy)acetic acid |
| 13 | 2-(4-chloro-2-(pyridin-2-ylethynyl)phenoxy)acetic acid |

-continued

| Ex. | Formula |
|---|---|
| 14 | 2-(4-chloro-2-(pyridin-3-ylethynyl)phenoxy)acetic acid |
| 15 | 2-(4-chloro-2-((4-methylpyridin-3-yl)ethynyl)phenoxy)acetic acid |
| 16 | 2-(4-chloro-2-((5-(N-ethylsulfamoyl)-2-methylphenyl)ethynyl)phenoxy)acetic acid |
| 17 | 2-(4-chloro-2-((3-(propylsulfonyl)phenyl)ethynyl)phenoxy)acetic acid |
| 18 | 2-(4-chloro-2-((3-(methylsulfonyl)phenyl)ethynyl)phenoxy)acetic acid |
| 19 | 2-(4-chloro-2-((3-((3-hydroxypropyl)sulfonyl)phenyl)ethynyl)phenoxy)acetic acid |

| Ex. | Formula |
|---|---|
| 20 | 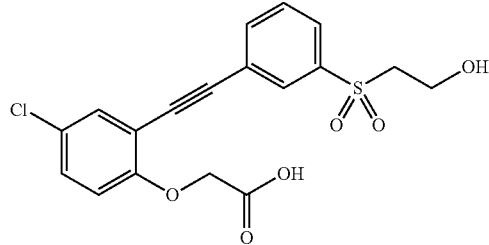 |
| 21 | 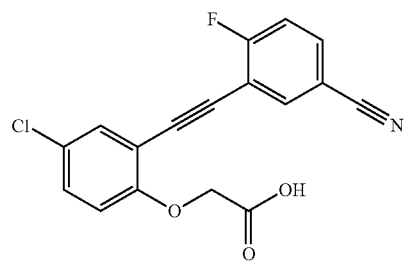 |
| 22 | 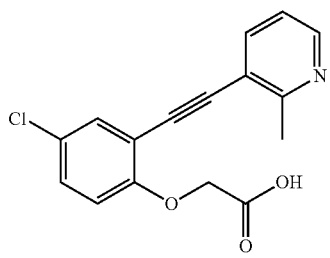 |
| 23 | 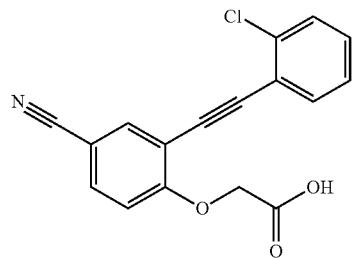 |
| 24 | 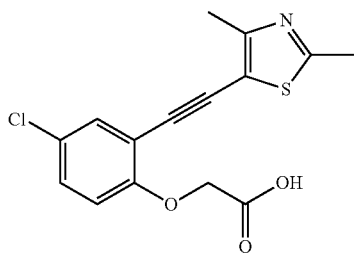 |
| 25 | 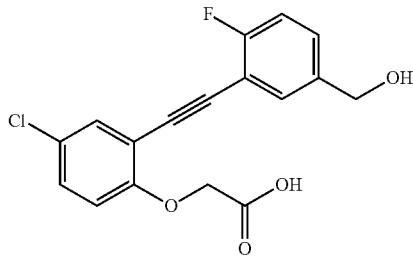 |
| Ex. | Formula |
|---|---|
| 26 | 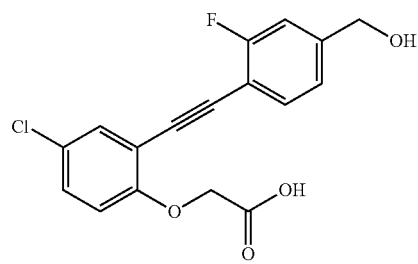 |
| 27 | 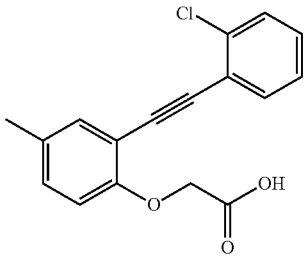 |
| 28 | 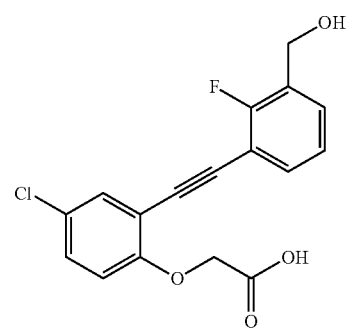 |
| 29 | 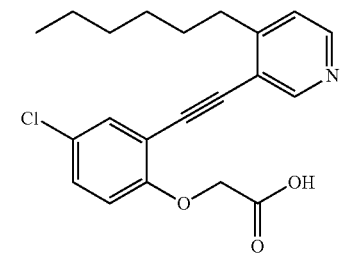 |
| 30 | 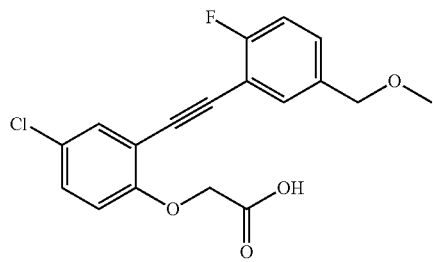 |

| Ex. | Formula |
|---|---|
| 31 | (4-chloro-2-((4-methyl-1-oxidopyridin-3-yl)ethynyl)phenoxy)acetic acid |
| 32 | (4-cyano-2-((3-(propylsulfonyl)phenyl)ethynyl)phenoxy)acetic acid |
| 33 | (4-chloro-2-((2-methyl-5-(methylsulfonyl)phenyl)ethynyl)phenoxy)acetic acid |
| 34 | (4-chloro-2-((2-fluoro-4-(methoxymethyl)phenyl)ethynyl)phenoxy)acetic acid |
| 35 | (4-chloro-2-((5-(N,N-dimethylsulfamoyl)pyridin-3-yl)ethynyl)phenoxy)acetic acid |

| Ex. | Formula |
|---|---|
| 36 | (4-chloro-2-((5-(methylsulfonyl)pyridin-3-yl)ethynyl)phenoxy)acetic acid |
| 37 | (2-((2-chlorophenyl)ethynyl)-5-fluorophenoxy)acetic acid |
| 38 | (4-chloro-2-((2-methyl-5-(propylsulfonyl)phenyl)ethynyl)phenoxy)acetic acid |
| 39 | (4-chloro-2-((5-(methylsulfonamido)pyridin-3-yl)ethynyl)phenoxy)acetic acid |

| Ex. | Formula |
|---|---|
| 40 | 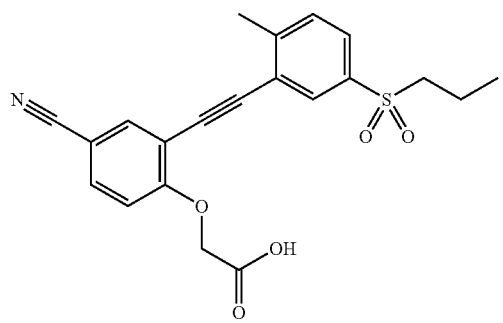 |
| 41 | 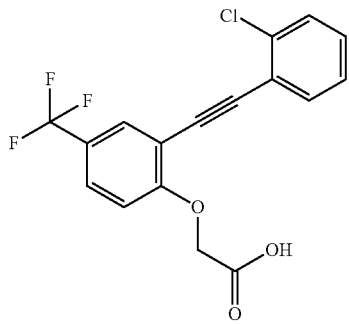 |
| 42 | 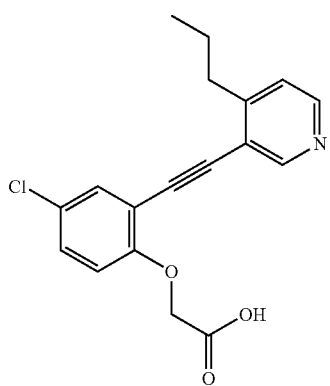 |
| 43 | 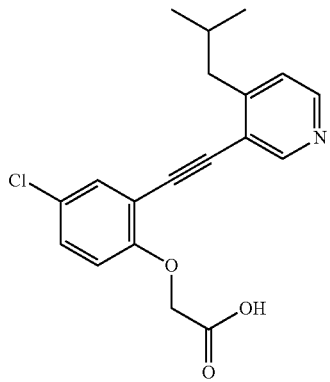 |
| Ex. | Formula |
|---|---|
| 44 | 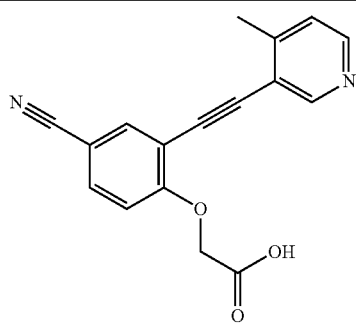 |
| 45 | 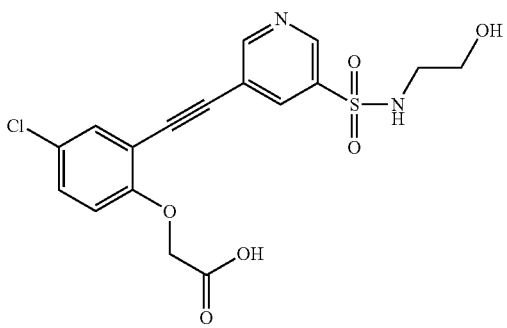 |
| 46 | 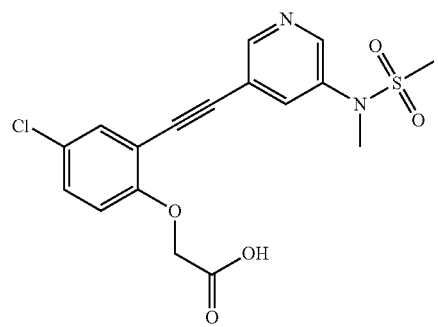 |
| 47 |  |

| Ex. | Formula |
|---|---|
| 48 | 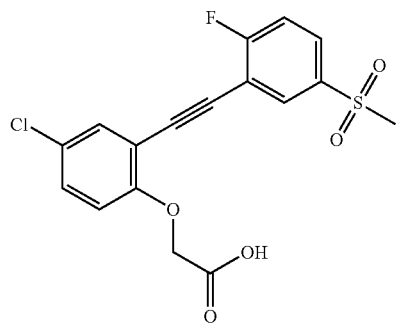 |
| 49 | 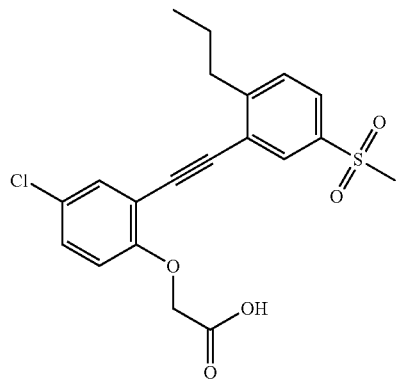 |
| 50 | 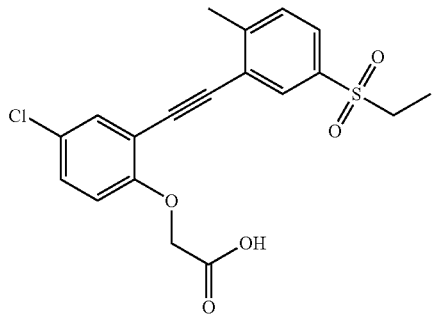 |
| 51 | 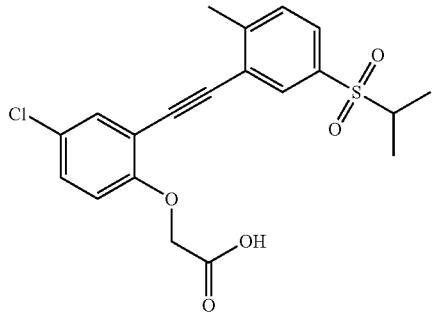 |
| Ex. | Formula |
|---|---|
| 52 | 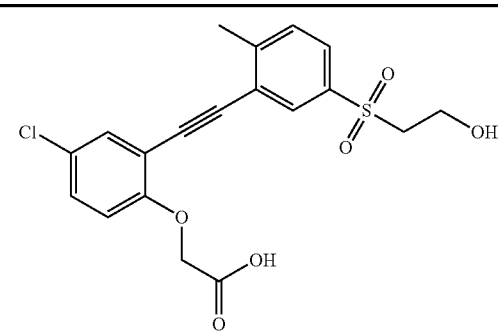 |
| 53 | 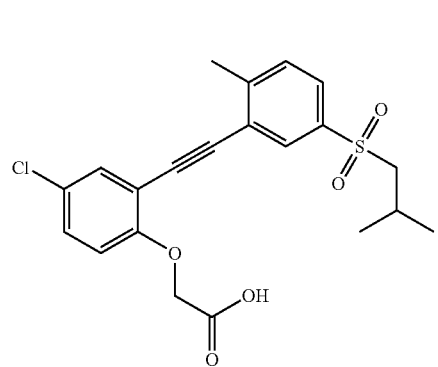 |
| 54 | 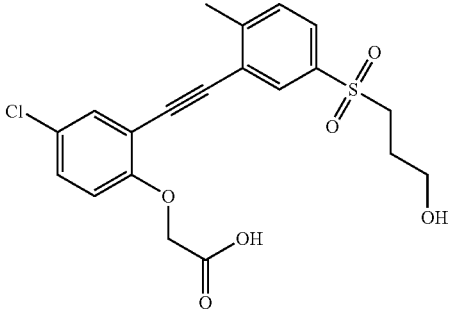 |
| 55 | 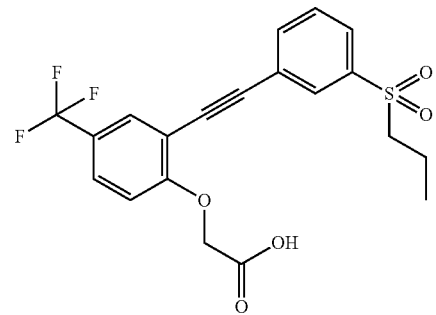 |

| Ex. | Formula |
|---|---|
| 56 | 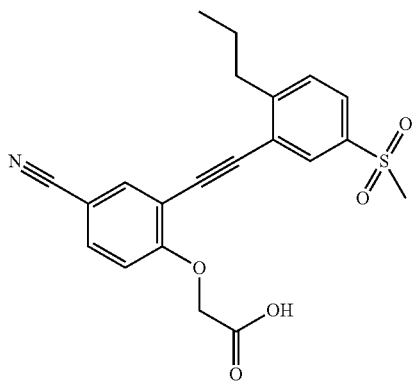 |
| 57 | 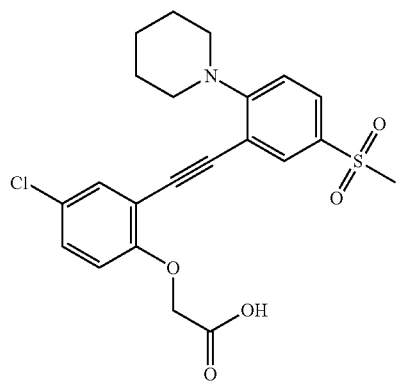 |
| 58 | 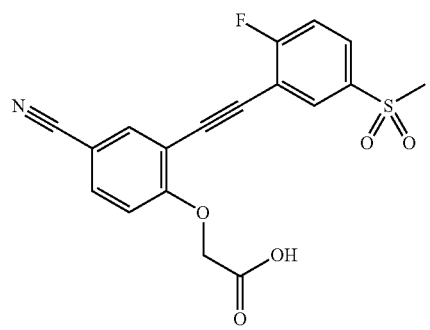 |
| 59 | 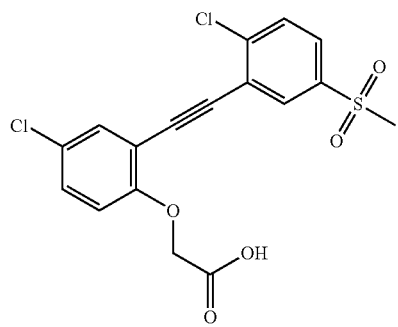 |
| 60 | 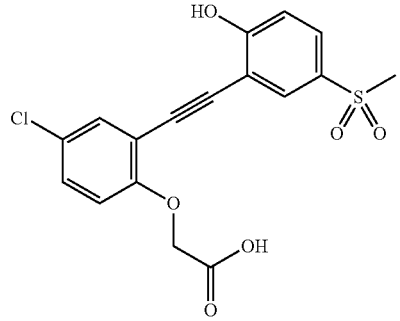 |
| 61 | 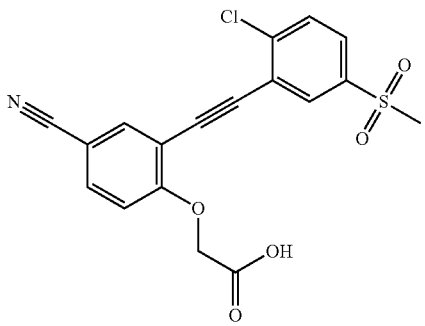 |
| 62 | 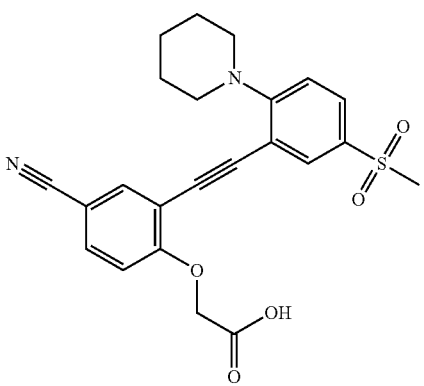 |
| 63 | 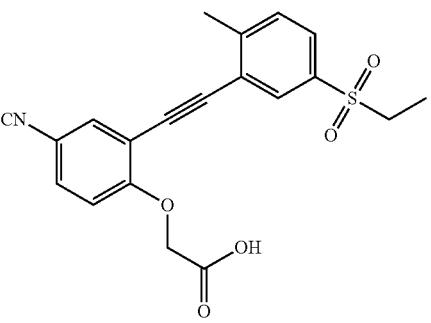 |

| Ex. | Formula |
|---|---|
| 64 | 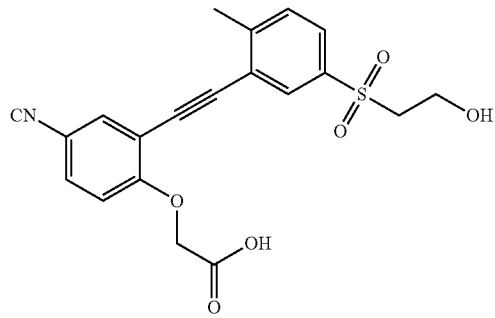 |
| 65 | 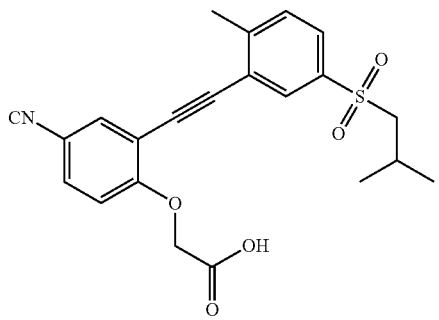 |
| 66 | 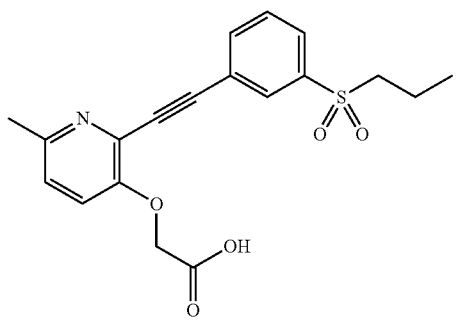 |
| 67 | 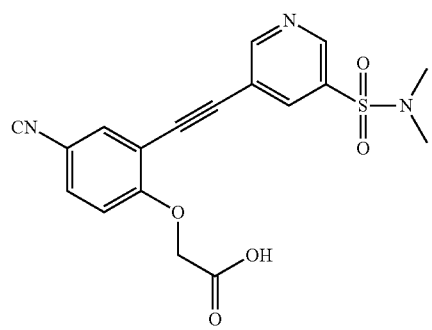 |
| 68 | 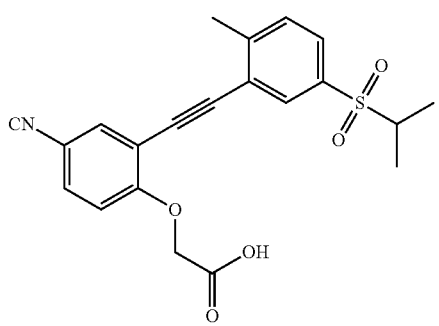 |
| Ex. | Formula |
|---|---|
| 69 | 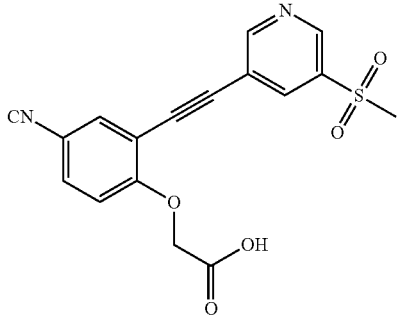 |
| 70 | 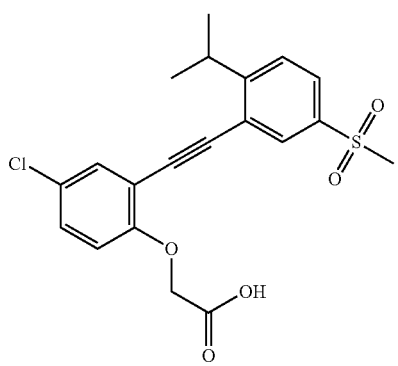 |
| 71 | 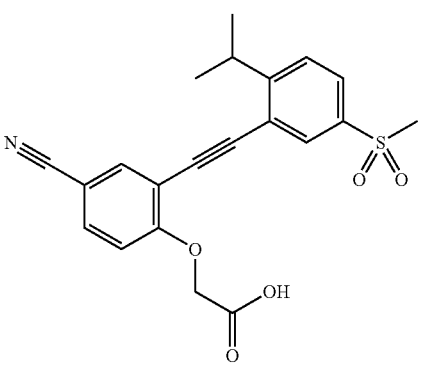 |
| 72 | 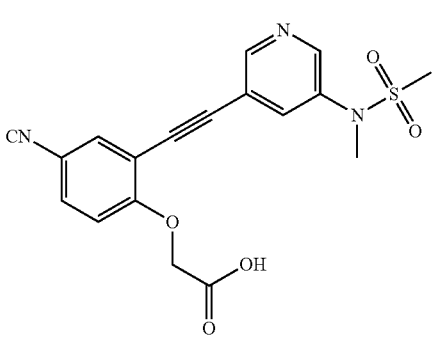 |

387
-continued
| Ex. | Formula |
|---|---|
| 73 | 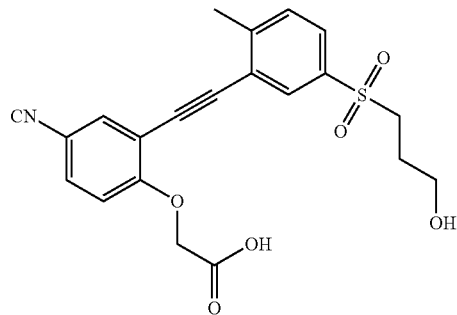 |
| 74 | 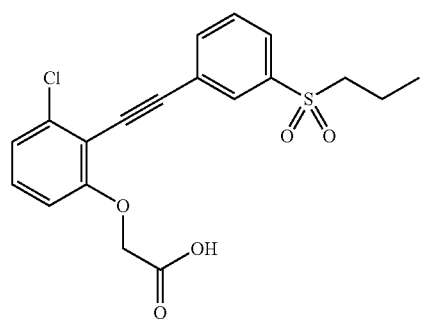 |
| 75 | 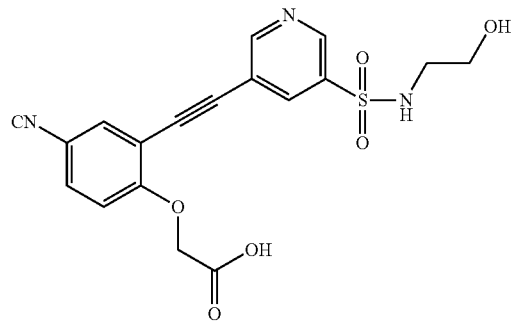 |
| 76 | 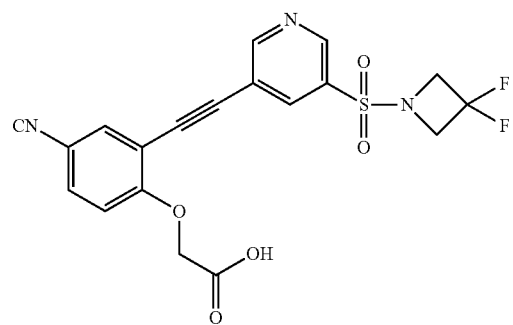 |
388
-continued
| Ex. | Formula |
|---|---|
| 77 | 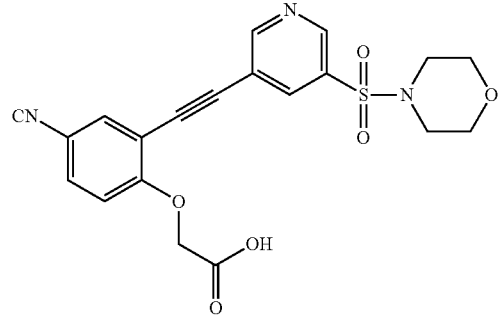 |
| 78 | |
| 79 | |
| 80 | 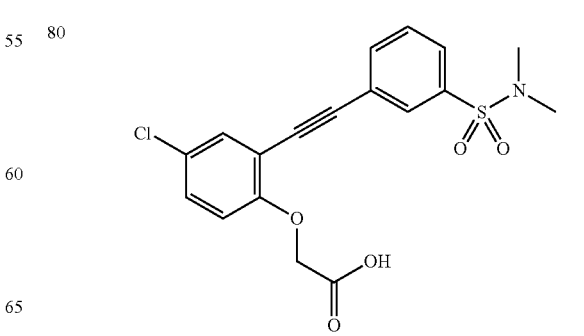 |

| Ex. | Formula |
|---|---|
| 81 | |
| 82 | |
| 83 | |
| 84 | |
| 85 | |
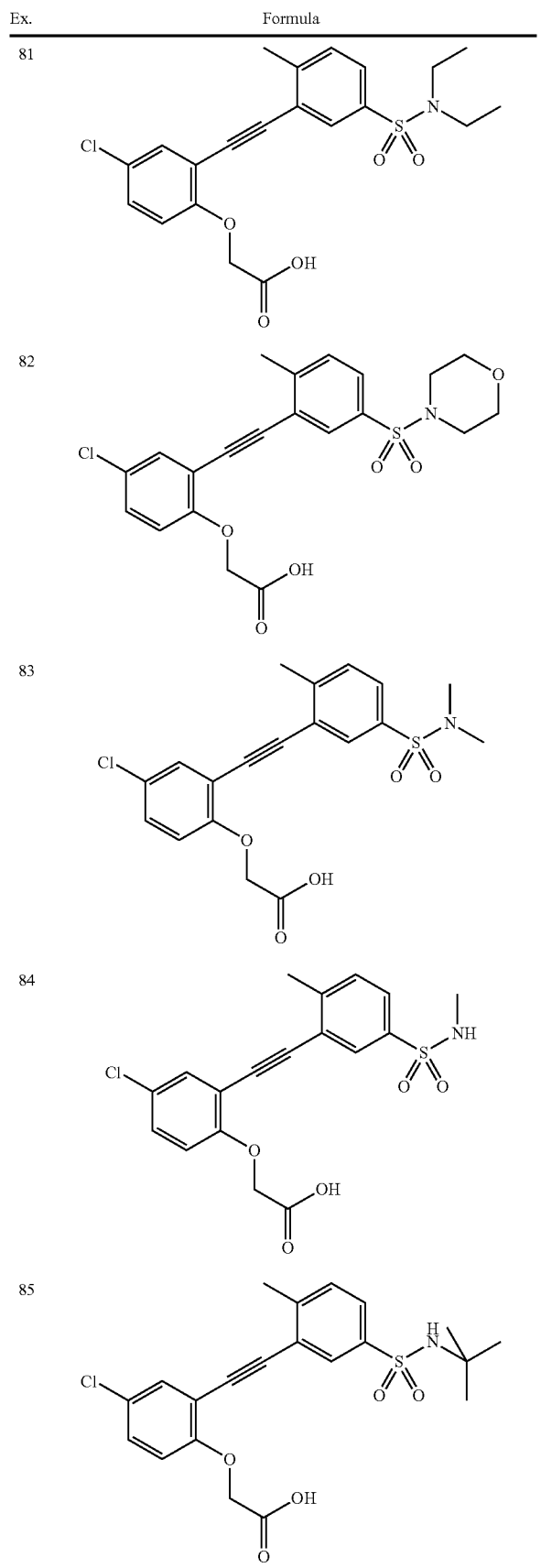
| Ex. | Formula |
|---|---|
| 86 | |
| 87 | |
| 88 | |
| 89 | |
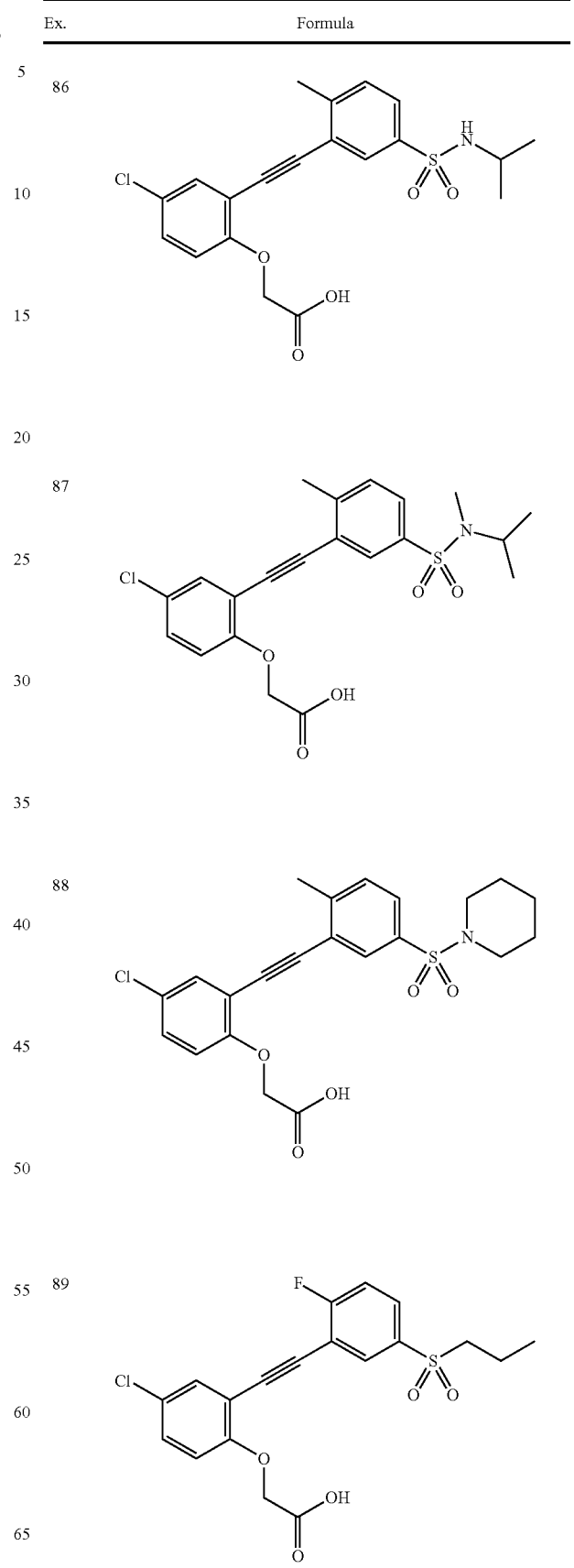

-continued
| Ex. | Formula |
|---|---|
| 90 | 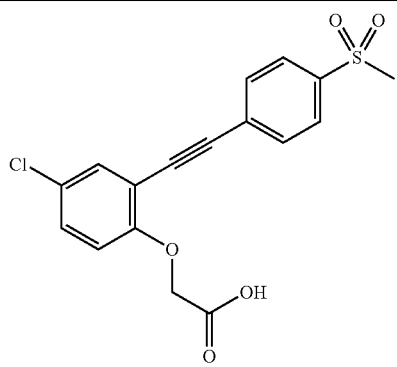 |
| 91 | 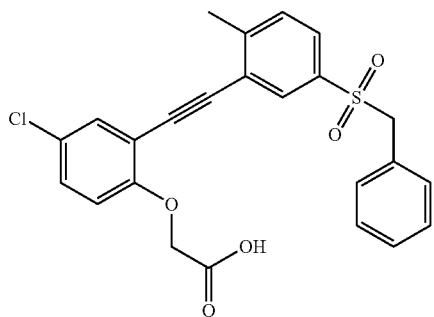 |
| 92 | 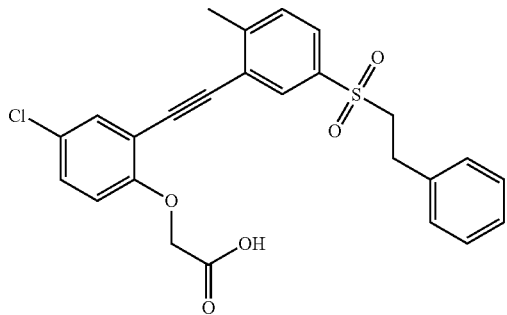 |
| 93 | 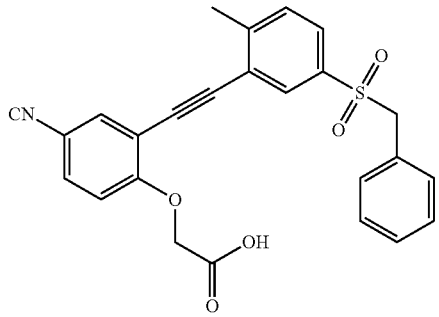 |
-continued
| Ex. | Formula |
|---|---|
| 94 | 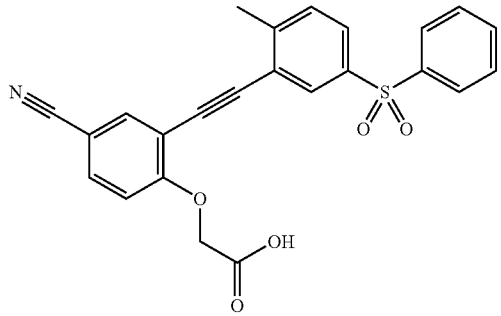 |
| 95 | 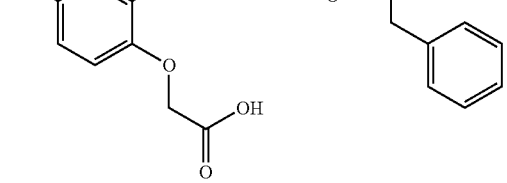 |
| 96 | 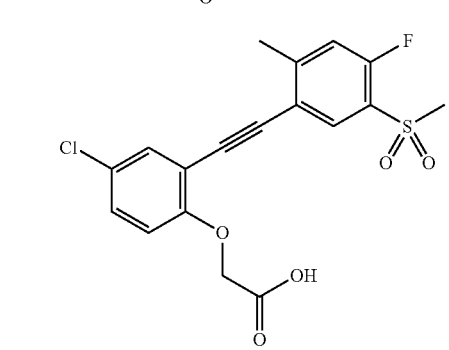 |
| 97 | 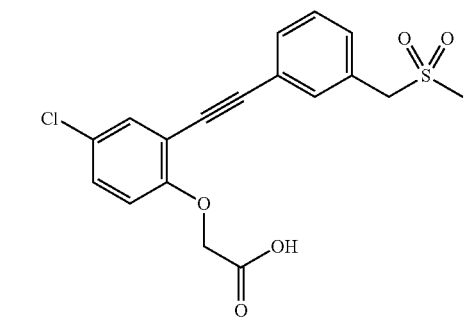 |
| 98 | |

| Ex. | Formula |
|---|---|
| 99 | 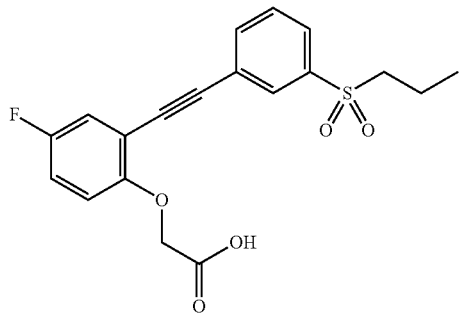 |
| 100 | 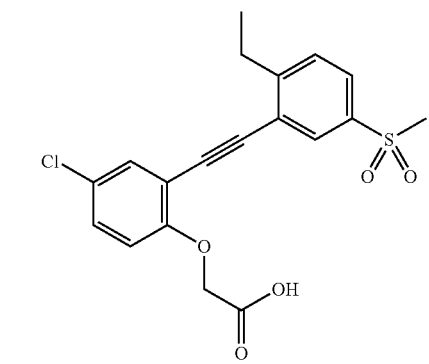 |
| 101 | 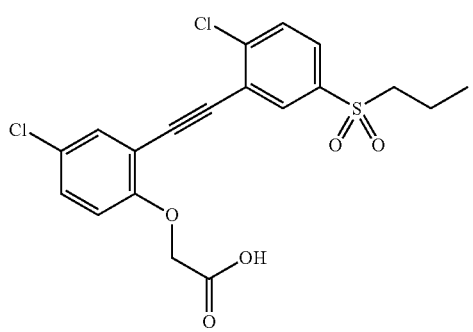 |
| 102 | 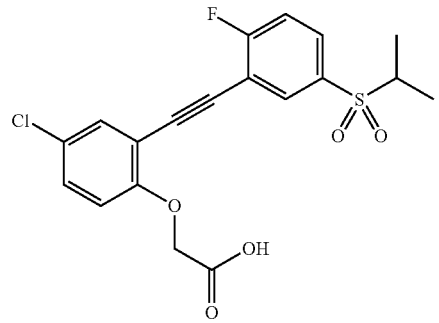 |
| Ex. | Formula |
|---|---|
| 103 | 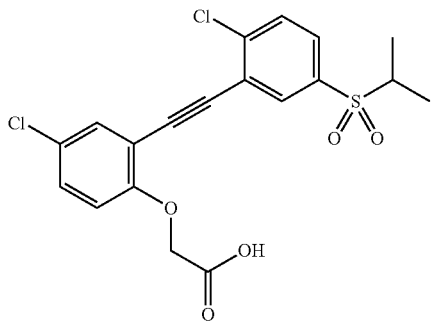 |
| 104 | 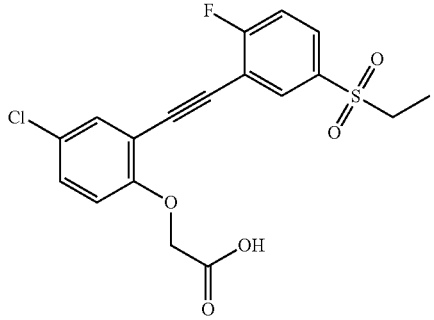 |
| 105 | 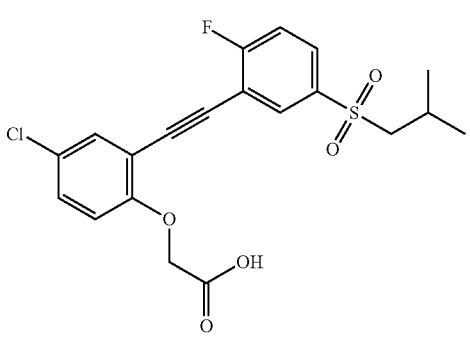 |
| 106 | 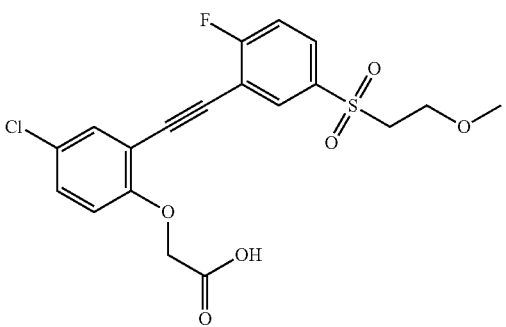 |

| Ex. | Formula |
|---|---|
| 107 | 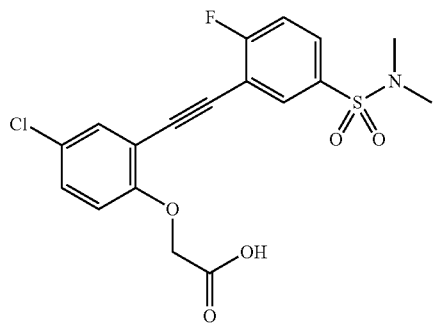 |
| 108 | 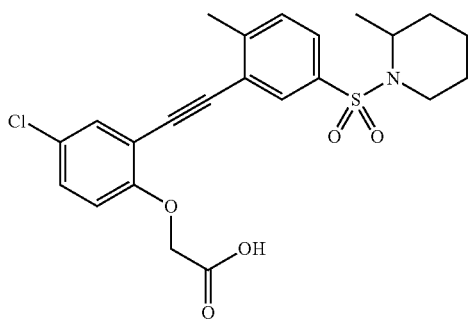 |
| 109 | 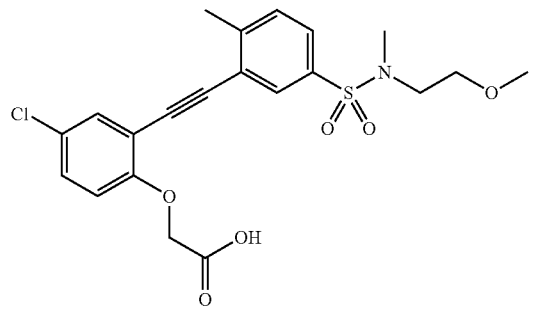 |
| 110 | 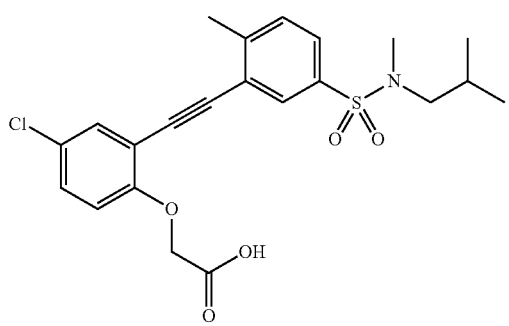 |
| 111 | 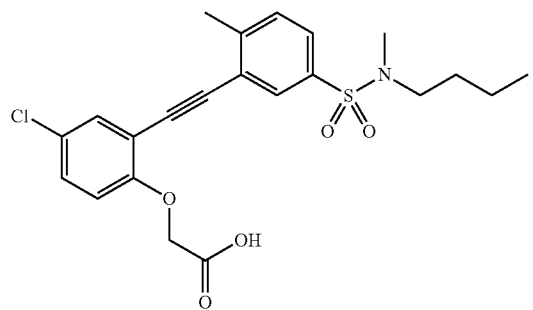 |
| 112 | 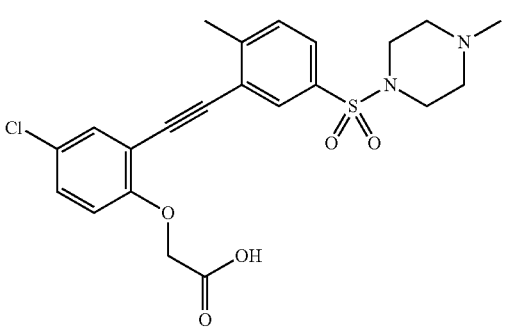 |
| 113 | 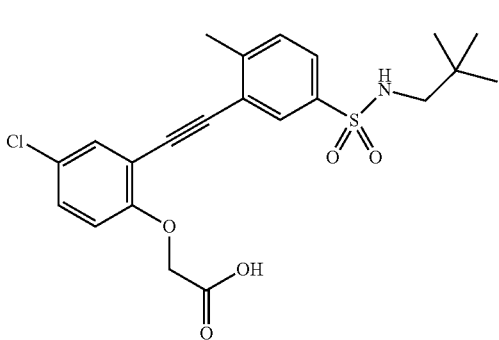 |
| 114 | 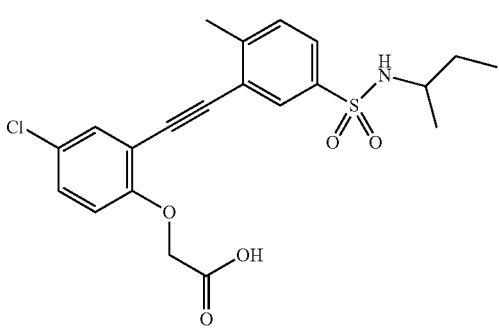 |
| 115 | 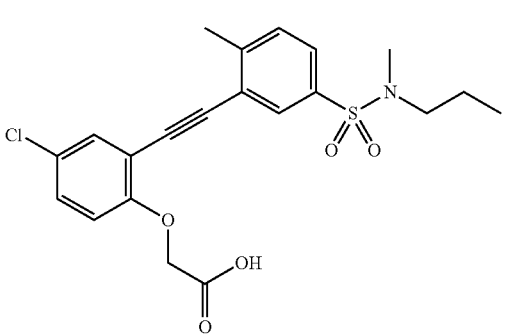 |

-continued
| Ex. | Formula |
|---|---|
| 116 | 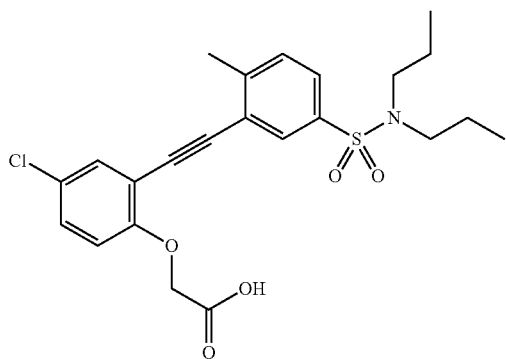 |
| 117 | 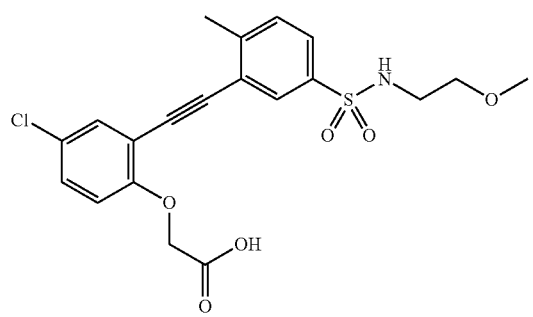 |
| 118 | 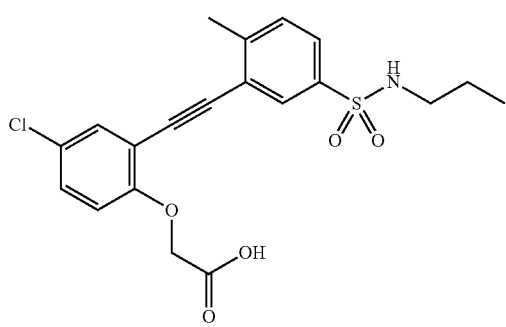 |
| 119 | 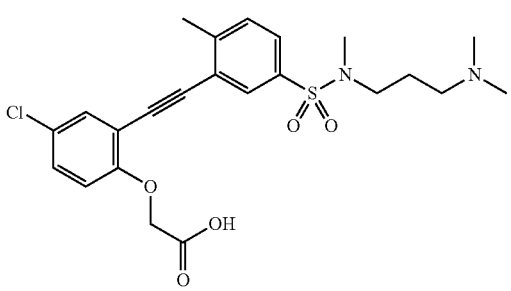 |
| 120 | 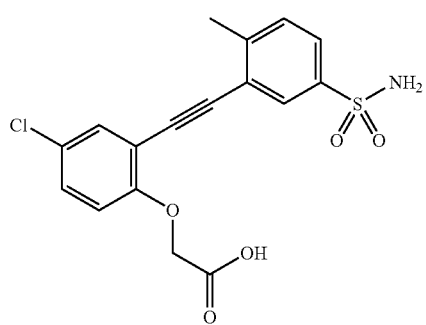 |
-continued
| Ex. | Formula |
|---|---|
| 121 | 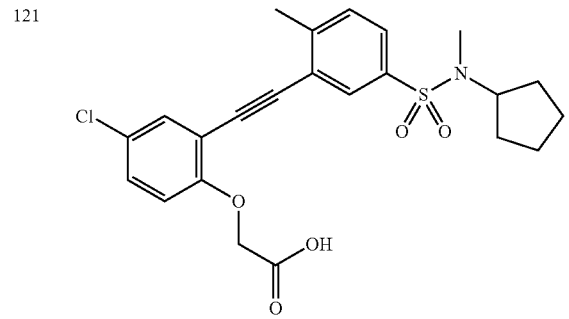 |
| 122 | 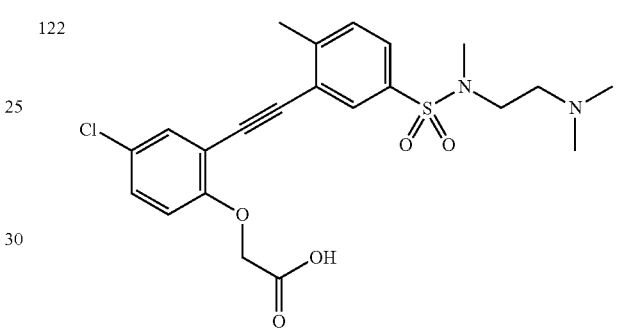 |
| 123 | 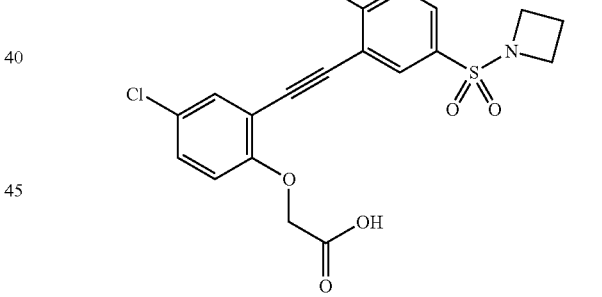 |
| 124 | 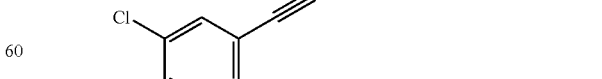 |

399
-continued
| Ex. | Formula |
|---|---|
| 125 | 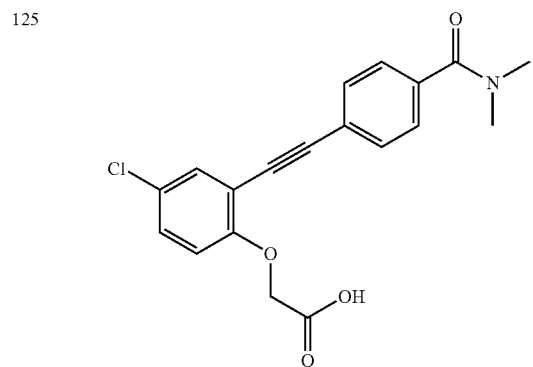 |
| 126 | 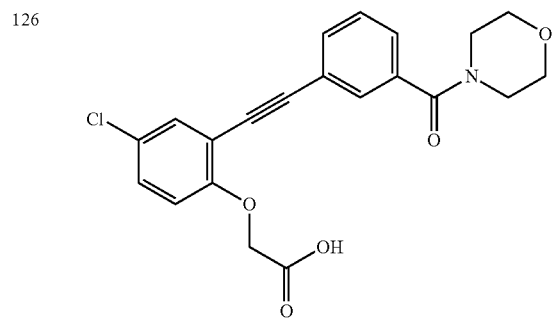 |
| 127 | 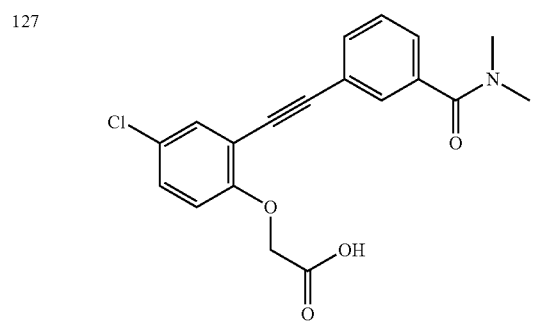 |
| 128 | 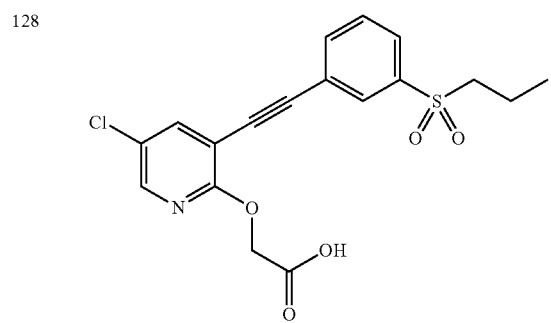 |
400
-continued
| Ex. | Formula |
|---|---|
| 129 | 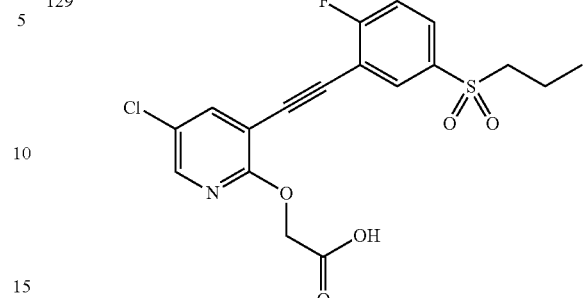 |
| 130 | 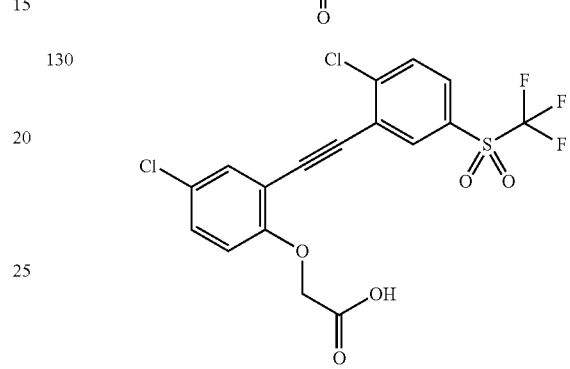 |
| 131 | 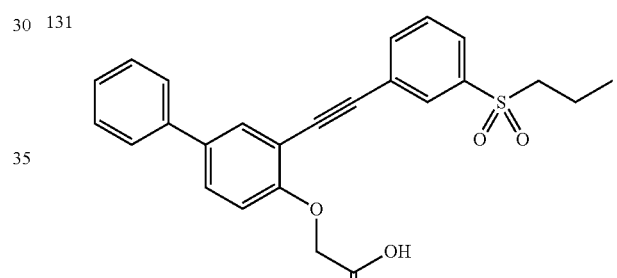 |
| 132 | 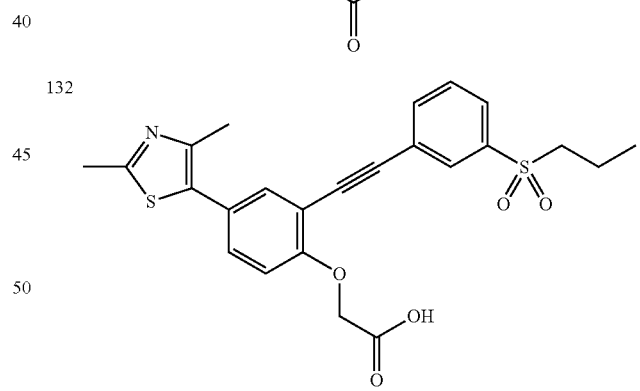 |
| 133 | 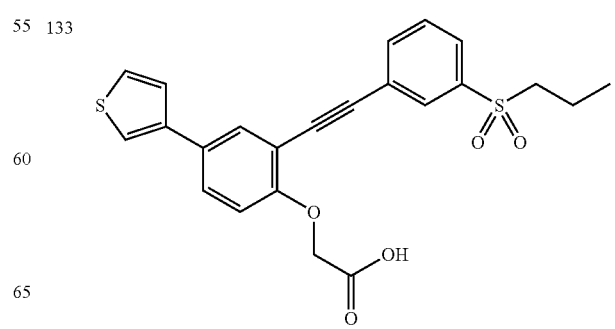 |

| Ex. | Formula |
|---|---|
| 134 | 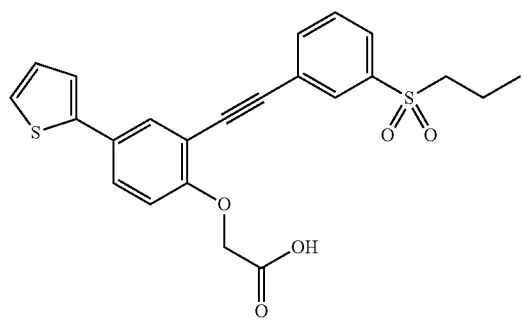 |
| 135 | 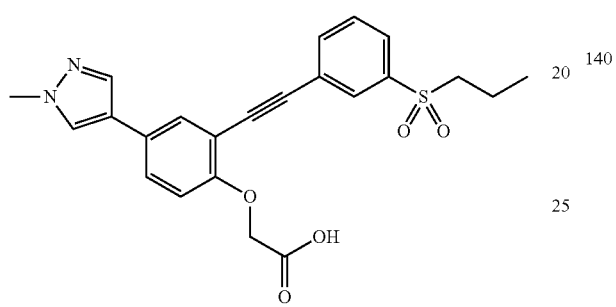 |
| 136 | 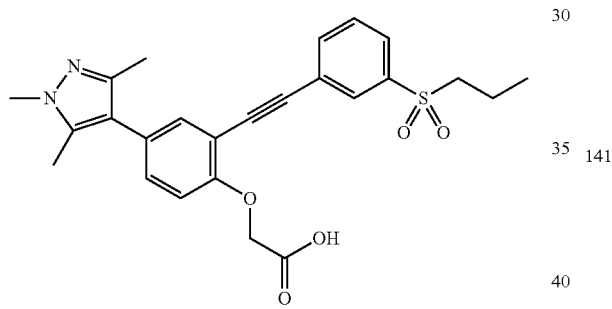 |
| 137 | 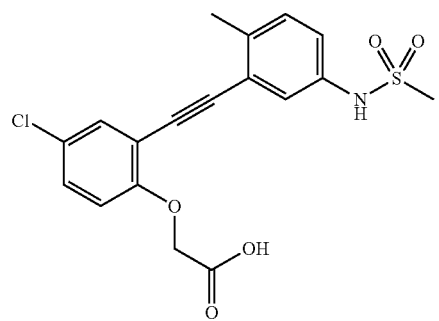 |
| 138 | 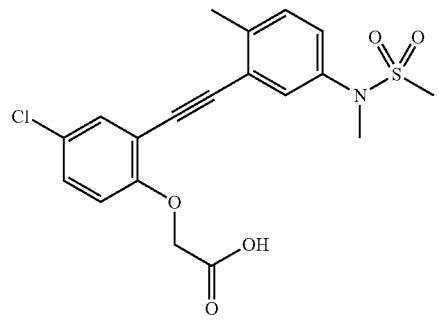 |
| Ex. | Formula |
|---|---|
| 139 | 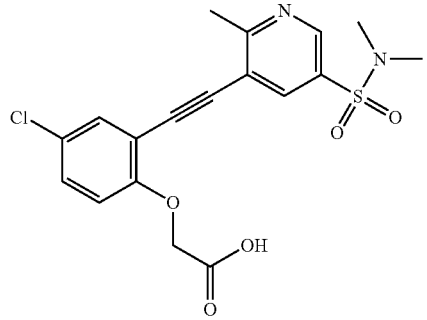 |
| 140 | 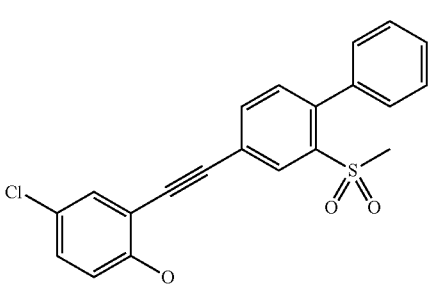 |
| 141 | 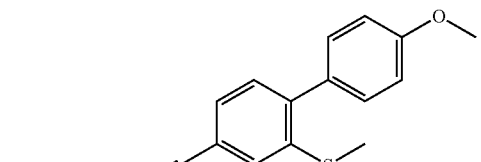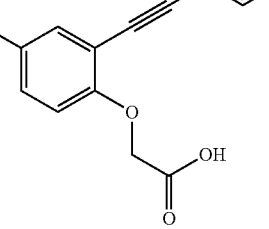 |
| 142 | 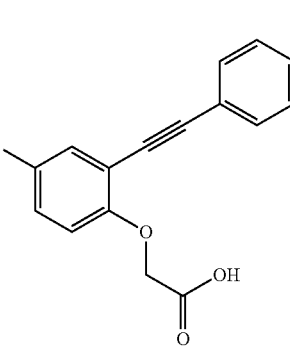 |

-continued

| Ex. | Formula |
|---|---|
| 143 | |
| 144 | |
| 145 | |
| 146 | |

-continued

| Ex. | Formula |
|---|---|
| 147 | |
| 148 | |
| 149 | |
| 150 | |

| Ex. | Formula |
|---|---|
| 151 | |
| 152 | |
| 153 | |
| 154 | |
| 155 | |
| 156 | |
| 157 | |
| 158 | |
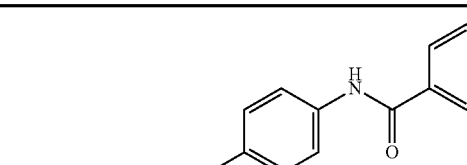

| Ex. | Formula |
|---|---|
| 159 | (structure) |
| 160 | (structure) |
| 161 | (structure) |
| 162 | (structure) |
| 163 | (structure) |
| 164 | (structure) |
| 165 | (structure) |
| 166 | (structure) |

| Ex. | Formula |
|---|---|
| 167 | 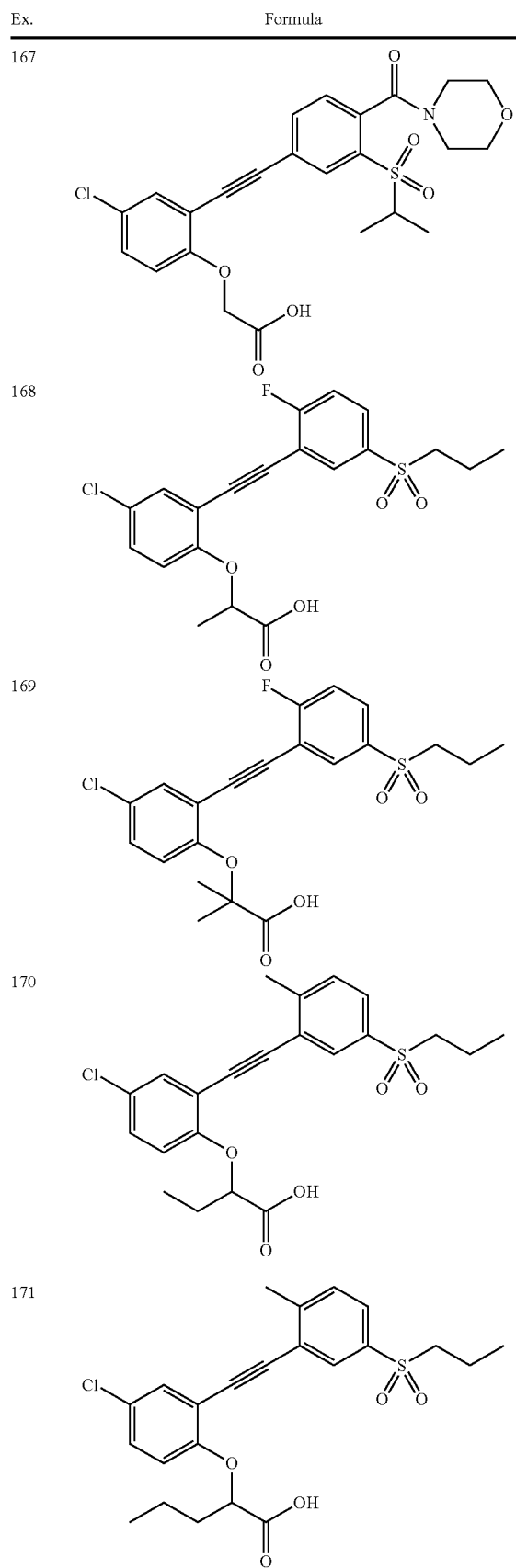 |
| 168 | |
| 169 | |
| 170 | |
| 171 | |

| Ex. | Formula |
|---|---|
| 172 | 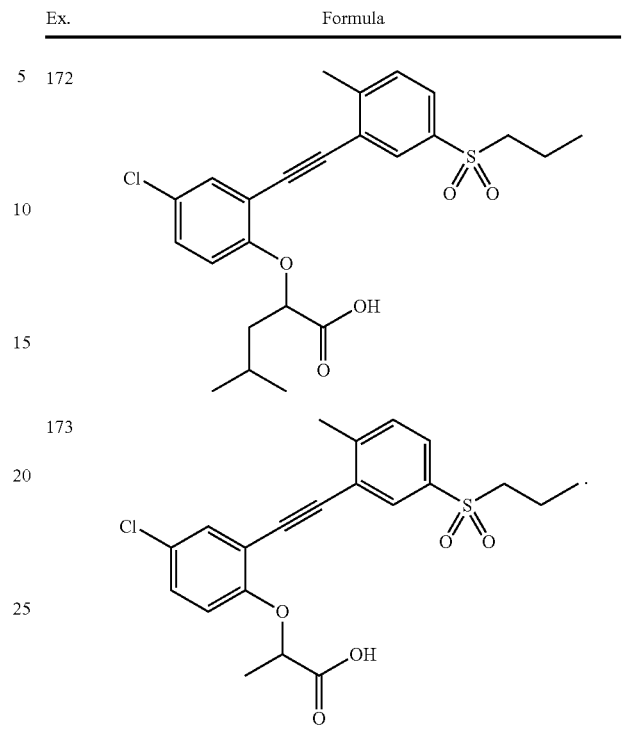 |
| 173 | |

6. A pharmaceutical composition containing at least one compound according to claim 1 and a pharmaceutically acceptable carrier, diluent or excipient.

7. A kit consisting of separate packs of:
   (a) an effective amount of a compound of claim 1; and
   (b) an effective amount of a second active ingredient.

8. A method of treating a disease in a subject comprising administering a composition comprising a compound according to claim 1 to a subject having a disease selected from the group consisting of allergic asthma, allergic rhinitis, allergic conjunctivitis, systemic anaphylaxis, chronic obstructive pulmonary disease (COPD), rheumatoid arthritis, osteoarthritis, inflammatory bowel disease, ulcerative colitis, Crohn's disease and hypersensitivity response.

9. A method of treating an inflammatory dermatosis in a subject comprising administering a composition comprising a compound according to claim 1 to a subject having an inflammatory dermatosis selected from the group consisting of atopic dermatitis, contact hypersensitivity, allergic contact dermatitis, eczema, myositis, chronic urticaria, chronic idiopathic/autoimmune urticaria, drug induced exanthems, photodermatosis or polymorphous light eruption and myosotis.

10. A process for the preparation of compounds of claim 1, wherein compounds of Formula (II)

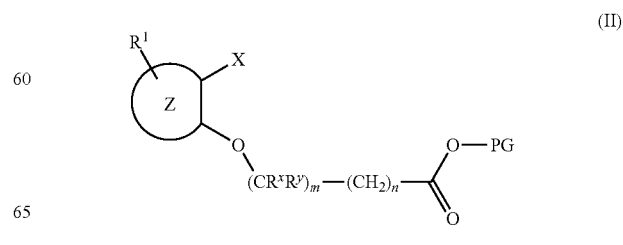

are reacted with compounds of Formula (III) in the presence of a catalyst

wherein $R^1$, Q, m and n are as defined in claim 1, PG denotes a protecting group, and
X denotes Cl, Br, I, or trifluoromethanesulfonate.

11. The process according to claim 10, wherein the catalyst is selected from dichlorobis(triphenylphosphine)palladium (II) or 1,1'-bis(diphenylphosphino)ferrocenedichloro palladium(II), $Pd(OAc)_2$, $Pd_2(dba)_3$, or Pd/C.

12. The process according to claim 11, further comprising the step of removing the protecting group.

* * * * *